US012459921B2

(12) United States Patent
Chen et al.

(10) Patent No.: US 12,459,921 B2
(45) Date of Patent: Nov. 4, 2025

(54) ISOINDOLINE COMPOUND, PREPARATION METHOD, PHARMACEUTICAL COMPOSITION AND USE THEREOF

(71) Applicant: SHANGHAI INSTITUTE OF MATERIA MEDICA, CHINESE ACADEMY OF SCIENCES, Shanghai (CN)

(72) Inventors: Xiaohua Chen, Shanghai (CN); Jia Li, Shanghai (CN); Yu Cheng, Shanghai (CN); Yubo Zhou, Shanghai (CN); Huijun Nie, Shanghai (CN); Yujie Wang, Shanghai (CN); Hongtao Tian, Shanghai (CN); Weijuan Kan, Shanghai (CN); Tian Mi, Shanghai (CN); Xiaobei Hu, Shanghai (CN); Binshan Zhou, Shanghai (CN); Kenian Yan, Shanghai (CN); Gaoya Xu, Shanghai (CN); Yuhua Zhong, Shanghai (CN); Lei Feng, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 1194 days.

(21) Appl. No.: 17/281,419

(22) PCT Filed: Sep. 30, 2019

(86) PCT No.: PCT/CN2019/109368

§ 371 (c)(1),
(2) Date: Mar. 30, 2021

(87) PCT Pub. No.: WO2020/064002

PCT Pub. Date: Apr. 2, 2020

(65) Prior Publication Data

US 2022/0041576 A1 Feb. 10, 2022

(30) Foreign Application Priority Data

Sep. 30, 2018 (CN) ......................... 201811156797.9

(51) Int. Cl.

| | |
|---|---|
| ***C07D 401/14*** | (2006.01) |
| ***A61K 45/06*** | (2006.01) |
| ***C07D 401/04*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/10*** | (2006.01) |
| ***C07D 491/107*** | (2006.01) |
| ***C07D 495/04*** | (2006.01) |
| ***C07D 498/20*** | (2006.01) |

(52) U.S. Cl.
CPC ............ *C07D 401/14* (2013.01); *A61K 45/06* (2013.01); *C07D 401/04* (2013.01); *C07D 405/14* (2013.01); *C07D 409/14* (2013.01); *C07D 413/14* (2013.01); *C07D 417/14* (2013.01); *C07D 471/10* (2013.01); *C07D 491/107* (2013.01); *C07D 495/04* (2013.01); *C07D 498/20* (2013.01)

(58) Field of Classification Search
None
See application file for complete search history.

(56) References Cited

U.S. PATENT DOCUMENTS

| | | | | |
|---|---|---|---|---|
| 8,153,659 B2 | 4/2012 | Ruchelman | | |
| 8,481,568 B2 | 7/2013 | Muller | | |
| 8,518,972 B2 | 8/2013 | Man | | |
| 8,877,780 B2 | 11/2014 | Muller | | |
| 9,181,216 B2 | 11/2015 | Ruchelman | | |
| 9,447,070 B2 | 9/2016 | Muller | | |
| 9,920,027 B2 | 3/2018 | Ruchelman | | |
| 10,017,492 B2 | 7/2018 | Ge | | |
| 2019/0192668 A1* | 6/2019 | Mainolfi | .............. | A61K 31/427 |
| 2022/0041578 A1* | 2/2022 | Chen | .................... | C07D 413/14 |

FOREIGN PATENT DOCUMENTS

| | | | |
|---|---|---|---|
| CN | 101291924 | A | 10/2008 |
| CN | 101679380 | A | 3/2010 |
| CN | 102822165 | A | 12/2012 |

(Continued)

OTHER PUBLICATIONS

Fischer et al., Structure of the DDB1-CRBN E3 ubiquitin ligase in complex with thalidomide. Nature. Aug. 7, 2014;512(7512):49-53 (Year: 2014).*
International Search Report issued Jan. 8, 2020 in corresponding PCT/CN2019/109368.
Written Opinion issued Jan. 8, 2020 in corresponding PCT/CN2019/109368.
Lohbeck, J., "Practical synthesis of a phthalimide-based Cereblon lignad to enable PROTAC development," Bioorganic & Medicinal Chemistry Letters, vol. 26, Sep. 19, 2016, pp. 5260-5262.
Papatzimas, J.W., et al., "A General Strategy for the Preparation of Thalidomide-Conjugate Linkers," Synlett, vol. 28, Aug. 23, 2017, pp. 2881-2885.

(Continued)

*Primary Examiner* — Jeffrey S Lundgren
*Assistant Examiner* — Anthony Joseph Seitz
(74) *Attorney, Agent, or Firm* — Ice Miller LLP

(57) ABSTRACT

The present invention relates to a polysubstituted isoindoline compound as shown in general formula (I), and a preparation method, a pharmaceutical composition and the use thereof. In particular, the polysubstituted isoindoline compound is provided in the present invention as a class of novel $CRL4^{CRBN}$ E3 ubiquitin ligase modulators in structure, wherein same has a stronger antitumor activity and antitumor spectrum, and can be used to prepare drugs for treating $CRL4^{CRBN}$ E3 ligase-related diseases.

14 Claims, No Drawings

(56) References Cited

FOREIGN PATENT DOCUMENTS

| | | | | | |
|---|---|---|---|---|---|
| CN | 102822165 | B | | 12/2012 | |
| CN | 105566290 | A | | 5/2016 | |
| WO | 2007027527 | A2 | | 3/2007 | |
| WO | 2008027542 | A2 | | 3/2008 | |
| WO | WO-2008115516 | A2 | * | 9/2008 | ......... A61K 31/4035 |
| WO | 2011100380 | A1 | | 8/2011 | |
| WO | 2012015986 | A2 | | 2/2012 | |
| WO | 2016065980 | A1 | | 5/2016 | |
| WO | 2017176958 | A1 | | 10/2017 | |
| WO | 2017197051 | A1 | | 11/2017 | |
| WO | WO-2017197240 | A1 | * | 11/2017 | ........... A61K 31/404 |
| WO | 2017212329 | A1 | | 12/2017 | |
| WO | 2017223452 | A1 | | 12/2017 | |
| WO | 2018119448 | A1 | | 6/2018 | |
| WO | 2019191112 | A1 | | 3/2019 | |
| WO | 2019133531 | A1 | | 7/2019 | |
| WO | WO-2019213005 | A1 | * | 11/2019 | ........... A61K 31/501 |
| WO | 2020106933 | A1 | | 5/2020 | |

OTHER PUBLICATIONS

Extended European Search Report issued May 12, 2022 in corresponding EP No. 19867602.

Lebraud, Honorine, et al., "Protein Degradation by In-Cell Self-Assembly of Proteolysis Targeting Chimeras," ACS Central Science, vol. 2, pp. 927-934 (2016).

Patani, G.A., et al, "Bioisosterism: A Rational Approach in Drug Design," Chem. Rev., vol. 96(8), pp. 3147-3176, Dec. 19, 1996.

Ito, Takumi, et al, "Identification of a Primary Target of Thalidomide Teratogenicity," Science, vol. 327, pp. 1345-1350, Mar. 12, 2010.

Kronke, Jan, et al, "Lenalidomide Causes Selective Degradation of IKZF1 and IKZF3 in Multiple Myeloma Cells," Science, vol. 343, 8 pages (2014).

Lu, Gang, et al, "The Myeloma Drug Lenalidomide Promotes the Cereblon-Dependent Destructions of Ikaros Proteins," Science, vol. 343, 8 pages (2014).

Kronke, Jan, et al, "Lenalidomide induces ubiquitination and degradation of CK1a in del(5q) MDS," Nature, vol. 523, 20 pages (2015).

* cited by examiner

ISOINDOLINE COMPOUND, PREPARATION METHOD, PHARMACEUTICAL COMPOSITION AND USE THEREOF

CROSS-REFERENCE TO RELATED APPLICATION

This application is a Section 371 of International Application No. PCT/CN2019/109368 filed Sep. 30, 2019, which was published in the Chinese language Apr. 2, 2020, under International Publication No. WO 2020/064002 A1, which claims priority to Chinese Application No. 2018111567979 filed Sep. 30, 2018, the disclosures of which are incorporated herein by reference in their entireties.

TECHNICAL FIELD

The present invention relates to a class of novel multi-substituted isoindoline compound, pharmaceutically acceptable salt, solvate, pharmaceutical composition, and use thereof in the preparation of drugs for the treatment or prevention of various diseases.

BACKGROUND OF THE INVENTION

Tight regulation of protein expression in cells plays an important role in cell function, cell survival and division. Many primary or acquired diseases usually involve abnormal protein function. Traditional protein dysfunction regulating method is mainly by designing targeted inhibitors or agonists. These targeted drugs play an important role in the treatment of diseases. Nevertheless, in order to obtain a satisfactory therapeutic effect, these inhibitors or agonists usually need to be maintained at a higher drug concentration to achieve an effective therapeutic effect, which to a certain extent also leads to adverse drug reactions. Another way to regulate the abnormal function of proteins is to change the dynamic balance of pathologically related proteins, which involves the synthesis and degradation of proteins, for example knock out or silence target protein genes by using small interfering RNA (siRNA), antisense oligonucleotides, or gene editing techniques. These nucleic acid-based technologies change protein synthesis by acting on the transcription and translation process of the target protein. The main limitation of this type of technology lies in low stability and bioavailability of nucleic acid in vivo, which to some extent further limited applications thereof. Another strategy to regulate the dynamic balance of proteins is to regulate the process of protein degradation, thus directly changing the expression of target proteins in cells by promoting or inhibiting the degradation of proteins. Ubiquitin-Proteasome System (UPS) plays an important role in the degradation of proteins. Under the action of a series of ubiquitin enzymes, the target protein can be labeled by ubiquitin, and proteins with specific ubiquitin tags can be transported to the proteasome for degradation.

There are various protein ubiquitination patterns, including monoubiquitination (substrate proteins bind to only one ubiquitin), multi-monoubiquitination (substrate proteins have multiple ubiquitination sites, each of which is monoubiquitinated), or polyubiquitination (forming an ubiquitin chain). In addition, the process of polyubiquitination can also occur on multiple lysine side chain amine groups or N terminal amine groups on the ubiquitin itself. Depending on different ubiquitination patterns, the protein ubiquitination can affect the process of the protein in the cell, including subcellular localization, protein storage, and protein-protein interaction, etc. it also affect the function of the protein, including protein function activation, inhibition or proteasome/lysosomal degradation, etc.

The process of protein ubiquitination is a series of multi-step reactions which mainly involves three types of enzymes: E1 ubiquitin activating enzyme, E2 ubiquitin conjugating enzyme, and E3 ubiquitin ligase. Firstly, the C terminal of ubiquitin is activated by ATP and forms an active thioester structure with the cysteine sulfhydryl of the active center of E1 ubiquitin activating enzyme. Then, the active intermediate covalently connects ubiquitin to the E2 ubiquitin-conjugating enzyme via the new thioester structure through transthioester reaction. Finally, E3 ubiquitin ligase recruits the substrate protein and simultaneously binds to the E2 ubiquitin conjugating enzyme-ubiquitin active intermediate, and transfers ubiquitin to the substrate protein to complete the ubiquitination of the substrate protein. In the entire ubiquitination process, E3 ubiquitin ligase plays an important role, it not only acts as a bridge to bring the two reaction components (E2 ubiquitin conjugating enzyme-ubiquitin conjugate and substrate protein) close to each other in space, but also acts as an enzyme catalysis to accelerate the rate of substrate protein ubiquitination. Because the E3 ubiquitin ligase needs to specifically recognize the substrate, the mammalian genome encodes more than 600 E3 ubiquitin ligases, while only two E1 ubiquitin activating enzymes and about 40 E2 ubiquitin conjugating enzymes have been discovered yet.

E3 ubiquitin ligases can be divided into three categories according to their conserved domains and action mode. E3 ubiquitin ligase of TECT family and RBR family, first transfers ubiquitin from E2 ubiquitin activating enzyme to itself, then transfers ubiquitin from E3 ubiquitin ligase to substrate protein during substrate ubiquitination. The RING family E3 ubiquitin ligase occupies a comparatively larger proportion in the entire E3 ubiquitin ligase. This type of E3 ubiquitin ligase contains the RING domain or RING like domains, which can bind to the E2 ubiquitin conjugating enzyme, and promote the direct transfer of ubiquitin from the E2 ubiquitin conjugating enzyme to the substrate protein.

$CRL4^{CRBN}$ E3 ubiquitin ligase belongs to the RING family E3 ubiquitin ligase, which is a protein complex assembled from multiple subunits. The complex consists of a substrate protein recognition module (CRBN), an E2 ubiquitin conjugating enzyme recognition module (RING domain) and a link (Cullin protein) between them. CRBN directly binds to the substrate in the entire protein complex and controls the substrate specificity of the entire ubiquitination process.

Small molecule modulators that act directly on CRBN can control the substrate selectivity of $CRL4^{CRBN}$E3 ubiquitin ligase. New research found that Cereblon (gene name: CRBN) is a direct target of immunomodulator-thalidomide and its analogues (Science, 2010, 327, 1345; Science, 2014, 343, 301; Science, 2014, 343, 305; Nature, 2015, 523, 183.). It has been demonstrated that dosamine immunomodulators can selectively induce ubiquitination and degradation of transcription factors IKZF1 and IKZF3 in multiple myeloma cell lines by regulating the activity of CRBN-ubiquitin ligase complex. This process changes the functions of T cells and B cells, and at the same time produces toxic effects on multiple myeloma cells, thus achieving therapeutic effect on malignant myeloid systems including multiple myeloma. Recent studies have shown that lenalidomide, an analog of thalidomide, can selectively induce the ubiquitination and degradation of CK1α through $CRL4^{CRBN}$E3 ubiquitin ligase, thus achieving the treatment of 5q deletion myelodysplastic syndrome (MDS). However, another structural analogue of thalidomide (CC-885) can selectively induce and degrade GSPT1 by acting on $CRL4^{CRBN}$E3 ligase, and exhibits strong cytotoxicity to a variety of tumor cells.

Existing research results show that different dosamine drug molecules have different specificity of substrate protein degradation after interacting with target CRBN. When lenalidomide is used in the treatment of multiple myeloma, its therapeutic effect is mainly achieved through the selective degradation of IKZF1 and IKZF3; while in the treatment of 5q deletion myelodysplastic syndrome (del(5q) MDS) mainly through degradation of CK1α. Lenalidomide is the main dosamine analogue developed presently which shows strong degradation activity against CK1α, thus being the most important clinically effective treatment for myelodysplastic syndrome del(5q) MDS dosamine drugs. With the development of new dosamine drugs and the development of clinical trials, the indications of dosamine drug molecules are also expanding, e.g., thalidomide approved by FDA for the treatment of erythema nodosum leprosy, lenalidomide for the treatment of prostate cancer in clinical trials, and pomalidomide for the treatment of myelofibrosis in clinical trials.

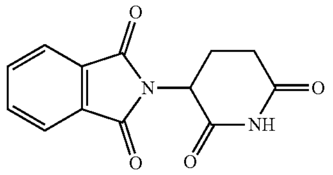

thalidomide

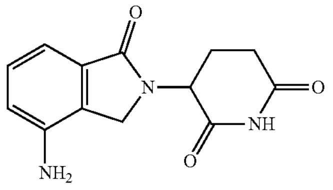

lenalidomide

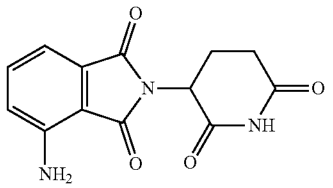

pomalidomide

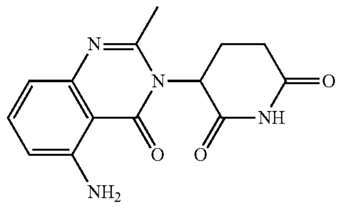

CC-122

-continued

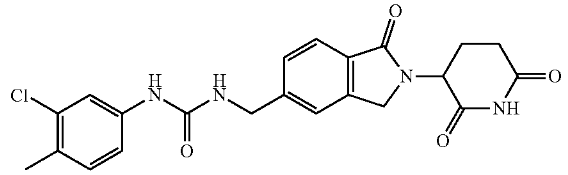

CC-885

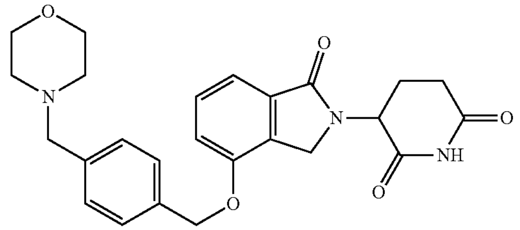

CC-220

The reported compounds lenalidomide, pomalidomide, CC-122, CC-220, CC-885 are similar to thalidomide in structure. The characteristic of this types of compounds lies that after structural changes and adjustments, the compounds have different pharmacological activity and completely different therapeutic effects, and can be used clinically to treat different indications.

WO2008115516A2, U.S. Pat. Nos. 8,153,659B2, 9,181,216B2, 9,920,027B2 have disclosed the compound represented by the general formula S1:

S1

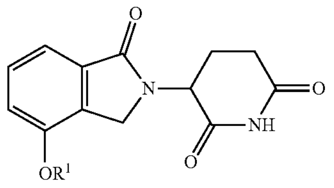

The main representative R1 in the general formula S1 is aryl, arylalkyl, heterocyclylalkyl, etc.

WO2011100380 A1 and CN102822165B have disclosed a class of compounds represented by the general formula S2:

S2

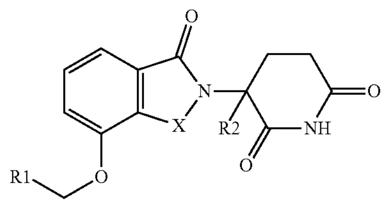

In the general formula S2, R1 is a variety of substituted aryl, and the representative compound is CC-220:

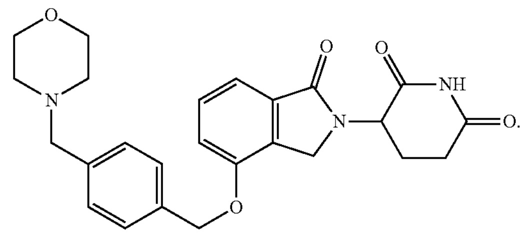

CC-220

WO2016065980A1, CN105566290A and U.S. Ser. No. 10/017,492B2

S3

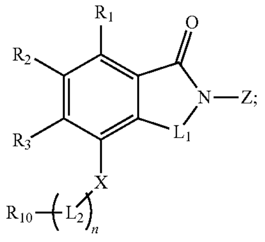

The representative compounds in the general formula S3 are:

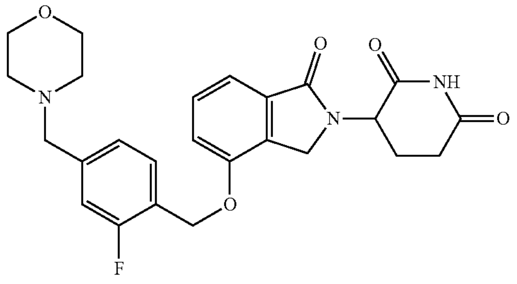

And

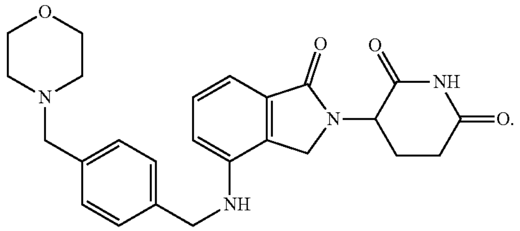

WO2007027527A2, CN101291924A and U.S. Pat. No. 8,481,568B2 have disclosed a class of compounds represented by the general formula S3:

S4

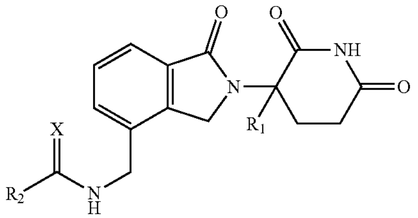

S5

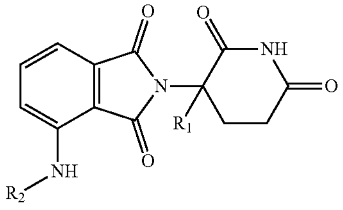

The representative compound in the general formula S4 and S5 are:

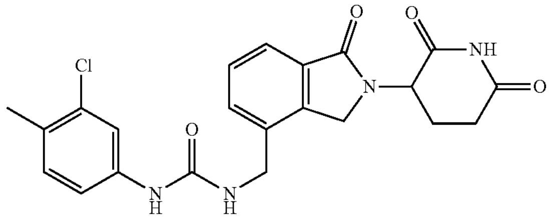

and

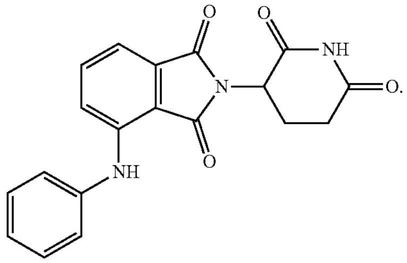

WO2008027542A2, U.S. Pat. No. 8,877,780B2 and U.S. Pat. No. 9,447,070B2 have disclosed a class of compounds represented by the general formula S3:

S6

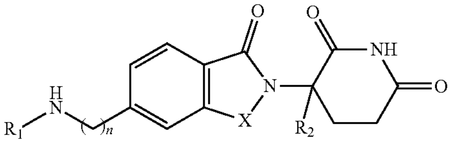

S7

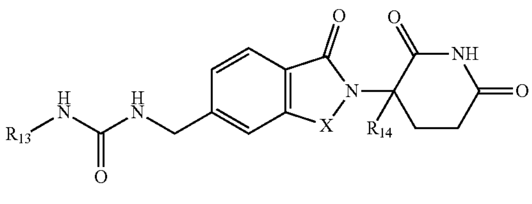

the representative compounds in the general formula S6 and S7 are:

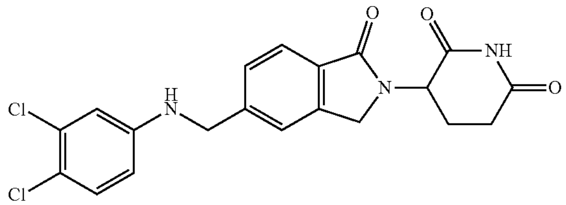

and

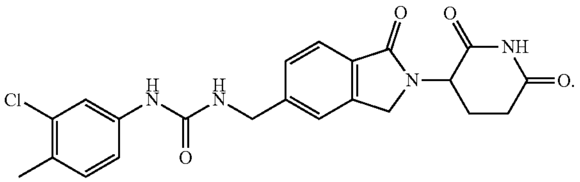

CC-885

The mechanism of action of lenalidomide and some of the above-mentioned molecules is that compounds of different structures can bind to CRBN, thus causing the conformational change of the CRBN binding part, thereby recruiting different endogenous biological macromolecules to bind with CRBN; and further ubiquitinate and degrade the potentially different endogenous substrate proteins, which can produce different pharmacological activities and used in clinical trials to treat different indications.

In summary, lenalidomide is mainly used for the treatment of multiple myeloma and myelodysplastic syndrome, but the effect is not ideal for other indications; other above-mentioned compounds such as CC-122, CC-885 and CC-220 are still in preclinical or clinical research. Therefore, the development of novel structural compounds as $CRL4^{CRBN}E3$ ubiquitin ligase modulators can further improve the therapeutic effect of tumors and expand the clinical needs of new indications of domide drugs. Domide molecules of the different structures are of unknown pharmacological activities and pharmacological properties, and the properties and effects in any aspects are uncertain. Based on the mechanism of action of the dosamine molecule, the development of a new structure of the dosamine molecule can realize the recruitment of new protein substrates, thereby achieving the improvement of the therapeutic effect and the expansion of new indications. Therefore, it is of great research value and practical significance to continue to develop novel structures of $CRL4^{CRBN}E3$ ubiquitin ligase modulators to expand new indications.

SUMMARY OF THE INVENTION

The inventors of the present invention obtained the following important information by analyzing the crystal structure of the complex between CRBN and small molecules (PDB ID: 4CI2, 5HXB): CRBN has multiple binding pockets with small molecules. Therefore, small molecules with complex structure and multiple binding sites can be developed to realize effective binding between CRBN and small molecules. At the same time, molecular dynamics simulation methods are used to analyze the structure dynamics and binding site of the interface between the model molecule and E3 ubiquitin ligase, combining molecular docking and complex-based pharmacophore matching, and scoring binding mode and interaction of the active site of the compound on the E3 ubiquitin ligase by scoring function to obtain a new specific CRBN small molecule modulator. Based on this information, we designed and synthesized a series of small molecule modulators of CRBN described in this application, and tested the activity of the compounds. The test results show that the new small molecule regulator has very high cell growth inhibitory activity. After the molecule acts on organisms, it can regulate the degradation of substrate proteins by regulating the ubiquitin-proteasome protein degradation pathway in organisms, so as to achieve effective disease therapy based on CRBN target.

An object of the present invention is to provide the compound represented by the following formula (I), the enantiomer, diastereomer, racemate, isotopic compound, metabolic precursor, metabolite, pharmaceutically acceptable salt, ester, prodrug or hydrate thereof.

Another object of the present invention is to provide important intermediates and preparation methods of the compound.

Another object of the present invention is to provide a pharmaceutical composition, wherein the pharmaceutical composition contains a therapeutically effective dose of the compound of formula (I), the enantiomer, diastereomer, racemate, pharmaceutically acceptable salt, ester, prodrug or hydrate thereof, and at least one pharmaceutically acceptable carrier.

Another object of the present invention is to provide a pharmaceutical composition, wherein the pharmaceutical composition contains a therapeutically effective dose of the compound of formula (I), the enantiomer, diastereomer, racemate, pharmaceutically acceptable salt, ester, prodrug or hydrate thereof, and one or more other ingredients with pharmaceutically therapeutic activity. The compound of formula (I) of the present invention, the enantiomer, diastereomer, racemate, pharmaceutically acceptable salt, ester, prodrug or hydrate thereof may be combined with one or more other ingredients with pharmaceutically therapeutic activity to produce synergistic effects in the prevention or treatment of specific diseases or dysfunctions. The compound of formula (I) of the present invention, the enantiomer, diastereomer, racemate, pharmaceutically acceptable salt, ester, prodrug or hydrate thereof can also reduce or eliminate the toxic and side effects of one or more other ingredients with pharmaceutically therapeutic activity in the prevention or treatment of specific diseases or dysfunctions, and vice versa.

Another object of the present invention is to provide another one or more ingredients with pharmaceutically therapeutic activity as described above, comprising macromolecular compound, such as protein, polysaccharide, nucleic acid, etc., and small molecular compound, such as inorganic compound, organometallic compound, synthetic or natural organic small molecule compound, etc.

Another object of the present invention is to provide a use of the compound of formula (I), the enantiomer, diastereomer, racemate, pharmaceutically acceptable salt, ester, prodrug or hydrate thereof, for the manufacture of a medicament for the treatment of diseases related to $CRL4^{CRBN}$ E3 ubiquitin ligase, preferably, the diseases include, but are not limited to cancer, pain, neurological diseases and immune system diseases.

In order to achieve the above object, the present invention provides the compound of formula (I) and the tautomer, enantiomer, diastereomer, racemate, metabolic precursor, metabolite, isotopic compound, pharmaceutically acceptable salt, ester, prodrug or hydrate thereof:

(I)

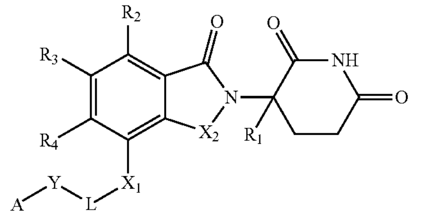

wherein $X_1$ is —$CH_2$— or —O—;

$X_2$ is —$CH_2$— or —CO—;

$R_1$ is hydrogen, deuterium, fluorine or linear or branched $C_1$-$C_6$hydrocarbon group;

$R_2$ and $R_4$ are each independently hydrogen or deuterium;

$R_3$ is hydrogen, deuterium or halogen;

L is substituted or unsubstituted linear alkylene group containing 2-8 carbon atoms, and the "substituted" means that one or more hydrogen atoms in the alkylene group are optionally substituted by the following substituents: deuterium, halogen, carbonyl, hydroxyl, amino, cyano, $C_1$-$C_6$ alkyl, $C_1$-$C_6$ haloalkyl, $C_3$-$C_8$ cycloalkyl, —NHC(O)$Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl unsubstituted or substituted by halogen, hydroxyl, cyano, or nitro, or $C_{3-6}$ cycloalkyl unsubstituted or substituted by halogen, hydroxyl, cyano, or nitro;

Y is absent, or —O—, —CO—, —CO—NH—, —NH—CO—, —NH—CO—NH—, —NH—CO—CH(NH$Ra_9$)— or —CH(NH$R_{a9}$)—;

and when Y is —O—, then A is 6-10 membered aryl, 5-10 membered heteroaryl, (6-10 membered aryl)-$(CH_2)_{b1}$—, or (5-10 membered heteroaryl)-$(CH_2)_{b1}$—, the aryl or heteroaryl is optionally substituted by one or more groups selected from: deuterium, halogen, cyano, nitro, amino, hydroxyl, $C_1$-$C_6$ alkyl, $C_1$-$C_6$ haloalkyl, hydroxyl-substituted $C_1$-$C_6$ alkyl, $C_1$-$C_6$ alkoxyl, $C_1$-$C_6$ alkoxycarbonyl, $C_1$-$C_6$ haloalkoxyl, hydroxyl-substituted $C_1$-$C_6$ alkoxyl, cyano-substituted $C_1$-$C_6$ alkoxyl, $C_3$-$C_6$ cycloalkyl, $C_3$-$C_6$ cycloalkyloxyl, phenyl, 5-6 membered heteroaryl, 3-6 membered heterocyclyl, —NHC(O)$Ra_5$, —NHC(O)O$Ra_6$ and —N$Ra_7$$Ra_8$, wherein $Ra_5$, $Ra_6$, $Ra_7$ and $Ra_8$ are each independently hydrogen, $C_{1-6}$ alkyl unsubstituted or substituted by halogen, hydroxyl, $C_1$-$C_6$ alkoxyl, cyano, or nitro, or $C_{3-6}$ cycloalkyl unsubstituted or substituted by halogen, hydroxyl, $C_1$-$C_6$ alkoxyl, cyano, or nitro;

$b_1$ is 1 or 2;

and when Y is absent, or —CO— or —CO—NH—, (the corresponding placement of Y, A and L is A-L-, A-CO-L-, A-CO—NH-L-) then A is i) heterocyclyl selected from the following:

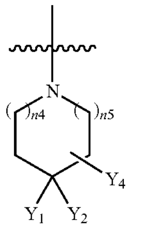

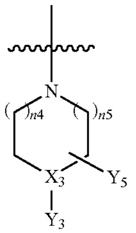

$X_3$ is C, N or O;

$n_4$ is 0, 1, 2 or 3;

$n_5$ is 0, 1, 2 or 3;

$Y_1$ and $Y_2$ are each independently selected from hydrogen, deuterium, halogen, cyano, carboxyl, nitro, hydroxyl, amino, aminocarbonyl, $C_1$-$C_6$ alkyl, $C_1$-$C_6$ alkoxyl, $C_1$-$C_6$ alkylcarbonyl, $C_1$-$C_6$ alkoxycarbonyl, $C_1$-$C_6$ alkylsulfonyl, $C_1$-$C_6$ alkylaminocarbonyl, $C_3$-$C_6$ cycloalkyl or heterocyclyl, $C_1$-$C_6$ acylamino, $C_1$-$C_6$ haloalkyl, $C_1$-$C_6$ haloalkoxyl, $C_1$-$C_3$ alkenyl, $C_1$-$C_3$ alkynyl, substituted or unsubstituted 6-10 membered aryl, substituted or unsubstituted 5-10 membered heteroaryl, linear or branched $C_1$-$C_3$ alkyl substituted by 6-10 membered aryl or 5-10 membered heteroaryl, wherein the substituted or unsubstituted 6-10 membered aryl or 5-10 membered heteroaryl is substituted by one or more substituents selected from: deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl;

when $Y_1$ and $Y_2$ are each independently hydrogen, deuterium, $C_1$-$C_6$ alkoxyl, halogen, $C_1$-$C_6$ alkyl, $C_3$-$C_6$ cycloalkyl, carboxyl, $C_1$-$C_6$ alkylaminocarbonyl, $C_1$-$C_6$ alkoxycarbonyl, nitro, amino, cyano, $C_1$-$C_6$ haloalkyl, hydroxyl, $C_1$-$C_6$ alkylsulfonyl, and when Y is absent, $X_1$ is other than —O—;

$Y_3$ is absent or hydrogen, $C_1$-$C_6$ alkyl, $C_3$-$C_6$ cycloalkyl, $C_1$-$C_6$ alkylaminocarbonyl, $C_1$-$C_6$ alkoxycarbonyl, $C_1$-$C_6$ haloalkyl, $C_1$-$C_6$ alkylsulfonyl, $C_1$-$C_6$ alkylcarbonyl, aminocarbonyl, $C_3$-$C_6$ heterocyclyl, $C_1$-$C_6$ acylamino, $C_1$-$C_6$ haloalkoxyl, $C_1$-$C_3$ alkenyl, $C_1$-$C_3$ alkynyl, substituted or unsubstituted 6-10 membered aryl, substituted or unsubstituted 5-10 membered heteroaryl, linear or branched $C_1$-$C_3$ alkyl substituted by $C_5$-$C_{10}$ aryl or heteroaryl, wherein the substituted or unsubstituted 6-10 membered aryl or 5-10 membered heteroaryl is substituted by one or more substituents selected from: deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl;

when $Y_3$ is hydrogen, $C_1$-$C_6$ alkyl, $C_3$-$C_6$ cycloalkyl, $C_1$-$C_6$ alkylaminocarbonyl, $C_1$-$C_6$ alkoxycarbonyl, $C_1$-$C_6$ haloalkyl, $C_1$-$C_6$ alkylsulfonyl or $Y_3$ is absent, and when Y is absent, $X_1$ is other than —O—;

$Y_4$ and $Y_5$ are one or more substituents on the heterocyclic ring, $Y_4$ and $Y_5$ are each independently deuterium, halogen, oxo, $C_1$-$C_3$ alkyl, $C_1$-$C_3$ cycloalkyl, $C_1$-$C_3$ haloalkyl or phenyl;

ii) fused heterocyclyl selected from:

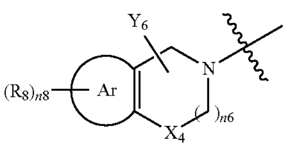

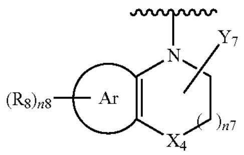

$X_4$ is C, N or O;

$n_6$ is 0, 1, 2 or 3;

$n_7$ is 0, 1, 2 or 3;

$n_8$ is 0, 1, 2, 3 or 4;

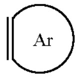

is 6-10 membered aryl ring or 5-10 membered heteroaryl ring, preferably, the

ring is selected from benzene ring, pyridine ring, thiophene ring, indole ring, benzothiophene ring, benzimidazole ring, naphthalene ring, quinoline ring or isoquinoline ring;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl;

when $R_8$ is each independently selected from the following optional substituents: hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, and when Y is absent, $X_1$ is other than —O—;

$Y_6$ and $Y_7$ are one or more substituents on the heterocyclic ring, and each is independently selected from deuterium, halogen, $C_1$-$C_3$ alkyl, $C_1$-$C_3$ cycloalkyl, $C_1$-$C_3$ haloalkyl;

or iii) spiroheterocyclic group selected from:

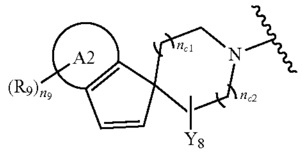

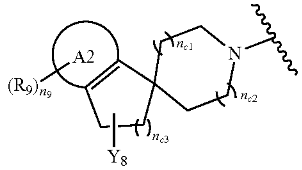

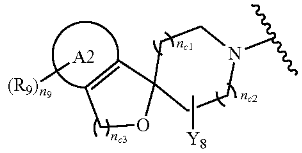

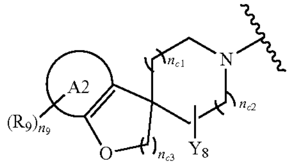

-continued

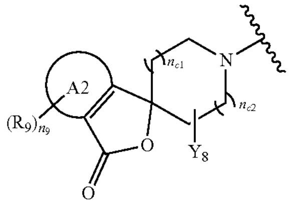

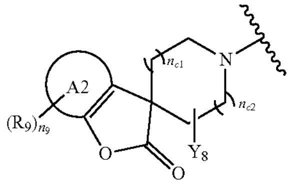

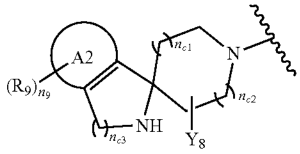

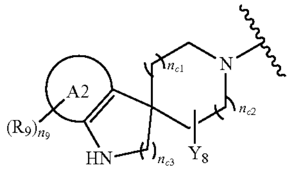

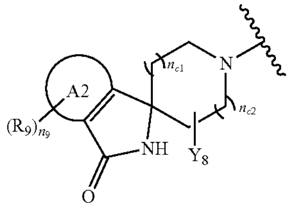

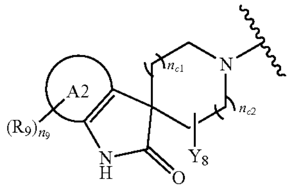

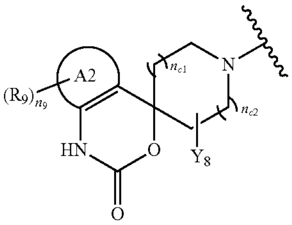

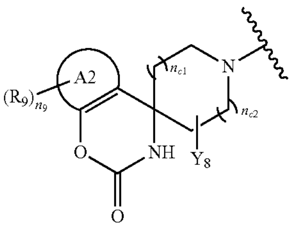

-continued

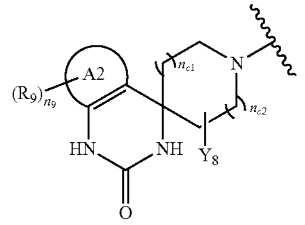 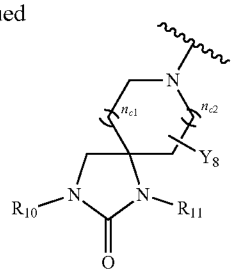

$n_{c1}$ is 0, 1, 2 or 3;
$n_{c3}$ is 1, 2 or 3;
$n_9$ is 0, 1, 2 or 4;

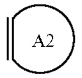

is 6-10 membered aryl ring or 5-10 heteroaryl ring;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkylaminocarbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl;

$R_{10}$ and $R_{11}$ are independently selected from hydrogen, substituted or unsubstituted 6-10 membered aryl, substituted or unsubstituted 5-10 membered heteroaryl, and the type of the substituent is the same as the above-mentioned substituent $R_9$ on the

ring;

$Y_8$ is a substituent which optionally replaces the hydrogen atom in the non-aromatic moiety of the spiro ring structure, and $Y_8$ is optionally substituted by deuterium, halogen, $C_1$-$C_3$ alkyl, $C_1$-$C_3$ cycloalkyl or $C_1$-$C_3$ haloalkyl;

when Y is selected from —NH—CO—, —NH—CO—NH—, —NH—CO—CH($NHR_{a9}$)— or —CH($NHR_{a9}$)—, the corresponding placement of Y, A and L is A-NH—CO-L-, A-NH—CO—NH-L-, A-NH—CO—CH($NHR_{a9}$)-L- or A-CH($NHR_{a9}$)-L-, wherein A is:

6-10 membered aryl, 5-10 membered heteroaryl, (6-10 membered aryl) —$CH_2$—, or (5-10 membered heteroaryl) —$CH_2$—, the aryl or heteroaryl is optionally substituted by one or more $R_5$ substituents, or A is selected from the following groups:

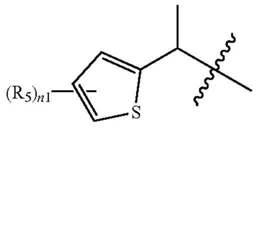 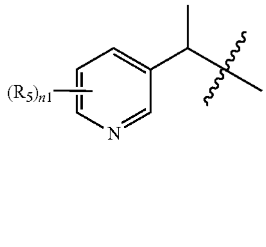

-continued

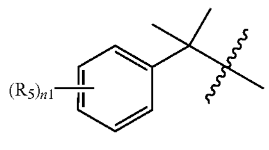 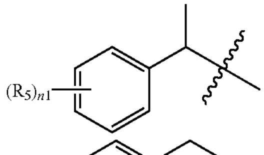

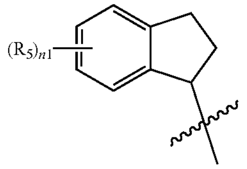 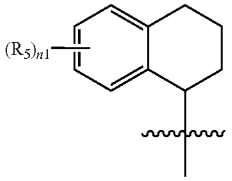

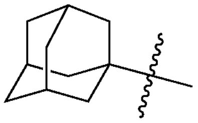 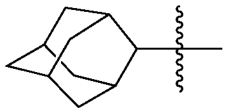

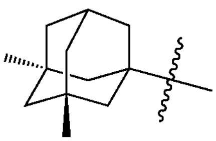 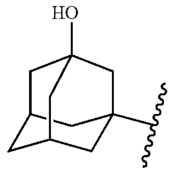

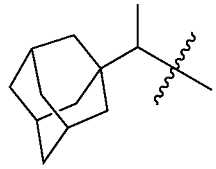 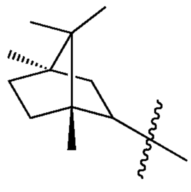

$n_1$ is 0, 1, 2, 3 or 4;

$R_5$ is each independently selected from deuterium, halogen, hydroxyl, amino, cyano, nitro, linear or branched $C_1$-$C_6$ alkyl, linear or branched $C_1$-$C_6$ alkoxyl, $C_1$-$C_3$ acylamino, aminocarbonyl, phenyl, 5-6 membered heteroaryl, 3-6 membered heterocyclyl, $C_3$-$C_6$ cycloalkyl, $C_3$-$C_6$ cycloalkyloxyl, $C_1$-$C_3$ alkylaminocarbonyl, $C_1$-$C_3$ alkylsulfonyl, phenyloxyl or 5-6 membered heteroaryloxyl, when $n_1>1$, each $R_5$ can be the same or different;

$R_{a9}$ is selected from hydrogen, substituted or unsubstituted $C_1$-$C_{10}$ alkylcarbonyl, substituted or unsubstituted $C_3$-$C_8$ cycloalkylcarbonyl, $C_1$-$C_8$ heterocycloalkylcarbonyl, wherein the "substituted" means that the terminal of carbon chain is substituted by hydroxyl or amino.

Preferably, the compound of formula (I), wherein $X_1$ is —$CH_2$— or —O—;

$X_2$ is —$CH_2$— or —CO—;

$R_1$ is hydrogen, deuterium, fluorine or linear or branched $C_1$-$C_3$hydrocarbon group;

$R_2$ and $R_4$ are each independently hydrogen or deuterium;

$R_3$ is hydrogen, deuterium or halogen;

L is substituted or unsubstituted linear alkylene group containing 2-8 carbon atoms, and the "substituted" means that one or more hydrogen atoms in the alkylene group are optionally substituted by the following substituents: deuterium, halogen, carbonyl, hydroxyl, amino, cyano, $C_1$-$C_6$ alkyl, $C_1$-$C_6$ haloalkyl, $C_3$-$C_6$ cycloalkyl, —NHC(O)$Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl substituted by halogen, hydroxyl, cyano, or nitro, or $C_{3-6}$ cycloalkyl substituted by halogen, hydroxyl, cyano, or nitro;

Y is absent, or —O—, —CO—, —CO—NH—, —NH—CO—, —NH—CO—NH—, —NH—CO—CH($NHRa_9$)— or —CH($NHR_{a9}$)—;

when Y is —O—, then A is substituted or unsubstituted 9-10 membered aryl, 9-10 membered heteroaryl, (9-10 membered aryl) —$(CH_2)_{b1}$—, or (9-10 membered heteroaryl)-$(CH_2)_{b1}$—, wherein, $b_1$ is 1 or 2;

the substituted or unsubstituted 9-10 membered aryl or 9-10 membered heteroaryl is selected from the following groups:

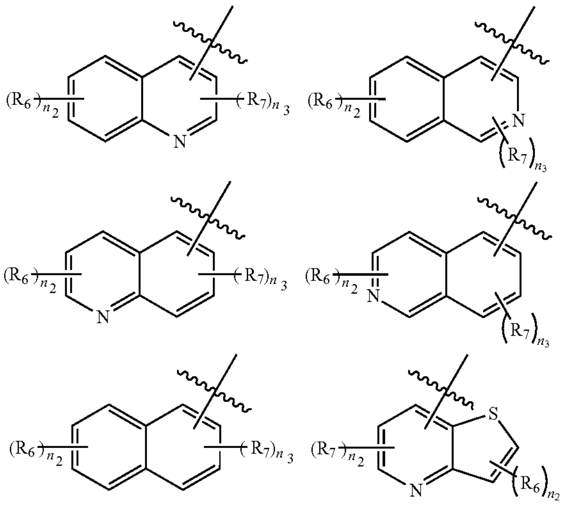

$n_2$ is 0, 1, 2 or 3;

$n_3$ is 0, 1, 2 or 3;

$R_6$ and $R_7$ each independently selected from the following groups: deuterium, halogen, cyano, nitro, amino, hydroxyl, $C_1$-$C_6$ alkyl, $C_1$-$C_6$ haloalkyl, hydroxyl-substituted $C_1$-$C_6$ alkyl, $C_1$-$C_6$ alkoxyl, $C_1$-$C_6$ alkoxycarbonyl, $C_1$-$C_6$ haloalkoxyl, hydroxyl-substituted $C_1$-$C_6$ alkoxyl, cyano-substituted $C_1$-$C_6$ alkoxyl, $C_3$-$C_6$ cycloalkyl, $C_3$-$C_6$ cycloalkyloxyl, phenyl, $C_5$-$C_6$ heteroaryl, $C_3$-$C_6$ heterocyclyl, —NHC(O)$Ra_5$, —NHC(O)O$Ra_6$, —$NRa_7Ra_8$; wherein $Ra_5$, $Ra_6$, $Ra_7$ and $Ra_8$ are each independently hydrogen, $C_{1-6}$ alkyl unsubstituted or substituted by halogen, hydroxyl, $C_1$-$C_6$ alkoxyl, cyano, or nitro, or $C_{3-6}$ cycloalkyl unsubstituted or substituted by halogen, hydroxyl, $C_1$-$C_6$ alkoxyl, cyano, or nitro, wherein when $n_2$>1 or $n_3$>1, $R_6$ and $R_7$ can be the same or different;

and when Y is absent, or —CO— or —CO—NH—, (the corresponding placement of Y, A and L is A-L-, A-CO-L-, A-CO—NH-L-), then A is:

i) heterocyclyl selected from the following:

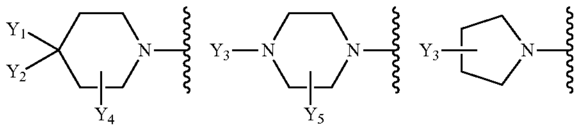

wherein, $Y_1$ and $Y_2$ are each independently selected from hydrogen, deuterium, halogen, cyano, carboxyl, nitro, hydroxyl, amino, aminocarbonyl, $C_1$-$C_6$ alkyl, $C_1$-$C_6$ alkoxyl, $C_1$-$C_6$ alkylcarbonyl, $C_1$-$C_6$ alkoxycarbonyl, $C_1$-$C_6$ alkylsulfonyl, $C_1$-$C_6$ alkylaminocarbonyl, $C_3$-$C_6$ cycloalkyl or heterocyclyl, $C_1$-$C_6$ acylamino, $C_1$-$C_6$ haloalkyl, $C_1$-$C_6$ haloalkoxyl, $C_1$-$C_3$ alkenyl, $C_1$-$C_3$ alkynyl, substituted or unsubstituted 6-10 membered aryl, substituted or unsubstituted 5-10 membered heteroaryl, linear or branched $C_1$-$C_3$ alkyl substituted by 6-10 membered aryl or 5-10 membered heteroaryl, wherein the substituted or unsubstituted 6-10 membered aryl or 5-10 membered heteroaryl is substituted by one or more substituents selected from: deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl;

when $Y_1$ and $Y_2$ are each independently hydrogen, deuterium, $C_1$-$C_6$ alkoxyl, halogen, $C_1$-$C_6$ alkyl, $C_3$-$C_6$ cycloalkyl, carboxyl, $C_1$-$C_6$ alkylaminocarbonyl, $C_1$-$C_6$ alkoxycarbonyl, nitro, amino, cyano, $C_1$-$C_6$ haloalkyl, hydroxyl, $C_1$-$C_6$ alkylsulfonyl, and when Y is absent, $X_1$ is other than —O—;

$Y_3$ is absent, or $C_1$-$C_6$ alkylcarbonyl, aminocarbonyl, $C_3$-$C_6$ heterocyclyl, $C_1$-$C_6$ acylamino, $C_1$-$C_6$ haloalkoxyl, $C_1$-$C_3$alkenyl, $C_1$-$C_3$ alkynyl, substituted or unsubstituted 6-10 membered aryl, substituted or unsubstituted 5-10 membered heteroaryl, linear or branched $C_1$-$C_3$ alkyl substituted by $C_5$-$C_{10}$ aryl or heteroaryl, wherein the substituted or unsubstituted 6-10 membered aryl or 5-10 membered heteroaryl is substituted by one or more of the following substituents: deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl; the 6-10 membered aryl is preferably selected from phenyl, naphthyl, the 5-10 membered heteroaryl is preferably selected from thienyl, pyridyl, benzothienyl, benzimidazolyl, indolyl, quinolinyl, isoquinolinyl;

when $Y_3$ is hydrogen, $C_1$-$C_6$ alkyl, $C_3$-$C_6$ cycloalkyl, $C_1$-$C_6$ alkylaminocarbonyl, $C_1$-$C_6$ alkoxycarbonyl, $C_1$-$C_6$ haloalkyl, $C_1$-$C_6$ alkylsulfonyl or $Y_3$ is absent, and when Y is absent, $X_1$ is other than —O—;

$Y_4$ and $Y_5$ are one or more substituents on the heterocyclic ring wherein $Y_4$ and $Y_5$ are each independently deuterium, halogen, oxo, $C_1$-$C_3$ alkyl, $C_1$-$C_3$ cycloalkyl or phenyl;

ii) fused heterocyclyl selected from:

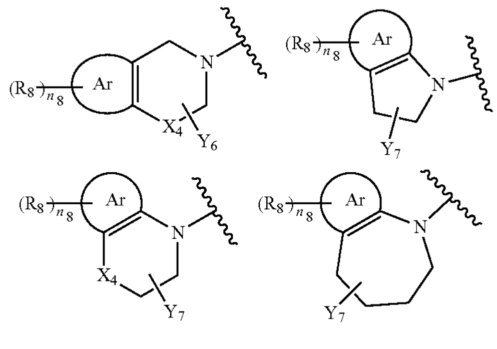

$n_8$ is 0, 1, 2, 3 or 4;

$X_4$ is C, N or O;

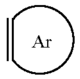

is 6-10 membered aryl ring or 5-10 membered heteroaryl ring, wherein the

ring is preferably selected from benzene ring, pyridine ring, thiophene ring, indole ring, naphthalene ring, benzothiophene ring, benzimidazole ring, quinoline ring or isoquinoline ring;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl;

when $R_8$ each independently selected from any of the following substituents: hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, and when Y is absent, $X_1$ is other than —O—;

$Y_6$ and $Y_7$ are one or more substituents on the heterocyclic ring, and each is independently selected from deuterium, halogen, $C_1$-$C_3$ alkyl, $C_1$-$C_3$ cycloalkyl, $C_1$-$C_3$ haloalkyl;

or iii) spiroheterocyclic group selected from:

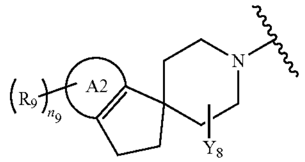

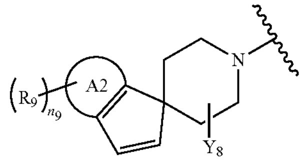

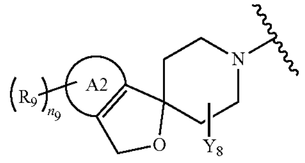

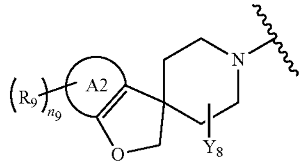

-continued

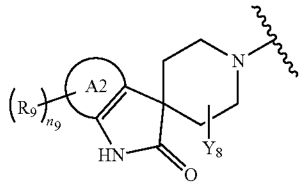

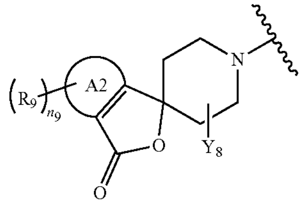

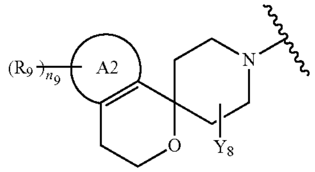

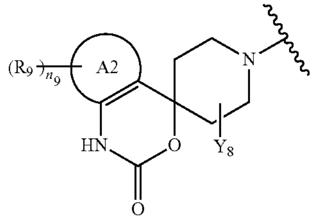

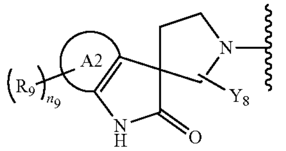

wherein $n_9$ is 0, 1, 2, 3 or 4;

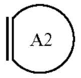

is 6-10 membered aryl ring or 5-10 heteroaryl ring, preferably, thiophene ring, pyrrole ring, benzene ring, pyridine ring, benzothiophene ring, benzimidazole ring, indole ring, quinoline ring and isoquinoline ring;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkylaminocarbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl; wherein when $n_9>1$, each $R_9$ can be the same or different;

$Y_8$ is a substituent which optionally replaces the hydrogen atom in the non-aromatic moiety of the spiro ring structure, and $Y_8$ is optionally substituted by deuterium, halogen, $C_1$-$C_3$ alkyl, $C_1$-$C_3$ cycloalkyl or $C_1$-$C_3$ haloalkyl;

when Y is selected from —NH—CO—, —NH—CO—NH—, —NH—CO—CH($NHR_{a9}$)— or —CH($NHR_{a9}$)—, the corresponding placement of Y, A and L is A-NH—CO-L-, A-NH—CO—NH-L-, A-NH—CO—CH($NHR_{a9}$)-L- or A-CH($NHR_{a9}$)-L-, wherein A is:

6-10 membered aryl, 5-10 membered heteroaryl, (6-10 membered aryl) —$CH_2$—, (5-10 membered heteroaryl) —$CH_2$—, the aryl or heteroaryl is optionally substituted by one or more $R_5$ substituents, or A is selected from the following groups:

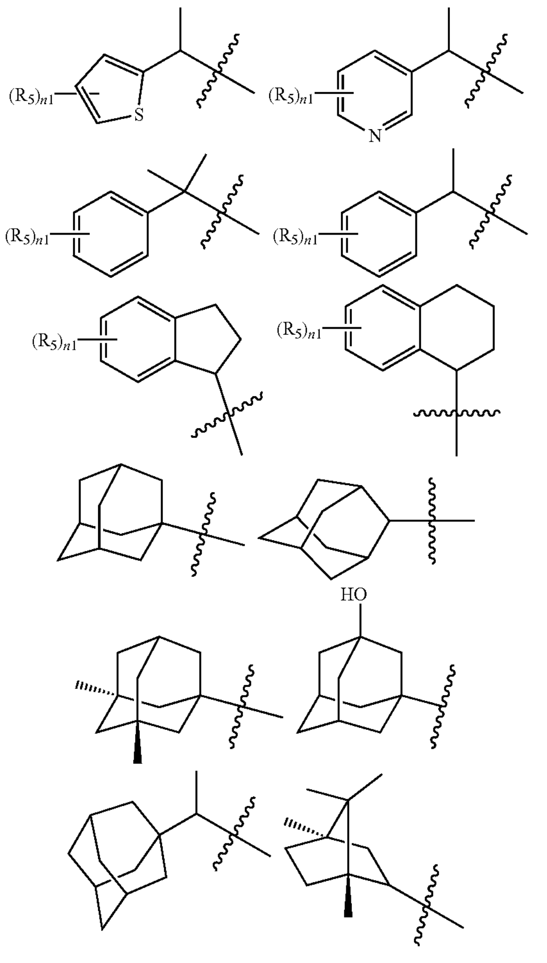

$n_1$ is 0, 1, 2, 3 or 4;

$R_5$ is each independently selected from deuterium, halogen, hydroxyl, amino, cyano, nitro, linear or branched $C_1$-$C_6$ alkyl, linear or branched $C_1$-$C_6$ alkoxyl, $C_1$-$C_3$ acylamino, aminocarbonyl, phenyl, 5-6 membered heteroaryl, 3-6 membered heterocyclyl, $C_3$-$C_6$ cycloalkyl, $C_3$-$C_6$ cycloalkyloxyl, $C_1$-$C_3$ alkylaminocarbonyl, $C_1$-$C_3$ alkylsulfonyl, phenyloxyl or 5-6 membered heteroaryloxyl, when $n_1$>1, each $R_5$ can be the same or different;

$R_{a9}$ is independently selected from hydrogen, substituted or unsubstituted $C_1$-$C_{10}$ alkylcarbonyl, substituted or unsubstituted $C_3$-$C_8$ cycloalkylcarbonyl, $C_1$-$C_8$ heterocycloalkylcarbonyl, wherein the "substituted" means that the terminal of carbon chain is substituted by hydroxyl or amino.

More preferably, the compound of formula (I), wherein $X_1$ is —$CH_2$— or —O—;

$X_2$ is —$CH_2$— or —CO—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —$NRa_3Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —O—, —CO—, —CO—NH—, —NH—CO—, —NH—CO—NH—, —NH—CO—CH($NHRa_9$)— or —CH($NHR_{a9}$)—;

when Y is —O—, A is selected from 9-10 membered aryl, 9-10 membered heteroaryl, (9-10 membered aryl)-$(CH_2)_{b1}$—, (9-10 membered heteroaryl)-$(CH_2)_{b1}$—, the 9-10 membered aryl or 9-10 membered heteroaryl can be unsubstituted or substituted;

the substituted or unsubstituted 9-10 membered aryl or 9-10 membered heteroaryl is selected from the following groups:

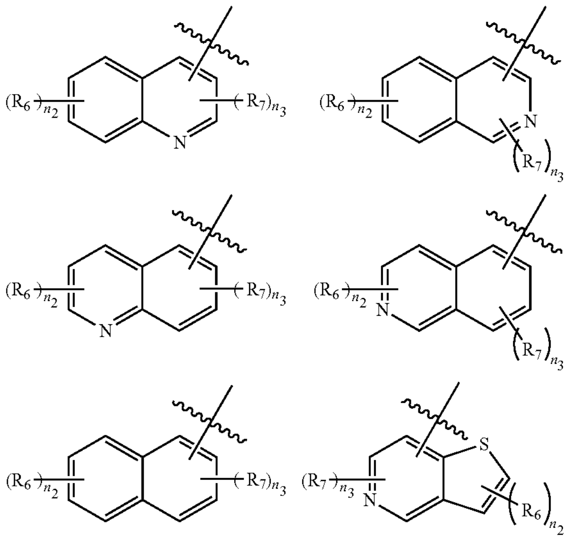

$b_1$ is 1 or 2;

$n_2$ is 0, 1, 2 or 3;

$n_3$ is 0, 1, 2 or 3;

$R_6$ and $R_7$ are each independently selected from the following groups: deuterium, halogen, cyano, nitro, amino, hydroxyl, $C_1$-$C_6$ alkyl, $C_1$-$C_6$ haloalkyl, hydroxyl-substituted $C_1$-$C_6$ alkyl, $C_1$-$C_6$ alkoxyl, $C_1$-$C_6$ alkoxycarbonyl, $C_1$-$C_6$ haloalkox, hydroxyl-substituted $C_1$-$C_6$ alkoxyl, cyano-substituted $C_1$-$C_6$ alkoxyl, $C_3$-$C_6$ cycloalkyl, $C_3$-$C_6$ cycloalkyloxyl, phenyl, $C_5$-$C_6$ heteroaryl, $C_3$-$C_6$ heterocyclyl, —NHC(O)$Ra_5$, —NHC(O)O$Ra_6$, —$NRa_7Ra_8$; wherein, $Ra_5$, $Ra_6$, $Ra_7$ and $Ra_8$ are each independently hydrogen, $C_{1-6}$ alkyl unsubstituted or substituted by halogen, hydroxyl, or cyano, or $C_{3-6}$ cycloalkyl unsubstituted or substituted by halogen, hydroxyl, or cyano, wherein when $n_2$>1 or $n_3$>1, $R_6$ and $R_7$ can be the same or different;

Y is absent, or is —CO— or —CO—NH—, (the corresponding placement of Y, A and L is -A-CO-L-, -A-CO—NH-L-, -A-L-), A moiety comprises at least one nitrogen atom and Y is connected to the nitrogen atom, then A is:

i) heterocyclyl selected from the following:

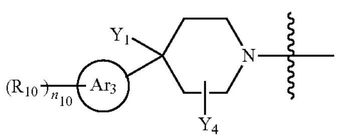

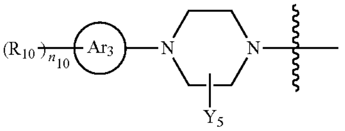

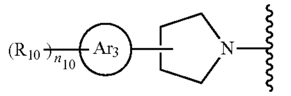

$n_{10}$ is 0, 1, 2, 3, 4 or 5;

$Y_1$ is selected from hydrogen, deuterium, halogen, cyano, carboxyl, nitro, hydroxyl, amino, aminocarbonyl, $C_1$-$C_6$ alkyl, $C_1$-$C_6$ alkoxyl, $C_1$-$C_6$ alkylcarbonyl, $C_1$-$C_6$ alkoxycarbonyl, $C_1$-$C_6$ alkylsulfonyl, $C_1$-$C_6$ alkylaminocarbonyl, $C_3$-$C_6$ cycloalkyl or heterocyclyl, $C_1$-$C_6$ acylamino, $C_1$-$C_6$ haloalkyl, $C_1$-$C_6$ haloalkoxyl, $C_1$-$C_3$ alkenyl, $C_1$-$C_3$ alkynyl, substituted or unsubstituted 6-10 membered aryl, substituted or unsubstituted 5-10 membered heteroaryl, linear or branched $C_1$-$C_3$ alkyl substituted by 6-10 membered aryl or 5-10 membered heteroaryl, wherein the substituted or unsubstituted 6-10 membered aryl or 5-10 membered heteroaryl is substituted by one or more substituents selected from: deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl;

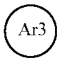

is selected from substituted or unsubstituted 6-10 membered aryl, substituted or unsubstituted 5-10 membered heteroaryl, preferably, the 6-10 membered aryl or 5-10 membered heteroaryl is selected from thienyl, pyridyl, phenyl, benzothienyl, benzimidazolyl, indolyl, naphthyl, quinolinyl, isoquinolinyl;

$R_{10}$ is each independently deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl, when $n_{10}$>1, $R_{10}$ can be the same or different;

$Y_4$ and $Y_5$ are one or more substituents on the heterocyclic ring, $Y_4$ and $Y_5$ are each independently deuterium, halogen, methyl, ethyl, cyclopropyl or phenyl;

ii) fused heterocyclyl selected from:

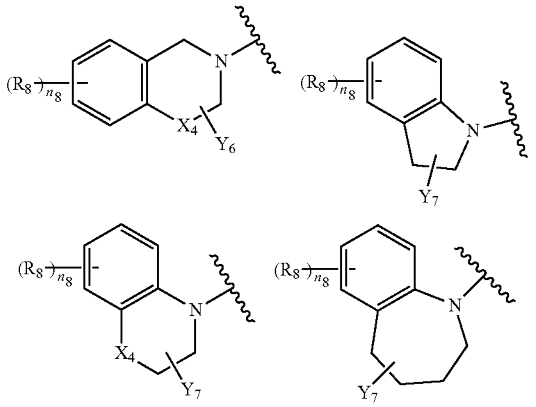

$n_8$ is 0, 1, 2, 3 or 4;

$X_4$ is C, N or O;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl; wherein when $n_8$>1, each $R_8$ can be the same or different;

when $R_8$ each independently selected from any of the following substituents: deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, and when Y is absent, $X_1$ is other than —O—;

$Y_6$ and $Y_7$ are one or more substituents on the heterocyclic ring, and each is independently selected from deuterium, halogen, methyl, ethyl, cyclopropyl or trifluoromethyl;

or iii) spiroheterocyclic group selected from:

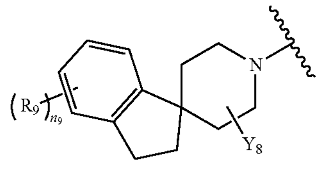

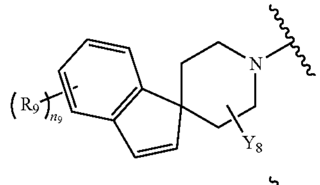

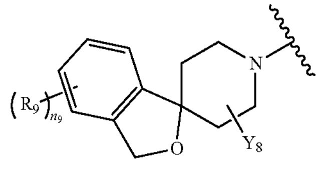

-continued

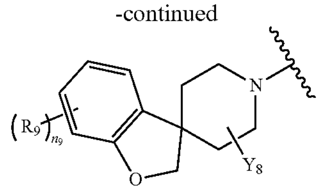

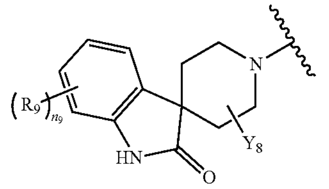

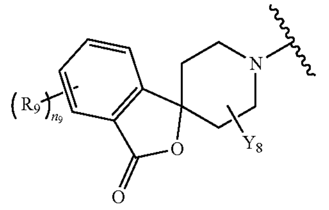

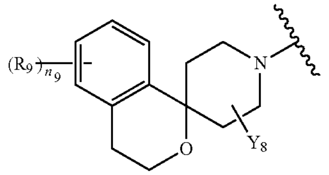

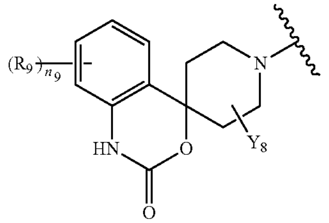

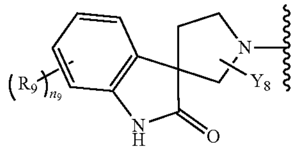

wherein, $n_9$ is 0, 1, 2, 3 or 4;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkylaminocarbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl; wherein when $n_9>1$, each $R_9$ can be the same or different;

$Y_8$ is a substituent which optionally substitute the hydrogen atom in the non-aromatic moiety of the spiro ring structure, and $Y_8$ is optionally substituted by deuterium, halogen, methyl, ethyl, cyclopropyl, or trifluoromethyl;

when Y is selected from —NH—CO—, —NH—CO—NH—, —NH—CO—CH(NHR$_{a9}$)— or —CH(NHR$_{a9}$)—, the corresponding placement of Y, A and L is A-NH—CO-L-, A-NH—CO—NH-L-, A-NH—CO—CH(NHR$_{a9}$)-L- or A-CH(NHR$_{a9}$)-L-, wherein A is:

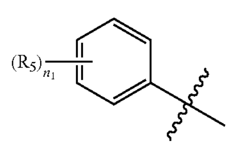

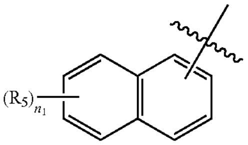

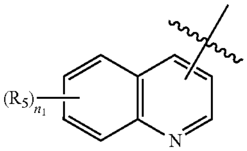

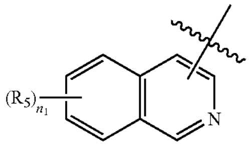

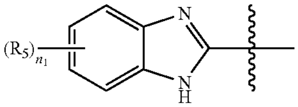

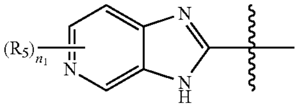

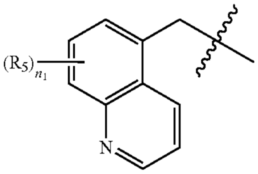

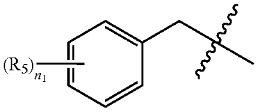

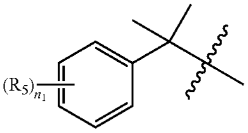

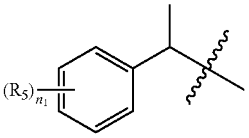

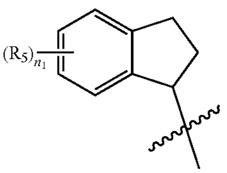

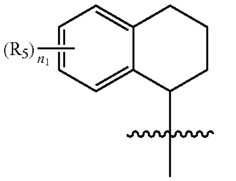

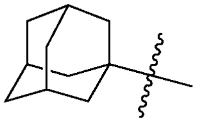

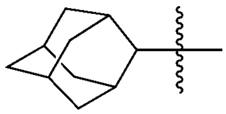

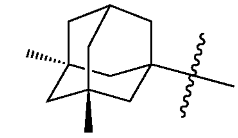

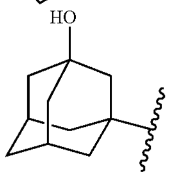

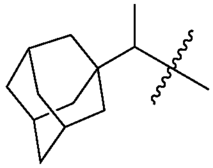

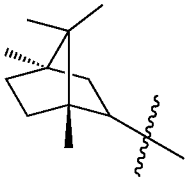

$n_1$ is 0, 1, 2, 3 or 4;

$R_5$ is each independently selected from deuterium, halogen, hydroxyl, amino, cyano, nitro, linear or branched $C_1$-$C_6$ alkyl, linear or branched $C_1$-$C_6$ alkoxyl, $C_1$-$C_3$ acylamino, aminocarbonyl, phenyl, 5-6 membered heteroaryl, 3-6 membered heterocyclyl, $C_3$-$C_6$ cycloalkyl, $C_3$-$C_6$ cycloalkyloxyl, $C_1$-$C_3$ alkylaminocarbonyl, $C_1$-$C_3$ alkylsulfonyl, phenyloxyl or 5-6 membered heteroaryloxyl, when $n_1$>1, each $R_5$ can be the same or different;

$R_{a9}$ is selected from hydrogen, substituted or unsubstituted $C_1$-$C_{10}$ alkylcarbonyl, substituted or unsubstituted $C_3$-$C_8$ cycloalkylcarbonyl, $C_1$-$C_8$ heterocycloalkylcarbonyl, wherein the "substituted" means that the terminal of carbon chain is substituted by hydroxyl or amino.

In a preferred embodiment, the compound of formula (I) is the compound of formula (I-1) to (I-8):

I-1

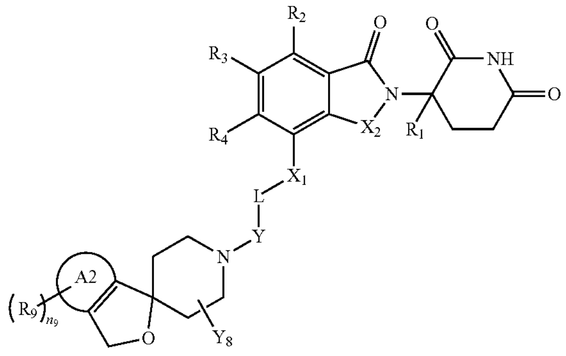

I-2

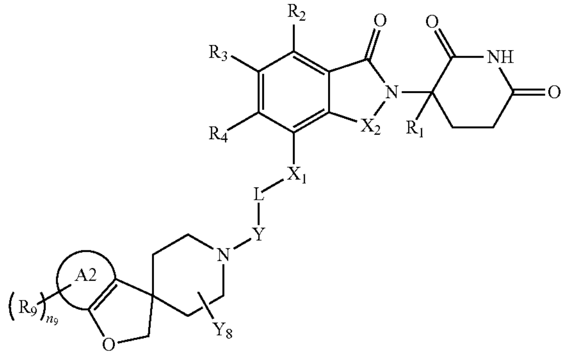

I-3

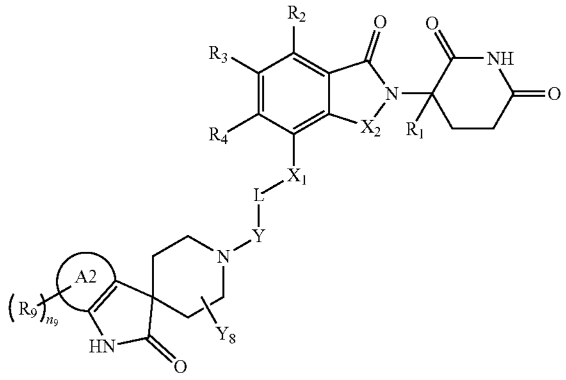

-continued

I-4

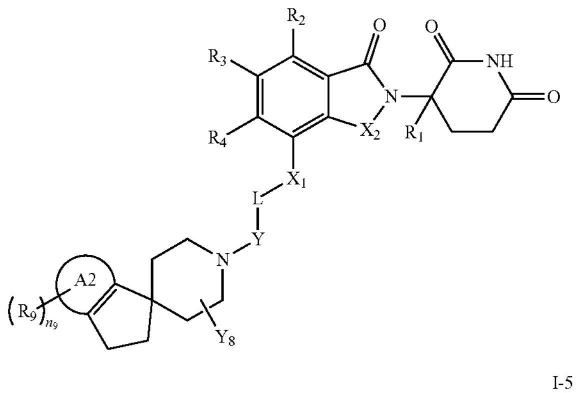

I-5

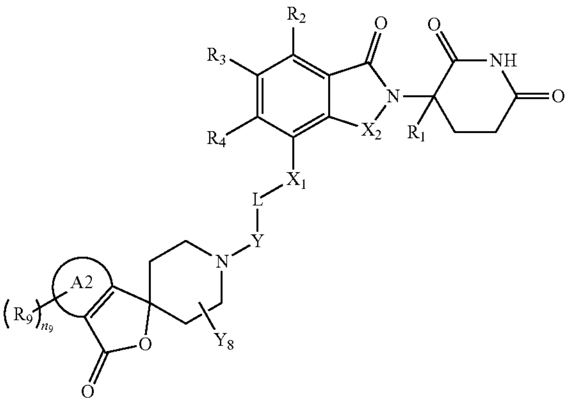

I-6

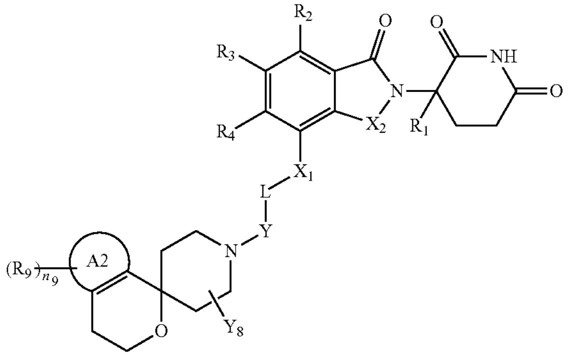

I-7

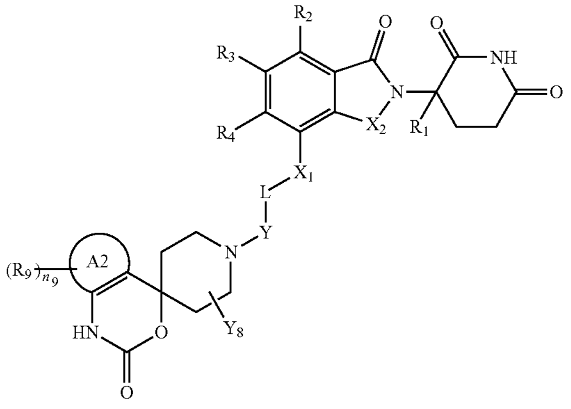

-continued

I-8

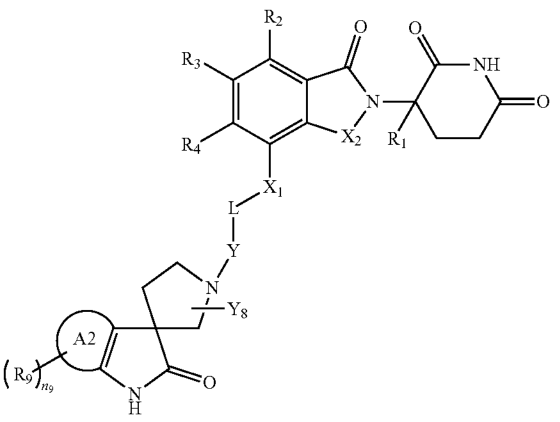

wherein $X_1$ is —$CH_2$— or —O—;

$X_2$ is —$CH_2$— or —CO—;

$R_1$ is hydrogen, deuterium or fluorine;

$R_2$ and $R_4$ are each independently selected from hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —$NRa_3Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —CO— or —CO—NH—;

$n_9$ is 0, 2, 3, 4;

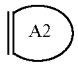

is a 6-10 membered aryl ring or 5-10 heteroaryl ring,

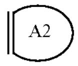

is fused with the spiro ring nucleus to form a spiro heterocyclic group, preferably,

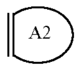

is thiophene ring, pyrrole ring, benzene ring, pyridine ring, benzothiophene ring, benzimidazole ring, indole ring, quinoline ring and isoquinoline ring;

$Y_8$ is a substituent which optionally substitute the hydrogen atom in the non-aromatic moiety of the spiro ring structure, and Y8 is optionally substituted by deuterium, halogen, methyl, ethyl, cyclopropyl, or trifluoromethyl;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkylaminocarbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl; wherein when $n_9$>1, each $R_9$ can be the same or different;

In a preferred embodiment, the compound of formula (I) is the compound of formula (I-9) to (I-16):

I-9

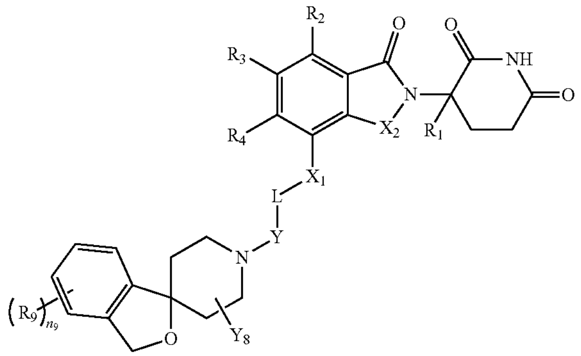

I-10

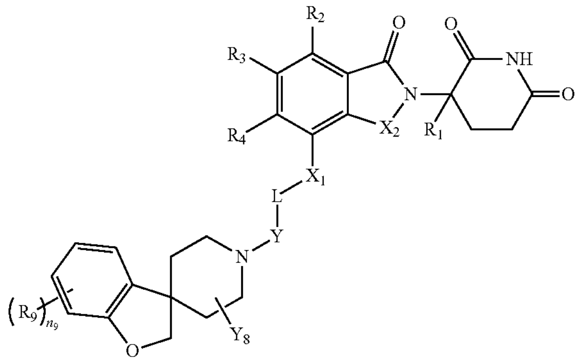

I-11

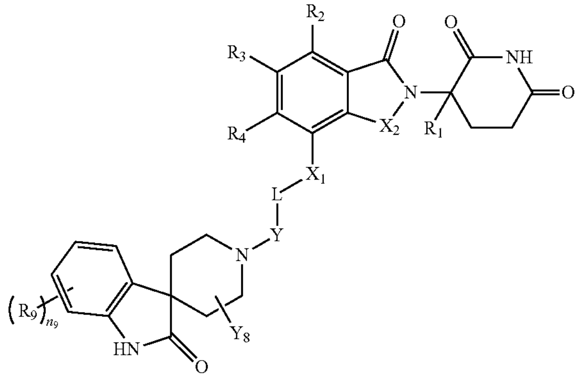

-continued

I-12

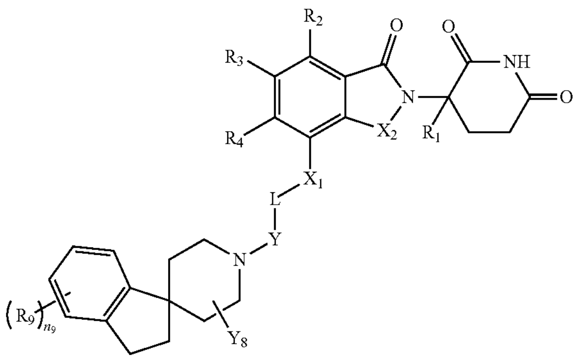

I-13

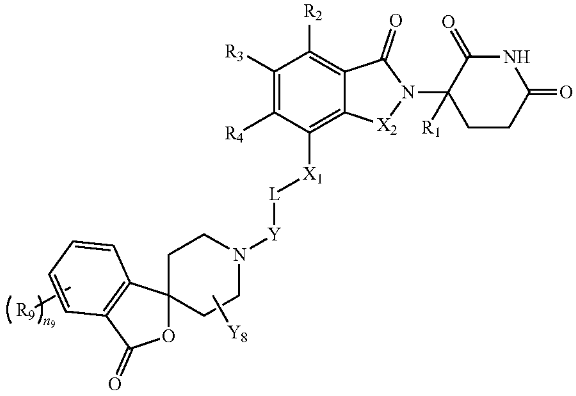

I-14

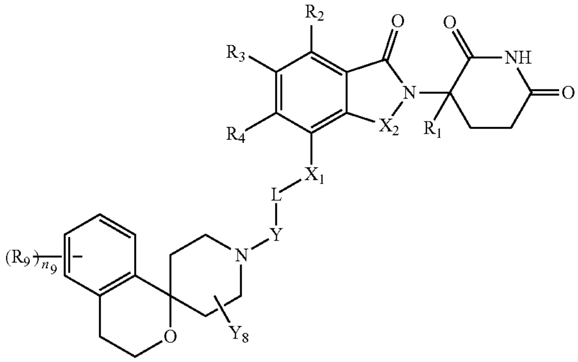

I-15

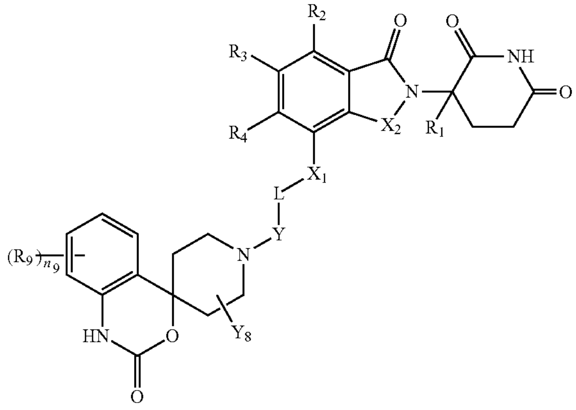

-continued

I-16

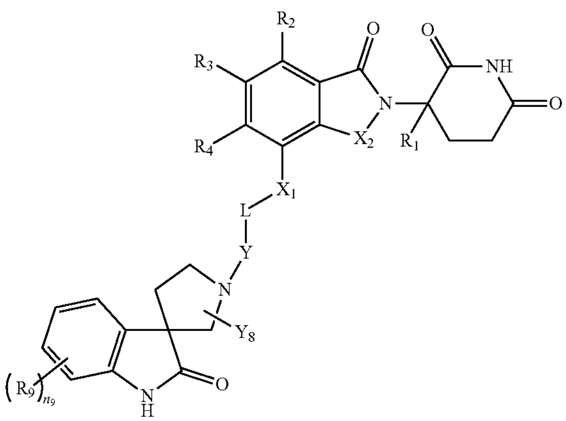

wherein $X_1$ is —$CH_2$— or —O—;

$X_2$ is —$CH_2$— or —CO—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —$NRa_3Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —CO— or —CO—NH—;

$n_9$ is 0, 1, 2, 3 or 4;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkylaminocarbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl; wherein when $n_9$>1, each $R_9$ can be the same or different;

$Y_8$ is a substituent which optionally substitute the hydrogen atom in the non-aromatic moiety of the spiro ring structure, and $Y_8$ is optionally substituted by deuterium, halogen, methyl, ethyl, cyclopropyl, or trifluoromethyl;

In a preferred embodiment, wherein the compound of formula (I) is the compound of formula (I-17) to (I-18):

I-17

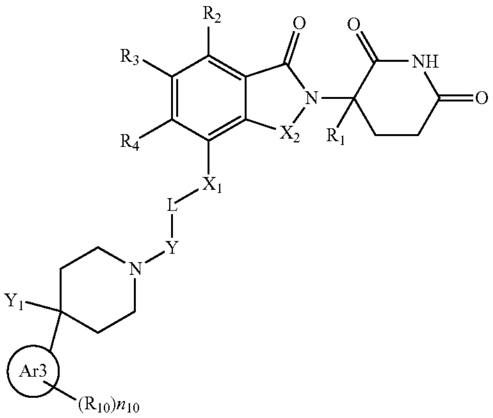

I-18

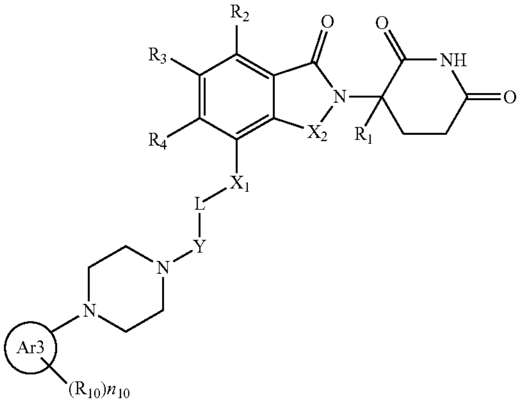

wherein $X_1$ is —$CH_2$— or —O—;

$X_2$ is —$CH_2$— or —CO—;

$R_1$ is hydrogen, deuterium or fluorine;

$R_2$ and $R_4$ are each independently hydrogen or deuterium;

$R_3$ is selected from hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —CO— or —CO—NH—;

$n_{10}$ is 0, 1, 2, 3, 4 or 5;

$Y_1$ is each independently selected from hydrogen, deuterium, halogen, cyano, carboxyl, nitro, hydroxyl, amino, aminocarbonyl, $C_1$-$C_6$ alkyl, $C_1$-$C_6$ alkoxyl, $C_1$-$C_6$ alkylcarbonyl, $C_1$-$C_6$ alkoxycarbonyl, $C_1$-$C_6$ alkylsulfonyl, $C_1$-$C_6$ alkylaminocarbonyl, $C_3$-$C_6$ cycloalkyl or heterocyclyl, $C_1$-$C_6$ acylamino, $C_1$-$C_6$ haloalkyl, $C_1$-$C_6$ haloalkoxyl, $C_1$-$C_3$ alkenyl, $C_1$-$C_3$ alkynyl, substituted or unsubstituted 6-10 membered aryl, substituted or unsubstituted 5-10 membered heteroaryl, linear or branched $C_1$-$C_3$ alkyl substituted by 6-10 membered aryl or 5-10 membered heteroaryl, wherein the substituted or unsubstituted 6-10 membered aryl or 5-10 membered heteroaryl is substituted by one or more substituents selected from: deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl;

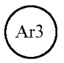

is selected from substituted or unsubstituted 6-10 membered aryl, substituted or unsubstituted 5-10 membered heteroaryl, preferably, the 6-10 membered aryl or 5-10 membered heteroaryl is selected from thienyl, pyridyl, phenyl, benzothienyl, benzimidazolyl, indolyl, naphthyl, quinolinyl, isoquinolinyl;

$R_{10}$ is each independently selected from deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl, when $n_{10}$>1, each $R_{10}$ can be the same or different;

In a preferred embodiment, the compound of formula (I) is the compound of formula (I-19) to (I-23):

I-19

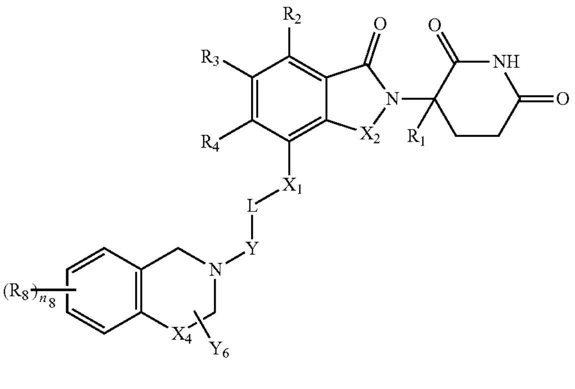

I-20

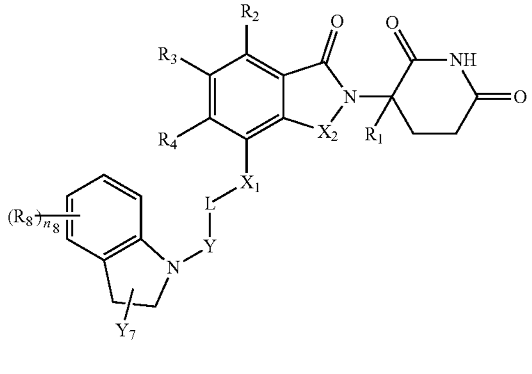

-continued

I-21

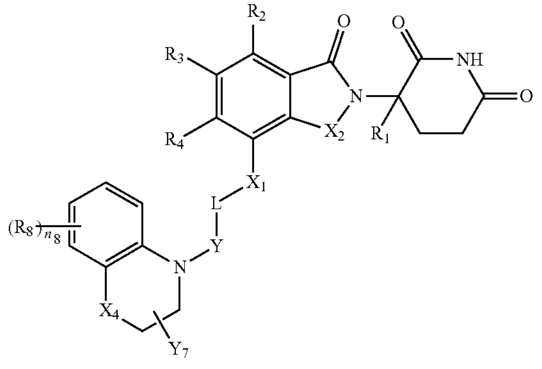

I-23

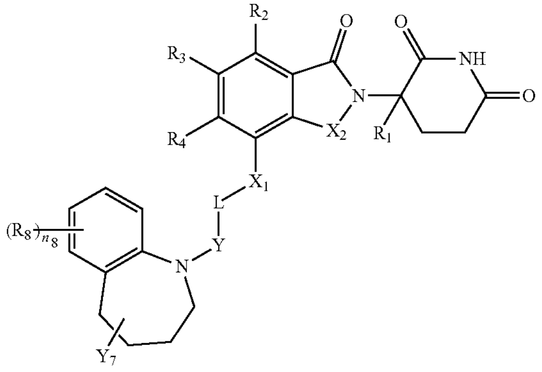

wherein $X_1$ is —$CH_2$— or —O—;

$X_2$ is —$CH_2$— or —CO—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —CO— or —CO—NH—;

$n_8$ is 0, 1, 2, 3 or 4;

$X_4$ is C, N or O;

$R_8$ is each independently hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxy carbonyl, nitro, amino, cyano, $C_1$-$C_3$ haloalkyl, hydroxyl, $C_1$-$C_3$ alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl; wherein when $n_8$>1, each $R_5$ can be the same or different;

when $R_8$ selected from any of the following substituents: deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, and when Y is absent, $X_1$ is other than —O—;

$Y_6$ and $Y_7$ are one or more substituents on the heterocyclic ring, and each is independently selected from deuterium, halogen, methyl, ethyl, cyclopropyl or trifluoromethyl;

In a preferred embodiment, the compound of formula (I) is the compound of formula (I-24) to (I-32):

I-24

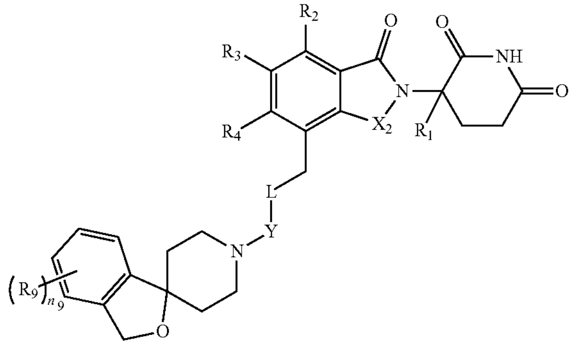

I-25

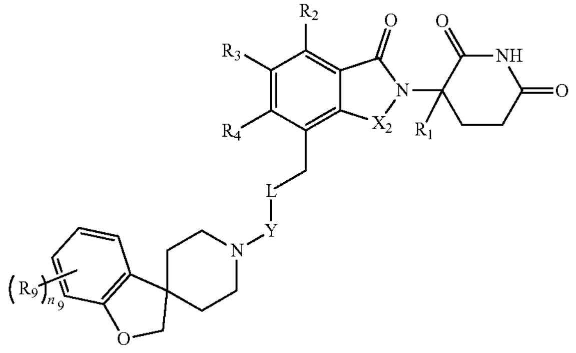

I-26

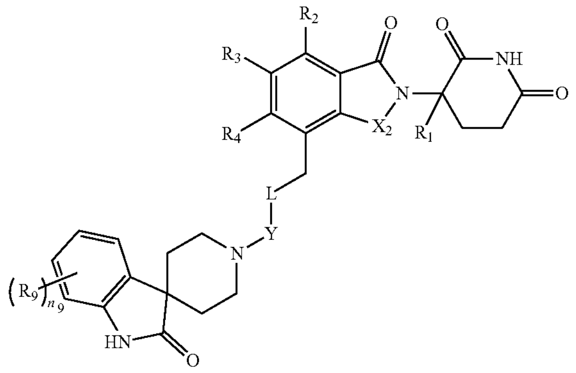

-continued

I-27

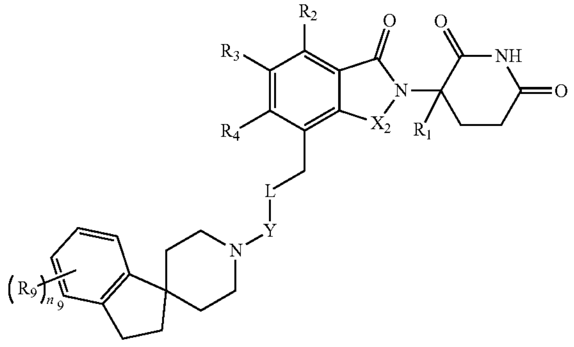

I-29

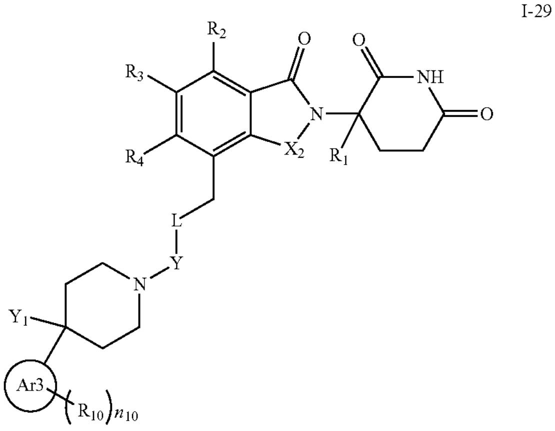

I-30

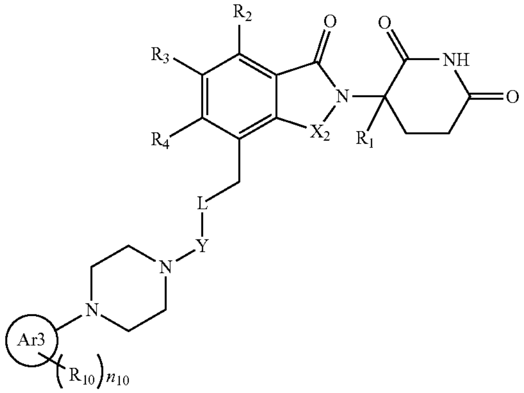

I-31

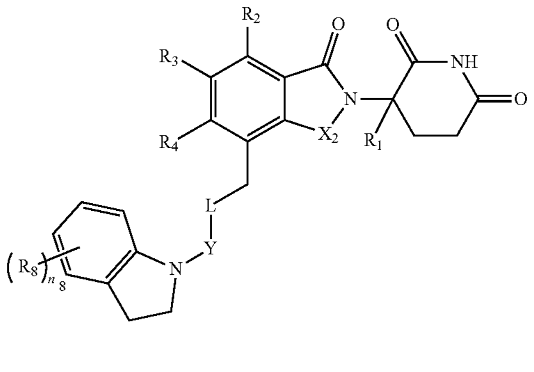

-continued

I-32

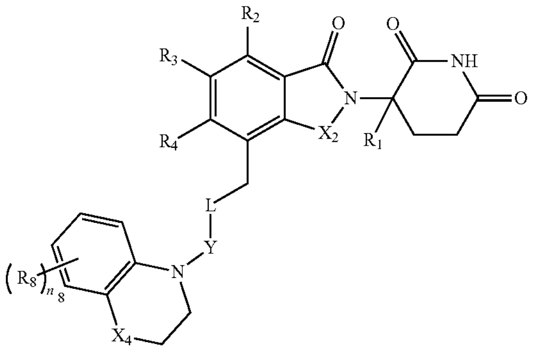

wherein, $X_2$ is —$CH_2$— or —CO—;

$R_1$ is hydrogen, deuterium or fluorine;

$R_2$ and $R_4$ are each independently hydrogen or deuterium;

$R_3$ is selected from hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —$NRa_3Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —CO— or —CO—NH—;

$n_8$, $n_9$ and $n_{10}$ are each independently selected from 0, 1, 2, 3, or 4;

$X_4$ is C, N or O;

$R_9$ is selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkyl amino carbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl; wherein when $n_9$>1, each $R_9$ can be the same or different;

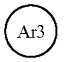

is selected from substituted or unsubstituted 6-10 membered aryl, substituted or unsubstituted 5-10 membered heteroaryl, preferably, the 6-10 membered aryl or 5-10 membered heteroaryl is selected from thienyl, pyridyl, phenyl, benzothienyl, benzimidazolyl, indolyl, naphthyl, quinolinyl, isoquinolinyl;

$R_{10}$ is each independently selected from deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl, when $n_{10}$>1, each $R_{10}$ can be the same or different;

$R_8$ is each independently hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl; wherein when $n_8$>1, each $R_8$ can be the same or different;

In a preferred embodiment, the compound of formula (I) is the compound of formula (I-33) to (I-40):

I-33

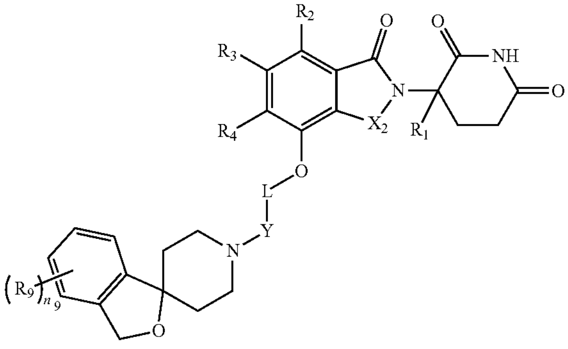

I-34

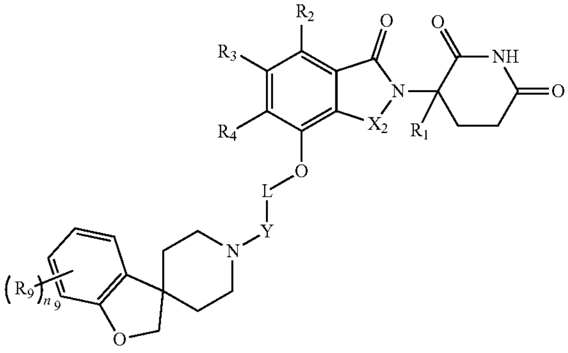

I-35

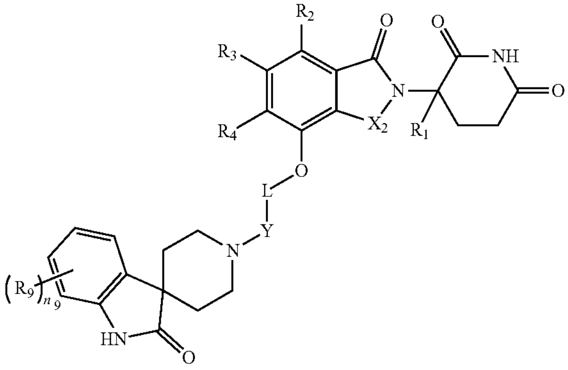

-continued

I-36

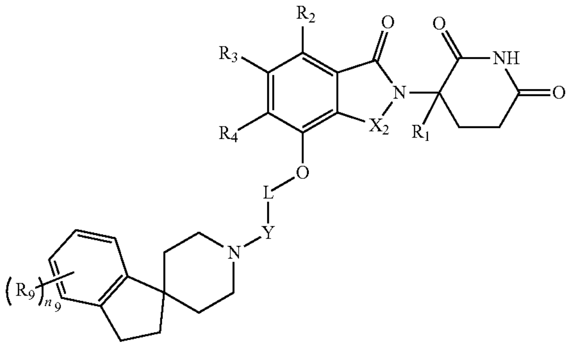

I-37

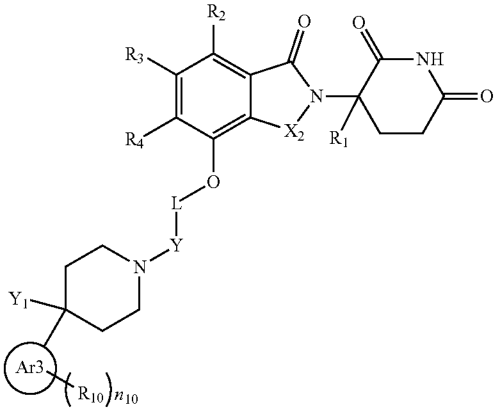

I-38

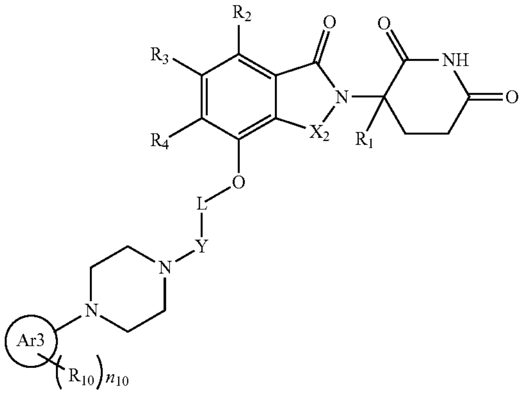

I-39

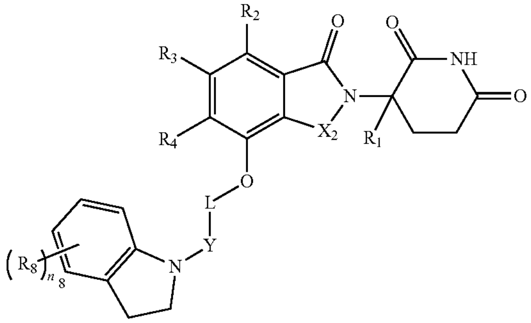

-continued

I-40

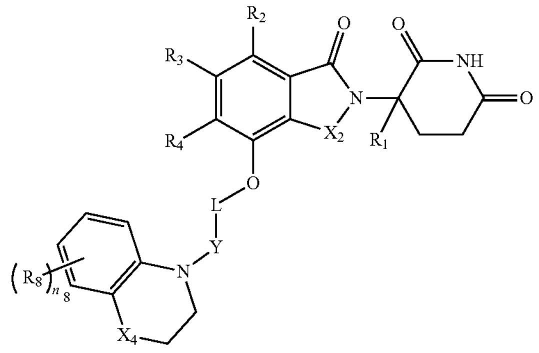

wherein $X_1$ is —$CH_2$— or —O—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is absent, or —CO— or —CO—NH—;

$n_8$, $n_9$ and $n_{10}$ are each independently 0, 1, 2, 3, or 4;

$X_4$ is selected from C, N or O;

$R_9$ is each independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$ cycloalkyloxyl, $C_3$-$C_6$ cycloalkyl or heterocycloalkyl, $C_1$-$C_3$ alkylaminocarbonyl, $C_1$-$C_3$ alkoxycarbonyl, $C_1$-$C_3$ alkylsulfonyl, $C_1$-$C_3$ haloalkyl, $C_1$-$C_3$ haloalkoxyl, phenyl, 5-6 membered heteroaryl; wherein when $n_9$>1, each $R_9$ can be the same or different;

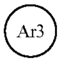

is selected from substituted or unsubstituted 6-10 membered aryl, substituted or unsubstituted 5-10 membered heteroaryl, preferably, the 6-10 membered aryl or 5-10 membered heteroaryl is selected from thienyl, pyridyl, phenyl, benzothienyl, benzimidazolyl, indolyl, naphthyl, quinolinyl, isoquinolinyl;

$R_{10}$ is each independently selected from deuterium, halogen, cyano, nitro, hydroxyl, amino, aminocarbonyl, $C_1$-$C_3$ alkyl, $C_1$-$C_3$ alkoxyl, $C_1$-$C_3$ alkylcarbonyl, $C_1$-$C_3$ alkoxycarbonyl, $C_1$-$C_3$ alkylsulfonyl, $C_1$-$C_3$ alkylaminocarbonyl, $C_3$-$C_6$ cycloalkyl or heterocyclyl, $C_1$-$C_3$ acylamino, $C_1$-$C_3$ haloalkyl, $C_1$-$C_3$ haloalkoxyl, when $n_{10}$>1, each $R_{10}$ can be the same or different;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl; wherein when $n_8$>1, each $R_8$ can be the same or different;

when $R_8$ selected from any of the following substituents: deuterium, $C_1$-$C_3$ alkoxyl, halogen, $C_1$-$C_3$ alkyl, $C_3$-$C_6$ cycloalkyl, carboxyl, $C_1$-$C_3$ alkylaminocarbonyl, $C_1$-$C_3$ alkoxycarbonyl, nitro, amino, cyano, $C_1$-$C_3$ haloalkyl, hydroxyl, $C_1$-$C_3$ alkylsulfonyl, and when Y is absent, $X_1$ is other than —O—;

In a preferred embodiment, the compound of formula (I) is the compound of formula (I-41) to (I-48):

I-41

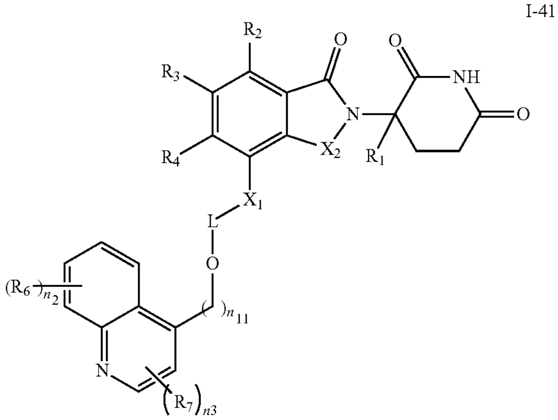

I-42

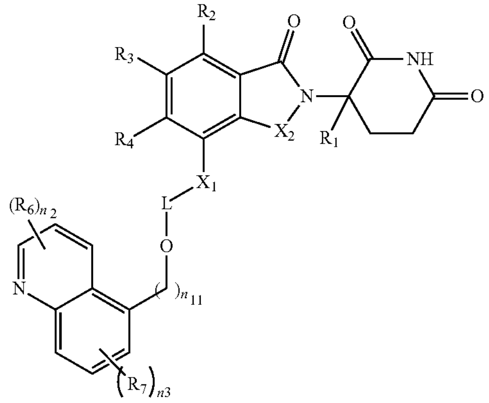

I-43

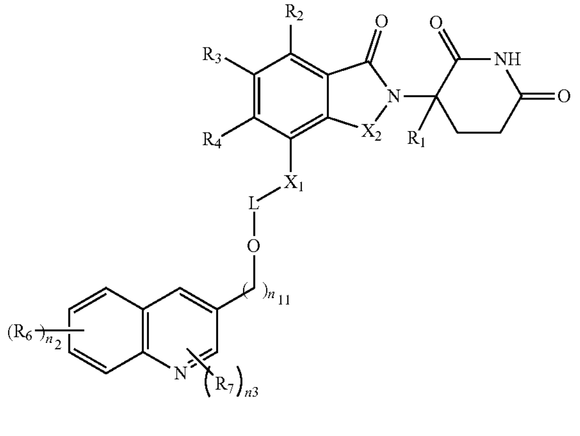

-continued

I-44

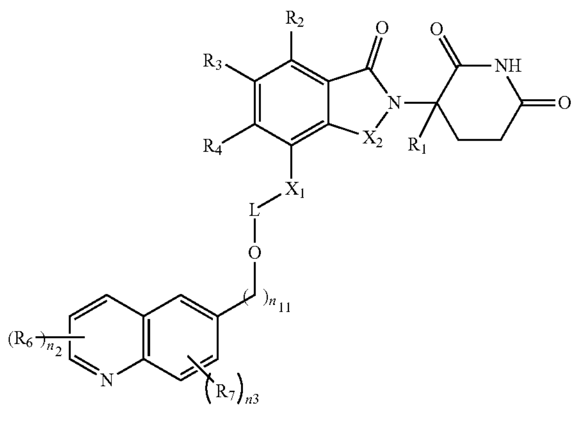

I-45

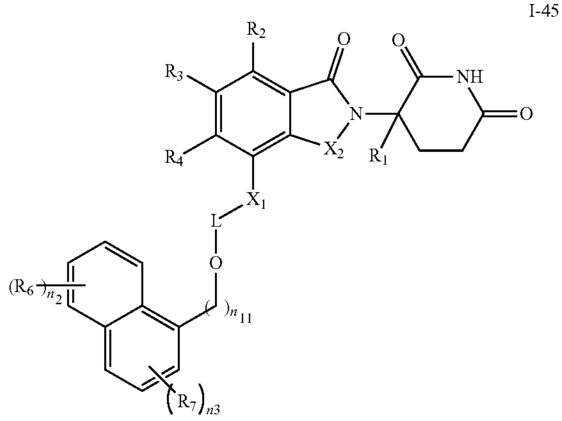

I-46

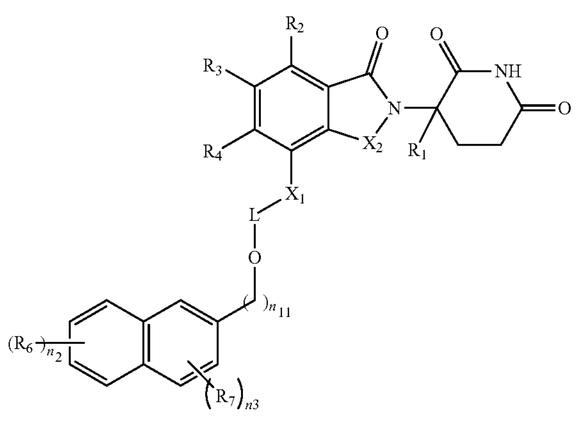

-continued

I-47

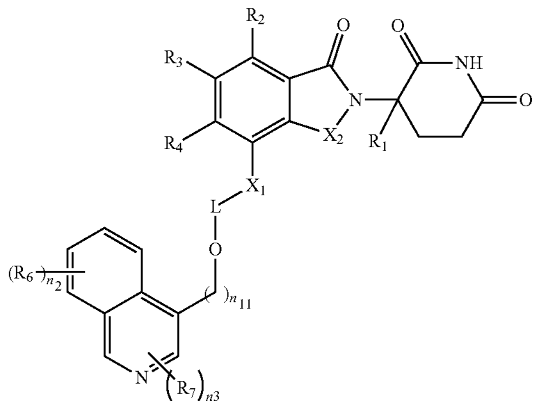

I-48

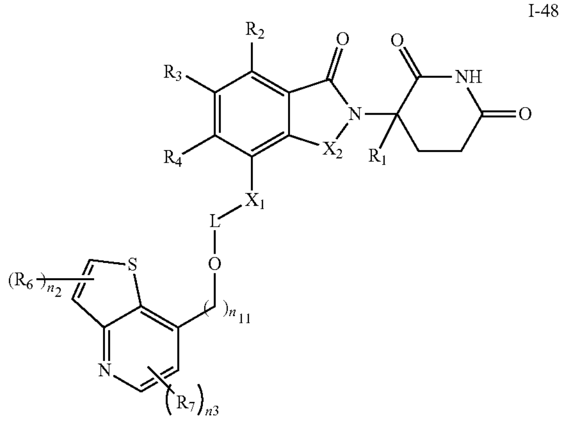

wherein $X_1$ is —$CH_2$— or —O—;

$X_2$ is —$CH_2$— or —CO—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

$n_2$ is 0, 1, 2 or 3;

$n_3$ is 0, 1, 2 or 3;

$R_6$ and $R_7$ are each independently selected from the following groups: deuterium, halogen, cyano, nitro, amino, hydroxyl, $C_1$-$C_6$ alkyl, $C_1$-$C_6$ haloalkyl, hydroxyl-substituted$C_1$-$C_6$ alkyl, $C_1$-$C_6$ alkoxyl, $C_1$-$C_6$ alkoxycarbonyl, $C_1$-$C_6$ haloalkox, hydroxyl-substituted $C_1$-$C_6$ alkoxyl, cyano-substituted $C_1$-$C_6$ alkoxyl, $C_3$-$C_6$ cycloalkyl, $C_3$-$C_6$ cycloalkyloxyl, phenyl, $C_5$-$C_6$ heteroaryl, $C_3$-$C_6$ heterocyclyl, —NHC(O)$Ra_5$, —NHC(O)O$Ra_6$, —N$Ra_7$$Ra_8$; wherein, $Ra_5$, $Ra_6$, $Ra_7$ and $Ra_8$ are each independently selected from hydrogen, $C_{1-6}$ alkyl unsubstituted or substituted by one or more substituents selected from halogen, hydroxyl, or cyano, or $C_{3-6}$ cycloalkyl unsubstituted or substituted by one or more substituents selected from halogen, hydroxyl, or cyano, wherein when $n_2>1$ or $n_3>1$, each $R_6$ and $R_7$ can be the same or different;

In a preferred embodiment, the compound of formula (I) is the compound of formula (I-49) to (I-53):

I-49

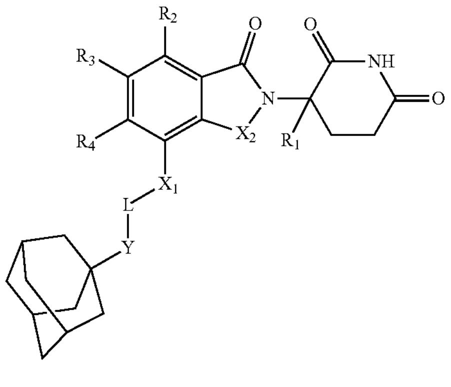

I-50

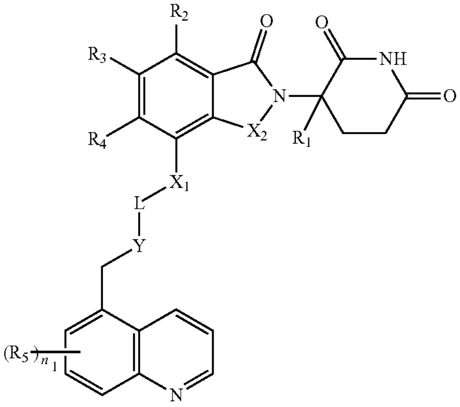

I-51

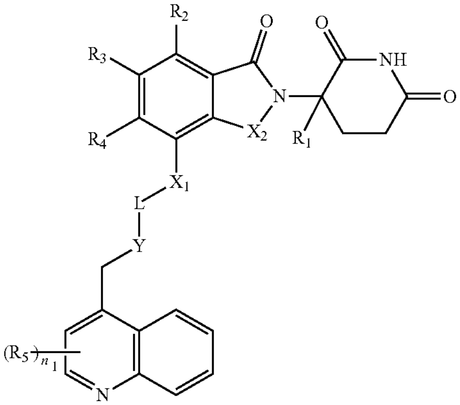

-continued

I-52

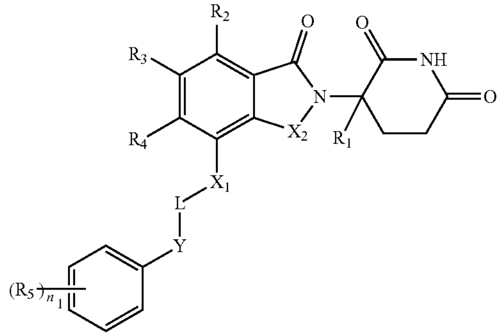

I-53

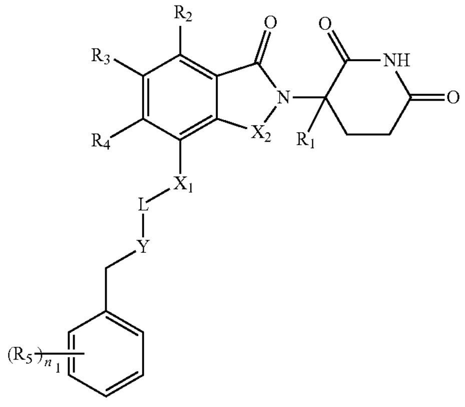

wherein $X_1$ is —$CH_2$— or —O—;

$X_2$ is —$CH_2$— or —CO—;

$R_1$ is hydrogen, deuterium or fluorine;

$R_2$ and $R_4$ are each independently selected from hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O)$Ra_1$, —NHC(O)O$Ra_2$, —$NRa_3Ra_4$, wherein $Ra_1$, $Ra_2$, $Ra_3$ and $Ra_4$ are each independently selected from hydrogen, $C_{1-6}$ alkyl unsubstituted or substituted by one or more halogens, or $C_{3-6}$ cycloalkyl unsubstituted or substituted by one or more halogens;

Y is selected from —NH—CO—, —NH—CO—NH—, —NH—CO—CH($NHR_{a9}$)— or —CH($NHR_{a9}$)—;

$n_1$ is 0, 1, 2, 3 or 4;

$R_5$ is each independently selected from deuterium, halogen, hydroxyl, amino, cyano, nitro, linear or branched $C_1$-$C_6$ alkyl, linear or branched $C_1$-$C_6$ alkoxyl, $C_1$-$C_3$ acylamino, aminocarbonyl, phenyl, 5-6 membered heteroaryl, 3-6 membered heterocyclyl, $C_3$-$C_6$ cycloalkyl, $C_3$-$C_6$ cycloalkyloxyl, $C_1$-$C_3$ alkylaminocarbonyl, $C_1$-$C_3$ alkylsulfonyl, phenyloxyl or 5-6 membered heteroaryloxyl, when $n_1>1$, each $R_5$ can be the same or different;

$R_{a9}$ is selected from hydrogen, substituted or unsubstituted $C_1$-$C_{10}$ alkylcarbonyl, substituted or unsubstituted $C_3$-$C_8$ cycloalkylcarbonyl, $C_1$-$C_8$ heterocycloalkylcarbonyl, wherein the "substituted" means that the terminal of carbon chain is substituted by hydroxyl or amino.

Most preferably, the compound of formula (I) is one of the following compounds:
| Serial number | Compound |
|---|---|
| 1 | 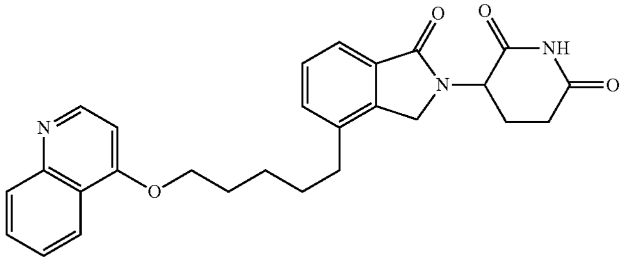 [SMILES: O=C1CCC(N2Cc3c(CCCCCOc4ccnc5ccccc45)cccc3C2=O)C(=O)N1] |
| 2 | 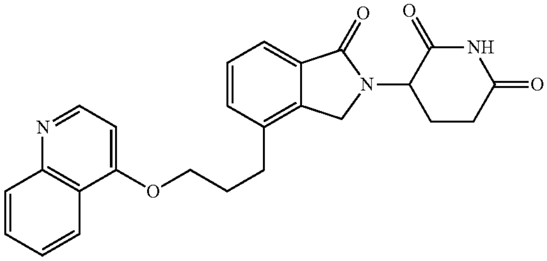 [SMILES: O=C1CCC(N2Cc3c(CCCOc4ccnc5ccccc45)cccc3C2=O)C(=O)N1] |
| 3 | 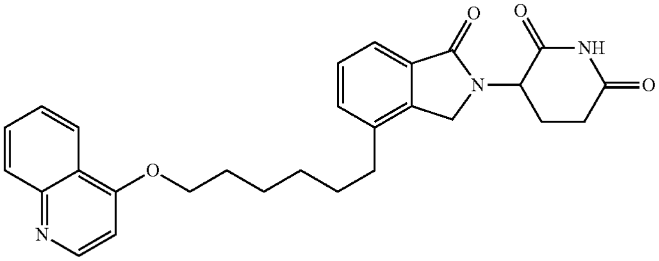 [SMILES: O=C1CCC(N2Cc3c(CCCCCCOc4ccnc5ccccc45)cccc3C2=O)C(=O)N1] |
| 4 | 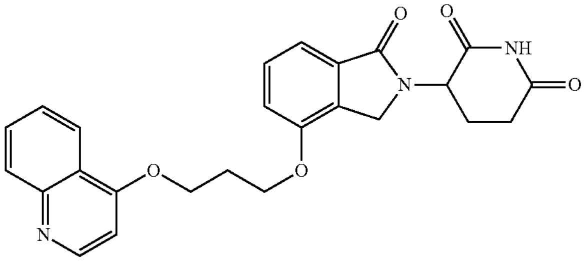 [SMILES: O=C1CCC(N2Cc3c(OCCCOc4ccnc5ccccc45)cccc3C2=O)C(=O)N1] |
| 5 | 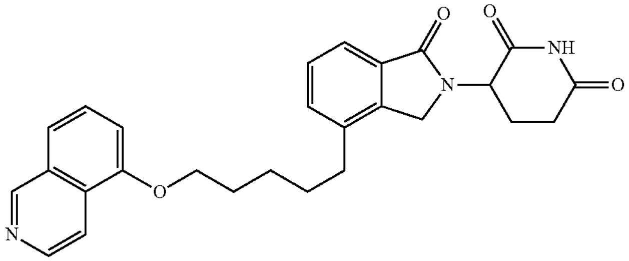 [SMILES: O=C1CCC(N2Cc3c(CCCCCOc4cccc5cnccc45)cccc3C2=O)C(=O)N1] |

-continued
| Serial number | Compound |
|---|---|
| 6 | 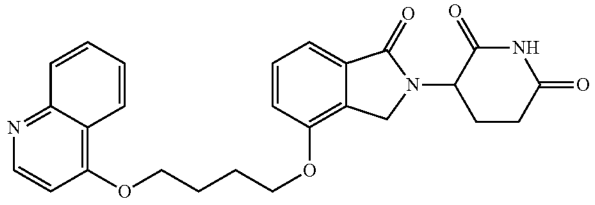 [SMILES: O=C1CCC(N2Cc3c(OCCCCOc4ccnc5ccccc45)cccc3C2=O)C(=O)N1] |
| 7 | 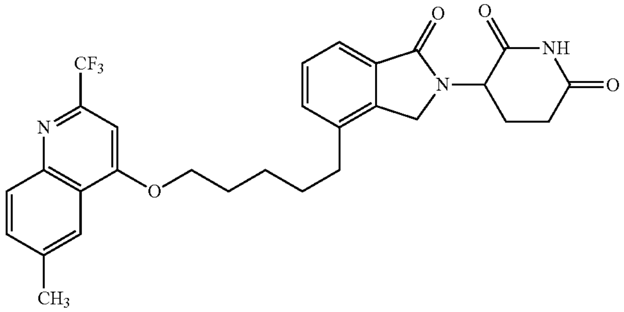 |
| 8 | 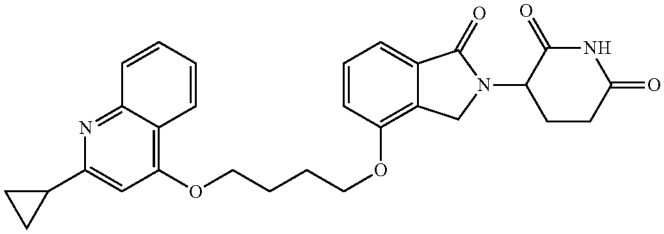 [SMILES: O=C1CCC(N2Cc3c(OCCCCOc4cc(C5CC5)nc5ccccc45)cccc3C2=O)C(=O)N1] |
| 9 | 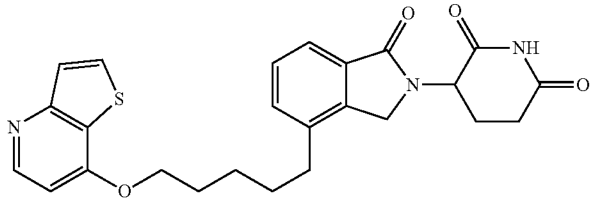 [SMILES: O=C1CCC(N2Cc3c(CCCCCOc4ccnc5ccsc45)cccc3C2=O)C(=O)N1] |
| 10 | 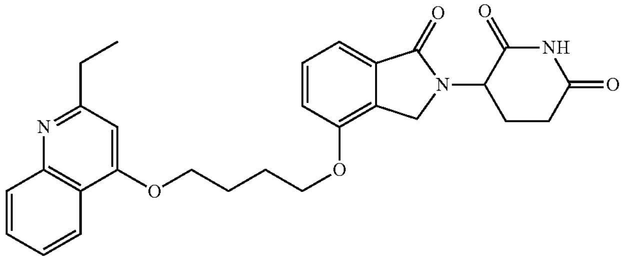 [SMILES: CCc1cc(OCCCCOc2cccc3c2CN(C2CCC(=O)NC2=O)C3=O)c2ccccc2n1] |
| 11 | 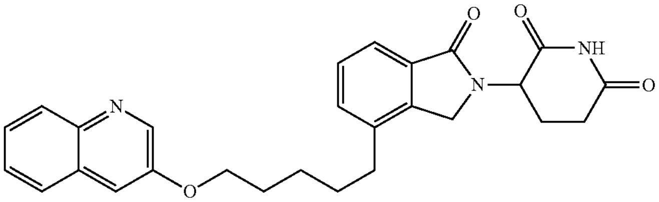 [SMILES: O=C1CCC(N2Cc3c(CCCCCOc4cnc5ccccc5c4)cccc3C2=O)C(=O)N1] |

-continued
| Serial number | Compound |
|---|---|
| 12 | 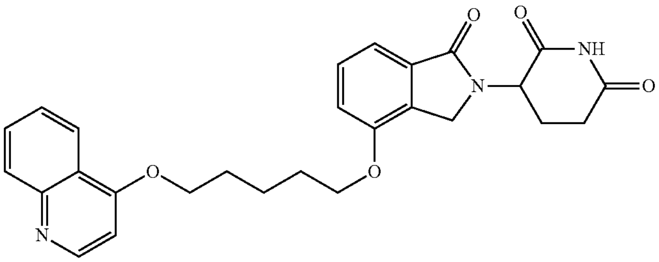 [SMILES: O=C1CCC(N2Cc3c(OCCCCCOc4ccnc5ccccc45)cccc3C2=O)C(=O)N1] |
| 13 | 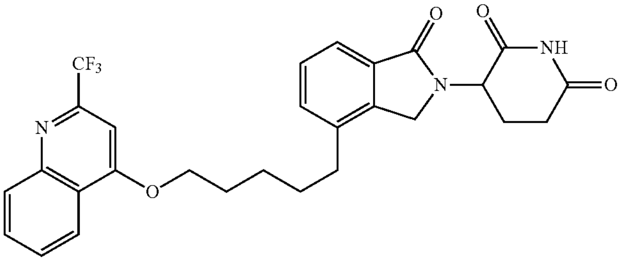 [SMILES: O=C1CCC(N2Cc3c(CCCCCOc4cc(C(F)(F)F)nc5ccccc45)cccc3C2=O)C(=O)N1] |
| 14 | 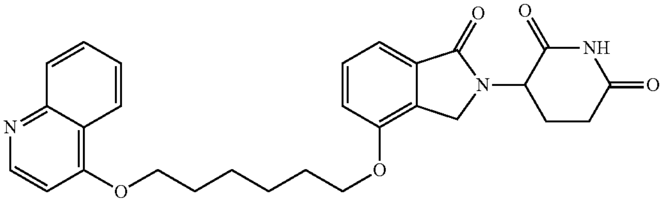 [SMILES: O=C1CCC(N2Cc3c(OCCCCCCOc4ccnc5ccccc45)cccc3C2=O)C(=O)N1] |
| 15 | 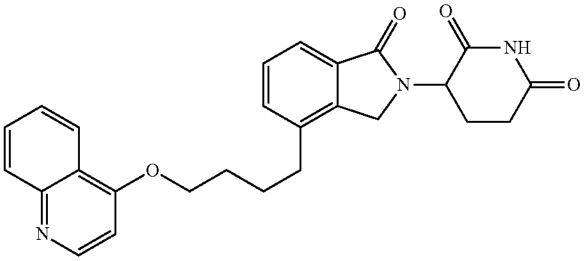 |
| 16 | 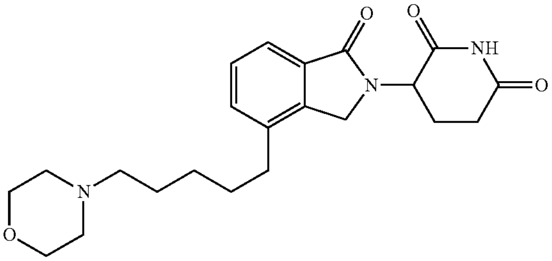 [SMILES: O=C1CCC(N2Cc3c(CCCCCN4CCOCC4)cccc3C2=O)C(=O)N1] |
| 17 | 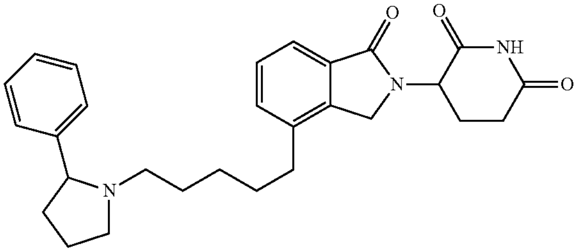 [SMILES: O=C1CCC(N2Cc3c(CCCCCN4CCCC4c4ccccc4)cccc3C2=O)C(=O)N1] |

-continued
| Serial number | Compound |
|---|---|
| 18 | 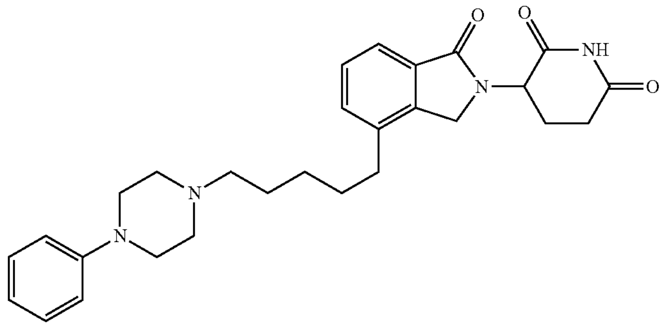 |
| 19 | 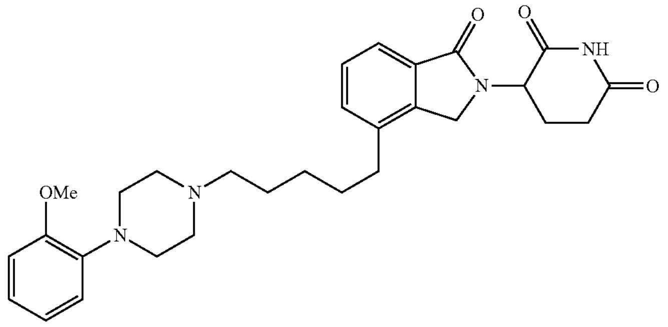 [SMILES: COc1ccccc1N1CCN(CCCCCc2cccc3c2CN(C2CCC(=O)NC2=O)C3=O)CC1] |
| 20 | 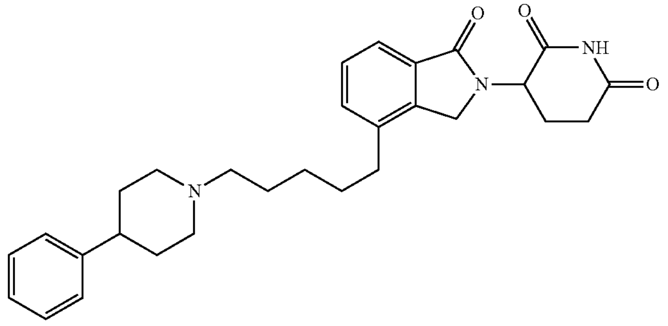 [SMILES: O=C1CCC(N2Cc3c(CCCCCN4CCC(c5ccccc5)CC4)cccc3C2=O)C(=O)N1] |
| 21 | 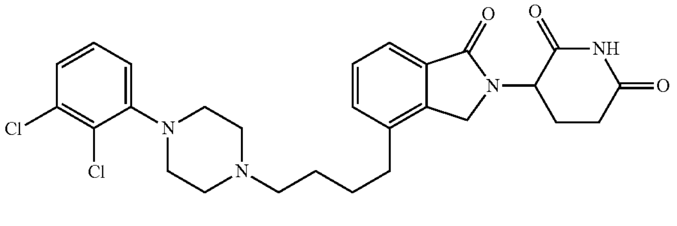 [SMILES: O=C1CCC(N2Cc3c(CCCCN4CCN(c5cccc(Cl)c5Cl)CC4)cccc3C2=O)C(=O)N1] |
| 22 | 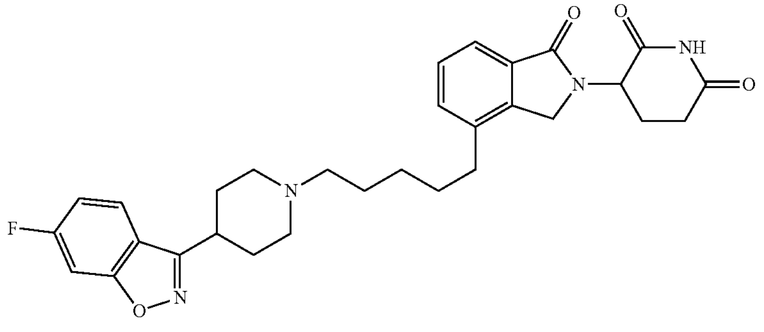 [SMILES: O=C1CCC(N2Cc3c(CCCCCN4CCC(c5noc6cc(F)ccc56)CC4)cccc3C2=O)C(=O)N1] |

-continued
| Serial number | Compound |
|---|---|
| 23 | 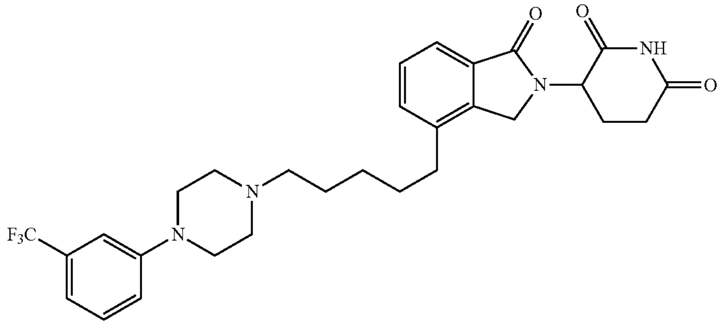 [SMILES: O=C1CCC(N2Cc3c(CCCCCN4CCN(c5cccc(C(F)(F)F)c5)CC4)cccc3C2=O)C(=O)N1] |
| 24 | 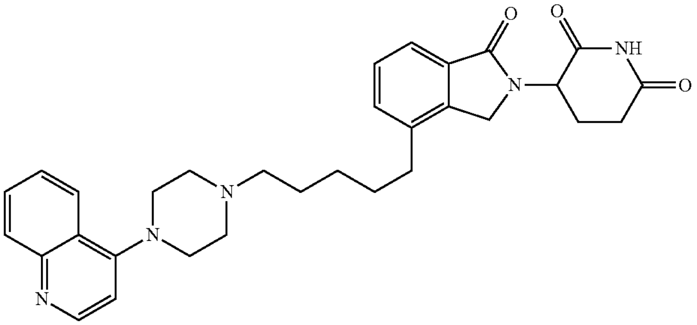 [SMILES: O=C1CCC(N2Cc3c(CCCCCN4CCN(c5ccnc6ccccc56)CC4)cccc3C2=O)C(=O)N1] |
| 25 | 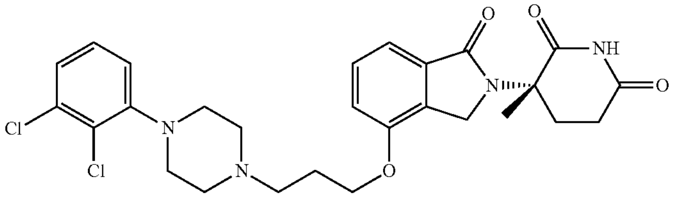 [SMILES: C[C@]1(N2Cc3c(OCCCN4CCN(c5cccc(Cl)c5Cl)CC4)cccc3C2=O)CCC(=O)NC1=O] |
| 26 | 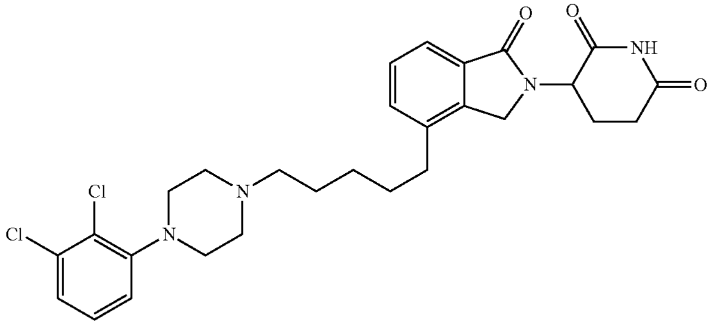 |
| 27 | 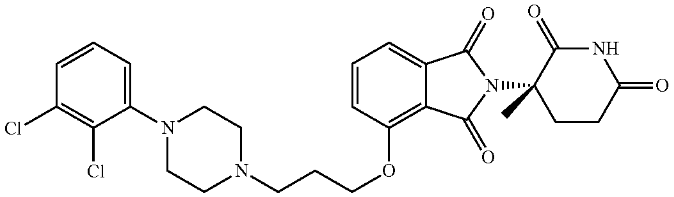 [SMILES: C[C@]1(N2C(=O)c3cccc(OCCCN4CCN(c5cccc(Cl)c5Cl)CC4)c3C2=O)CCC(=O)NC1=O] |

-continued
| Serial number | Compound |
| --- | --- |
| 28 | 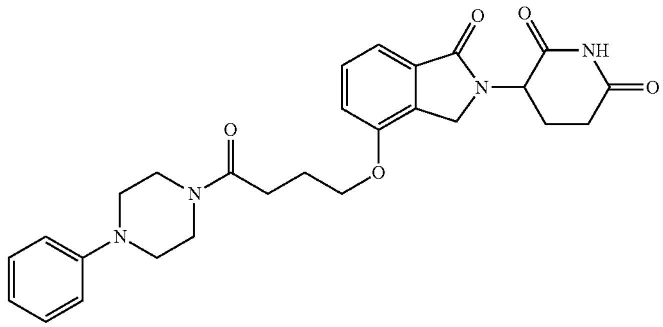 [SMILES: O=C1CCC(N2Cc3c(OCCCC(=O)N4CCN(c5ccccc5)CC4)cccc3C2=O)C(=O)N1] |
| 29 | 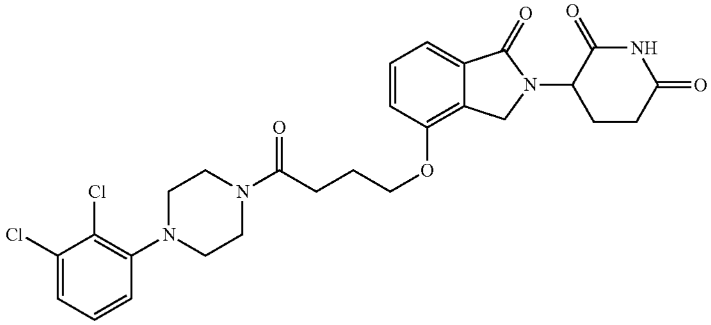 [SMILES: O=C1CCC(N2Cc3c(OCCCC(=O)N4CCN(c5cccc(Cl)c5Cl)CC4)cccc3C2=O)C(=O)N1] |
| 30 | 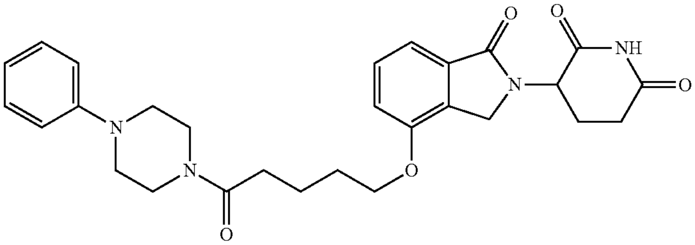 [SMILES: O=C1CCC(N2Cc3c(OCCCCC(=O)N4CCN(c5ccccc5)CC4)cccc3C2=O)C(=O)N1] |
| 31 | 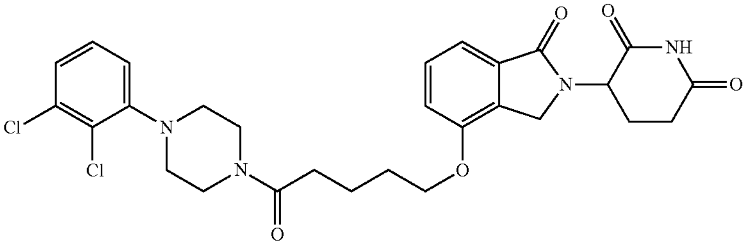 [SMILES: O=C1CCC(N2Cc3c(OCCCCC(=O)N4CCN(c5cccc(Cl)c5Cl)CC4)cccc3C2=O)C(=O)N1] |
| 32 | 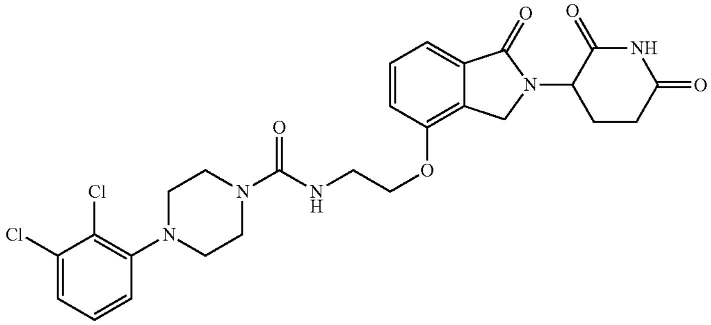 [SMILES: O=C1CCC(N2Cc3c(OCCNC(=O)N4CCN(c5cccc(Cl)c5Cl)CC4)cccc3C2=O)C(=O)N1] |

-continued
| Serial number | Compound |
|---|---|
| 33 | 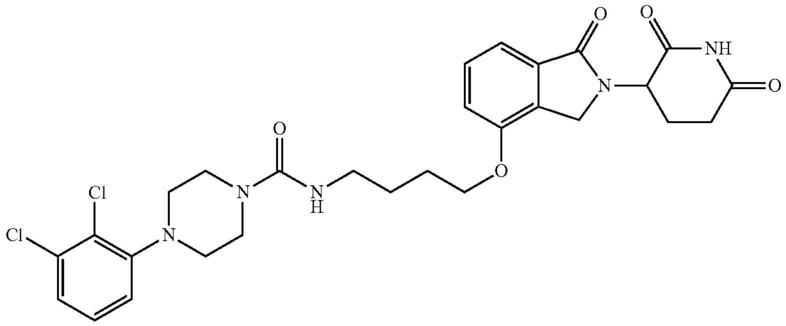 [SMILES: O=C1CCC(N2Cc3c(OCCCCNC(=O)N4CCN(c5cccc(Cl)c5Cl)CC4)cccc3C2=O)C(=O)N1] |
| 34 | 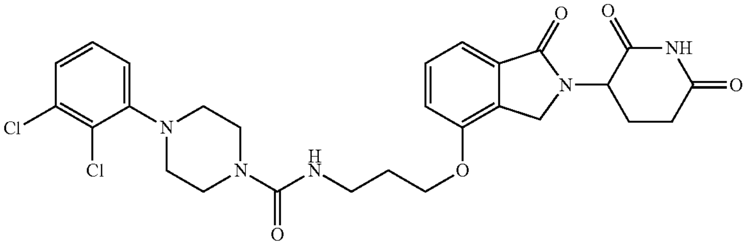 [SMILES: O=C1CCC(N2Cc3c(OCCCNC(=O)N4CCN(c5cccc(Cl)c5Cl)CC4)cccc3C2=O)C(=O)N1] |
| 35 | 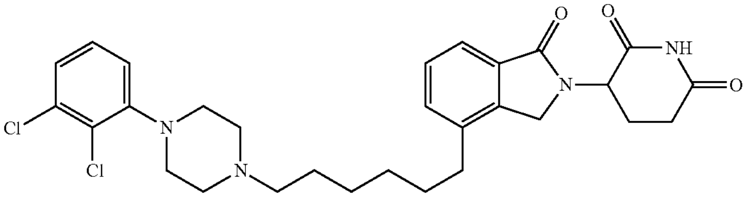 [SMILES: O=C1CCC(N2Cc3c(CCCCCCN4CCN(c5cccc(Cl)c5Cl)CC4)cccc3C2=O)C(=O)N1] |
| 36 | 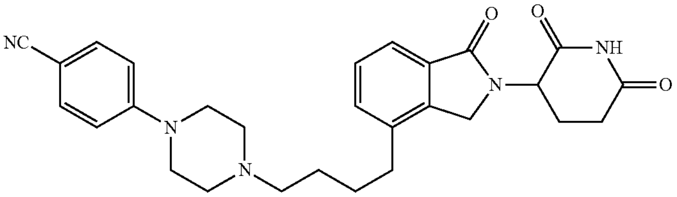 [SMILES: N#Cc1ccc(N2CCN(CCCCc3cccc4c3CN(C3CCC(=O)NC3=O)C4=O)CC2)cc1] |
| 37 | 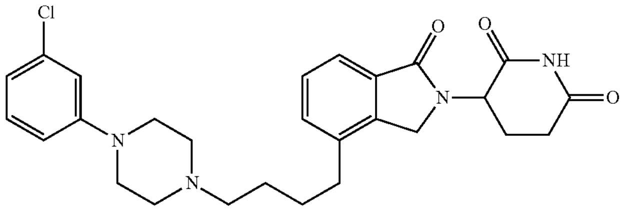 [SMILES: O=C1CCC(N2Cc3c(CCCCN4CCN(c5cccc(Cl)c5)CC4)cccc3C2=O)C(=O)N1] |
| 38 | 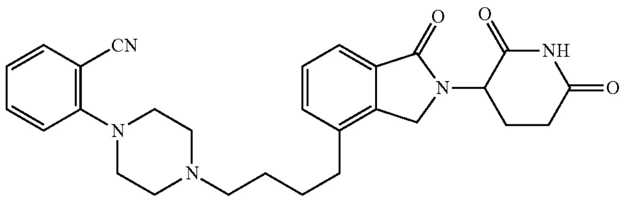 |

-continued
| Serial number | Compound |
|---|---|
| 39 | 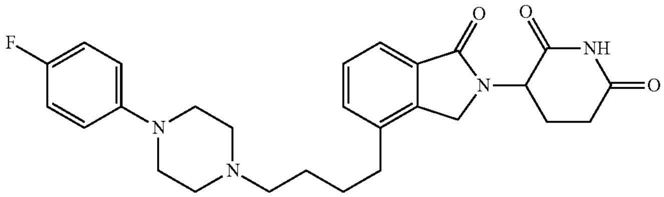 [SMILES: O=C1CCC(N2Cc3c(CCCCN4CCN(c5ccc(F)cc5)CC4)cccc3C2=O)C(=O)N1] |
| 40 | 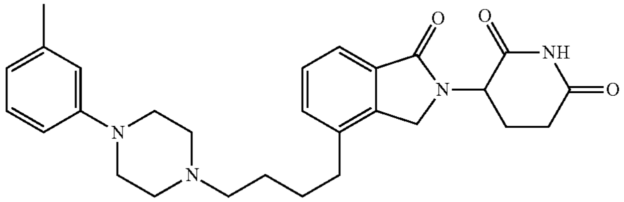 [SMILES: Cc1cccc(N2CCN(CCCCc3cccc4c3CN(C3CCC(=O)NC3=O)C4=O)CC2)c1] |
| 41 | 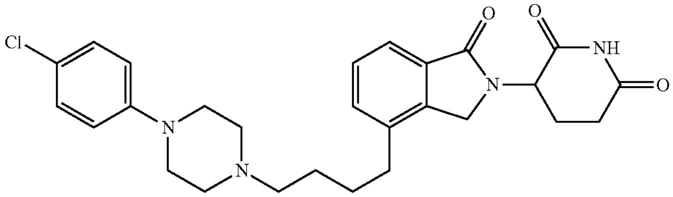 [SMILES: O=C1CCC(N2Cc3c(CCCCN4CCN(c5ccc(Cl)cc5)CC4)cccc3C2=O)C(=O)N1] |
| 42 | 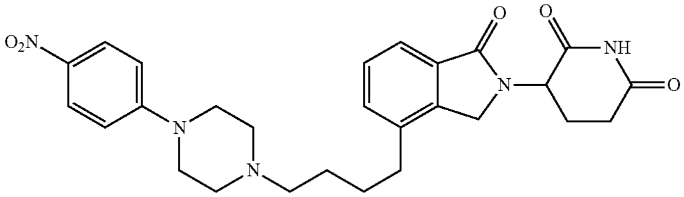 [SMILES: O=C1CCC(N2Cc3c(CCCCN4CCN(c5ccc([N+](=O)[O-])cc5)CC4)cccc3C2=O)C(=O)N1] |
| 43 | 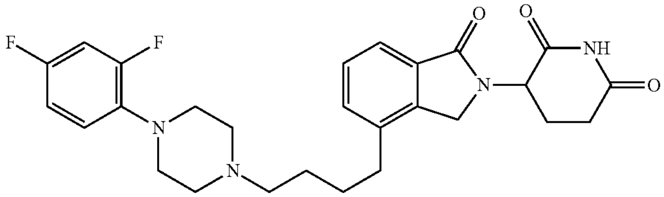 [SMILES: O=C1CCC(N2Cc3c(CCCCN4CCN(c5ccc(F)cc5F)CC4)cccc3C2=O)C(=O)N1] |
| 44 | 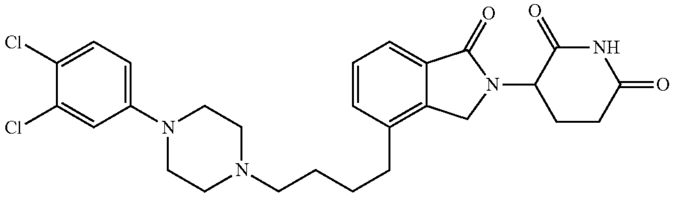 [SMILES: O=C1CCC(N2Cc3c(CCCCN4CCN(c5ccc(Cl)c(Cl)c5)CC4)cccc3C2=O)C(=O)N1] |
| 45 | 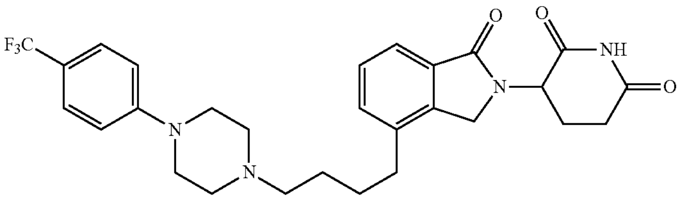 |

-continued
| Serial number | Compound |
|---|---|
| 46 | 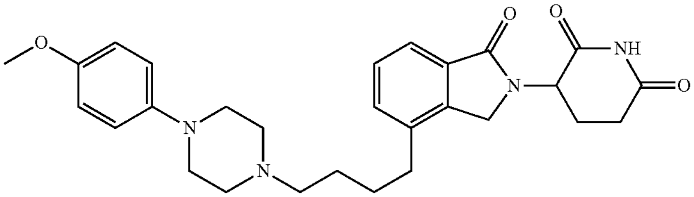 [SMILES: COc1ccc(N2CCN(CCCCc3cccc4c3CN(C3CCC(=O)NC3=O)C4=O)CC2)cc1] |
| 47 | 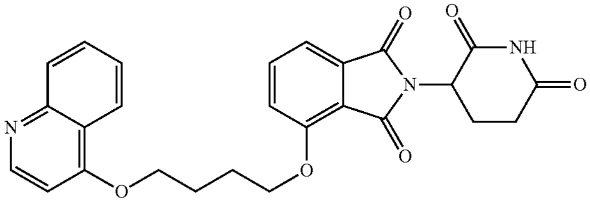 [SMILES: O=C1CCC(N2C(=O)c3cccc(OCCCCOc4ccnc5ccccc45)c3C2=O)C(=O)N1] |
| 48 | 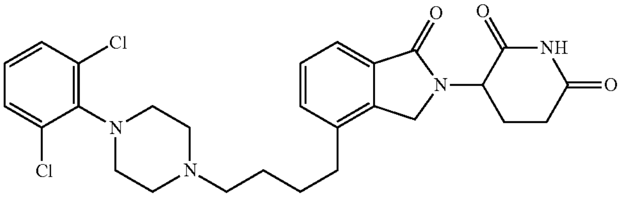 [SMILES: O=C1CCC(N2Cc3c(CCCCN4CCN(c5c(Cl)cccc5Cl)CC4)cccc3C2=O)C(=O)N1] |
| 49 | 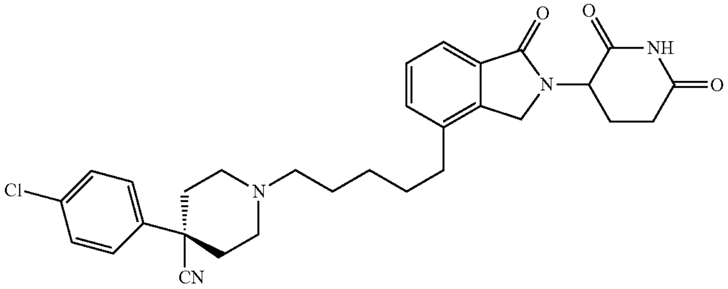 |
| 50 | 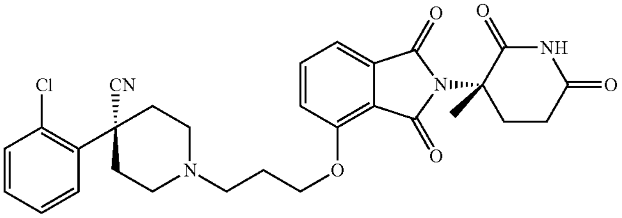 |
| 51 | 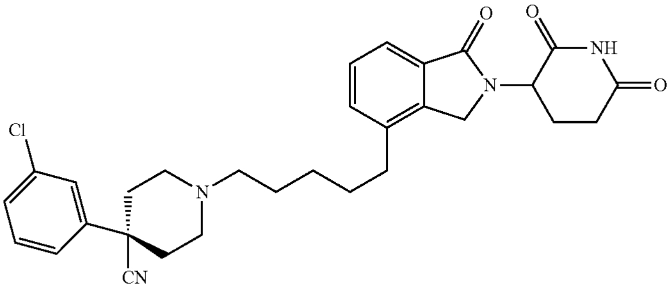 |

-continued
| Serial number | Compound |
| --- | --- |
| 52 | 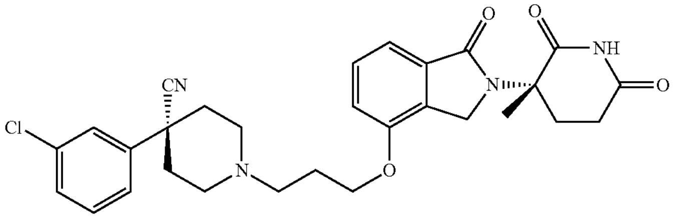 |
| 53 | 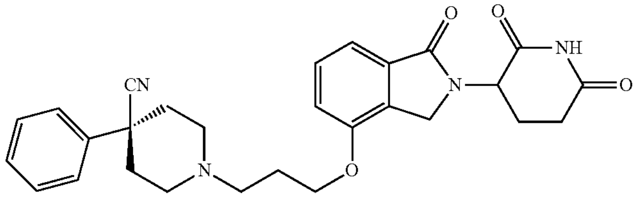 |
| 54 | 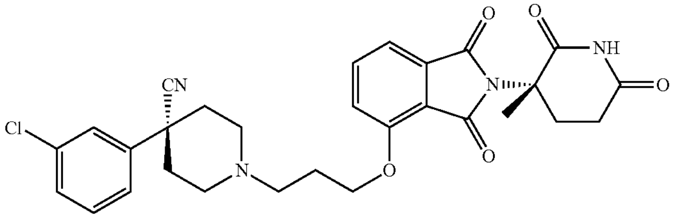 |
| 55 | 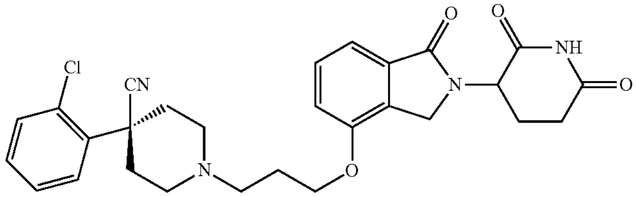 |
| 56 | 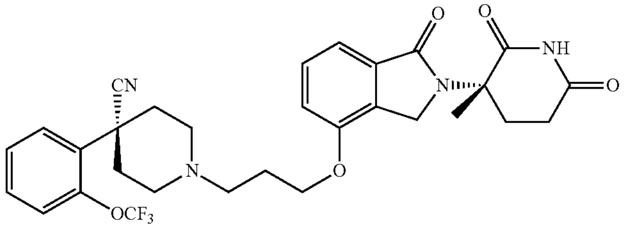 |
| 57 | 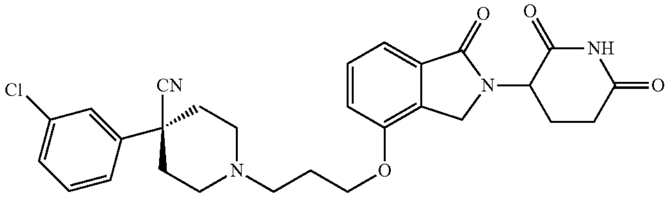 |
| 58 | 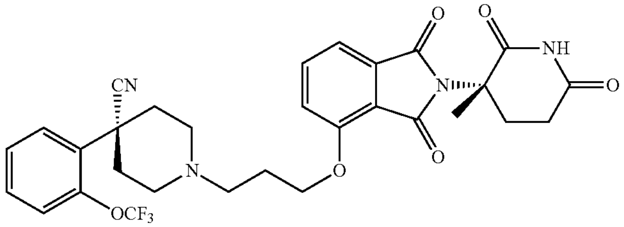 |

-continued
| Serial number | Compound |
|---|---|
| 59 | 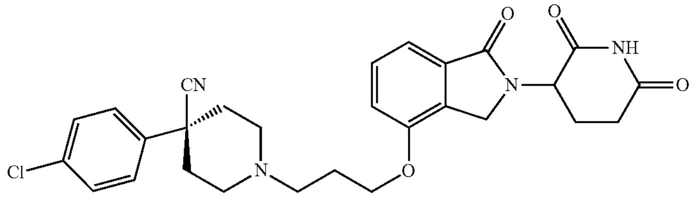 |
| 60 | 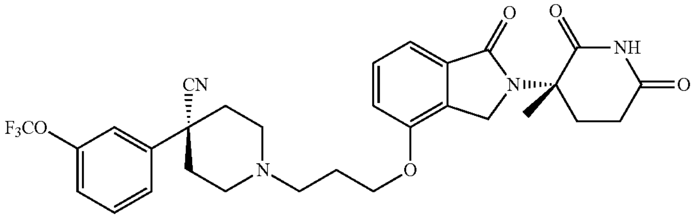 |
| 61 | 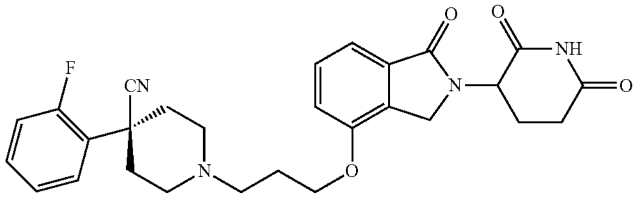 |
| 62 | 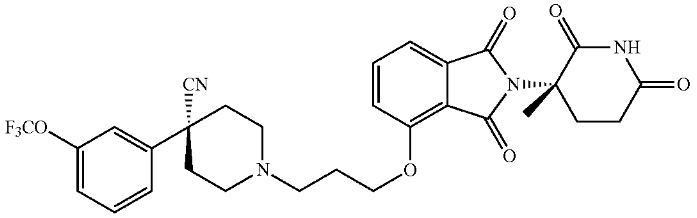 |
| 63 | 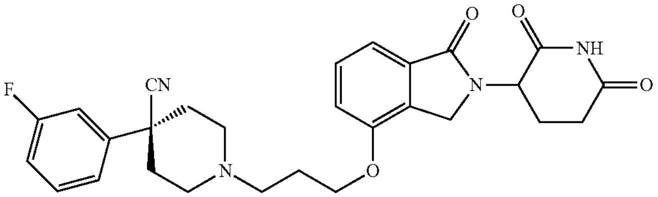 |
| 64 | 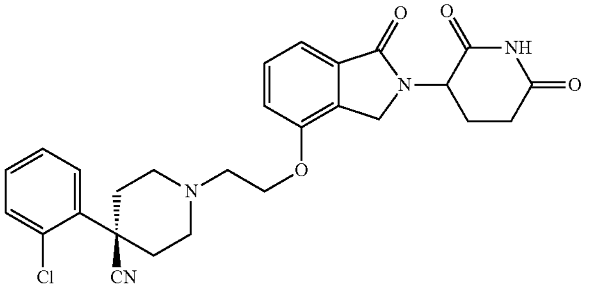 |
| 65 | 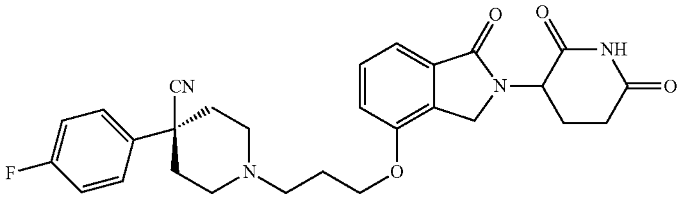 |

-continued
| Serial number | Compound |
|---|---|
| 66 | 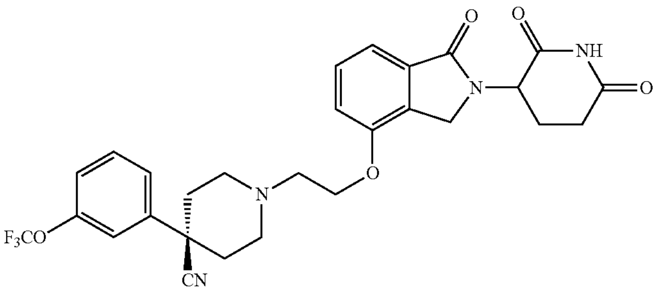 |
| 67 | 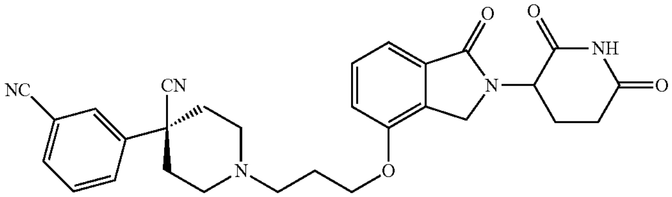 |
| 68 | 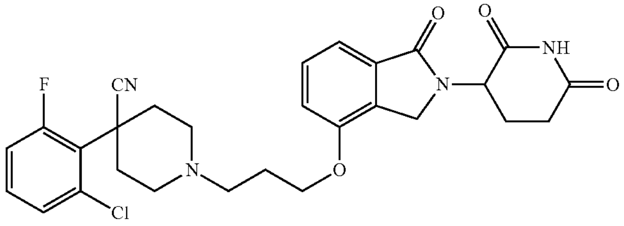 [SMILES: N#CC1(c2c(F)cccc2Cl)CCN(CCCOc2cccc3c2CN(C2CCC(=O)NC2=O)C3=O)CC1] |
| 69 | 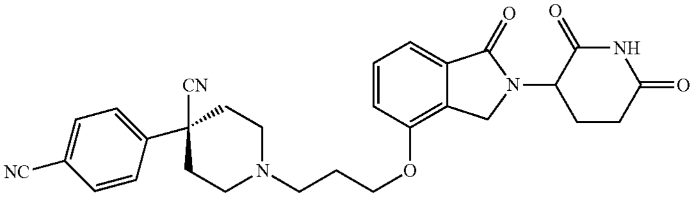 |
| 70 | 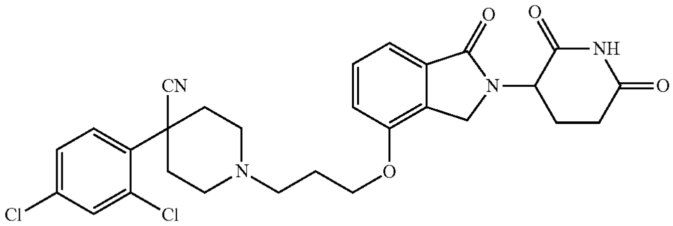 [SMILES: N#CC1(c2ccc(Cl)cc2Cl)CCN(CCCOc2cccc3c2CN(C2CCC(=O)NC2=O)C3=O)CC1] |
| 71 | 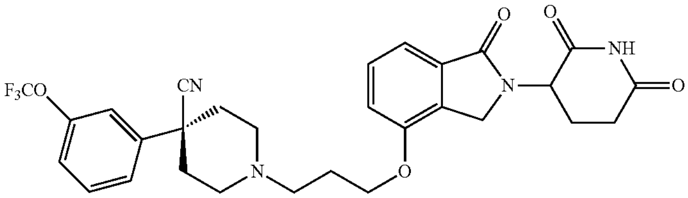 |

-continued
| Serial number | Compound |
|---|---|
| 72 | 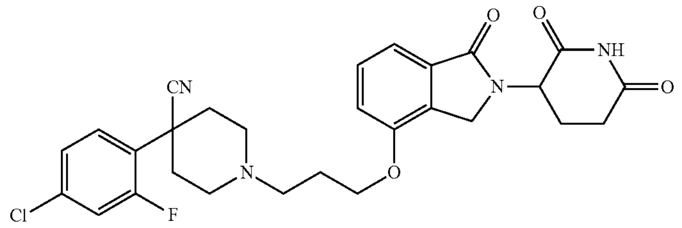 [SMILES: N#CC1(c2ccc(Cl)cc2F)CCN(CCCOc2cccc3c2CN(C2CCC(=O)NC2=O)C3=O)CC1] |
| 73 | 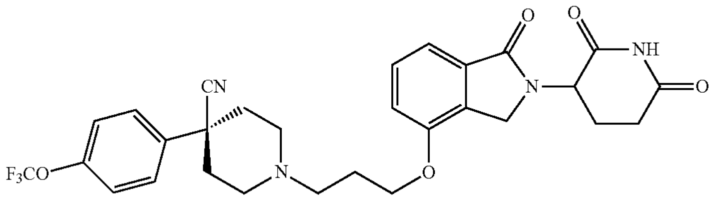 |
| 74 | 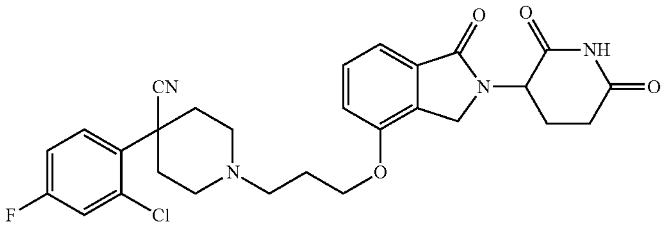 [SMILES: N#CC1(c2ccc(F)cc2Cl)CCN(CCCOc2cccc3c2CN(C2CCC(=O)NC2=O)C3=O)CC1] |
| 75 | 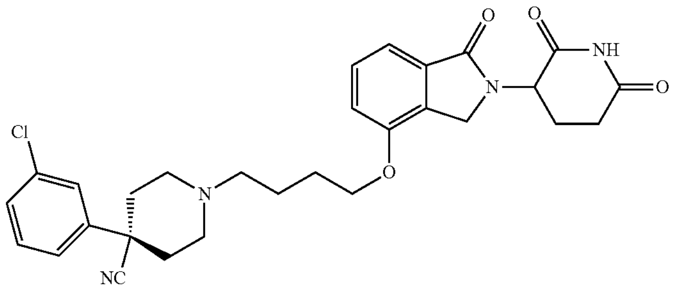 |
| 76 | 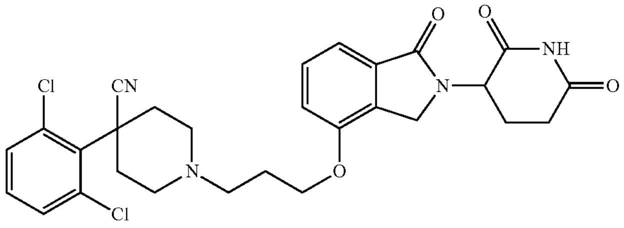 |
| 77 | 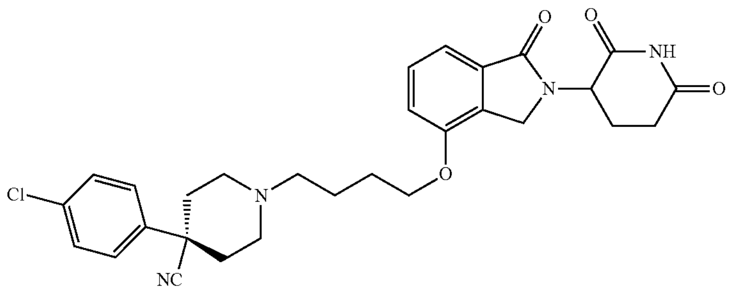 |

-continued
| Serial number | Compound |
|---|---|
| 78 | 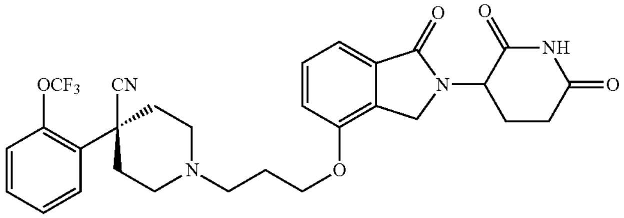 |
| 79 | 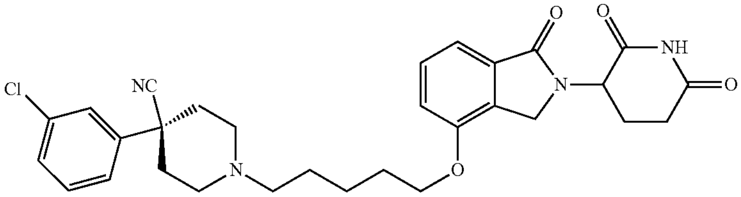 |
| 80 | 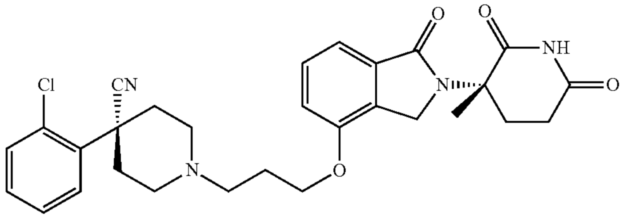 |
| 81 | 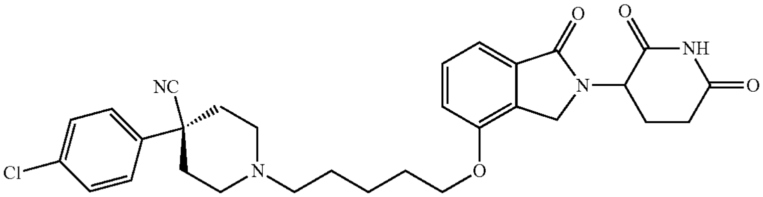 |
| 82 | 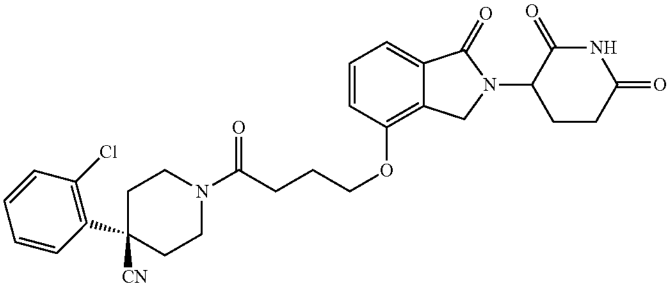 |
| 83 | 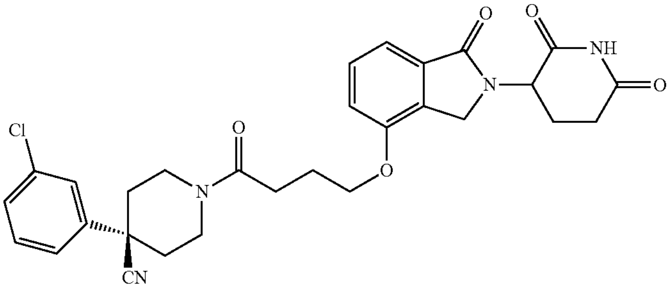 |

-continued
| Serial number | Compound |
|---|---|
| 84 | 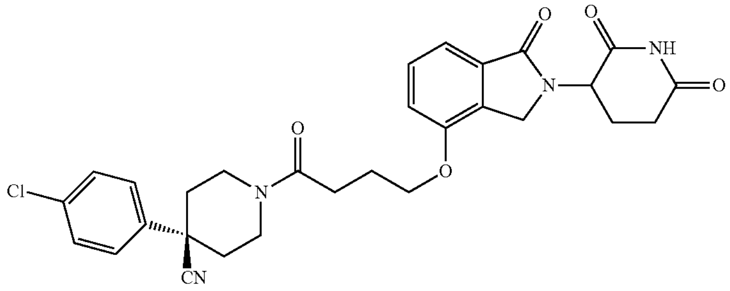 |
| 85 | 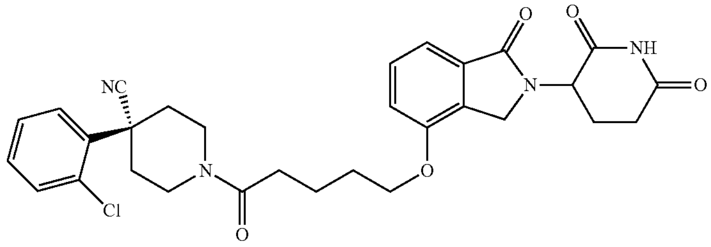 |
| 86 | 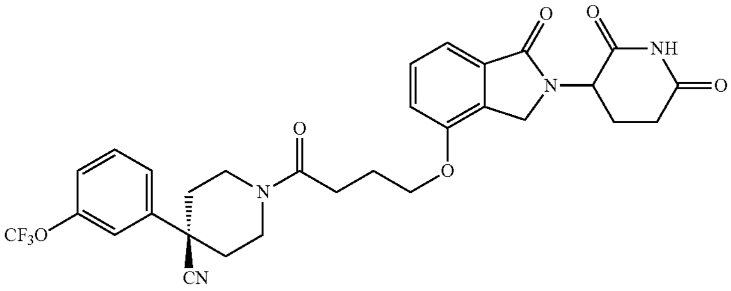 |
| 87 | 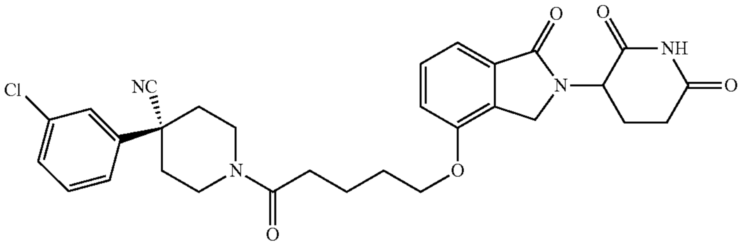 |
| 88 | 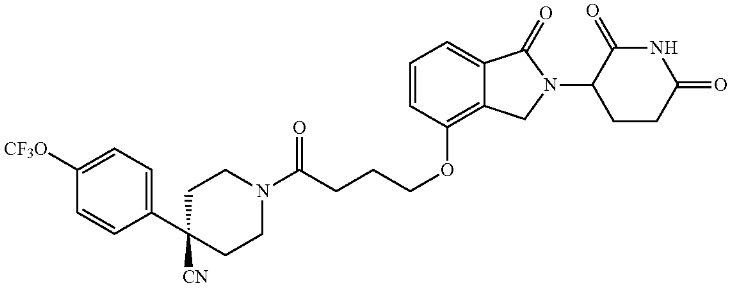 |

-continued
| Serial number | Compound |
|---|---|
| 89 | 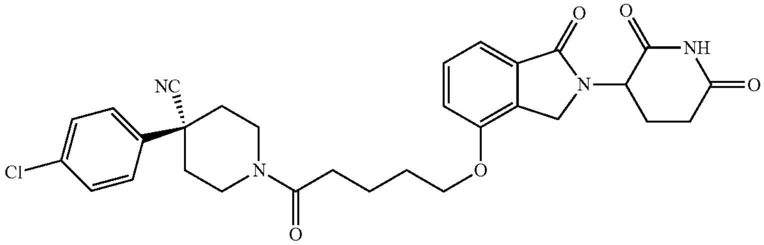 |
| 90 | 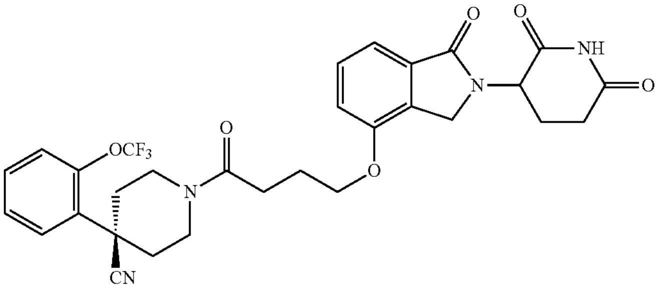 |
| 91 | 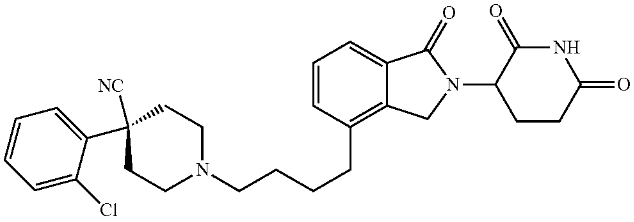 |
| 92 | 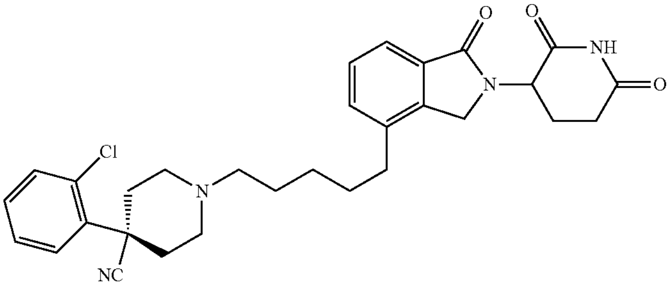 |
| 93 | 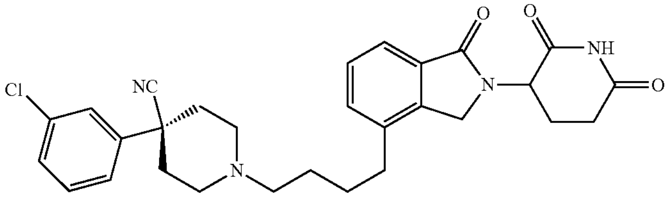 |
| 94 | 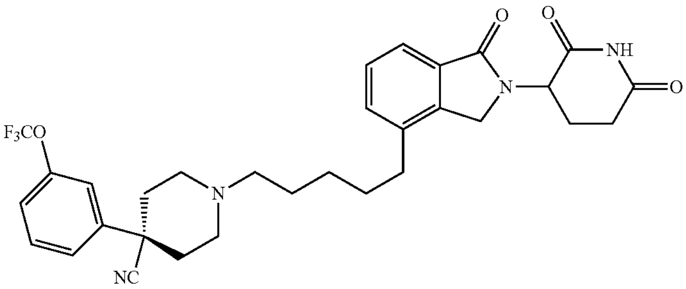 |

-continued
| Serial number | Compound |
|---|---|
| 95 | 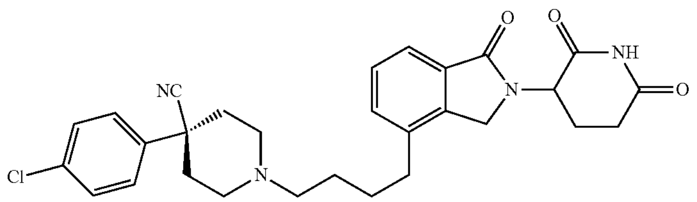 |
| 96 | 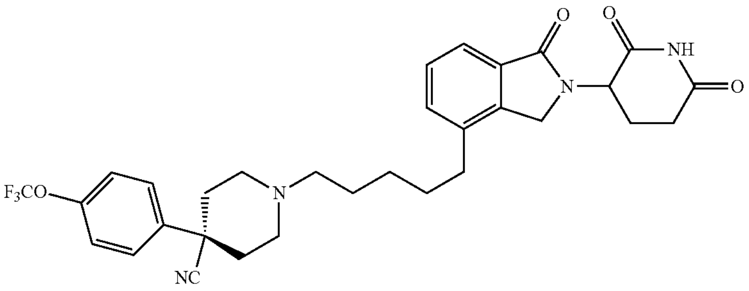 |
| 97 | 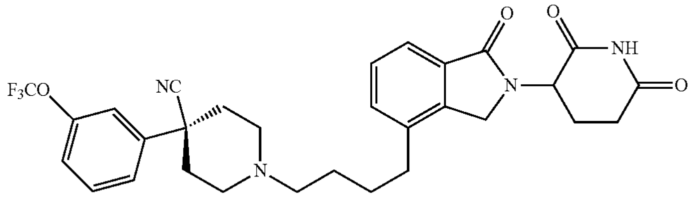 |
| 98 | 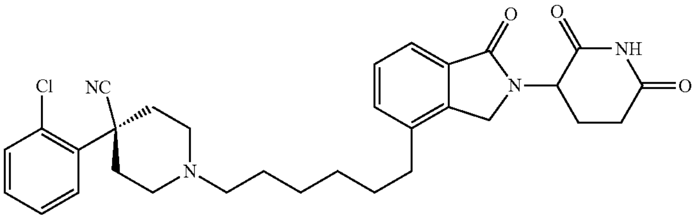 |
| 99 | 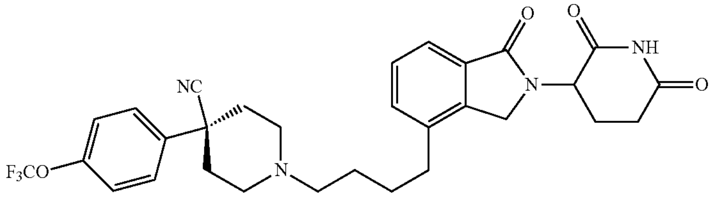 |
| 100 | 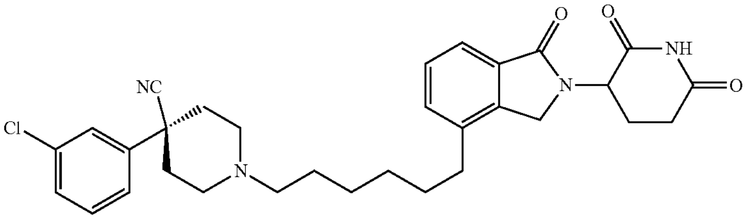 |

-continued
| Serial number | Compound |
|---|---|
| 101 | 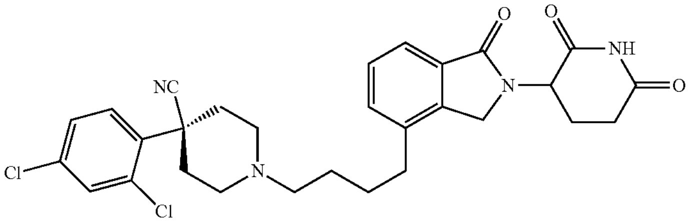 |
| 102 | 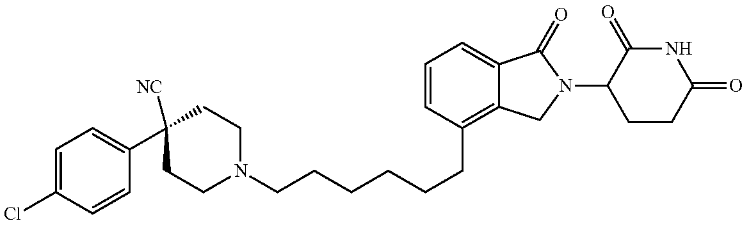 |
| 103 | 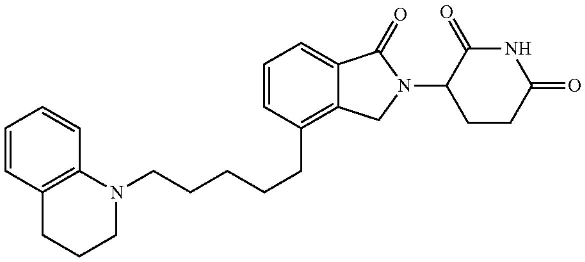 [SMILES: O=C1CCC(N2Cc3c(CCCCCN4CCCc5ccccc54)cccc3C2=O)C(=O)N1] |
| 104 | 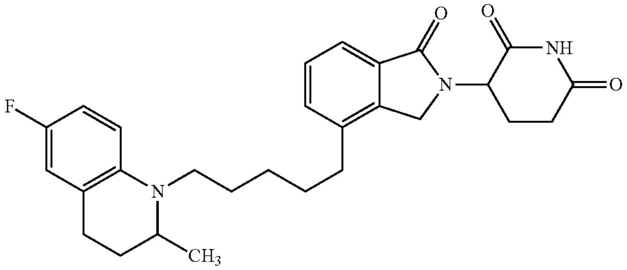 [SMILES: CC1CCc2cc(F)ccc2N1CCCCCc1cccc2c1CN(C1CCC(=O)NC1=O)C2=O] |
| 105 | 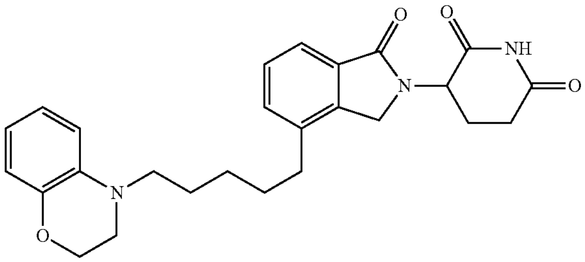 [SMILES: O=C1CCC(N2Cc3c(CCCCCN4CCOc5ccccc54)cccc3C2=O)C(=O)N1] |
| 106 | 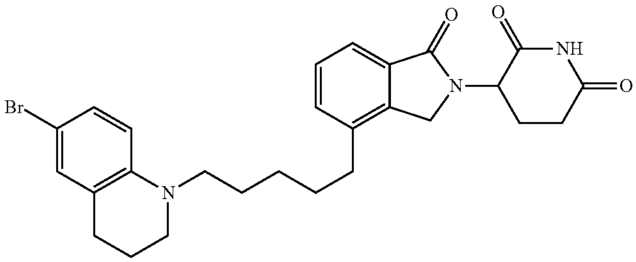 |

-continued
| Serial number | Compound |
| --- | --- |
| 107 | 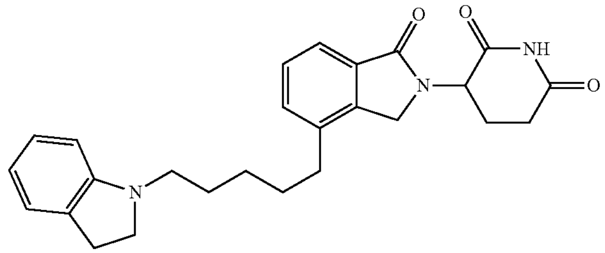 [SMILES: O=C1CCC(N2Cc3c(CCCCCN4CCc5ccccc54)cccc3C2=O)C(=O)N1] |
| 108 | 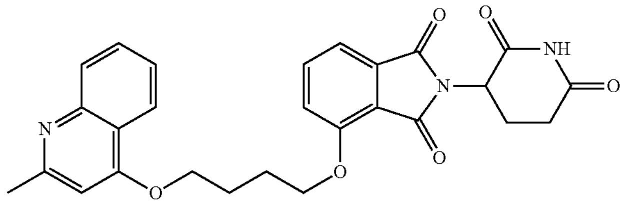 [SMILES: Cc1cc(OCCCCOc2cccc3c2C(=O)N(C2CCC(=O)NC2=O)C3=O)c2ccccc2n1] |
| 109 | 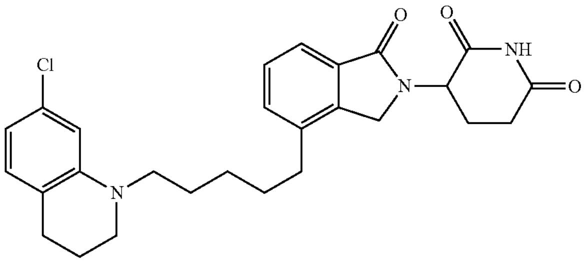 [SMILES: O=C1CCC(N2Cc3c(CCCCCN4CCCc5ccc(Cl)cc54)cccc3C2=O)C(=O)N1] |
| 110 | 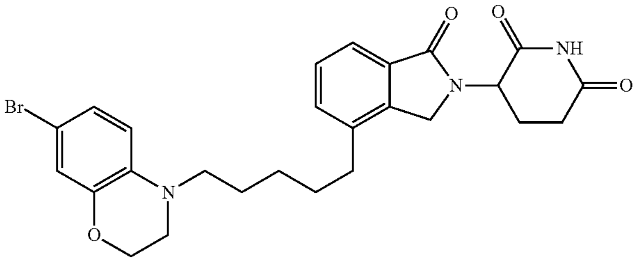 |
| 111 | 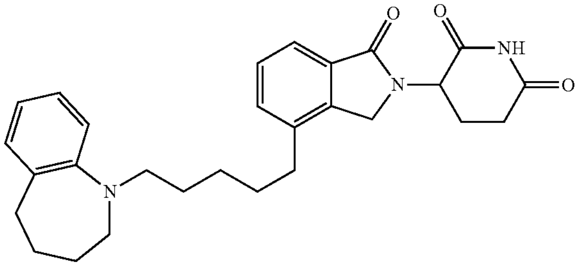 [SMILES: O=C1CCC(N2Cc3c(CCCCCN4CCCCc5ccccc54)cccc3C2=O)C(=O)N1] |
| 112 | 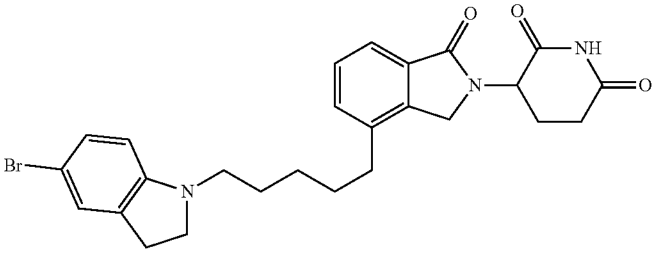 [SMILES: O=C1CCC(N2Cc3c(CCCCCN4CCc5cc(Br)ccc54)cccc3C2=O)C(=O)N1] |

-continued
| Serial number | Compound |
|---|---|
| 113 | 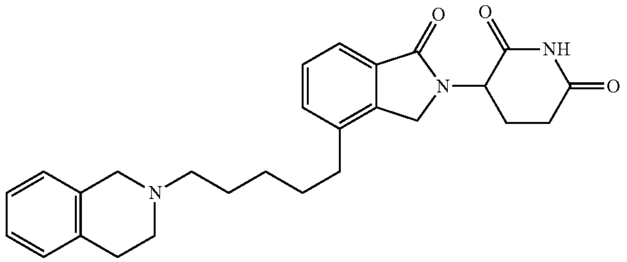 [SMILES: O=C1CCC(N2Cc3c(CCCCCN4CCc5ccccc5C4)cccc3C2=O)C(=O)N1] |
| 114 | 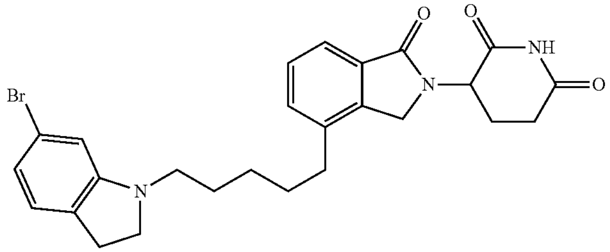 [SMILES: O=C1CCC(N2Cc3c(CCCCCN4CCc5ccc(Br)cc54)cccc3C2=O)C(=O)N1] |
| 115 | 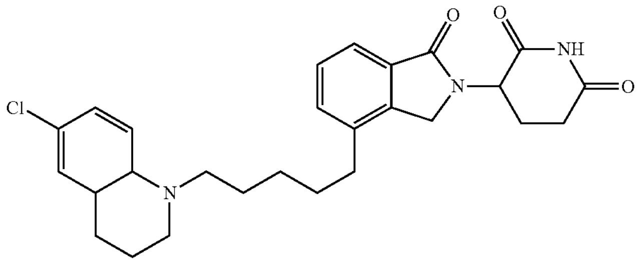 [SMILES: O=C1CCC(N2Cc3c(CCCCCN4CCCC5C=C(Cl)C=CC54)cccc3C2=O)C(=O)N1] |
| 116 | 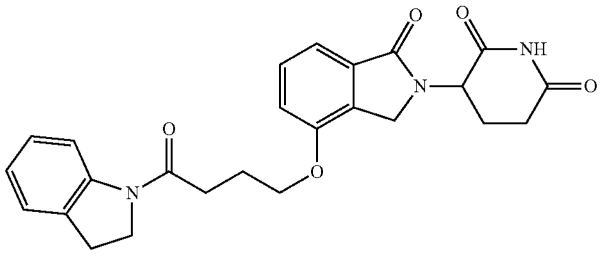 [SMILES: O=C1CCC(N2Cc3c(OCCCC(=O)N4CCc5ccccc54)cccc3C2=O)C(=O)N1] |
| 117 | 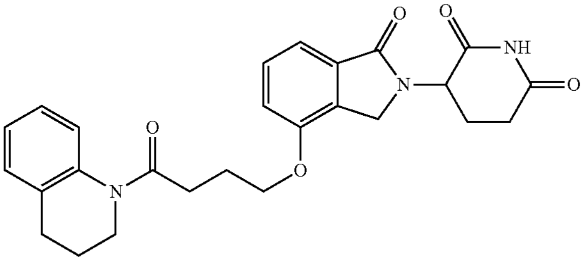 [SMILES: O=C1CCC(N2Cc3c(OCCCC(=O)N4CCCc5ccccc54)cccc3C2=O)C(=O)N1] |
| 118 | 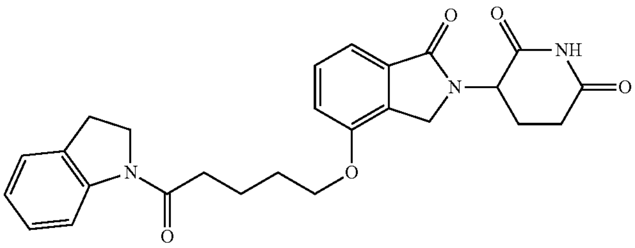 [SMILES: O=C1CCC(N2Cc3c(OCCCCC(=O)N4CCc5ccccc54)cccc3C2=O)C(=O)N1] |

-continued
| Serial number | Compound |
|---|---|
| 119 | 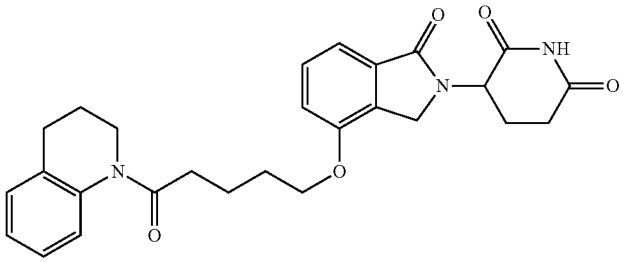 [SMILES: O=C1CCC(N2Cc3c(OCCCCC(=O)N4CCCc5ccccc54)cccc3C2=O)C(=O)N1] |
| 120 | 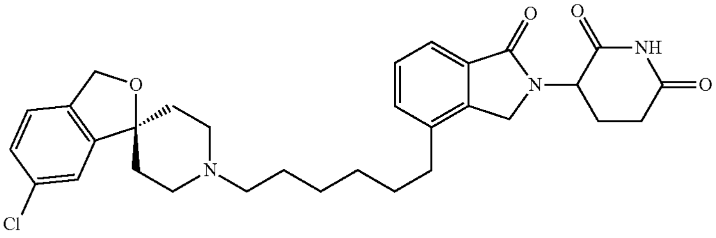 |
| 121 | 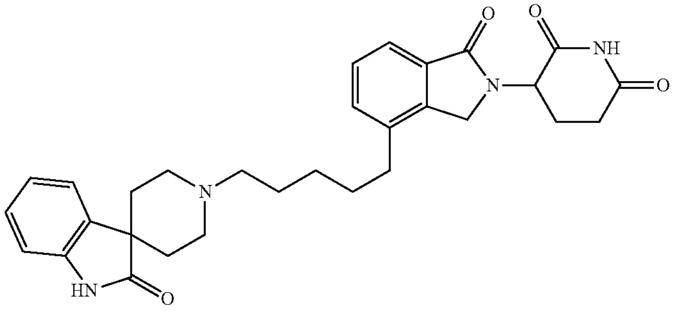 [SMILES: O=C1CCC(N2Cc3c(CCCCCN4CCC5(CC4)C(=O)Nc4ccccc45)cccc3C2=O)C(=O)N1] |
| 122 | 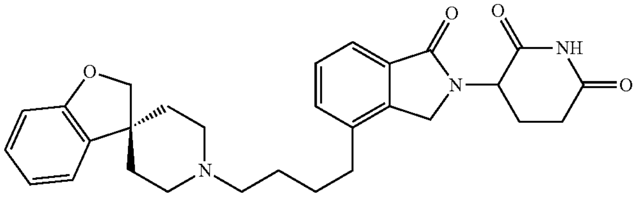 |
| 123 | 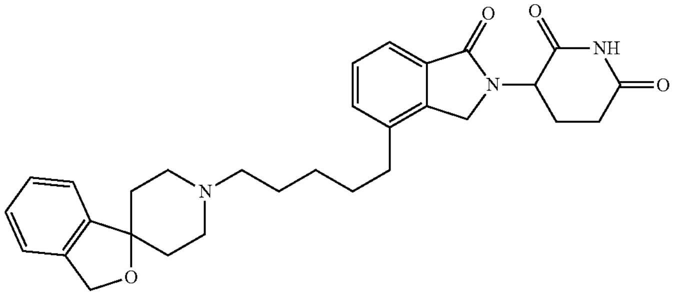 [SMILES: O=C1CCC(N2Cc3c(CCCCCN4CCC5(CC4)OCc4ccccc45)cccc3C2=O)C(=O)N1] |

-continued
| Serial number | Compound |
|---|---|
| 124 | 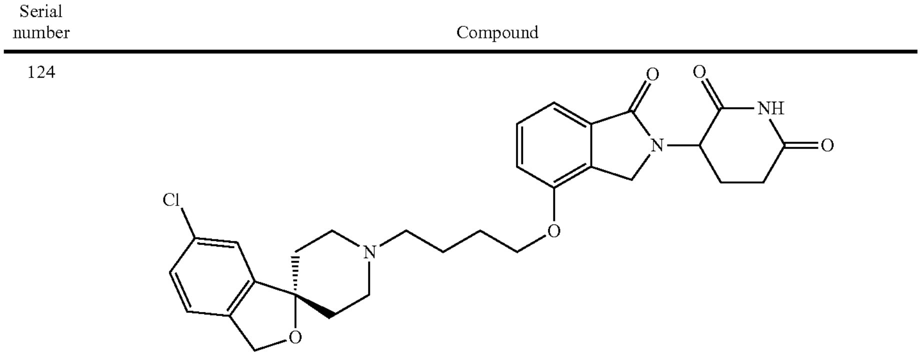 |
| 125 | 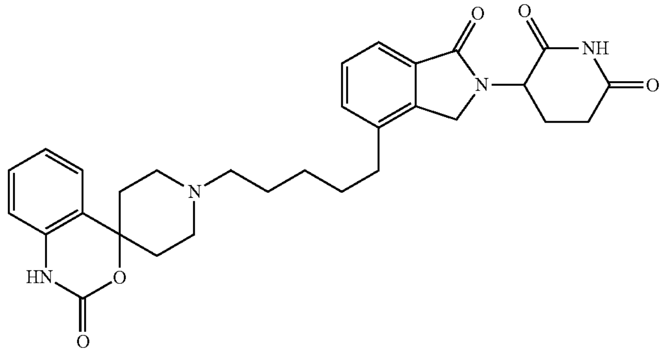 [SMILES: O=C1CCC(N2Cc3c(CCCCCN4CCC5(CC4)OC(=O)Nc4ccccc45)cccc3C2=O)C(=O)N1] |
| 126 | 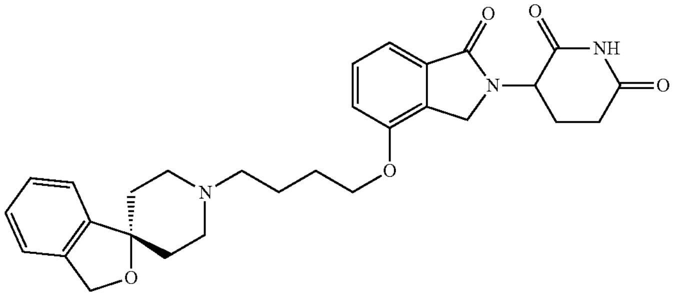 |
| 127 | 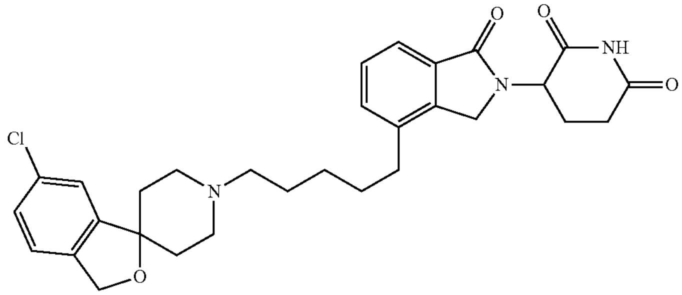 [SMILES: O=C1CCC(N2Cc3c(CCCCCN4CCC5(CC4)OCc4ccc(Cl)cc45)cccc3C2=O)C(=O)N1] |
| 128 | 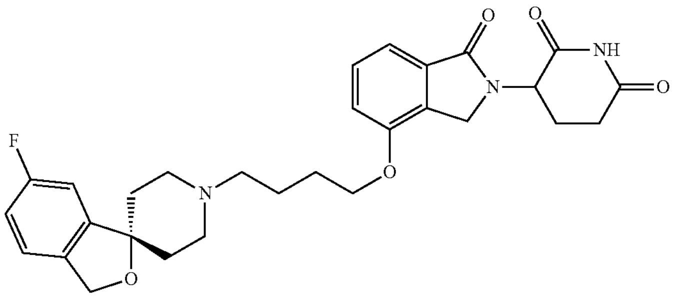 |

-continued
| Serial number | Compound |
|---|---|
| 129 | 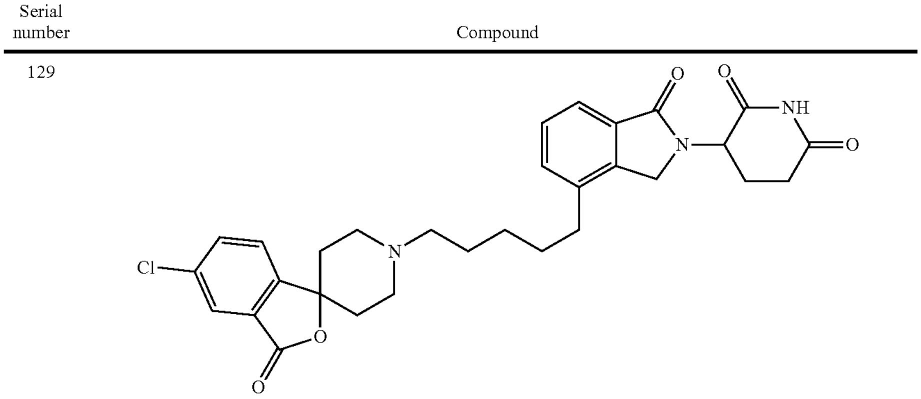 |
| 130 | 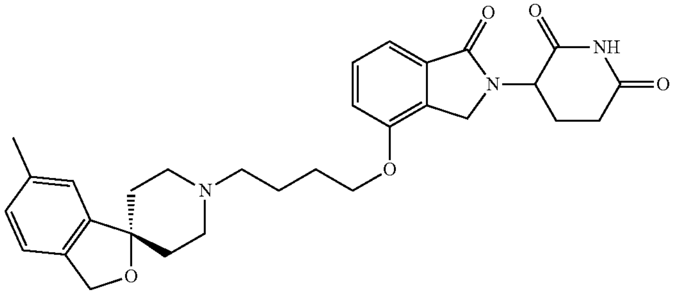 |
| 131 | 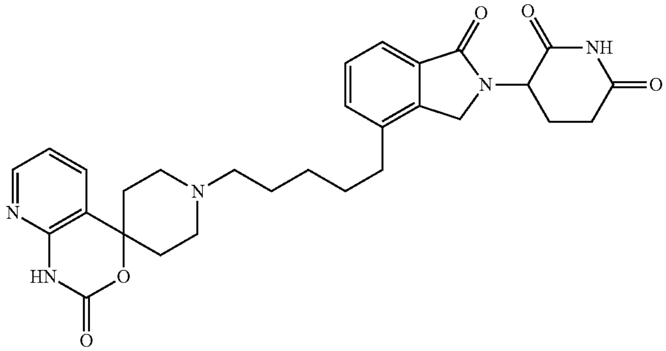 [SMILES: O=C1CCC(N2Cc3c(CCCCCN4CCC5(CC4)OC(=O)Nc4ncccc45)cccc3C2=O)C(=O)N1] |
| 132 | 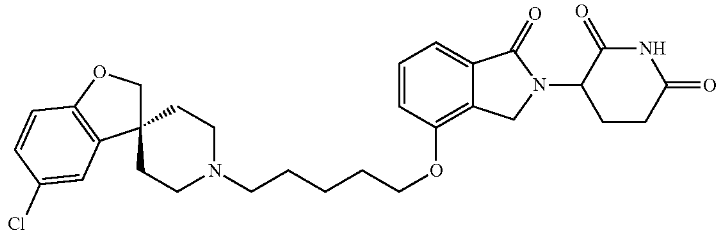 |
| 133 | 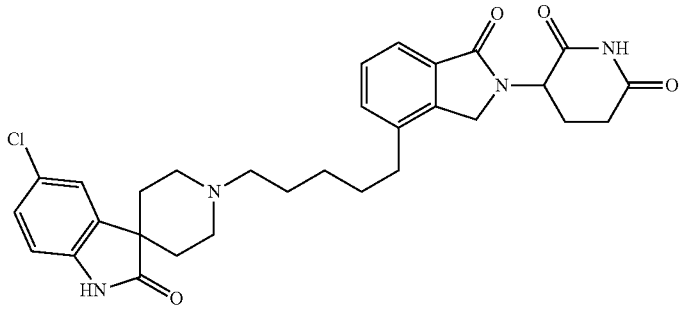 [SMILES: O=C1CCC(N2Cc3c(CCCCCN4CCC5(CC4)C(=O)Nc4ccc(Cl)cc45)cccc3C2=O)C(=O)N1] |

-continued
| Serial number | Compound |
| --- | --- |
| 134 | 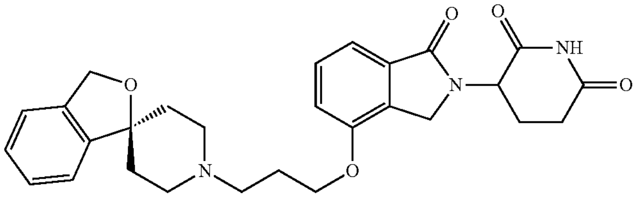 |
| 135 | 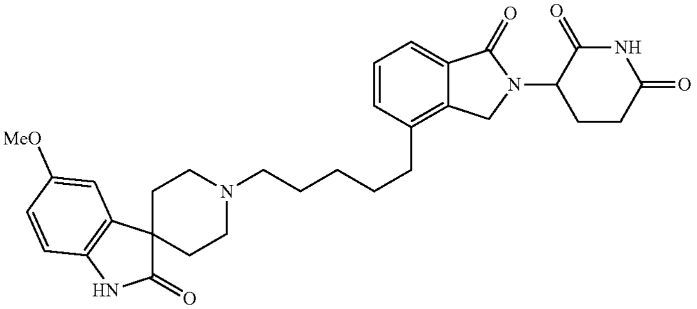 [SMILES: COc1ccc2c(c1)C1(CCN(CCCCCc3cccc4c3CN(C3CCC(=O)NC3=O)C4=O)CC1)C(=O)N2] |
| 136 | 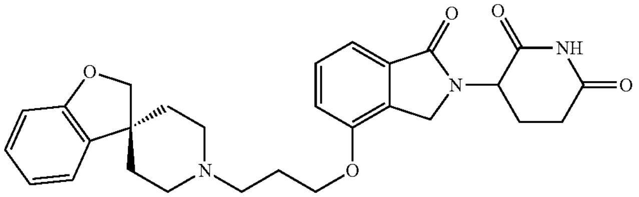 |
| 137 | 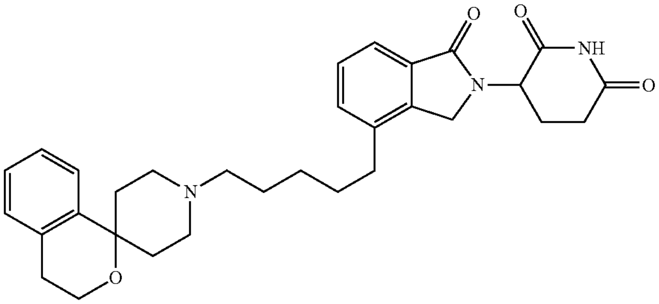 [SMILES: O=C1CCC(N2Cc3c(CCCCCN4CCC5(CC4)OCCc4ccccc45)cccc3C2=O)C(=O)N1] |
| 138 | 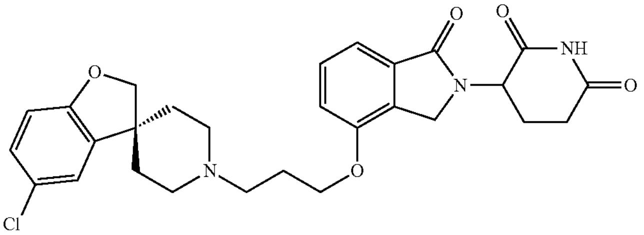 |
| 139 | 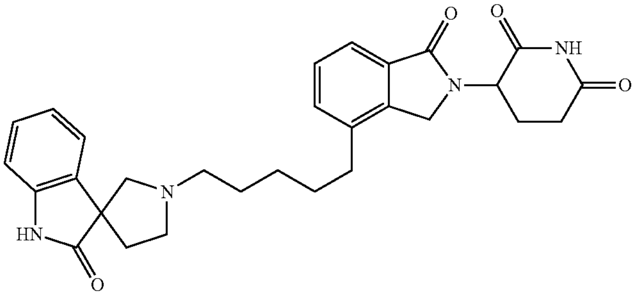 [SMILES: O=C1CCC(N2Cc3c(CCCCCN4CCC5(C4)C(=O)Nc4ccccc45)cccc3C2=O)C(=O)N1] |

-continued
| Serial number | Compound |
|---|---|
| 140 | 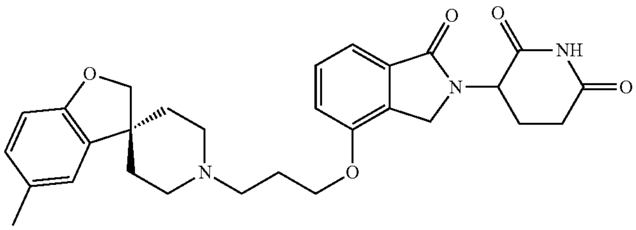 |
| 141 | 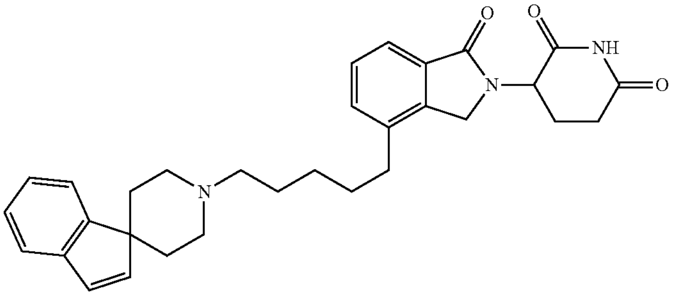 [SMILES: O=C1CCC(N2Cc3c(CCCCCN4CCC5(C=Cc6ccccc65)CC4)cccc3C2=O)C(=O)N1] |
| 142 | 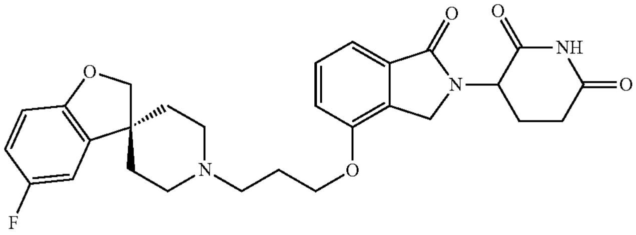 |
| 143 | 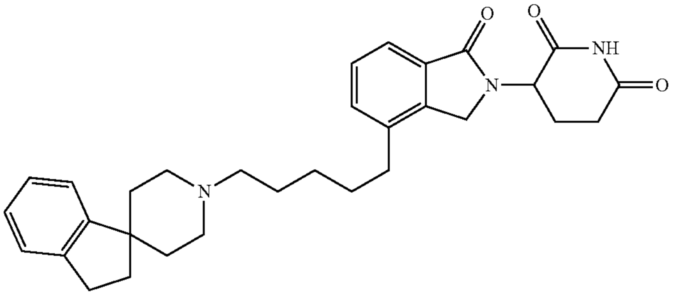 |
| 144 | 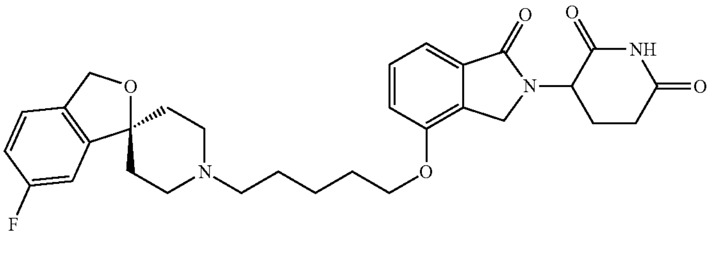 |

-continued
| Serial number | Compound |
| --- | --- |
| 145 | 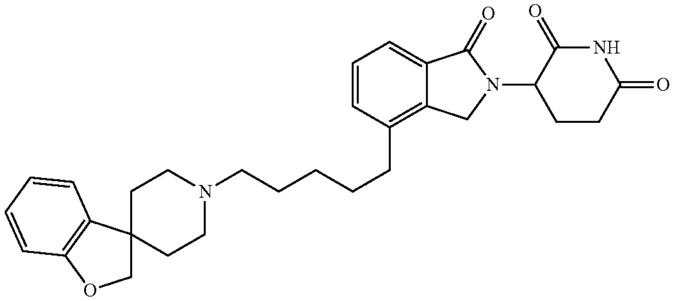 [SMILES: O=C1CCC(N2Cc3c(CCCCCN4CCC5(CC4)COc4ccccc45)cccc3C2=O)C(=O)N1] |
| 146 | 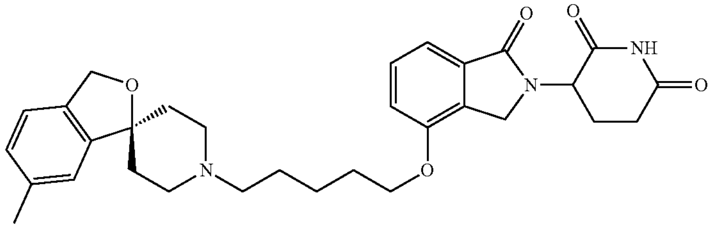 |
| 147 | 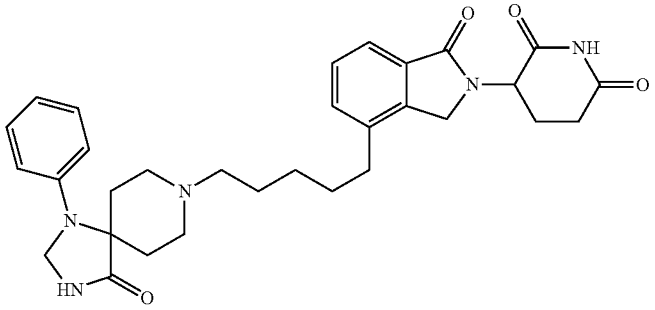 [SMILES: O=C1CCC(N2Cc3c(CCCCCN4CCC5(CC4)C(=O)NCN5c4ccccc4)cccc3C2=O)C(=O)N1] |
| 148 | 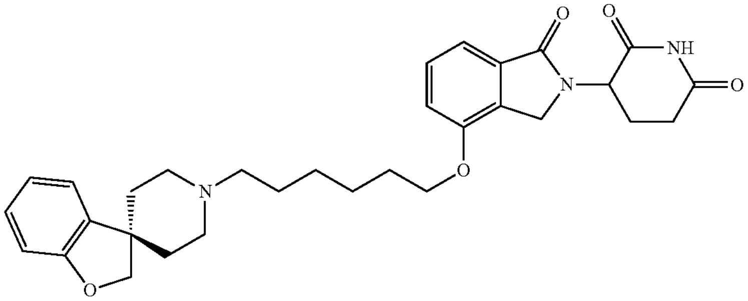 |
| 149 | 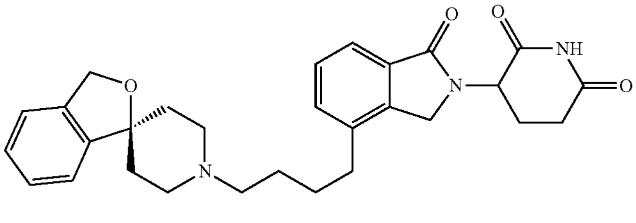 |

-continued
| Serial number | Compound |
|---|---|
| 150 | 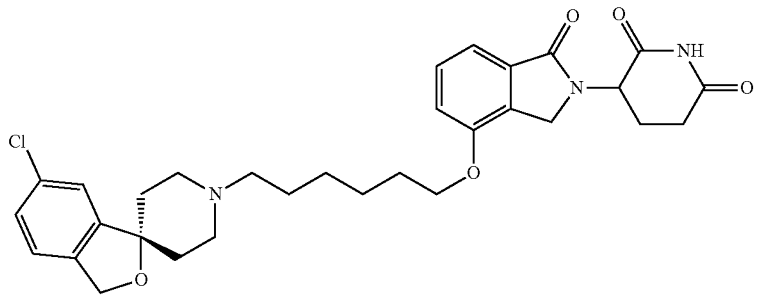 |
| 151 | 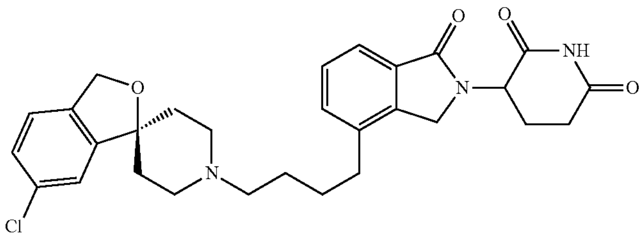 |
| 152 | 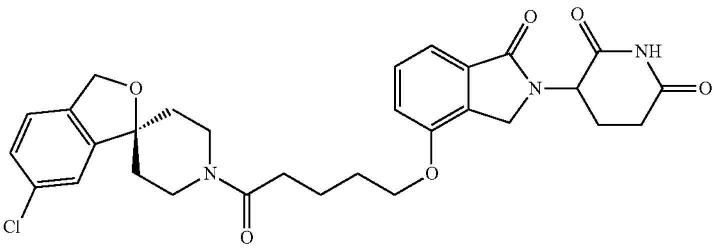 |
| 153 | 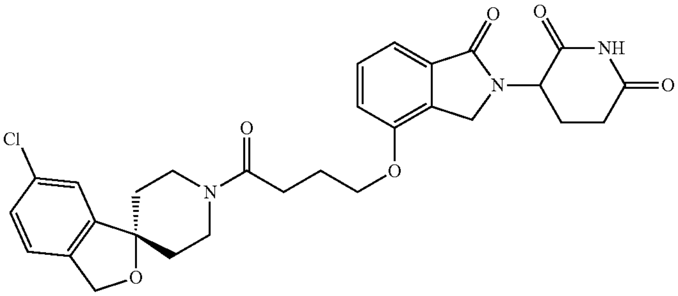 |
| 154 | 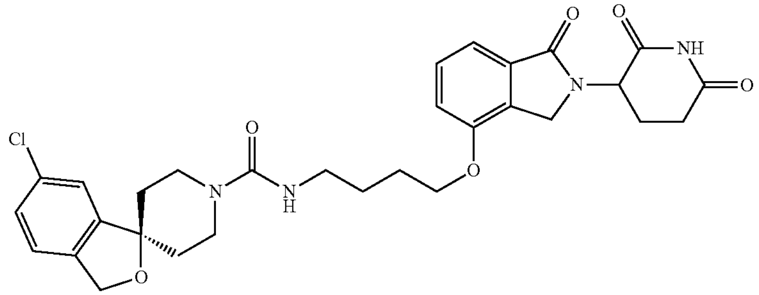 |

-continued
| Serial number | Compound |
|---|---|
| 155 | 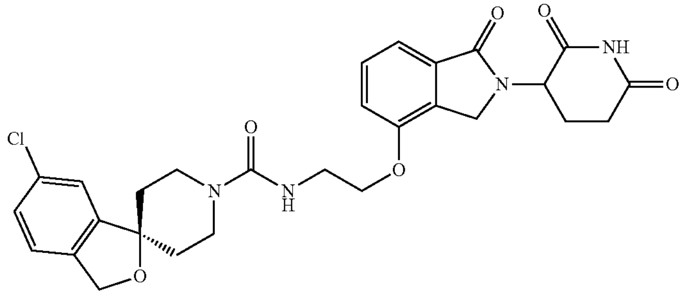 |
| 156 | 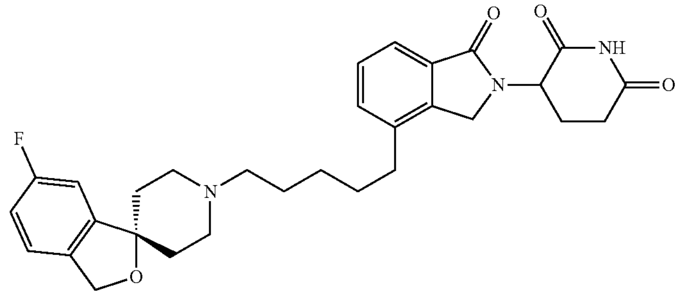 |
| 157 | 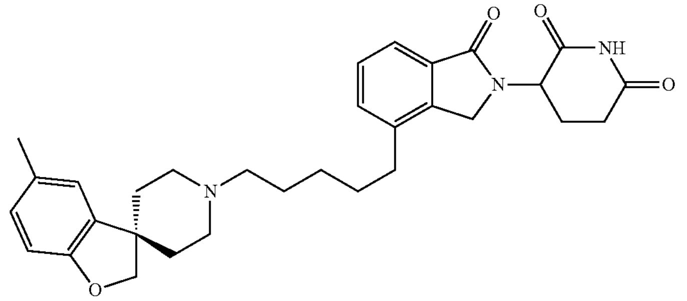 |
| 158 | 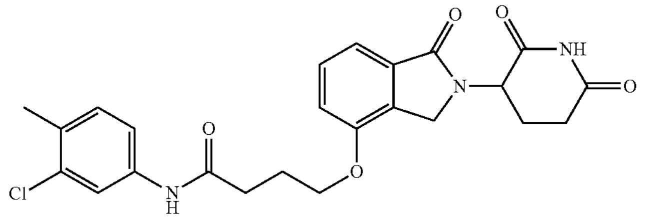 [SMILES: Cc1ccc(NC(=O)CCCOc2cccc3c2CN(C2CCC(=O)NC2=O)C3=O)cc1Cl] |
| 159 | 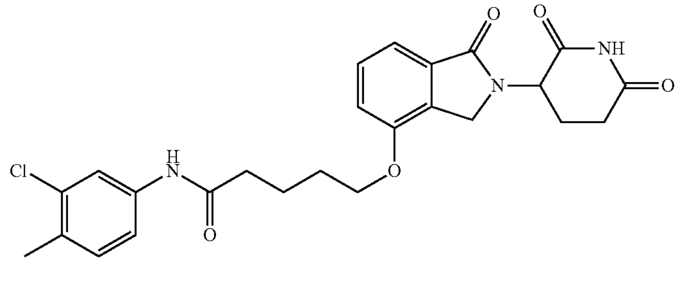 [SMILES: Cc1ccc(NC(=O)CCCCOc2cccc3c2CN(C2CCC(=O)NC2=O)C3=O)cc1Cl] |

-continued
| Serial number | Compound |
|---|---|
| 160 | 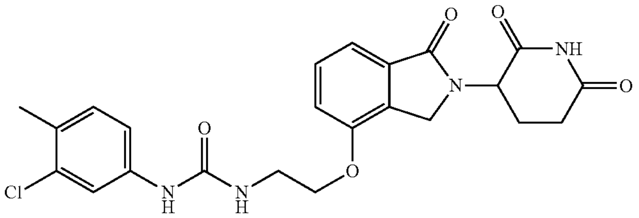 [SMILES: Cc1ccc(NC(=O)NCCOc2cccc3c2CN(C2CCC(=O)NC2=O)C3=O)cc1Cl] |
| 161 | 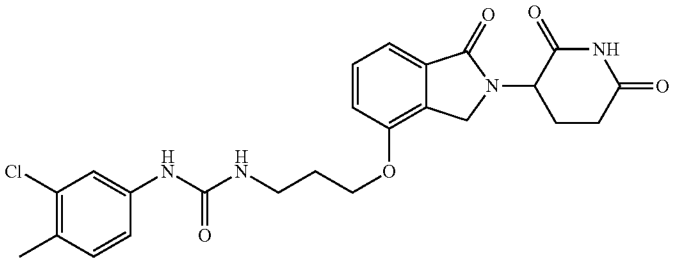 [SMILES: Cc1ccc(NC(=O)NCCCOc2cccc3c2CN(C2CCC(=O)NC2=O)C3=O)cc1Cl] |
| 162 | 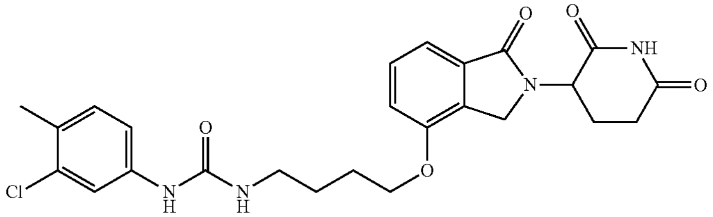 [SMILES: Cc1ccc(NC(=O)NCCCCOc2cccc3c2CN(C2CCC(=O)NC2=O)C3=O)cc1Cl] |
| 163 | 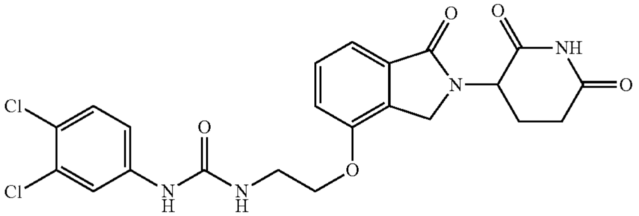 [SMILES: O=C1CCC(N2Cc3c(OCCNC(=O)Nc4ccc(Cl)c(Cl)c4)cccc3C2=O)C(=O)N1] |
| 164 | 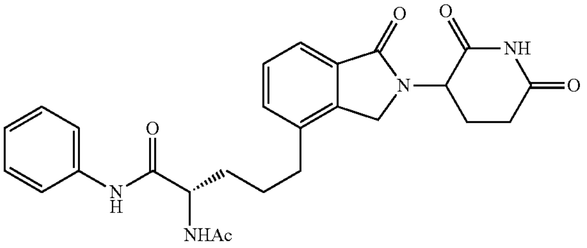 [SMILES: CC(=O)N[C@@H](CCCc1cccc2c1CN(C1CCC(=O)NC1=O)C2=O)C(=O)Nc1ccccc1] |
| 165 | 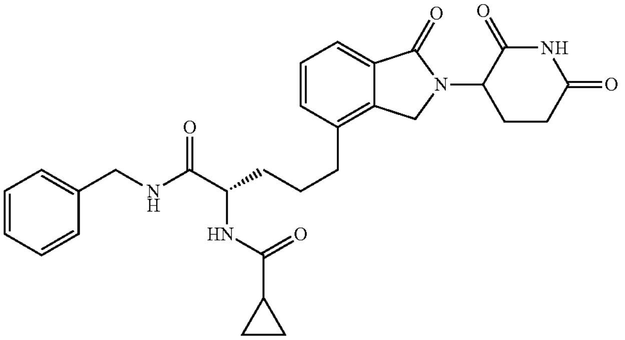 [SMILES: O=C1CCC(N2Cc3c(CCC[C@H](NC(=O)C4CC4)C(=O)NCc4ccccc4)cccc3C2=O)C(=O)N1] |

-continued
| Serial number | Compound |
|---|---|
| 166 | 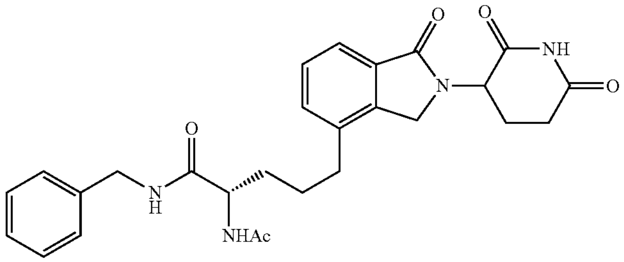 |
| 167 | 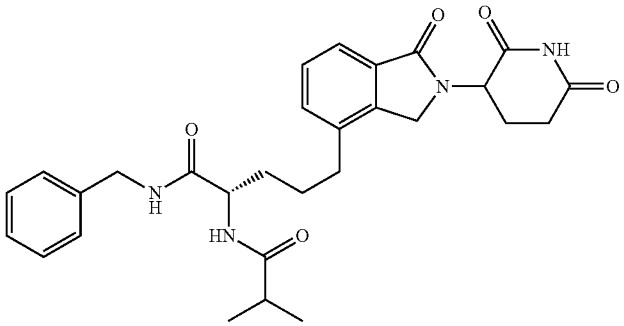 [SMILES: CC(C)C(=O)N[C@@H](CCCc1cccc2c1CN(C1CCC(=O)NC1=O)C2=O)C(=O)NCc1ccccc1] |
| 168 | 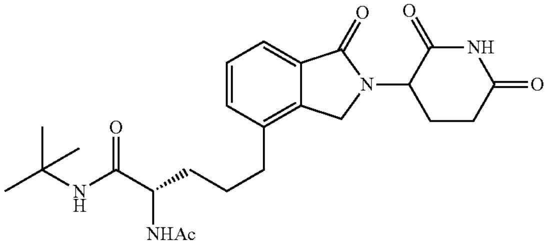 [SMILES: CC(=O)N[C@@H](CCCc1cccc2c1CN(C1CCC(=O)NC1=O)C2=O)C(=O)NC(C)(C)C] |
| 169 | 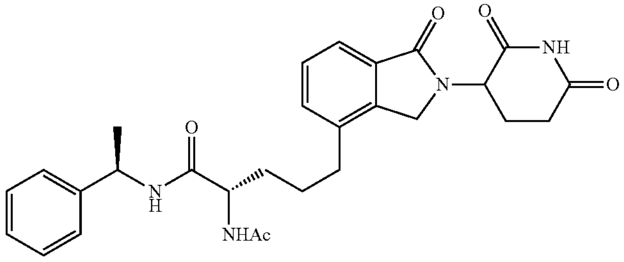 [SMILES: CC(=O)N[C@@H](CCCc1cccc2c1CN(C1CCC(=O)NC1=O)C2=O)C(=O)N[C@H](C)c1ccccc1] |
| 170 | 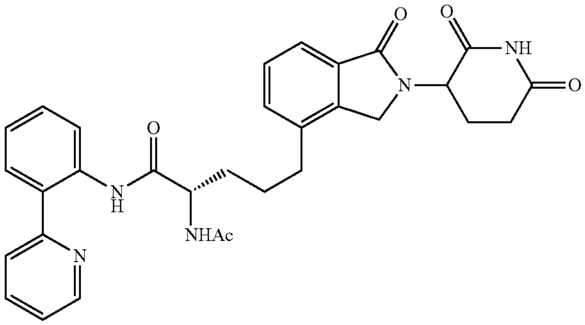 |

-continued
| Serial number | Compound |
|---|---|
| 171 | 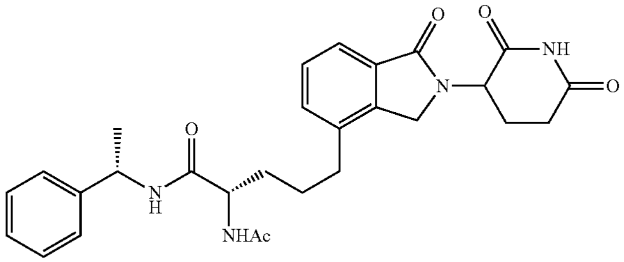 [SMILES: CC(=O)N[C@@H](CCCc1cccc2c1CN(C1CCC(=O)NC1=O)C2=O)C(=O)N[C@@H](C)c1ccccc1] |
| 172 | 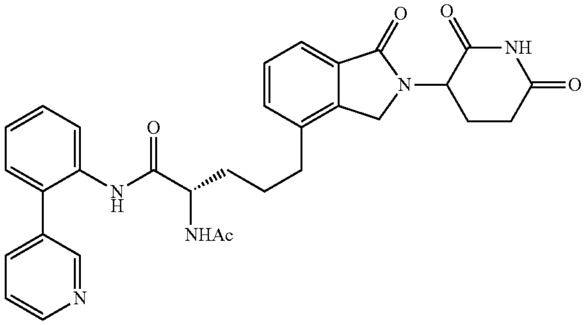 [SMILES: CC(=O)N[C@@H](CCCc1cccc2c1CN(C1CCC(=O)NC1=O)C2=O)C(=O)Nc1ccccc1-c1cccnc1] |
| 173 | 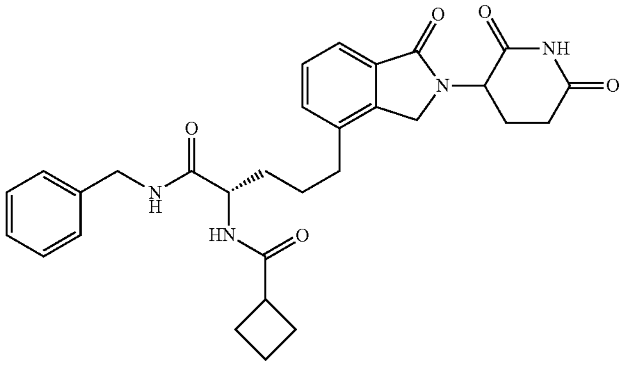 [SMILES: O=C1CCC(N2Cc3c(CCC[C@H](NC(=O)C4CCC4)C(=O)NCc4ccccc4)cccc3C2=O)C(=O)N1] |
| 174 | 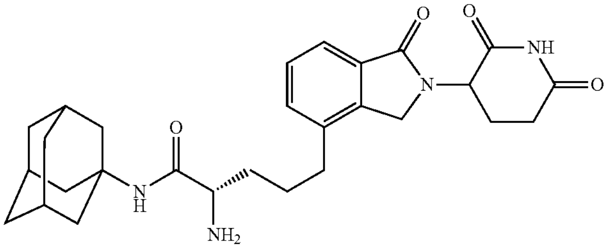 [SMILES: N[C@@H](CCCc1cccc2c1CN(C1CCC(=O)NC1=O)C2=O)C(=O)NC12CC3CC(CC(C3)C1)C2] |
| 175 | 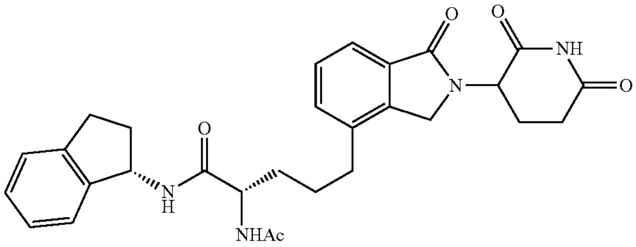 [SMILES: CC(=O)N[C@@H](CCCc1cccc2c1CN(C1CCC(=O)NC1=O)C2=O)C(=O)N[C@H]1CCc2ccccc21] |

-continued
| Serial number | Compound |
|---|---|
| 176 | 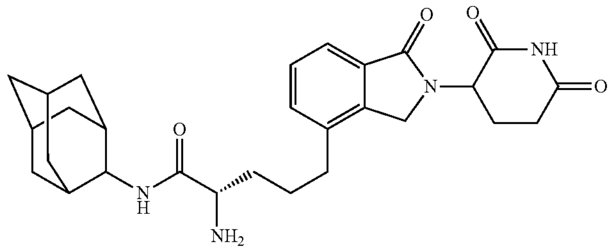 [SMILES: N[C@@H](CCCc1cccc2c1CN(C1CCC(=O)NC1=O)C2=O)C(=O)NC1C2CC3CC(C2)CC1C3] |
| 177 | 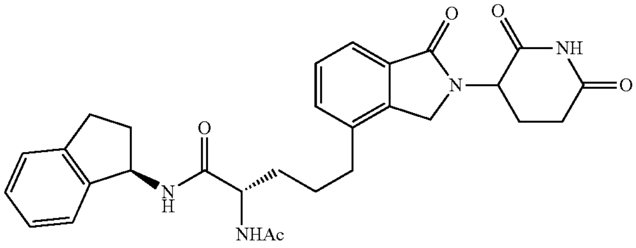 [SMILES: CC(=O)N[C@@H](CCCc1cccc2c1CN(C1CCC(=O)NC1=O)C2=O)C(=O)N[C@@H]1CCc2ccccc21] |
| 178 | 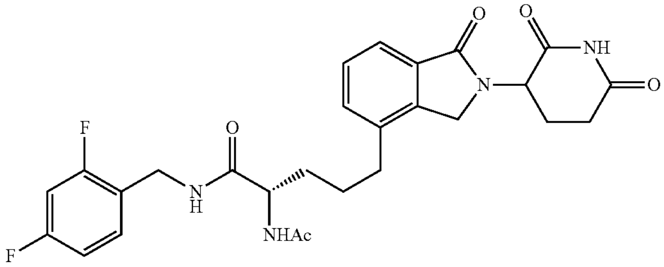 [SMILES: CC(=O)N[C@@H](CCCc1cccc2c1CN(C1CCC(=O)NC1=O)C2=O)C(=O)NCc1ccc(F)cc1F] |
| 179 | 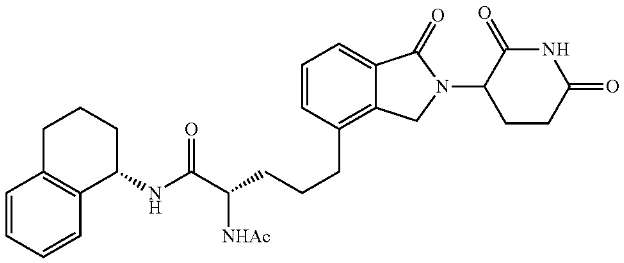 [SMILES: CC(=O)N[C@@H](CCCc1cccc2c1CN(C1CCC(=O)NC1=O)C2=O)C(=O)N[C@H]1CCCc2ccccc21] |
| 180 | 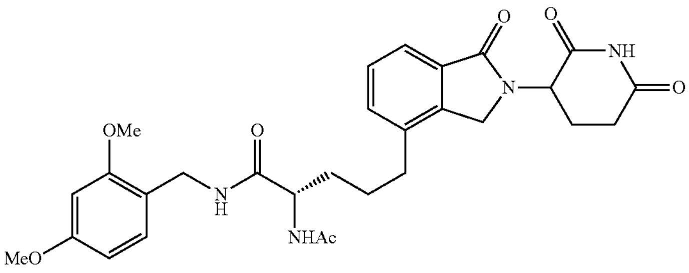 [SMILES: COc1ccc(CNC(=O)[C@H](CCCc2cccc3c2CN(C2CCC(=O)NC2=O)C3=O)NC(C)=O)c(OC)c1] |

-continued
| Serial number | Compound |
|---|---|
| 181 | 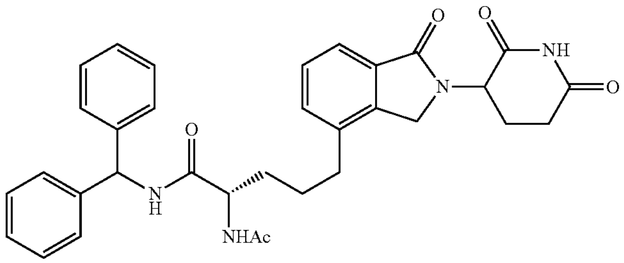 [SMILES: CC(=O)N[C@@H](CCCc1cccc2c1CN(C1CCC(=O)NC1=O)C2=O)C(=O)NC(c1ccccc1)c1ccccc1] |
| 182 | 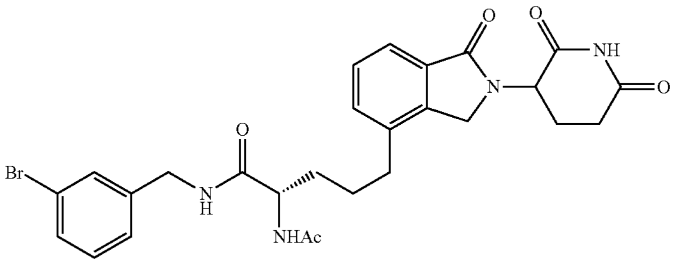 |
| 183 | 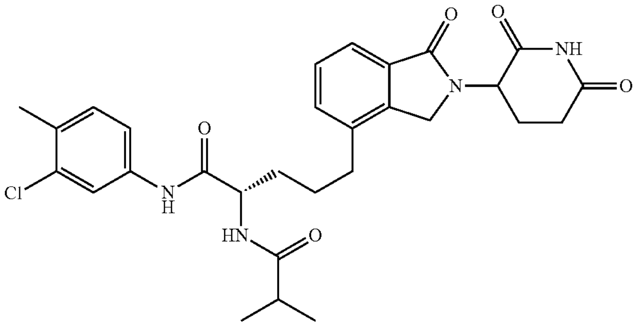 [SMILES: Cc1ccc(NC(=O)[C@H](CCCc2cccc3c2CN(C2CCC(=O)NC2=O)C3=O)NC(=O)C(C)C)cc1Cl] |
| 184 | 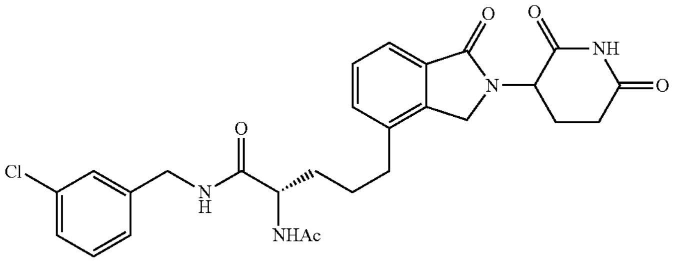 [SMILES: CC(=O)N[C@@H](CCCc1cccc2c1CN(C1CCC(=O)NC1=O)C2=O)C(=O)NCc1cccc(Cl)c1] |
| 185 | 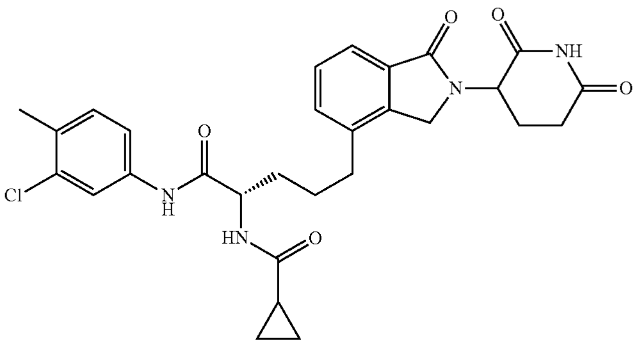 [SMILES: Cc1ccc(NC(=O)[C@H](CCCc2cccc3c2CN(C2CCC(=O)NC2=O)C3=O)NC(=O)C2CC2)cc1Cl] |

-continued
| Serial number | Compound |
|---|---|
| 186 | 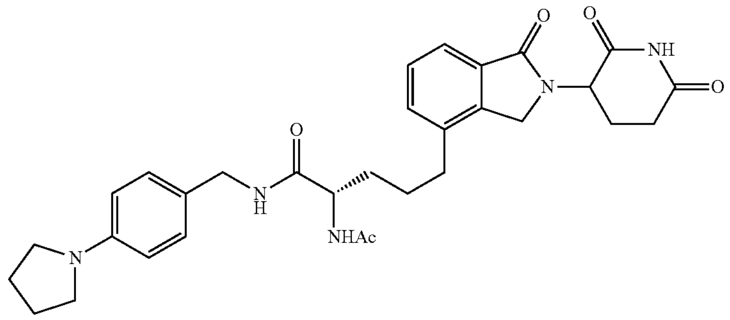 [SMILES: CC(=O)N[C@@H](CCCc1cccc2c1CN(C1CCC(=O)NC1=O)C2=O)C(=O)NCc1ccc(N2CCCC2)cc1] |
| 187 | 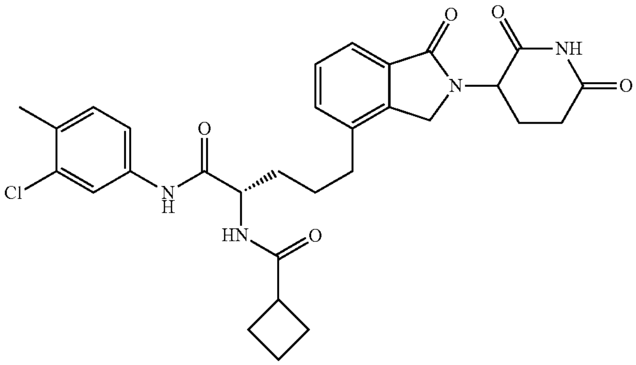 [SMILES: Cc1ccc(NC(=O)[C@H](CCCc2cccc3c2CN(C2CCC(=O)NC2=O)C3=O)NC(=O)C2CCC2)cc1Cl] |
| 188 | 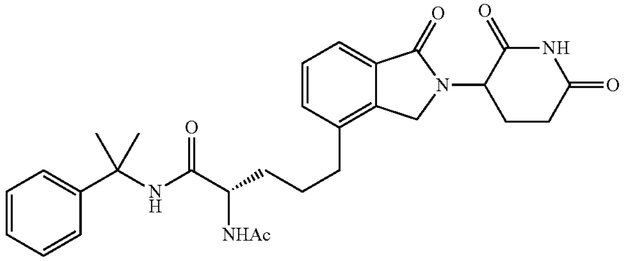 [SMILES: CC(=O)N[C@@H](CCCc1cccc2c1CN(C1CCC(=O)NC1=O)C2=O)C(=O)NC(C)(C)c1ccccc1] |
| 189 | 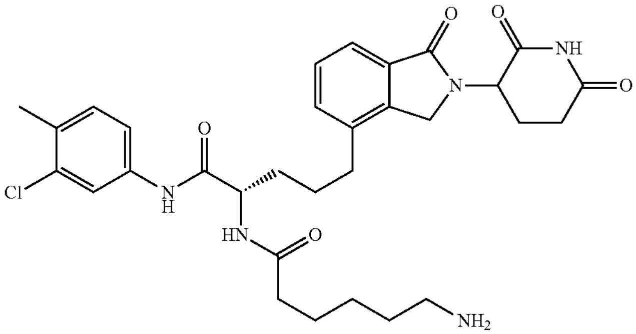 [SMILES: Cc1ccc(NC(=O)[C@H](CCCc2cccc3c2CN(C2CCC(=O)NC2=O)C3=O)NC(=O)CCCCCN)cc1Cl] |
| 190 | 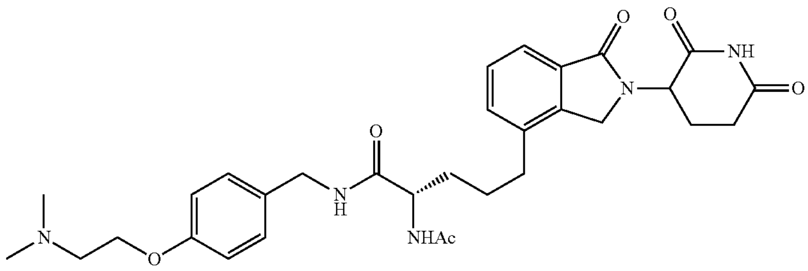 [SMILES: CC(=O)N[C@@H](CCCc1cccc2c1CN(C1CCC(=O)NC1=O)C2=O)C(=O)NCc1ccc(OCCN(C)C)cc1] |

-continued
| Serial number | Compound |
|---|---|
| 191 | 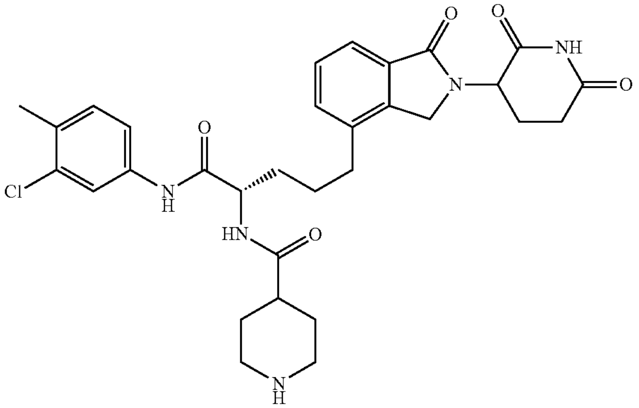 [SMILES: Cc1ccc(NC(=O)[C@H](CCCc2cccc3c2CN(C2CCC(=O)NC2=O)C3=O)NC(=O)C2CCNCC2)cc1Cl] |
| 192 | 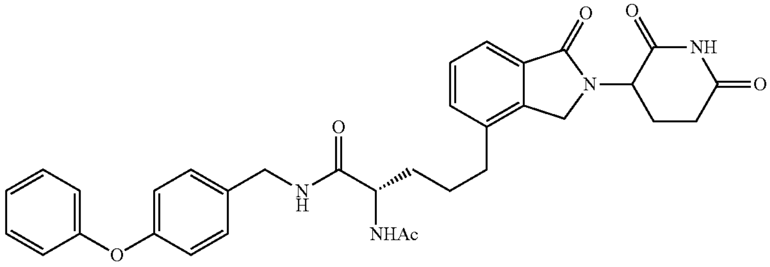 [SMILES: CC(=O)N[C@@H](CCCc1cccc2c1CN(C1CCC(=O)NC1=O)C2=O)C(=O)NCc1ccc(Oc2ccccc2)cc1] |
| 193 | 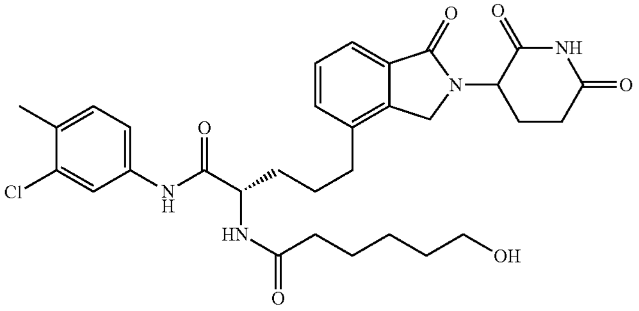 [SMILES: Cc1ccc(NC(=O)[C@H](CCCc2cccc3c2CN(C2CCC(=O)NC2=O)C3=O)NC(=O)CCCCCO)cc1Cl] |
| 194 | 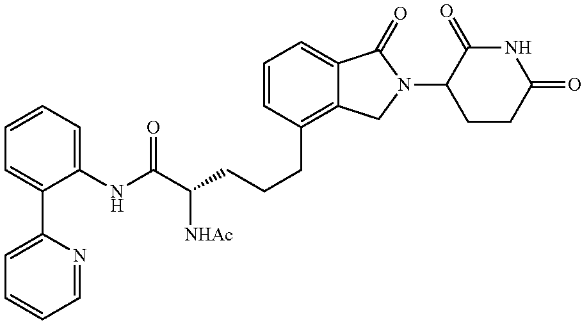 [SMILES: CC(=O)N[C@@H](CCCc1cccc2c1CN(C1CCC(=O)NC1=O)C2=O)C(=O)Nc1ccccc1-c1ccccn1] |

-continued
| Serial number | Compound |
|---|---|
| 195 | 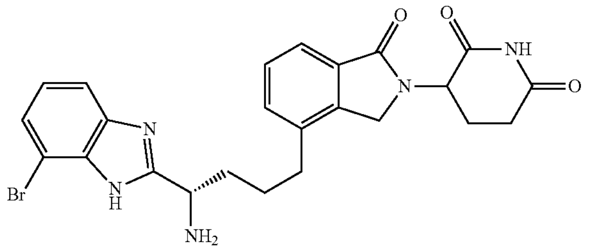 [SMILES: N[C@@H](CCCc1cccc2c1CN(C1CCC(=O)NC1=O)C2=O)c1nc2cccc(Br)c2[nH]1] |
| 196 | 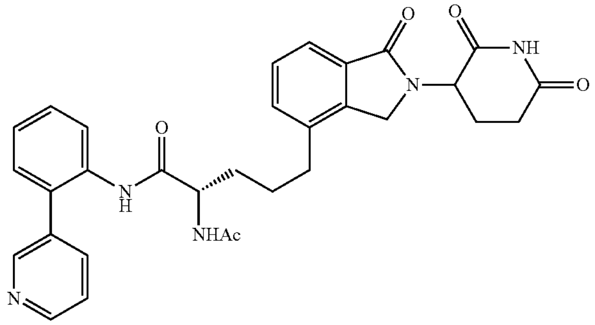 [SMILES: CC(=O)N[C@@H](CCCc1cccc2c1CN(C1CCC(=O)NC1=O)C2=O)C(=O)Nc1ccccc1-c1cccnc1] |
| 197 | 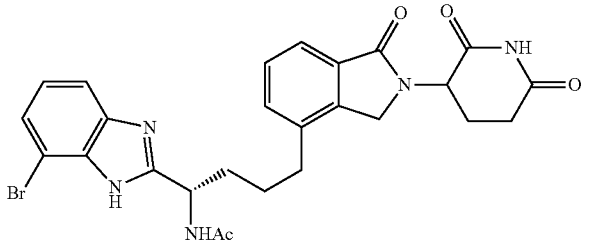 [SMILES: CC(=O)N[C@@H](CCCc1cccc2c1CN(C1CCC(=O)NC1=O)C2=O)c1nc2cccc(Br)c2[nH]1] |
| 198 | 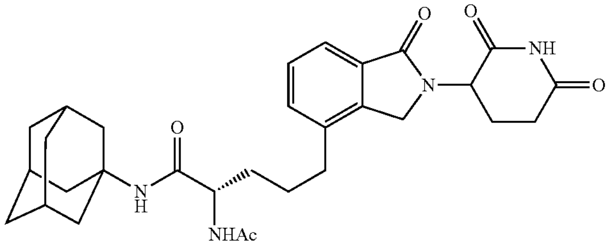 [SMILES: CC(=O)N[C@@H](CCCc1cccc2c1CN(C1CCC(=O)NC1=O)C2=O)C(=O)NC12CC3CC(CC(C3)C1)C2] |
| 199 | 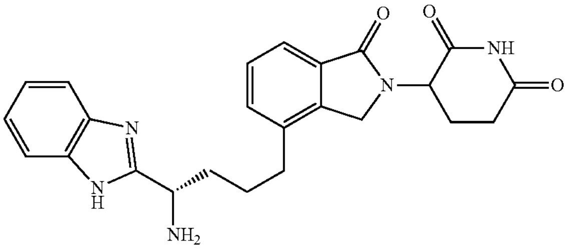 [SMILES: N[C@@H](CCCc1cccc2c1CN(C1CCC(=O)NC1=O)C2=O)c1nc2ccccc2[nH]1] |

-continued
| Serial number | Compound |
|---|---|
| 200 | 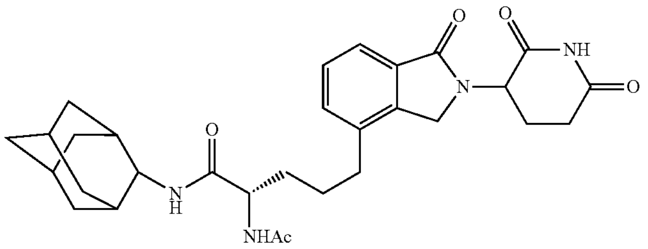 [SMILES: CC(=O)N[C@@H](CCCc1cccc2c1CN(C1CCC(=O)NC1=O)C2=O)C(=O)NC1C2CC3CC(C2)CC1C3] |
| 201 | 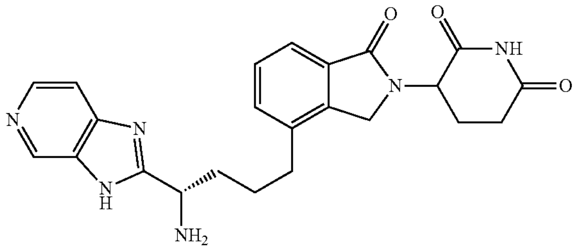 [SMILES: N[C@@H](CCCc1cccc2c1CN(C1CCC(=O)NC1=O)C2=O)c1nc2ccncc2[nH]1] |
| 202 | 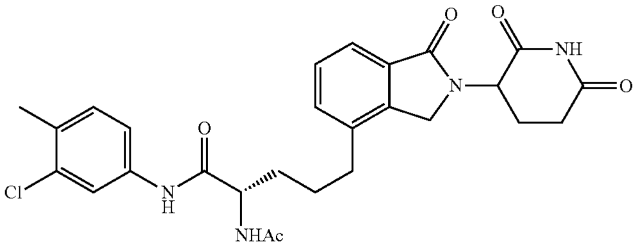 [SMILES: CC(=O)N[C@@H](CCCc1cccc2c1CN(C1CCC(=O)NC1=O)C2=O)C(=O)Nc1ccc(C)c(Cl)c1] |
| 203 | 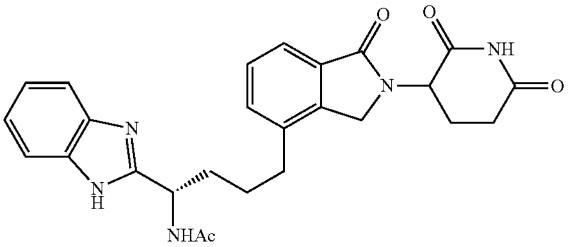 [SMILES: CC(=O)N[C@@H](CCCc1cccc2c1CN(C1CCC(=O)NC1=O)C2=O)c1nc2ccccc2[nH]1] |
| 204 | 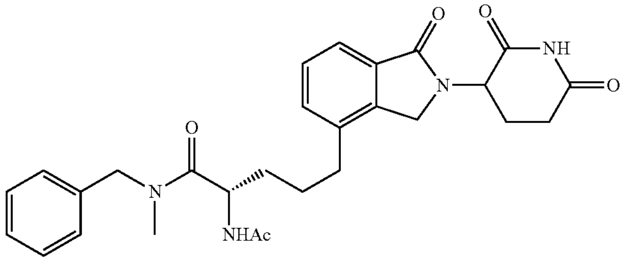 [SMILES: CC(=O)N[C@@H](CCCc1cccc2c1CN(C1CCC(=O)NC1=O)C2=O)C(=O)N(C)Cc1ccccc1] |
| 205 | 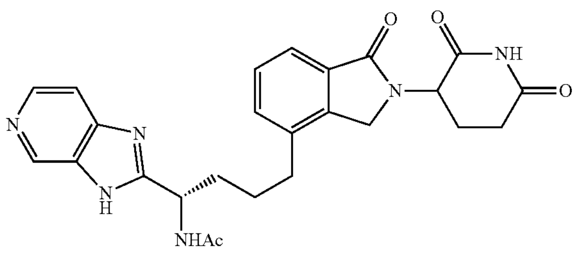 [SMILES: CC(=O)N[C@@H](CCCc1cccc2c1CN(C1CCC(=O)NC1=O)C2=O)c1nc2ccncc2[nH]1] |

-continued
| Serial number | Compound |
|---|---|
| 206 | 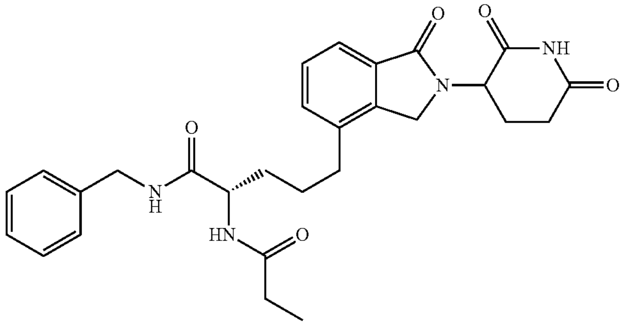 [SMILES: CCC(=O)N[C@@H](CCCc1cccc2c1CN(C1CCC(=O)NC1=O)C2=O)C(=O)NCc1ccccc1] |
| 207 | 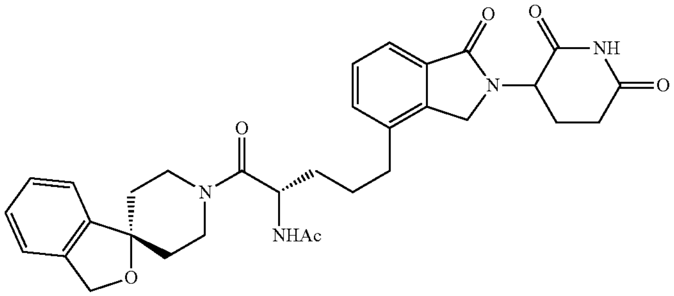 |
| 208 | 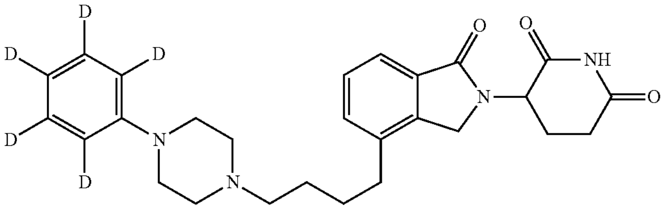 [SMILES: [2H]c1c([2H])c([2H])c(N2CCN(CCCCc3cccc4c3CN(C3CCC(=O)NC3=O)C4=O)CC2)c([2H])c1[2H]] |
| 209 | 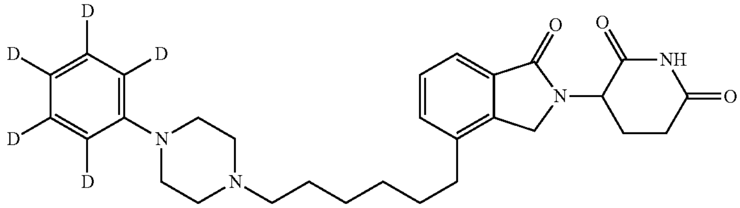 [SMILES: [2H]c1c([2H])c([2H])c(N2CCN(CCCCCCc3cccc4c3CN(C3CCC(=O)NC3=O)C4=O)CC2)c([2H])c1[2H]] |
| 210 | 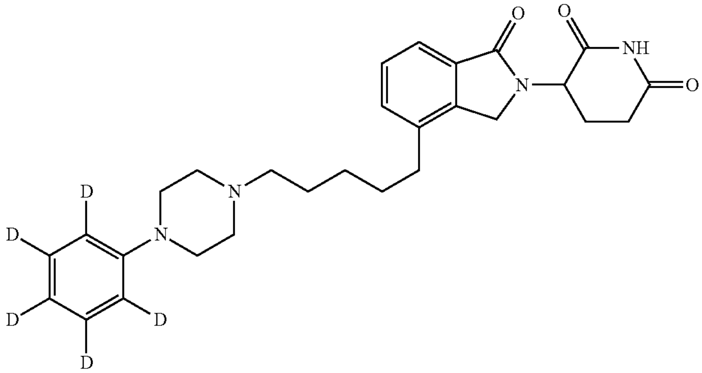 [SMILES: [2H]c1c([2H])c([2H])c(N2CCN(CCCCCc3cccc4c3CN(C3CCC(=O)NC3=O)C4=O)CC2)c([2H])c1[2H]] |

-continued
| Serial number | Compound |
|---|---|
| 211 | 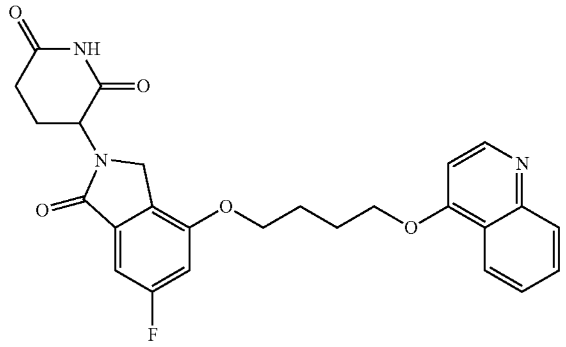 [SMILES: O=C1CCC(N2Cc3c(OCCCCOc4ccnc5ccccc45)cc(F)cc3C2=O)C(=O)N1] |
| 212 | 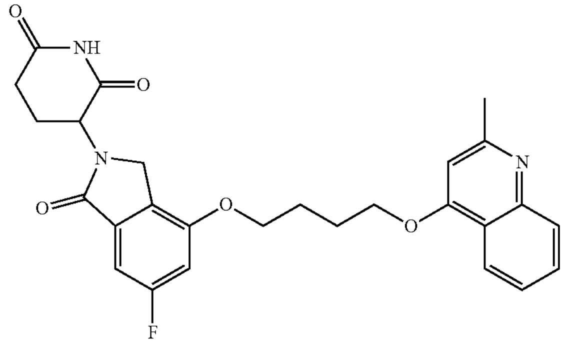 [SMILES: Cc1cc(OCCCCOc2cc(F)cc3c2CN(C2CCC(=O)NC2=O)C3=O)c2ccccc2n1] |
| 213 | 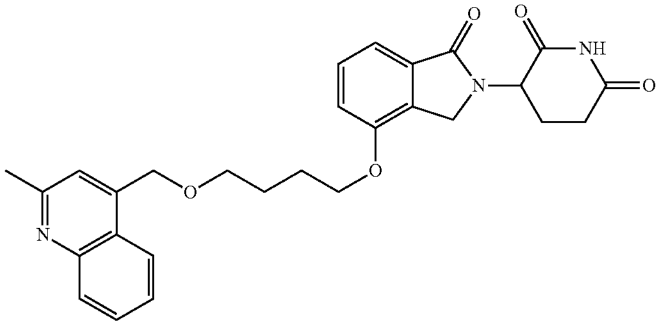 [SMILES: Cc1cc(COCCCCOc2cccc3c2CN(C2CCC(=O)NC2=O)C3=O)c2ccccc2n1] |
| 214 | 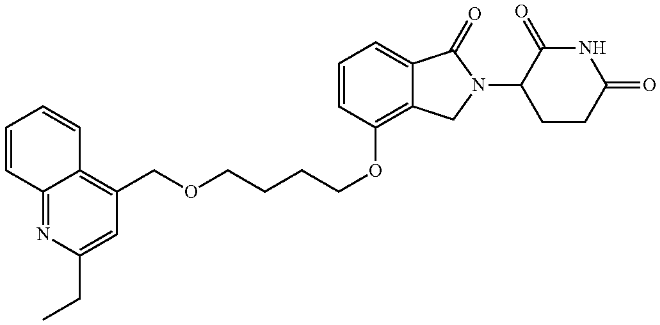 [SMILES: CCc1cc(COCCCCOc2cccc3c2CN(C2CCC(=O)NC2=O)C3=O)c2ccccc2n1] |
| 215 | 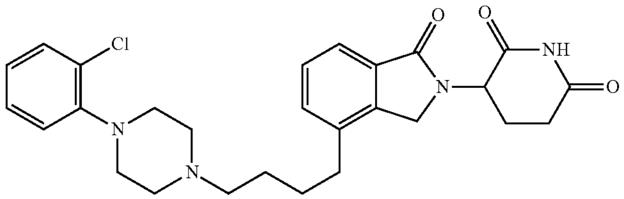 [SMILES: O=C1CCC(N2Cc3c(CCCCN4CCN(c5ccccc5Cl)CC4)cccc3C2=O)C(=O)N1] |

-continued
| Serial number | Compound |
| --- | --- |
| 216 | 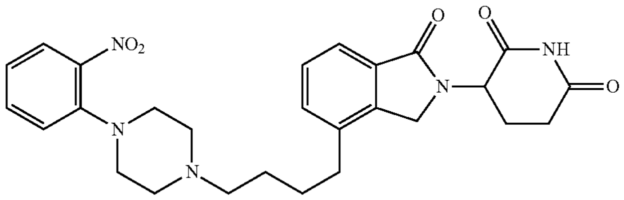 [SMILES: O=C1CCC(N2Cc3c(CCCCN4CCN(c5ccccc5[N+](=O)[O-])CC4)cccc3C2=O)C(=O)N1] |
| 217 | 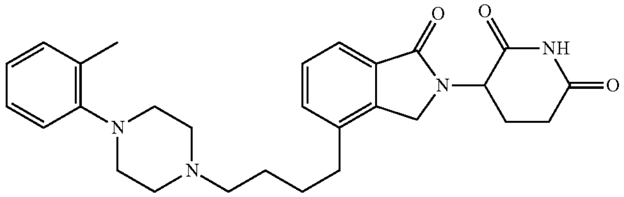 |
| 218 | 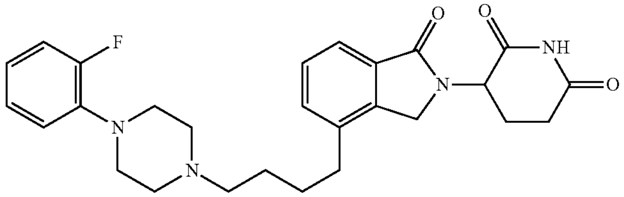 |
| 219 | 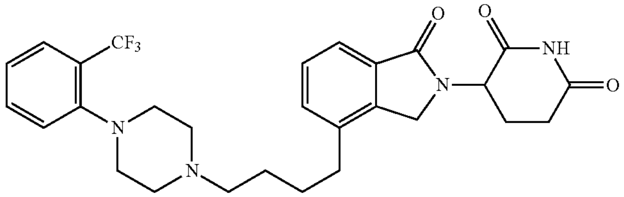 |
| 220 | 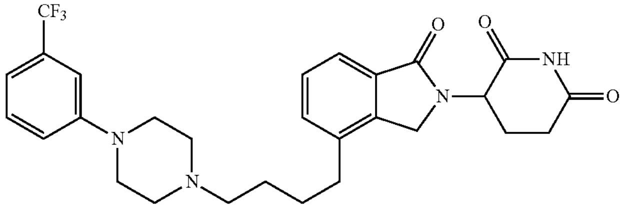 |
| 221 | 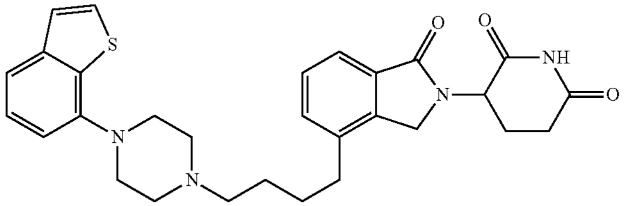 [SMILES: O=C1CCC(N2Cc3c(CCCCN4CCN(c5cccc6ccsc56)CC4)cccc3C2=O)C(=O)N1] |
| 222 | 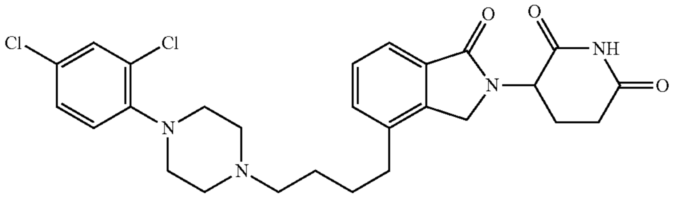 [SMILES: O=C1CCC(N2Cc3c(CCCCN4CCN(c5ccc(Cl)cc5Cl)CC4)cccc3C2=O)C(=O)N1] |

-continued
| Serial number | Compound |
|---|---|
| 223 | 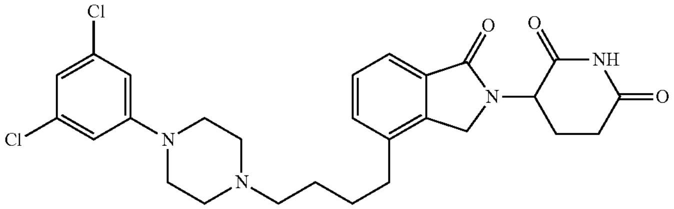 [SMILES: O=C1CCC(N2Cc3c(CCCCN4CCN(c5cc(Cl)cc(Cl)c5)CC4)cccc3C2=O)C(=O)N1] |
| 224 | 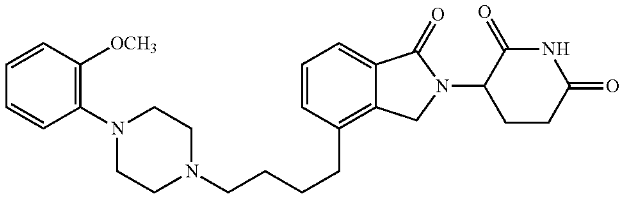 [SMILES: COc1ccccc1N1CCN(CCCCc2cccc3c2CN(C2CCC(=O)NC2=O)C3=O)CC1] |
| 225 | 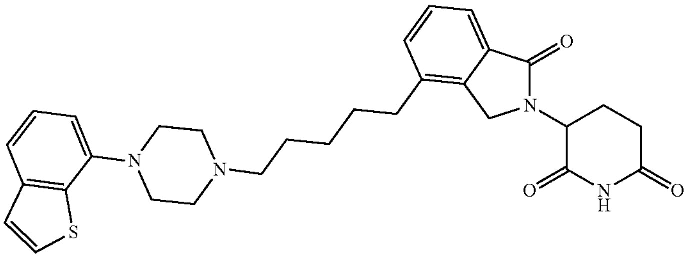 [SMILES: O=C1CCC(N2Cc3c(CCCCCN4CCN(c5cccc6ccsc56)CC4)cccc3C2=O)C(=O)N1] |
| 226 | 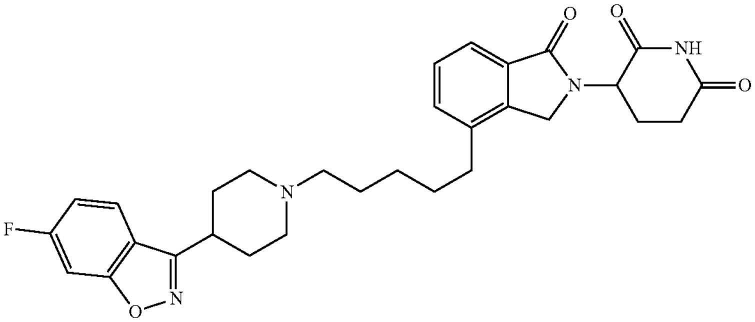 [SMILES: O=C1CCC(N2Cc3c(CCCCCN4CCC(c5noc6cc(F)ccc56)CC4)cccc3C2=O)C(=O)N1] |
| 227 | 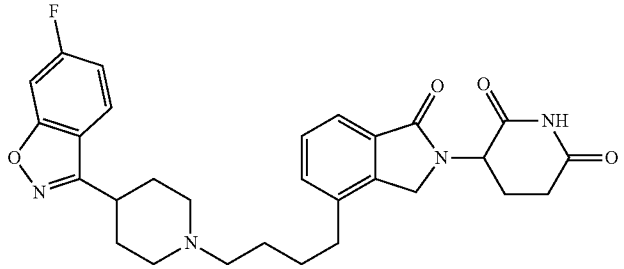 [SMILES: O=C1CCC(N2Cc3c(CCCCN4CCC(c5noc6cc(F)ccc56)CC4)cccc3C2=O)C(=O)N1] |
| 228 | 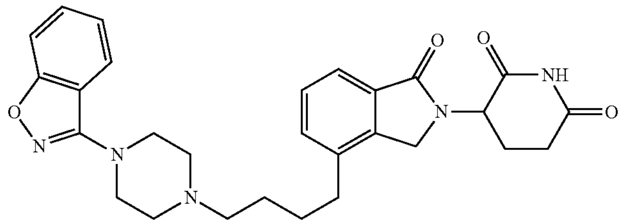 [SMILES: O=C1CCC(N2Cc3c(CCCCN4CCN(c5noc6ccccc56)CC4)cccc3C2=O)C(=O)N1] |

-continued
| Serial number | Compound |
|---|---|
| 229 | 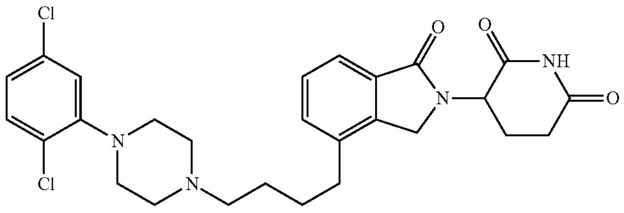 [SMILES: O=C1CCC(N2Cc3c(CCCCN4CCN(c5cc(Cl)ccc5Cl)CC4)cccc3C2=O)C(=O)N1] |
| 230 | 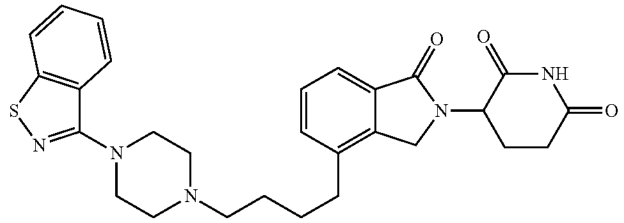 [SMILES: O=C1CCC(N2Cc3c(CCCCN4CCN(c5nsc6ccccc56)CC4)cccc3C2=O)C(=O)N1] |
| 231 | 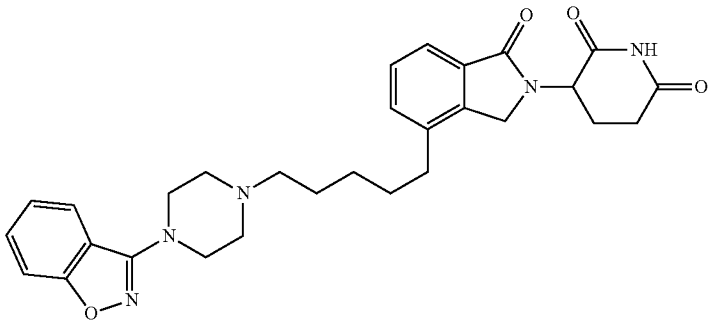 |
| 232 | 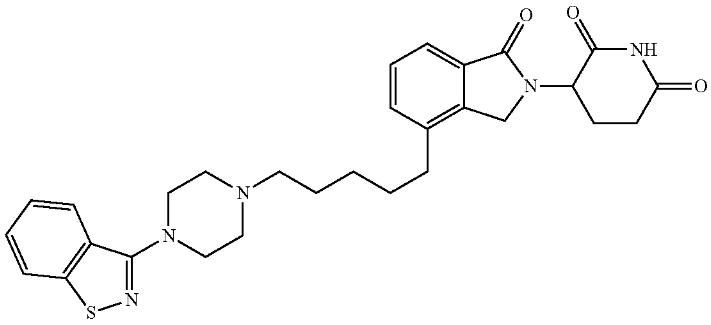 [SMILES: O=C1CCC(N2Cc3c(CCCCCN4CCN(c5nsc6ccccc56)CC4)cccc3C2=O)C(=O)N1] |
| 233 | 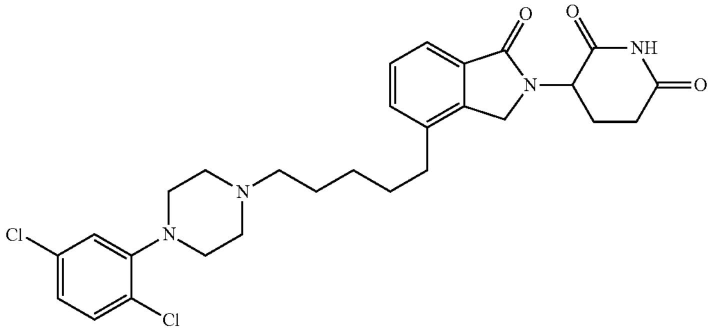 [SMILES: O=C1CCC(N2Cc3c(CCCCCN4CCN(c5cc(Cl)ccc5Cl)CC4)cccc3C2=O)C(=O)N1] |

-continued
| Serial number | Compound |
| --- | --- |
| 234 | 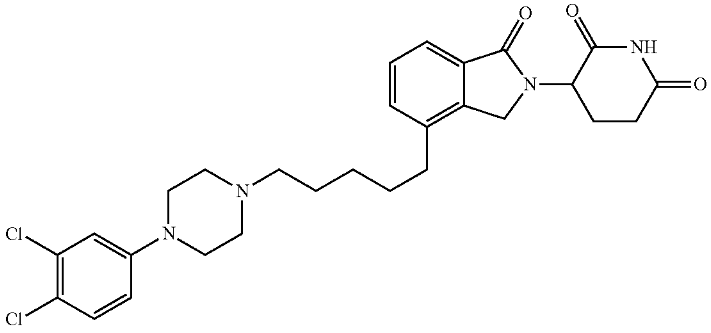 [SMILES: O=C1CCC(N2Cc3c(CCCCCN4CCN(c5ccc(Cl)c(Cl)c5)CC4)cccc3C2=O)C(=O)N1] |
| 235 | 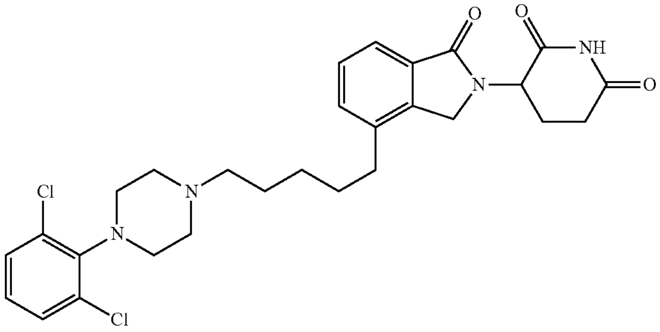 [SMILES: O=C1CCC(N2Cc3c(CCCCCN4CCN(c5c(Cl)cccc5Cl)CC4)cccc3C2=O)C(=O)N1] |
| 236 | 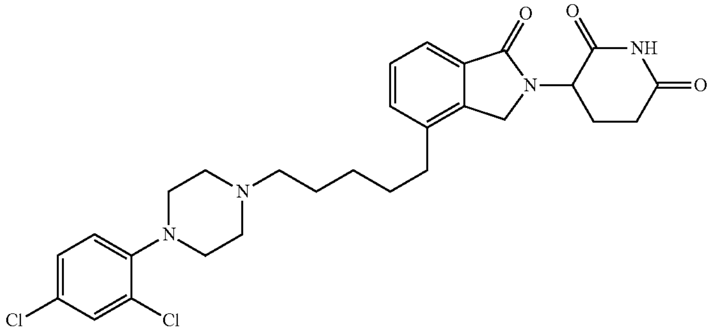 [SMILES: O=C1CCC(N2Cc3c(CCCCCN4CCN(c5ccc(Cl)cc5Cl)CC4)cccc3C2=O)C(=O)N1] |
| 237 | 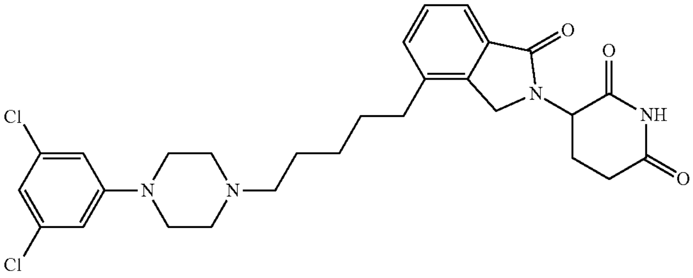 [SMILES: O=C1CCC(N2Cc3c(CCCCCN4CCN(c5cc(Cl)cc(Cl)c5)CC4)cccc3C2=O)C(=O)N1] |
| 238 | 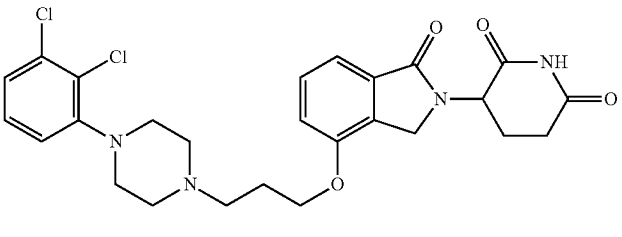 [SMILES: O=C1CCC(N2Cc3c(OCCCN4CCN(c5cccc(Cl)c5Cl)CC4)cccc3C2=O)C(=O)N1] |

-continued
| Serial number | Compound |
|---|---|
| 239 | 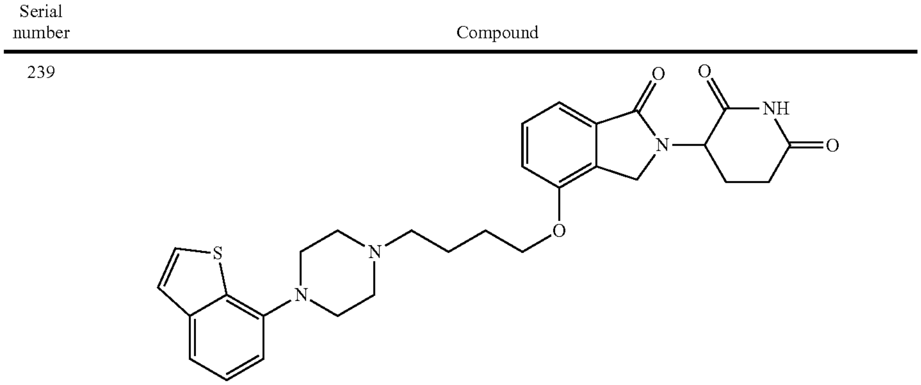 |
| 240 | 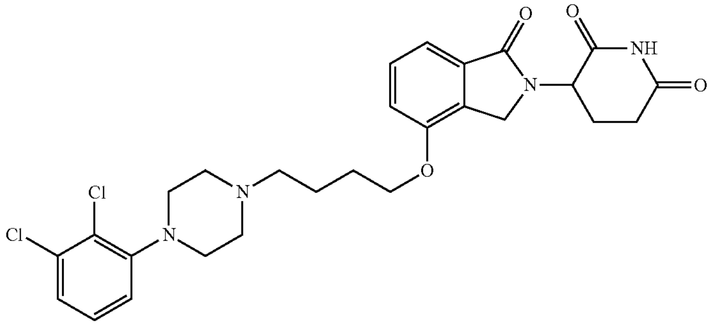 [SMILES: O=C1CCC(N2Cc3c(OCCCCN4CCN(c5cccc(Cl)c5Cl)CC4)cccc3C2=O)C(=O)N1] |
| 241 | 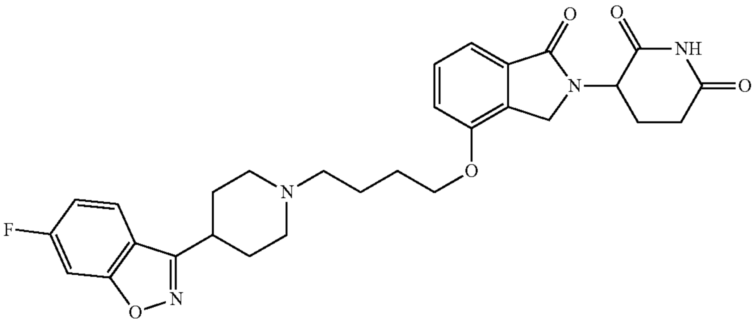 |
| 242 | 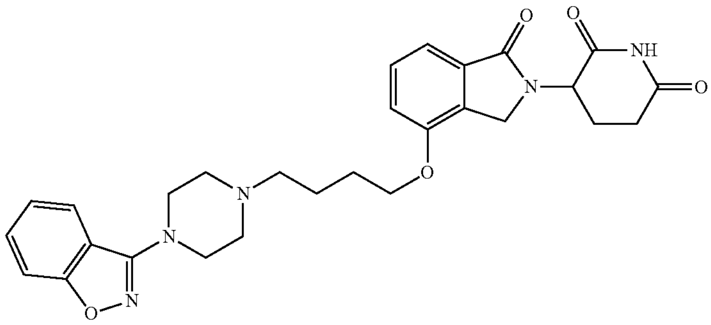 |

-continued
| Serial number | Compound |
|---|---|
| 243 | 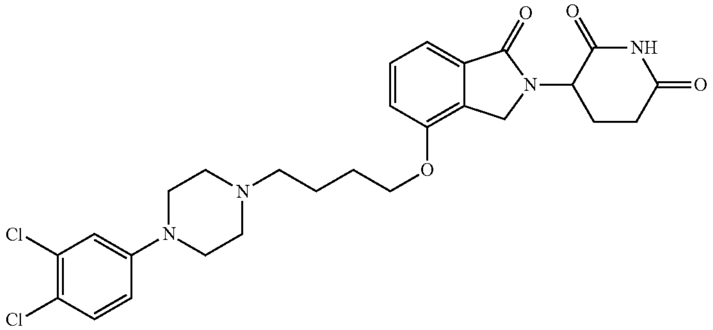 |
| 244 | 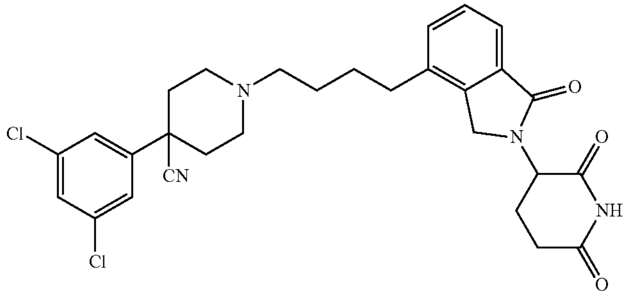 [SMILES: N#CC1(c2cc(Cl)cc(Cl)c2)CCN(CCCCc2cccc3c2CN(C2CCC(=O)NC2=O)C3=O)CC1] |
| 245 | 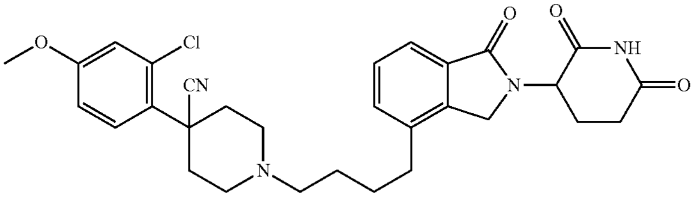 [SMILES: COc1ccc(C2(C#N)CCN(CCCCc3cccc4c3CN(C3CCC(=O)NC3=O)C4=O)CC2)c(Cl)c1] |
| 246 | 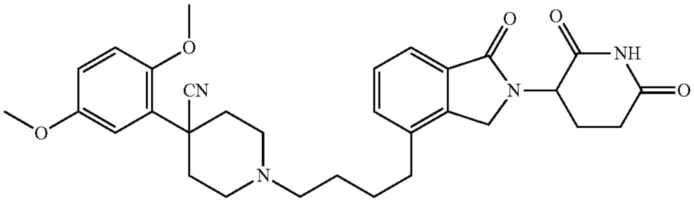 [SMILES: COc1ccc(OC)c(C2(C#N)CCN(CCCCc3cccc4c3CN(C3CCC(=O)NC3=O)C4=O)CC2)c1] |
| 247 | 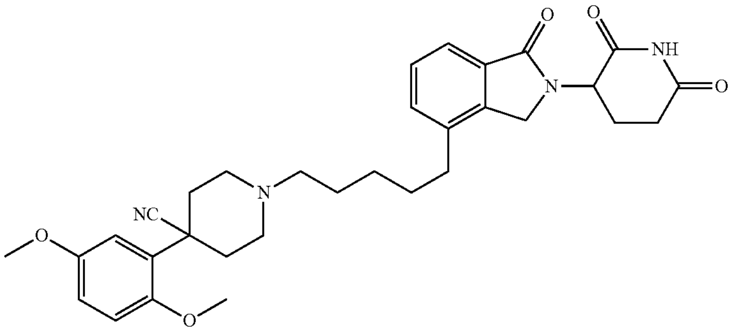 [SMILES: COc1ccc(OC)c(C2(C#N)CCN(CCCCCc3cccc4c3CN(C3CCC(=O)NC3=O)C4=O)CC2)c1] |

-continued
| Serial number | Compound |
|---|---|
| 248 | 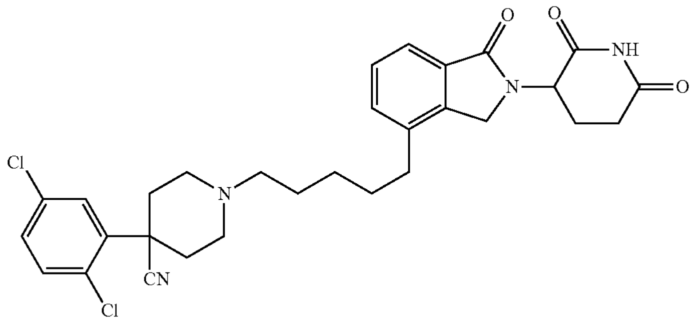 [SMILES: N#CC1(c2cc(Cl)ccc2Cl)CCN(CCCCCc2cccc3c2CN(C2CCC(=O)NC2=O)C3=O)CC1] |
| 249 | 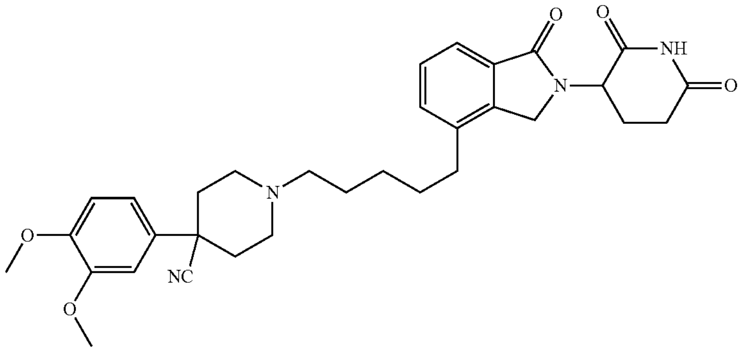 [SMILES: COc1ccc(C2(C#N)CCN(CCCCCc3cccc4c3CN(C3CCC(=O)NC3=O)C4=O)CC2)cc1OC] |
| 250 | 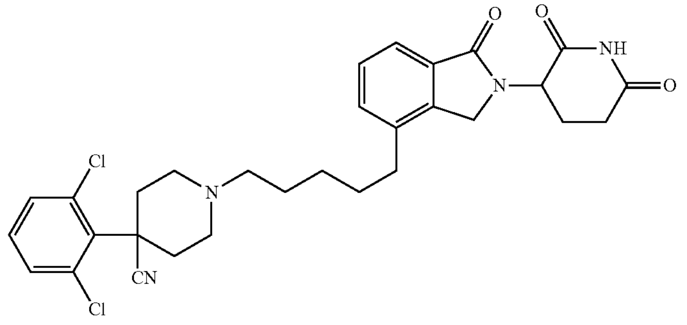 [SMILES: N#CC1(c2c(Cl)cccc2Cl)CCN(CCCCCc2cccc3c2CN(C2CCC(=O)NC2=O)C3=O)CC1] |
| 251 | 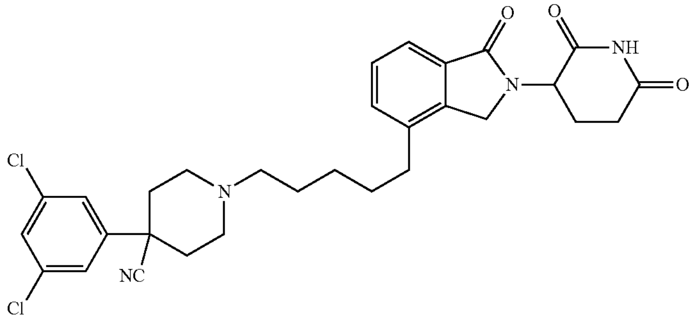 [SMILES: N#CC1(c2cc(Cl)cc(Cl)c2)CCN(CCCCCc2cccc3c2CN(C2CCC(=O)NC2=O)C3=O)CC1] |

-continued
| Serial number | Compound |
|---|---|
| 252 | 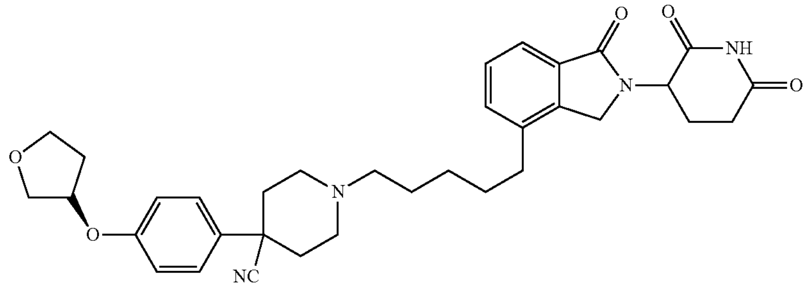 |
| 253 | 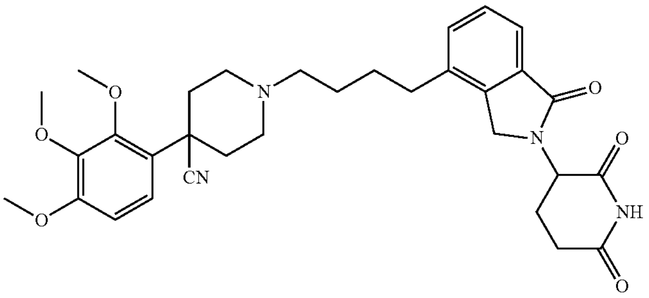 [SMILES: COc1ccc(C2(C#N)CCN(CCCCc3cccc4c3CN(C3CCC(=O)NC3=O)C4=O)CC2)c(OC)c1OC] |
| 254 | 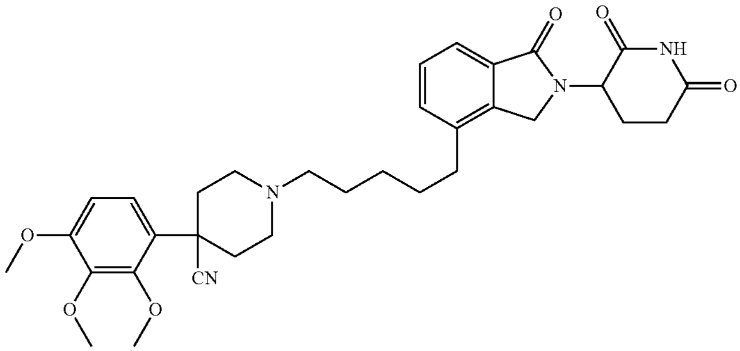 [SMILES: COc1ccc(C2(C#N)CCN(CCCCCc3cccc4c3CN(C3CCC(=O)NC3=O)C4=O)CC2)c(OC)c1OC] |
| 255 | 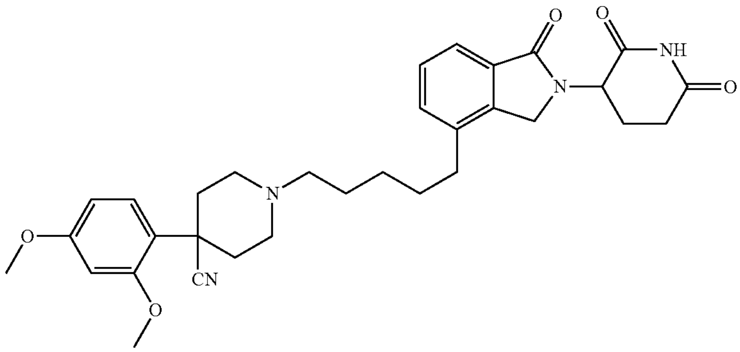 [SMILES: COc1ccc(C2(C#N)CCN(CCCCCc3cccc4c3CN(C3CCC(=O)NC3=O)C4=O)CC2)c(OC)c1] |
| 256 | 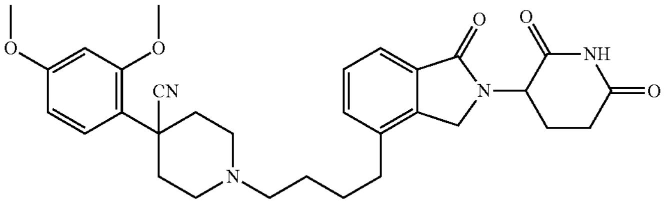 [SMILES: COc1ccc(C2(C#N)CCN(CCCCc3cccc4c3CN(C3CCC(=O)NC3=O)C4=O)CC2)c(OC)c1] |

-continued
| Serial number | Compound |
|---|---|
| 257 | 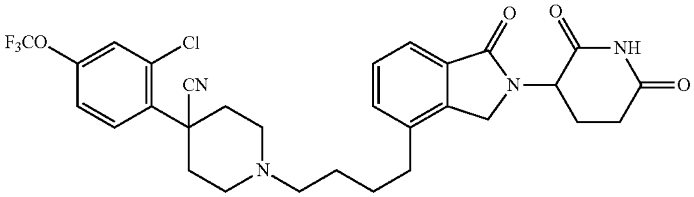 [SMILES: N#CC1(c2ccc(OC(F)(F)F)cc2Cl)CCN(CCCCc2cccc3c2CN(C2CCC(=O)NC2=O)C3=O)CC1] |
| 258 | 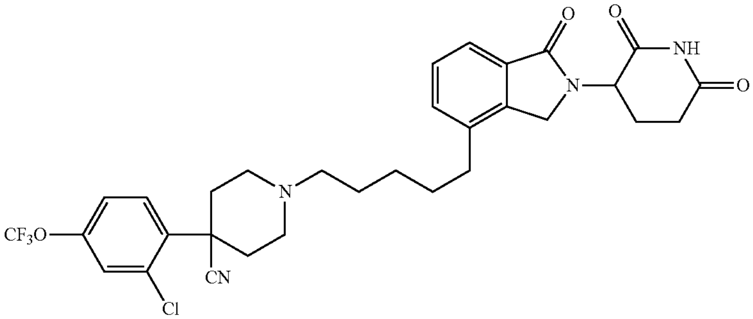 |
| 259 | 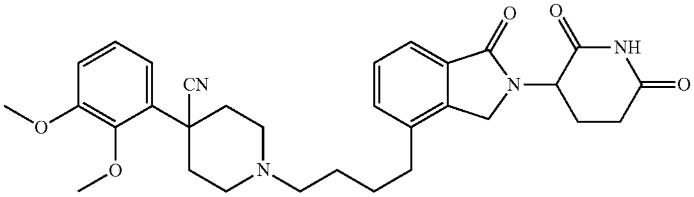 [SMILES: COc1cccc(C2(C#N)CCN(CCCCc3cccc4c3CN(C3CCC(=O)NC3=O)C4=O)CC2)c1OC] |
| 260 | 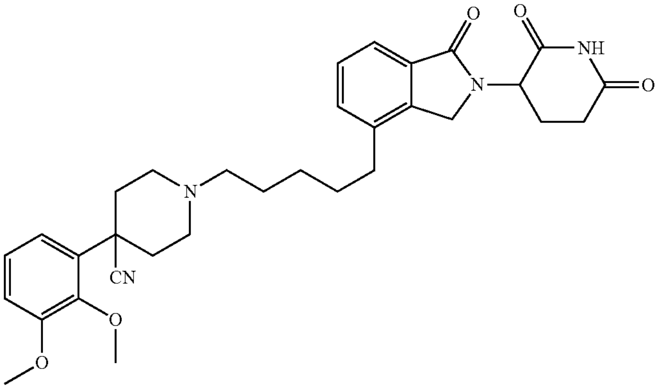 [SMILES: COc1cccc(C2(C#N)CCN(CCCCCc3cccc4c3CN(C3CCC(=O)NC3=O)C4=O)CC2)c1OC] |
| 261 | 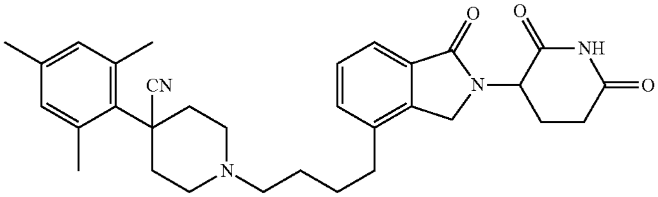 [SMILES: Cc1cc(C)c(C2(C#N)CCN(CCCCc3cccc4c3CN(C3CCC(=O)NC3=O)C4=O)CC2)c(C)c1] |

-continued
| Serial number | Compound |
|---|---|
| 262 | 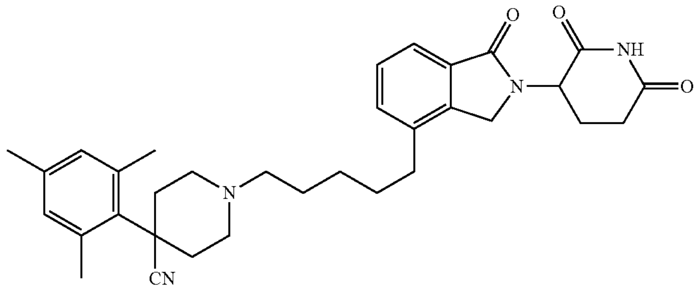 [SMILES: Cc1cc(C)c(C2(C#N)CCN(CCCCCc3cccc4c3CN(C3CCC(=O)NC3=O)C4=O)CC2)c(C)c1] |
| 263 | 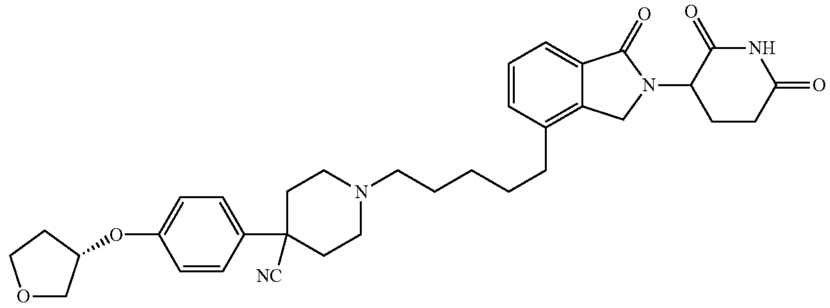 [SMILES: N#CC1(c2ccc(O[C@H]3CCOC3)cc2)CCN(CCCCCc2cccc3c2CN(C2CCC(=O)NC2=O)C3=O)CC1] |
| 264 | 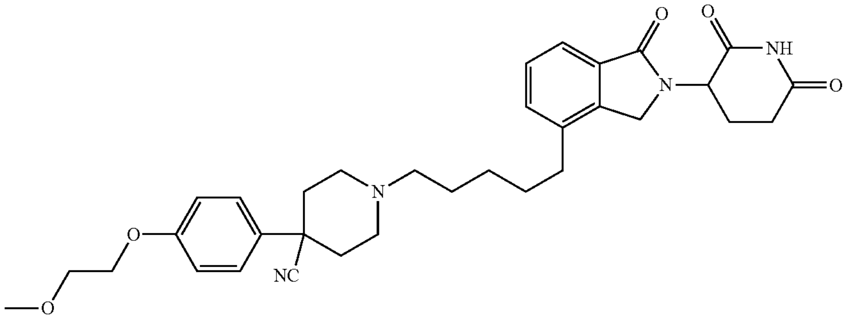 [SMILES: COCCOc1ccc(C2(C#N)CCN(CCCCCc3cccc4c3CN(C3CCC(=O)NC3=O)C4=O)CC2)cc1] |
| 265 | 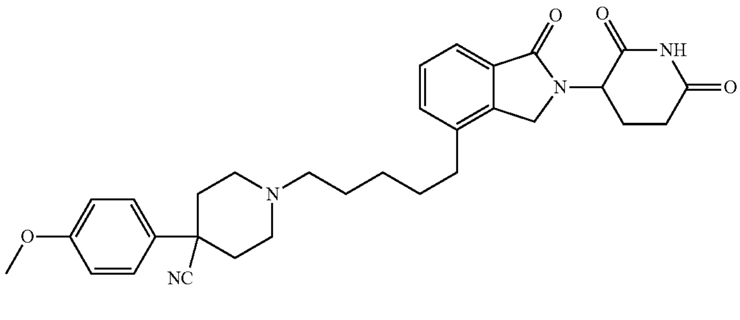 [SMILES: COc1ccc(C2(C#N)CCN(CCCCCc3cccc4c3CN(C3CCC(=O)NC3=O)C4=O)CC2)cc1] |
| 266 | 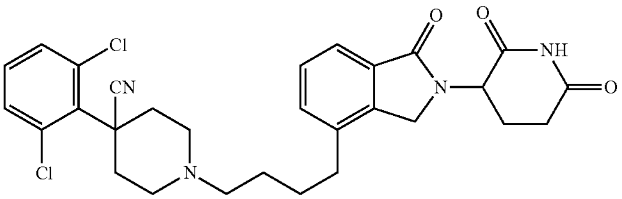 |

-continued
| Serial number | Compound |
|---|---|
| 267 | 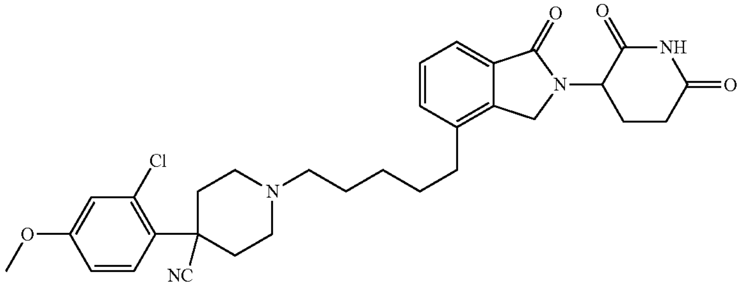 [SMILES: COc1ccc(C2(C#N)CCN(CCCCCc3cccc4c3CN(C3CCC(=O)NC3=O)C4=O)CC2)c(Cl)c1] |
| 268 | 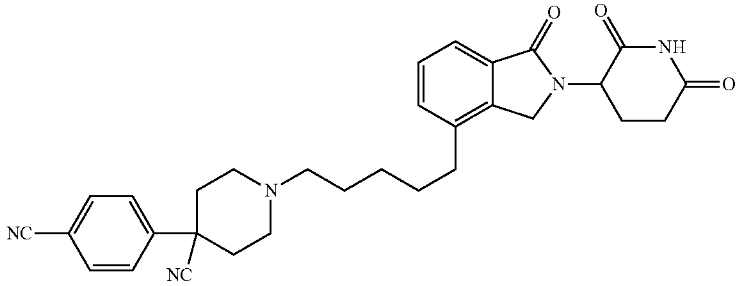 [SMILES: N#Cc1ccc(C2(C#N)CCN(CCCCCc3cccc4c3CN(C3CCC(=O)NC3=O)C4=O)CC2)cc1] |
| 269 | 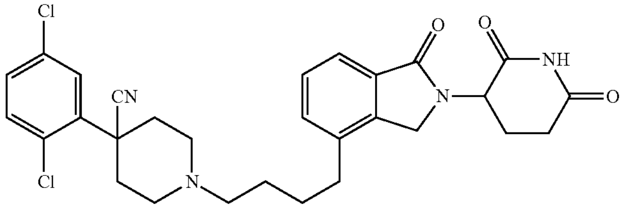 [SMILES: N#CC1(c2cc(Cl)ccc2Cl)CCN(CCCCc2cccc3c2CN(C2CCC(=O)NC2=O)C3=O)CC1] |
| 270 | 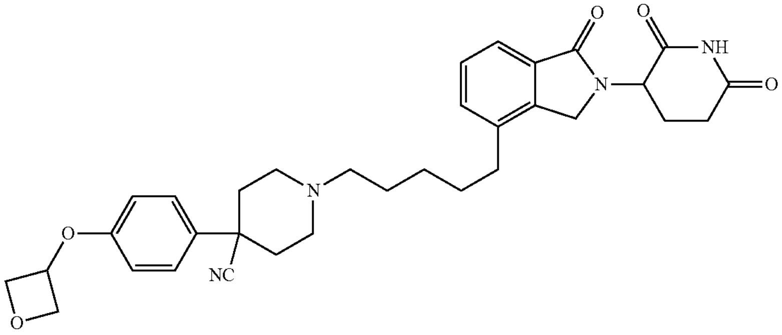 [SMILES: N#CC1(c2ccc(OC3COC3)cc2)CCN(CCCCCc2cccc3c2CN(C2CCC(=O)NC2=O)C3=O)CC1] |
| 271 | 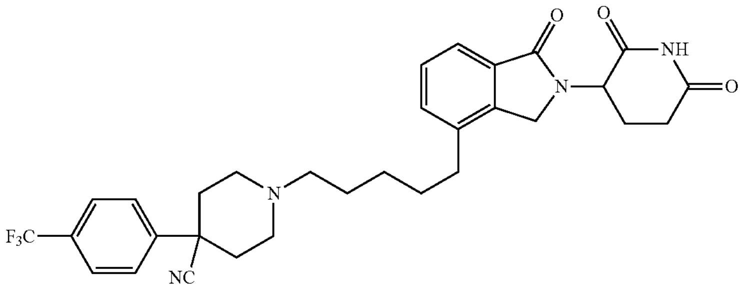 [SMILES: N#CC1(c2ccc(C(F)(F)F)cc2)CCN(CCCCCc2cccc3c2CN(C2CCC(=O)NC2=O)C3=O)CC1] |

-continued
| Serial number | Compound |
|---|---|
| 272 | 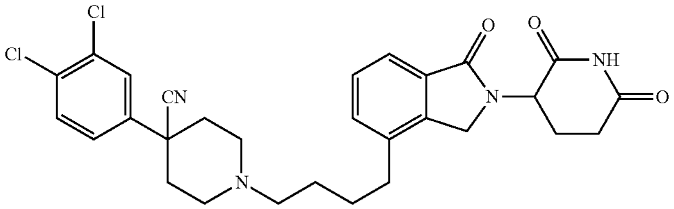 [SMILES: N#CC1(c2ccc(Cl)c(Cl)c2)CCN(CCCCc2cccc3c2CN(C2CCC(=O)NC2=O)C3=O)CC1] |
| 273 | 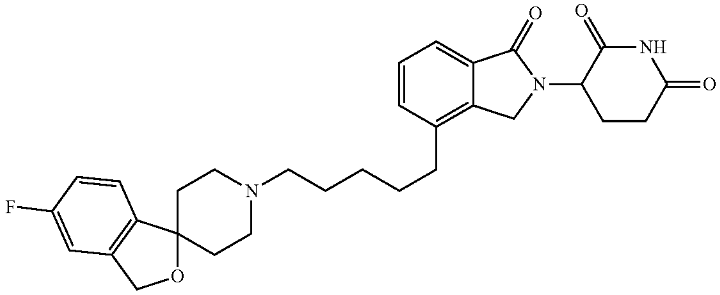 [SMILES: O=C1CCC(N2Cc3c(CCCCCN4CCC5(CC4)OCc4cc(F)ccc45)cccc3C2=O)C(=O)N1] |
| 274 | 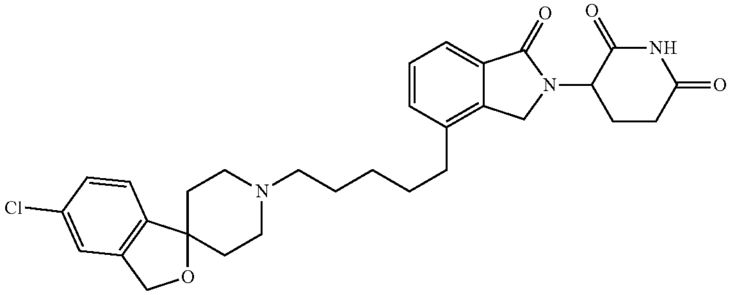 [SMILES: O=C1CCC(N2Cc3c(CCCCCN4CCC5(CC4)OCc4cc(Cl)ccc45)cccc3C2=O)C(=O)N1] |
| 275 | 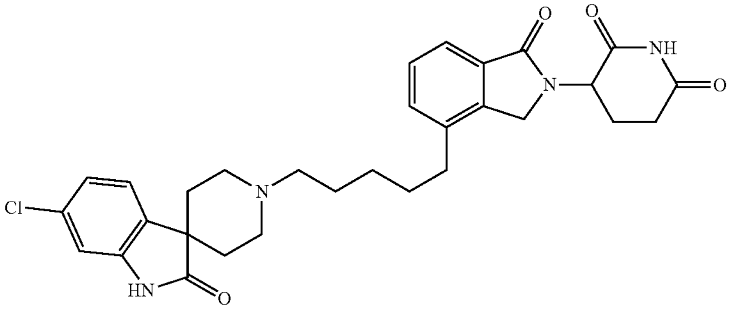 [SMILES: O=C1CCC(N2Cc3c(CCCCCN4CCC5(CC4)C(=O)Nc4cc(Cl)ccc45)cccc3C2=O)C(=O)N1] |
| 276 | 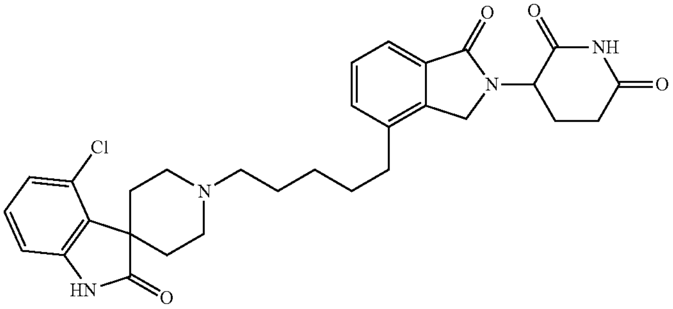 [SMILES: O=C1CCC(N2Cc3c(CCCCCN4CCC5(CC4)C(=O)Nc4cccc(Cl)c45)cccc3C2=O)C(=O)N1] |

-continued

| Serial number | Compound |
|---|---|
| 277 | 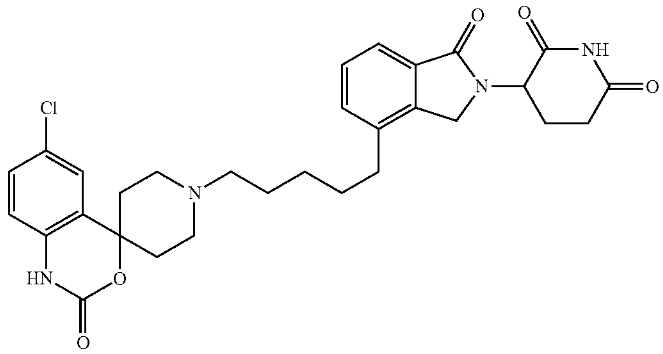 [SMILES: O=C1CCC(N2Cc3c(CCCCCN4CCC5(CC4)OC(=O)Nc4ccc(Cl)cc45)cccc3C2=O)C(=O)N1] |
| 278 | 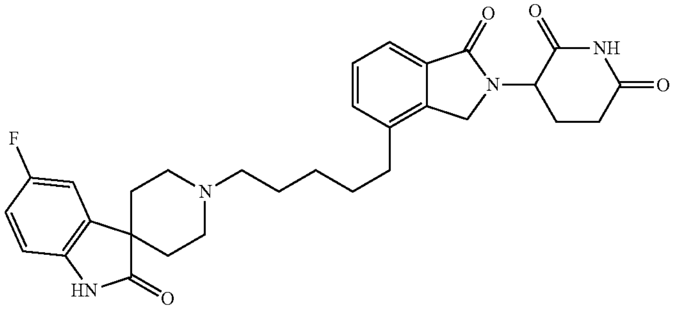 [SMILES: O=C1CCC(N2Cc3c(CCCCCN4CCC5(CC4)C(=O)Nc4ccc(F)cc45)cccc3C2=O)C(=O)N1] |
| 279 | 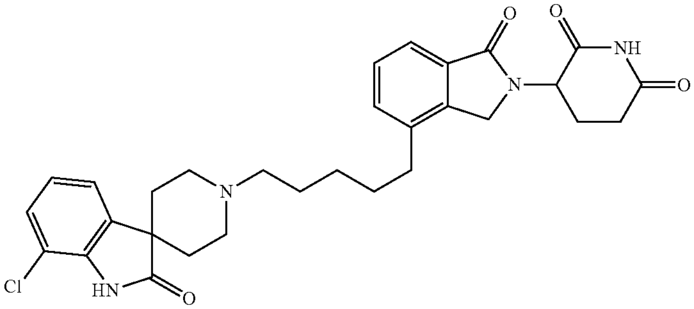 [SMILES: O=C1CCC(N2Cc3c(CCCCCN4CCC5(CC4)C(=O)Nc4c(Cl)cccc45)cccc3C2=O)C(=O)N1] |
| 280 | 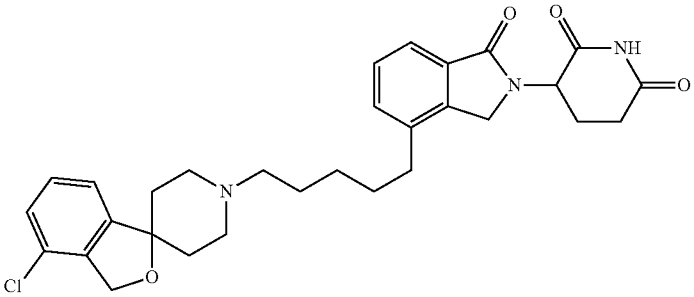 [SMILES: O=C1CCC(N2Cc3c(CCCCCN4CCC5(CC4)OCc4c(Cl)cccc45)cccc3C2=O)C(=O)N1] |

the tautomer, enantiomer, diastereomer, racemate, metabolite, metabolic precursor, isotopic compound, pharmaceutically acceptable salt, ester, prodrug or hydrate thereof.

The compound of formula (I) may contain one or more asymmetric or chiral centers, and therefore may exist a different stereoisomers. The compound of the present invention includes all stereoisomeric forms, including but not limited to diastereomer, enantiomer, atropisomer and the mixture thereof (such as racemates), which all are included in the scope of the present invention.

The term "substitution" refers to the substitution of one or more hydrogen atoms on a specific group by specific substituent. The specific substituents are those described in the preceding paragraph or those present in each example. Unless otherwise specified, any substituent may have a substituent selected from a specific group at any substitutable position of the group, and the substituent may be the same or different in each position. Cyclic substituents, such as heterocycloalkyl, can be attached to another ring, such as cycloalkyl, to form a spirobicyclic ring system, for example, two rings share one carbon atom.

Those skilled in the art should understand that the combinations of substituents contemplated by the present invention are those that are stable or chemically achievable. Substitution on the relevant structure in the present invention includes substituted and unsubstituted, for example, "optionally" substituted by a certain substituent, which includes the meaning of being substituted or unsubstituted by a certain substituent.

In the present invention, when the number of substituent is more than 1, the R substituents can be the same or different substituents, which means that when the number of substituent in a certain structure is more than one, the combination of R substituents can be selected from multiple different types of substituents.

The term "substitution" can only apply to the site that can be substituted by substituent, and does not include substitution that cannot be achieved on the basis of existing chemical knowledge.

The compound of formula (I) may also exist in different tautomeric forms, all of which are included in the scope of the invention.

The term "tautomer" refers to the constitutional isomers with different energies that are mutually converted via a low energy barrier. The reaction generally results in the shift of hydrogen atoms or protons accompanying the conversion of single bonds and adjacent double bonds.

The term "enantiomer" refers to stereoisomers that are mirror images of each other and are not superimposable.

"Diastereomers" refer to stereoisomers that have two or more chiral centers and are not mirror images.

"Racemate" refers to two stereoisomers that are mirror images of each other, the opposite optical activity of which neutralizes their optical activity.

"Pharmaceutically acceptable salt" refers to the drug molecule forms a corresponding salt with the corresponding organic acid, inorganic acid or organic base or inorganic base, such as hydrochloric acid, formic acid, trifluoroacetic acid, succinic acid, methylsulfonic acid and the like.

"Prodrug" refers to a class of compounds that are inactive or less active in vitro, and release active drugs through enzymatic or non-enzymatic transformation in vivo to exert their medicinal effects.

"Hydrate" refers to a compound containing water.

The term "halogen" includes fluorine, chlorine, bromine or iodine.

The term "hydrocarbyl" refers to a substituent containing only carbon atoms and hydrogen atoms, and includes but not limited to methyl, ethyl, isopropyl, propyl, cyclohexyl, phenyl, etc.

The term "C1-C6 alkyl" refers to a straight or branched chain alkyl having from 1 to 6 carbon atoms, including but not limited to methyl, ethyl, propyl, isopropyl, butyl, isobutyl, sec-butyl, tert-butyl, pentyl and hexyl etc.

The term "C1-C6 alkoxyl" refers to a straight or branched chain alkoxyl having from 1 to 6 carbon atoms, including but not limited to methoxyl, ethoxyl, propoxyl, isopropoxyl and butoxyl, etc.

The term "C1-C6 alkoxycarbonyl" includes but not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl and hexoxycarbonyl, etc.

The term "cycloalkyl" refers to a saturated or partially unsaturated monocyclic or polycyclic cyclic hydrocarbon substituent. Monocyclic cycloalkyl includes but not limited to cyclopropyl, cyclobutyl, cyclopentenyl, and cyclohexyl. Polycyclic cycloalkyl includes spiro, fused, and bridged cycloalkyl.

The term "heterocyclyl" refers to a cyclic substituent containing one or more saturated and/or partially saturated monocyclic or polycyclic, wherein one or more ring atoms are selected from nitrogen, oxygen, sulfur or $S(O)_m$ (wherein, m is an integer from 0 to 2), and the remaining ring atoms are carbon; such as epoxypropane, tetrahydrofuranyl, pyrrolidinyl, tetrahydropyranyl, piperidinyl, piperazinyl, morpholinyl, thiomorpholinyl; heterocyclyl can be fused with aryl, heteroaryl, or cycloalkyl ring, and the ring attached to the core structure is heterocyclyl.

The term "aryl" refers to 6-14 membered all-carbon monocyclic or fused polycyclic group with conjugated p electron system, preferably 6 to 10 membered ring, more preferably phenyl and naphthyl, most preferably phenyl. The aryl ring may fuse to heteroaryl, heterocyclyl or cycloalkyl ring, and the ring attached to the core structure is aryl ring.

The term "heteroaryl" refers to 5-14 membered aryl having 1 to 4 heteroatoms as ring atoms, and the remaining ring atoms are carbon, wherein the heteroatoms include oxygen, sulfur and nitrogen, preferably 5-10 membered ring. The heteroaryl is preferably 5 or 6 membered ring, such as thienyl, pyridyl, pyrrolyl and the like. The heteroaryl ring may be fused to aryl, heterocyclyl or cycloalkyl ring, wherein the ring attached to the core structure is heteroaryl ring.

The term "spiroheterocyclic group" refers to polycyclicheterocyclyl that shares one atom between single rings (referred to spiro atom), in which one or more ring atoms are heteroatom selected from nitrogen and oxygen, sulfur or S(O)m (wherein m is an integer from 0 to 2), and the remaining ring atoms are carbon. Spiroheterocyclic ring can be fused with 6-10 membered aryl or 5-10 membered heteroaryl ring, wherein the ring attached to the core structure is spiroheterocyclic ring.

The term "haloalkyl" refers to a linear, branched or cyclic alkyl substituted by single or multiple halogens, and includes but not limited to 2-bromoethyl, 2-bromopropyl, etc.

The term "alkenyl" refers to alkenyl of 2-10 carbons, such as vinyl, propenyl, butenyl, styryl, phenpropenyl.

The term "alkynyl" refers to alkynyl of 2-10 carbons, such as ethynyl, propynyl, butynyl, phenylethynyl, phenylpropynyl.

The term "C3-C8 cycloalkyl" refers to a cyclic alkyl having 3 to 8 carbon atoms in the ring, and includes but not limited to cyclopropyl, cyclobutyl, cyclopentyl, and cyclohexyl, etc.

The term "5-10 membered heterocyclyl" means containing one or more saturated and/or partially saturated rings, which includes 5 to 10 ring atoms, of which one or more ring atoms are heteroatoms selected from nitrogen, oxygen, sulfur or S(O)m (wherein m is an integer from 0 to 2), and the remaining ring atoms are carbon; such as epoxypropane, tetrahydrofuranyl, pyrrolidinyl, tetrahydropyranyl, piperidinyl, piperazinyl, morpholinyl, thiomorpholinyl.

The term "C3-C6 heterocyclyl" refers to containing one or more saturated and/or partially saturated rings, which include 3 to 6 ring atoms, of which one or more ring atoms are heteroatoms selected from nitrogen, oxygen, sulfur or S(O)m (where m is an integer from 0 to 2), and the remaining ring atoms are carbon; such as epoxypropyl, tetrahydrofuranyl, pyrrolidinyl, tetrahydropyranyl, piperidinyl, piperazinyl The term "hydroxyl-substituted alkyl" refers to a linear, branched or cyclic alkyl substituted by single or multiple hydroxyls, including but not limited to (S)-1-hydroxy-isobutyl-2-yl and (R)-1-hydroxyisobutyl-2-yl, etc.

In the present invention, unless otherwise specified, the terms used have the general meanings known to those skilled in the art.

The present invention also includes any of the new intermediates disclosed herein.

An aspect of the present invention provides a method for preparing the compound of formula (I), and the method is selected from one of the following methods:

The synthetic references of starting compounds 1A, 2A, 3D, 4A, 5A, 6A and 7A see WO2008115516A2, WO2011100380 A1, WO2016065980A1, WO2007027527A2 and WO2008027542A2.

Synthesis Method 1

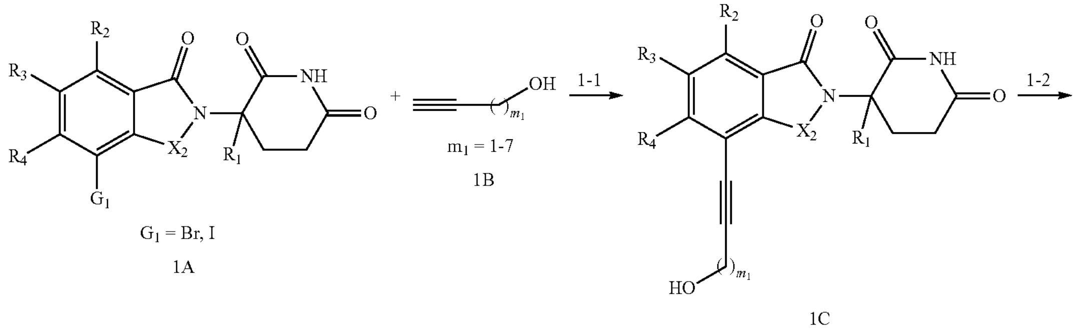

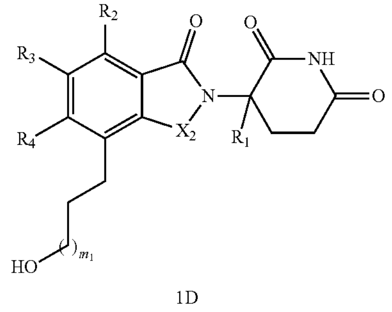

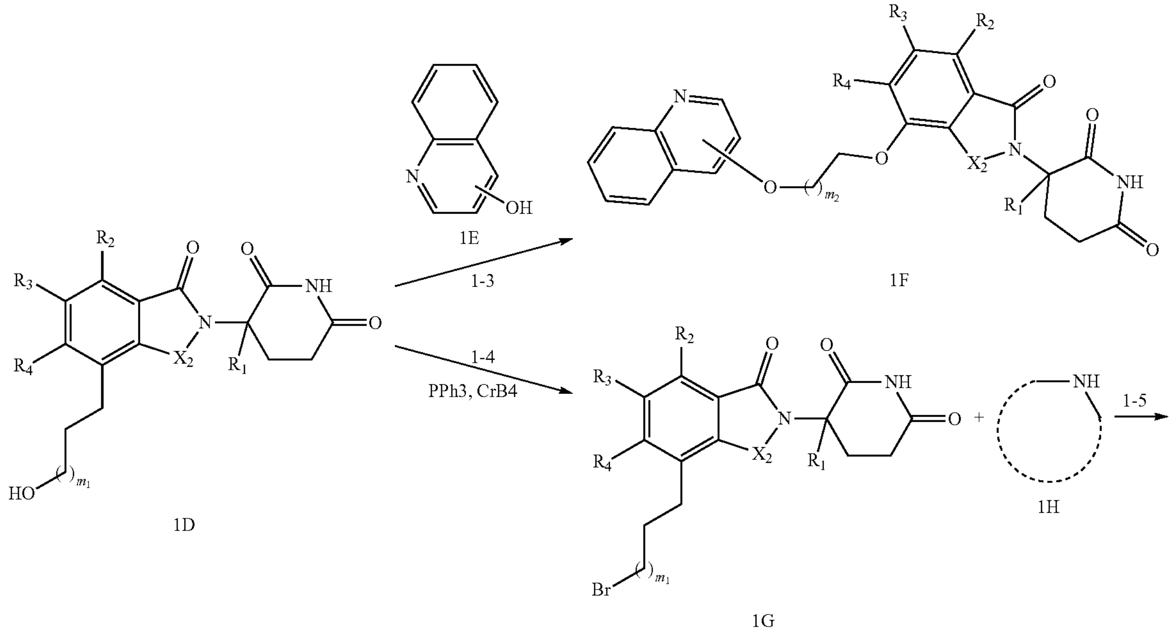

-continued

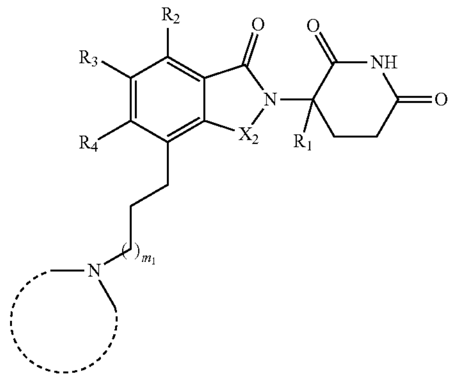

1I wherein, the definitions of $R_1$, $R_2$, $R_3$, $R_4$ and $X_2$ are the same as the aforementioned definitions;

$m_1$ is an integer from 1 to 7;

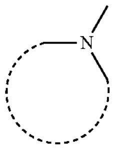

has the same definition as i) heterocyclyl, ii) fused heterocyclyl, and iii) spiroheterocyclic group in the definition of the above-mentioned A;

Step 1-1: compound 1C is obtained by Sonogashira coupling reaction of compounds 1A and 1B at room temperature or under heating in dipole organic solvents such as DMF or DMA, etc., with the presence of Pd catalyst (such as $Pd(PPh_3)_4$ or $Pd(PPh_3)_2Cl_2$, etc.), monovalent copper catalyst (Copper(I) iodide) and base (such as triethylamine or diisopropylethylamine, etc.);

Step 1-2: compound 1C is reduced to compound 1D by hydrogen under Pd/C catalytic condition, Raney nickel or other metal catalyst (such as Wilkinson's catalyst), Step 1-3: compound 1F is obtained by reacting compound 1D with hydroxyquinoline 1E (or substituted or unsubstituted hydroxyquinoline and its analogs, substituted or unsubstituted naphthol and its analogs, etc.) under the condition of triphenylphosphine and diisopropyl azodiformate;

Step 1-4: compound 1D is reacted to obtain compound 1G with the presence of triphenylphosphine and carbon tetrabromide;

Step 1-5: compound 1G and nitrogen-containing heterocyclic compound 1H (compound 1H is a variety of amine compounds containing A group as defined above) are reacted to obtain compound 1I in the presence of sodium iodide;

Synthesis Method 2

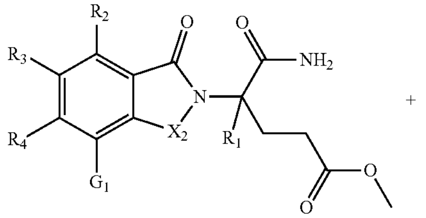

G1 = Br, I

2A

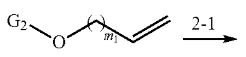

$m_1$ = 1-7

2B

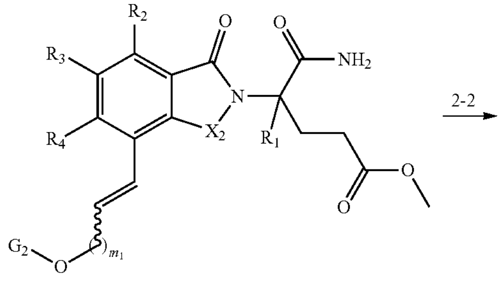

2C

-continued

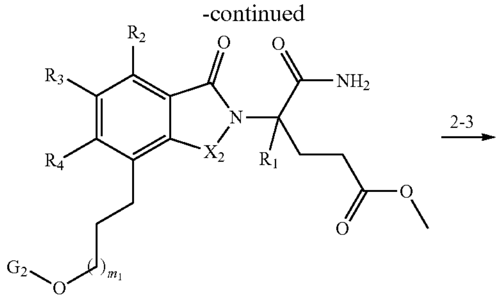

2D

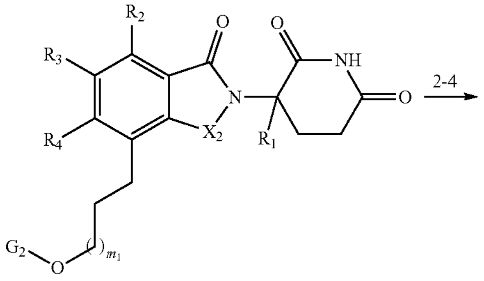

2E

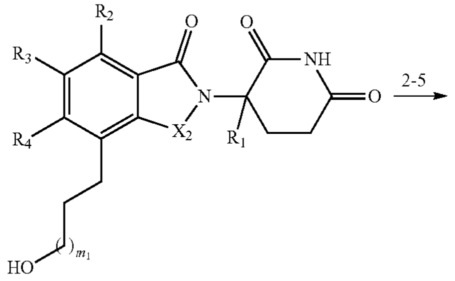

2F

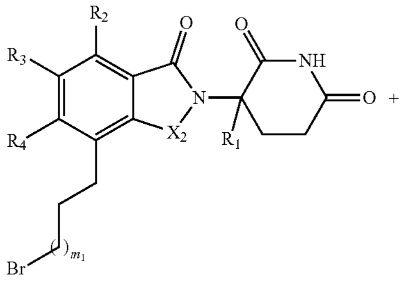

2G

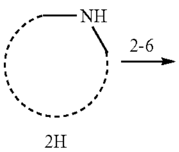

2H

-continued

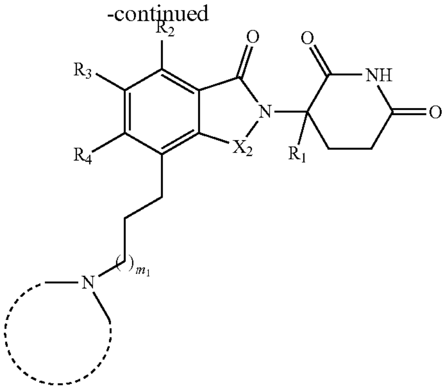

2I wherein, the definitions of $R_1$, $R_2$, $R_3$, $R_4$ and $X_2$ are the same as the aforementioned definitions;

$m_1$ is an integer from 1 to 7;

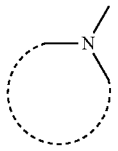

has the same definition as i) heterocyclyl, ii) fused heterocyclyl, and iii) spiroheterocyclic group in the definition of the above-mentioned A;

G2 is a protecting group selected from TBS, Trit, benzyl;

Step 2-1: multi-substituted olefin derivative 2C is obtained by reacting compounds 2A and 2B under heating condition in the presence of aprotic solvent (such as acetonitrile or DMF, etc.), Pd catalyst (Palladium (II) acetate or Pd (PPh3)4, etc.), phosphine ligand (such as triphenylphosphine, s-Phos, etc.), organic base (triethylamine or diisopropylethylamine, etc.) (Heck coupling reaction);

Step 2-2: compound 2C is reduced to compound 2D by hydrogen under catalytic condition of Pd/C, Raney nickel or other metal catalyst (such as Wilkinson's catalyst), Step 2-3: the piperidone derivative 2E is obtained by ring-closing in the presence of potassium tert-butoxide in dry tetrahydrofuran;

Step 2-4: compound 2F is obtained by removing the protective group of compound 2E under acidic condition or in the presence of TBAF;

Step 2-5: compound 2F is reacted to obtain compound 2G in the presence of triphenylphosphine and carbon tetrabromide;

Step 2-6: compound 2G and nitrogen-containing heterocyclic compound 2H (compound 2H is a variety of amine compounds containing A group as defined above) are reacted to obtain compound 2I in the presence of sodium iodide;

Synthesis Method 3

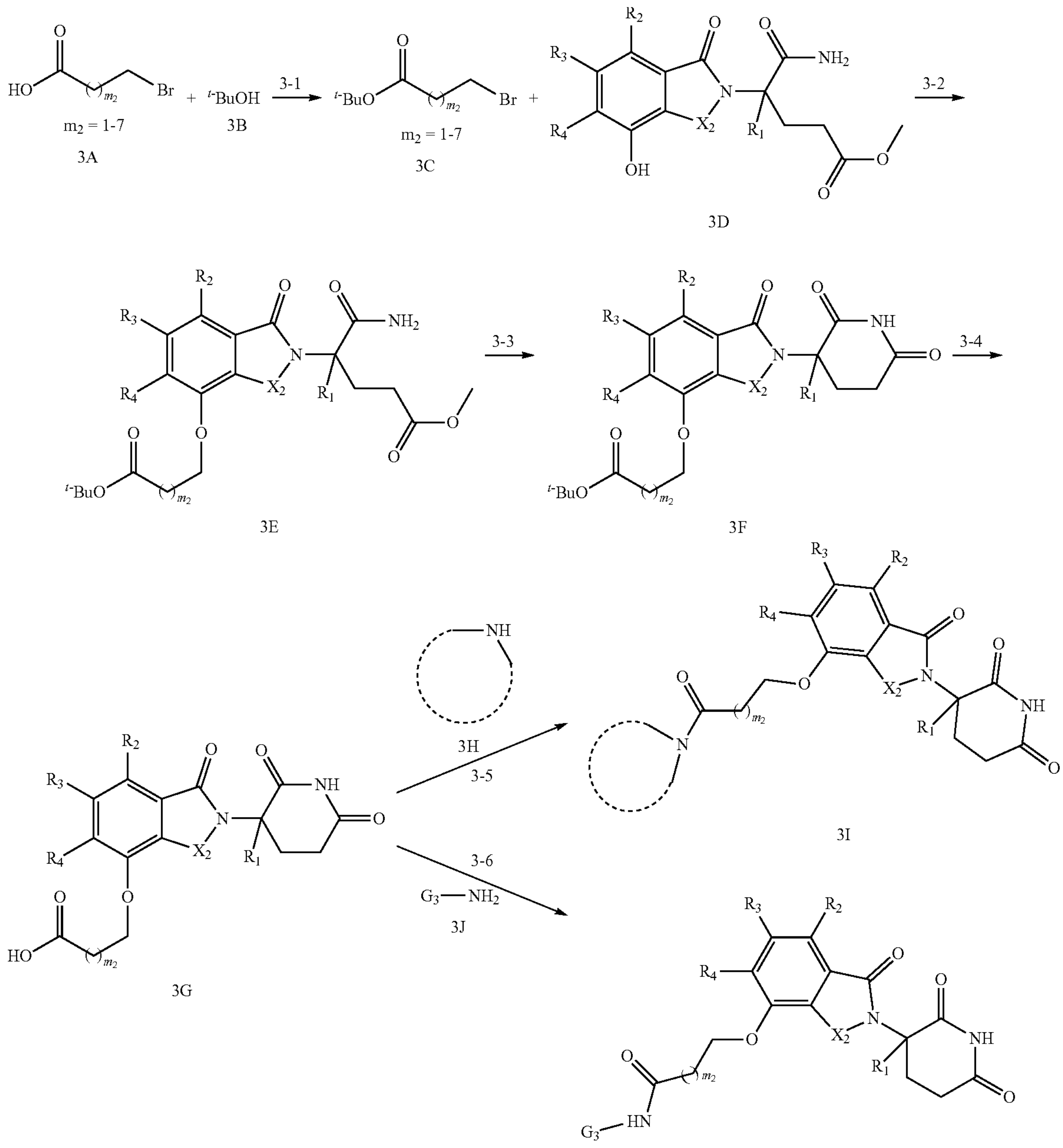

wherein, the definitions of $R_1$, $R_2$, $R_3$, $R_4$ and $X_2$ are the same as the aforementioned definitions;

$m_2$ is an integer from 1 to 7;

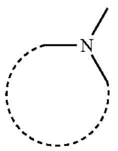

has the same definition as i) heterocyclyl, ii) fused heterocyclyl, and iii) spiroheterocyclic group in the definition of the above-mentioned A;

$G_3$-$NH_2$ are various aromatic amine or aliphatic amine compounds used in the examples of the present invention;

Step 3-1: compounds 3A and 3B are reacted in the presence of trifluoroacetic anhydride and tert-butanol to obtain compound 3C;

Step 3-2: compounds 3C and 3D are reacted in the presence of potassium carbonate to obtain compound 3E;

Step 3-3: piperidone derivative 3F is obtained by ring-closing of compound 3E in the presence of potassium tert-butoxide;

Step 3-4: compound 3G is obtained by removing the protective group of compound 3F under hydrochloric acid condition;

Step 3-5: compound 31 is obtained by condensation reaction of compound 3G and nitrogen-containing heterocyclic compound 3H (compound 3H is a variety of amine compounds containing A group in the aforementioned definition) in the presence of condensing agent (HATU or HOBt) and base (triethylamine);

Step 3-6: compound 3G and compound 3J are condensed in the presence of condensing agent (HATU or HOBt) and base (triethylamine) to obtain compound 3K;

Synthesis Method 4 perature or under heating condition in the presence of Pd catalyst (such as $Pd(PPh_3)_4$ or $Pd(PPh_3)_2Cl_2$, etc.), monovalent copper catalyst (Copper(I) iodide) and base (such as triethylamine or diisopropylethylamine, etc.);

Step 4-2: compound 4C is reduced to compound 4D by hydrogen under catalytic condition of Pd/C, Raney nickel or other metal catalyst (such as Wilkinson's catalyst), Step 4-3: compound 4D is condensed under the condition of amine derivative 4E and condensing agent HATU and HOBt to obtain compound 4F;

Step 4-4: the protective group of compound 4F is removed under hydrochloric acid condition, and after reaction, spin-dried, and reacted with the corresponding acyl chloride or carboxylic acid to obtain compound 4G;

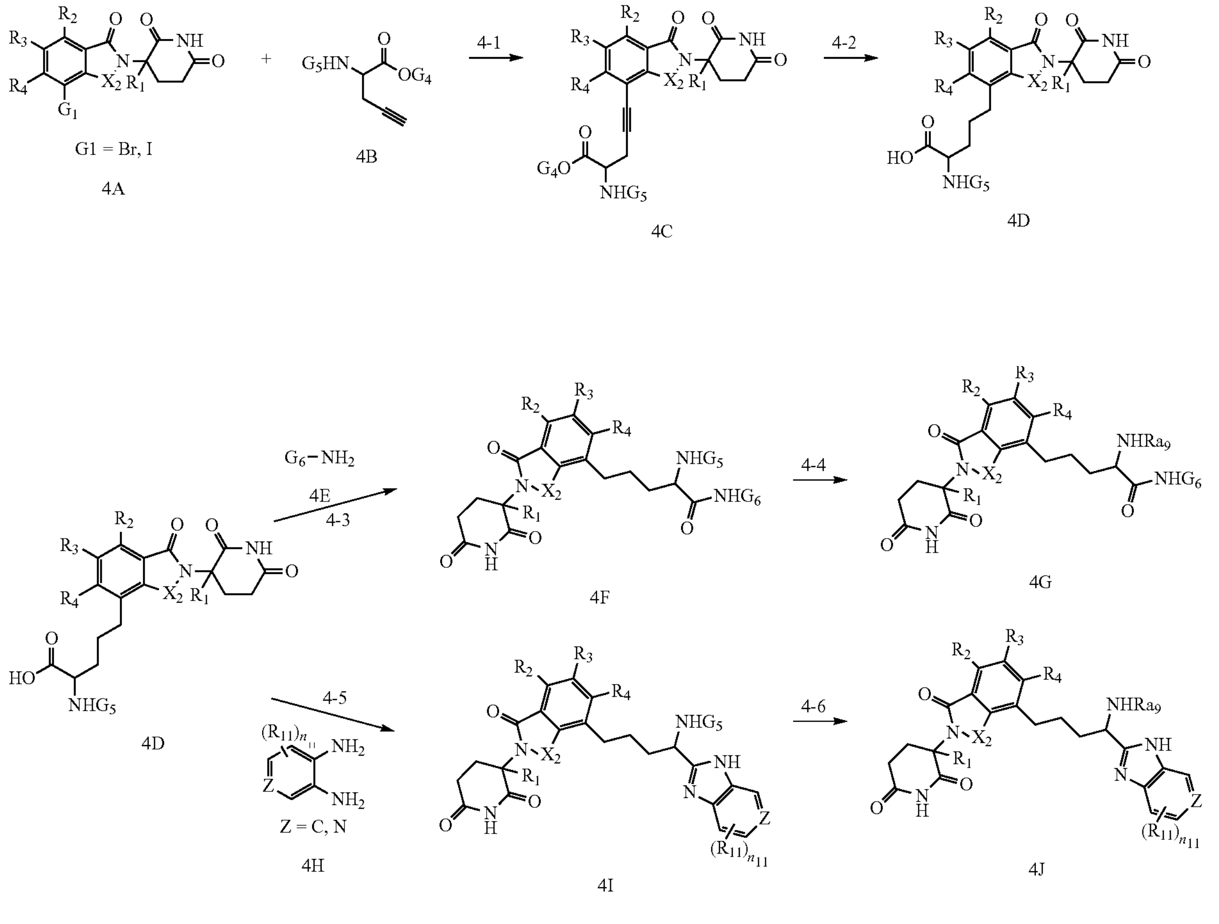

wherein, the definitions of $R_1$, $R_2$, $R_3$, $R_4$, $X_2$, $R_{a9}$, $R_{11}$ and $n_{11}$ are the same as the aforementioned definitions;

$G_4$ and $G_5$ are protective groups selected from tert-butoxycarbonyl or benzyl;

$G_6$-$NH_2$ is an aromatic amine or aliphatic amine compound;

Step 4-1: compound 4C is obtained by Sonogashira coupling reaction of compounds 4A and 4B at room temperature or under heating condition in the presence of Pd catalyst (see above);

Step 4-5: compound 4D and o-phenylenediamine derivative 4H are reacted under condensing agent HATU and HOBt, and then heated under acidic condition to obtain compound 41;

Step 4-6: the protective group of compound 41 is removed under hydrochloric acid condition, and after reaction, spin-dried, and reacted with the corresponding acyl chloride or carboxylic acid to obtain compound 4J;

Synthesis Method 5

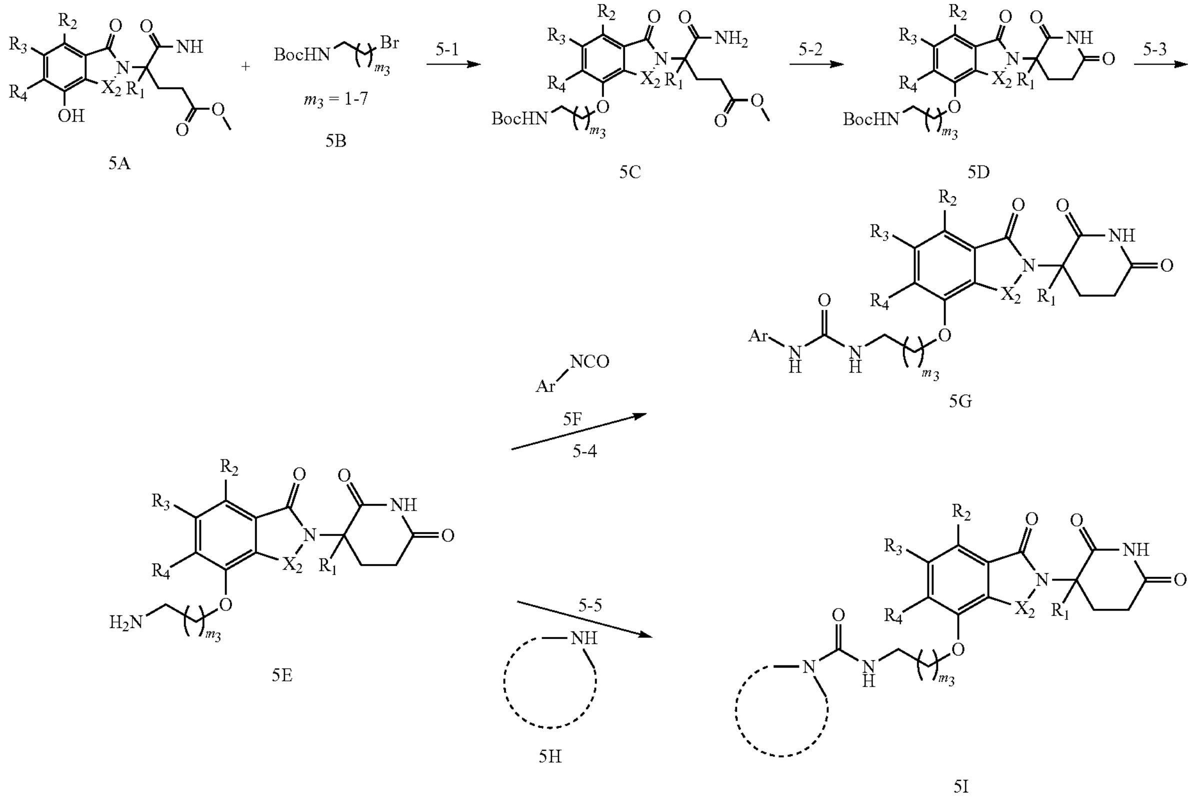

5A 5B 5C 5D 5E 5F 5G 5H 5I wherein, the definitions of $R_1$, $R_2$, $R_3$, $R_4$ and $X_2$ are the same as the aforementioned definitions;

$m_3$ is an integer from 1 to 7;

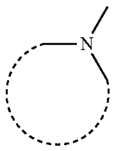

has the same definition as heterocyclyl, fused heterocyclyl, and spiroheterocyclic group in the definition of the above-mentioned A;

Ar is 6-10 membered aryl, 5-10 membered heteroaryl, the aryl or heteroaryl is optionally substituted by one or more $R_5$ substituents, and $R_5$ definition is the same as the above-mentioned definition;

Step 5-1: compounds 5A and 5B are reacted under condition of triphenylphosphine and diisopropyl azodicarboxylate to obtain compound 5C;

Step 5-2: compounds 5C is reacted in the presence of potassium carbonate to obtain compound 5D;

Step 5-3: compound 5E is obtained by removing the protective group of compound 5D under hydrochloric acid condition;

Step 5-4: compound 5E and compound 5F are reacted under basic condition (such as triethylamine or diisopropylethylamine, etc.) to obtain compound 5G;

Step 5-5: compound 5E and nitrogen-containing heterocyclic compound 5H (compound 5H is a variety of amine compounds containing A group in the aforementioned definition) are reacted to obtain compound 51 in the presence of N,N-carbonyldiimidazole and basic condition.

Synthesis Method 6

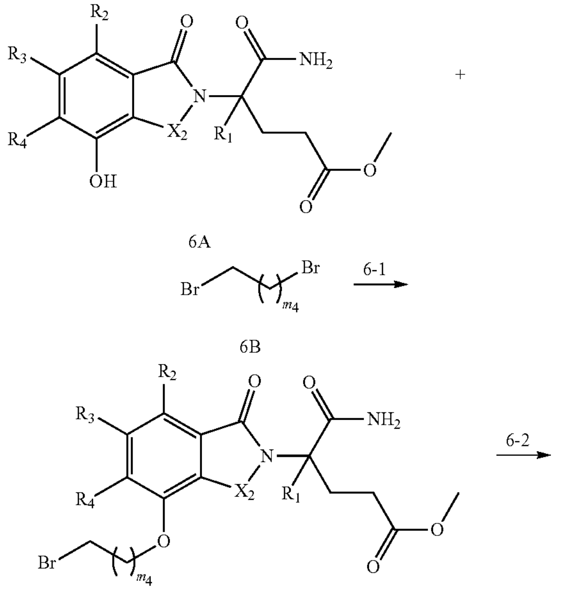

6A 6B 6C

-continued

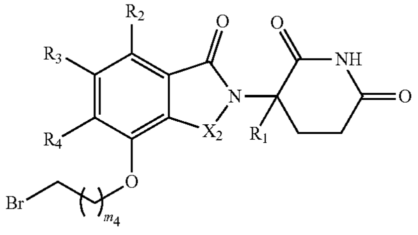

6D

-continued

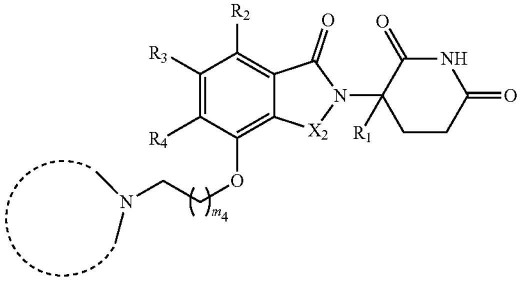

6F

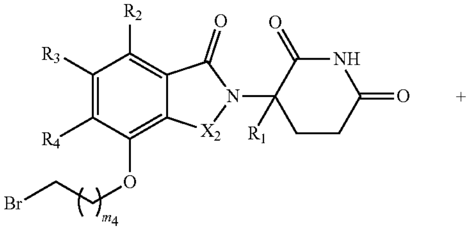

6D

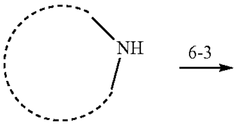

6E wherein, the definitions of $R_1$, $R_2$, $R_3$, $R_4$ and $X_2$ are the same as the aforementioned definitions;

an integer from 1 to 7;

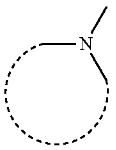

has the same definition as heterocyclyl, fused heterocyclyl, and spiroheterocyclic group in the definition of the abovementioned A;

Step 6-1: compounds 6A and 6B are reacted in the presence of potassium carbonate to obtain compound 6C;

Step 6-2: compounds 6C is reacted in the presence of potassium tert-butoxide to obtain compound 6D;

Step 6-3: compound 6D and nitrogen-containing heterocyclic compound 6E (compound 6E is a variety of amine compounds containing A group in the aforementioned definition) are reacted to obtain compound 6F under basic condition.

Synthesis Method 7

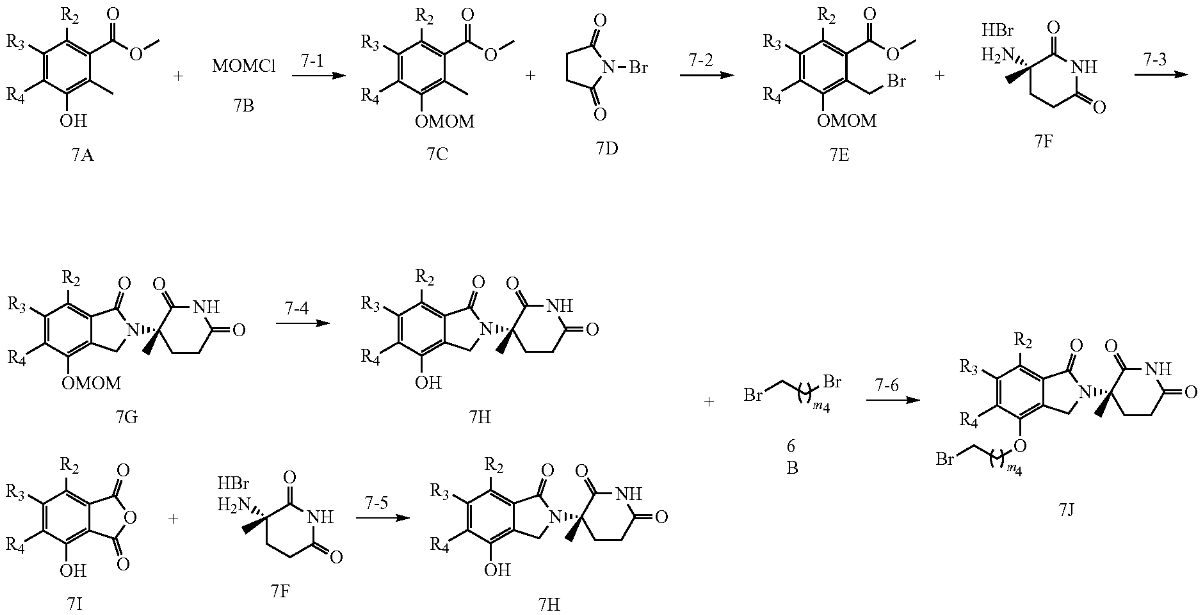

7A 7B 7C 7D 7E 7F 7G 7H 6B 7J 7I 7F 7H

-continued

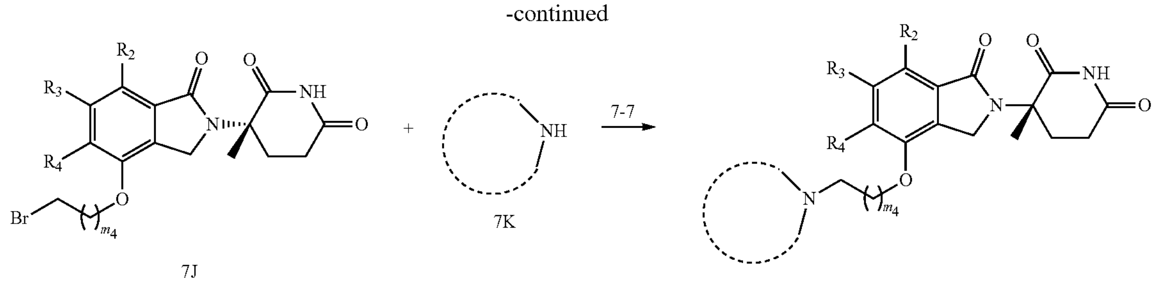

7J 7K 7L wherein, the definitions of $R_1$, $R_2$, $R_3$, and $R_4$ are the same as the aforementioned definitions;

$m_4$ is an integer from 1 to 7;

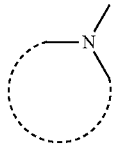

has the same definition as heterocyclyl, fused heterocyclyl, and spiroheterocyclic group in the definition of the above-mentioned A;

Step 7-1: compound 7A and 7B chloromethyl methyl ether are reacted in the presence of sodium hydride to obtain compound 7C;

Step 7-2: compound 7C is reacted in the presence of 7D and azodiisobutyronitrile to obtain compound 7E;

Step 7-3: compound 7E and compound 7F are reacted under basic condition (such as triethylamine or diisopropylethylamine, etc.) to obtain compound 7G;

Step 7-4: compound 7G is reacted under acidic condition (hydrochloric acid and dioxane) to obtain compound 7H;

Step 7-5: compound 7I and compound 7F are reacted under basic condition (such as triethylamine or diisopropylethylamine, etc.) to obtain compound 7H;

Step 7-6: compounds 7H and 6B are reacted in the presence of potassium carbonate to obtain compound 7J;

Step 7-7: compound 7J and nitrogen-containing heterocyclic compound 7K (compound 7K is a variety of amine compounds containing A group in the aforementioned definition) are reacted to obtain compound 7L under basic condition.

Another object of the present invention is to provide the compound of formula (I), the tautomer, diastereomer, racemate, metabolic precursor, metabolite, isotopic compound, pharmaceutically acceptable salt, ester, prodrug or hydrate thereof for use in regulating the activity of $CRL4^{CRBN}$E3ubiquitin ligase.

Another object of the present invention is to provide a pharmaceutical composition, wherein the pharmaceutical composition contains a therapeutically effective dose of the compound of formula (I), the tautomer, diastereomer, diastereomers, racemate, metabolic precursor, metabolite, isotopic compound, pharmaceutically acceptable salt, ester, prodrug or hydrate thereof, and at least one pharmaceutically acceptable carrier.

Another object of the present invention is to provide a pharmaceutical composition, wherein the pharmaceutical composition contains a therapeutically effective dose of the compound of formula (I), the tautomer, diastereomer, racemate, metabolic precursor, metabolite, isotopic compound, pharmaceutically acceptable salt, ester, prodrug or hydrate thereof, and one or more other ingredients with pharmaceutically therapeutic activity. The compound of formula (I) described in claim 1 of the present invention, the enantiomer, diastereomer, racemate, pharmaceutically acceptable salt, ester, prodrug or hydrate thereof may be combined with one or more other ingredients with pharmaceutically therapeutic activity to produce synergistic effects in the prevention or treatment of specific diseases or dysfunctions. The compound of formula (I) described in claim 1 of the present invention, the enantiomer, diastereomer, racemate, pharmaceutically acceptable salt, ester, prodrug or hydrate thereof can also reduce or eliminate the toxic and side effects of one or more other ingredients with pharmaceutically therapeutic activity in the prevention or treatment of specific diseases or dysfunctions, and vice versa.

Another object of the present invention is to provide another one or more ingredients with pharmaceutically therapeutic activity as described above, comprising macromolecular compound, such as protein, polysaccharide, nucleic acid, etc., and small molecular compound, such as inorganic compound, organometallic compound, synthetic or natural organic small molecule compound, etc.

Another object of the present invention is to provide a use of the compound of formula (I), the enantiomer, diastereomer, racemate, metabolic precursor, metabolite, isotopic compound, pharmaceutically acceptable salt, ester, prodrug or hydrate thereof, for the preparation of a medicament for the treatment of diseases related to $CRL4^{CRBN}$E3 ubiquitin ligase, preferably, the diseases non-limiting include cancer, inflammation disease, pain, neurological diseases and immune system diseases.

The compound of the present invention can be prepared into pharmaceutically acceptable salts when containing basic groups, which includes inorganic acid salts and organic acid salts. The acids suitable for formulating salt include but not limited to inorganic acids such as hydrochloric acid, hydrobromic acid, hydrofluoric acid, sulfuric acid, nitric acid, and phosphoric acid; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, and benzenesulfonic acid; and acidic amino acids such as aspartic acid and glutamic acid.

Another object of the present invention is to provide a pharmaceutical composition, which includes one or more of therapeutically effective amount of compound of formula (I), the tautomer, diastereomer, racemate, metabolic precursor, metabolite, isotopic compound, pharmaceutically acceptable salt, prodrugs, solvates, hydrates and crystal form thereof, and at least one excipient, diluent or carrier.

A typical formulation is prepared by mixing the compound of formula (I) of the present invention with carrier, diluent or excipient. Suitable carriers, diluents or excipients are well known to those skilled in the art, including such as carbohydrates, waxes, water-soluble and/or swellable polymers, hydrophilic or hydrophobic substances, gelatin, oils, solvents, water and other substances. The specific carrier, diluent or excipient used will depend on the mode and purpose of the compound of the present invention. The solvent is generally selected on the basis of the solvent considered by those skilled in the art to be safe and effective for administration to mammals. Generally speaking, safe solvents are non-toxic aqueous solvents such as pharmaceutical water, and other non-toxic solvents that are soluble or miscible with water. Suitable aqueous solvents include one or more of water, ethanol, propylene glycol, polyethylene glycol (e.g. PEG400 or PEG300) and the like. The formulation may also include one or more of buffer, stabilizer, surfactant, wetting agent, lubricant, emulsifier, suspending agent, preservative, antioxidant, opalizer, glidant, processing aid, coloring agent, sweetening agent, spices, flavoring agent or other known additives, so that the compound of formula (I) can be manufactured or used in an acceptable form.

When the compound of formula (I) of the present invention is used in combination with at least one other drug, the two drugs or more drugs can be used separately or in combination, and are preferably administered in the form of pharmaceutical composition. The compound or pharmaceutical composition of formula (I) of the present invention can be administered separately in any known oral, intravenous, rectal, vaginal, transdermal, or other local or systemic administration form, separately or together administered to the subject.

These pharmaceutical compositions may also contain one or more of buffer, stabilizer, surfactant, wetting agent, lubricant, emulsifier, suspending agent, preservative, antioxidant, opalizer, glidant, processing aid, coloring agent, sweetening agent, spices, flavoring agent or other known additives, so that the pharmaceutical composition can be manufactured or used in an acceptable form.

The drug of the present invention is preferably administered by oral route. Solid-state formulations for oral administration may include capsules, tablets, powders, or pellets, In the solid-state formulation, the compound or pharmaceutical composition of the present invention is mixed with at least one inert excipient, diluent or carrier. Suitable excipients, diluents or carriers include substances such as sodium citrate or dicalcium phosphate, or starch, lactose, sucrose, mannose alcohol, silicic acid, etc.; binders such as carboxymethyl cellulose, alginate, gelatin, polyvinylpyrrolidone, sucrose, Arabic Gum, etc.; wetting agents such as glycerin, etc.; disintegrating agents such as agar, calcium carbonate, potato or tapioca starch, alginic acid, specific complexing silicate, sodium carbonate, etc.; solution blockers such as paraffin, etc.; absorption promoters such as quaternary ammonium compounds, etc.; adsorbents such as kaolin, bentonite, etc.; lubricants such as talc, calcium stearate, magnesium stearate, solid polyethylene glycol, sodium lauryl sulfate, etc. In the case of capsules and tablets, the formulation may also include buffer. Similar types of solid compositions can also be used as fillers for soft and hard filled gelatin capsules, where lactose and high molecular weight polyethylene glycol are used as excipients.

Liquid formulations for oral administration include pharmaceutically acceptable emulsions, solutions, suspensions, syrups and elixirs. In addition to the compound of the present invention or the composition thereof, the liquid formulations may contain an inert diluent commonly used in the art, such as water or other solvents; solubilizers and emulsifiers such as ethanol, isopropanol, ethyl carbonate, ethyl acetate, benzyl alcohol, benzyl benzoate, propylene glycol, 1,3-butanediol, dimethylformamide; oils (such as cottonseed oil, peanut oil, olive oil, castor oil, sesame oil, etc.); glycerin; tetrahydrofurfuryl alcohol; fatty acid esters of polyethylene glycol and sorbitan; or a mixture of several of these substances, etc.

In addition to these inert diluents, the composition may also contain one or more of excipients, such as wetting agent, emulsifier, suspending agent, sweetening agent, flavoring agent and spices.

Regarding to suspension, in addition to the compound or composition of the present invention, it may further contain carrier such as suspending agent, such as ethoxylated stearyl alcohol, polyoxyethylene sorbitol, sorbitan ester, microcrystalline cellulose, aluminum metahydroxide, bentonite, agar and tragacanth, or a mixture of several of these substances.

The composition for rectal or vaginal administration is preferably suppository, which can be prepared by mixing the compound or composition of the present invention with suitable non-irritating excipient or carrier, such as cocoa butter, polyethylene glycol or suppository wax. The excipient or carrier is solid at normal room temperature and liquid at body temperature, and can be melt in the rectum or vagina to release the active compound.

The compound or pharmaceutical composition of the present invention can be administered in other topical formulations, including ointment, powder, spray and inhalant. The compound can be mixed under sterile conditions with pharmacically acceptable excipient, diluent or carrier and with any preservative, buffer or propellant as required. Ophthalmic formulation, ophthalmic ointment, powder and solution are also intended to be included within the scope of the present invention.

Another object of the present invention is to provide the compound of formula (I), the tautomer, diastereomer, racemate, metabolic precursor, metabolite, isotopic compound, pharmaceutically acceptable salt, ester, prodrug, or hydrate thereof, or crystal form, for use in monotherapy or combination therapy. When used in combination therapy, it contains a therapeutically effective dose of the compound of formula (I) described in claim 1, the enantiomer, diastereomer, racemate and the mixture thereof, as well as the pharmaceutically acceptable sals, crystalline hydrate and solvate, as well as one or more ingredients with pharmaceutically therapeutic activity. The other one or more ingredients with pharmaceutically therapeutic activity comprising macromolecular compound, such as protein (antibody or polypeptide), polysaccharide, nucleic acid (DNA or RNA), etc., and small molecular compound, such as inorganic compound, organometallic compound, synthetic or natural organic small molecule compound, etc. In addition, it also includes radiation, surgery, cell therapy, hormone therapy or cytokine therapy, etc. The compound of formula (I) described in claim 1 of the present invention, the prodrug, enantiomer, diastereomer, racemate and mixture thereof, and the pharmaceutically acceptable salt, crystalline hydrate and solvate may be combined with one or more other ingredients with pharmaceutically therapeutic activity to produce synergistic effects in the prevention or treatment of specific diseases or dysfunctions. The compound of formula (I)

described in claim 1 of the present invention, the prodrug, enantiomer, diastereomer, racemate and mixture thereof, and the pharmaceutically acceptable salt, crystalline hydrate and solvate can also reduce or eliminate the toxic and side effects of one or more other ingredients with pharmaceutically therapeutic activity in the prevention or treatment of specific diseases or dysfunctions, and vice versa.

Another object of the present invention is to provide a use of compound of general formula (I), the tautomer, diastereomer, racemate, metabolic precursor, metabolite, isotopic compound, and pharmaceutically acceptable salt, ester, prodrug or hydrate thereof, for the manufacture of a medicament for the treatment of diseases related to $CRL4^{CRBN}$E3ubiquitin ligase. The related diseases described in the present invention that are related to $CRL4^{CRBN}$E3 ubiquitin ligase non-limiting include tumors, central system diseases and immune diseases.

In a preferred embodiment, the disease or dysfunction includes but is not limited to cancer, angiogenesis-related diseases or dysfunction, pain (including but not limited to complex local pain syndrome), macular degeneration and related dysfunction, skin diseases, pulmonary dysfunction, immunodeficiency diseases, central nervous system damage and dysfunction, TNFα related diseases or dysfunctions.

In another preferred embodiment, the cancer includes (but is not limited to) skin cancer (such as melanoma), lymphatic system cancer, breast cancer, cervical cancer, uterine cancer, cancer inalimentary canal, lung cancer, ovarian cancer, prostate cancer, colon cancer, rectal cancer, oral cancer, brain tumor, head and neck cancer, throat cancer, testicular cancer, kidney cancer, pancreatic cancer, spleen cancer, liver cancer, bladder cancer, laryngeal cancer and cancers related to AIDS. The compound provided by the present invention is also effective to hematologic tumor and myeloma, such as useful to treat multiple myeloma, lymphoma and acute and chronic leukemia. The compounds provided by the present invention can also be used to prevent or treat primary tumors and metastatic tumors.

The term "deuterium (D)" used in the present invention is a stable non-radioactive isotope of hydrogen with an atomic weight of 2.0144. Natural hydrogen is present as a mixture of H (hydrogen or protium) D(2H or deuterium) and T(3H or tritium) isotopes, in which the abundance of deuteriumis 0.0156. According to the general technical knowledge of the field, of all compounds in the structural formulas of all compounds containing natural hydrogen atoms, are actually a mixture of H, D, and T. Therefore, when the deuterium abundance at any site in a compound is greater than its natural abundance 0.0156%, these compounds should be considered unnatural or deuterium-enriched.

The term "isotopic compound" used in the present invention refers to the compound of formula (I) of the present invention, the pharmaceutically acceptable salt, solvate, stereoisomer, metabolite, or prodrug containing one or more atomic isotopes of natural or unnatural abundance. The present invention also covers isotopically-labeled compounds of the present invention, except for the fact that one or more atoms are replaced by the atom with atomic mass or the mass number different from the atomic mass or mass number common in nature. It is the same as the one mentioned here. Examples of isotopes that can be included in the compounds of the present invention include the isotopes of hydrogen, carbon, nitrogen, oxygen, phosphorus, sulfur, fluorine, iodine, and chlorine, such as: $^{2}$hydrogen, $^{3}$hydrogen, $^{11}$carbon, $^{13}$carbon, $^{14}$carbon, $^{13}$nitrogen, $^{15}$nitrogen, $^{15}$oxygen, $^{17}$oxygen, $^{18}$oxygen, $^{31}$phosphorus, $^{32}$phosphorus, $^{35}$sulfur, $^{18}$fluorine, $^{123}$iodine, $^{125}$iodine and $^{36}$chlorine.

Certain isotopically labeled compounds of the present invention (such as those labeled with 3H and 14C) are used in compound and/or substrate tissue distribution tests. Tritium (3H) and carbon-14 (14C) isotopes are particularly preferred because they are easy to prepare and detect. Moreover, replacement of heavier isotopes such as deuterium (i.e. 2H) can provide some therapeutic advantages (for example, increased half-life in vivo or reduced dosage requirements) by providing greater metabolic stability, so it may be preferable in some cases. Positron emission isotopes, such as 15O, 13N, 11C and 18F are used for positron emission tomography (PET) study to check substrate receptor occupancy rate. Isotopically-labeled compound of the present invention can generally be prepared by following methods similar to those disclosed in the scheme and/or the examples below, by substituting isotopically-labeled reagents for non-isotopically-labeled reagents. All isotopic variants of the compounds of the present invention, whether radioactive or not, are included within the scope of the present invention.

DETAILED DESCRIPTION OF THE INVENTION

The present invention will be further described below in conjunction with specific examples, but these examples do not limit the scope of the present invention.

I. Preparation Examples

In all the examples, $^{1}$H NMR was recorded by a Bruker Avance III-300 or Avance III-400 nuclear magnetic resonance instrument, and the chemical shift was expressed as δ (ppm); the mass spectrum was measured by MS Mass Spectra UPLC-MS (ESI); wherein UPLC model is Waters HPLC H-CLASS, MS (ESI) model is Waters SQ Detector 2. Anhydrous tetrahydrofuran was prepared by refluxing benzophenone/metal sodium for drying and deoxygenation. Anhydrous toluene and anhydrous dichloromethane were prepared by refluxing with calcium chloride to dry. Petroleum ether, ethyl acetate, dichloromethane and other solvents used in the mobile phase of column chromatography were purchased from Sinopharm Chemical Reagent Co., Ltd. The thin layer chromatography silica gel plate (HSGF254) used in the reaction detection was from Sinopharm Chemical Reagent Co., Ltd. 200-300 mesh silica gel for compound separation was from Sinopharm Chemical Reagent Co., Ltd. The raw materials in the present invention can be commercially purchased, for example, the main reagents were purchased from Sinopharm Chemical Reagent Co., Ltd., or prepared by methods known in this field, or prepared according to the methods described in the present invention.

1. Synthesis of Intermediate Compounds

Intermediates were synthesised by referring to the synthesis methods in the above methods 1-7.

Methyl 3-bromo-2-bromomethyl benzoate

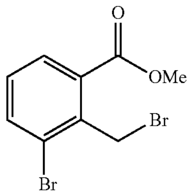 [SMILES: COC(=O)c1cccc(Br)c1CBr]

3-bromo-2-methylbenzoic acid (4.0 g, 17.46 mmol) was dissolved in 40 mL benzene, NBS (3.73 g, 20.95 mmol) and BPO (424 mg, 1.75 mmol) were added, the reaction mixture was heated at 95° C. overnight. After the reaction was completed, the solvent was removed under reduced pressure. The residue obtained was purified by silica gel column chromatography to obtain colorless oil methyl 3-bromo-2-bromomethyl benzoate 5.3 g, yield 98%; $^1$H NMR (400 MHz, $CDCl_3$) δ 7.88 (dd, J=7.8, 1.3 Hz, 1H), 7.76 (dd, J=8.0, 1.3 Hz, 1H), 7.22 (t, J=7.9 Hz, 1H), 5.12 (s, 2H), 3.95 (s, 3H).

3-(4-bromo-1-oxoisoindoline-2-)piperidine-2,6-dione

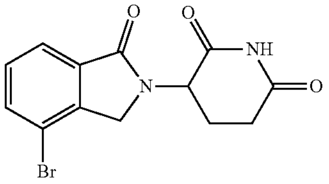 [SMILES: O=C1CCC(N2Cc3c(Br)cccc3C2=O)C(=O)N1]

Methyl 3-bromo-2-bromomethyl benzoate (5.3 g, 17.2 mmol) was dissolved in 50 mL acetonitrile, 3-amino-piperidine-2,6-dione hydrochloride (3.45 g, 21.0 mmol) and triethylamine (3.18 mL, 22.88 mmol) were successively added, the reaction mixture was reacted at 80° C. for 18 h. After the reaction was completed, the solvent was removed under reduced pressure, and the product was dispersed in a mixed solution of water-ethyl acetate-petroleum ether (v/v/v, 2:1:1), and the resulting precipitate was filtered and dried, 3-(4-bromo-1-oxoisoindoline-2-)piperidine-2,6-dione (3.35 g, 60%) was obtained under reduced pressure. $^1$H NMR (400 MHz, DMSO) δ 11.03 (s, 1H), 7.87 (dd, J=7.9, 0.7 Hz, 1H), 7.79-7.75 (m, 1H), 7.51 (t, J=7.7 Hz, 1H), 5.15 (dd, J=13.3, 5.1 Hz, 1H), 4.42 (d, J=17.6 Hz, 1H), 4.26 (d, J=17.6 Hz, 1H), 2.92 (ddd, J=17.5, 13.7, 5.4 Hz, 1H), 2.64-2.55 (m, 1H), 2.55-2.39 (m, 1H), 2.02 (dtd, J=12.5, 5.2, 2.0 Hz, 1H).

3-(4-(5-hydroxypentyl-1-yne-1-)-1-oxoisoindoline-2-)piperidine-2,6-dione

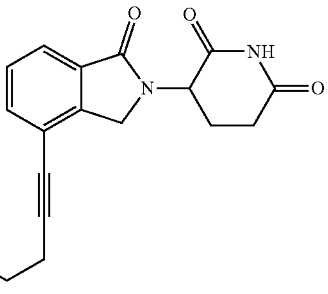

3-(4-bromo-1-oxoisoindoline-2-)piperidine-2,6-dione (1.0 g, 3.09 mmol), 4-pentyne-1-ol (521 mg, 6.19 mmol), $Pd(PPh_3)_2Cl_2$ (218 mg, 0.31 mmol) and CuI (118 mg, 0.62 mmol) were dissolved in 10 mL dry DMF. The reaction solution was replaced with high-purity nitrogen for 3 times, then 10 mL of triethylamine was added, and the reaction solution was replaced with high-purity nitrogen once more. The reaction solution was heated to 60° C. overnight. After the reaction was completed, the solvent was removed under reduced pressure. The crude product was purified by silica gel column chromatography to obtain 1.03 g of product 3-(4-(5-hydroxypentyl-1-yne-1-)-1-oxoisoindoline-2-)piperidine-2,6-dione, as a white solid, yield 100%; $^1$H NMR (400 MHz, DMSO) δ 11.02 (s, 1H), 7.71 (d, J=7.6 Hz, 0.8 Hz, 1H), 7.64 (dd, J=7.6, 0.8 Hz, 1H), 7.53 (t, J=7.6 Hz, 1H), 5.15 (dd, J=13.3, 5.1 Hz, 1H), 4.57 (t, J=5.1 Hz, 1H), 4.46 (d, J=17.8 Hz, 1H), 4.31 (d, J=17.8 Hz, 1H), 3.54 (dd, J=11.4, 6.1 Hz, 2H), 2.99-2.86 (m, 1H), 2.65-2.57 (m, 1H), 2.56-2.39 (m, 3H), 2.06-1.97 (m, 1H), 1.77-1.67 (m, 2H).

3-(4-(6-hydroxyhexyl-1-yne-1-)-1-oxoisoindoline-2-)piperidine-2,6-dione

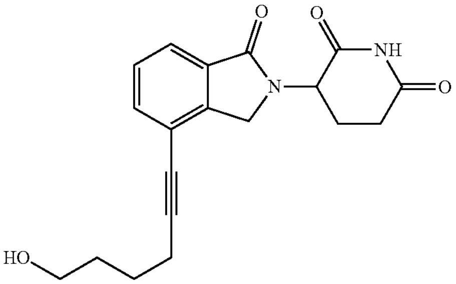 [SMILES: O=C1CCC(N2Cc3c(C#CCCCCO)cccc3C2=O)C(=O)N1]

3-(4-bromo-1-oxoisoindoline-2-)piperidine-2,6 dione and 5-hexyn-1-ol were used as raw materials, and the preparation method was the same as 3-(4-(5-hydroxypentyl-1-yne-1-)-1-oxoisoindoline-2-)piperidine-2,6-dione to afford 665 mg 3-(4-(6-hydroxyhexyl-1-yne-1-)-1-oxoisoindoline-2-)piperidine-2,6-dione as a light yellow solid, yield 84%; $^1$H N MR (400 MHz, DMSO) δ 11.00 (s, 1H), 7.70 (d, J=7.0 Hz, 1H), 7.63 (d, J=7.6 Hz, 1H), 7.51 (t, J=7.6 Hz, 1H), 5.14 (dd, J=13.3, 5.1 Hz, 1H), 4.50-4.40 (m, 2H), 4.30 (d, J=17.7 Hz, 1H), 3.44 (q, J=5.9 Hz, 2H), 2.91 (ddd, J=17.5, 13.7, 5.4 Hz, 1H), 2.64-2.55 (m, 1H), 2.50-2.40 (m, 3H), 2.01 (ddd, J=10.2, 5.0, 3.2 Hz, 1H), 1.58 (ddd, J=11.3, 6.4, 2.6 Hz, 4H).

3-(4-(5-hydroxypentyl)-1-oxoisoindoline-2-)piperidine-2,6-dione

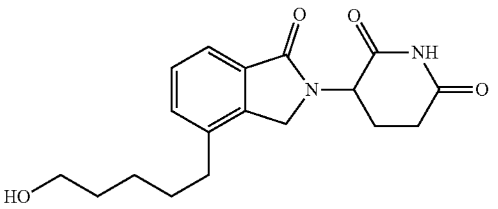 [SMILES: O=C1CCC(N2Cc3c(CCCCCO)cccc3C2=O)C(=O)N1]

3-(4-(5-hydroxypentyl-1-yne-1-)-1-oxoisoindoline-2-)piperidine-2,6-dione (1.0 g, 3.09 mmol) was dissolved in 30 mL of tetrahydrofuran, 10% Pd/C (200 mg) was added to the reaction solution, and heated to 40° C. under hydrogen (260 psi) for 7 h. After the reaction was completed, the catalyst was removed by filtration. The filtrate was concentrated under reduced pressure and purified by silica gel column chromatography to obtain 1.02 g 3-(4-(5-hydroxypentyl)-1-oxoisoindoline-2-)piperidine-2,6-dione as a white solid, yield 100%; $^{1}$H NMR (400 MHz, DMSO) δ 10.99 (s, 1H), 7.58-7.53 (m, 1H), 7.48-7.43 (m, 2H), 5.13 (dd, J=13.2, 5.2 Hz, 1H), 4.46 (d, J=17.1 Hz, 1H), 4.35 (t, J=5.1 Hz, 1H), 4.30 (d, J=17.1 Hz, 1H), 3.38 (dd, J=11.6, 6.4 Hz, 2H), 2.92 (ddd, J=17.4, 13.8, 5.6 Hz, 1H), 2.68-2.56 (m, 3H), 2.48-2.37 (m, 1H), 2.06-1.96 (m, 1H), 1.66-1.54 (m, 2H), 1.45 (td, J=13.4, 6.5 Hz, 2H), 1.33 (dt, J=9.4, 7.5 Hz, 2H).

3-(4-(5-bromopentyl)-1-oxoisoindoline-2-)piperidine-2,6-dione

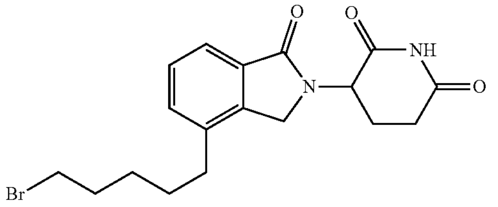 [SMILES: O=C1CCC(N2Cc3c(CCCCCBr)cccc3C2=O)C(=O)N1]

3-(4-(5-hydroxypentyl))-1-oxoisoindoline-2-)piperidine-2,6-dione (500 mg, 1.513 mmol) and triphenylphosphine (794 mg, 3.036 mmol) were dissolved in 40 mL of dry tetrahydrofuran. Carbon tetrabromide (1.506 g, 4.54 mmol) was added to the reaction solution, and the resulting mixture was reacted at room temperature for 1 h. After the reaction was completed, the solvent was removed under reduced pressure, and the resulting residue was purified by silica gel column chromatography to obtain 588 mg 3-(4-(5-bromopentyl)-1-oxoisoindoline-2-)piperidine-2,6-dione as a white solid, yield 99%; 1H NMR (500 MHz, DMSO) δ 11.01 (s, 1H), 7.62 (dd, J=11.8, 7.3 Hz, 1H), 7.56 (dd, J=6.5, 4.0 Hz, 1H), 7.48-7.43 (m, 1H), 5.14 (dd, J=13.4, 5.2 Hz, 1H), 4.47 (d, J=17.1 Hz, 1H), 4.31 (d, J=17.1 Hz, 1H), 3.54 (t, J=6.6 Hz, 2H), 2.98-2.87 (m, 1H), 2.63 (dd, J=22.8, 14.8 Hz, 3H), 2.43 (ddd, J=26.4, 13.4, 4.3 Hz, 1H), 2.06-1.97 (m, 1H), 1.94-1.76 (m, 2H), 1.63 (dt, J=15.3, 7.6 Hz, 2H), 1.44 (dt, J=14.8, 7.5 Hz, 2H).

3-(4-(4-hydroxybutyl)-1-oxoisoindoline-2-)piperidine-2,6-dione

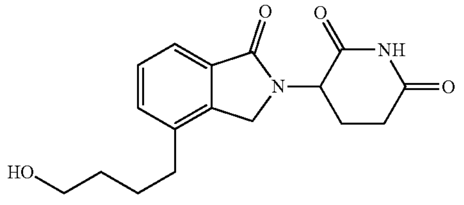 [SMILES: O=C1CCC(N2Cc3c(CCCCO)cccc3C2=O)C(=O)N1]

3-(4-(4-hydroxybutyl-1-yne-)-1-oxoisoindoline-2-)piperidine-2,6-dione (0.74 g, 2.37 mmol) was add to the mixed solution of 30 mL tetrahydrofuran and 10 mL methanol, and Raney nickel was added. The resulting mixture was reacted for 30 h under 260 psi hydrogen pressure. After the reaction was completed, the reaction solution was filtered through Celite, the filtrate was concentrated under reduced pressure, and the residue obtained was purified by silica gel column chromatography to obtain 0.75 g 3-(4-(4-hydroxybutyl)-1-oxoisoindoline-2-)piperidine-2,6-dione, yield 100%; $^{1}$H NMR (400 MHz, DMSO) δ 11.01 (s, 1H), 7.58-7.54 (m, 1H), 7.46 (d, J=4.3 Hz, 2H), 5.14 (dd, J=13.3, 5.0 Hz, 1H), 4.46 (d, J=17.2 Hz, 1H), 4.41 (t, J=5.2 Hz, 1H), 4.30 (d, J=17.1 Hz, 1H), 3.42 (dd, J=11.7, 6.3 Hz, 2H), 3.14-3.04 (m, 1H), 2.98-2.87 (m, 1H), 2.69-2.60 (m, 3H), 2.05-1.96 (m, 1H), 1.68-1.57 (m, 2H), 1.50-1.42 (m, 2H), 1.17 (t, J=7.4 Hz, 1H). ESI-MS $[M+H]^+$ m/z=317.24.

3-(4-(3-hydroxypropyl-1-oxoisoindoline-2-)piperidine-2,6-dione

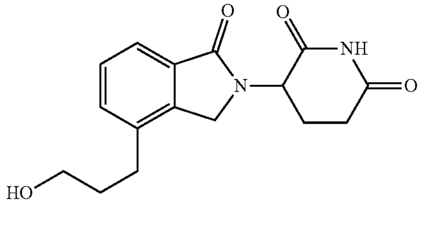 [SMILES: O=C1CCC(N2Cc3c(CCCO)cccc3C2=O)C(=O)N1]

The preparation method was the same as 3-(4-(4-hydroxybutyl)-1-oxoisoindoline-2-)piperidine-2,6-dione; $^{1}$H NMR (400 MHz, DMSO) δ 10.96 (s, 1H), 7.56 (p, J=3.8 Hz, 1H), 7.46 (s, 2H), 5.13 (dd, J=13.3, 5.1 Hz, 1H), 4.46 (d, J=17.2 Hz, 1H), 4.39 (t, J=5.2 Hz, 1H), 4.30 (d, J=17.2 Hz, 1H), 3.42 (dd, J=11.6, 6.3 Hz, 2H), 2.92 (ddd, J=17.5, 13.7, 4.7 Hz, 1H), 2.69-2.56 (m, 3H), 2.48-2.36 (m, 1H), 2.01 (ddd, J=9.8, 4.9, 2.9 Hz, 1H), 1.70-1.56 (m, 2H), 1.51-1.40 (m, 2H).

3-(4-(2-bromoethoxy)-1-oxoisoindoline-2-)piperidine-2,6-dione

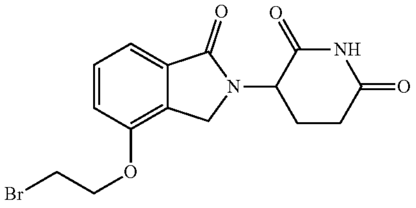 [SMILES: O=C1CCC(N2Cc3c(OCCBr)cccc3C2=O)C(=O)N1]

Step 1: methyl 5-amino-4-(4-hydroxy-1-oxoisoindoline-2-)-5-oxopentanoate (200 mg, 0.68 mmol, 1.0 eq) was dissolved in 10 mL anhydrous acetonitrile, 1,2-dibromoethane (643 mg, 3.42 mmol, 5.0 eq) and anhydrous potassium carbonate (96 mg, 0.68 mmol, 1.0 eq) were added, and stirred vigorously for 24 h at 50° C. After the reaction was completed, the acetonitrile was spun off and purified by column chromatography to obtain 100 mg white solid with a yield of 37%; $^1$H NMR (400 MHz, DMSO) δ 7.61 (s, 1H), 7.47 (t, J=7.8 Hz, 1H), 7.32 (d, J=7.3 Hz, 1H), 7.25 (d, J=8.0 Hz, 1H), 7.20 (d, J=9.8 Hz, 1H), 4.74 (dd, J=10.4, 5.0 Hz, 1H), 4.55 (d, J=17.6 Hz, 1H), 4.51-4.43 (m, 2H), 4.39 (d, J=17.6 Hz, 1H), 3.91-3.81 (m, 2H), 3.53 (d, J=14.0 Hz, 3H), 2.33-2.14 (m, 3H), 2.12-2.03 (m, 1H).

Step 2: methyl 5-amino-4-(4-(2-bromoethoxy)-1-oxoisoindoline-2-)-5-oxopentanoate (100 mg, 0.25 mmol, 1.0 eq) was dissolved in 20 mL of anhydrous tetrahydrofuran and stirred at −78° C. for 15 min. Potassium tert-butoxide (31 mg, 0.28 mmol, 1.1 eq) was added, and the reaction was continued for 90 minutes. After the reaction was completed, 1 mL of 1N hydrochloric acid was added to quench the reaction at −78° C. The reaction system was gradually warmed to room temperature, the solvent was spun off, and 90 mg white solid was obtained by column chromatography, yield 98%; $^1$H NMR (400 MHz, DMSO) δ 10.97 (s, 1H), 7.49 (t, J=7.8 Hz, 1H), 7.35 (d, J=7.4 Hz, 1H), 7.27 (d, J=8.1 Hz, 1H), 5.12 (dd, J=13.3, 5.1 Hz, 1H), 4.47 (dt, J=8.1, 4.9 Hz, 2H), 4.43-4.34 (m, 1H), 4.26 (d, J=17.4 Hz, 1H), 3.83 (t, J=5.3 Hz, 2H), 2.90 (ddd, J=13.6, 12.4, 5.4 Hz, 1H), 2.58 (d, J=18.1 Hz, 1H), 2.49-2.40 (m, 1H), 1.99 (s, 1H).

3-(4-(3-bromopropoxyl)-1-oxoisoindoline-2-)piperidine-2,6-dione

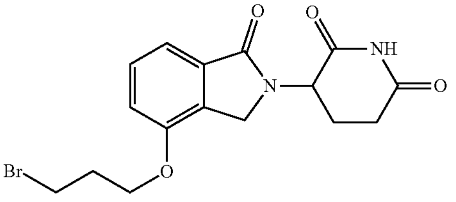 [SMILES: O=C1CCC(N2Cc3c(OCCCBr)cccc3C2=O)C(=O)N1]

1,2-dibromoethane was replaced with 1,3-dibromopropane, while the synthesis method was the same as 3-(4-(2-bromoethoxy)-1-oxoisoindoline-2-)piperidine-2,6-dione to afford 634 mg of 3-(4-(3-bromopropoxy)-1-oxoisoindoline-2-)piperidine-2,6-dione as a white solid, yield 95%; $^1$H NMR (400 MHz, DMSO) δ 11.00 (s, 1H), 7.49 (t, J=7.8 Hz, 1H), 7.32 (d, J=7.4 Hz, 1H), 7.27 (d, J=8.0 Hz, 1H), 5.12 (dd, J=13.3, 5.0 Hz, 1H), 4.41 (d, J=17.5 Hz, 1H), 4.23 (dd, J=14.3, 8.4 Hz, 3H), 3.71 (t, J=6.6 Hz, 2H), 2.96-2.86 (m, 1H), 2.58 (d, J=17.2 Hz, 1H), 2.47-2.38 (m, 2H), 2.32-2.22 (m, 2H), 2.03-1.94 (m, 1H).

3-(4-(5-bromopentyloxy)-1-oxoisoindoline-2-)piperidine-2,6-dione

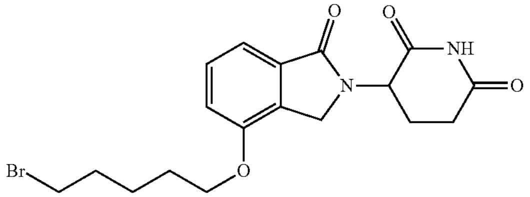 [SMILES: O=C1CCC(N2Cc3c(OCCCCCBr)cccc3C2=O)C(=O)N1]

1,2-Dibromoethane was replaced with 1,5-dibromopentane, while the synthesis method was the same as 3-(4-(2-bromoethoxy)-1-oxoisoindoline-2-)piperidine-2,6-dione to afford 322 mg of 3-(4-(5-bromopentyloxy)-1-oxoisoindoline-2-)piperidine-2,6-dione as a white solid, yield 97%; $^1$H NMR (400 MHz, $CDCl_3$) δ 8.00 (s, 1H), 7.48 (dd, J=7.6, 0.9 Hz, 1H), 7.43 (t, J=7.7 Hz, 1H), 7.04-6.99 (m, 1H), 5.23 (dd, J=13.3, 5.1 Hz, 1H), 4.43 (d, J=16.5 Hz, 1H), 4.30 (d, J=16.5 Hz, 1H), 4.08 (t, J=6.2 Hz, 2H), 3.45 (t, J=6.7 Hz, 2H), 2.86 (ddd, J=23.2, 15.9, 4.1 Hz, 2H), 2.44-2.32 (m, 1H), 2.22 (dtd, J=10.3, 5.2, 2.6 Hz, 1H), 1.99-1.90 (m, 2H), 1.89-1.79 (m, 2H), 1.71-1.60 (m, 2H).

3-(4-(6-bromohexyloxy)-1-oxoisoindoline-2-)piperidine-2,6-dione

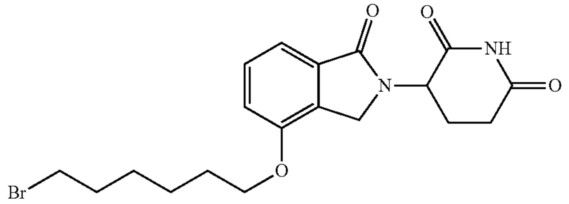 [SMILES: O=C1CCC(N2Cc3c(OCCCCCCBr)cccc3C2=O)C(=O)N1]

1,2-Dibromoethane was replaced with 1,6-dibromohexane, the synthesis method was the same as 3-(4-(2-bromoethoxy)-1-oxoisoindoline-2-)piperidine-2,6-dione to afford 474 mg of 3-(4-(6-bromohexyloxy)-1-oxoisoindoline-2-)piperidine-2,6-dione as a white solid, yield of 95%; $^1$H NMR (400 MHz, DMSO) δ 10.97 (s, 1H), 7.47 (t, J=7.8 Hz, 1H), 7.30 (d, J=7.4 Hz, 1H), 7.23 (d, J=8.1 Hz, 1H), 5.10 (dd, J=13.3, 5.1 Hz, 1H), 4.37 (d, J=17.4 Hz, 1H), 4.22 (d, J=17.4 Hz, 1H), 4.11 (t, J=6.3 Hz, 2H), 3.54 (t, J=6.7 Hz, 2H), 2.99-2.84 (m, 1H), 2.58 (d, J=18.0 Hz, 1H), 2.45 (dd, J=13.1, 4.4 Hz, 1H), 1.99 (t, J=5.1 Hz, 1H), 1.89-1.68 (m, 4H), 1.46 (dd, J=7.1, 3.5 Hz, 4H).

Benzyl (S)-2-((tert-butoxycarbonyl)amino)-4-pentynoate

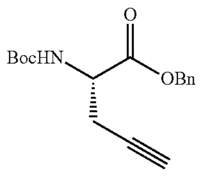 [SMILES: C#CC[C@H](NC(=O)OC(C)(C)C)C(=O)OCc1ccccc1]

L-propargylalanine protected by tert-butoxycarbonyl (3.0 g, 14.07 mmol), DMAP (172 mg, 1.41 mmol) and DIPEA (4.88 mL, 29.55 mmol) were dissolve in 150 mL of dry dichloromethane. The reaction solution was cooled to 0° C., benzyl chloroformate (2.08 mL, 14.77 mmol) was added dropwise to the reaction solution. The resulting reaction solution reacted at 0° C. for 4 h. After the reaction was completed, the reaction solution was washed with 1N potassium hydrogen sulfate aqueous solution in turn, the organic phase was dried over anhydrous sodium sulfate, and the reaction solution was filtered, and concentrated under reduced pressure. The resulting residue was passed through a silica gel column chromatography to obtain 3.321 g of the target product, as a colorless oil, yield 78%.

Benzyl (2R)-2-tert-butoxycarbonylamino-5-(2-(2,6-dioxopiperidine-3-)-1-oxoisoindoline-4-) -4-pentynoate

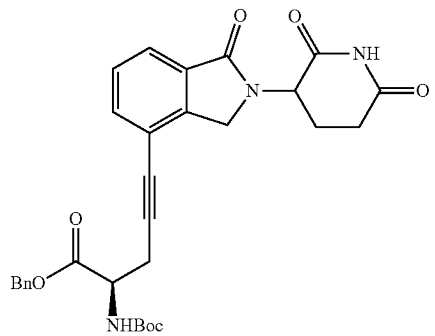 [SMILES: CC(C)(C)OC(=O)N[C@H](CC#Cc1cccc2c1CN(C1CCC(=O)NC1=O)C2=O)C(=O)OCc1ccccc1]

Benzyl (S)-2-((tert-butoxycarbonyl)amino)-4-pentynoate (3.18 g, 10.47 mmol), 3-(4-bromo-1-oxoisoindoline-2-)piperidine-2,6-dione (2.26 g, 6.98 mmol), bistriphenylphosphine palladium dichloride (491 mg, 0.70 mmol) and CuI (267 mg, 1.40 mmol)) were added to a 100 mL reaction flask, the reaction system was replaced with nitrogen, dry DMF (20 mL) and dry triethylamine (20 mL) were added under the protection of nitrogen, and the solution was heated to 60° C. to react overnight. After the reaction was completed, the solvent was removed under reduced pressure, and the residue was purified by silica gel column chromatography to obtain 3.64 g of benzyl (2R)-2-tert-butoxycarbonylamino-5-(2-(2,6-dioxopiperidine-3-)-1-oxoisoindoline-4-)-4-pentynoate, as an off-white solid, yield 95%.

(2R)-2-tert-butoxycarbonylamino-5-(2-(2,6-dioxopiperidine-3-)-1-oxoisoindoline-4-)pentanoic acid

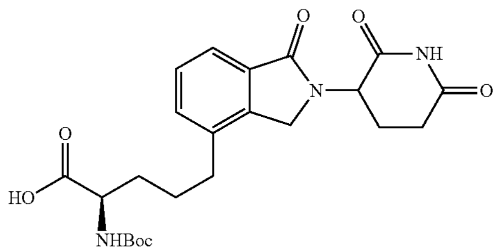 [SMILES: CC(C)(C)OC(=O)N[C@H](CCCc1cccc2c1CN(C1CCC(=O)NC1=O)C2=O)C(=O)O]

Benzyl (2R)-2-tert-butoxycarbonylamino-5-(2-(2,6-dioxopiperidine-3-)-1-oxoisoindoline-4-)-4-pentynoate (127 mg, 0.23 mmol) was dissolved in 50 mL of tetrahydrofuran, 10% Pd/C (50 mg) was added, and the solution was reacted overnight under hydrogen (8 bar) condition. After the reaction was completed, the catalyst was removed by filtration and the filtrate was concentrated under reduced pressure to obtain 107 mg of compound (2R)-2-tert-butoxycarbonylamino-5-(2-(2,6-dioxopiperidine-3-)-1-oxoisoindoline-4-) pentanoic acid, yield 100%; $^1$H NMR (400 MHz, DMSO) δ 12.43 (s, 1H), 10.99 (s, 1H), 7.57 (dd, J=6.5, 2.0 Hz, 1H), 7.49-7.41 (m, 2H), 7.09 (d, J=7.8 Hz, 1H), 5.75 (s, 1H), 5.14 (ddd, J=13.3, 4.9, 2.0 Hz, 1H), 4.46 (d, J=17.1 Hz, 1H), 4.30 (dd, J=17.2, 1.3 Hz, 1H), 3.97-3.86 (m, 1H), 3.00-2.87 (m, 1H), 2.71-2.57 (m, 3H), 2.41 (ddd, J=26.4, 13.3, 4.2 Hz, 1H), 2.09-1.91 (m, 1H), 1.78-1.56 (m, 4H), 1.37 (s, 9H).

2. SYNTHESIS OF EXAMPLES

Compounds were synthesized by referring to the above methods 1-7.

Example 1: 3-(1-oxo-4-(5-(quinoline-4-oxy)pentyl)isoindoline-2-)piperidine-2,6-dione (1)

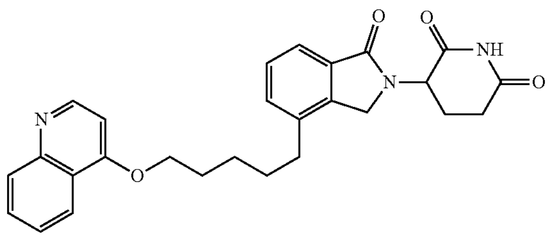 [SMILES: O=C1CCC(N2Cc3c(CCCCCOc4ccnc5ccccc45)cccc3C2=O)C(=O)N1]

3-(4-(5-hydroxypentyl)-1-oxoisoindoline-2-)piperidine-2,6-dione (100 mg, 0.303 mmol, 1 eq.), 4-hydroxyquinoline (132 mg, 0.909 mmol, 3 eq.) and triphenylphosphine (159 mg, 0.605 mmol, 2 eq.) were dissolved in 20 mL of dry THF, and diisopropyl azodicarboxylate (120 μL, 0.605 mmol, 2 eq.) was added under the protection of nitrogen. The resulting mixture was stirred to react at room temperature for 2 h. After the reaction was completed, the solvent was removed under reduced pressure. The obtained residue was separated by silica gel column chromatography, and then purified by HPLC to obtain 52 mg of 3-(1-oxo-4-(5-(quinoline-4-oxy)pentyl)isoindoline-2-)piperidine-2,6-dione, as a white solid, yield 38%; $^1$H NMR (400 MHz, DMSO) δ 11.00 (s, 1H), 8.71 (d, J=5.2 Hz, 1H), 8.12-8.07 (m, 1H), 7.93 (dd, J=8.4, 0.5 Hz, 1H), 7.73 (ddd, J=8.4, 6.9, 1.5 Hz, 1H), 7.57 (dd, J=7.3, 1.3 Hz, 1H), 7.55-7.51 (m, 1H), 7.48 (dd, J=7.5, 1.4 Hz, 1H), 7.47-7.42 (m, 1H), 7.01 (d, J=5.3 Hz, 1H), 5.13 (dd, J=13.3, 5.1 Hz, 1H), 4.47 (d, J=17.1 Hz, 1H), 4.32 (d, J=17.1 Hz, 1H), 4.26 (t, J=6.3 Hz, 2H), 2.91 (ddd, J=17.6, 13.8, 5.3 Hz, 1H), 2.74-2.67 (m, 2H), 2.63-2.55 (m, 1H), 2.39 (ddd, J=17.4, 13.1, 4.8 Hz, 1H), 2.01-1.88 (m, 3H), 1.79-1.68 (m, 2H), 1.63-1.52 (m, 2H).

Example 2: 3-(1-oxo-4-(3-(quinoline-4-oxy)propyl) isoindoline-2-)piperidine-2,6-dione (2)

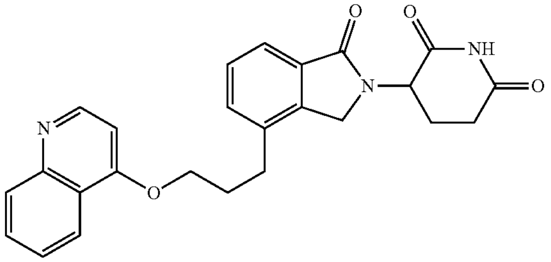 [SMILES: O=C1CCC(N2Cc3c(CCCOc4ccnc5ccccc45)cccc3C2=O)C(=O)N1]

3-(4-(3-hydroxypropyl)-1-oxoisoindoline-2-)piperidine-2,6-dione (48 mg, 0.16 mmol), 4-hydroxyquinoline (70 mg, 0.48 mmol) and triphenylphosphine (84 mg, 0.32 mmol) were added to a 100 mL round bottom flask under nitrogen protection, 20 mL of tetrahydrofuran was added, and the mixture was stirred vigorously. Then diisopropyl azodicarboxylate (65 mg, 0.32 mmol) was added. After the reaction was completed, the solvent was spun off, purified by HPLC to afford 17.6 mg of product, yield 26%; $^1$H NMR (400 MHz, DMSO) δ 10.96 (s, 1H), 9.10 (d, J=6.4 Hz, 1H), 8.26 (d, J=7.7 Hz, 1H), 8.13 (d, J=8.4 Hz, 1H), 8.08-8.01 (m, 1H), 7.79 (t, J=11.3 Hz, 1H), 7.56 (t, J=6.4 Hz, 2H), 7.46 (dd, J=10.5, 4.4 Hz, 2H), 5.11 (dd, J=13.3, 5.1 Hz, 1H), 4.52 (t, J=5.9 Hz, 2H), 4.47 (d, J=17.1 Hz, 1H), 4.31 (d, J=17.1 Hz, 1H), 3.00-2.84 (m, 3H), 2.6 (m, 1H), 2.36-2.14 (m, 3H), 1.97-1.86 (m, 1H).

Example 3: 3-(1-oxo-4-(6-(quinoline-4-oxy)hexyl) isoindoline-2-)piperidine-2,6-dione (3)

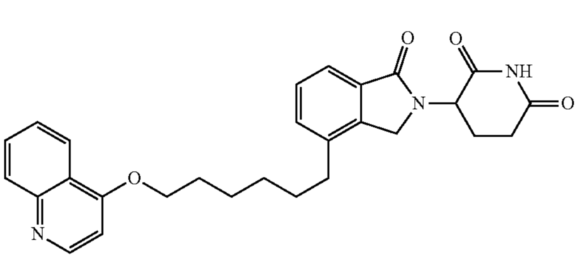 [SMILES: O=C1CCC(N2Cc3c(CCCCCCOc4ccnc5ccccc45)cccc3C2=O)C(=O)N1]

3-(4-(5-hydroxypentyl)-1-oxoisoindoline-2-)piperidine-2,6-dione was replaced with 3-(4-(6-hydroxyhexyl)-1-oxoisoindoline-2-)piperidine-2,6-dione, the preparation method was the same as 3-(1-oxo-4-(5-(quinoline-4-oxy)pentyl) isoindoline-2-)piperidine-2,6-dione, 47.2 mg, yield 50%; $^1$H NMR (400 MHz, DMSO) δ 11.00 (s, 1H), 8.72 (d, J=5.3 Hz, 1H), 8.14 (dd, J=8.3, 0.9 Hz, 1H), 7.97-7.91 (m, 1H), 7.74 (ddd, J=8.4, 6.9, 1.5 Hz, 1H), 7.56 (tdd, J=4.7, 3.9, 1.2 Hz, 2H), 7.48-7.40 (m, 2H), 7.02 (d, J=5.3 Hz, 1H), 5.13 (dd, J=13.2, 5.2 Hz, 1H), 4.46 (d, J=17.2 Hz, 1H), 4.30 (d, J=17.1 Hz, 1H), 4.25 (t, J=6.3 Hz, 2H), 2.92 (ddd, J=17.5, 13.5, 5.5 Hz, 1H), 2.70-2.63 (m, 2H), 2.59 (dd, J=16.3, 2.0 Hz, 1H), 2.41 (ddd, J=26.5, 13.4, 4.6 Hz, 1H), 2.05-1.95 (m, 1H), 1.92-1.83 (m, 2H), 1.71-1.62 (m, 2H), 1.61-1.51 (m, 2H), 1.44 (dt, J=15.9, 8.0 Hz, 2H).

Example 4: 3-(1-oxo-4-(3-(quinoline-4-oxy) propoxy) isoindoline-2-)piperidine-2,6-dione (4)

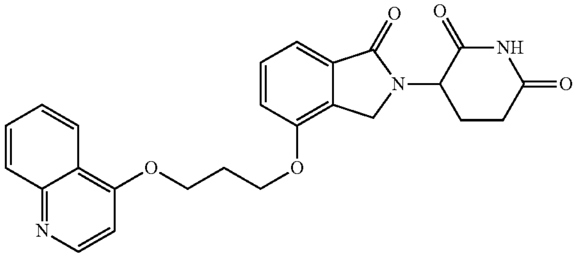

Step 1: 1,3-propanediol (5.0 g, 6.57 mmol) was dissolved in 60 mL of dry tetrahydrofuran, sodium hydride (2.39 g, 5.97 mmol) was added under ice bath, and stirred for 30 minutes. Then tert-butyldimethylchlorosilane (9.0 g, 5.97 mmol) was added, and the reaction was continued for 1 h. After the reaction was completed, saturated ammonium chloride was added to quench, extracted with ethyl acetate, washed with saturated sodium chloride, dried, concentrated, and purified by column chromatography to obtain a colorless oil (10.06 g, 90%). $^1$H NMR (400 MHz, $CDCl_3$) δ 3.87-3.76 (m, 4H), 2.65 (t, J=5.2 Hz, 1H), 1.83-1.73 (m, 2H), 0.89 (s, 9H), 0.07 (s, 6H).

Step 2: compound methyl 5-amino-4-(4-hydroxy-1-oxoisoindoline-2-)-5-oxopentanoate (100 mg, 0.34 mmol, 1.0 eq) was added to 100 ml round bottom flask, 3-tert-butyldimethylsiloxy-1-propanol (174 mg, 0.85 mmol, 2.5 eq) and triphenylphosphine (178 mg, 0.68 mmol, 2 eq) were added. The reaction system was replaced with nitrogen, and 20 mL of dry tetrahydrofuran was added. Diisopropyl azodicarboxylate (134 μL, 0.68 mmol, 2 eq) was added to the reaction system to react at room temperature for 1 h. After the reaction was completed, the solvent was spun off, and the target product was obtained by column chromatography. ESI-MS $[M+H]^+$ m/z=465.60.

Step 3: the obtained product in the previous step was added into a 50 mL round bottom flask, 20 mL tetrahydrofuran was added, and tetrabutylammonium fluoride (0.64 ml, 0.64 mmol) was added to react at room temperature overnight. After the reaction was completed, the solvent was removed under reduced pressure, and the product was purified by column chromatography to obtain 211 mg of white solid with a yield of 78%; $^1$H NMR (400 MHz, DMSO) δ 10.99 (s, 1H), 7.49 (t, J=7.8 Hz, 1H), 7.31 (d, J=7.2 Hz, 1H), 7.25 (d, J=8.0 Hz, 1H), 5.12 (dd, J=13.3, 5.1 Hz, 1H), 4.59 (t, J=6.0 Hz, 1H), 4.38 (d, J=17.4 Hz, 1H), 4.22 (d, J=17.3 Hz, 1H), 4.19 (t, J=6.2 Hz, 2H), 3.58 (dd, J=11.4, 6.1 Hz, 2H), 2.97-2.85 (m, 1H), 2.63-2.54 (m, 1H), 2.48-2.38 (m, 1H), 2.05-1.93 (m, 1H), 1.89 (p, J=6.1 Hz, 2H). ESI-MS $[M+H]^+$ m/z=319.26

Step 4: compound 3-(4-(3-hydroxypropoxy)-1-oxoisoindoline-2-)piperidine-2,6-dione (50 mg, 0.16 mmol, 1.0 eq) was added into a 100 mL round bottom flask, 4-hydroxyquinoline (68 mg, 0.47 mmol, 3 eq) and triphenylphosphine (82 mg, 0.31 mmol, 2 eq) were added. The system was replaced with $N_2$ and tetrahydrofuran (20 ml) was added. Diisopropyl azodicarboxylate (62 ul, 0.31 mmol, 2 eq) was added to react at room temperature for 1 h. After the reaction was completed, the solvent was removed under reduced pressure, purified by HPLC, and 27.6 mg of product was obtained with a yield of 39%; $^1$H NMR (400 MHz, DMSO) δ 11.01 (s, 1H), 9.13 (d, J=6.2 Hz, 1H), 8.37 (d, J=8.4 Hz, 1H), 8.12 (d, J=8.4 Hz, 1H), 8.05 (t, J=7.7 Hz, 1H), 7.81 (t, J=7.7 Hz, 1H), 7.54 (d, J=6.3 Hz, 1H), 7.48 (t, J=7.8 Hz, 1H), 7.36-7.28 (m, 2H), 5.10 (dd, J=13.3, 5.0 Hz, 1H), 4.71 (t, J=5.8 Hz, 2H), 4.41 (t, J=5.8 Hz, 2H), 4.32 (d, J=17.4 Hz, 1H), 4.17 (d, J=17.4 Hz, 1H), 2.99-2.84 (m, 1H), 2.62-2.53 (m, 1H), 2.48-2.39 (m, 2H), 2.29 (qd, J=13.4, 4.4 Hz, 1H), 1.99-1.89 (m, 1H). ESI-MS $[M+H]^+$ m/z=446.33.

Example 5: 3-(4-(5-(isoindoline-5-oxy)pentyl)-1-oxoisoindoline-2-)piperidine-2,6-dione (5)

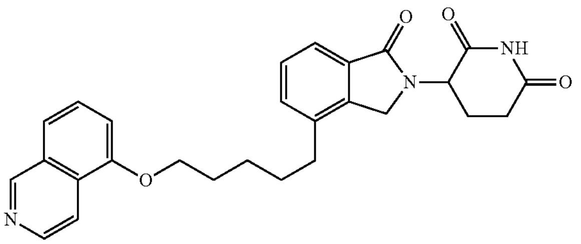 [SMILES: O=C1CCC(N2Cc3c(CCCCCOc4cccc5cnccc45)cccc3C2=O)C(=O)N1]

4-Hydroxyquinoline was replaced with 5-hydroxyisoquinoline, and the preparation method was the same as 3-(1-oxo-4-(5-(quinoline-4-oxy)pentyl)isoindoline-2-)piperidine-2,6-dione, 26 mg, yield 38%; $^1$H NMR (400 MHz, DMSO) δ 11.00 (s, 1H), 9.30 (s, 1H), 8.49 (d, J=5.9 Hz, 1H), 7.92 (d, J=5.9 Hz, 1H), 7.67 (d, J=8.2 Hz, 1H), 7.63-7.54 (m, 2H), 7.46 (dt, J=14.5, 7.2 Hz, 2H), 7.24 (d, J=7.6 Hz, 1H), 5.13 (dd, J=13.3, 5.1 Hz, 1H), 4.47 (d, J=17.2 Hz, 1H), 4.32 (d, J=17.1 Hz, 1H), 4.20 (t, J=6.3 Hz, 2H), 2.92 (ddd, J=17.5, 13.8, 5.5 Hz, 1H), 2.71 (t, J=7.6 Hz, 2H), 2.64-2.55 (m, 1H), 2.40 (qd, J=13.5, 4.5 Hz, 1H), 1.98 (ddd, J=10.5, 5.0, 2.4 Hz, 1H), 1.91 (dd, J=14.5, 7.0 Hz, 2H), 1.78-1.68 (m, 2H), 1.63-1.53 (m, 2H).

Example 6: 3-(1-oxo-4-(4-(quinoline-4-oxy) butoxy) isoindoline-2-)piperidine-2,6-dione (6)

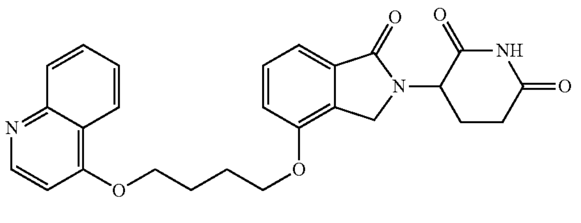 [SMILES: O=C1CCC(N2Cc3c(OCCCCOc4ccnc5ccccc45)cccc3C2=O)C(=O)N1]

Step 1: 1,4-butanediol (1.0 g, 11.10 mmol, 1.1 eq.) was dissolved in 20 mL of tetrahydrofuran, sodium hydride (0.40 g, 10.09 mmol, 1 eq.) was added under ice bath, and stirred for 30 min. Then tert-butyldimethylchlorosilane (1.52 g, 10.09 mmol, 1 eq) was added, and the reaction was continued for 1 h. After the reaction was completed, saturated ammonium chloride was added to quench, extracted with ethyl acetate, washed with saturated sodium chloride, dried, concentrated, and purified by column chromatography to obtain 1.75 g colorless oil, yield 78%. $^1$H NMR (400 MHz, $CDCl_3$) δ 9.71-3.60 (m, 4H), 2.59 (t, J=5.5 Hz, 1H), 1.70-1.58 (m, 4H), 0.90 (s, 9H), 0.07 (s, 6H).

Step 2: compound methyl 5-amino-4-(4-hydroxy-1-oxoisoindoline-2-)-5-oxopentanoate (100 mg, 0.34 mmol, 1.0 eq) was added to 100 mL round bottom flask, 4-tert-butyldimethylsiloxy-1-butanol (174 mg, 0.85 mmol, 2.5 eq) and triphenylphosphine (178 mg, 0.68 mmol, 2 eq) were added. The reaction system was protected with nitrogen and tetrahydrofuran (20 ml) was added. Diisopropyl azodicarboxylate (134 ul, 0.68 mmol, 2 eq) was added to the reaction system to react at room temperature for 1 h. After the reaction was completed, the solvent was spun off, and the mixture of product and triphenylphosphine oxide was obtained by column chromatography purification; ESI-MS $[M+H]^+$ m/z=479.42.

Step 3: the obtained mixture in the previous step was added into a 50 mL round bottom flask, 20 mL tetrahydrofuran was added, and tetrabutylammonium fluoride (0.34 ml, 0.34 mmol, 1 eq) was added to react at room temperature overnight. After the reaction was completed, the solvent was spun off, and purified by column chromatography to obtain 96 mg product, as a white solid, yield 85%; $^1$H NMR (400 MHz, DMSO) δ 10.99 (s, 1H), 7.47 (t, J=7.8 Hz, 1H), 7.30 (d, J=7.4 Hz, 1H), 7.23 (d, J=8.1 Hz, 1H), 5.11 (dd, J=13.3, 5.1 Hz, 1H), 4.47 (t, J=5.1 Hz, 1H), 4.37 (d, J=17.4 Hz, 1H), 4.21 (d, J=17.4 Hz, 1H), 4.12 (t, J=6.4 Hz, 2H), 3.45 (dd, J=11.6, 6.3 Hz, 2H), 2.96-2.86 (m, 1H), 2.62-2.54 (m, 1H), 2.48-2.39 (m, 1H), 2.03-1.94 (m, 1H), 1.82-1.73 (m, 2H), 1.63-1.53 (m, 2H). ESI-MS $[M+H]^+$ m/z=333.27.

Step 4: compound-(4-(4-hydroxybutoxy)-1-oxoisoindoline-2-)piperidine-2,6-dione (50 mg, 0.15 mmol, 1.0 eq) was added into a 100 mL round bottom flask, 4-hydroxyquinoline (65 mg, 0.45 mmol, 3 eq) and triphenylphosphine (79 mg, 0.30 mmol, 2 eq) were added. The system was replaced with $N_2$ and tetrahydrofuran (20 ml) was added. Diisopropyl azodicarboxylate (59 ul, 0.30 mmol, 2 eq) was added to the reaction system, and reacted at room temperature for 1 h. After the reaction was completed, the solvent was removed under reduced pressure. The residue was purified by HPLC to obtain 9.9 mg product, yield 14%; $^1$H NMR (400 MHz, DMSO) δ 10.97 (s, 1H), 9.16 (d, J=6.4 Hz, 1H), 8.32 (d, J=8.3 Hz, 1H), 8.15-8.06 (m, 2H), 7.82 (t, J=7.6 Hz, 1H), 7.55 (d, J=6.6 Hz, 1H), 7.46 (t, J=7.8 Hz, 1H), 7.27 (dd, J=14.2, 7.8 Hz, 2H), 5.10 (dd, J=13.5, 5.1 Hz, 1H), 4.63 (t, J=5.9 Hz, 2H), 4.33 (d, J=17.4 Hz, 1H), 4.27 (t, J=5.9 Hz, 2H), 4.19 (d, J=17.4 Hz, 1H), 2.97-2.85 (m, 1H), 2.63-2.54 (m, 1H), 2.36 (dt, J=13.4, 8.7 Hz, 1H), 2.18-2.09 (m, 2H), 2.09-1.92 (m, 3H). ESI-MS $[M+H]^+$ m/z=460.34.

Example 7: 3-(4-(5-((6-methyl-2-(trifluoromethyl) quinoline-4-)oxy)pentyl)-1-oxoisoindoline-2-)piperidine-2,6-dione (7)

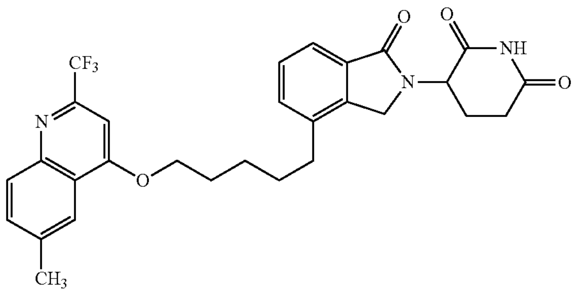 [SMILES: Cc1ccc2nc(C(F)(F)F)cc(OCCCCCc3cccc4c3CN(C3CCC(=O)NC3=O)C4=O)c2c1]

4-hydroxyquinoline was replaced with 6-methyl-2-trifluoromethyl-4-hydroxyquinoline, and the preparation method was the same as 3-(1-oxo-4-(5-(quinoline-4-oxy)pentyl)isoindoline-2-)piperidine-2,6-dione, 71 mg, yield 87%; $^{1}$H NMR (400 MHz, DMSO) δ 10.99 (s, 1H), 7.98 (d, J=8.6 Hz, 1H), 7.94 (s, 1H), 7.72 (dd, J=8.7, 2.0 Hz, 1H), 7.57 (dd, J=7.2, 1.2 Hz, 1H), 7.46 (dt, J=14.7, 6.8 Hz, 2H), 7.35 (s, 1H), 5.12 (dd, J=13.1, 5.1 Hz, 1H), 4.47 (d, J=17.1 Hz, 1H), 4.38 (t, J=6.4 Hz, 2H), 4.32 (d, J=17.2 Hz, 1H), 2.91 (ddd, J=17.8, 13.6, 5.2 Hz, 1H), 2.75-2.68 (m, 2H), 2.62-2.55 (m, 1H), 2.52 (s, 3H), 2.39 (ddd, J=17.4, 12.9, 4.0 Hz, 1H), 1.96 (ddd, J=18.1, 8.7, 4.9 Hz, 3H), 1.81-1.71 (m, 2H), 1.64-1.54 (m, 2H).

Example 8: 3-(4-(4-((2-cyclopropylquinoline-4-)oxy)butoxy)-1-oxoisoindoline-2-)piperidine-2,6-dione (8)

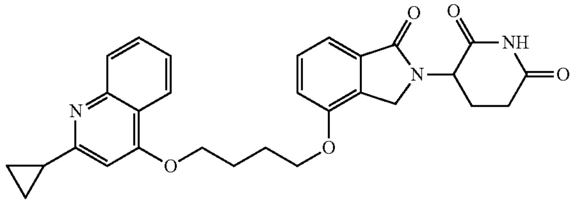 [SMILES: O=C1CCC(N2Cc3c(OCCCCOc4cc(C5CC5)nc5ccccc45)cccc3C2=O)C(=O)N1]

Step 1: 2-cyclopropyl-4-hydroxyquinoline (120 mg, 0.65 mmol, 1 eq), 1,4-butanediol (0.87 g, 9.72 mmol, 15 eq), triphenylphosphine (2.56 g, 9.72 mmol, 15 eq) were added under the protection of nitrogen, then 60 mL tetrahydrofuran was added and stirred vigorously. Then diisopropyl azodicarboxylate (1.91 ml, 9.72 mmol, 15 eq) was added. The mixture was reacted at room temperature for 1 h. After the reaction was completed, the solvent was removed under reduced pressure, and triphenylphosphine oxide and 1,4-butanediol were removed by column chromatography purification. The resulting mixture was directly used in the next step without further purification. ESI-MS [M+H]$^{+}$ m/z=258.57.

Step 2: Under the protection of nitrogen, the obtained mixture in the previous step, methyl 5-amino-4-(4-hydroxy-1-oxoisoindoline-2-)-5-oxopentanoate (50 mg, 0.7 mmol, 1 eq) and triphenylphosphine (89 mg, 0.34 mmol, 2 eq) were added into a 100 mL round bottom flask, then 20 mL of tetrahydrofuran was added and stirred vigorously. Then diisopropyl azodicarboxylate (67 ul, 0.34 mmol, 2 eq) was added to react at room temperature for hour. After the reaction was completed, the solvent was spun off, and purified by column chromatography to obtain 77 mg product, as a light yellow oil, yield 85%; ESI-MS [M+H]$^{+}$ m/z=532.31.

Step 3: methyl 5-amino-4-(4-(4-((2-cyclopropylquinoline-4-)oxy)butoxy)-1-oxoisoindoline-2-)-5-oxopentanoate (40 mg, 0.075 mmol, 1 eq) was dissolved in 10 mL of dry tetrahydrofuran, potassium tert-butoxide (8.5 mg, 0.075 mmol, 1 eq) was added under ice bath condition, and the reaction was detected 10 min later. After the reaction was completed, 5 ul formic acid was added to quench the reaction, the solvent was spun off, and purified by HPLC to obtain 21.5 mg of the product as a white solid with a yield of 57%. $^{1}$H NMR (400 MHz, DMSO) δ 10.97 (s, 1H), 8.20 (d, J=8.1 Hz, 1H), 8.08-7.97 (m, 2H), 7.72 (t, J=6.9 Hz, 1H), 7.47 (t, J=7.8 Hz, 1H), 7.30 (d, J=7.4 Hz, 1H), 7.25 (d, J=8.2 Hz, 1H), 6.94 (s, 1H), 5.10 (dd, J=13.3, 5.1 Hz, 1H), 4.57 (t, J=6.0 Hz, 2H), 4.33 (d, J=17.4 Hz, 2H), 4.26 (t, J=6.0 Hz, 2H), 4.17 (s, 1H), 2.99-2.84 (m, 1H), 2.63-2.53 (m, 1H), 2.48-2.42 (m, 1H), 2.41-2.28 (m, 1H), 2.15-2.07 (m, 2H), 2.05-1.94 (m, 3H), 1.48-1.40 (m, 4H). ESI-MS [M+H]$^{+}$ m/z=500.47.

Example 9: 3-(1-oxo-4-(5-(thieno[3,2-b]pyridine-7-oxy)pentyl)isoindoline-2-)piperidine-2,6-dione (9)

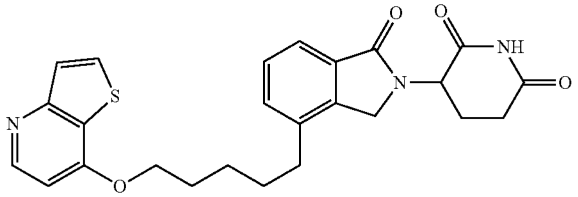 [SMILES: O=C1CCC(N2Cc3c(CCCCCOc4ccnc5ccsc45)cccc3C2=O)C(=O)N1]

4-hydroxyquinoline was replaced with thieno[3,2-b]pyridine-7-phenol, the preparation method was the same as 3-(1-oxo-4-(5-(quinoline-4-oxy)pentyl) isoindoline-2-)piperidine-2,6-dione, 31 mg, yield 44%; $^{1}$H NMR (400 MHz, DMSO) δ 11.00 (s, 1H), 8.52 (d, J=5.4 Hz, 1H), 8.04 (d, J=5.4 Hz, 1H), 7.56 (dd, J=6.9, 1.7 Hz, 1H), 7.51 (d, J=5.4 Hz, 1H), 7.49-7.40 (m, 2H), 7.00 (d, J=5.4 Hz, 1H), 5.13 (dd, J=13.4, 5.1 Hz, 1H), 4.47 (d, J=17.1 Hz, 1H), 4.30 (dd, J=15.0, 8.5 Hz, 3H), 2.92 (ddd, J=17.0, 13.4, 5.3 Hz, 1H), 2.72-2.65 (m, 2H), 2.63-2.56 (m, 1H), 2.40 (ddd, J=26.4, 13.5, 4.7 Hz, 1H), 1.98 (ddd, J=8.7, 7.3, 4.8 Hz, 1H), 1.92-1.81 (m, 2H), 1.71 (dt, J=15.5, 7.9 Hz, 2H), 1.58-1.46 (m, 2H).

Example 10: 3-(4-(4-((2-ethylquinoline-4-)oxy)butoxy)-1-oxoisoindoline-2-)piperidine-2,6-dione (10)

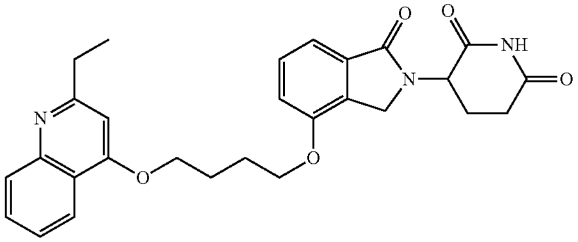 [SMILES: CCc1cc(OCCCCOc2cccc3c2CN(C2CCC(=O)NC2=O)C3=O)c2ccccc2n1]

Step 1: 1.4-butanediol (10.0 g, 110.96 mmol, 5 eq) was dissolve in 50 ml of dichloromethane, and TEA (4.63 ml, 33.29 mmol, 1.5 eq) was added under ice bath condition. Then methyl methyl ether (1.69 ml, 1.79 mmol, 1 eq) was added dropwise, and reacted at room temperature for 5 h. After the reaction was completed, saturated ammonium chloride was added to quench, and the mixture was extracted with dichloromethane, dried, concentrated, and purified by column chromatography to obtain 1.10 g (37%) of a colorless liquid. $^{1}$H NMR (400 MHz, $CDCl_3$) δ 4.63 (s, 1H), 3.67 (s, 1H), 3.57 (t, J=5.9 Hz, 1H), 3.36 (s, 1H), 1.93 (s, 1H), 1.70-1.64 (m, 2H).

Step 2: 2-ethylquinoline-1-phenol (100 mg, 0.57 mmol, 1 eq), 4-methoxymethoxy-1-butanol (1.16 g, 8.66 mmol, 15 eq), triphenylphosphine (2.27 g, 8.66 mmol, 15 eq) were dissolved in 40 mL of tetrahydrofuran, diisopropyl azodicarboxylate (1.75 g, 8.66 mmol, 15 eq) was added at room temperature, and reacted at room temperature for 2 h. After the reaction was completed, the solvent was spun off, and 147 mg of product was obtained by TLC purification, as a light yellow oil, yield 90%; J=8.2 Hz, 1H), 7.65 (t, J=6.9 Hz, 1H), 7.45-7.40 (m, 1H), 6.63 (s, 1H), 4.66 (s, 2H), 4.22 (t, J=6.3 Hz, 2H), 3.65 (t, J=6.3 Hz, 2H), 3.39 (s, 3H), 2.94 (q, J=7.6 Hz, 2H), 2.05 (d, J=27.7 Hz, 2H), 1.92-1.86 (m, 2H), 1.38 (t, J=7.6 Hz, 3H). ESI-MS $[M+H]^+$ m/z=290.61.

Step 3: The compound 2-ethyl-4-(4-(methoxymethoxy) butoxy) quinoline (147 mg, 0.51 mmol) was transferred to a 100 ml round bottom flask, 10 ml dioxane hydrochloride and 1 ml methanol were added. The resulting mixed system was stirred at room temperature for 1 h. After the reaction was completed, the solvent was spun off, a small amount of aminomethanol was added, and the solvent was spun off. 75 mg of white solid was obtained by column chromatography purification, yield 100%; ESI-MS $[M+H]^+$ m/z=246.65.

Step 4: The compound methyl 5-amino-4-(4-hydroxy-1-oxoisoindoline-2-)-5-oxopentanoate (50 mg, 0.17 mmol, 1 eq), 2-ethyl-4-(4-hydroxybutoxy)quinoline (100 mg, 0.34 mmol, 2 eq), triphenylphosphine (90 mg, 0.34 mmol, 2 eq) were added to a 50 mL round bottom flask, 20 mL of tetrahydrofuran was added, and then diisopropyl azodicarboxylate (67 ul, 0.34 mmol, 2 eq) was added to reacted at room temperature for 2 h. After the reaction was completed, the solvent was spun off, and the product was purified by TLC to obtain 72 mg of white solid with a yield of 81%; $^1H$ NMR (400 MHz, $CDCl_3$) δ 8.14 (d, J=7.3 Hz, 1H), 7.99 (d, J=8.4 Hz, 1H), 7.68 (t, J=8.4 Hz, 1H), 7.49-7.41 (m, 1H), 7.06 (dd, J=6.8, 2.1 Hz, 1H), 6.68 (s, 1H), 6.29 (s, 1H), 5.32 (s, 1H), 4.92 (dd, J=8.8, 6.2 Hz, 1H), 4.44 (q, J=17.5 Hz, 1H), 4.32 (t, J=5.5 Hz, 1H), 4.23 (d, J=5.8 Hz, 1H), 3.67 (s, 1H), 2.98 (q, J=7.6 Hz, 1H), 2.50-2.39 (m, 1H), 2.24-2.14 (m, 2H), 1.42 (t, J=7.6 Hz, 1H). ESI-MS $[M+H]^+$ m/z=520.35.

Step 5: methyl 5-amino-4-(4-(4-((2-ethylquinoline-4-)oxy)butoxy)-1-oxoisoquinoline-2-)-5-oxopentanoate (72 mg, 0.14 mmol, 1.0 eq) was dissolved in 10 mL of dry tetrahydrofuran, potassium tert-butoxide (16 mg, 0.14 mmol, 1 eq) was added under ice bath, and the reaction was detected 10 min later. After the reaction was completed, 5 ul formic acid was added to quench the reaction, the solvent was spun off, and purified by HPLC to obtain 54 mg of the product as a white solid with a yield of 79%. $^1H$ NMR (400 MHz, DMSO) δ 10.98 (s, 1H), 8.27 (d, J=8.2 Hz, 1H), 8.08 (dt, J=8.5, 7.6 Hz, 2H), 7.82-7.75 (m, 1H), 7.52 (s, 1H), 7.47 (t, J=7.8 Hz, 1H), 7.28 (dd, J=17.6, 7.8 Hz, 2H), 5.11 (dd, J=13.3, 5.1 Hz, 1H), 4.62 (t, J=6.0 Hz, 2H), 4.33 (d, J=17.4 Hz, 1H), 4.26 (t, J=6.0 Hz, 2H), 4.19 (d, J=17.4 Hz, 1H), 3.11 (q, J=7.6 Hz, 2H), 2.98-2.84 (m, 1H), 2.62-2.53 (m, 1H), 2.35 (qd, J=13.3, 4.4 Hz, 1H), 2.19-2.09 (m, 2H), 2.08-1.92 (m, 4H), 1.40 (t, J=7.6 Hz, 3H). ESI-MS $[M+H]^+$ m/z=488.43.

Example 11: 3-(1-oxo-4-(5-(quinoline-3-oxy)pentyl) isoindoline-2-)piperidine-2,6-dione (11)

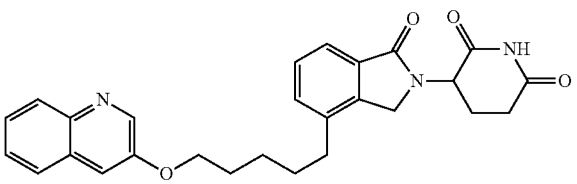 [SMILES: O=C1CCC(N2Cc3c(CCCCCOc4cnc5ccccc5c4)cccc3C2=O)C(=O)N1]

4-hydroxyquinoline was replaced with 3-hydroxyquinoline, and the preparation method was the same as 3-(1-oxo-4-(5-(quinoline-4-oxy)pentyl)isoindoline-2-)piperidine-2,6-dione, 51 mg, yield 74%; $^1H$ NMR (400 MHz, DMSO) δ 11.00 (s, 1H), 8.61 (d, J=2.9 Hz, 1H), 7.96-7.91 (m, 1H), 7.89-7.84 (m, 1H), 7.76 (d, J=2.9 Hz, 1H), 7.60-7.52 (m, 3H), 7.51-7.43 (m, 2H), 5.13 (dd, J=13.3, 5.2 Hz, 1H), 4.48 (d, J=17.2 Hz, 1H), 4.33 (d, J=17.1 Hz, 1H), 4.15 (t, J=6.5 Hz, 2H), 2.92 (ddd, J=17.6, 13.9, 5.5 Hz, 1H), 2.73-2.65 (m, 2H), 2.58 (ddd, J=16.7, 4.2, 2.1 Hz, 1H), 2.42 (ddd, J=18.3, 13.1, 4.4 Hz, 1H), 2.03-1.95 (m, 1H), 1.91-1.81 (m, 2H), 1.76-1.66 (m, 2H), 1.53 (dt, J=15.3, 7.8 Hz, 2H).

Example 12: 3-(1-oxo-4-((5-(quinoline-4-oxy) pentyl)oxy)isoindoline-2-)piperidine-2,6-dione (12)

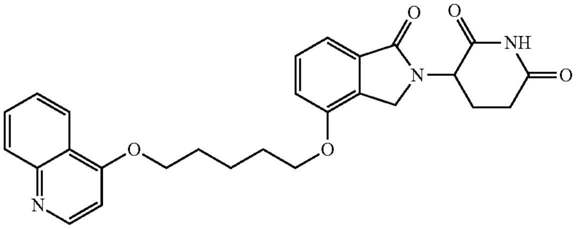 [SMILES: O=C1CCC(N2Cc3c(OCCCCCOc4ccnc5ccccc45)cccc3C2=O)C(=O)N1]

Step 1: 1,5-pentanediol (5.00 g, 48.00 mmol, 5 eq) was dissolve in 20 ml of dichloromethane, and TEA (2.0 ml, 14.40 mmol, 1.5 eq) was added under ice bath condition. Then bromomethyl methyl ether (0.75 ml, 9.6 mmol, 1 eq) was added dropwise, and reacted at room temperature for 5 h. After the reaction was completed, saturated ammonium chloride was added to quench, extracted with dichloromethane, dried, concentrated, and purified by column chromatography to obtain 0.57 g of a colorless liquid, yield 40%. $^1H$ NMR (400 MHz, $CDCl_3$) δ 4.61 (s, 1H), 3.64 (t, J=6.5 Hz, 1H), 3.53 (t, J=6.5 Hz, 1H), 3.35 (s, 1H), 1.64-1.58 (m, 1H), 1.54 (s, 1H), 1.47-1.41 (m, 1H).

Step 2: 5-(methoxymethoxy)-1-pentanol (296 mg, 2.04 mmol, 3.0 eq) was added into a 100 ml round bottom flask, 4-hydroxyquinoline (110 mg, 0.68 mmol, 1 eq) and triphenylphosphine (357 mg, 1.36 mmol, 2 eq) were added. The system was replaced with $N_2$ and tetrahydrofuran (20 ml) was added. Diisopropyl azodicarboxylate (268 ul, 1.36 mmol, 2 eq) was added to the reaction system. Reacted at room temperature for 1 h. After the reaction was completed, the solvent was spun off, and purified by column chromatography to obtain 147 mg product, as a colorless oil, yield 79%; $^1H$ NMR (400 MHz, $CDCl_3$) δ 8.73 (d, J=5.2 Hz, 1H), 8.21 (dd, J=8.3, 1.0 Hz, 1H), 8.02 (d, J=8.4 Hz, 1H), 7.69 (ddd, J=8.4, 6.9, 1.4 Hz, 1H), 7.49 (t, J=8.3 Hz, 1H), 6.71 (d, J=5.2 Hz, 1H), 4.63 (s, 2H), 4.20 (t, J=6.3 Hz, 2H), 3.58 (t, J=6.2 Hz, 2H), 3.37 (s, 3H), 2.01-1.96 (m, 2H), 1.76-1.63 (m, 4H).

Step 3: The compound 4-(5-(methoxymethoxy)pentoxy) quinoline (147 mg, 0.53 mmol) was transferred to a 100 ml round bottom flask, then 10 ml dioxane hydrochloride and lml methanol were added. The resulting mixture was stirred at room temperature for 1 h. After the reaction was completed, the solvent was spun off, a small amount of aminomethanol was added, and the solvent was spun off. 124 mg (100%) of white solid was obtained by column chromatography. ESI-MS $[M+H]^+$ m/z=276.57.

Step 4: The compound methyl 5-amino-4-(4-hydroxy-1-oxoisoindoline-2-)-5-oxopentanoate (50 mg, 0.17 mmol, 1 eq), 5-(quinoline-4-oxo)-1-pentanol (100 mg, 0.34 mmol, 2 eq), triphenylphosphine (90 mg, 0.34 mmol, 2 eq) were added to a 50 mL round bottom flask, 20 mL of tetrahydrofuran was added, and then diisopropyl azodicarboxylate (67 ul, 0.34 mmol, 2 eq) was added to react at room temperature for 2 h. After the reaction was completed, the solvent was spun off, and the product was purified by TLC to obtain 65 mg of white solid at a yield of 76%; $^1$H NMR (400 MHz, $CDCl_3$) δ 8.74 (d, J=5.2 Hz, 1H), 8.23-8.18 (m, 1H), 8.02 (d, J=8.4 Hz, 1H), 7.69 (t, J=8.4 Hz, 1H), 7.49 (dd, J=11.2, 4.0 Hz, 1H), 7.44-7.39 (m, 2H), 7.01 (dq, J=7.9, 4.1 Hz, 1H), 6.75 (d, J=5.2 Hz, 1H), 6.40 (s, 1H), 5.43 (s, 1H), 4.91 (dd, J=8.8, 6.2 Hz, 1H), 4.41 (q, J=17.6 Hz, 2H), 4.25 (t, J=6.3 Hz, 2H), 4.11 (t, J=10.9, 2H), 3.63 (s, 3H), 2.42-1.81 (m, 10H). ESI-MS $[M+H]^+$ m/z=506.83.

Step 5: methyl 5-amino-4-(5-(4-((2-quinoline-4-)oxy) pentoxy)-1-oxoisoindoline-2-)-5-oxopentanoate (85 mg, 0.17 mmol, 1 eq) was dissolved in 10 mL of dry tetrahydrofuran, potassium tert-butoxide (17 mg, 0.17 mmol, 1 eq) was added under ice bath condition, and the reaction was detected 10 min later. After the reaction was completed, 5 ul formic acid was added to quench the reaction, the solvent was spun off, and purified by HPLC to obtain 29.6 mg of the product as a white solid with a yield of 34%. $^1$H NMR (400 MHz, DMSO) δ 10.98 (s, 1H), 9.14 (d, J=6.5 Hz, 1H), 8.33 (d, J=8.4 Hz, 1H), 8.14 (d, J=8.6 Hz, 1H), 8.07 (t, J=8.6 Hz, 1H), 7.82 (t, J=7.7 Hz, 1H), 7.53 (d, J=6.5 Hz, 1H), 7.46 (t, J=7.8 Hz, 1H), 7.30 (d, J=7.3 Hz, 1H), 7.24 (d, J=8.1 Hz, 1H), 5.10 (dd, J=13.3, 5.1 Hz, 1H), 4.56 (t, J=6.3 Hz, 2H), 4.35 (d, J=17.4 Hz, 1H), 4.25-4.14 (m, 3H), 3.00-2.84 (m, 1H), 2.56 (m, 1H), 2.38 (qd, J=13.1, 4.3 Hz, 1H), 2.06-1.80 (m, 5H), 1.78-1.67 (m, 2H). ESI-MS $[M+H]^+$ m/z=506.31.

Example 13: 3-(1-oxo-4-(5-((2-(trifluoromethyl) quinoline-4-)oxy)pentyl)isoindoline-2-)piperidine-2, 6-ditone (13)

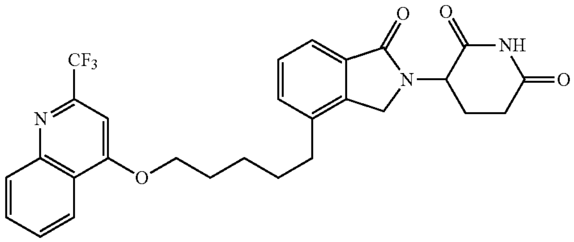 [SMILES: O=C1CCC(N2Cc3c(CCCCCOc4cc(C(F)(F)F)nc5ccccc45)cccc3C2=O)C(=O)N1]

4-hydroxyquinoline was replaced with 2-trifluoromethyl 4-hydroxyquinoline, and the preparation method was the same as 3-(1-oxo-4-(5-(quinoline-4-oxy) pentyl)isoindoline-2-)piperidine-2,6-dione, 37 mg, yield 47%; $^1$H NMR (400 MHz, DMSO) δ 10.99 (s, 1H), 8.19 (dd, J=8.3, 0.7 Hz, 1H), 8.08 (d, J=8.4 Hz, 1H), 7.89 (ddd, J=8.4, 6.9, 1.4 Hz, 1H), 7.75-7.69 (m, 1H), 7.57 (dd, J=7.2, 1.1 Hz, 1H), 7.50-7.42 (m, 2H), 7.40 (s, 1H), 5.13 (dd, J=13.3, 5.1 Hz, 1H), 4.47 (d, J=17.4 Hz, 1H), 4.40 (t, J=6.3 Hz, 2H), 4.32 (d, J=17.2 Hz, 1H), 2.92 (ddd, J=17.4, 13.9, 5.9 Hz, 1H), 2.76-2.67 (m, 2H), 2.58 (ddd, J=6.0, 3.3, 1.7 Hz, 1H), 2.39 (ddd, J=26.7, 13.7, 5.0 Hz, 1H), 2.02-1.89 (m, 3H), 1.81-1.70 (m, 2H), 1.65-1.53 (m, 2H).

Example 14: 3-(1-oxo-4-((6-(quinoline-4-oxy)hexyl) oxy)isoindoline-2-)piperidine-2,6-dione (14)

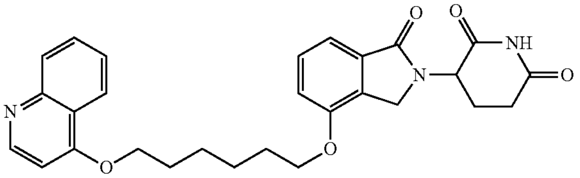 [SMILES: O=C1CCC(N2Cc3c(OCCCCCCOc4ccnc5ccccc45)cccc3C2=O)C(=O)N1]

Step 1: 1,6-hexanediol (10.00 g, 84.62 mmol, 5 eq) was dissolved in 20 ml of dichloromethane, and TEA (3.53 ml, 25.38 mmol, 1.5 eq) was added under ice bath. Then bromomethyl methyl ether (1.33 ml, 16.92 mmol, 1 eq) was added dropwise, and reacted at room temperature for 5 h. After the reaction was completed, saturated ammonium chloride was added to quench, extracted with dichloromethane, dried, concentrated, and purified by column chromatography to obtain 1.11 g of a colorless liquid, yield 41%. $^1$H NMR (400 MHz, $CDCl_3$) δ 4.61 (s, 2H), 3.63 (t, J=6.6 Hz, 1H), 3.51 (t, J=6.6 Hz, 1H), 3.35 (s, 1H), 1.63-1.53 (m, 2H), 1.51 (s, 1H), 1.43-1.34 (m, 2H).

Step 2: 6-(methoxymethoxy)-1-hexanol (180 mg, 1.24 mmol, 2.0 eq) was add into a 100 mL round bottom flask, then 4-hydroxyquinoline (100 mg, 0.62 mmol, 1 eq), and triphenylphosphine (330 mg, 1.24 mmol, 2 eq) were added. The system was replaced with $N_2$ and tetrahydrofuran (20 ml) was added. Diisopropyl azodicarboxylate (207 ul, 1.24 mmol, 2 eq) was added to the reaction system to react at room temperature for 1 h. After the reaction was completed, the solvent was spun off, and purified by column chromatography to obtain 140 mg of colorless oil, yield 78%; $^1$H NMR (400 MHz, $CDCl_3$) δ 8.75 (d, J=5.2 Hz, 1H), 8.23 (d, J=8.3 Hz, 1H), 8.04 (d, J=8.5 Hz, 1H), 7.72 (d, J=8.1 Hz, 1H), 7.51 (t, J=8.3 Hz 1H), 6.73 (d, J=5.2 Hz, 1H), 4.65 (s, 2H), 4.21 (t, J=6.3 Hz, 2H), 3.57 (t, J=8.1 Hz 2H), 3.39 (s, 3H), 2.02-1.93 (m, 3H), 1.71-1.49 (m, 6H). $[M+H]^+$ m/z=290.39.

Step 3: The compound 4-(6-(methoxymethoxy)hexyloxy) quinoline (140 mg, 0.48 mmol) was transferred to a 100 mL round bottom flask, and 10 mL dioxane hydrochloride and 1 mL methanol were added. The resulting mixed system was stirred at room temperature for 1 h. After the reaction was completed, the solvent was spun off, a small amount of aminomethanol was added, and the solvent was spun off. 118 mg (100%) of white solid was obtained by column chromatography purification, yield 100%; $^1$H NMR (400 MHz, $CDCl_3$) δ 8.72 (d, J=5.2 Hz, 1H), 8.21 (dd, J=8.3, 0.8 Hz, 1H), 8.02 (d, J=8.4 Hz, 1H), 7.72-7.66 (m, 1H), 7.53-7.47 (m, 1H), 6.71 (d, J=5.2 Hz, 1H), 4.18 (t, J=6.4 Hz, 2H), 3.69 (t, J=6.5 Hz, 2H), 1.95 (dd, J=14.5, 6.7 Hz, 2H), 1.62 (qd, J=14.5, 7.0 Hz, 4H), 1.54-1.45 (m, 2H). $[M+H]^+$ m/z=246.72.

Step 4: The compound methyl 5-amino-4-(4-hydroxy-1-oxoisoindoline-2-)-5-oxopentanoate (50 mg, 0.17 mmol, 1 eq), 5-(quinoline-4-oxy)-1-hexanol (83 mg, 0.34 mmol, 2 eq), triphenylphosphine (90 mg, 0.34 mmol, 2 eq) were added to a 50 mL round bottom flask, 20 mL of tetrahydrofuran and diisopropyl azodicarboxylate (67 ul, 0.34 mmol, 2 eq) were added to react at room temperature for 2 h. After the reaction was completed, the solvent was spun off and purified by TLC to obtain 63 mg of white solid with a yield of 71%; $^1$H NMR (400 MHz, $CDCl_3$) δ 8.73 (d, J=5.2 Hz, 1H), 8.20 (d, J=8.3 Hz, 1H), 8.01 (d, J=8.4 Hz, 1H), 7.68 (t, J=7.0 Hz, 1H), 7.47 (t, J=7.6 Hz, 1H), 7.39 (d, J=1.1 Hz, 1H), 6.98 (p, J=4.0 Hz, 1H), 6.73 (d, J=5.2 Hz, 1H), 6.54 (s, 1H), 5.61 (s, 1H), 4.92 (dd, J=8.8, 6.1 Hz, 1H), 4.40 (dd, J=38.8, 17.6 Hz, 1H), 4.22 (t, J=6.3 Hz, 1H), 4.11-4.02 (m, 1H), 3.62 (s, 1H), 2.46-2.27 (m, 1H), 2.22-2.12 (m, 1H), 2.05-1.96 (m, 1H), 1.93-1.82 (m, 1H), 1.70-1.66 (m, 2H). $[M+H]^+$ m/z=520.35.

Step 5: methyl 5-amino-5-oxo-4-(1-oxo-4-((6-(quinoline-4-oxy)hexyl)oxy)isoindoline-2-)oxopentanoate (63 mg, 0.19 mmol, 1.0 eq) was dissolved in 10 ml of dry tetrahydrofuran, potassium tert-butoxide (22 mg, 0.19 mmol, 1 eq) was added under ice bath condition, and the reaction was detected 10 min later. After the reaction was completed, 5 ul formic acid was added to quench the reaction, the solvent was spun off, and purified by HPLC to obtain 42 mg of the product as a white solid with a yield of 45%. $^1$H NMR (400 MHz, DMSO) δ 10.98 (s, 1H), 9.15 (d, J=6.5 Hz, 1H), 8.34 (d, J=8.4 Hz, 1H), 8.15 (d, J=8.6 Hz, 1H), 8.09 (t, J=8.4 Hz, 1H), 7.83 (t, J=8.4 Hz, 1H), 7.54 (d, J=6.6 Hz, 1H), 7.45 (t, J=7.8 Hz, 1H), 7.28 (d, J=7.3 Hz, 1H), 7.22 (d, J=8.1 Hz, 1H), 5.10 (dd, J=13.2, 5.1 Hz, 1H), 4.55 (t, J=6.3 Hz, 2H), 4.34 (d, J=17.4 Hz, 1H), 4.21 (d, J=17.4 Hz, 1H), 4.14 (t, J=6.3 Hz, 2H), 2.97-2.84 (m, 1H), 2.61-2.53 (m, 1H), 2.41 (qd, J=13.3, 4.5 Hz, 1H), 2.03-1.91 (m, 3H), 1.86-1.72 (m, 2H), 1.67-1.52 (m, 4H). ESI-MS $[M+H]^+$ m/z=488.76.

Example 15: 3-(1-oxo-4-(4-(quinoline-4-oxy)butyl) isoindoline-2-)piperidine-2,6-dione (15)

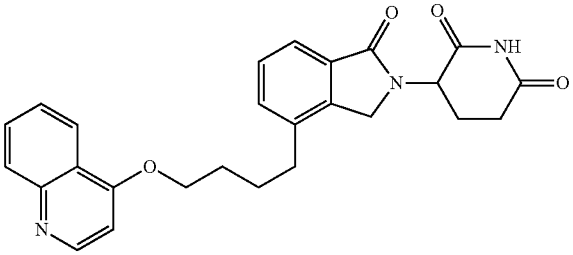

3-(4-(4-hydroxybutyl)-1-oxoisoindoline-2-)piperidine-2,6-dione (50 mg, 0.16 mmol), 4-hydroxyquinoline (70 mg, 0.48 mmol), and triphenylphosphine (84 mg, 0.32 mmol) were added to a 100 mL round bottom flask, 20 mL of dry tetrahydrofuran was added under nitrogen protection, stirred the reaction system until it became homogeneous, and then diisopropyl azodicarboxylate (65 mg, 0.32 mmol) was added and stirred at room temperature for 30 min. After the reaction was completed, the solvent was removed under reduced pressure, and the residue was separated by HPLC to obtain 21.7 mg of the product with a yield of 31%; $^1$H NMR (400 MHz, DMSO) δ 11.04 (s, 1H), 9.19 (d, J=6.4 Hz, 1H), 8.36 (d, J=8.4 Hz, 1H), 8.21-8.06 (m, 2H), 7.88 (t, J=7.4 Hz, 1H), 7.60-7.44 (m, 4H), 5.15 (dd, J=13.3, 4.9 Hz, 1H), 4.59 (t, J=5.8 Hz, 2H), 4.48 (d, J=17.2 Hz, 1H), 4.32 (d, J=17.1 Hz, 1H), 3.00-2.87 (m, 1H), 2.86-2.71 (m, 2H), 2.54 (s, 2H), 2.38-2.26 (m, 1H), 2.05-1.82 (m, 5H).

Example 16: 3-(4-(5-morpholinpentyl)-1-oxoisoindoline-2)-piperidine-2,6-dione (16)

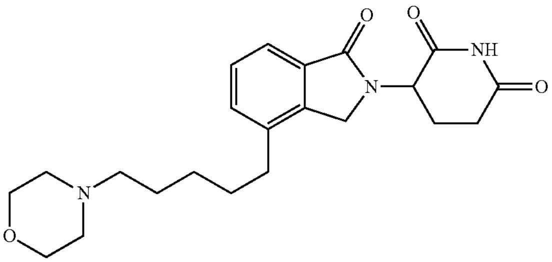 [SMILES: O=C1CCC(N2Cc3c(CCCCCN4CCOCC4)cccc3C2=O)C(=O)N1]

The compound 3-(4-(5-bromopentyl)-1-oxoisoindoline-2-)piperidine-2,6-dione (78 mg, 0.198 mmol, 1 eq.) and morpholine (34 mg, 0.396 mmol, 2 eq.) were dissolved in 5 mL dry DMF, potassium iodide (50 mg, 0.297 mmol, 2 eq.) was added under stirring at room temperature, and the resulting reaction solution was stirred overnight at room temperature. After the reaction was completed, the resulting reaction solution was directly separated by HPLC to obtain 3-(4-(5-morpholinpentyl)-1-oxoisoindoline-2-)piperidine-2,6-dione 13.4 mg, as a white solid, yield 17%; $^1$H NMR (400 MHz, DMSO) δ 11.00 (s, 1H), 7.59-7.53 (m, 1H), 7.45 (dd, J=6.2, 2.5 Hz, 2H), 5.13 (dd, J=13.3, 5.1 Hz, 1H), 4.46 (d, J=17.1 Hz, 1H), 4.30 (d, J=17.1 Hz, 1H), 3.59-3.50 (m, 4H), 2.98-2.86 (m, 1H), 2.67-2.56 (m, 3H), 2.42 (ddd, J=12.6, 9.7, 6.9 Hz, 1H), 2.31 (s, 4H), 2.28-2.21 (m, 2H), 2.06-1.96 (m, 1H), 1.61 (dt, J=15.3, 7.5 Hz, 2H), 1.51-1.39 (m, 2H), 1.32 (dt, J=14.9, 7.3 Hz, 2H).

Example 17: 3-(1-oxo-4-(5-(2-phenylpyrroline-1-) pentyl)indoline-2-)piperidine-2,6-dione (17)

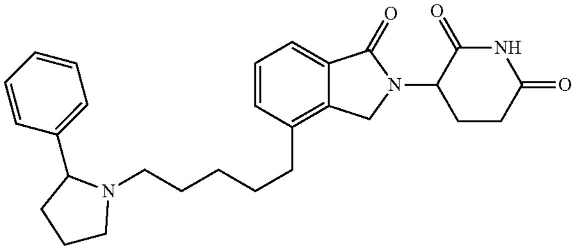 [SMILES: O=C1CCC(N2Cc3c(CCCCCN4CCCC4c4ccccc4)cccc3C2=O)C(=O)N1]

The compound 3-(4-(5-bromopentyl)-1-oxoisoindoline-2-)piperidine-2,6-dione (50 mg, 0.127 mmol) was dissolved in 3 mL dry dimethyl sulfoxide, 2-phenylpyrroline (28 mg, 0.193 mmol) and triethylamine (10 uL, 0.386 mmol) successively added under stirring at room temperature, and stirred at room temperature for 24 h. LC-MS tracked that the reaction was completed. The product was directly separated by HPLC to obtain 30.5 mg of white solid, yield 52%; $^1$H NMR (400 MHz, DMSO) δ 11.01 (s, 1H), 7.55 (d, J=7.3 Hz, 1H), 7.44 (t, J=7.4 Hz, 1H), 7.38 (d, J=7.4 Hz, 1H), 7.35-7.26 (m, 4H), 7.22 (t, J=6.5 Hz, 1H), 5.13 (dd, J=13.3, 5.1 Hz, 1H), 4.42 (dd, J=17.2, 3.9 Hz, 1H), 4.26 (d, J=17.1 Hz, 1H), 3.31-3.19 (m, 2H), 2.98-2.87 (m, 1H), 2.69-2.31 (m, 15H), 2.24-1.94 (m, 4H), 1.79 (ddd, J=19.8, 16.0, 8.8 Hz, 2H), 1.61-1.36 (m, 5H), 1.35-1.14 (m, 2H).

Example 18: 3-(1-oxo-4-(5-(4-phenylpiperazine-1-)pentyl)indoline-2-)piperidine-2,6-dione (18)

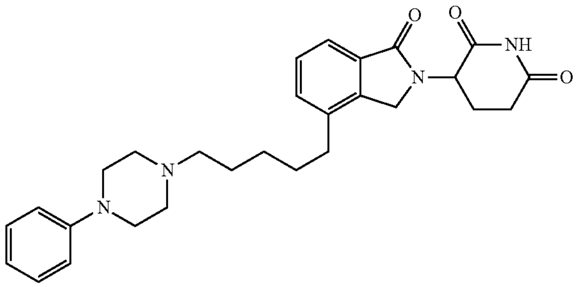 [SMILES: O=C1CCC(N2Cc3c(CCCCCN4CCN(c5ccccc5)CC4)cccc3C2=O)C(=O)N1]

The preparation method was the same as 3-(1-oxo-4-(5-(2-phenylpyrroline-1-)pentyl)indoline-2-)piperidine-2,6-dione, 22.4 mg, yield 37%; $^1H$ NMR (400 MHz, DMSO) δ 10.99 (s, 1H), 7.60-7.54 (m, 1H), 7.50-7.41 (m, 2H), 7.20 (dd, J=8.5, 7.4 Hz, 2H), 6.91 (d, J=8.0 Hz, 2H), 6.76 (t, J=7.2 Hz, 1H), 5.14 (dd, J=13.3, 5.1 Hz, 1H), 4.47 (d, J=17.2 Hz, 1H), 4.31 (d, J=17.1 Hz, 1H), 3.15-3.05 (m, 4H), 2.92 (ddd, J=17.6, 13.7, 5.4 Hz, 1H), 2.69-2.57 (m, 3H), 2.57-2.51 (m, 4H), 2.43 (dd, J=13.1, 4.3 Hz, 1H), 2.38-2.30 (m, 2H), 2.06-1.95 (m, 1H), 1.64 (dt, J=15.2, 7.6 Hz, 2H), 1.52 (dt, J=14.8, 7.6 Hz, 2H), 1.41-1.28 (m, 2H).

Example 19: 3-(4-(5-(4-(2-methoxyphenyl)piperazine-1-)pentyl)-1-oxoindoline-2-)piperidine-2,6-dione (19)

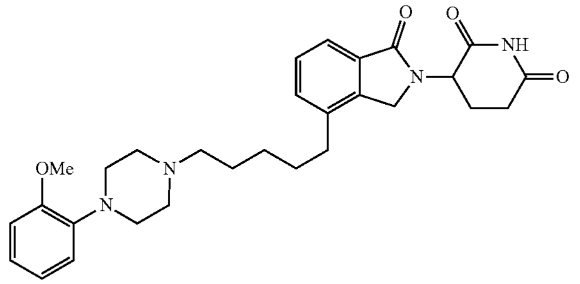 [SMILES: COc1ccccc1N1CCN(CCCCCc2cccc3c2CN(C2CCC(=O)NC2=O)C3=O)CC1]

The preparation method was the same as 3-(1-oxo-4-(5-(2-phenylpyrroline-1-)pentyl)indoline-2-)piperidine-2,6-dione, 26.3 mg, yield 41%; $^1H$ NMR (400 MHz, DMSO) δ 11.01 (s, 1H), 7.56 (dt, J=7.8, 3.9 Hz, 1H), 7.50-7.42 (m, 2H), 6.97-6.90 (m, 2H), 6.87 (d, J=3.8 Hz, 2H), 5.14 (dd, J=13.3, 5.1 Hz, 1H), 4.47 (d, J=17.2 Hz, 1H), 4.31 (d, J=17.2 Hz, 1H), 3.76 (s, 3H), 3.03-2.85 (m, 5H), 2.70-2.52 (m, 5H), 2.48-2.24 (m, 4H), 2.05-1.96 (m, 1H), 1.68-1.58 (m, 2H), 1.56-1.46 (m, 2H), 1.40-1.18 (m, 3H).

Example 20: 3-(1-oxo-4-(5-(4-phenylpiperidine-1-)pentyl)indoline-2-)piperidine-2,6-dione (20)

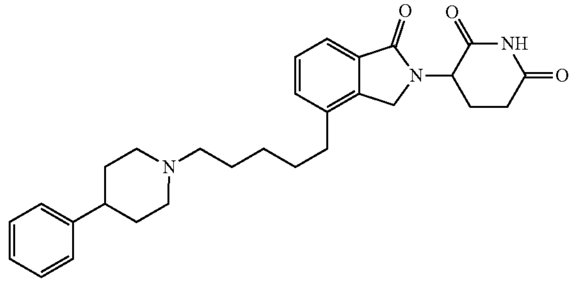 [SMILES: O=C1CCC(N2Cc3c(CCCCCN4CCC(c5ccccc5)CC4)cccc3C2=O)C(=O)N1]

The preparation method was the same as 3-(1-oxo-4-(5-(2-phenylpyrroline-1-)pentyl)indoline-2-)piperidine-2,6-dione, 15.6 mg, yield 26%; $^1H$ NMR (400 MHz, DMSO) δ 11.00 (s, 1H), 8.25 (s, 1H), 7.61-7.54 (m, 1H), 7.51-7.42 (m, 2H), 7.33-7.16 (m, 5H), 5.14 (dd, J=13.3, 5.1 Hz, 1H), 4.47 (d, J=17.2 Hz, 1H), 4.31 (d, J=17.1 Hz, 1H), 3.09 (d, J=11.3 Hz, 2H), 2.99-2.86 (m, 1H), 2.71-2.56 (m, 3H), 2.53-2.36 (m, 4H), 2.22 (dd, J=11.5, 9.7 Hz, 2H), 2.01 (ddd, J=10.2, 5.0, 3.0 Hz, 1H), 1.83-1.48 (m, 8H), 1.41-1.26 (m, 2H).

Example 21: 3-(4-(4-(4-(2,3-dichlorophenyl)piperazine-1-)butyl)-1-oxoisoindoline-2-)piperidine-2,6-dione (21)

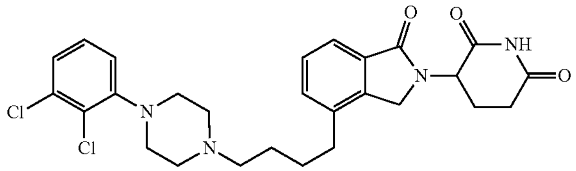 [SMILES: O=C1CCC(N2Cc3c(CCCCN4CCN(c5cccc(Cl)c5Cl)CC4)cccc3C2=O)C(=O)N1]

The preparation method was the same as 3-(1-oxo-4-(5-(2-phenylpyrroline-1-)pentyl)indoline-2-)piperidine-2,6-dione, 30.9 mg, yield 33%; $^1H$ NMR (400 MHz, DMSO) δ 11.02 (s, 1H), 8.15 (s, 1H), 7.61-7.55 (m, 1H), 7.50-7.45 (m, 2H), 7.34-7.27 (m, 2H), 7.17-7.10 (m, 1H), 5.15 (dd, J=13.3, 5.2 Hz, 1H), 4.48 (d, J=17.2 Hz, 1H), 4.33 (d, J=17.2 Hz, 1H), 3.04-2.86 (m, 5H), 2.68 (t, J=7.6 Hz, 2H), 2.65-2.53 (m, 5H), 2.47-2.35 (m, 3H), 2.07-1.98 (m, 1H), 1.71-1.59 (m, 2H), 1.52 (dt, J=14.2, 7.1 Hz, 2H).

Example 22: 3-(4-(5-(4-(6-fluorobenzo[d]isoxazole-3-)piperidine-1-)pentyl)-1-oxoisoindoline-2-)piperidine-2,6-dione (22)

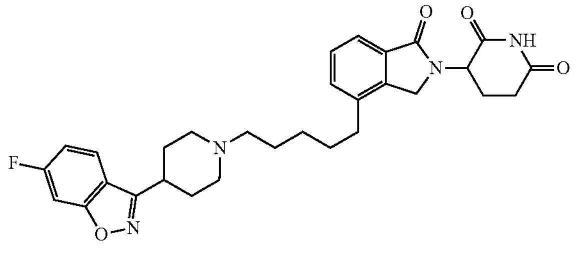 [SMILES: O=C1CCC(N2Cc3c(CCCCCN4CCC(c5noc6cc(F)ccc56)CC4)cccc3C2=O)C(=O)N1]

The preparation method was the same as 3-(1-oxo-4-(5-(2-phenylpyrroline-1-)pentyl)indoline-2-)piperidine-2,6-dione, 20.4 mg, yield 30%; $^1$H NMR (400 MHz, DMSO) δ 10.99 (s, 1H), 8.17 (s, 1H), 8.00 (dd, J=8.7, 5.3 Hz, 1H), 7.69 (dd, J=9.1, 2.1 Hz, 1H), 7.56 (dt, J=7.7, 3.9 Hz, 1H), 7.51-7.43 (m, 2H), 7.28 (td, J=9.1, 2.1 Hz, 1H), 5.14 (dd, J=13.3, 5.1 Hz, 1H), 4.47 (d, J=17.2 Hz, 1H), 4.31 (d, J=17.1 Hz, 1H), 3.23-3.12 (m, 1H), 3.05 (d, J=11.6 Hz, 2H), 2.93 (ddd, J=17.7, 13.8, 5.3 Hz, 1H), 2.71-2.55 (m, 3H), 2.47-2.35 (m, 3H), 2.23 (t, J=11.0 Hz, 2H), 2.09-1.97 (m, 3H), 1.93-1.78 (m, 2H), 1.70-1.59 (m, 2H), 1.58-1.48 (m, 2H), 1.41-1.30 (m, 2H).

Example 23: 3-(1-oxo-4-(5-(4-(3-trifluoromethylphenyl)piperazine-1-)pentyl)isoindoline-2-)piperidine-2,6-dione (23)

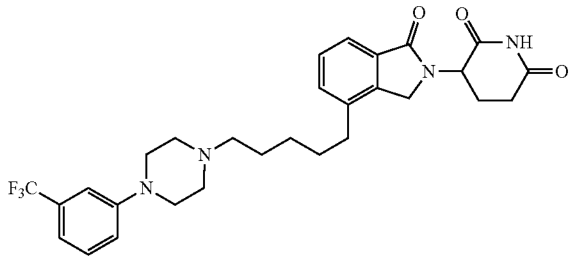 [SMILES: O=C1CCC(N2Cc3c(CCCCCN4CCN(c5cccc(C(F)(F)F)c5)CC4)cccc3C2=O)C(=O)N1]

The preparation method was the same as 3-(1-oxo-4-(5-(2-phenylpyrroline-1-)pentyl)indoline-2-)piperidine-2,6-dione, 25.5 mg, yield 30%; $^1$H NMR (400 MHz, DMSO) δ 11.01 (s, 1H), 7.57 (dd, J=5.0, 2.0 Hz, 1H), 7.49-7.44 (m, 2H), 7.41 (t, J=8.1 Hz, 1H), 7.21 (dd, J=8.6, 2.1 Hz, 1H), 7.15 (s, 1H), 7.06 (d, J=7.4 Hz, 1H), 5.14 (dd, J=13.2, 5.3 Hz, 1H), 4.47 (d, J=17.2 Hz, 1H), 4.31 (d, J=17.0 Hz, 1H), 3.28 (d, J=48.8 Hz, 7H), 2.98-2.87 (m, 1H), 2.63 (dt, J=22.0, 15.0 Hz, 4H), 2.46-2.30 (m, 3H), 2.05-1.95 (m, 1H), 1.70-1.58 (m, 2H), 1.52 (dt, J=9.8, 6.2 Hz, 2H), 1.41-1.28 (m, 2H).

Example 24: 3-(1-oxo-4-(5-(4-(quinoline-4-)piperazine-1-)pentyl)isoindoline-2-)piperidine-2,6-dione (24)

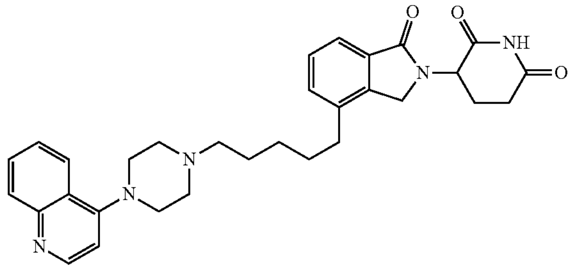 [SMILES: O=C1CCC(N2Cc3c(CCCCCN4CCN(c5ccnc6ccccc56)CC4)cccc3C2=O)C(=O)N1]

The preparation method was the same as 3-(1-oxo-4-(5-(2-phenylpyrroline-1-)pentyl)indoline-2-)piperidine-2,6-dione, 16.2 mg, yield 24%; $^1$H NMR (400 MHz, DMSO) δ 11.03 (s, 1H), 8.69 (d, J=4.9 Hz, 1H), 8.16 (s, 2H), 8.01 (d, J=8.1 Hz, 1H), 7.95 (d, J=8.3 Hz, 1H), 7.73-7.66 (m, 1H), 7.60-7.52 (m, 2H), 7.51-7.44 (m, 2H), 6.98 (d, J=5.0 Hz, 1H), 5.15 (dd, J=13.3, 5.0 Hz, 1H), 4.49 (d, J=17.2 Hz, 1H), 4.32 (d, J=17.2 Hz, 1H), 3.24-3.09 (m, 4H), 3.00-2.88 (m, 1H), 2.73-2.57 (m, 6H), 2.48-2.38 (m, 3H), 2.06-1.97 (m, 1H), 1.66 (dt, J=15.3, 7.7 Hz, 2H), 1.60-1.49 (m, 2H), 1.44-1.32 (m, 2H).

Example 25: (S)-3-(4-(3-(4-(2,3-dichlorophenyl)piperazine-1-)propoxy)-1-oxoisoindoline-2-)-3-methylpiperidine-2,6-dione (25)

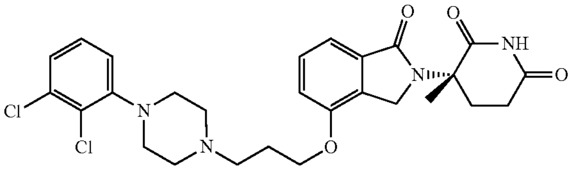 [SMILES: C[C@]1(N2Cc3c(OCCCN4CCN(c5cccc(Cl)c5Cl)CC4)cccc3C2=O)CCC(=O)NC1=O]

The preparation method was the same as 3-(1-oxo-4-(5-(2-phenylpyrroline-1-)pentyl)indoline-2-)piperidine-2,6-dione, and obtained 15 mg of final product, as a white solid, yield 27%; 1H NMR (400 MHz, DMSO) δ 10.87 (s, 1H), 7.46 (t, J=7.8 Hz, 1H), 7.34-7.11 (m, 5H), 4.65 (d, J=17.5 Hz, 1H), 4.54 (d, J=17.7 Hz, 1H), 4.19 (t, J=5.9 Hz, 2H), 3.00 (s, 3H), 2.67 (ddd, J=51.9, 30.3, 22.3 Hz, 7H), 2.00-1.83 (m, 3H), 1.70 (s, 3H).

Example 26: 3-(4-(5-(4-(2,3-dichlorophenyl)piperazine-1-)pentyl)-1-oxoisoindoline-2-)piperidine-2,6-dione (26)

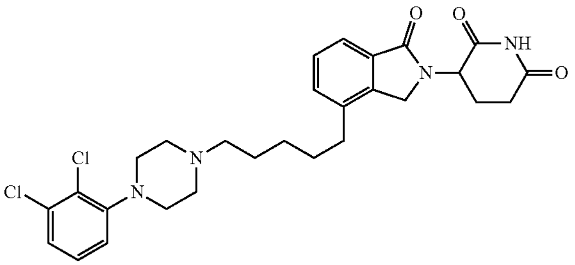 [SMILES: O=C1CCC(N2Cc3c(CCCCCN4CCN(c5cccc(Cl)c5Cl)CC4)cccc3C2=O)C(=O)N1]

The preparation method was the same as 3-(1-oxo-4-(5-(2-phenylpyrroline-1-)pentyl)indoline-2-)piperidine-2,6-dione, 29.0 mg, yield 42%; $^1$H NMR (400 MHz, DMSO) δ 10.99 (s, 1H), 8.16 (s, 1H), 7.60-7.53 (m, 1H), 7.49-7.42 (m, 2H), 7.33-7.26 (m, 2H), 7.16-7.10 (m, 1H), 5.75 (s, 1H), 5.14 (dd, J=13.3, 5.1 Hz, 1H), 4.47 (d, J=17.2 Hz, 1H), 4.31 (d, J=17.2 Hz, 1H), 3.01-2.86 (m, 5H), 2.69-2.63 (m, 2H), 2.58 (s, 1H), 2.53 (d, J=6.6 Hz, 4H), 2.47-2.38 (m, 1H), 2.37-2.29 (m, 2H), 2.06-1.96 (m, 1H), 1.63 (dt, J=15.3, 7.8 Hz, 2H), 1.57-1.43 (m, 2H), 1.40-1.29 (m, 2H).

Example 27: (S)-4-(3-(4-(2,3-dichlorophenyl)piperazine-1-)propoxy)-2-(3-methyl-2,6-dioxopiperidine-3-)isoindoline-1,3-dione (27)

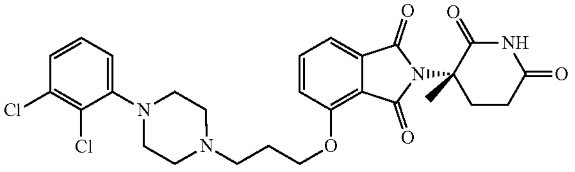 [SMILES: C[C@]1(N2C(=O)c3cccc(OCCCN4CCN(c5cccc(Cl)c5Cl)CC4)c3C2=O)CCC(=O)NC1=O]

The preparation method was the same as 3-(1-oxo-4-(5-(2-phenylpyrroline-1-)pentyl)indoline-2-)piperidine-2,6-dione, and obtained 25 mg of final product, as a white solid, yield 45%; 1H NMR (400 MHz, DMSO) δ 11.00 (s, 1H), 7.78 (t, J=7.9 Hz, 1H), 7.50 (d, J=8.5 Hz, 1H), 7.37 (d, J=7.2 Hz, 1H), 7.33-7.27 (m, 2H), 7.14 (dd, J=5.8, 3.6 Hz, 1H), 4.24 (t, J=6.0 Hz, 2H), 2.98 (s, 4H), 2.75-2.51 (m, 9H), 2.08-1.91 (m, 3H), 1.86 (d, J=6.1 Hz, 3H).

Example 28: 3-(1-oxo-4-(4-oxo-4-(4-phenylpiperazine-1-)butoxy)isoindoline-2-)piperidine-2,6-dione (28)

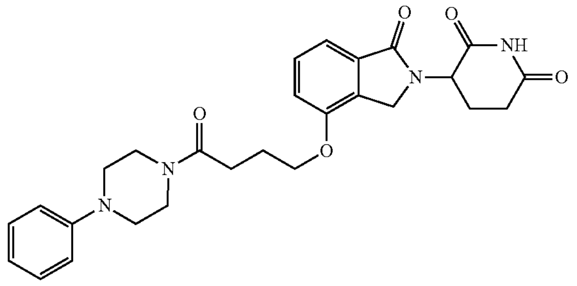 [SMILES: O=C1CCC(N2Cc3c(OCCCC(=O)N4CCN(c5ccccc5)CC4)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and obtained 26 mg of final product, as a white solid, yield 56%; $^1$H NMR (400 MHz, DMSO) δ 10.98 (s, 1H), 7.47 (t, J=7.8 Hz, 1H), 7.30 (d, J=7.5 Hz, 1H), 7.23 (dd, J=15.1, 7.6 Hz, 3H), 6.93 (d, J=8.0 Hz, 2H), 6.80 (t, J=7.2 Hz, 1H), 5.11 (dd, J=13.3, 5.1 Hz, 1H), 4.40 (d, J=17.4 Hz, 1H), 4.24 (d, J=17.4 Hz, 1H), 4.16 (t, J=6.3 Hz, 2H), 3.60 (d, J=4.6 Hz, 4H), 3.10 (dd, J=9.7, 4.7 Hz, 4H), 2.99-2.85 (m, 1H), 2.56 (dd, J=16.8, 9.9 Hz, 3H), 2.47-2.37 (m, 1H), 2.06-1.93 (m, 3H).

Example 29: 3-(4-(4-(4-(2,3-dichlorophenyl)piperazine-1-)-4-oxobutoxy)-1-oxoisoindoline-2-)piperidine-2,6-dione (29)

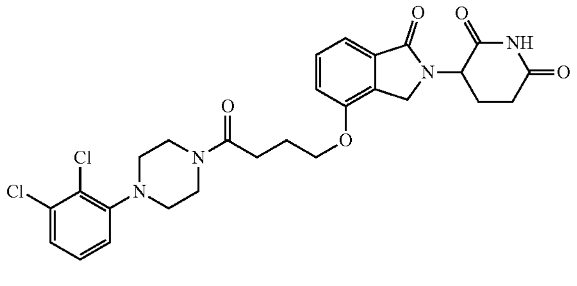 [SMILES: O=C1CCC(N2Cc3c(OCCCC(=O)N4CCN(c5cccc(Cl)c5Cl)CC4)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and obtained 21 mg of final product, as a white solid, yield 26%; $^1$H NMR (400 MHz, DMSO) δ 10.97 (s, 1H), 7.48 (t, J=7.8 Hz, 1H), 7.37-7.28 (m, 3H), 7.25 (d, J=8.1 Hz, 1H), 7.13-7.07 (m, 1H), 5.11 (dd, J=13.3, 5.1 Hz, 1H), 4.40 (d, J=17.4 Hz, 1H), 4.25 (d, J=17.4 Hz, 1H), 4.16 (t, J=6.3 Hz, 2H), 3.62 (d, J=3.6 Hz, 4H), 2.91 (td, J=14.2, 7.7 Hz, 5H), 2.64-2.53 (m, 3H), 2.48-2.35 (m, 1H), 2.06-1.94 (m, 3H).

Example 30: 3-(1-oxo-4-((5-oxo-5-(4-phenylpiperazine-1-)pentyloxy)isoindoline-2-)piperidine-2,6-dione (30)

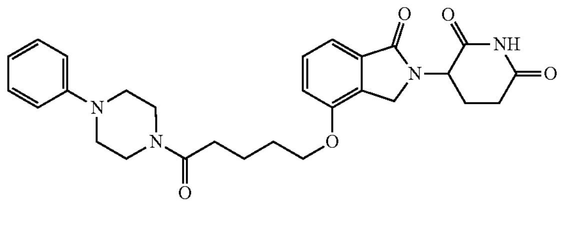 [SMILES: O=C1CCC(N2Cc3c(OCCCCC(=O)N4CCN(c5ccccc5)CC4)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and obtained 26 mg of final product, as a white solid, yield 37%; $^1$H NMR (400 MHz, DMSO) δ 10.97 (s, 1H), 7.48 (t, J=7.8 Hz, 1H), 7.31 (d, J=7.4 Hz, 1H), 7.27-7.16 (m, 3H), 6.95 (d, J=7.9 Hz, 2H), 6.81 (t, J=7.3 Hz, 1H), 5.10 (dd, J=13.3, 5.1 Hz, 1H), 4.38 (d, J=17.4 Hz, 1H), 4.23 (d, J=17.4 Hz, 1H), 4.15 (t, J=6.2 Hz, 2H), 3.65-3.56 (m, 4H), 3.19-3.04 (m, 4H), 2.98-2.85 (m, 1H), 2.57 (d, J=18.5 Hz, 1H), 2.50-2.37 (m, 4H), 2.04-1.93 (m, 1H), 1.74 (ddd, J=21.7, 14.2, 6.9 Hz, 4H).

Example 31: 3-(4-((5-(4-(2,3-dichlorophenyl)piperazine-1-)-5-oxopentyl)oxy)-1-oxopentyl-2-)piperidine-2,6-dione (31)

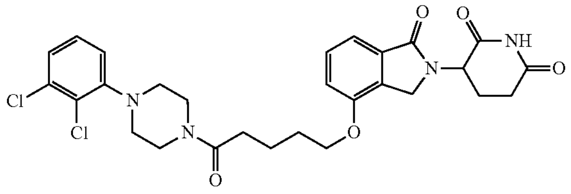 [SMILES: O=C1CCC(N2Cc3c(OCCCCC(=O)N4CCN(c5cccc(Cl)c5Cl)CC4)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, 20 mg of final product was afforded as a white solid, yield 25%; $^1$H NMR (400 MHz, DMSO) δ 10.96 (s, 1H), 7.48 (t, J=7.8 Hz, 1H), 7.37-7.27 (m, 3H), 7.25 (d, J=8.1 Hz, 1H), 7.12 (dd, J=6.3, 3.3 Hz, 1H), 5.10 (dd, J=13.3, 5.1 Hz, 1H), 4.37 (d, J=17.4 Hz, 1H), 4.23 (d, J=17.3 Hz, 1H), 4.15 (t, J=6.2 Hz, 2H), 3.60 (d, J=4.6 Hz, 4H), 3.00-2.81 (m, 5H), 2.56 (d, J=18.6 Hz, 1H), 2.49-2.36 (m, 4H), 2.02-1.92 (m, 1H), 1.74 (ddd, J=21.8, 14.3, 7.0 Hz, 4H).

Example 32: 4-(2,3-dichlorophenyl)-N-(2-((2-(2,6-dioxopiperidine-3-)-1-oxoisoindoline-4-)oxy)ethyl) piperazine-1-carboxamide (32)

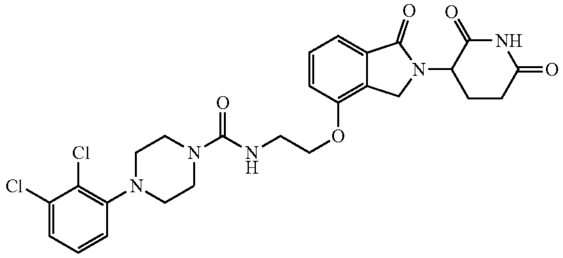 [SMILES: O=C1CCC(N2Cc3c(OCCNC(=O)N4CCN(c5cccc(Cl)c5Cl)CC4)cccc3C2=O)C(=O)N1]

3-(4-(2-aminoethoxy)-1-oxoisoindoline-2-)piperidine-2,6-dione hydrochloride (50 mg, 0.147 mmol) was dissolved in 3 mL dry DMSO, triethylamine (61 μL, 0.44 mmol) and carbonyldiimidazole (36 mg, 0.22 mmol) were added at room temperature while stirring. The resulting reaction solution was stirred and reacted at 40° C. for 0.5 h. After completely converted into active intermediate, 4-(2,3-dichlorophenyl)piperazine hydrochloride (59 mg, 0.22 mmol) was added to the reaction solution. The resulting reaction solution was stirred and reacted at 40° C. for 2 h. After the reaction was completed, the reaction solution was separated by HPLC to afford 39.6 mg target product, yield 48%; $^1$H NMR (400 MHz, DMSO) δ 10.97 (s, 1H), 7.48 (t, J=7.8 Hz, 1H), 7.35-7.26 (m, 3H), 7.16-7.09 (m, 1H), 6.81 (t, J=5.3 Hz, 1H), 5.11 (dd, J=13.3, 5.1 Hz, 1H), 4.39 (d, J=17.4 Hz, 1H), 4.25 (d, J=17.3 Hz, 1H), 4.17 (t, J=5.9 Hz, 2H), 3.58-3.37 (m, 6H), 3.01-2.80 (m, 5H), 2.63-2.55 (m, 1H), 2.41 (ddd, J=26.1, 13.1, 4.4 Hz, 1H), 2.04-1.94 (m, 1H).

Example 33: 4-(2,3-dichlorophenyl)-N-(4-((2-(2,6-dioxopiperidine-3-)-1-oxoisoindoline-4-)oxy)butyl) piperazine-1-carboxamide (33)

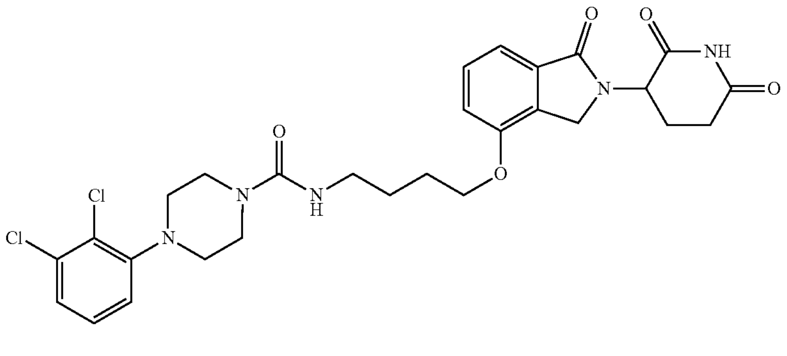 [SMILES: O=C1CCC(N2Cc3c(OCCCCNC(=O)N4CCN(c5cccc(Cl)c5Cl)CC4)cccc3C2=O)C(=O)N1]

The preparation method was the same as 4-(2,3-dichlorophenyl)-N-(2-((2-(2,6-dioxopiperidine-3-)-1-oxoisoindoline-4-)oxy)ethyl)piperazine-1-carboxamide, and obtained white solid compound, 44.6 mg, yield 56%; $^1$H NMR (400 MHz, DMSO) δ 10.96 (s, 1H), 7.48 (t, J=7.8 Hz, 1H), 7.31 (t, J=5.8 Hz, 3H), 7.24 (d, J=8.1 Hz, 1H), 7.16-7.12 (m, 1H), 6.60 (t, J=5.4 Hz, 1H), 5.11 (dd, J=13.2, 5.0 Hz, 1H), 4.39 (d, J=17.4 Hz, 1H), 4.23 (d, J=17.4 Hz, 1H), 4.13 (t, J=6.3 Hz, 2H), 3.46-3.39 (m, 4H), 3.12 (dd, J=12.7, 6.8 Hz, 2H), 2.97-2.85 (m, 5H), 2.58 (d, J=18.6 Hz, 1H), 2.50-2.40 (m, 1H), 2.03-1.95 (m, 1H), 1.79-1.72 (m, 2H), 1.64-1.54 (m, 2H).

Example 34: 4-(2,3-dichlorophenyl)-N-(3-((2-(2,6-dioxopiperidine-3-)-1-oxoisoindole-4-)oxy)propyl) piperidine-1-carboxamide (34)

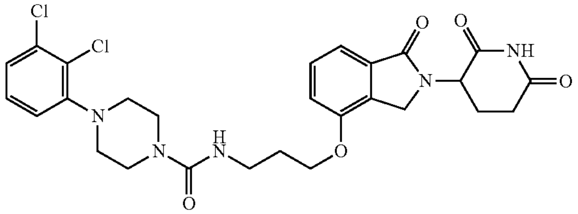 [SMILES: O=C1CCC(N2Cc3c(OCCCNC(=O)N4CCN(c5cccc(Cl)c5Cl)CC4)cccc3C2=O)C(=O)N1]

The preparation method was the same as 4-(2,3-dichlorophenyl)-N-(2-((2-(2,6-dioxopiperidine-3-)-1-oxoisoindoline-4-)oxy)ethyl)piperazine-1-carboxamide, and 20.3 mg of white solid was obtained, yield 29%; $^1$H NMR (400 MHz, DMSO) δ 10.97 (s, 1H), 7.48 (t, J=8.0 Hz, 1H), 7.34-7.29 (m, 3H), 7.24 (d, J=8.1 Hz, 1H), 7.15-7.11 (m, 1H), 6.68 (t, J=5.4 Hz, 1H), 5.11 (dd, J=13.0, 5.0 Hz, 1H), 4.39 (d, J=17.5 Hz, 1H), 4.24 (d, J=17.5 Hz, 1H), 4.15 (t, J=6.0 Hz, 2H), 3.44 (t, 4H), 3.26-3.19 (m, 2H), 2.90 (t, 4H), 2.63-2.55 (m, 1H), 2.45-2.32 (m, 1H), 2.04-1.86 (m, 3H).

Example 35: 3-(4-(6-(4-(2,3-dichlorophenyl)piperazine-1-)hexyl)-1-oxoisoindoline-2-)piperidine-2,6-dione (35)

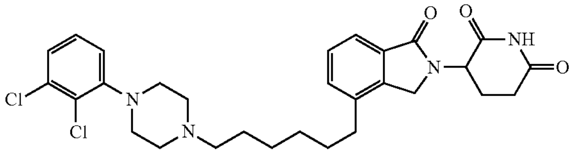 [SMILES: O=C1CCC(N2Cc3c(CCCCCCN4CCN(c5cccc(Cl)c5Cl)CC4)cccc3C2=O)C(=O)N1]

The preparation method was the same as 3-(1-oxo-4-(5-(2-phenylpyrroline-1-)pentyl)indoline-2-)piperidine-2,6-dione, 30.5 mg, yield 30%; $^1$H NMR (400 MHz, DMSO) δ 10.99 (s, 1H), 7.56 (dd, J=8.2, 4.5 Hz, 1H), 7.46 (d, J=3.5 Hz, 2H), 7.30 (dd, J=9.1, 5.3 Hz, 2H), 7.13 (dd, J=6.3, 3.1 Hz, 1H), 5.13 (dd, J=13.3, 5.1 Hz, 1H), 4.46 (d, J=17.1 Hz, 1H), 4.31 (d, J=17.2 Hz, 1H), 3.32 (s, 4H), 3.0-2.88 (m, 5H), 2.68-2.56 (m, 3H), 2.47-2.37 (m, 1H), 2.32 (s, 2H), 2.04-1.96 (m, 1H), 1.66-1.56 (m, 2H), 1.50-1.40 (m, 2H), 1.38-1.27 (m, 4H).

Example 36: 4-(4-(4-(2-(2,6-dioxopiperidine-3-)-1-oxoisoindoline-4-)butyl)piperazine-1-)benzonitrile (36)

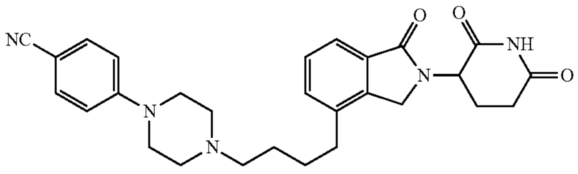 [SMILES: N#Cc1ccc(N2CCN(CCCCc3cccc4c3CN(C3CCC(=O)NC3=O)C4=O)CC2)cc1]

The preparation method was the same as 3-(1-oxo-4-(5-(2-phenylpyrroline-1-)pentyl)indoline-2-)piperidine-2,6-dione, 12.5 mg white solid, yield 20%; $^1$H NMR (400 MHz, DMSO) δ 10.99 (s, 1H), 7.60-7.53 (m, 3H), 7.49-7.44 (m, 2H), 7.00 (d, J=9.0 Hz, 2H), 5.13 (dd, J=13.3, 5.2 Hz, 1H), 4.47 (d, J=17.2 Hz, 1H), 4.31 (d, J=17.2 Hz, 1H), 3.32-3.28 (m, 4H), 2.97-2.86 (m, 1H), 2.67 (t, J=7.6 Hz, 2H), 2.58 (d, J=16.3 Hz, 1H), 2.47-2.43 (m, 4H), 2.42-2.32 (m, 3H), 2.05-1.96 (m, 1H), 1.69-1.60 (m, 2H), 1.54-1.46 (m, 2H).

Example 37: 3-(4-(4-(4-(3-chlorophenyl)piperazine-1-)butyl)-1-oxoisoindoline-2-)piperidine-2,6-dione (37)

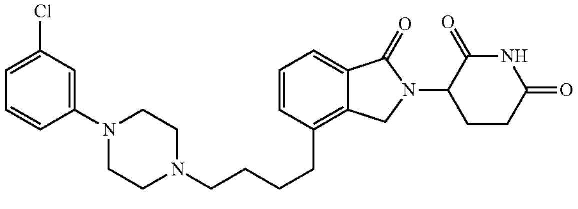 [SMILES: O=C1CCC(N2Cc3c(CCCCN4CCN(c5cccc(Cl)c5)CC4)cccc3C2=O)C(=O)N1]

The preparation method was the same as 3-(1-oxo-4-(5-(2-phenylpyrroline-1-)pentyl)indoline-2-)piperidine-2,6-dione, 21 mg white solid, yield 32.6%; $^1$H NMR (400 MHz, DMSO) δ 10.99 (s, 1H), 7.57 (dt, J=7.7, 3.9 Hz, 1H), 7.49-7.43 (m, 2H), 7.19 (t, J=8.1 Hz, 1H), 6.94-6.84 (m, 2H), 6.77 (dd, J=7.8, 1.4 Hz, 1H), 5.13 (dd, J=13.3, 5.1 Hz, 1H), 4.47 (d, J=17.2 Hz, 1H), 4.32 (d, J=17.1 Hz, 1H), 3.20-3.10 (m, 4H), 2.98-2.86 (m, 1H), 2.67 (t, J=7.5 Hz, 2H), 2.59 (d, J=17.0 Hz, 1H), 2.49-2.46 (m, 4H), 2.45-2.35 (m, 3H), 2.05-1.96 (m, 1H), 1.69-1.59 (m, 2H), 1.56-1.46 (m, 2H).

Example 38: 2-(4-(4-(2-(2,6-dioxopiperidine-3-)-1-oxoisoindoline-4-)butyl)piperazine-1-)benzonitrile (38)

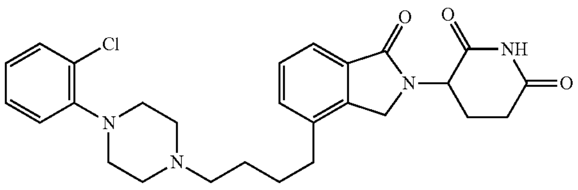 [SMILES: O=C1CCC(N2Cc3c(CCCCN4CCN(c5ccccc5Cl)CC4)cccc3C2=O)C(=O)N1]

The preparation method was the same as 3-(1-oxo-4-(5-(2-phenylpyrroline-1-)pentyl)indoline-2-)piperidine-2,6-dione, 20 mg yellow solid, yield 31.7%; $^1$H NMR (400 MHz, DMSO) δ 10.99 (s, 1H), 7.69 (dd, J=7.7, 1.5 Hz, 1H), 7.62-7.55 (m, 2H), 7.49-7.45 (m, 2H), 7.14 (d, J=8.2 Hz, 1H), 7.08 (t, J=7.6 Hz, 1H), 5.14 (dd, J=13.2, 5.1 Hz, 1H), 4.48 (d, J=17.1 Hz, 1H), 4.32 (d, J=17.1 Hz, 1H), 3.17-3.10 (m, 4H), 2.97-2.87 (m, 1H), 2.72-2.65 (m, 2H), 2.60 (d, J=17.2 Hz, 1H), 2.54 (t, 4H), 2.47-2.36 (m, 3H), 2.06-1.98 (m, 1H), 1.65 (dt, J=15.6, 6.3 Hz, 2H), 1.52 (dt, J=14.8, 7.5 Hz, 2H).

Example 39: 3-(4-(4-(4-(4-fluorophenyl)piperazine-1-)butyl)-1-oxoisoindoline-2-)piperidine-2,6-dione (39)

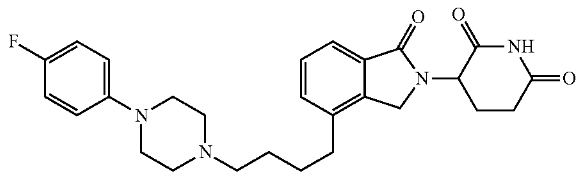 [SMILES: O=C1CCC(N2Cc3c(CCCCN4CCN(c5ccc(F)cc5)CC4)cccc3C2=O)C(=O)N1]

The preparation method was the same as 3-(1-oxo-4-(5-(2-phenylpyrroline-1-)pentyl)indoline-2-)piperidine-2,6-dione, 41.4 mg white solid, yield 66.5%; $^1$H NMR (400 MHz, DMSO) δ 10.99 (s, 1H), 7.57 (dd, J=5.2, 3.4 Hz, 1H), 7.49-7.44 (m, 2H), 7.03 (t, J=8.9 Hz, 2H), 6.96-6.89 (m, 2H), 5.13 (dd, J=13.2, 5.0 Hz, 1H), 4.47 (d, J=17.2 Hz, 1H), 4.32 (d, J=17.1 Hz, 1H), 3.08-3.01 (m, 4H), 2.97-2.86 (m, 1H), 2.68 (t, J=7.6 Hz, 2H), 2.58 (d, J=17.6 Hz, 1H), 2.49-2.46 (m, 4H), 2.44-2.34 (m, 3H), 2.01 (dt, J=10.4, 5.0 Hz, 1H), 1.69-1.59 (m, 2H), 1.51 (dt, J=14.2, 7.1 Hz, 2H).

Example 40: 3-(1-oxo-4-(4-(4-(3-methylphenyl) piperazine-1-)butyl)isoindoline-2-)piperidine-2,6-dione (40)

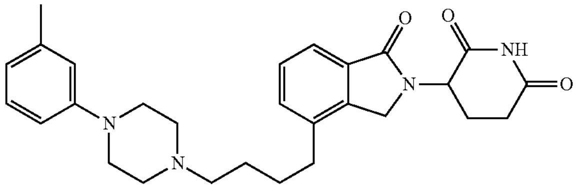 [SMILES: Cc1cccc(N2CCN(CCCCc3cccc4c3CN(C3CCC(=O)NC3=O)C4=O)CC2)c1]

The preparation method was the same as 3-(1-oxo-4-(5-(2-phenylpyrroline-1-)pentyl)indoline-2-)piperidine-2,6-dione, 45.2 mg white solid, yield 73.3%; $^1$H NMR (400 MHz, DMSO) δ 10.99 (s, 1H), 7.57 (dd, J=5.4, 3.2 Hz, 1H), 7.50-7.44 (m, 2H), 7.07 (t, J=7.8 Hz, 1H), 6.76-6.66 (m, 2H), 6.58 (d, J=7.3 Hz, 1H), 5.13 (dd, J=13.3, 5.1 Hz, 1H), 4.47 (d, J=17.2 Hz, 1H), 4.32 (d, J=17.2 Hz, 1H), 3.12-3.07 (m, 4H), 2.97-2.86 (m, 1H), 2.68 (t, J=7.5 Hz, 2H), 2.58 (d, J=17.4 Hz, 1H), 2.44-2.34 (m, 3H), 2.23 (s, 3H), 2.05-1.96 (m, 1H), 1.69-1.59 (m, 2H), 1.51 (dt, J=14.7, 7.5 Hz, 2H).

Example 41: 3-(4-(4-(4-(4-chlorophenyl)piperazine-1-)butyl)-1-oxoisoindoline-2-)piperidine-2,6-dione (41)

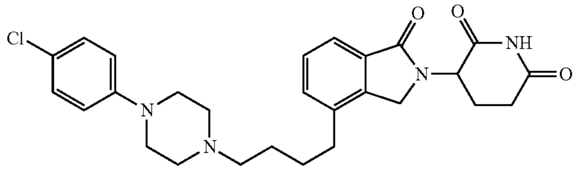 [SMILES: O=C1CCC(N2Cc3c(CCCCN4CCN(c5ccc(Cl)cc5)CC4)cccc3C2=O)C(=O)N1]

The preparation method was the same as 3-(1-oxo-4-(5-(2-phenylpyrroline-1-)pentyl)indoline-2-)piperidine-2,6-dione, 42.8 mg white solid, yield 66.5%; $^1$H NMR (400 MHz, DMSO) δ 10.99 (s, 1H), 7.57 (dd, J=5.4, 3.2 Hz, 1H), 7.49-7.45 (m, 2H), 7.22 (d, J=9.0 Hz, 2H), 6.93 (d, J=9.0 Hz, 2H), 5.14 (dd, J=13.2, 5.1 Hz, 1H), 4.47 (d, J=17.1 Hz, 1H), 4.32 (d, J=17.2 Hz, 1H), 3.14 (s, 4H), 2.98-2.86 (m, 1H), 2.68 (t, J=7.5 Hz, 2H), 2.62-2.53 (m, 5H), 2.48-2.35 (m, 3H), 2.05-1.95 (m, 1H), 1.65 (dt, J=15.5, 6.9 Hz, 2H), 1.53 (dt, J=15.2, 7.6 Hz, 2H).

Example 42: 3-(4-(4-(4-(4-nitrophenyl)piperazine-1-)butyl)-1-oxoisoindoline-2-)piperidine-2,6-dione (42)

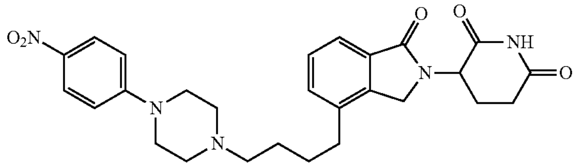 [SMILES: O=C1CCC(N2Cc3c(CCCCN4CCN(c5ccc([N+](=O)[O-])cc5)CC4)cccc3C2=O)C(=O)N1]

The preparation method was the same as 3-(1-oxo-4-(5-(2-phenylpyrroline-1-)pentyl)indoline-2-)piperidine-2,6-dione, 34.9 mg yellow solid, yield 53%; $^1$H NMR (400 MHz, DMSO) δ 10.99 (s, 1H), 8.05 (d, J=9.4 Hz, 2H), 7.57 (dd, J=5.4, 3.2 Hz, 1H), 7.50-7.45 (m, 2H), 7.01 (d, J=9.5 Hz, 2H), 5.14 (dd, J=13.3, 5.0 Hz, 1H), 4.47 (d, J=17.2 Hz, 1H), 4.32 (d, J=17.2 Hz, 1H), 3.45-3.41 (m, 4H), 2.97-2.87 (m, 1H), 2.68 (t, J=7.6 Hz, 2H), 2.59 (d, J=17.2 Hz, 1H), 2.49-2.44 (m, 4H), 2.44-2.33 (m, 3H), 2.06-1.96 (m, 1H), 1.70-1.59 (m, 2H), 1.51 (dt, J=15.2, 7.7 Hz, 2H).

Example 43: 3-(4-(4-(4-(2,4-difluorophenyl)piperazine-1-)butyl)-1-oxoisoindoline-2-)piperidine-2,6-dione (43)

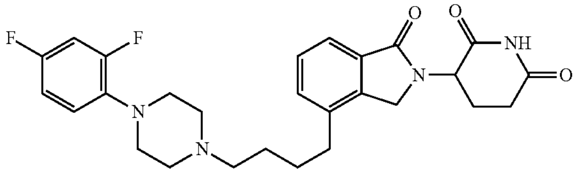 [SMILES: O=C1CCC(N2Cc3c(CCCCN4CCN(c5ccc(F)cc5F)CC4)cccc3C2=O)C(=O)N1]

The preparation method was the same as 3-(1-oxo-4-(5-(2-phenylpyrroline-1-)pentyl)indoline-2-)piperidine-2,6-dione, 13.3 mg white solid, yield 20.6%; $^1$H NMR (400 MHz, DMSO) δ 10.99 (s, 1H), 7.56 (dt, J=7.7, 3.9 Hz, 1H), 7.49-7.44 (m, 2H), 7.22-7.14 (m, 1H), 7.08-6.94 (m, 2H), 5.14 (dd, J=13.2, 4.9 Hz, 1H), 4.47 (d, J=17.1 Hz, 1H), 4.32 (d, J=17.2 Hz, 1H), 2.98-2.87 (m, 5H), 2.67 (t, J=7.6 Hz, 2H), 2.59 (d, J=17.6 Hz, 1H), 2.46-2.30 (m, 7H), 2.06-1.97 (m, 1H), 1.68-1.57 (m, 2H), 1.55-1.45 (m, 2H).

Example 44: 3-(4-(4-(4-(3,4-dichlorophenyl)piperazine-1-)butyl)-1-oxoisoindoline-2-)piperidine-2,6-dione (44)

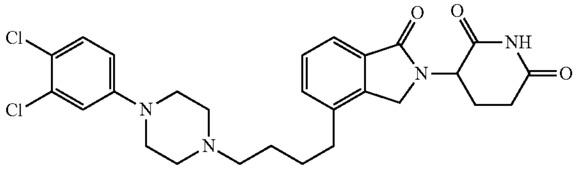 [SMILES: O=C1CCC(N2Cc3c(CCCCN4CCN(c5ccc(Cl)c(Cl)c5)CC4)cccc3C2=O)C(=O)N1]

The preparation method was the same as 3-(1-oxo-4-(5-(2-phenylpyrroline-1-)pentyl)indoline-2-)piperidine-2,6-dione, 45.8 mg white solid, yield 66.5%; $^1$H NMR (400 MHz, DMSO) δ 10.99 (s, 1H), 7.56 (dd, J=8.1, 4.8 Hz, 1H), 7.49-7.45 (m, 2H), 7.38 (d, J=9.0 Hz, 1H), 7.10 (d, J=2.8 Hz, 1H), 6.91 (dd, J=9.1, 2.9 Hz, 1H), 5.13 (dd, J=13.3, 5.0 Hz, 1H), 4.47 (d, J=17.2 Hz, 1H), 4.31 (d, J=17.2 Hz, 1H), 3.16 (m, 4H), 2.98-2.86 (m, 1H), 2.67 (t, J=7.6 Hz, 2H), 2.59 (d, J=16.4 Hz, 1H), 2.48-2.31 (m, 7H), 2.05-1.96 (m, 1H), 1.64 (dt, J=15.1, 7.2 Hz, 2H), 1.56-1.45 (m, 2H).

Example 45: 3-(1-oxo-4-(4-(4-(4-trifluoromethylphenyl)piperazine-1-)butyl)isoindoline-2-)piperidine-2,6-dione (45)

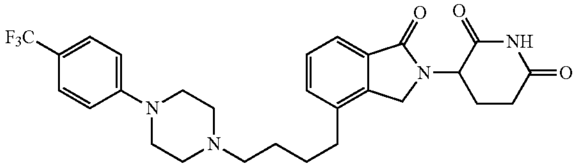 [SMILES: O=C1CCC(N2Cc3c(CCCCN4CCN(c5ccc(C(F)(F)F)cc5)CC4)cccc3C2=O)C(=O)N1]

The preparation method was the same as 3-(1-oxo-4-(5-(2-phenylpyrroline-1-)pentyl)indoline-2-)piperidine-2,6-dione, 27.6 mg white solid, yield 40.6%; $^1$H NMR (400 MHz, DMSO) δ 10.99 (s, 1H), 7.58 (dd, J=5.5, 3.0 Hz, 1H), 7.55-7.46 (m, 4H), 7.07 (d, J=7.9 Hz, 2H), 5.14 (dd, J=13.4, 5.3 Hz, 1H), 4.48 (d, J=17.2 Hz, 1H), 4.32 (d, J=17.1 Hz, 1H), 3.20-3.10 (m, 4H), 2.99-2.87 (m, 1H), 2.72-2.65 (m, 2H), 2.60 (d, J=16.5 Hz, 1H), 2.46-2.30 (m, 7H), 2.05-1.96 (m, 1H), 1.67-1.54 (m, 4H).

Example 46: 3-(4-(4-(4-(4-methoxyphenyl)piperazine-1-)butyl)-1-oxoisoindoline-2-)piperidine-2,6-dione (46)

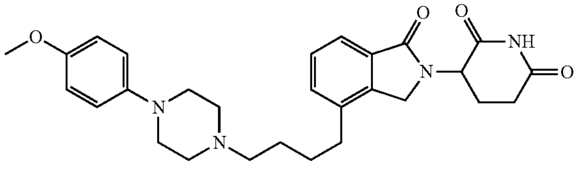 [SMILES: COc1ccc(N2CCN(CCCCc3cccc4c3CN(C3CCC(=O)NC3=O)C4=O)CC2)cc1]

The preparation method was the same as 3-(1-oxo-4-(5-(2-phenylpyrroline-1-)pentyl)indoline-2-)piperidine-2,6-dione, 43.3 mg white solid, yield 68%; $^1$H NMR (400 MHz, DMSO) δ 11.00 (s, 1H), 7.58 (dd, J=5.5, 3.2 Hz, 1H), 7.51-7.46 (m, 2H), 6.89 (d, J=9.2 Hz, 2H), 6.82 (d, J=9.1 Hz, 2H), 5.14 (dd, J=13.2, 5.1 Hz, 1H), 4.48 (d, J=17.2 Hz, 1H), 4.33 (d, J=17.2 Hz, 1H), 3.69 (s, 3H), 3.08-2.87 (m, 5H), 2.73-2.66 (m, 2H), 2.60 (d, J=17.9 Hz, 1H), 2.48-2.31 (m, 7H), 2.06-1.97 (m, 1H), 1.70-1.50 (m, 4H).

Example 47: 2-(2,6-dioxopiperidine-3-)-4-(4-(quinoline-4-oxy)butoxy)isoindoline-1,3-dione (47)

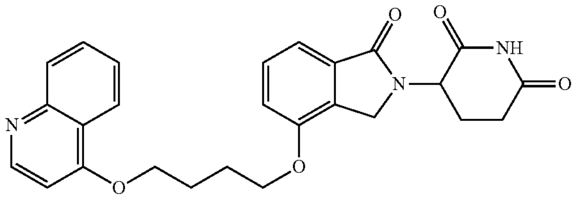 [SMILES: O=C1CCC(N2Cc3c(OCCCCOc4ccnc5ccccc45)cccc3C2=O)C(=O)N1]

Step 1:4-hydroxyquinoline (100 mg, 0.69 mmol, 1.0 eq) was added in a 50 ml round bottom flask, 4-methoxymethoxy-1-butanol (278 mg, 2.07 mmol, 2 eq), and triphenylphosphine (543 mg, 2.07 mmol, 2 eq) were added. The reaction system was replaced with nitrogen, and 15 mL of dry tetrahydrofuran was added. Diisopropyl azodicarboxylate (408 μL, 2.07 mmol, 2 eq) was added to the reaction system to react at room temperature for 1 h. TLC monitored that the reaction was completed, and concentrated under reduced pressure, and 173 mg target product was obtained by column chromatography, yield 96%.

Step 2: 4-(4-methoxymethoxybutoxy)quinoline was added in a 50 mL round bottom flask, and 10 mL 4M dioxane hydrochloride and 1 mL methanol were added to react at room temperature for 1 h. LC-MS monitored that the reaction was-completed, and then concentrated under reduced pressure. Saturated sodium bicarbonate solution was added, extracted with ethyl acetate, and separated. The organic layer was washed with saturated sodium chloride, dried, and 140 mg white solid was obtained by column chromatography, yield 100%.

Step 3:2-(2,6-dioxopiperidine-3-)-4-hydroxyisoindoline-1,3-dione (35 mg, 0.128 mmol) was added in a 50 ml round bottom flask, and 4-(quinoline-4-oxy)-1-butanol (56 mg, 0.256 mmol, 2 eq) and triphenylphosphine (67 mg, 0.256 mmol, 2 eq) were added. The reaction system was replaced with nitrogen, and 5 mL of dry tetrahydrofuran was added. Diisopropyl azodicarboxylate (51 μL, 0.256 mmol, 2 eq) was added to the reaction system to react at room temperature for 1 h. TLC monitored that the reaction was completed, and then concentrated under reduced pressure, 20.3 mg of white solid was obtained by HPLC, yield 33.4%; $^1$H NMR (400 MHz, DMSO) δ 11.11 (s, 1H), 8.75 (d, J=5.3 Hz, 1H), 8.16-8.11 (m, 1H), 7.94 (d, J=8.4 Hz, 1H), 7.83-7.72 (m, 2H), 7.54 (t, J=7.7 Hz, 2H), 7.43 (d, J=7.2 Hz, 1H), 7.08 (d, J=5.4 Hz, 1H), 5.08 (dd, J=12.7, 5.4 Hz, 1H), 4.41 (t, J=6.1 Hz, 2H), 4.35 (t, J=5.8 Hz, 2H), 2.87 (dd, J=8.5, 5.3 Hz, 1H), 2.70-2.55 (m, 1H), 2.18-1.95 (m, 6H).

Example 48: 3-(4-(4-(4-(2,6-dichlorophenyl)piperazine-1-)butyl)-1-oxoisoindoline-2-)piperidine-2,6-dione (48)

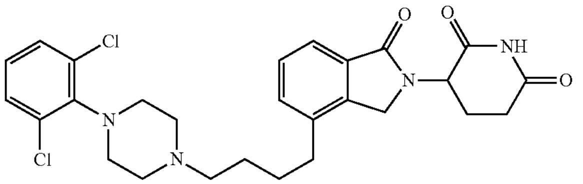 [SMILES: O=C1CCC(N2Cc3c(CCCCN4CCN(c5c(Cl)cccc5Cl)CC4)cccc3C2=O)C(=O)N1]

The preparation method was the same as 3-(1-oxo-4-(5-(2-phenylpyrroline-1-)pentyl)indoline-2-)piperidine-2,6-dione, 39.3 mg white solid, yield 43%; $^1$H NMR (400 MHz, DMSO) δ 10.99 (s, 1H), 7.58 (dd, J=5.8, 2.7 Hz, 1H), 7.50-7.46 (m, 2H), 7.41 (d, J=8.1 Hz, 2H), 7.17-7.12 (m, 1H), 5.14 (dd, J=13.5, 5.1 Hz, 1H), 4.48 (d, J=17.1 Hz, 1H), 4.33 (d, J=17.1 Hz, 1H), 3.13 (s, 4H), 2.99-2.87 (m, 2H), 2.72-2.66 (m, 2H), 2.61 (d, J=19.2 Hz, 1H), 2.48-2.45 (m, 4H), 2.42-2.33 (dd, J=14.2, 6.7 Hz, 3H), 2.07-1.99 (m, 1H), 1.70-1.61 (m, 1H), 1.56-1.47 (m, 1H).

Example 49: 4-(4-chlorophenyl)-1-(5-(2-(2,6-dioxopiperidine-3-)-1-oxoisoindoline-4-)pentyl) piperidine-4-carbonitrile (49)

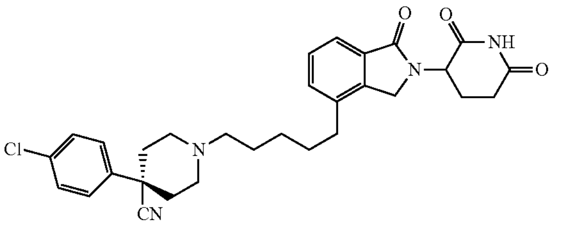

The preparation method was the same as 3-(1-oxo-4-(5-(2-phenylpyrroline-1-)pentyl)indoline-2-)piperidine-2,6-dione, 19.9 mg, yield 26%; $^1$H NMR (400 MHz, DMSO) δ 11.01 (s, 1H), 7.60-7.54 (m, 2H), 7.54-7.49 (m, 2H), 7.49-7.45 (m, 2H), 5.15 (dd, J=13.3, 5.4 Hz, 1H), 4.47 (d, J=17.0

Hz, 1H), 4.31 (d, J=17.2 Hz, 1H), 2.99-2.88 (m, 1H), 2.72-2.56 (m, 3H), 2.48-2.20 (m, 5H), 2.12 (d, J=14.0 Hz, 2H), 2.06-1.88 (m, 3H), 1.70-1.59 (m, 2H), 1.52 (dt, J=13.4, 6.7 Hz, 2H), 1.36 (dd, J=14.7, 5.1 Hz, 2H).

Example 50: (S)-4-(2-chlorophenyl)-1-(3-((2-(3-methyl-2,6-dioxopiperidine-3-)-1,3-dioxoisoindoline-4-)oxy)propyl)piperidine-4-carbonitrile (50)

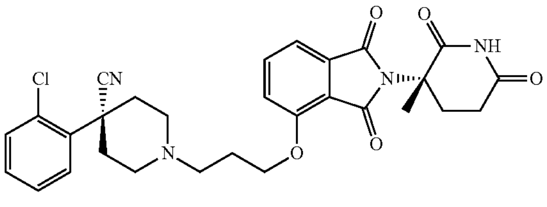

Step 1: Add 4-hydroxyisobenzofuran-1,3-dione (200 mg, 1.22 mmol, 1.0 eq), (S)-3-amino-3-methylpiperidine-2,6-dione hydrobromic acid monohydrate (294 mg, 1.22 mmol, 1.0 eq) was dissolved in 20 ml of toluene. Triethylamine (136 mg, 1.34 mmol, 1.1 eq) was added to reflux at 120° C. for 24 h. After the reaction was completed, the toluene was spun off and purified by column chromatography to obtain 200 mg of white solid with a yield of 57%. $^1$H NMR (400 MHz, DMSO) δ 11.07 (s, 1H), 10.97 (s, 1H), 7.62 (dd, J=8.3, 7.3 Hz, 1H), 7.22 (dd, J=15.6, 7.7 Hz, 2H), 2.75-2.62 (m, 1H), 2.57-2.52 (m, 1H), 2.06-1.97 (m, 1H), 1.86 (s, 3H), 1.29-1.18 (m, 1H).

Step 2: (S)-4-hydroxyl-2-(3-methyl-2,6-dioxopiperidine-3-)isoindoline-1,3-dione (200 mg, 0.69 mmol, 1.0 eq) was dissolved in 20 mL acetonitrile, and 1,3-dibromopropane (681 mg, 3.54 mmol, 3.0 eq) and anhydrous potassium carbonate (96 mg, 0.69 mmol, 1.0 eq) were added. The reaction system reacted at 50° C. for 24 h. After the reaction was completed, the solvent was spun off, diluted with ethyl acetate, washed with saturated sodium chloride, dried with anhydrous sodium sulfate. The solvent was removed under reduced pressure, and purified by column chromatography to obtain 243 mg of white solid with a yield of 86%. $^1$H NMR (400 MHz, DMSO) δ 10.98 (s, 1H), 7.83-7.78 (m, 1H), 7.52 (d, J=8.5 Hz, 1H), 7.40 (d, J=7.1 Hz, 1H), 4.29 (t, J=5.8 Hz, 2H), 3.72 (t, J=6.5 Hz, 1H), 2.68 (s, 1H), 2.31 (dd, J=13.8, 7.7 Hz, 1H), 2.03 (d, J=18.2 Hz, 1H), 1.88 (s, 1H).

Step 3: (S)-4-(3-bromopropyl)-2-(3-methyl-2,6-dioxopiperidine-3-)isoindoline-1,3-dione (40 mg, 0.098 mmol, 1.0 eq) was dissolved in 3 mL DMSO, and 4-(2-chlorophenyl) piperidine-4-carbonitrile hydrochloride (38 mg, 0.147 mmol, 1.5 eq), and triethylamine (9.89 mg, 0.980 mmol, 10.0 eq) were added, and reacted at 40° C. overnight. After the reaction was completed, the solution was diluted with 20 mL ethyl acetate, washed with saturated sodium chloride, dried over anhydrous sodium sulfate, concentrated under reduced pressure, purified by thin layer chromatography and high performance liquid chromatography to obtain 23 mg of product, as a white solid, yield 43%; 1H NMR (400 MHz, DMSO) δ 10.99 (d, J=5.1 Hz, 1H), 7.81-7.75 (m, 1H), 7.59-7.51 (m, 2H), 7.49 (d, J=8.6 Hz, 1H), 7.47-7.40 (m, 2H), 7.37 (d, J=7.2 Hz, 1H), 4.23 (t, J=6.0 Hz, 2H), 3.05 (d, J=9.4 Hz, 2H), 2.76-2.62 (m, 1H), 2.55 (dd, J=12.7, 5.3 Hz, 3H), 2.38 (dd, J=29.5, 18.0 Hz, 5H), 2.00 (dd, J=16.1, 10.9 Hz, 5H), 1.87 (s, 3H).

Example 51: 4-(3-chlorophenyl)-1-(5-(2-(2,6-dioxopiperidine-3-)-1-oxoisoindoline-4-)pentyl) piperidine-4-carbonitrile (51)

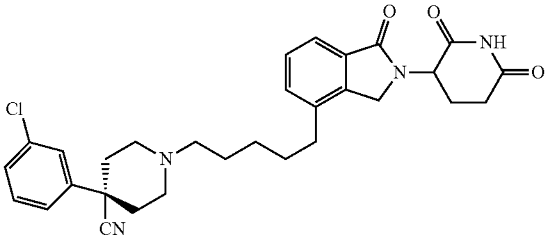

The preparation method was the same as 3-(1-oxo-4-(5-(2-phenylpyrroline-1-)pentyl)indoline-2-)piperidine-2,6-dione, 21.6 mg, yield 28%; $^1$H NMR (400 MHz, DMSO) δ 11.01 (s, 1H), 7.60-7.49 (m, 3H), 7.49-7.43 (m, 3H), 5.15 (dd, J=13.6, 5.2 Hz, 1H), 4.48 (d, J=17.1 Hz, 1H), 4.31 (d, J=17.2 Hz, 1H), 2.99 (d, J=12.2 Hz, 2H), 2.95-2.87 (m, 1H), 2.69-2.64 (m, 2H), 2.64-2.57 (m, 1H), 2.49-2.41 (m, 1H), 2.40-2.32 (m, 2H), 2.24 (td, J=11.9, 1.3 Hz, 2H), 2.14 (dd, J=12.7, 1.5 Hz, 2H), 2.06-1.93 (m, 3H), 1.64 (dt, J=15.3, 7.7 Hz, 2H), 1.56-1.46 (m, 2H), 1.35 (dd, J=15.1, 7.2 Hz, 2H).

Example 52: (S)-4-(3-chlorophenyl)-1-(3-((2-(3-methyl-2,6-dioxopiperidine-3-)-1-oxoisoindole-4-)oxy)propyl)piperidine-4-carbonitrile (52)

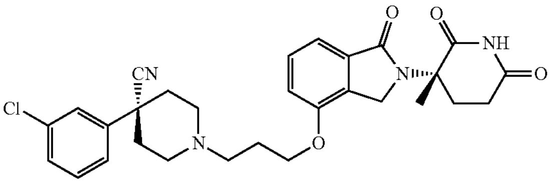

The preparation method was the same as (S)-4-(2-chlorophenyl)-1-(3-((2-(3-methyll-2,6-dioxopiperidine-3-)-1-oxoisoindoline-4-)oxy)propyl)piperidine-4-carbonitrile, and obtained 14 mg of final product, as a white solid, yield 26%; $^1$H NMR (400 MHz, DMSO) δ 10.88 (s, 1H), 7.60 (s, 1H), 7.50 (dt, J=17.6, 7.7 Hz, 4H), 7.24 (dd, J=12.5, 7.8 Hz, 2H), 4.66 (d, J=17.6 Hz, 1H), 4.54 (d, J=17.6 Hz, 1H), 4.20 (t, J=6.0 Hz, 2H), 3.05 (d, J=10.6 Hz, 2H), 2.80-2.52 (m, 5H), 2.35-2.24 (m, 2H), 2.16 (d, J=12.4 Hz, 2H), 1.94 (ddd, J=23.3, 12.4, 8.2 Hz, 5H), 1.70 (s, 3H).

Example 53: 1-(3-((2-(2,6-dioxopiperidine-3-)-1-oxoisoindoline-4-)oxy)propyl)-4-phenylpiperidine-4-carboxonitrile 53)

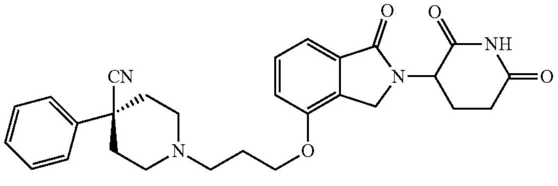

3-(4-(3-bromopropoxy)-1-oxoisoindoline-2-)piperidine-2,6-dione (40 mg, 0.11 mmol) was dissolved in 3 mL dry DMSO, 4-phenylpiperidine-4-carbonitrile hydrochloride (0.16 mmol, 1.5 eq), and triethylamine (110 mg, 1.1 mmol, 10.0 eq) were added to react at 40° C. overnight. After the reaction was completed, the reaction solution was diluted with 20 mL ethyl acetate. The organic phase was washed with saturated sodium chloride, dried over anhydrous sodium sulfate, concentrated, and purified by thin layer chromatography and high performance liquid chromatography to obtain 26.3 mg of final product, as a white solid, yield 41%; $^1$H NMR (400 MHz, DMSO) δ 10.99 (s, 1H), 7.53 (dt, J=3.1, 2.1 Hz, 2H), 7.46 (ddd, J=13.1, 11.8, 7.1 Hz, 3H), 7.36 (ddd, J=8.3, 4.3, 1.7 Hz, 1H), 7.31 (d, J=7.4 Hz, 1H), 7.25 (d, J=8.1 Hz, 1H), 5.11 (dd, J=13.3, 5.1 Hz, 1H), 4.39 (d, J=17.4 Hz, 1H), 4.24 (d, J=17.4 Hz, 1H), 4.18 (t, J=6.2 Hz, 2H), 3.03 (d, J=12.2 Hz, 2H), 2.91 (ddd, J=17.4, 13.7, 5.4 Hz, 1H), 2.58 (dd, J=12.2, 4.8 Hz, 3H), 2.48-2.38 (m, 1H), 2.30 (dd, J=12.0, 11.3 Hz, 2H), 2.11 (d, J=13.0 Hz, 2H), 2.05-1.89 (m, 5H). ESI-MS [M+H]$^+$ m/z=487.65.

Example 54: (S)-4-(3-chlorophenyl)-1-(3-((2-(3-methyl-2,6-dioxopiperidine-3-)-1,3-dioxo isoindoline-4-)oxy)propyl)piperidine-4-carbonitrile (54)

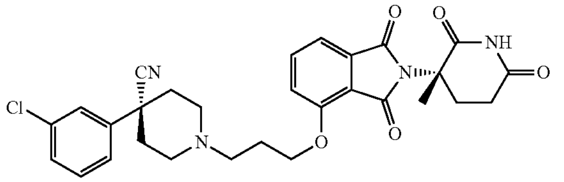

The preparation method was the same as (S)-4-(2-chlorophenyl)-1-(3-((2-(3-methyll-2,6-dioxopiperidine-3-)-1,3-dioxoisoindoline-4-)oxy)propyl)piperidine-4-carbonitrile, and obtained 18 mg of final product, as a white solid, yield 34%; 1H NMR (400 MHz, DMSO) δ 11.00 (s, 1H), 7.81-7.75 (m, 1H), 7.58 (s, 1H), 7.55-7.41 (m, 4H), 7.37 (d, J=7.2 Hz, 1H), 4.24 (t, J=6.0 Hz, 2H), 3.02 (d, J=11.3 Hz, 2H), 2.74-2.63 (m, 1H), 2.62-2.51 (m, 4H), 2.28 (t, J=11.4 Hz, 2H), 2.14 (d, J=12.2 Hz, 2H), 2.08-1.93 (m, 5H), 1.87 (s, 3H).

Example 55: 4-(2-chlorophenyl)-1-(3-((2-(2,6-dioxopiperidine-3-)-1-oxoisoindoline-4-)oxy)propyl) piperidine-4-carbonitrile (55)

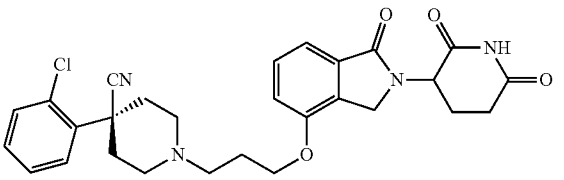

The preparation method was the same as 1-(3-((2-(2,6-dioxopiperidine-3-)-1-oxoisoindoline-4-)oxy)propyl)-4-phenylpiperidine-4-carbonitrile, 21.0 mg, yield 31%; $^1$H NMR (400 MHz, DMSO) δ 10.99 (s, 1H), 7.61-7.52 (m, 2H), 7.51-7.39 (m, 3H), 7.31 (d, J=7.0 Hz, 1H), 7.25 (d, J=8.2 Hz, 1H), 5.12 (dd, J=13.1, 6.1 Hz, 1H), 4.39 (d, J=17.4 Hz, 1H), 4.24 (d, J=17.2 Hz, 1H), 4.20-4.13 (m, 2H), 3.12-3.00 (m, 2H), 2.97-2.85 (m, 1H), 2.68-2.53 (m, 3H), 2.38 (ddd, J=16.4, 14.0, 6.7 Hz, 5H), 1.98 (ddd, J=21.0, 12.0, 4.6 Hz, 5H). ESI-MS [M+H]$^+$ m/z=522.28.

Example 56: (S)-1-(3-((2-(3-methyl-2,6-dioxopiperidine-3-)-1-oxoisoindoline-4-)oxy)propyl)-4-(2-(trifluoromethoxy)phenyl)piperidine-4-carbonitrile 56)

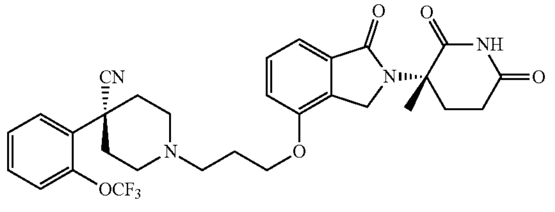

The preparation method was the same as (S)-4-(2-chlorophenyl)-1-(3-((2-(3-methyll-2,6-dioxopiperidine-3-)-1-oxoisoindoline-4-)oxy)propyl)piperidine-4-carbonitrile, and obtained 16 mg of final product, as a white solid, yield 30%; 1H NMR (400 MHz, DMSO) δ 10.87 (s, 1H), 7.57 (dd, J=18.0, 7.6 Hz, 2H), 7.44 (dd, J=15.4, 7.6 Hz, 3H), 7.22 (dd, J=10.7, 7.9 Hz, 2H), 4.65 (d, J=17.5 Hz, 1H), 4.53 (d, J=17.6 Hz, 1H), 4.18 (t, J=5.9 Hz, 2H), 3.06 (d, J=11.1 Hz, 2H), 2.82-2.52 (m, 5H), 2.41-2.22 (m, 4H), 2.11-1.84 (m, 5H), 1.69 (s, 3H).

Example 57: 4-(3-chlorophenyl)-1-(3-((2-(2,6-dioxopiperidine-3-)-1-oxoisoindoline-4-)oxy)propyl) piperidine-4-carbonitrile (57)

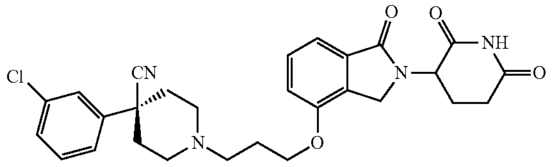

The preparation method was the same as 1-(3-((2-(2,6-dioxopiperidine-3-)-1-oxoisoindoline-4-)oxy)propyl)-4-phenylpiperidine-4-carbonitrile, 25.7 mg, yield 38%; $^1$H NMR (400 MHz, DMSO) δ 11.00 (s, 1H), 7.62-7.58 (m, 1H), 7.56-7.44 (m, 4H), 7.32 (d, J=7.2 Hz, 1H), 7.26 (d, J=7.9 Hz, 1H), 5.12 (dd, J=13.4, 5.1 Hz, 1H), 4.39 (d, J=17.5 Hz, 1H), 4.24 (d, J=17.4 Hz, 1H), 4.18 (t, J=6.2 Hz, 2H), 3.05 (dd, J=10.8, 2.7 Hz, 2H), 2.92 (ddd, J=17.4, 13.3, 5.0 Hz, 1H), 2.62-2.55 (m, 3H), 2.49-2.40 (m, 1H), 2.38-2.25 (m, 2H), 2.17 (d, J=12.0 Hz, 2H), 1.99 (ddd, J=21.0, 15.7, 9.3 Hz, 5H).

Example 58: (S)-1-(3-((2-(3-methyl-2,6-dioxopiperidine-3-)-1,3-dioxoisoindoline-4-)oxy)propyl)-4-(2-(trifluoromethoxy)phenyl)piperidine-4-carbonitrile (58)

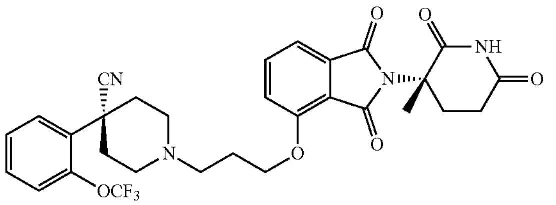

The preparation method was the same as (S)-4-(2-chlorophenyl)-1-(3-((2-(3-methyll-2,6-dioxopiperidine-3-)-1,3-dioxoisoindoline-4-)oxy)propyl)piperidine-4-carbonitrile, and obtained 21 mg of final product, as a white solid, yield 36%; 1H NMR (400 MHz, DMSO) δ 11.00 (s, 1H), 7.81-7.74 (m, 1H), 7.56 (dd, J=15.7, 7.6 Hz, 2H), 7.51-7.40 (m, 3H), 7.37 (d, J=7.2 Hz, 1H), 4.23 (t, J=6.0 Hz, 2H), 3.04 (d, J=11.9 Hz, 2H), 2.68 (dd, J=12.5, 6.4 Hz, 1H), 2.60-2.51 (m, 4H), 2.43-2.18 (m, 4H), 2.10-1.92 (m, 5H), 1.87 (s, 3H).

Example 59: 4-(4-chlorophenyl)-1-(3-((2-(2,6-dioxopiperidine-3-)-1-oxoisoindoline-4-)oxy)propyl) piperidine-4-carbonitrile (59)

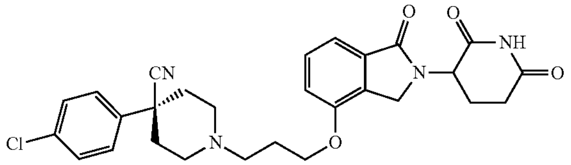

The preparation method was the same as 1-(3-((2-(2,6-dioxopiperidine-3-)-1-oxoisoindoline-4-)oxy)propyl)-4-phenylpiperidine-4-carbonitrile, 24.6 mg, yield 36%; $^1$H NMR (400 MHz, DMSO) δ 11.00 (s, 1H), 7.60-7.55 (m, 2H), 7.54-7.50 (m, 2H), 7.48 (d, J=7.8 Hz, 1H), 7.32 (d, J=7.5 Hz, 1H), 7.26 (d, J=8.1 Hz, 1H), 5.12 (dd, J=13.1, 5.0 Hz, 1H), 4.40 (d, J=17.4 Hz, 1H), 4.25 (d, J=17.4 Hz, 1H), 4.19 (t, J=6.0 Hz, 2H), 3.18-3.00 (m, 2H), 2.92 (ddd, J=18.5, 13.0, 4.4 Hz, 1H), 2.59 (ddd, J=16.3, 3.5, 1.3 Hz, 3H), 2.49-2.39 (m, 2H), 2.38-2.32 (m, 1H), 2.16 (d, J=15.1 Hz, 2H), 2.09-1.92 (m, 5H). ESI-MS $[M+H]^+$ m/z=522.28.

Example 60: (S)-1-(3-((2-(3-methyl-2,6-dioxopiperidine-3-)-1-oxoisoindoline-4-)oxy)propyl)-4-(3-(trifluoromethoxy)phenyl)piperidine-4-carbonitrile 60

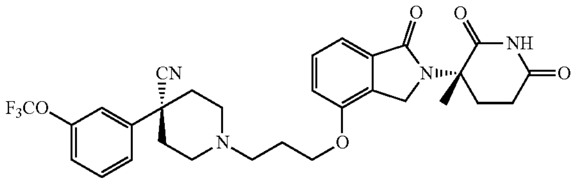

The preparation method was the same as (S)-4-(2-chlorophenyl)-1-(3-((2-(3-methyll-2,6-dioxopiperidine-3-)-1-oxoisoindoline-4-)oxy)propyl)piperidine-4-carbonitrile, and obtained 18 mg of final product, as a white solid, yield 34%; 1H NMR (400 MHz, DMSO) δ 10.87 (s, 1H), 7.61 (d, J=7.0 Hz, 2H), 7.54-7.37 (m, 3H), 7.23 (dd, J=12.8, 7.8 Hz, 2H), 4.65 (d, J=17.6 Hz, 1H), 4.54 (d, J=17.6 Hz, 1H), 4.19 (t, J=5.9 Hz, 2H), 3.05 (d, J=10.4 Hz, 2H), 2.82-2.51 (m, 5H), 2.37-2.24 (m, 2H), 2.17 (d, J=12.3 Hz, 2H), 2.11-1.85 (m, 5H).

Example 61: 1-(3-((2-(2,6-dioxopiperidine-3-)-1-oxoisoindoline-4-)oxy)propyl)-4-(2-fluorophenyl) piperidine-4-carbonitrile (61)

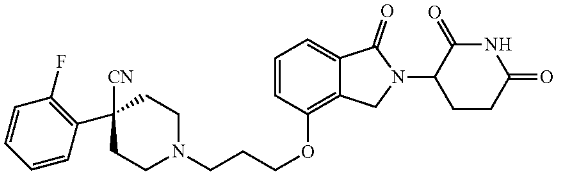

The preparation method was the same as 1-(3-((2-(2,6-dioxopiperidine-3-)-1-oxoisoindoline-4-)oxy)propyl)-4-phenylpiperidine-4-carbonitrile, 23.6 mg, yield 36%; $^1$H NMR (400 MHz, DMSO) δ 10.99 (s, 1H), 7.50 (dd, J=15.4, 7.3 Hz, 3H), 7.37-7.22 (m, 4H), 5.12 (dd, J=13.4, 5.2 Hz, 1H), 4.40 (d, J=17.4 Hz, 1H), 4.24 (d, J=17.8 Hz, 1H), 4.18 (t, J=5.8 Hz, 2H), 3.05 (ddd, J=12.6, 7.5, 3.9 Hz, 2H), 2.98-2.86 (m, 1H), 2.65-2.55 (m, 3H), 2.49-2.43 (m, 1H), 2.40-2.20 (m, 4H), 2.10-1.89 (m, 5H). ESI-MS $[M+H]^+$ m/z=505.66.

Example 62: (S)-1-(3-((2-(3-methyl-2,6-dioxopiperidine-3-)-1,3-dioxoisoindoline-4-)oxy)propyl)-4-(3-(trifluoromethoxy)phenyl)piperidine-4-carbonitrile (62)

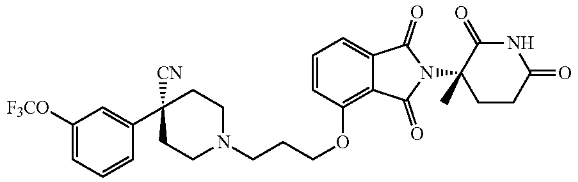

The preparation method was the same as (S)-4-(2-chlorophenyl)-1-(3-((2-(3-methyll-2,6-dioxopiperidine-3-)-1,3-dioxoisoindoline-4-)oxy)propyl)piperidine-4-carbonitrile, and obtained 21 mg of final product, as a white solid, yield 36%; 1H NMR (400 MHz, DMSO) δ 11.00 (s, 1H), 7.78 (t, J=7.9 Hz, 1H), 7.65-7.56 (m, 2H), 7.49 (d, J=8.8 Hz, 2H), 7.38 (t, J=9.1 Hz, 2H), 4.24 (t, J=5.8 Hz, 2H), 3.02 (d, J=10.4 Hz, 2H), 2.68 (dd, J=12.4, 6.5 Hz, 1H), 2.55 (dd, J=12.8, 4.6 Hz, 4H), 2.29 (t, J=11.6 Hz, 2H), 2.16 (d, J=12.9 Hz, 2H), 2.08-1.91 (m, 5H), 1.87 (s, 3H).

Example 63: 1-(3-((2-(2,6-dioxopiperidine-3-)-1-oxoisoindoline-4-)oxy)propyl)-4-(3-fluorophenyl) piperidine-4-carbonitrile (63)

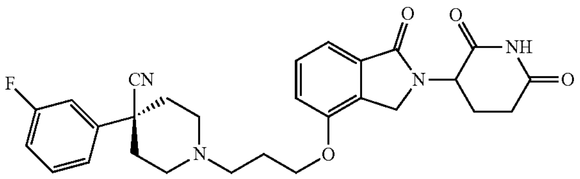

The preparation method was the same as 1-(3-((2-(2,6-dioxopiperidine-3-)-1-oxoisoindoline-4-)oxy)propyl)-4-phenylpiperidine-4-carbonitrile, 23.6 mg, yield 36%; $^{1}$H NMR (400 MHz, DMSO) δ 11.00 (s, 1H), 7.54-7.46 (m, 2H), 7.44-7.37 (m, 2H), 7.32 (d, J=7.3 Hz, 1H), 7.28-7.19 (m, 2H), 5.12 (dd, J=13.3, 5.1 Hz, 1H), 4.39 (d, J=17.5 Hz, 1H), 4.24 (d, J=17.5 Hz, 1H), 4.18 (t, J=6.2 Hz, 2H), 3.03 (d, J=12.4 Hz, 2H), 2.97-2.86 (m, 1H), 2.63-2.55 (m, 3H), 2.49-2.41 (m, 1H), 2.30 (t, J=12.2 Hz, 2H), 2.15 (d, J=12.4 Hz, 2H), 2.08-1.89 (m, 5H). ESI-MS $[M+H]^+$ m/z=505.66.

Example 64: 4-(2-chlorophenyl)-1-(2-((2-(2,6-dioxopiperidine-3-)-1-oxoisoindoline-4-)oxy)ethyl) piperidine-4-carbonitrile (64)

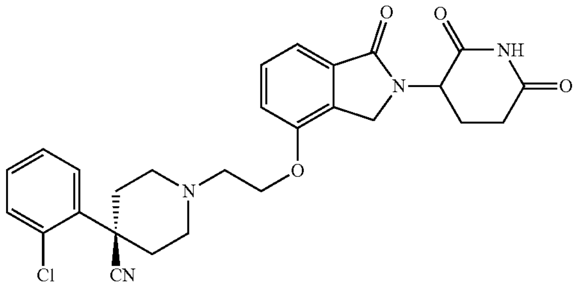

The preparation method was the same as 1-(3-((2-(2,6-dioxopiperidine-3-)-1-oxoisoindoline-4-)oxy)propyl)-4-phenylpiperidine-4-carbonitrile, and obtained 16 mg of final product, as a white solid, yield 29%; 1H NMR (400 MHz, DMSO) δ 10.98 (s, 1H), 7.59-7.40 (m, 5H), 7.30 (dd, J=11.8, 7.8 Hz, 2H), 5.11 (dd, J=13.3, 5.0 Hz, 1H), 4.39 (d, J=17.4 Hz, 1H), 4.26 (t, J=12.6 Hz, 3H), 3.13 (d, J=12.2 Hz, 2H), 3.00-2.79 (m, 3H), 2.57 (d, J=22.0 Hz, 3H), 2.46 (d, J=13.6 Hz, 3H), 1.98 (t, J=9.0 Hz, 3H), 1.23 (s, 3H).

Example 65: 1-(3-((2-(2,6-dioxopiperidine-3-)-1-oxoisoindoline-4-)oxy)propyl)-4-(4-fluorophenyl) piperidine-4-carbonitrile (65)

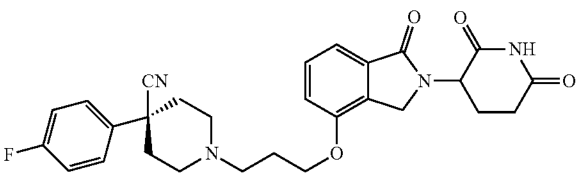

The preparation method was the same as 1-(3-((2-(2,6-dioxopiperidine-3-)-1-oxoisoindoline-4-)oxy)propyl)-4-phenylpiperidine-4-carbonitrile, 22.3 mg, yield 34%; $^{1}$H NMR (400 MHz, DMSO) δ 10.99 (s, 1H), 7.58 (ddd, J=8.7, 5.5, 2.8 Hz, 2H), 7.48 (t, J=7.8 Hz, 1H), 7.33-7.22 (m, 4H), 5.11 (dd, J=13.3, 5.2 Hz, 1H), 4.39 (d, J=17.5 Hz, 1H), 4.23 (d, J=17.5 Hz, 1H), 4.17 (t, J=6.2 Hz, 2H), 3.09-2.98 (m, 2H), 2.91 (ddd, J=17.7, 13.8, 5.5 Hz, 1H), 2.64-2.54 (m, 3H), 2.48-2.38 (m, 1H), 2.35-2.23 (m, 2H), 2.18-2.08 (m, 2H), 2.05-1.89 (m, 5H). ESI-MS $[M+H]^+$ m/z=505.61.

Example 66: 1-(2-((2-(2,6-dioxopiperidine-3-)-1-oxoisoindoline-4-)oxy)ethyl)-4-(3-(trifluoromethoxy)phenyl)piperidine-4-carbonitrile (66)

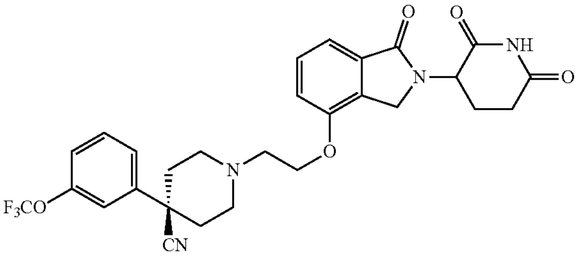

The preparation method was the same as 1-(3-((2-(2,6-dioxopiperidine-3-)-1-oxoisoindoline-4-)oxy)propyl)-4-phenylpiperidine-4-carbonitrile, and obtained 12 mg of final product, as a white solid, yield 20%; 1H NMR (400 MHz, DMSO) δ 10.99 (s, 1H), 7.64-7.56 (m, 2H), 7.53-7.46 (m, 2H), 7.40 (d, J=6.2 Hz, 1H), 7.31 (dd, J=12.8, 7.8 Hz, 2H), 5.11 (dd, J=13.3, 5.0 Hz, 1H), 4.39 (d, J=17.5 Hz, 1H), 4.25 (t, J=10.6 Hz, 3H), 3.11 (d, J=11.8 Hz, 2H), 2.98-2.80 (m, 3H), 2.61-2.52 (m, 1H), 2.49-2.37 (m, 3H), 2.16 (d, J=12.6 Hz, 2H), 2.10-1.91 (m, 3H).

Example 67: 4-(3-cyanophenyl)-1-(3-((2-(2,6-dioxopiperidine-3-)-1-oxoisoindoline-4-)oxy)propyl) piperidine-4-carbonitrile (67)

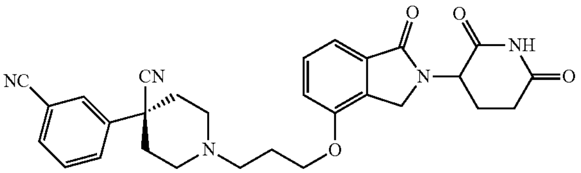

The preparation method was the same as 1-(3-((2-(2,6-dioxopiperidine-3-)-1-oxoisoindoline-4-)oxy)propyl)-4-phenylpiperidine-4-carbonitrile, 16.9 mg, yield 25%; $^{1}$H NMR (400 MHz, DMSO) δ 10.99 (s, 1H), 8.03 (t, J=1.5 Hz, 1H), 7.93 (ddd, J=8.0, 2.1, 1.1 Hz, 1H), 7.90-7.85 (m, 1H), 7.67 (t, J=7.8 Hz, 1H), 7.49 (t, J=7.9 Hz, 1H), 7.32 (d, J=7.6 Hz, 1H), 7.26 (d, J=7.9 Hz, 1H), 5.16-5.08 (m, 1H), 4.40 (d, J=17.5 Hz, 1H), 4.24 (d, J=17.6 Hz, 1H), 4.18 (t, J=6.6 Hz, 2H), 3.04 (dt, J=8.5, 3.7 Hz, 2H), 2.98-2.86 (m, 1H), 2.63-2.55 (m, 3H), 2.48-2.40 (m, 1H), 2.30 (t, J=11.3 Hz, 2H), 2.19 (d, J=12.1 Hz, 2H), 2.09-1.90 (m, 5H). ESI-MS $[M+H]^+$ m/z=512.63.

Example 68: 4-(2-chloro-6-fluorophenyl)-1-(3-((2-(2,6-dioxopiperidine-3-)-1-oxoisoindoline-4-)oxy)propyl)piperidine-4-carbonitrile (68)

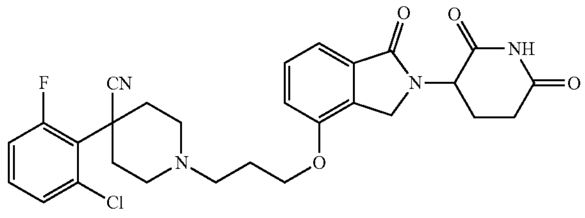 [SMILES: N#CC1(c2c(F)cccc2Cl)CCN(CCCOc2cccc3c2CN(C2CCC(=O)NC2=O)C3=O)CC1]

The preparation method was the same as 1-(3-((2-(2,6-dioxopiperidine-3-)-1-oxoisoindoline-4-)oxy)propyl)-4-phenylpiperidine-4-carbonitrile, 30 mg, as a white solid, yield 37%; 1H NMR (400 MHz, DMSO) δ 10.98 (s, 1H), 7.52-7.41 (m, 3H), 7.35-7.22 (m, 3H), 5.11 (dd, J=13.3, 5.0 Hz, 1H), 4.39 (d, J=17.4 Hz, 1H), 4.27-4.11 (m, 3H), 3.03 (d, J=10.9 Hz, 2H), 2.91 (s, 2H), 2.57 (d, J=24.3 Hz, 4H), 2.48-2.22 (m, 6H), 2.03-1.89 (m, 3H).

Example 69: 4-(4-cyanophenyl)-1-(3-((2-(2,6-dioxopiperidine-3-)-1-oxoisoindoline-4-)oxy)propyl)piperidine-4-carbonitrile (69)

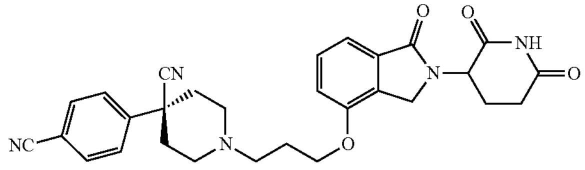

The preparation method was the same as 1-(3-((2-(2,6-dioxopiperidine-3-)-1-oxoisoindoline-4-)oxy)propyl)-4-phenylpiperidine-4-carbonitrile, 20.0 mg, yield 30%; $^1$H NMR (400 MHz, DMSO) δ 10.99 (s, 1H), 7.93 (d, J=8.5 Hz, 2H), 7.76 (d, J=8.6 Hz, 2H), 7.48 (t, J=7.8 Hz, 1H), 7.31 (d, J=7.3 Hz, 1H), 7.25 (d, J=8.1 Hz, 1H), 5.11 (dd, J=13.3, 5.2 Hz, 1H), 4.39 (d, J=17.5 Hz, 1H), 4.24 (d, J=17.4 Hz, 1H), 4.18 (t, J=6.1 Hz, 2H), 3.15-2.99 (m, 2H), 2.97-2.85 (m, 1H), 2.64-2.55 (m, 3H), 2.48-2.39 (m, 1H), 2.38-2.25 (m, 2H), 2.23-2.11 (m, 2H), 2.09-1.89 (m, 5H). ESI-MS $[M+H]^+$ m/z=512.68.

Example 70: 4-(2,4-chlorophenyl)-1-(3-((2-(2,6-dioxopiperidine-3-)-1-oxoisoindoline-4-)oxy)propyl)piperidine-4-carbonitrile (70)

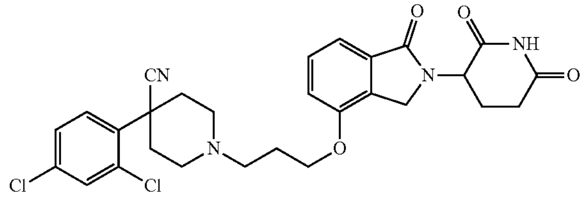 [SMILES: N#CC1(c2ccc(Cl)cc2Cl)CCN(CCCOc2cccc3c2CN(C2CCC(=O)NC2=O)C3=O)CC1]

The preparation method was the same as 1-(3-((2-(2,6-dioxopiperidine-3-)-1-oxoisoindoline-4-)oxy)propyl)-4-phenylpiperidine-4-carbonitrile, 38 mg, as a white solid, yield 46%; 1H NMR (400 MHz, DMSO) δ 10.98 (s, 1H), 7.75 (d, J=1.9 Hz, 1H), 7.58-7.44 (m, 3H), 7.30 (d, J=7.4 Hz, 1H), 7.24 (d, J=8.1 Hz, 1H), 5.11 (dd, J=13.3, 5.1 Hz, 1H), 4.39 (d, J=17.5 Hz, 1H), 4.23 (d, J=17.5 Hz, 1H), 4.17 (t, J=6.1 Hz, 2H), 3.05 (d, J=10.6 Hz, 2H), 2.97-2.86 (m, 1H), 2.58 (d, J=17.1 Hz, 3H), 2.49-2.26 (m, 5H), 2.04-1.88 (m, 5H).

Example 71: 1-(3-((2-(2,6-dioxopiperidine-3-)-1-oxoisoindoline-4-)oxy)propyl)-4-(3-trifluoromethoxyphenyl)piperidine-4-carbonitrile (71)

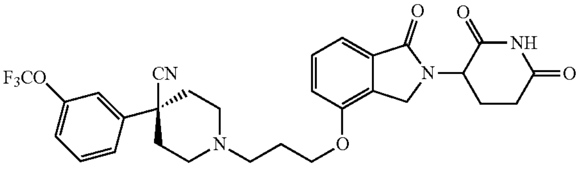

The preparation method was the same as 1-(3-((2-(2,6-dioxopiperidine-3-)-1-oxoisoindoline-4-)oxy)propyl)-4-phenylpiperidine-4-carbonitrile, 27.4 mg, yield 47%; $^1$H NMR (400 MHz, DMSO) δ 10.97 (s, 1H), 7.63-7.56 (m, 2H), 7.51 (d, J=2.4 Hz, 1H), 7.47 (d, J=7.8 Hz, 1H), 7.42-7.37 (m, 1H), 7.31 (d, J=7.4 Hz, 1H), 7.25 (d, J=8.1 Hz, 1H), 5.11 (dd, J=13.3, 5.1 Hz, 1H), 4.39 (d, J=17.5 Hz, 1H), 4.24 (d, J=17.4 Hz, 1H), 4.18 (t, J=6.1 Hz, 2H), 3.05 (d, J=9.8 Hz, 2H), 2.91 (ddd, J=18.7, 13.7, 5.4 Hz, 1H), 2.58 (dd, J=13.5, 2.3 Hz, 3H), 2.49-2.39 (m, 1H), 2.32 (t, J=11.7 Hz, 2H), 2.18 (d, J=12.8 Hz, 2H), 2.10-1.87 (m, 5H). ESI-MS $[M+H]^+$ m/z=571.66.

Example 72: 4-(4-chloro-2-fluorophenyl)-1-(3-((2-(2,6-dioxopiperidine-3-)-1-oxoisoindoline-4-)oxy)propyl)piperidine-4-carbonitrile (72)

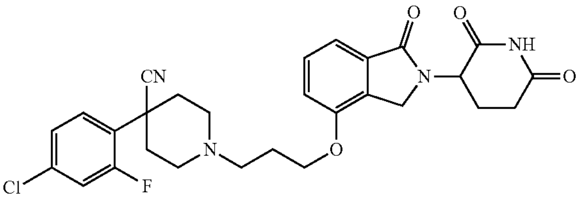 [SMILES: N#CC1(c2ccc(Cl)cc2F)CCN(CCCOc2cccc3c2CN(C2CCC(=O)NC2=O)C3=O)CC1]

The preparation method was the same as 1-(3-((2-(2,6-dioxopiperidine-3-)-1-oxoisoindoline-4-)oxy)propyl)-4-phenylpiperidine-4-carbonitrile, and finally obtained 27 mg of white solid, yield 33%; 1H NMR (400 MHz, DMSO) δ 10.98 (s, 1H), 7.59 (d, J=11.8 Hz, 1H), 7.56-7.45 (m, 2H), 7.39 (d, J=8.6 Hz, 1H), 7.31 (d, J=7.4 Hz, 1H), 7.25 (d, J=8.1 Hz, 1H), 5.11 (dd, J=13.2, 5.0 Hz, 1H), 4.39 (d, J=17.4 Hz, 1H), 4.24 (d, J=17.4 Hz, 1H), 4.17 (t, J=6.0 Hz, 2H), 3.20-2.82 (m, 4H), 2.58 (d, J=18.6 Hz, 2H), 2.48-2.18 (m, 5H), 2.09-1.89 (m, 5H).

Example 73: 1-(3-((2-(2,6-dioxopiperidine-3-)-1-oxoisoindoline-4-)oxy)propyl)-4-(4-trifluoromethoxyphenyl)piperidine-4-carbonitrile (73)

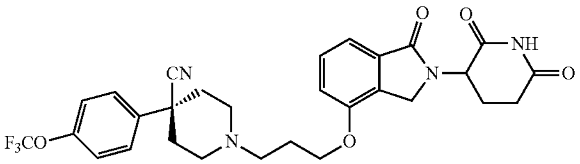

The preparation method was the same as 1-(3-((2-(2,6-dioxopiperidine-3-)-1-oxoisoindoline-4-)oxy)propyl)-4-phenylpiperidine-4-carbonitrile, 26.9 mg, yield 36%; $^1$H NMR (400 MHz, DMSO) δ 10.98 (s, 1H), 7.68 (d, J=8.8 Hz, 2H), 7.52-7.41 (m, 3H), 7.31 (d, J=7.4 Hz, 1H), 7.25 (d, J=8.2 Hz, 1H), 5.11 (dd, J=13.5, 5.0 Hz, 1H), 4.39 (d, J=17.4 Hz, 1H), 4.24 (d, J=17.5 Hz, 1H), 4.18 (t, J=6.0 Hz, 2H), 3.03 (ddd, J=7.4, 4.6, 1.9 Hz, 2H), 2.98-2.85 (m, 1H), 2.69-2.52 (m, 3H), 2.48-2.39 (m, 1H), 2.36-2.23 (m, 2H), 2.14 (dd, J=13.2, 5.0 Hz, 2H), 2.08-1.86 (m, 5H). ESI-MS $[M+H]^+$ m/z=571.66.

Example 74: 4-(2-chloro-4-fluorophenyl)-1-(3-((2-(2,6-dioxopiperidine-3-)-1-oxoisoindoline-4-)oxy)propyl)piperidine-4-carbonitrile (74)

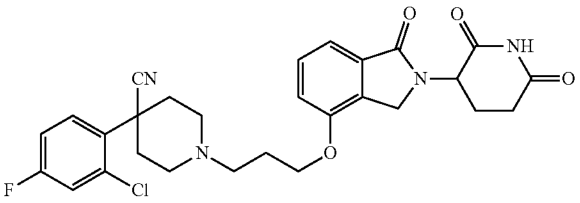 [SMILES: N#CC1(c2ccc(F)cc2Cl)CCN(CCCOc2cccc3c2CN(C2CCC(=O)NC2=O)C3=O)CC1]

The preparation method was the same as 1-(3-((2-(2,6-dioxopiperidine-3-)-1-oxoisoindoline-4-)oxy)propyl)-4-phenylpiperidine-4-carbonitrile, 28 mg white solid, yield 47%; 1H NMR (400 MHz, DMSO) δ 10.98 (s, 1H), 7.63-7.54 (m, 2H), 7.48 (t, J=7.8 Hz, 1H), 7.32 (dd, J=15.2, 5.0 Hz, 2H), 7.24 (d, J=8.1 Hz, 1H), 5.11 (dd, J=13.3, 5.1 Hz, 1H), 4.39 (d, J=17.4 Hz, 1H), 4.24 (d, J=17.4 Hz, 1H), 4.17 (t, J=5.9 Hz, 2H), 3.05 (d, J=11.7 Hz, 2H), 2.97-2.85 (m, 1H), 2.56 (t, J=13.0 Hz, 3H), 2.45 (d, J=13.1 Hz, 3H), 2.35 (t, J=11.6 Hz, 2H), 2.03-1.88 (m, 5H).

Example 75: 4-(3-chlorophenyl)-1-(4-((2-(2,6-dioxopiperidine-3-)-1-oxoisoindoline-4-)oxy)butyl)piperidine-4-carbonitrile (75)

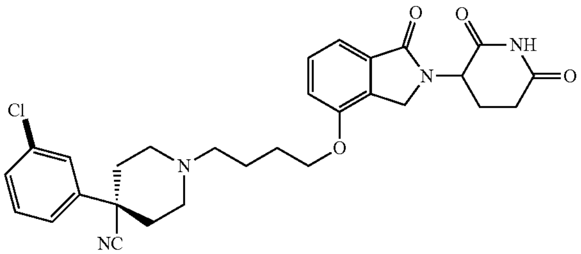

The preparation method was the same as 1-(3-((2-(2,6-dioxopiperidine-3-)-1-oxoisoindoline-4-)oxy)propyl)-4-phenylpiperidine-4-carbonitrile, 18.5 mg, yield 27%; $^1$H NMR (400 MHz, DMSO) δ 10.99 (s, 1H), 7.57 (s, 1H), 7.55-7.40 (m, 4H), 7.30 (d, J=7.5 Hz, 1H), 7.23 (d, J=8.2 Hz, 1H), 5.14 (dd, J=13.3, 5.0 Hz, 1H), 4.40 (d, J=17.2 Hz, 1H), 4.24 (d, J=17.5 Hz, 1H), 4.17 (t, J=5.7 Hz, 2H), 3.02 (d, J=12.0 Hz, 2H), 2.98-2.86 (m, 1H), 2.60 (dt, J=10.3, 5.1 Hz, 1H), 2.45 (t, J=6.4 Hz, 3H), 2.27 (t, J=12.0 Hz, 2H), 2.12 (d, J=12.7 Hz, 2H), 2.02-1.88 (m, 3H), 1.80 (dt, J=13.3, 6.8 Hz, 2H), 1.70-1.59 (m, 2H).

Example 76: 4-(2,6-chlorophenyl)-1-(3-((2-(2,6-dioxopiperidine-3-)-1-oxoisoindoline-4-)oxy)propyl)piperidine-4-carbonitrile (76)

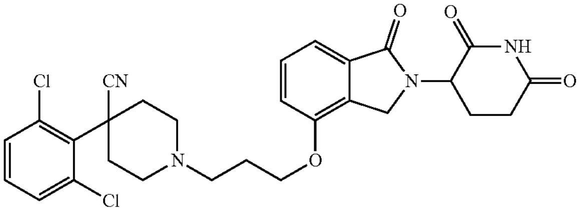 [SMILES: N#CC1(c2c(Cl)cccc2Cl)CCN(CCCOc2cccc3c2CN(C2CCC(=O)NC2=O)C3=O)CC1]

The preparation method was the same as 1-(3-((2-(2,6-dioxopiperidine-3-)-1-oxoisoindoline-4-)oxy)propyl)-4-phenylpiperidine-4-carbonitrile, and finally obtained 33 mg of white solid, yield 40%; 1H NMR (400 MHz, DMSO) δ 10.98 (s, 1H), 7.56 (d, J=8.0 Hz, 2H), 7.48 (t, J=7.8 Hz, 1H), 7.40 (t, J=8.0 Hz, 1H), 7.31 (d, J=7.5 Hz, 1H), 7.25 (d, J=8.2 Hz, 1H), 5.11 (dd, J=13.3, 5.1 Hz, 1H), 4.39 (d, J=17.5 Hz, 1H), 4.24 (d, J=17.4 Hz, 1H), 4.17 (t, J=5.9 Hz, 2H), 3.07 (d, J=11.3 Hz, 2H), 2.96-2.86 (m, 1H), 2.56 (t, J=12.2 Hz, 6H), 2.39 (d, J=11.7 Hz, 4H), 2.04-1.87 (m, 3H).

Example 77: 4-(4-chlorophenyl)-1-(4-((2-(2,6-dioxopiperidine-3-)-1-oxoisoindoline-4-)oxy)butyl)piperidine-4-carbonitrile (77)

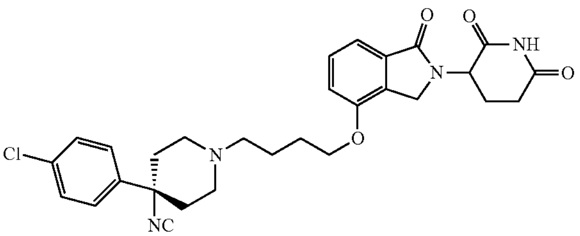

The preparation method was the same as 1-(3-((2-(2,6-dioxopiperidine-3-)-1-oxoisoindoline-4-)oxy)propyl)-4-phenylpiperidine-4-carbonitrile, 18.5 mg, yield 27%; $^1$H NMR (400 MHz, DMSO) δ 10.98 (s, 1H), 7.50 (dt, J=11.2, 8.4 Hz, 5H), 7.30 (d, J=7.5 Hz, 1H), 7.25 (d, J=8.0 Hz, 1H), 5.11 (dd, J=13.3, 5.0 Hz, 1H), 4.38 (d, J=17.2 Hz, 1H), 4.22 (d, J=17.5 Hz, 1H), 4.15 (t, J=5.7 Hz, 2H), 3.00 (d, J=12.0 Hz, 2H), 2.96-2.85 (m, 1H), 2.59 (dt, J=10.3, 5.1 Hz, 1H), 2.43 (t, J=6.4 Hz, 3H), 2.24 (t, J=12.0 Hz, 2H), 2.10 (d, J=12.7 Hz, 2H), 2.02-1.87 (m, 3H), 1.78 (dt, J=13.3, 6.8 Hz, 2H), 1.69-1.57 (m, 2H).

Example 78: 1-(3-((2-(2,6-dioxopiperidine-3-)-1-oxoisoindoline-4-)-oxy-)propyl)-4-(2-trifluoromethoxyphenyl)piperidine-4-carbonitrile (78)

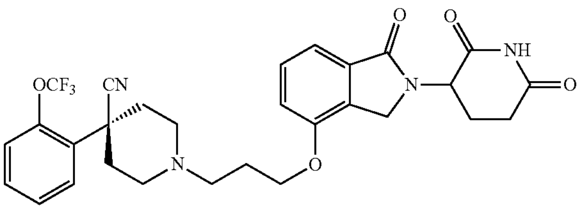

The preparation method was the same as that of Example 59, and finally 17 mg white solid was obtained, yield 28%; 1H NMR (400 MHz, DMSO) δ 10.97 (s, 1H), 7.61-7.52 (m, 2H), 7.51-7.38 (m, 3H), 7.30 (d, J=7.4 Hz, 1H), 7.24 (d, J=8.1 Hz, 1H), 5.11 (dd, J=13.3, 5.1 Hz, 1H), 4.39 (d, J=17.4 Hz, 1H), 4.24 (d, J=17.4 Hz, 1H), 4.17 (t, J=6.1 Hz, 2H), 3.04 (d, J=12.3 Hz, 2H), 2.96-2.85 (m, 1H), 2.56 (t, J=12.2 Hz, 3H), 2.48-2.41 (m, 1H), 2.35 (t, J=11.9 Hz, 2H), 2.26 (d, J=13.2 Hz, 2H), 2.05-1.88 (m, 5H).

Example 79: 4-(3-chlorophenyl)-1-(5-((2-(2,6-dioxopiperidine-3-)-1-oxoisoindoline-4-)oxy)pentyl) piperidine-4-carbonitrile (79)

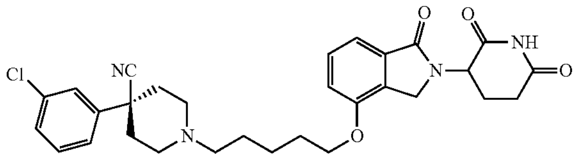

The preparation method was the same as 1-(3-((2-(2,6-dioxopiperidine-3-)-1-oxoisoindoline-4-)oxy)propyl)-4-phenylpiperidine-4-carbonitrile, and finally 25 mg 4-(3-chlorophenyl)-1-(5-((2-(2,6-dioxopiperidine-3-)-1-oxoisoindole-4-)oxy)pentyl)piperidine-4-carbonitrile, as a white solid, yield 37%; 1H NMR (400 MHz, DMSO) δ 10.97 (s, 1H), 7.58 (s, 1H), 7.54-7.41 (m, 4H), 7.30 (d, J=7.5 Hz, 1H), 7.24 (d, J=8.2 Hz, 1H), 5.10 (dd, J=13.3, 5.1 Hz, 1H), 4.37 (d, J=17.4 Hz, 1H), 4.22 (d, J=17.4 Hz, 1H), 4.12 (t, J=6.3 Hz, 2H), 2.99 (d, J=12.2 Hz, 2H), 2.96-2.84 (m, 1H), 2.56 (d, J=18.3 Hz, 2H), 2.48-2.35 (m, 3H), 2.25 (t, J=11.5 Hz, 2H), 2.13 (d, J=12.4 Hz, 1H), 1.98 (t, J=11.2 Hz, 3H), 1.82-1.72 (m, 2H), 1.50 (dt, J=16.5, 10.5 Hz, 4H).

Example 80: (S)-4-(2-chlorophenyl)-1-(3-((2-(3-methyl-2,6-dioxopiperidine-3-)-1-oxoisoindoline-4-)oxy)propyl)piperidine-4-carbonitrile (80)

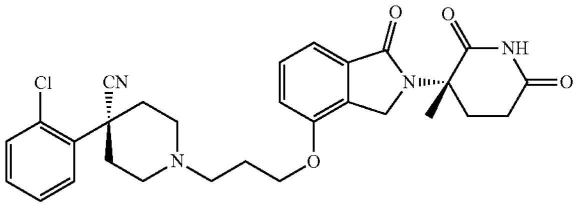

Step 1: methyl 3-hydroxy-2-methylbenzoate (20.54 g, 123.56 mmol, 1.0 eq) was dissolved in 200 mL DMF under ice bath for 15 min, sodium hydride (5.93 g, 148.27 mmol, 1.2 eq) was added, then MOMCl (11.94 g, 148.27 mmol, 1.2 eq) was added, and reacted at room temperature for 1 h. After the reaction was completed, saturated ammonium chloride was added to quench the reaction, extracted with ethyl acetate three times, washed with saturated ammonium chloride three times, dried, concentrated under reduced pressure, and purified by column chromatography to obtain 25.98 g of yellow oil with a yield of 100%. $^1H$ NMR (400 MHz, $CDCl_3$) δ 7.47 (dd, J=7.5, 1.4 Hz, 1H), 7.24-7.14 (m, 2H), 5.21 (s, 2H), 3.89 (s, 3H), 3.49 (s, 3H), 2.49-2.41 (m, 3H).

Step 2: methyl 3-methoxymethoxy-2-methylbenzoate (25.98 g, 123.56 mmol, 1.0 eq) was dissolved in 200 ml carbon tetrachloride, and NBS (23.09 mmol, 129.24 mmol, 1.05 mmol), and AIBN (2.03 g, 12.36 mmol, 0.1 eq) were added, and refluxed at 88° C. for 6 h. After the reaction was completed, the solvent was spun off under reduced pressure and purified by column chromatography to obtain 35.73 g of brown solid. Yield 100%. $^1H$ NMR (400 MHz, $CDCl_3$) δ 7.58 (dd, J=6.5, 2.5 Hz, 1H), 7.35-7.27 (m, 1H), 5.30 (s, 1H), 5.10-5.05 (m, 1H), 3.94 (s, 1H), 3.53 (s, 1H).

Step 3: methyl 2-bromomethyl-3-methoxymethoxybenzoate (353 mg, 1.22 mmol, 1.0 eq), and (S)-3-amino(o-3-methylpiperidine)-2,6-dione hydrochloride monohydrate (294 mg, 1.22 mmol, 1.0 eq) were dissolved in 20 ml of toluene. Triethylamine (136 mg, 1.34 mmol, 1.1 eq) was added, and refluxed at 120° C. for 24 h. After the reaction was completed, the toluene was spun off and purified by column chromatography to obtain 232 mg of white solid with a yield of 61%.

Step 4: (S)-3-(4-methoxymethoxy-1-oxoisoindoline-2-)-3-methylpiperidine-2,6-dione (232 mg, 0.73 mmol, 1.0 eq) was added in a 50 mL round-bottom flask, and 20 mL hydrochloric acid dioxane and 200 uL methanol were added. The mixture was reacted at room temperature for 1 h. After the reaction was completed, the solvent was spun off, and directly used in the next step without further purification.

Step 5: (S)-3-(4-hydroxy-1-oxoisoindoline-2-)-3-methylpiperidine-2,6-dione (200 mg, 0.73 mmol, 1.0 eq) was dissolved in 20 mL acetonitrile. 1,2-dibromopropane (736 mg, 3.65 mmol, 5.0 eq), and anhydrous potassium carbonate (101 mg, 0.73 mmol, 1.0 eq) were added, and reacted at 50° C. for 24 h. After the reaction was completed, the solvent was spun off, diluted with ethyl acetate, washed with saturated sodium chloride, and purified by column chromatography to obtain 200 mg of white solid with a yield of 69%.

Step 6: (S)-3-(4-(3-bromopropoxy)-1-oxoisoindoline-2-)-3-methylpiperidine-2,6-dione (40 mg, 0.10 mmol, 1.0 eq) was dissolved in 3 mL DMSO, 4-(2-chlorophenyl)piperidine-4-carbonitrile hydrochloride (39 mg, 0.15 mmol, 1.5 eq), and triethylamine (102 mg, 1.01 mmol, 10.0 eq) were added, and reacted at 40° C. overnight. After the reaction was completed, diluted with 20 mL of ethyl acetate, washed with saturated sodium chloride, and purified by thin layer chromatography and high performance liquid chromatography to obtain 15 mg of the product, as a white solid, yield 28%; 1H NMR (400 MHz, DMSO) δ 10.87 (s, 1H), 7.61-7.51 (m, 2H), 7.45 (dd, J=12.1, 6.3 Hz, 3H), 7.22 (dd, J=11.7, 7.8 Hz, 2H), 4.65 (d, J=17.5 Hz, 1H), 4.54 (d, J=17.6 Hz, 1H), 4.18 (t, J=6.1 Hz, 2H), 3.07 (d, J=11.7 Hz, 2H), 2.80-2.51 (m, 7H), 2.37 (t, J=12.3 Hz, 2H), 2.08-1.84 (m, 5H), 1.69 (s, 3H).

Example 81: 4-(4-chlorophenyl)-1-(5-((2-(2,6-dioxopiperidine-3-)-1-oxoisoindoline-4-)oxy)pentyl) piperidine-4-carbonitrile (81)

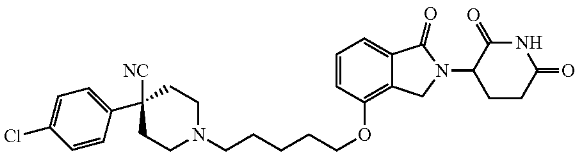

The preparation method was the same as 1-(3-((2-(2,6-dioxopiperidine-3-)-1-oxoisoindoline-4-)oxy)propyl)-4-phenylpiperidine-4-carbonitrile, and finally 21 mg 4-(4-chlorophenyl)-1-(5-((2-(2,6-dioxopiperidine-3-)-1-oxoisoindole-4-)oxy)pentyl)piperidine-4-carbonitrile, as a white solid, yield 22%; $^1$H NMR (400 MHz, DMSO) δ 10.97 (s, 1H), 7.55 (d, J=8.5 Hz, 2H), 7.52-7.43 (m, 3H), 7.30 (d, J=7.5 Hz, 1H), 7.24 (d, J=8.1 Hz, 1H), 5.11 (dd, J=13.3, 5.0 Hz, 1H), 4.37 (d, J=17.4 Hz, 1H), 4.22 (d, J=17.4 Hz, 1H), 4.12 (t, J=6.2 Hz, 2H), 2.98 (d, J=11.9 Hz, 2H), 2.94-2.84 (m, 1H), 2.56 (d, J=17.6 Hz, 1H), 2.48-2.34 (m, 3H), 2.24 (t, J=11.7 Hz, 2H), 2.09 (d, J=12.8 Hz, 2H), 1.95 (dd, J=17.2, 8.5 Hz, 3H), 1.77 (dd, J=13.4, 6.6 Hz, 2H), 1.58-1.38 (m, 4H).

Example 82: 4-(2-chlorophenyl)-1-(4-((2-(2,6-dioxopiperidine-3-)-1-oxoisoindoline-4-)oxy)butyryl) piperidine-4-carbonitrile (82)

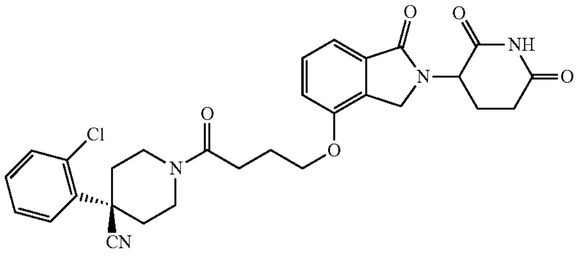

The synthesis method was the same as N-(3-chloro-4-methylphenyl)-4-((2-(2,6-dioxopiperidine-3-)-1-oxoisoindoline-4-)oxy)butanamide, and obtained 52 mg of final product, as a white solid, yield 66%; $^1$H NMR (400 MHz, DMSO) δ 10.97 (s, 1H), 7.60-7.54 (m, 1H), 7.51-7.40 (m, 4H), 7.30 (d, J=7.5 Hz, 1H), 7.24 (d, J=8.2 Hz, 1H), 5.11 (dd, J=13.2, 5.0 Hz, 1H), 4.64 (d, J=13.4 Hz, 1H), 4.39 (d, J=17.5 Hz, 1H), 4.25 (d, J=17.4 Hz, 1H), 4.13 (d, J=16.2 Hz, 3H), 3.37 (d, J=12.8 Hz, 1H), 2.89 (q, J=13.3 Hz, 2H), 2.64-2.53 (m, 3H), 2.44 (dd, J=16.8, 8.0 Hz, 4H), 2.05-1.92 (m, 4H), 1.84 (d, J=12.5 Hz, 1H).

Example 83: 4-(3-chlorophenyl)-1-(4-((2-(2,6-dioxopiperidine-3-)-1-oxoisoindoline-4-)oxy)butyryl) piperidine-4-carbonitrile (83)

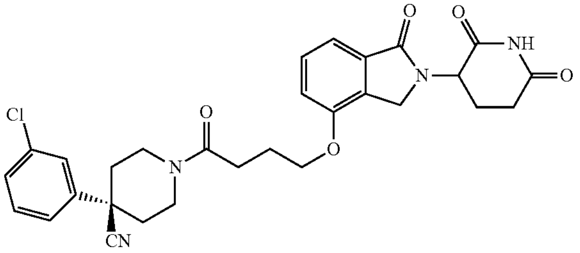

The synthesis method was the same as N-(3-chloro-4-methylphenyl)-4-((2-(2,6-dioxopiperidine-3-)-1-oxoisoindoline-4-)oxy)butanamide, and finally obtained 39 mg of product, as a white solid, yield 49%; 1H NMR (400 MHz, DMSO) δ 10.97 (s, 1H), 7.61 (s, 1H), 7.56-7.43 (m, 4H), 7.30 (d, J=7.4 Hz, 1H), 7.25 (d, J=8.1 Hz, 1H), 5.11 (dd, J=13.3, 5.0 Hz, 1H), 4.62 (d, J=14.0 Hz, 1H), 4.39 (d, J=17.4 Hz, 1H), 4.24 (d, J=17.4 Hz, 1H), 4.16 (t, J=6.2 Hz, 2H), 4.09 (d, J=14.4 Hz, 1H), 3.27 (d, J=13.2 Hz, 1H), 2.98-2.74 (m, 2H), 2.56 (dd, J=13.3, 6.2 Hz, 3H), 2.43 (dd, J=13.2, 4.4 Hz, 1H), 2.24-1.79 (m, 7H).

Example 84: 4-(4-chlorophenyl)-1-(4-((2-(2,6-dioxopiperidine-3-)-1-oxoisoindoline-4-)oxy)butyryl) piperidine-4-carbonitrile (84)

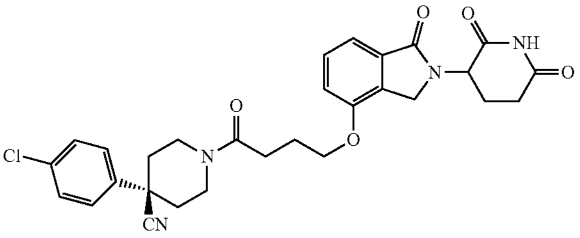

The synthesis method was the same as N-(3-chloro-4-methylphenyl)-4-((2-(2,6-dioxopiperidine-3-)-1-oxoisoindoline-4-)oxy)butanamide, and finally obtained 38 mg of product, as a white solid, yield 47%; $^1$H NMR (400 MHz, DMSO) δ 10.97 (s, 1H), 7.60-7.43 (m, 5H), 7.27 (dd, J=21.4, 7.8 Hz, 2H), 5.11 (dd, J=13.3, 5.1 Hz, 1H), 4.62 (d, J=13.5 Hz, 1H), 4.39 (d, J=17.5 Hz, 1H), 4.24 (d, J=17.4 Hz, 1H), 4.16 (t, J=6.2 Hz, 2H), 4.09 (d, J=13.6 Hz, 1H), 3.27 (d, J=12.6 Hz, 1H), 2.99-2.75 (m, 2H), 2.56 (dd, J=13.2, 7.1 Hz, 3H), 2.43 (dd, J=13.0, 4.4 Hz, 3H), 2.13 (d, J=13.3 Hz, 2H), 2.05-1.92 (m, 4H), 1.86 (d, J=12.6 Hz, 1H).

Example 85: 4-(2-chlorophenyl)-1-(5-((2-(2,6-dioxopiperidine-3-)-1-oxoisoindoline-4-)oxy)valeryl) piperidine-4-carbonitrile (85)

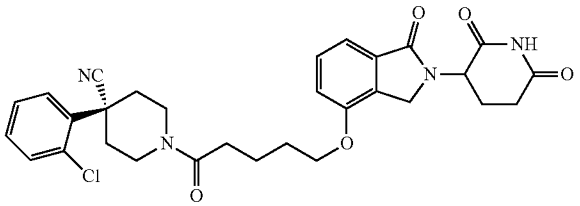

The synthesis method was the same as N-(3-chloro-4-methylphenyl)-4-((2-(2,6-dioxopiperidine-3-)-1-oxoisoindoline-4-)oxy)butanamide, and finally obtained 26 mg of product, as a white solid, yield 33%; 1H NMR (400 MHz, DMSO) δ 10.96 (s, 1H), 7.57 (dt, J=7.3, 3.7 Hz, 1H), 7.54-7.41 (m, 4H), 7.30 (d, J=7.4 Hz, 1H), 7.24 (d, J=8.1 Hz, 1H), 5.10 (dd, J=13.3, 5.1 Hz, 1H), 4.63 (d, J=14.1 Hz, 1H), 4.37 (d, J=17.4 Hz, 1H), 4.22 (d, J=17.4 Hz, 1H), 4.13 (dd, J=14.7, 8.6 Hz, 3H), 3.37 (d, J=12.7 Hz, 1H), 2.89 (ddd, J=25.1, 15.0, 8.7 Hz, 2H), 2.59 (s, 1H), 2.51-2.37 (m, 9H), 1.99 (dd, J=16.4, 8.8 Hz, 2H), 1.91-1.62 (m, 5H).

Example 86: 1-(4-((2-(2,6-dioxopiperidine-3-)-1-oxoisoindoline-4-)-oxy-)butyryl)-4-(4-tri fluoromethoxyphenyl)piperidine-4-carbonitrile (86)

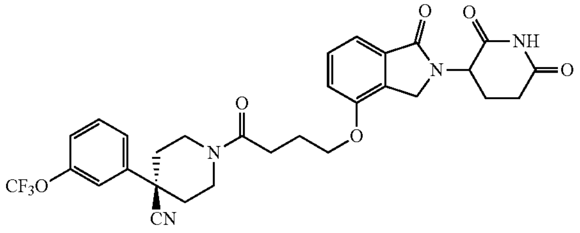

The synthesis method was the same as N-(3-chloro-4-methylphenyl)-4-((2-(2,6-dioxopiperidine-3-)-1-oxoisoindoline-4-)oxy)butanamide, and obtained 32 mg of final product, as a white solid, yield 35%; $^{1}H$ NMR (400 MHz, DMSO) δ 10.98 (s, 1H), 7.67 (d, J=8.5 Hz, 2H), 7.47 (dd, J=15.0, 7.9 Hz, 3H), 7.27 (dd, J=19.9, 7.8 Hz, 2H), 5.11 (dd, J=13.4, 5.0 Hz, 1H), 4.63 (d, J=13.7 Hz, 1H), 4.40 (d, J=17.4 Hz, 1H), 4.25 (d, J=17.3 Hz, 1H), 4.20-4.06 (m, 3H), 3.28 (d, J=13.4 Hz, 1H), 2.99-2.77 (m, 2H), 2.65-2.54 (m, 3H), 2.43 (dd, J=13.3, 4.4 Hz, 1H), 2.16 (d, J=13.0 Hz, 2H), 2.01 (dd, J=13.1, 6.8 Hz, 4H), 1.92-1.80 (m, 1H).

Example 87: 4-(3-chlorophenyl)-1-(5-((2-(2,6-dioxopiperidine-3-)-1-oxoisoindoline-4-)oxy)valeryl) piperidine-4-carbonitrile (87)

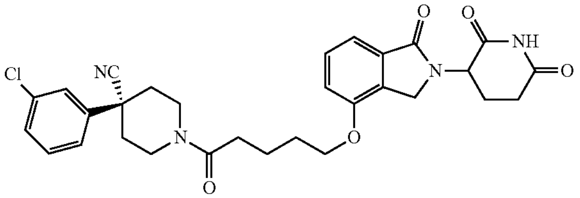

The synthesis method was the same as N-(3-chloro-4-methylphenyl)-4-((2-(2,6-dioxopiperidine-3-)-1-oxoisoindoline-4-)oxy)butanamide, and finally obtained 33 mg of product, as a white solid, yield 42%; 1H NMR (400 MHz, DMSO) δ 10.96 (s, 1H), 7.62 (s, 1H), 7.56-7.43 (m, 4H), 7.30 (d, J=7.4 Hz, 1H), 7.24 (d, J=8.1 Hz, 1H), 5.10 (dd, J=13.3, 5.1 Hz, 1H), 4.61 (d, J=13.6 Hz, 1H), 4.37 (d, J=17.4 Hz, 1H), 4.22 (d, J=17.4 Hz, 1H), 4.15 (t, J=6.2 Hz, 2H), 4.09 (d, J=14.2 Hz, 1H), 3.27 (t, J=9.6 Hz, 1H), 2.97-2.84 (m, 1H), 2.79 (t, J=12.6 Hz, 1H), 2.56 (d, J=17.9 Hz, 1H), 2.50-2.34 (m, 6H), 2.23-1.60 (m, 10H).

Example 88: 1-(4-((2-(2,6-dioxopiperidine-3-)-1-oxoisoindoline-4-)-oxy-)butyryl)-4-(3-trifluoromethoxyphenyl)piperidine-4-carbonitrile (88)

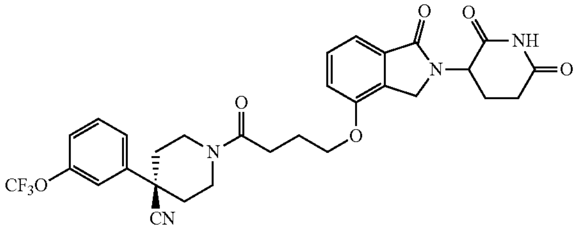

The synthesis method was the same as N-(3-chloro-4-methylphenyl)-4-((2-(2,6-dioxopiperidine-3-)-1-oxoisoindoline-4-)oxy)butanamide, and obtained 32 mg of final product, as a white solid, yield 56%; $^{1}H$ NMR (400 MHz, DMSO) δ 10.98 (s, 1H), 7.67 (d, J=8.5 Hz, 2H), 7.47 (dd, J=15.0, 7.9 Hz, 3H), 7.27 (dd, J=19.9, 7.8 Hz, 2H), 5.11 (dd, J=13.4, 5.0 Hz, 1H), 4.63 (d, J=13.7 Hz, 1H), 4.40 (d, J=17.4 Hz, 1H), 4.25 (d, J=17.3 Hz, 1H), 4.20-4.06 (m, 3H), 3.28 (d, J=13.4 Hz, 1H), 2.99-2.77 (m, 2H), 2.65-2.54 (m, 3H), 2.43 (dd, J=13.3, 4.4 Hz, 1H), 2.16 (d, J=13.0 Hz, 2H), 2.01 (dd, J=13.1, 6.8 Hz, 4H), 1.92-1.80 (m, 1H).

Example 89: 4-(3-chlorophenyl)-1-(5-((2-(2,6-dioxopiperidine-3-)-1-oxoisoindoline-4-)oxy)valeryl) piperidine-4-carbonitrile (89)

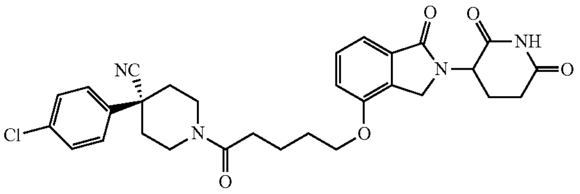

The synthesis method was the same as N-(3-chloro-4-methylphenyl)-4-((2-(2,6-dioxopiperidine-3-)-1-oxoisoindoline-4-)oxy)butanamide, and finally obtained 64 mg of product, as a white solid, yield 82%; 1H NMR (400 MHz, DMSO) δ 10.96 (s, 1H), 7.57 (d, J=8.8 Hz, 2H), 7.51 (d, J=8.8 Hz, 2H), 7.47 (d, J=7.8 Hz, 1H), 7.30 (d, J=7.5 Hz, 1H), 7.24 (d, J=8.1 Hz, 1H), 5.10 (dd, J=13.3, 5.1 Hz, 1H), 4.61 (d, J=12.4 Hz, 1H), 4.37 (d, J=17.4 Hz, 1H), 4.22 (d, J=17.4 Hz, 1H), 4.15 (t, J=6.1 Hz, 2H), 4.08 (d, J=14.9 Hz, 1H), 3.28 (s, 1H), 2.88 (d, J=12.1 Hz, 1H), 2.79 (s, 1H), 2.56 (d, J=18.5 Hz, 1H), 2.45 (t, J=7.4 Hz, 6H), 2.14 (d, J=12.5 Hz, 2H), 2.10-1.92 (m, 2H), 1.92-1.60 (m, 6H).

Example 90: 1-(4-((2-(2,6-dioxopiperidine-3-)-1-oxoisoindoline-4-)-oxy-)butyryl)-4-(2-trifluoromethoxyphenyl)piperidine-4-carbonitrile (90)

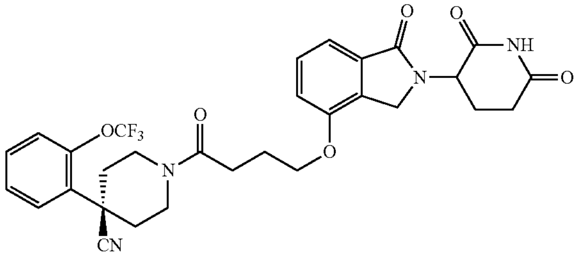

The synthesis method was the same as N-(3-chloro-4-methylphenyl)-4-((2-(2,6-dioxopiperidine-3-)-1-oxoisoindoline-4-)oxy)butanamide, and obtained 47 mg of final product, as a white solid, yield 88%; 1H NMR (400 MHz, DMSO) δ 10.97 (s, 1H), 7.60-7.40 (m, 5H), 7.30 (d, J=7.5 Hz, 1H), 7.24 (d, J=8.1 Hz, 1H), 5.11 (dd, J=13.3, 5.0 Hz, 1H), 4.63 (d, J=13.8 Hz, 1H), 4.39 (d, J=17.4 Hz, 1H), 4.25 (d, J=17.3 Hz, 1H), 4.15 (t, J=6.0 Hz, 3H), 3.35 (s, 1H), 2.97-2.82 (m, 2H), 2.56 (t, J=10.2 Hz, 3H), 2.45 (s, 1H), 2.28 (d, J=13.1 Hz, 2H), 2.07-1.93 (m, 4H), 1.91-1.77 (m, 1H).

Example 91: 4-(2-chlorophenyl)-1-(4-(2-(2,6-dioxopiperidine-3-)-1-oxoisoindoline-4-)butyl)piperidine-4-carbonitrile (91)

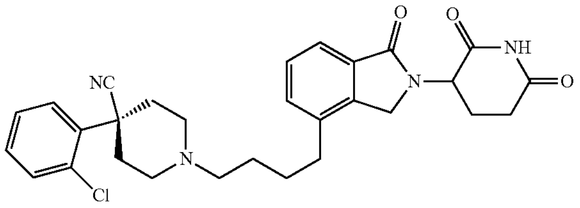

The preparation method was the same as 1-(3-((2-(2,6-dioxopiperidine-3-)-1-oxoisoindoline-4-)oxy)propyl)-4-phenylpiperidine-4-carbonitrile, 17.4 mg, yield 17%. $^1$H NMR (400 MHz, DMSO) δ 10.99 (s, 1H), 7.55 (ddd, J=11.7, 5.3, 2.8 Hz, 3H), 7.44 (ddd, J=7.1, 5.1, 2.8 Hz, 4H), 5.13 (dd, J=13.2, 5.1 Hz, 1H), 4.47 (d, J=17.2 Hz, 1H), 4.32 (d, J=17.2 Hz, 1H), 2.99 (d, J=12.3 Hz, 2H), 2.96-2.85 (m, 1H), 2.67 (t, J=7.6 Hz, 2H), 2.58 (d, J=17.6 Hz, 1H), 2.48-2.36 (m, 5H), 2.30 (t, J=11.9 Hz, 2H), 2.04-1.89 (m, 3H), 1.63 (dt, J=15.3, 7.7 Hz, 2H), 1.56-1.45 (m, 2H).

Example 92: 4-(2-chlorophenyl)-1-(5-(2-(2,6-oxopiperidine-3-)-1-oxoisoindoline-4-)pentyl)piperidine-4-carbonitrile (92)

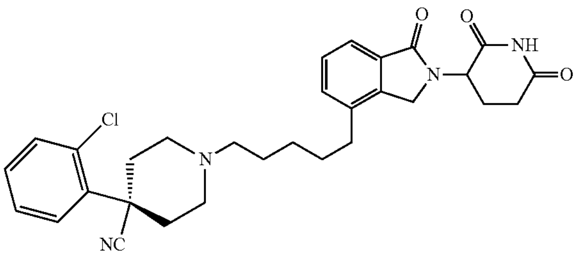

The preparation method was the same as 1-(3-((2-(2,6-dioxopiperidine-3-)-1-oxoisoindoline-4-)oxy)propyl)-4-phenylpiperidine-4-carbonitrile, 10.5 mg, yield 10%; $^1$H NMR (400 MHz, DMSO) δ 11.00 (s, 1H), 7.59-7.51 (m, 3H), 7.44 (dt, J=4.4, 3.4 Hz, 4H), 5.13 (dd, J=13.3, 5.1 Hz, 1H), 4.46 (d, J=17.2 Hz, 1H), 4.31 (d, J=17.2 Hz, 1H), 3.00 (d, J=12.0 Hz, 2H), 2.96-2.86 (m, 1H), 2.67-2.56 (m, 3H), 2.44 (d, J=12.9 Hz, 3H), 2.39-2.25 (m, 4H), 2.05-1.88 (m, 3H), 1.63 (dt, J=15.6, 7.9 Hz, 2H), 1.55-1.44 (m, 2H), 1.34 (dt, J=14.8, 7.5 Hz, 2H).

Example 93: 4-(3-chlorophenyl)-1-(4-(2-(2,6-dioxopiperidine-3-)-1-oxoisoindoline-4-)butyl)piperidine-4-carbonitrile (93)

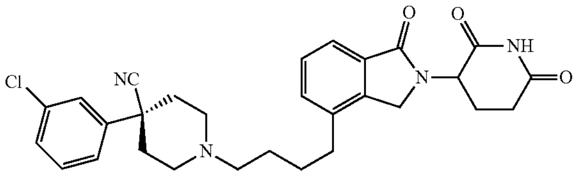

The preparation method was the same as 3-(1-oxo-4-(5-(2-phenylpyrroline-1-)pentyl)indoline-2-)piperidine-2,6-dione, 27 mg, yield 26%; $^1$H NMR (400 MHz, DMSO) δ 10.99 (s, 1H), 7.61-7.41 (m, 7H), 5.13 (dd, J=13.3, 5.1 Hz, 1H), 4.47 (d, J=17.2 Hz, 1H), 4.32 (d, J=17.2 Hz, 1H), 3.02-2.84 (m, 3H), 2.67 (t, J=7.6 Hz, 2H), 2.59 (d, J=16.8 Hz, 1H), 2.46-2.35 (m, 3H), 2.23 (t, J=11.3 Hz, 2H), 2.13 (d, J=12.6 Hz, 2H), 2.05-1.93 (m, 3H), 1.65 (dt, J=16.6, 6.8 Hz, 2H), 1.51 (dt, J=15.2, 7.5 Hz, 2H).

Example 94: 1-(5-(2-(2,6-dioxopiperidine-3-)-1-oxoisoindoline-4-)pentyl)-4-(3-trifluoromethoxyphenyl) piperidine-4-carbonitrile (94)

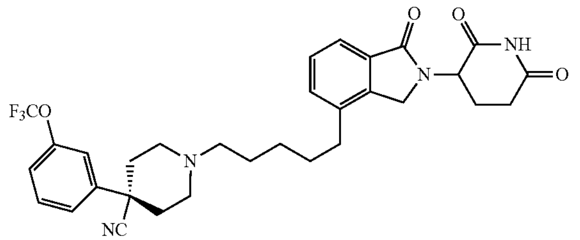

The preparation method was the same as 3-(1-oxo-4-(5-(2-phenylpyrroline-1-)pentyl)indoline-2-)piperidine-2,6-dione, 9 mg, yield 8%; $^1$H NMR (400 MHz, DMSO) δ 11.00 (s, 1H), 7.62-7.58 (m, 2H), 7.56 (dd, J=5.9, 2.7 Hz, 1H), 7.50 (s, 1H), 7.48-7.45 (m, 2H), 7.40 (d, J=4.1 Hz, 1H), 5.14 (dd, J=13.3, 5.1 Hz, 1H), 4.47 (d, J=17.2 Hz, 1H), 4.31 (d, J=17.1 Hz, 1H), 2.98 (d, J=11.5 Hz, 2H), 2.94-2.87 (m, 1H), 2.67-2.56 (m, 3H), 2.45-2.38 (m, 1H), 2.39-2.31 (m, 2H), 2.23 (t, J=11.4 Hz, 2H), 2.14 (d, J=12.3 Hz, 2H), 2.06-1.93 (m, 3H), 1.63 (dt, J=15.1, 7.6 Hz, 2H), 1.50 (dt, J=14.8, 7.6 Hz, 2H), 1.39-1.29 (m, 2H).

Example 95: 4-(4-chlorophenyl)-1-(4-(2-(2,6-dioxopiperidine-3-)-1-oxoisoindoline-4-)butyl)piperidine-4-carbonitrile (95)

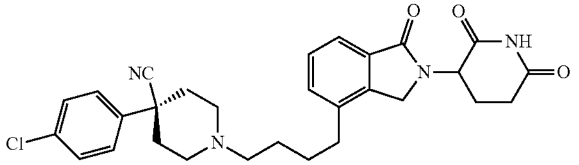

The preparation method was the same as 3-(1-oxo-4-(5-(2-phenylpyrroline-1-)pentyl)indoline-2-)piperidine-2,6-dione, 32.8 mg, yield 31.6%; $^1$H NMR (400 MHz, DMSO) δ 11.00 (s, 1H), 5.13 (dd, J=13.3, 5.0 Hz, 1H), 4.47 (d, J=17.2 Hz, 1H), 4.32 (d, J=17.2 Hz, 1H), 3.00-2.86 (m, 3H), 2.67 (t, J=7.5 Hz, 2H), 2.62-2.55 (m, 1H), 2.47-2.36 (m, 3H), 2.24 (t, J=11.9 Hz, 2H), 2.09 (d, J=12.9 Hz, 2H), 2.04-1.90 (m, 3H), 1.69-1.58 (m, 2H), 1.51 (dt, J=14.1, 7.1 Hz, 2H), 1.23-1.23 (m, 1H).

Example 96: 1-(5-(2-(2,6-dioxopiperidine-3-)-1-oxoisoindoline-4-)pentyl)-4-(4-trifluoromethoxyphenyl)piperidine-4-carbonitrile (96)

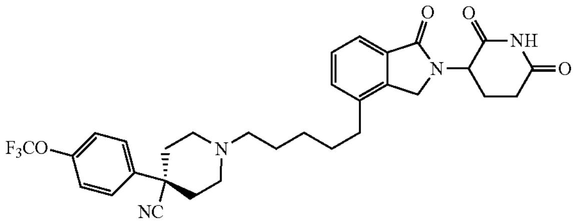

The preparation method was the same as 3-(1-oxo-4-(5-(2-phenylpyrroline-1-)pentyl)indoline-2-)piperidine-2,6-dione, 19.9 mg, yield 18%; $^1$H NMR (400 MHz, DMSO) δ 11.00 (s, 1H), 7.66 (dd, J=7.0, 4.9 Hz, 2H), 7.56 (dt, J=7.7, 3.8 Hz, 1H), 7.45 (dd, J=8.8, 5.8 Hz, 4H), 5.14 (dd, J=13.3, 5.1 Hz, 1H), 4.47 (d, J=17.2 Hz, 1H), 4.31 (d, J=17.1 Hz, 1H), 2.98 (d, J=11.3 Hz, 2H), 2.94-2.86 (m, 1H), 2.67-2.56 (m, 3H), 2.43 (dt, J=13.5, 9.1 Hz, 1H), 2.38-2.33 (m, 2H), 2.24 (t, J=11.4 Hz, 2H), 2.12 (d, J=12.3 Hz, 2H), 2.05-1.90 (m, 3H), 1.63 (dt, J=15.2, 7.7 Hz, 2H), 1.55-1.45 (m, 2H), 1.34 (dt, J=14.9, 7.6 Hz, 2H).

Example 97: 1-(4-(2-(2,6-dioxopiperidine-3-)-1-oxoisoindoline-4-)butyl)-4-(3-trifluoromethoxyphenyl) piperidine-4-carbonitrile (97)

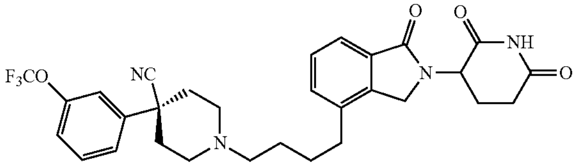

The preparation method was the same as 3-(1-oxo-4-(5-(2-phenylpyrroline-1-)pentyl)indoline-2-)piperidine-2,6-dione, 13 mg, yield 11%; $^1$H NMR (400 MHz, DMSO) δ 10.99 (s, 1H), 7.63-7.54 (m, 3H), 7.52-7.44 (m, 3H), 7.39 (d, J=6.6 Hz, 1H), 5.13 (dd, J=13.3, 5.1 Hz, 1H), 4.47 (d, J=17.2 Hz, 1H), 4.32 (d, J=17.2 Hz, 1H), 3.02-2.86 (m, 3H), 2.67 (t, J=7.6 Hz, 2H), 2.59 (d, J=17.1 Hz, 1H), 2.47-2.36 (m, 3H), 2.24 (t, J=11.6 Hz, 2H), 2.14 (d, J=12.2 Hz, 2H), 2.06-1.94 (m, 3H), 1.64 (dt, J=15.7, 6.5 Hz, 2H), 1.51 (dt, J=14.5, 7.2 Hz, 2H).

Example 98: 4-(2-chlorophenyl)-1-(6-(2-(2,6-dioxopiperidine-3-)-1-oxoisoindoline-4-)hexyl)piperidine-4-carbonitrile (98)

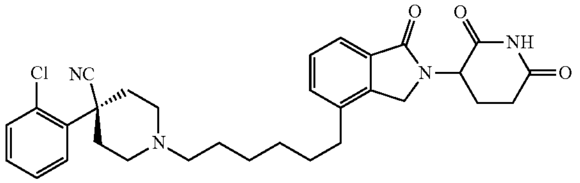

The preparation method was the same as 3-(1-oxo-4-(5-(2-phenylpyrroline-1-)pentyl)indoline-2-)piperidine-2,6-dione, 11.9 mg, yield 11.7%; $^1$H NMR (400 MHz, DMSO) δ 10.99 (s, 1H), 7.55 (dd, J=10.3, 6.6 Hz, 3H), 7.48-7.40 (m, 4H), 5.13 (dd, J=13.3, 5.0 Hz, 1H), 4.46 (d, J=17.2 Hz, 1H), 4.30 (d, J=17.1 Hz, 1H), 3.01 (d, J=12.2 Hz, 2H), 2.98-2.86 (m, 1H), 2.68-2.56 (m, 3H), 2.47-2.41 (m, 3H), 2.40-2.27 (m, 4H), 2.05-1.90 (m, 3H), 1.65-1.57 (m, 2H), 1.50-1.40 (m, 2H), 1.38-1.27 (m, 4H).

Example 99: 1-(4-(2-(2,6-dioxopiperidine-3-)-1-oxoisoindoline-4-)butyl)-4-(4-trifluoromethoxyphenyl)piperidine-4-carbonitrile (99)

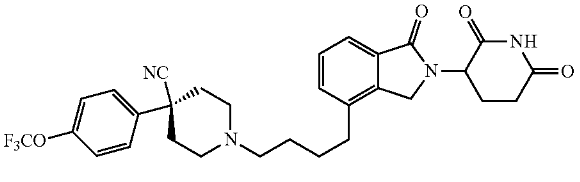

The preparation method was the same as 3-(1-oxo-4-(5-(2-phenylpyrroline-1-)pentyl)indoline-2-)piperidine-2,6-dione, 18.5 mg, yield 16%; $^1$H NMR (400 MHz, DMSO) δ 11.00 (s, 1H), 7.67 (d, J=8.9 Hz, 2H), 7.56 (dt, J=7.6, 3.8 Hz, 1H), 7.46 (dt, J=13.1, 6.3 Hz, 4H), 5.14 (dd, J=13.3, 5.1 Hz, 1H), 4.47 (d, J=17.2 Hz, 1H), 4.32 (d, J=17.1 Hz, 1H), 2.97 (d, J=12.0 Hz, 2H), 2.94-2.86 (m, 1H), 2.67 (t, J=7.6 Hz, 2H), 2.59 (d, J=16.8 Hz, 1H), 2.42 (dd, J=14.1, 7.5 Hz, 3H), 2.25 (t, J=11.9 Hz, 2H), 2.12 (d, J=12.5 Hz, 2H), 2.01-1.95 (m, 3H), 1.63 (dd, J=14.1, 6.6 Hz, 2H), 1.52 (dd, J=13.9, 7.1 Hz, 2H).

Example 100: 4-(3-chlorophenyl)-1-(6-(2-(2,6-dioxopiperidine-3-)-1-oxoisoindoline-4-)hexyl)piperidine-4-carbonitrile (100)

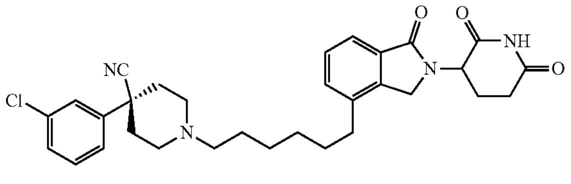

The preparation method was the same as 3-(1-oxo-4-(5-(2-phenylpyrroline-1-)pentyl)indoline-2-)piperidine-2,6-dione, 13.2 mg, yield 13%; $^1$H NMR (400 MHz, DMSO) δ 11.00 (s, 1H), 7.60-7.42 (m, 7H), 5.14 (dd, J=13.3, 5.1 Hz, 1H), 4.46 (d, J=17.2 Hz, 1H), 4.30 (d, J=17.1 Hz, 1H), 3.04-2.86 (m, 3H), 2.68-2.56 (m, 3H), 2.47-2.33 (m, 3H), 2.26 (t, J=11.5 Hz, 2H), 2.14 (d, J=12.3 Hz, 2H), 2.05-1.95 (m, 3H), 1.66-1.56 (m, 2H), 1.51-1.41 (m, 2H), 1.38-1.27 (m, 4H).

Example 101: 4-(2,4-chlorophenyl)-1-(4-(2-(2,6-dioxopiperidine-3-)-1-oxoisoindoline-4-)butyl)piperidine-4-carbonitrile (101)

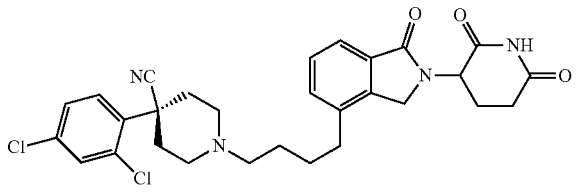

The preparation method was the same as 3-(1-oxo-4-(5-(2-phenylpyrroline-1-)pentyl)indoline-2-)piperidine-2,6-dione, 31 mg, yield 29%. $^1$H NMR (400 MHz, DMSO) δ 10.99 (s, 1H), 7.74 (d, J=2.0 Hz, 1H), 7.54 (qd, J=8.7, 3.7 Hz, 3H), 7.48-7.44 (m, 2H), 5.13 (dd, J=13.3, 5.1 Hz, 1H), 4.47 (d, J=17.2 Hz, 1H), 4.31 (d, J=17.1 Hz, 1H), 2.99 (d, J=11.9 Hz, 2H), 2.95-2.86 (m, 1H), 2.67 (t, J=7.6 Hz, 2H), 2.62-2.54 (m, 1H), 2.47-2.36 (m, 5H), 2.30 (t, J=12.0 Hz, 2H), 2.04-1.91 (m, 3H), 1.69-1.57 (m, 2H), 1.54-1.47 (m, 2H).

Example 102: 4-(4-chlorophenyl)-1-(6-(2-(2,6-dioxopiperidine-3-)-1-oxoisoindoline-4-)hexyl)piperidine-4-carbonitrile (102)

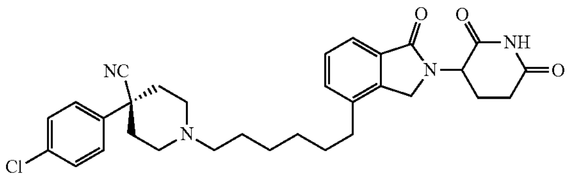

The preparation method was the same as 3-(1-oxo-4-(5-(2-phenylpyrroline-1-)pentyl)indoline-2-)piperidine-2,6-dione, 32.9 mg, yield 32.5%; $^1$H NMR (400 MHz, DMSO) δ 10.99 (s, 1H), 7.58-7.53 (m, 3H), 7.53-7.48 (m, 2H), 7.47-7.44 (m, 2H), 5.13 (dd, J=13.3, 5.1 Hz, 1H), 4.46 (d, J=17.2 Hz, 1H), 4.30 (d, J=17.1 Hz, 1H), 3.02-2.87 (m, 3H), 2.68-2.56 (m, 3H), 2.46-2.31 (m, 3H), 2.24 (t, J=11.5 Hz, 2H), 2.10 (d, J=12.0 Hz, 2H), 2.05-1.90 (m, 4H), 1.66-1.56 (m, 2H), 1.50-1.40 (m, 2H), 1.38-1.27 (m, 4H).

Example 103: 3-(4-(5-(3,4-dihydroquinoline-1(2H))pentyl)-1-oxoisoindoline-2-)piperidine-2,6-dione (103)

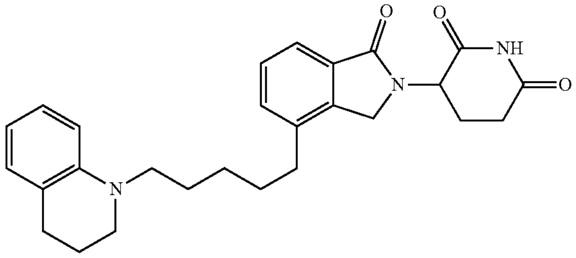

The compound 3-(4-(5-bromopentyl)-1-oxoisoindoline-2-)piperidine-2,6-dione (77 mg, 0.196 mmol, 1 eq.) and 1,2,3,4-tetrahydroquinoline (78 mg, 0.587 mmol, 3 eq.) were dissolved in 5 mL of dry DMF, sodium iodide (44 mg, 0.294 mmol, 1.5 eq.) was added under stirring at room temperature, and the resulting reaction solution was reacted at 80° C. overnight. After the reaction was completed, the resulting reaction solution was directly separated by HPLC to obtain 8.5 mg 3-(4-(5-(3,4-dihydroquinoline-1(2H))pentyl)-1-oxoisoindoline-2-)piperidine-2,6-dione, as a white solid, yield 10%; $^1$H NMR (400 MHz, DMSO) δ 11.00 (s, 1H), 7.56 (p, J=3.9 Hz, 1H), 7.46 (dd, J=7.6, 4.0 Hz, 2H), 6.95-6.89 (m, 1H), 6.83 (dd, J=7.2, 1.3 Hz, 1H), 6.54-6.48 (m, 1H), 6.42 (td, J=7.2, 0.7 Hz, 1H), 5.13 (dd, J=13.4, 5.2 Hz, 1H), 4.46 (d, J=17.1 Hz, 1H), 4.30 (d, J=17.1 Hz, 1H), 3.20 (dd, J=9.8, 4.9 Hz, 4H), 2.92 (ddd, J=17.6, 13.4, 5.2 Hz, 1H), 2.61 (ddd, J=8.7, 6.6, 4.9 Hz, 5H), 2.45-2.31 (m, 1H), 2.04-1.94 (m, 1H), 1.87-1.77 (m, 2H), 1.65 (dt, J=8.8, 7.0 Hz, 2H), 1.54 (dt, J=14.8, 7.3 Hz, 2H), 1.36 (dd, J=14.4, 7.6 Hz, 2H).

Example 104: 3-(4-(5-(6-fluoro-2-methyl-3,4-dihydroquinoline-1(2H))pentyl)-1-oxoisoindoline-2-) piperidine-2,6-dione (104)

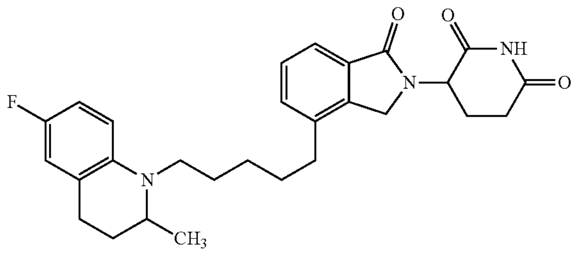 [SMILES: CC1CCc2cc(F)ccc2N1CCCCCc1cccc2c1CN(C1CCC(=O)NC1=O)C2=O]

Tetrahydroquinoline was replaced with 2-methyl-6-fluorotetrahydroquinoline, the preparation method was the same as 3-(4-(5-(3,4-dihydroquinoline-1(2H)) pentyl)-1-oxoisoindoline-2-)piperidine-2,6-dione, 17 mg, yield 28%; $^1$H NMR (400 MHz, DMSO) δ 11.00 (s, 1H), 7.60-7.53 (m, 1H), 7.45 (d, J=4.3 Hz, 2H), 6.76 (ddt, J=12.2, 5.8, 3.0 Hz, 2H), 6.42 (dd, J=8.8, 4.8 Hz, 1H), 5.13 (dd, J=13.3, 5.1 Hz, 1H), 4.46 (dd, J=17.2, 1.9 Hz, 1H), 4.30 (dd, J=17.2, 1.7 Hz, 1H), 3.45-3.37 (m, 1H), 3.31-3.20 (m, 1H), 3.12-3.02 (m, 1H), 2.92 (ddd, J=17.1, 13.6, 5.4 Hz, 1H), 2.75-2.55 (m, 5H), 2.42 (ddd, J=26.0, 13.1, 4.3 Hz, 1H), 2.04-1.94 (m, 1H), 1.66 (ddd, J=9.5, 8.0, 4.6 Hz, 4H), 1.59-1.43 (m, 2H), 1.40-1.28 (m, 2H), 1.03 (d, J=6.4 Hz, 3H).

Example 105: 3-(4-(5-(2,3-dihydro-4H-benzo[b][1,4]oxazine-4-)pentyl)-1-oxoisoindoline-2-)piperidine-2,6-dione (105)

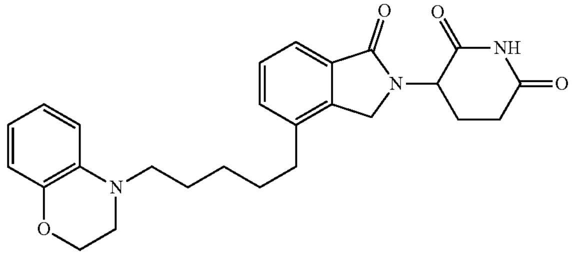 [SMILES: O=C1CCC(N2Cc3c(CCCCCN4CCOc5ccccc54)cccc3C2=O)C(=O)N1]

1,2,3,4-Tetrahydroquinoline was replaced with benzomorpholine, the preparation method was the same as 3-(4-(5-(3,4-dihydroquinoline-1(2H)) pentyl)-1-oxoisoindoline-2-)piperidine-2,6-dione, 23 mg, yield 25%; $^1$H NMR (400 MHz, DMSO) δ 10.99 (s, 1H), 7.56 (dd, J=8.2, 4.5 Hz, 1H), 7.49-7.43 (m, 2H), 6.77-6.70 (m, 1H), 6.68-6.61 (m, 2H), 6.47 (td, J=7.8, 1.4 Hz, 1H), 5.13 (dd, J=13.3, 5.1 Hz, 1H), 4.46 (d, J=17.1 Hz, 1H), 4.30 (d, J=17.1 Hz, 1H), 4.15-4.07 (m, 2H), 3.29-3.25 (m, 2H), 3.24-3.18 (m, 2H), 2.92 (ddd, J=17.7, 13.7, 5.4 Hz, 1H), 2.63 (dd, J=22.5, 14.7 Hz, 3H), 2.42 (ddd, J=26.3, 13.2, 4.4 Hz, 1H), 2.07-1.94 (m, 1H), 1.71-1.61 (m, 2H), 1.60-1.49 (m, 2H), 1.36 (dt, J=15.2, 7.7 Hz, 2H).

Example 106: 3-(4-(5-(6-bromo-3,4-dihydroquinoline-1(2H))pentyl)-1-oxoisoindoline-2-)piperidine-2,6-dione (106)

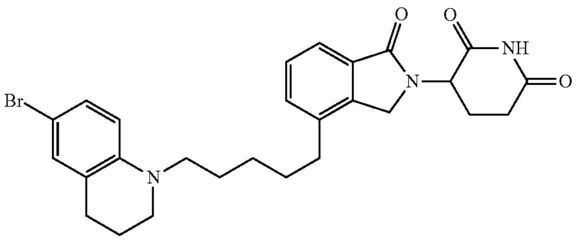 [SMILES: O=C1CCC(N2Cc3c(CCCCCN4CCCc5cc(Br)ccc54)cccc3C2=O)C(=O)N1]

Tetrahydroquinoline was replaced with 6-bromotetrahydroquinoline, the preparation method was the same as 3-(4-(5-(3,4-dihydroquinoline-1(2H))pentyl)-1-oxoisoindoline-2-)piperidine-2,6-dione, 10.3 mg, yield 10%; $^1$H NMR (400 MHz, DMSO) δ 11.00 (s, 1H), 7.56 (p, J=3.9 Hz, 1H), 7.47-7.42 (m, 2H), 7.05 (dd, J=8.8, 2.5 Hz, 1H), 6.99 (d, J=2.5 Hz, 1H), 6.46 (d, J=8.9 Hz, 1H), 5.13 (dd, J=13.2, 5.1 Hz, 1H), 4.46 (d, J=17.0 Hz, 1H), 4.30 (d, J=17.3 Hz, 1H), 3.26-3.12 (m, 4H), 2.92 (ddd, J=17.3, 13.3, 5.3 Hz, 1H), 2.64 (dd, J=9.6, 5.9 Hz, 5H), 2.47-2.31 (m, 2H), 2.05-1.95 (m, 1H), 1.83-1.74 (m, 2H), 1.68-1.58 (m, 2H), 1.52 (dt, J=14.5, 7.4 Hz, 2H), 1.40-1.28 (m, 2H).

Example 107: 3-(4-(5-(indoline-1-)pentyl)-1-oxoisoindoline-2-)piperidine-2,6-dione (107)

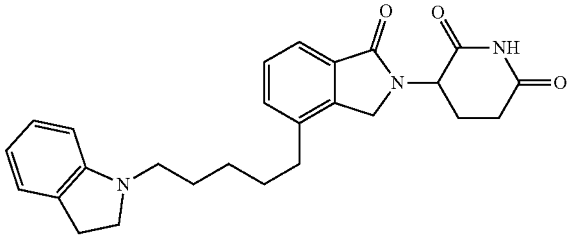 [SMILES: O=C1CCC(N2Cc3c(CCCCCN4CCc5ccccc54)cccc3C2=O)C(=O)N1]

1,2,3,4-Tetrahydroquinoline was replaced with hydrogenated indole, the preparation method was the same as 3-(4-(5-(3,4-dihydroquinoline-1(2H))pentyl)-1-oxoisoindoline-2-)piperidine-2,6-dione, 46.3 mg, yield 45%; $^1$H NMR (400 MHz, DMSO) δ 10.99 (s, 1H), 7.56 (dd, J=6.1, 2.4 Hz, 1H), 7.49-7.43 (m, 2H), 7.03-6.90 (m, 2H), 6.53 (t, J=7.2 Hz, 1H), 6.45 (d, J=7.8 Hz, 1H), 5.13 (dd, J=13.3, 5.1 Hz, 1H), 4.46 (d, J=17.2 Hz, 1H), 4.31 (d, J=17.1 Hz, 1H), 3.26 (t, J=8.4 Hz, 2H), 3.01 (t, J=7.2 Hz, 2H), 2.97-2.89 (m, 1H), 2.85 (t, J=8.3 Hz, 2H), 2.69-2.64 (m, 2H), 2.63-2.56 (m, 1H), 2.41 (ddd, J=17.6, 13.5, 4.7 Hz, 1H), 2.00 (ddd, J=10.5, 6.9, 3.3 Hz, 1H), 1.73-1.53 (m, 4H), 1.47-1.35 (m, 2H).

Example 108: 2-(2,6-dioxopiperidine-3-)-4-(4-((2-methylquinoline-4-)oxy)butoxy)isoindoline-1,3-dione 108)

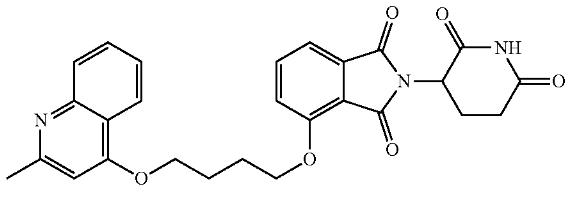 [SMILES: Cc1cc(OCCCCOc2cccc3c2C(=O)N(C2CCC(=O)NC2=O)C3=O)c2ccccc2n1]

The preparation method was the same as 2-(2,6-dioxopiperidine-3-)-4-(4-(quinoline-4-oxo)butoxy)isoindoline-1,3-dione, and obtained 12.5 mg of white solid, yield 20%; $^1$H NMR (400 MHz, DMSO) δ 11.10 (s, 1H), 8.15 (d, J=9.0 Hz, 1H), 7.92 (d, J=8.1 Hz, 1H), 7.88-7.78 (m, 2H), 7.55 (t, J=11.0 Hz, 2H), 7.44 (d, J=7.2 Hz, 1H), 7.20 (s, 1H), 5.07 (dd, J=12.8, 5.4 Hz, 1H), 4.49 (s, 2H), 4.35 (t, J=5.9 Hz, 2H), 2.88 (ddd, J=16.8, 14.0, 5.4 Hz, 1H), 2.69 (s, 3H), 2.63-2.55 (m, 1H), 2.18-1.95 (m, 6H).

Example 109: 3-(4-(5-(7-chloro-3,4-dihydroquinoline-1(2H))pentyl)-1-oxoisoindoline-2-)piperidine-2,6-dione (109)

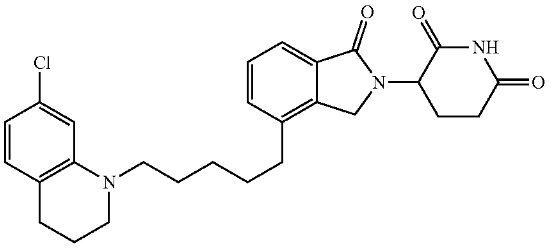 [SMILES: O=C1CCC(N2Cc3c(CCCCCN4CCCc5ccc(Cl)cc54)cccc3C2=O)C(=O)N1]

Tetrahydroquinoline was replaced with 7-chloro-1,2,3,4-tetrahydroquinoline, the preparation method was the same as 3-(4-(5-(3,4-dihydroquinoline-1(2H))pentyl)-1-oxoisoindoline-2-)piperidine-2,6-dione, 4.5 mg, yield 5%; $^1$H NMR (400 MHz, DMSO) δ 10.98 (s, 1H), 7.56 (dt, J=7.7, 3.9 Hz, 1H), 7.47-7.43 (m, 2H), 6.83 (d, J=7.9 Hz, 1H), 6.48 (d, J=1.9 Hz, 1H), 6.42 (dd, J=7.9, 1.9 Hz, 1H), 5.13 (dd, J=13.3, 5.1 Hz, 1H), 4.46 (d, J=17.2 Hz, 1H), 4.31 (d, J=17.1 Hz, 1H), 3.21 (dd, J=9.3, 5.6 Hz, 4H), 2.98-2.86 (m, 1H), 2.72-2.56 (m, 5H), 2.47-2.35 (m, 1H), 2.01 (ddd, J=10.7, 5.0, 2.7 Hz, 1H), 1.83-1.73 (m, 2H), 1.71-1.60 (m, 2H), 1.59-1.49 (m, 2H), 1.35 (dt, J=15.4, 7.7 Hz, 2H).

Example 110: 3-(4-(5-(7-bromo-2,3-dihydro-4H-benzo[b][1,4]oxazine-4-)pentyl)-1-oxoisoindoline-2-)piperidine-2,6-dione (110)

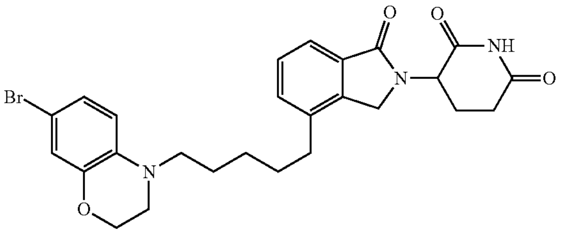

Tetrahydroquinoline was replaced with 6-bromobenzomorpholine, and the preparation method was the same as 3-(4-(5-(3,4-dihydroquinoline-1(2H)-)pentyl)-1-oxoisoindoline-2-)piperidine-2,6-dione, 14.9 mg, yield 28%; $^1$H NMR (400 MHz, DMSO) δ 10.99 (s, 1H), 7.56 (t, J=4.3 Hz, 1H), 7.45 (d, J=4.3 Hz, 2H), 6.87 (dd, J=8.6, 2.3 Hz, 1H), 6.80 (d, J=2.3 Hz, 1H), 6.61 (d, J=8.7 Hz, 1H), 5.13 (dd, J=13.3, 5.1 Hz, 1H), 4.46 (d, J=17.1 Hz, 1H), 4.30 (d, J=17.1 Hz, 1H), 4.20-4.05 (m, 2H), 3.30-3.25 (m, 2H), 3.24-3.17 (m, 2H), 2.99-2.85 (m, 1H), 2.63 (dd, J=20.5, 12.8 Hz, 3H), 2.47-2.35 (m, 1H), 2.07-1.93 (m, 1H), 1.64 (dt, J=15.1, 7.7 Hz, 2H), 1.54 (dt, J=14.9, 7.6 Hz, 2H), 1.41-1.27 (m, 2H).

Example 111: 3-(1-oxo-4-(5-(2,3,4,5-tetrahydro-TH-benzo[b]azepine-1-)pentyl)isoindoline-2-)piperidine-2,6-dione (111)

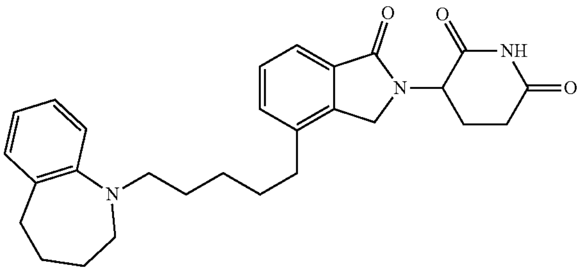 [SMILES: O=C1CCC(N2Cc3c(CCCCCN4CCCCc5ccccc54)cccc3C2=O)C(=O)N1]

1,2,3,4-Tetrahydroquinoline was replaced with benzazepine, and the preparation method was the same as 3-(4-(5-(3,4-dihydroquinoline-1(2H)-)pentyl)-1-oxoisoindoline-2-)piperidine-2,6-dione, 14.8 mg, yield 25%; $^1$H NMR (400 MHz, DMSO) δ 10.98 (d, J=5.3 Hz, 1H), 7.55 (dd, J=8.2, 4.2 Hz, 1H), 7.43 (dd, J=11.7, 8.0 Hz, 2H), 7.11-6.98 (m, 2H), 6.88 (t, J=6.9 Hz, 1H), 6.77 (dd, J=13.5, 6.7 Hz, 1H), 5.17-5.04 (m, 1H), 4.43 (dd, J=16.7, 6.2 Hz, 1H), 4.28 (dd, J=17.0, 6.2 Hz, 1H), 3.07 (dd, J=12.5, 6.2 Hz, 2H), 2.98-2.76 (m, 3H), 2.60 (d, J=18.9 Hz, 4H), 2.45-2.34 (m, 1H), 1.99 (dd, J=12.1, 4.6 Hz, 1H), 1.68-1.44 (m, 7H), 1.43-1.32 (m, 2H).

Example 112: 3-(4-(5-(indoline-1-)pentyl)-1-oxoisoindoline-2-)piperidine-2,6-dione (112)

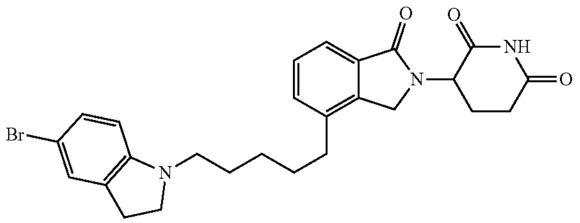 [SMILES: O=C1CCC(N2Cc3c(CCCCCN4CCc5cc(Br)ccc54)cccc3C2=O)C(=O)N1]

Tetrahydroquinoline was replaced with 5-bromohydroindole, and the preparation method was the same as 3-(4-(5-(3,4-dihydroquinoline-1(2H)-)pentyl)-1-oxoisoindoline-2-)piperidine-2,6-dione, 29.7 mg, yield 46%; $^1$H NMR (400 MHz, DMSO) δ 10.99 (s, 1H), 7.56 (dt, J=7.7, 3.8 Hz, 1H), 7.49-7.44 (m, 2H), 7.12 (d, J=1.7 Hz, 1H), 7.08 (dd, J=8.3, 2.0 Hz, 1H), 6.39 (d, J=8.3 Hz, 1H), 5.75 (s, 1H), 5.13 (dd, J=13.3, 5.1 Hz, 1H), 4.46 (d, J=17.1 Hz, 1H), 4.30 (d, J=17.1 Hz, 1H), 3.30 (t, J=8.5 Hz, 2H), 3.01 (t, J=7.3 Hz, 2H), 2.98-2.91 (m, 1H), 2.87 (t, J=8.2 Hz, 2H), 2.70-2.56 (m, 3H), 2.42 (ddd, J=26.6, 13.4, 4.5 Hz, 1H), 2.00 (dtd, J=6.8, 4.9, 1.8 Hz, 1H), 1.65 (dt, J=15.5, 7.8 Hz, 2H), 1.56 (dt, J=14.8, 7.5 Hz, 2H), 1.38 (dt, J=15.0, 7.7 Hz, 2H).

Example 113: 3-(4-(5-(3,4-dihydroisoquinoline-2 (1H)-)pentyl)-1-oxoisoindoline-2-)piperidine-2,6-dione (113)

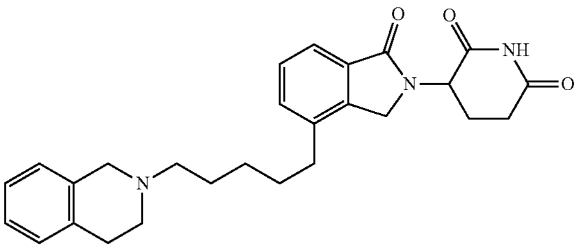 [SMILES: O=C1CCC(N2Cc3c(CCCCCN4CCc5ccccc5C4)cccc3C2=O)C(=O)N1]

-1,2,3,4-Tetrahydroquinoline was replaced with 1,2,3,4-tetrahydroisoquinoline, the preparation method was the same as 3-(1-oxo-4-(5-(2-phenylpyrrolidine-1-)pentyl)indoline-2-)piperidine-2,6-dione, 20 mg, yield 35%; $^1$H NMR (400 MHz, DMSO) δ 11.00 (s, 1H), 7.50 (dt, J=20.8, 6.9 Hz, 3H), 7.23-7.03 (m, 4H), 5.14 (dd, J=13.1, 4.7 Hz, 1H), 4.49 (d, J=17.3 Hz, 1H), 4.32 (d, J=17.1 Hz, 1H), 3.46-3.16 (m, 6H), 3.07-2.76 (m, 5H), 2.74-2.65 (m, 2H), 2.60 (dd, J=18.5, 1.8 Hz, 1H), 2.48-2.37 (m, 1H), 2.09-1.96 (m, 1H), 1.79-1.58 (m, 4H), 1.39 (dd, J=14.9, 7.9 Hz, 2H).

Example 114: 3-(4-(5-(5-bromoindoline-1-)pentyl)-1-oxoisoindoline-2-)piperidine-2,6-dione (114)

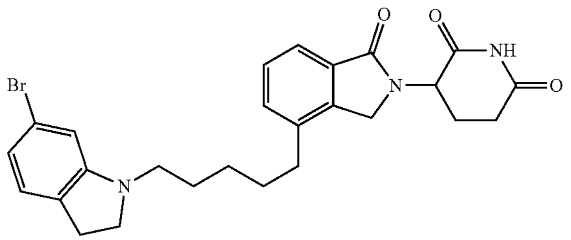 [SMILES: O=C1CCC(N2Cc3c(CCCCCN4CCc5ccc(Br)cc54)cccc3C2=O)C(=O)N1]

Tetrahydroquinoline was replaced with 6-bromohydroindole, and the preparation method was the same as 3-(4-(5-(3,4-dihydroquinoline-1(2H)-)pentyl)-1-oxoisoindoline-2-) piperidine-2,6-dione, 25.3 mg, yield 39%; $^1$H NMR (400 MHz, DMSO) δ 10.99 (s, 1H), 7.60-7.53 (m, 1H), 7.48-7.41 (m, 2H), 6.90 (d, J=7.6 Hz, 1H), 6.63 (dd, J=7.6, 1.7 Hz, 1H), 6.59 (d, J=1.6 Hz, 1H), 5.13 (dd, J=13.3, 5.1 Hz, 1H), 4.46 (d, J=17.2 Hz, 1H), 4.31 (d, J=17.1 Hz, 1H), 3.37-3.31 (m, 2H), 3.04 (t, J=7.2 Hz, 2H), 2.92 (ddd, J=17.6, 13.7, 5.4 Hz, 1H), 2.83 (t, J=8.4 Hz, 2H), 2.71-2.57 (m, 3H), 2.42 (ddd, J=26.5, 13.3, 4.5 Hz, 1H), 2.01 (ddd, J=12.3, 6.2, 4.0 Hz, 1H), 1.66 (dt, J=15.5, 7.7 Hz, 2H), 1.56 (dt, J=14.8, 7.5 Hz, 2H), 1.38 (dt, J=14.8, 7.6 Hz, 2H).

Example 115: 3-(4-(5-(6-chloro-3,4-dihydroisoquinoline-1(2H))pentyl)-1-oxoisoindoline-2-)piperidine-2,6-dione (115)

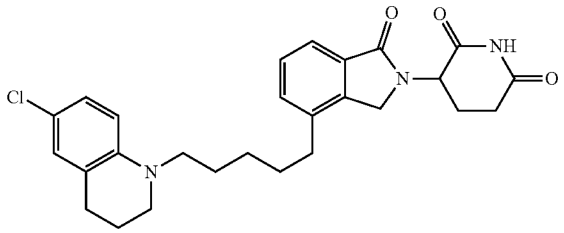 [SMILES: O=C1CCC(N2Cc3c(CCCCCN4CCCc5cc(Cl)ccc54)cccc3C2=O)C(=O)N1]

Tetrahydroquinoline was replaced with 6-chlorotetrahydroquinoline, the preparation method was the same as 3-(4-(5-(3,4-dihydroquinoline-1(2H))pentyl)-1-oxoisoindoline-2-)piperidine-2,6-dione, 19 mg, yield 31%; $^1$H NMR (400 MHz, DMSO) δ 11.00 (s, 1H), 7.56 (p, J=3.8 Hz, 1H), 7.45 (d, J=4.4 Hz, 2H), 6.93 (dd, J=8.8, 2.7 Hz, 1H), 6.88 (d, J=2.6 Hz, 1H), 6.50 (d, J=8.9 Hz, 1H), 5.13 (dd, J=13.4, 5.1 Hz, 1H), 4.46 (d, J=17.2 Hz, 1H), 4.30 (d, J=17.2 Hz, 1H), 3.19 (dd, J=9.8, 5.4 Hz, 4H), 2.92 (ddd, J=17.2, 12.9, 5.5 Hz, 1H), 2.69-2.56 (m, 5H), 2.48-2.32 (m, 1H), 2.05-1.96 (m, 1H), 1.84-1.74 (m, 2H), 1.64 (dt, J=16.2, 8.0 Hz, 2H), 1.53 (dt, J=14.3, 7.3 Hz, 2H), 1.34 (dt, J=14.2, 7.0 Hz, 2H).

Example 116: 3-(4-(4-(indoline-1-)-4-oxobutoxy)-1-oxoisoindoline-2-)piperidine-2,6-dione (116)

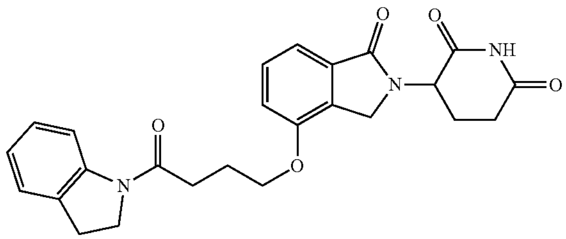 [SMILES: O=C1CCC(N2Cc3c(OCCCC(=O)N4CCc5ccccc54)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and obtained 41 mg of final product, as a white solid, yield 64%; $^1$H NMR (400 MHz, DMSO) δ 10.96 (s, 1H), 8.10 (d, J=8.0 Hz, 1H), 7.48 (t, J=7.8 Hz, 1H), 7.34-7.16 (m, 3H), 7.13 (t, J=7.6 Hz, 1H), 6.96 (t, J=7.4 Hz, 1H), 5.07 (dd, J=13.4, 5.0 Hz, 1H), 4.31 (d, J=17.3 Hz, 1H), 4.18 (dd, J=15.4, 11.7 Hz, 3H), 4.09 (t, J=8.5 Hz, 2H), 3.13 (t, J=8.4 Hz, 2H), 2.95-2.82 (m, 1H), 2.64 (t, J=6.7 Hz, 2H), 2.55 (d, J=10.6 Hz, 1H), 2.30-2.04 (m, 3H), 1.97-1.87 (m, 1H).

Example 117: 3-(4-(4-(3,4-dihydroquinoline-1(2H)-)-4-oxobutoxy)-1-oxoisoindoline-2-)piperidine-2,6-dione (117)

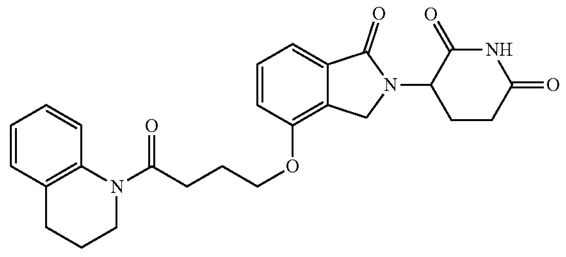 [SMILES: O=C1CCC(N2Cc3c(OCCCC(=O)N4CCCc5ccccc54)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and finally obtained 47 mg of white solid, yield 71%; $^1$H NMR (400 MHz, DMSO) δ 11.00 (s, 1H), 7.46 (t, J=7.8 Hz, 2H), 7.29 (d, J=7.5 Hz, 1H), 7.21 (d, J=8.1 Hz, 1H), 7.18-7.10 (m, 2H), 7.06 (t, J=7.3 Hz, 1H), 5.09 (dd, J=13.3, 5.1 Hz, 1H), 4.25-4.02 (m, 4H), 3.68 (td, J=12.6, 6.2 Hz, 2H), 3.29 (s, 1H), 2.99-2.86 (m, 1H), 2.77-2.55 (m, 5H), 2.34 (dd, J=13.1, 4.2 Hz, 1H), 2.09-1.94 (m, 3H), 1.86-1.77 (m, 2H).

Example 118: 3-(4-((5-(indoline-1-)-5-oxopentyl)oxy)-1-oxoisoindoline-2-)piperidine-2,6-dione (118)

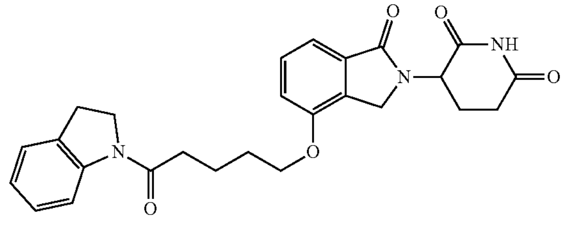 [SMILES: O=C1CCC(N2Cc3c(OCCCCC(=O)N4CCc5ccccc54)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and finally obtained 29 mg of product, as a white solid, yield 39%; $^1$H NMR (400 MHz, DMSO) δ 10.96 (s, 1H), 8.07 (d, J=8.0 Hz, 1H), 7.48 (t, J=7.8 Hz, 1H), 7.30 (d, J=7.4 Hz, 1H), 7.25 (d, J=8.1 Hz, 1H), 7.21 (d, J=7.3 Hz, 1H), 7.13 (t, J=7.7 Hz, 1H), 6.96 (t, J=7.4 Hz, 1H), 5.10 (dd, J=13.3, 5.1 Hz, 1H), 4.37 (d, J=17.4 Hz, 1H), 4.27-4.13 (m, 3H), 4.08 (t, J=8.5 Hz, 2H), 3.12 (t, J=8.4 Hz, 2H), 2.96-2.84 (m, 1H), 2.55 (dd, J=12.5, 7.6 Hz, 3H), 2.44-2.31 (m, 1H), 2.02-1.92 (m, 1H), 1.90-1.71 (m, 4H).

Example 119: 3-(4-((5-(3,4-dihydroquinoline-1(2H)-)-5-oxopentyl)oxy)-1-oxoisoindoline-2-)piperidine-2,6-dione (119)

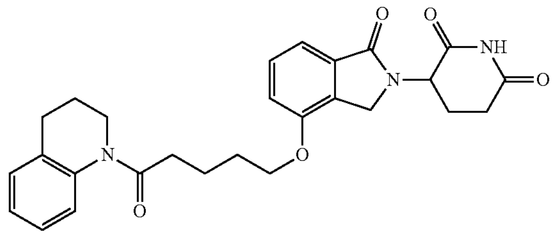 [SMILES: O=C1CCC(N2Cc3c(OCCCCC(=O)N4CCCc5ccccc54)cccc3C2=O)C(=O)N1]

The synthesis method was the same as N-(3-chloro-4-methylphenyl)-4-((2-(2,6-dioxopiperidine-3-)-1-oxoisoindoline-4-)oxy)butanamide, and finally obtained 19 mg of white solid, yield 39%; $^1$H NMR (400 MHz, DMSO) δ 10.97 (s, 1H), 7.45 (d, J=7.7 Hz, 2H), 7.30 (d, J=7.5 Hz, 1H), 7.23-7.01 (m, 4H), 5.10 (dd, J=13.3, 5.1 Hz, 1H), 4.31 (s, 1H), 4.21 (s, 1H), 4.08 (s, 2H), 3.67 (t, J=6.4 Hz, 2H), 2.96-2.84 (m, 1H), 2.66 (d, J=6.5 Hz, 2H), 2.55 (d, J=7.0 Hz, 3H), 2.40 (ddd, J=35.4, 17.8, 9.0 Hz, 1H), 2.05-1.93 (m, 1H), 1.89-1.80 (m, 2H), 1.72 (s, 4H).

Example 120: 3-(4-(6-(6-chloro-3H-spiro[isobenzofuran-1,4'-piperidine]-1'-)hexyl)-1-oxoisoindoline-2-)piperidine-2,6-dione (120)

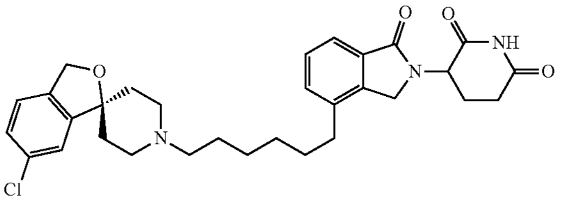

The preparation method was the same as 3-(1-oxo-4-(5-(2-phenylpyrroline-1-)pentyl)indoline-2-)piperidine-2,6-dione, 34 mg, yield 33.4%; $^1$H NMR (400 MHz, DMSO) δ 10.99 (s, 1H), 7.56 (dd, J=8.2, 4.5 Hz, 1H), 7.46 (d, J=3.7 Hz, 2H), 7.36 (s, 1H), 7.34-7.27 (m, 2H), 5.13 (dd, J=13.3, 5.1 Hz, 1H), 4.94 (s, 2H), 4.47 (d, J=17.1 Hz, 1H), 4.31 (d, J=17.1 Hz, 1H), 2.99-2.86 (m, 2H), 2.79 (d, J=10.0 Hz, 2H), 2.68-2.56 (m, 3H), 2.46-2.23 (m, 5H), 2.05-1.97 (m, 1H), 1.92 (dd, J=12.7, 9.1 Hz, 2H), 1.61 (d, J=11.7 Hz, 4H), 1.46 (s, 2H), 1.38-1.27 (m, 4H).

Example 121: 3-(1-oxo-4-(5-(2-oxospiro[indoline-3,4'-piperidine]-1'-)pentyl)indoline-2-)piperidine-2,6-dione (121)

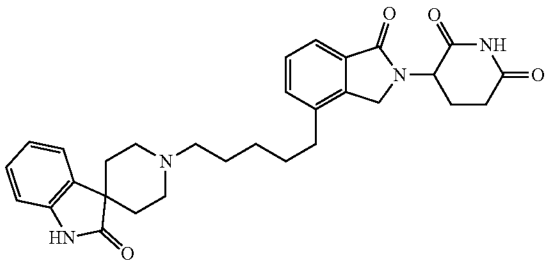 [SMILES: O=C1CCC(N2Cc3c(CCCCCN4CCC5(CC4)C(=O)Nc4ccccc45)cccc3C2=O)C(=O)N1]

The preparation method was the same as 3-(1-oxo-4-(5-(2-phenylpyrroline-1-)pentyl)indoline-2-)piperidine-2,6-dione, 24.6 mg, yield 38%; $^1$H NMR (400 MHz, DMSO) δ 11.02 (s, 1H), 10.40 (s, 1H), 8.19 (s, 1H), 7.58 (dd, J=6.2, 2.4 Hz, 1H), 7.52-7.42 (m, 3H), 7.19 (t, J=7.5 Hz, 1H), 6.96 (t, J=7.5 Hz, 1H), 6.85 (d, J=7.7 Hz, 1H), 5.15 (dd, J=13.3, 5.1 Hz, 1H), 4.49 (d, J=17.2 Hz, 1H), 4.32 (d, J=17.2 Hz, 1H), 2.99-2.85 (m, 3H), 2.73-2.57 (m, 5H), 2.48-2.37 (m, 1H), 2.07-1.97 (m, 1H), 1.88-1.76 (m, 2H), 1.73-1.49 (m, 6H), 1.37 (dt, J=14.4, 7.4 Hz, 2H).

Example 122: 3-(4-(4-(2H-spiro[benzofuran-3,4-piperidine]-1-)butyl)-1-oxoisoindoline-2-)piperidine-2,6-dione (122)

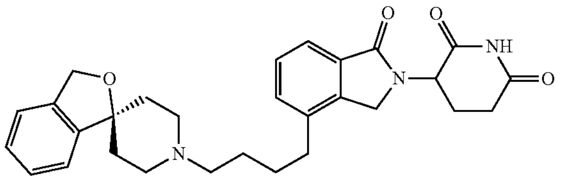

The preparation method was the same as 3-(1-oxo-4-(5-(2-phenylpyrroline-1-)pentyl)indoline-2-)piperidine-2,6-dione, 29.0 mg, yield 33%; $^1$H NMR (400 MHz, DMSO) δ 11.01 (s, 1H), 8.17 (s, 1H), 7.61-7.54 (m, 1H), 7.50-7.44 (m, 2H), 7.19 (dd, J=7.4, 0.9 Hz, 1H), 7.10 (td, J=7.9, 1.3 Hz, 1H), 6.84 (dd, J=7.8, 7.0 Hz, 1H), 6.75 (d, J=7.9 Hz, 1H), 5.14 (dd, J=13.2, 5.1 Hz, 1H), 4.47 (d, J=17.2 Hz, 1H), 4.32 (d, J=16.4 Hz, 3H), 2.93 (ddd, J=17.5, 14.0, 5.5 Hz, 1H), 2.84 (d, J=11.8 Hz, 2H), 2.67 (t, J=7.5 Hz, 2H), 2.65-2.57 (m, 1H), 2.48-2.30 (m, 3H), 2.01 (dd, J=17.2, 6.7 Hz, 3H), 1.84 (td, J=12.8, 3.7 Hz, 2H), 1.69-1.57 (m, 4H), 1.57-1.45 (m, 2H).

Example 123: 3-(4-(5-(3H-spiro[isobenzofuran-1,4'-piperidine]-1'-)pentyl)-1-oxoisoindoline-2-)piperidine-2,6-dione (123)

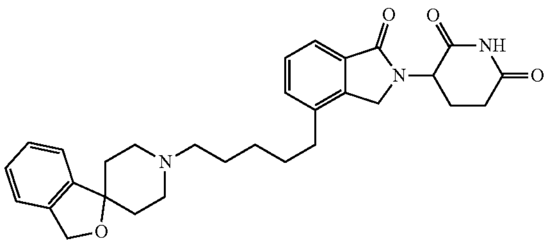 [SMILES: O=C1CCC(N2Cc3c(CCCCCN4CCC5(CC4)OCc4ccccc45)cccc3C2=O)C(=O)N1]

The preparation method was the same as 3-(1-oxo-4-(5-(2-phenylpyrroline-1-)pentyl)indoline-2-)piperidine-2,6-dione, 11.2 mg, yield 17%; $^1$H NMR (400 MHz, DMSO) δ 10.99 (s, 1H), 8.19 (s, 1H), 7.60-7.55 (m, 1H), 7.49-7.44 (m, 2H), 7.30-7.20 (m, 3H), 5.14 (dd, J=13.3, 5.1 Hz, 1H), 4.97 (s, 2H), 4.47 (d, J=17.2 Hz, 1H), 4.32 (d, J=17.2 Hz, 1H), 2.92 (ddd, J=17.9, 11.8, 4.6 Hz, 3H), 2.71-2.56 (m, 3H), 2.43 (dd, J=21.2, 8.6 Hz, 5H), 1.98 (dddd, J=26.0, 16.8, 8.7, 2.8 Hz, 3H), 1.65 (t, J=12.0 Hz, 4H), 1.54 (dd, J=14.6, 7.7 Hz, 2H), 1.40-1.29 (m, 2H).

Example 124: 3-(4-(4-(6-chloro-3H-spiro[isobenzofuran-1,4'-piperidine]-1'-)butoxy)-1-oxoisoindoline-2-)piperidine-2,6-dione (124)

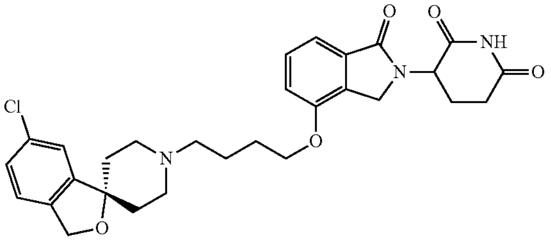

The preparation method was the same as 1-(3-((2-(2,6-dioxopiperidine-3-)-1-oxoisoindoline-4-)oxy)propyl)-4-phenylpiperidine-4-carbonitrile, 25.9 mg, yield 38%; $^1$H NMR (400 MHz, DMSO) δ 10.97 (s, 1H), 7.49 (t, J=7.8 Hz, 1H), 7.35-7.23 (m, 5H), 5.11 (dd, J=13.3, 5.1 Hz, 1H), 4.93 (s, 2H), 4.38 (d, J=17.4 Hz, 1H), 4.23 (d, J=17.4 Hz, 1H), 4.16 (t, J=6.3 Hz, 2H), 2.97-2.85 (m, 1H), 2.79 (d, J=10.7 Hz, 2H), 2.58 (d, J=18.2 Hz, 1H), 2.48-2.36 (m, 3H), 2.26 (t, J=10.9 Hz, 2H), 2.03-1.94 (m, 1H), 1.88 (dd, J=17.6, 7.6 Hz, 2H), 1.83-1.72 (m, 2H), 1.63 (dd, J=21.1, 9.9 Hz, 4H).

Example 125: 3-(1-oxo-4-(5-(2-oxo-1,2-dihydrospiro[benzo[d][1,3]oxazine-4,4'-piperidine]-1'-)pentyl)isoindoline-2-)piperidine-2,6-dione (125)

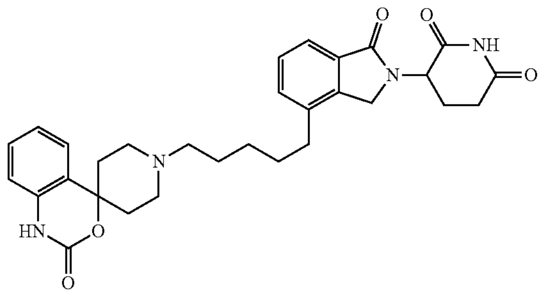 [SMILES: O=C1CCC(N2Cc3c(CCCCCN4CCC5(CC4)OC(=O)Nc4ccccc45)cccc3C2=O)C(=O)N1]

The preparation method was the same as 3-(1-oxo-4-(5-(2-phenylpyrroline-1-)pentyl)indoline-2-)piperidine-2,6-dione, 14.4 mg, yield 21%; $^1$H NMR (400 MHz, DMSO) δ 10.99 (s, 1H), 10.18 (s, 1H), 8.18 (s, 1H), 7.59-7.54 (m, 1H), 7.50-7.43 (m, 2H), 7.30-7.19 (m, 2H), 7.05-6.98 (m, 1H), 6.91-6.85 (m, 1H), 5.13 (dd, J=13.2, 5.1 Hz, 1H), 4.47 (d, J=17.2 Hz, 1H), 4.31 (d, J=17.2 Hz, 1H), 2.98-2.86 (m, 1H), 2.75 (d, J=10.6 Hz, 2H), 2.70-2.56 (m, 3H), 2.40 (ddd, J=24.4, 15.6, 7.6 Hz, 5H), 1.98 (ddd, J=39.2, 21.1, 8.9 Hz, 5H), 1.64 (dt, J=15.3, 7.6 Hz, 2H), 1.57-1.45 (m, 2H), 1.35 (dt, J=14.8, 7.5 Hz, 2H).

Example 126: 3-(4-(4-(2H-spiro[benzofuran-3,4'-piperidine]-1'-)butoxy)-1-oxoisoindoline-2-)piperidine-2,6-dione (126)

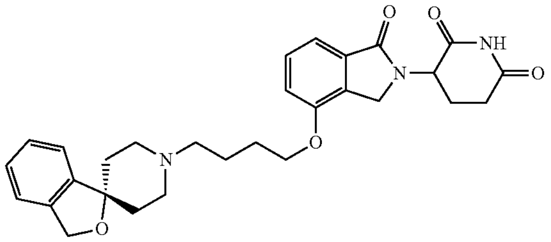

The preparation method was the same as 1-(3-((2-(2,6-dioxopiperidine-3-)-1-oxoisoindoline-4-)oxy)propyl)-4-phenylpiperidine-4-carbonitrile, 28.0 mg, yield 44%; $^1$H NMR (400 MHz, DMSO) δ 10.97 (s, 1H), 7.49 (t, J=7.8 Hz, 1H), 7.31 (d, J=7.4 Hz, 1H), 7.25 (d, J=8.1 Hz, 1H), 7.18 (d, J=7.1 Hz, 1H), 7.14-7.05 (m, 1H), 6.84 (t, J=7.4 Hz, 1H), 6.75 (d, J=7.9 Hz, 1H), 5.11 (dd, J=13.3, 5.1 Hz, 1H), 4.38 (d, J=17.4 Hz, 1H), 4.34 (s, 2H), 4.23 (d, J=17.4 Hz, 1H), 4.15 (t, J=6.2 Hz, 2H), 2.92 (dd, J=22.7, 8.6 Hz, 3H), 2.60 (s, 1H), 2.48-2.39 (m, 3H), 2.00 (ddd, J=13.9, 10.4, 7.6 Hz, 3H), 1.89-1.73 (m, 4H), 1.65 (t, J=11.5 Hz, 4H).

Example 127: 3-(4-(5-(6-chloro-3H-spiro[isobenzofuran-1,4'-piperidine]-1'-)pentyl-1-oxoisoindoline-2-)piperidine-2,6-dione (127)

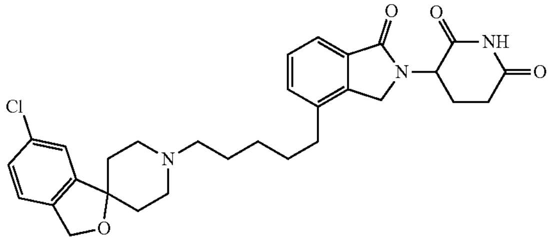 [SMILES: O=C1CCC(N2Cc3c(CCCCCN4CCC5(CC4)OCc4ccc(Cl)cc45)cccc3C2=O)C(=O)N1]

The preparation method was the same as 3-(1-oxo-4-(5-(2-phenylpyrroline-1-)pentyl)indoline-2-)piperidine-2,6-dione, 24.4 mg, yield 36%; $^1$H NMR (400 MHz, DMSO) δ 10.99 (s, 1H), 7.56 (dt, J=7.6, 3.9 Hz, 1H), 7.49-7.43 (m, 2H), 7.39-7.25 (m, 3H), 5.14 (dd, J=13.3, 5.1 Hz, 1H), 4.93 (s, 2H), 4.47 (d, J=17.2 Hz, 1H), 4.31 (d, J=17.1 Hz, 1H), 2.99-2.86 (m, 1H), 2.82-2.53 (m, 5H), 2.48-2.37 (m, 1H), 2.35-2.27 (m, 2H), 2.26-2.15 (m, 2H), 2.02 (ddd, J=9.9, 4.9, 2.9 Hz, 1H), 1.94-1.81 (m, 2H), 1.69-1.55 (m, 4H), 1.54-1.43 (m, 2H), 1.34 (dt, J=14.8, 7.3 Hz, 2H).

Example 128: 3-(4-(4-(6-fluoro-3H-spiro[isobenzofuran-1,4'-piperidine]-1'-)butoxy)-1-oxoisoindoline-2-)piperidine-2,6-dione (128)

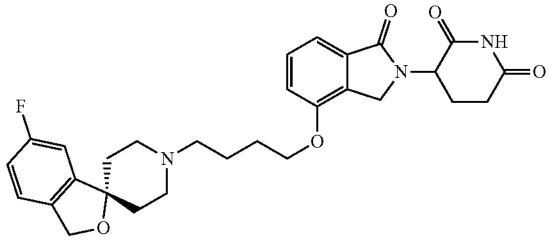

The preparation method was the same as 1-(3-((2-(2,6-dioxopiperidine-3-)-1-oxoisoindoline-4-)oxy)propyl)-4-phenylpiperidine-4-carbonitrile, 22.9 mg, yield 35%; $^1$H NMR (400 MHz, DMSO) δ 10.98 (s, 1H), 7.48 (t, J=7.8 Hz, 1H), 7.33-7.22 (m, 3H), 7.14 (dd, J=8.9, 2.2 Hz, 1H), 7.12-7.05 (m, 1H), 5.11 (dd, J=13.3, 5.0 Hz, 1H), 4.93 (s, 2H), 4.38 (d, J=17.4 Hz, 1H), 4.23 (d, J=17.4 Hz, 1H), 4.15 (t, J=6.2 Hz, 2H), 2.97-2.85 (m, 1H), 2.81 (d, J=11.0 Hz, 2H), 2.57 (d, J=18.0 Hz, 1H), 2.47-2.38 (m, 3H), 2.29 (t, J=11.5 Hz, 2H), 2.02-1.95 (m, 1H), 1.95-1.85 (m, 2H), 1.83-1.73 (m, 2H), 1.64 (dd, J=19.0, 10.7 Hz, 4H).

Example 129: 3-(4-(5-(5-chloro-3-oxo-3H-spiro[isobenzofuran-1,4'-piperidine]-1'-)pentyl)-1-oxoisoindoline-2-)piperidine-2,6-dione (129)

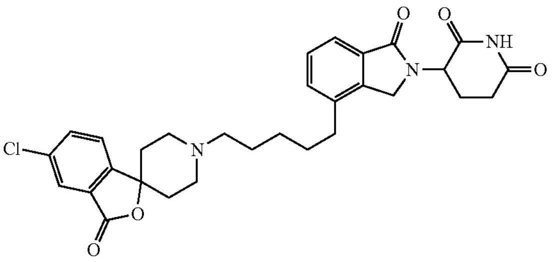 [SMILES: O=C1CCC(N2Cc3c(CCCCCN4CCC5(CC4)OC(=O)c4cc(Cl)ccc45)cccc3C2=O)C(=O)N1]

The preparation method was the same as 3-(1-oxo-4-(5-(2-phenylpyrroline-1-)pentyl)indoline-2-)piperidine-2,6-dione, 23.2 mg, yield 48%; $^1$H NMR (400 MHz, DMSO) δ 10.99 (s, 1H), 8.15 (s, 1H), 7.87 (d, J=1.4 Hz, 1H), 7.82 (dt, J=13.8, 5.0 Hz, 2H), 7.57 (dt, J=7.7, 3.8 Hz, 1H), 7.51-7.41 (m, 2H), 5.75 (s, 1H), 5.14 (dd, J=13.3, 5.1 Hz, 1H), 4.48 (d, J=17.2 Hz, 1H), 4.32 (d, J=17.1 Hz, 1H), 2.99-2.85 (m, 3H), 2.71-2.56 (m, 3H), 2.47-2.37 (m, 3H), 2.36-2.27 (m, 2H), 2.21 (t, J=12.1 Hz, 2H), 2.07-1.95 (m, 1H), 1.64 (dd, J=13.9, 8.5 Hz, 4H), 1.58-1.48 (m, 2H), 1.36 (dt, J=14.8, 7.5 Hz, 2H).

Example 130: 3-(4-(4-(6-methyl-3H-spiro[isobenzofuran-1,4'-piperidine]-1'-)butoxy)-1-oxoisoindoline-2-)piperidine-2,6-dione (130)

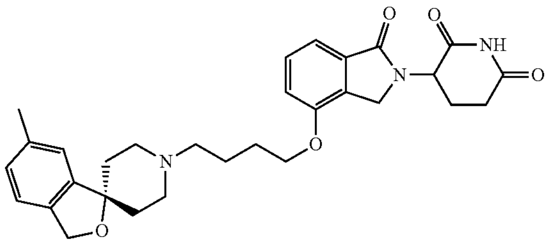

The preparation method was the same as 1-(3-((2-(2,6-dioxopiperidine-3-)-1-oxoisoindoline-4-)oxy)propyl)-4-phenylpiperidine-4-carbonitrile, 16.2 mg white solid, yield 29%; $^1$H NMR (400 MHz, DMSO) δ 10.97 (s, 1H), 7.49 (t, J=7.8 Hz, 1H), 7.31 (d, J=7.5 Hz, 1H), 7.25 (d, J=8.1 Hz, 1H), 7.13 (d, J=7.6 Hz, 1H), 7.07 (d, J=7.7 Hz, 1H), 7.00 (s, 1H), 5.11 (dd, J=13.3, 5.1 Hz, 1H), 4.90 (s, 2H), 4.38 (d, J=17.4 Hz, 1H), 4.23 (d, J=17.4 Hz, 1H), 4.16 (t, J=6.3 Hz, 2H), 2.98-2.85 (m, 1H), 2.80 (d, J=11.0 Hz, 2H), 2.57 (d, J=18.4 Hz, 1H), 2.48-2.38 (m, 3H), 2.35-2.23 (m, 5H), 2.03-1.93 (m, 1H), 1.90-1.73 (m, 4H), 1.63 (dt, J=20.6, 10.0 Hz, 4H).

Example 131: 3-(1-oxo-4-(5-(2'-oxo-1',2'-dihydrospiro[piperidine-4,4'-pyrido[2,3-d][1,3)oxazine)-1-)pentyl)isoindoline-2-)piperidine-2,6-dione (131)

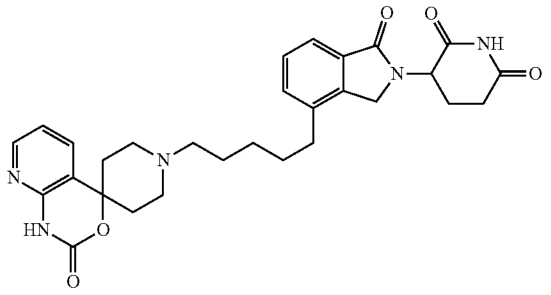 [SMILES: O=C1CCC(N2Cc3c(CCCCCN4CCC5(CC4)OC(=O)Nc4ncccc45)cccc3C2=O)C(=O)N1]

The preparation method was the same as 3-(1-oxo-4-(5-(2-phenylpyrroline-1-)pentyl)indoline-2-)piperidine-2,6-dione, 18.0 mg, yield 27%; $^1$H NMR (400 MHz, DMSO) δ 10.99 (s, 1H), 10.74 (s, 1H), 8.19 (dd, J=4.9, 1.3 Hz, 1H), 8.16 (s, 1H), 7.72 (dd, J=7.6, 1.1 Hz, 1H), 7.59-7.54 (m, 1H), 7.50-7.43 (m, 2H), 7.07 (dd, J=7.6, 5.0 Hz, 1H), 5.75 (s, 1H), 5.13 (dd, J=13.2, 5.1 Hz, 1H), 4.47 (d, J=17.2 Hz, 1H), 4.31 (d, J=17.1 Hz, 1H), 2.99-2.86 (m, 1H), 2.78 (d, J=10.6 Hz, 2H), 2.64 (dd, J=22.3, 14.4 Hz, 3H), 2.47-2.29 (m, 5H), 2.09-1.88 (m, 5H), 1.64 (dt, J=15.4, 7.7 Hz, 2H), 1.56-1.44 (m, 2H), 1.41-1.29 (m, 2H).

Example 132: 3-(4-((5-(6-chloro-3H-spiro[isobenzofuran-1,4-piperidine]-1-)pentyl)oxy)-1-oxoisoindoline-2-)piperidine-2,6-dione (132)

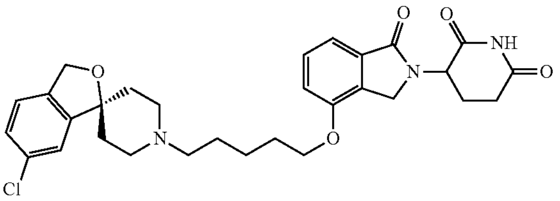

The preparation method was the same as 1-(3-((2-(2,6-dioxopiperidine-3-)-1-oxoisoindoline-4-)oxy)propyl)-4-phenylpiperidine-4-carbonitrile, and finally obtained 32 mg of white solid, yield 48%; $^1$H NMR (400 MHz, DMSO) δ 10.97 (s, 1H), 7.48 (t, J=7.8 Hz, 1H), 7.36 (s, 1H), 7.33-7.27 (m, 3H), 7.24 (d, J=8.1 Hz, 1H), 5.11 (dd, J=13.3, 5.1 Hz, 1H), 4.93 (s, 2H), 4.37 (d, J=17.4 Hz, 1H), 4.23 (d, J=17.4 Hz, 1H), 4.13 (t, J=6.3 Hz, 2H), 2.97-2.84 (m, 1H), 2.78 (d, J=10.5 Hz, 2H), 2.56 (d, J=18.0 Hz, 1H), 2.45 (dd, J=13.1, 4.4 Hz, 1H), 2.37 (t, J=7.0 Hz, 2H), 2.27 (t, J=11.5 Hz, 2H), 2.02-1.85 (m, 3H), 1.82-1.71 (m, 2H), 1.61 (d, J=12.4 Hz, 2H), 1.48 (ddd, J=22.2, 14.8, 9.1 Hz, 4H).

Example 133: 3-(4-(5-(5-chloro-2-oxospiro[indoline-3,4'-piperidine]-1'-)pentyl)-1-oxoisoindoline-2-)piperidine-2,6-dione (133)

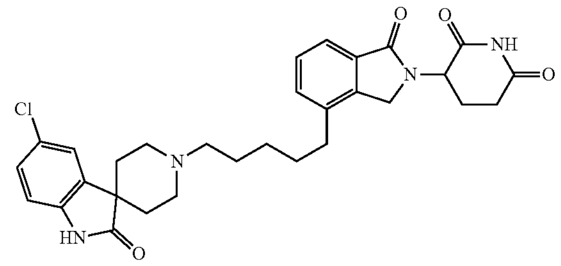 [SMILES: O=C1CCC(N2Cc3c(CCCCCN4CCC5(CC4)C(=O)Nc4ccc(Cl)cc45)cccc3C2=O)C(=O)N1]

The preparation method was the same as 3-(1-oxo-4-(5-(2-phenylpyrroline-1-)pentyl)indoline-2-)piperidine-2,6-dione, 36.2 mg, yield 55%; $^1$H NMR (400 MHz, DMSO) δ 10.99 (s, 1H), 10.51 (s, 1H), 8.18 (s, 1H), 7.57 (dd, J=6.0, 2.6 Hz, 1H), 7.53-7.43 (m, 3H), 7.24 (dd, J=8.3, 2.1 Hz, 1H), 6.85 (d, J=8.3 Hz, 1H), 5.14 (dd, J=13.3, 5.1 Hz, 1H), 4.48 (d, J=17.2 Hz, 1H), 4.32 (d, J=17.1 Hz, 1H), 3.01-2.84 (m, 3H), 2.63 (ddd, J=21.4, 16.7, 4.4 Hz, 5H), 2.53 (d, J=6.9 Hz, 2H), 2.48-2.36 (m, 1H), 2.02 (ddd, J=10.2, 5.0, 3.1 Hz, 1H), 1.86-1.70 (m, 4H), 1.69-1.61 (m, 2H), 1.60-1.50 (m, 2H), 1.37 (dt, J=14.7, 7.5 Hz, 2H).

Example 134: 3-(4-((5-(3H-spiro[isobenzofuran-1,4'-piperidin]-1'-yl)pentyl)oxy)-1-oxoisoindoline-2-yl)piperidine-2,6-dione (134)

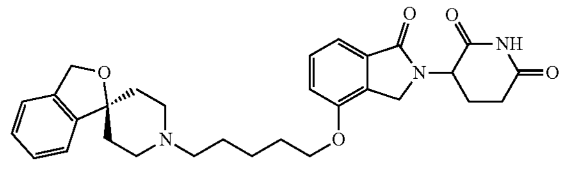

The preparation method was the same as 1-(3-((2-(2,6-dioxopiperidine-3-)-1-oxoisoindoline-4-)oxy)propyl)-4-phenylpiperidine-4-carbonitrile, and finally 35 mg 3-(4-((5-(2H-spiro[benzofuran-3,4'-piperidine]-1'-)pentyl)oxy)-1-oxoisoindole-2-)piperidine-2,6-dione was afforded as a white solid, yield 37%; $^1$H NMR (400 MHz, DMSO) δ 10.98 (s, 1H), 7.49 (t, J=7.8 Hz, 1H), 7.31 (d, J=7.5 Hz, 1H), 7.25 (d, J=8.1 Hz, 1H), 7.19 (d, J=7.3 Hz, 1H), 7.11 (td, J=7.8, 1.2 Hz, 1H), 6.85 (t, J=7.4 Hz, 1H), 6.76 (d, J=7.9 Hz, 1H), 5.12 (dd, J=13.3, 5.1 Hz, 1H), 4.42-4.31 (m, 3H), 4.24 (d, J=17.4 Hz, 1H), 4.14 (t, J=6.3 Hz, 2H), 2.91 (ddd, J=13.4, 11.9, 5.7 Hz, 3H), 2.59 (s, 1H), 2.45 (dd, J=13.1, 4.3 Hz, 1H), 2.38 (t, J=6.8 Hz, 2H), 2.10-1.94 (m, 3H), 1.91-1.72 (m, 4H), 1.63 (d, J=13.0 Hz, 2H), 1.59-1.39 (m, 4H).

Example 135: 3-(4-(5-(5-methoxy-2-oxospiro[indoline-3,4'-piperidine]-1'-)pentyl)-1-oxoisoindoline-2-)piperidine-2,6-dione (135)

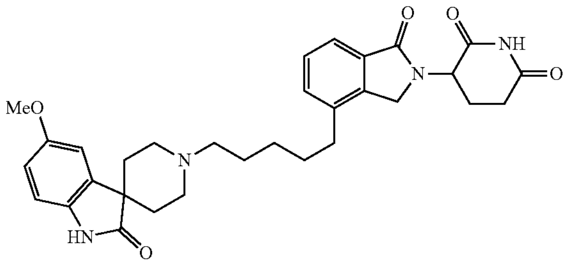 [SMILES: COc1ccc2c(c1)C1(CCN(CCCCCc3cccc4c3CN(C3CCC(=O)NC3=O)C4=O)CC1)C(=O)N2]

The preparation method was the same as 3-(1-oxo-4-(5-(2-phenylpyrroline-1-)pentyl)indoline-2-)piperidine-2,6-dione, 32.1 mg, yield 46%; $^1$H NMR (400 MHz, DMSO) δ 10.99 (s, 1H), 10.19 (s, 1H), 8.18 (s, 1H), 7.56 (dt, J=7.9, 3.9 Hz, 1H), 7.51-7.43 (m, 2H), 7.02 (s, 1H), 6.75 (s, 2H), 5.75 (s, 2H), 5.14 (dd, J=13.2, 5.1 Hz, 1H), 4.48 (d, J=17.2 Hz, 1H), 4.32 (d, J=17.1 Hz, 1H), 3.71 (s, 3H), 2.92 (ddd, J=13.0, 12.2, 5.1 Hz, 3H), 2.71-2.57 (m, 5H), 2.54 (s, 2H), 2.47-2.37 (m, 1H), 2.02 (ddd, J=10.4, 5.0, 3.6 Hz, 1H), 1.90-1.47 (m, 8H), 1.44-1.28 (m, 2H).

Example 136: 3-(4-(3-(2H-spiro[isobenzofuran-1,4'-piperidine]-1'-)propoxy)-1-oxoisoindoline-2-)piperidine-2,6-dione (136)

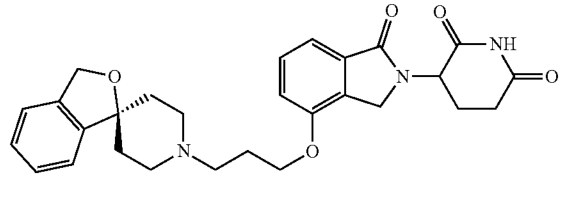

The preparation method was the same as 1-(3-((2-(2,6-dioxopiperidine-3-)-1-oxoisoindoline-4-)oxy)propyl)-4-phenylpiperidine-4-carbonitrile, 26.9 mg, yield 42%; $^1$H NMR (400 MHz, DMSO) δ 10.98 (s, 1H), 7.49 (t, J=7.8 Hz, 1H), 7.32 (d, J=7.5 Hz, 1H), 7.26 (d, J=8.1 Hz, 1H), 7.20 (d, J=6.9 Hz, 1H), 7.11 (t, J=7.7 Hz, 1H), 6.86 (t, J=7.4 Hz, 1H), 6.76 (d, J=8.0 Hz, 1H), 5.12 (dd, J=13.3, 5.1 Hz, 1H), 4.39 (d, J=14.5 Hz, 3H), 4.29-4.13 (m, 3H), 3.57-3.12 (m, 4H), 3.07-2.83 (m, 3H), 2.63-2.55 (m, 1H), 2.47-2.37 (m, 1H), 2.09-1.81 (m, 5H), 1.69 (d, J=12.4 Hz, 2H).

Example 137: 3-(1-oxo-4-(5-(spiro[isochroman-1,4'-piperidine]-1'-)pentyl)isoindoline-2-)piperidine-2,6-dione (137)

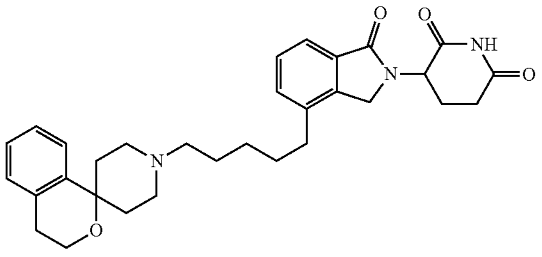 [SMILES: O=C1CCC(N2Cc3c(CCCCCN4CCC5(CC4)OCCc4ccccc45)cccc3C2=O)C(=O)N1]

The preparation method was the same as 3-(1-oxo-4-(5-(2-phenylpyrroline-1-)pentyl)indoline-2-)piperidine-2,6-dione, 20.6 mg, yield 33%; $^1$H NMR (400 MHz, DMSO) δ 10.99 (s, 1H), 7.57 (dt, J=7.5, 3.8 Hz, 1H), 7.51-7.40 (m, 2H), 7.21-7.05 (m, 4H), 5.14 (dd, J=13.2, 5.0 Hz, 1H), 4.47 (d, J=17.2 Hz, 1H), 4.32 (d, J=17.1 Hz, 1H), 3.81 (t, J=5.4 Hz, 2H), 2.99-2.86 (m, 1H), 2.74 (dd, J=14.1, 8.6 Hz, 4H), 2.69-2.57 (m, 3H), 2.46-2.31 (m, 5H), 2.06-1.87 (m, 3H), 1.78 (d, J=13.1 Hz, 2H), 1.70-1.59 (m, 2H), 1.53 (dd, J=12.4, 6.0 Hz, 2H), 1.36 (dd, J=13.7, 7.5 Hz, 2H).

Example 138: 3-(4-(3-(6-chloro-3H-spiro[isobenzofuran-1,4'-piperidine]-1'-)propoxy)-1-oxoisoindoline-2-)piperidine-2,6-dione (138)

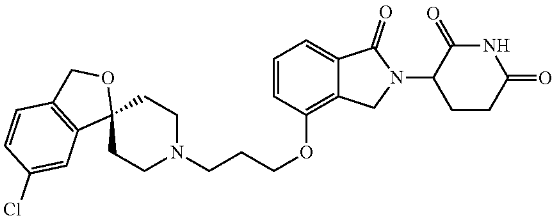

The preparation method was the same as 1-(3-((2-(2,6-dioxopiperidine-3-)-1-oxoisoindoline-4-)oxy)propyl)-4-phenylpiperidine-4-carbonitrile, 42 mg, yield 61%; $^1$H NMR (400 MHz, DMSO) δ 10.99 (s, 1H), 7.50 (t, J=7.8 Hz, 1H), 7.40-7.30 (m, 3H), 7.27 (t, J=7.0 Hz, 2H), 5.12 (dd, J=13.3, 5.1 Hz, 1H), 4.99 (s, 2H), 4.41 (d, J=17.4 Hz, 1H), 4.24 (dd, J=17.8, 11.6 Hz, 3H), 3.47-3.16 (m, 6H), 2.97-2.87 (m, 1H), 2.59 (dd, J=17.2, 1.0 Hz, 1H), 2.47-2.37 (m, 1H), 2.36-2.05 (m, 4H), 2.04-1.97 (m, 1H), 1.85-1.67 (m, 2H).

Example 139: 3-(1-oxo-4-(5-(2-oxospiro[indoline-3,3'-pyrroline]-1'-)pentyl)isoindoline-2-)piperidine-2,6-dione (139)

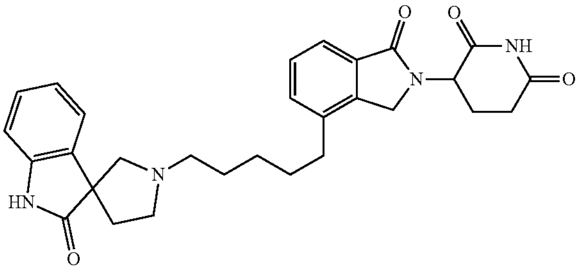 [SMILES: O=C1CCC(N2Cc3c(CCCCCN4CCC5(C4)C(=O)Nc4ccccc45)cccc3C2=O)C(=O)N1]

The preparation method was the same as 3-(1-oxo-4-(5-(2-phenylpyrroline-1-)pentyl)indoline-2-)piperidine-2,6-dione, 39.5 mg, yield 65%; $^1$H NMR (400 MHz, DMSO) δ 10.98 (s, 1H), 10.35 (s, 1H), 8.15 (s, 1H), 7.56 (dt, J=7.8, 3.9 Hz, 1H), 7.49-7.40 (m, 2H), 7.27 (dd, J=7.1, 4.0 Hz, 1H), 7.15 (td, J=7.6, 0.6 Hz, 1H), 6.94 (tdd, J=7.6, 2.6, 0.8 Hz, 1H), 6.81 (d, J=7.7 Hz, 1H), 5.75 (s, 2H), 5.13 (dd, J=13.3, 5.1 Hz, 1H), 4.46 (dd, J=17.2, 2.9 Hz, 1H), 4.30 (d, J=17.1 Hz, 1H), 3.09 (td, J=8.1, 4.7 Hz, 1H), 2.98-2.85 (m, 1H), 2.81 (dd, J=9.0, 2.0 Hz, 1H), 2.70-2.52 (m, 6H), 2.39 (ddd, J=25.6, 12.8, 4.3 Hz, 1H), 2.16 (ddd, J=12.1, 7.9, 4.1 Hz, 1H), 1.99 (dd, J=11.5, 5.5 Hz, 1H), 1.88 (dt, J=12.5, 7.6 Hz, 1H), 1.64 (dt, J=14.9, 7.4 Hz, 2H), 1.57-1.46 (m, 2H), 1.45-1.33 (m, 2H).

Example 140: 3-(4-(3-(6-methyl-3H-spiro[isobenzofuran-1,4'-piperidine]-1'-)propoxy)-1-oxoisoindoline-2-)piperidine-2,6-dione (140)

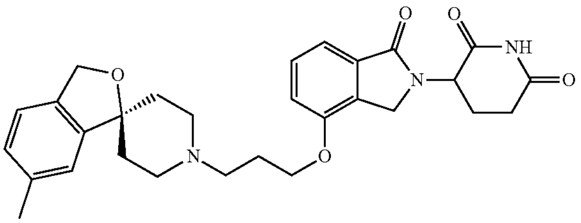

The preparation method was the same as 1-(3-((2-(2,6-dioxopiperidine-3-)-1-oxoisoindoline-4-)oxy)propyl)-4-phenylpiperidine-4-carbonitrile, 34.7 mg, yield 52%; $^1$H NMR (400 MHz, DMSO) δ 11.00 (s, 1H), 7.50 (t, J=7.8 Hz, 1H), 7.33 (d, J=7.5 Hz, 1H), 7.27 (d, J=8.1 Hz, 1H), 7.18 (d, J=7.6 Hz, 1H), 7.12 (d, J=7.6 Hz, 1H), 6.98 (s, 1H), 5.13 (dd, J=13.3, 5.0 Hz, 1H), 4.96 (s, 2H), 4.41 (d, J=17.4 Hz, 1H), 4.31-4.17 (m, 3H), 3.37 (dd, J=17.2, 16.7 Hz, 6H), 2.97-2.88 (m, 1H), 2.59 (d, J=17.2 Hz, 1H), 2.46-2.37 (m, 1H), 2.33 (s, 3H), 2.17 (dt, J=36.9, 32.7 Hz, 4H), 2.01 (dd, J=8.9, 3.3 Hz, 1H), 1.83-1.63 (m, 2H).

Example 141: 3-(1-oxo-4-(5-(spiro[indene-1,4'-piperidine]-1'-)pentyl)isoindoline-2-)piperidine-2,6-dione (141)

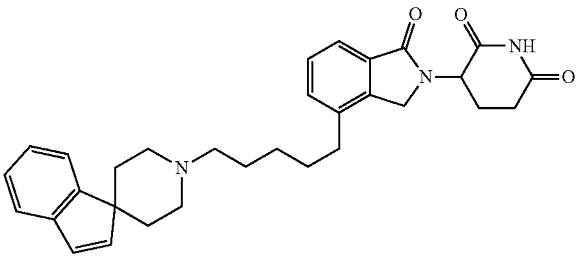 [SMILES: O=C1CCC(N2Cc3c(CCCCCN4CCC5(C=Cc6ccccc65)CC4)cccc3C2=O)C(=O)N1]

The preparation method was the same as 3-(1-oxo-4-(5-(2-phenylpyrroline-1-)pentyl)indoline-2-)piperidine-2,6-dione, 18.8 mg, yield 30%; $^1$H NMR (400 MHz, DMSO) δ 11.00 (s, 1H), 8.19 (s, 1H), 7.58 (dd, J=5.9, 2.6 Hz, 1H), 7.52-7.44 (m, 2H), 7.39 (d, J=7.0 Hz, 1H), 7.33 (d, J=7.0 Hz, 1H), 7.26-7.15 (m, 2H), 6.97 (d, J=5.6 Hz, 1H), 6.80 (d, J=5.6 Hz, 1H), 5.75 (s, 2H), 5.14 (dd, J=13.3, 5.0 Hz, 1H), 4.47 (dd, J=17.1, 8.0 Hz, 1H), 4.31 (dd, J=17.1, 7.9 Hz, 1H), 3.06 (d, J=11.6 Hz, 2H), 2.99-2.87 (m, 1H), 2.72-2.53 (m, 5H), 2.46-2.35 (m, 2H), 2.19-2.07 (m, 2H), 2.06-1.94 (m, 1H), 1.63 (qd, J=14.8, 8.1 Hz, 4H), 1.43-1.31 (m, 2H), 1.23 (d, J=12.9 Hz, 2H).

Example 142: 3-(4-(3-(6-fluoro-3H-spiro[isobenzofuran-1,4'-piperidine]-1'-)propoxy)-1-oxoisoindoline-2-)piperidine-2,6-dione (142)

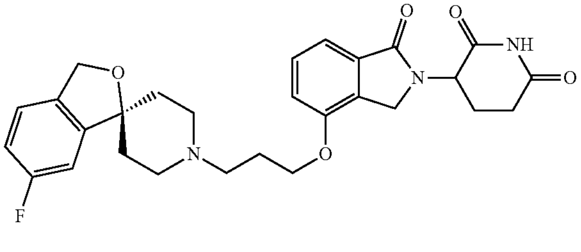

The preparation method was the same as 1-(3-((2-(2,6-dioxopiperidine-3-)-1-oxoisoindoline-4-)oxy)propyl)-4-phenylpiperidine-4-carbonitrile, 37.3 mg, yield 56%; $^1$H NMR (400 MHz, DMSO) δ 10.99 (s, 1H), 7.49 (t, J=7.8 Hz, 1H), 7.34-7.22 (m, 3H), 7.17 (dd, J=8.9, 2.2 Hz, 1H), 7.08 (td, J=9.4, 2.3 Hz, 1H), 5.11 (dd, J=13.3, 5.1 Hz, 1H), 4.93 (s, 2H), 4.38 (d, J=17.4 Hz, 1H), 4.23 (d, J=17.4 Hz, 1H), 4.18 (t, J=6.1 Hz, 2H), 2.97-2.86 (m, 1H), 2.82 (d, J=10.2 Hz, 2H), 2.63-2.52 (m, 3H), 2.48-2.39 (m, 1H), 2.31 (t, J=11.1 Hz, 2H), 2.04-1.86 (m, 5H), 1.62 (d, J=12.5 Hz, 2H).

Example 143: 3-(4-(5-(2,3-dihydrospiro[indene-1,4'-piperidine]-1'-)pentyl)-1-oxoisoindoline-2-)piperidine-2,6-dione (143)

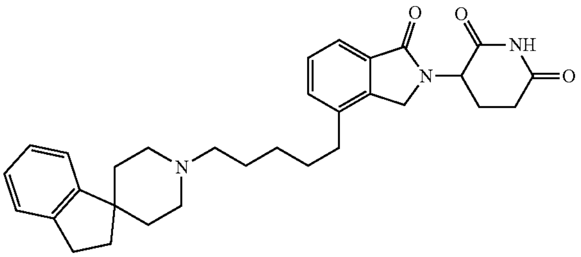 [SMILES: O=C1CCC(N2Cc3c(CCCCCN4CCC5(CCc6ccccc65)CC4)cccc3C2=O)C(=O)N1]

The preparation method was the same as 3-(1-oxo-4-(5-(2-phenylpyrroline-1-)pentyl)indoline-2-)piperidine-2,6-dione, 31.1 mg, yield 49%; $^1$H NMR (400 MHz, DMSO) δ 11.00 (s, 1H), 7.57 (dt, J=7.7, 3.9 Hz, 1H), 7.50-7.43 (m, 2H), 7.23-7.09 (m, 4H), 5.75 (s, 1H), 5.14 (dd, J=13.2, 5.0 Hz, 1H), 4.48 (d, J=17.2 Hz, 1H), 4.32 (d, J=17.2 Hz, 1H), 3.03-2.88 (m, 3H), 2.84 (t, J=7.3 Hz, 2H), 2.71-2.57 (m, 4H), 2.47-2.37 (m, 2H), 2.35-2.20 (m, 2H), 2.06-1.92 (m, 3H), 1.90-1.78 (m, 2H), 1.69-1.60 (m, 2H), 1.55 (dd, J=13.9, 7.3 Hz, 2H), 1.47 (d, J=12.6 Hz, 2H), 1.39-1.30 (m, 2H).

Example 144: 3-(4-((5-(6-fluoro-3H-spiro[isobenzofuran-1,4-piperidine]-1-)pentyl)oxy)-1-oxoisoindoline-2-)piperidine-2,6-dione (144)

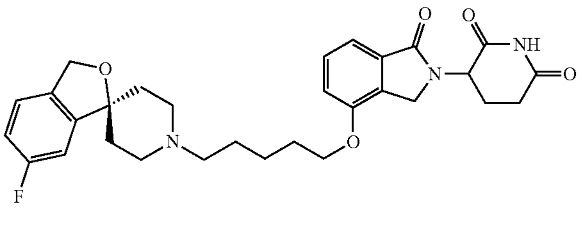

The preparation method was the same as 1-(3-((2-(2,6-dioxopiperidine-3-)-1-oxoisoindoline-4-)oxy)propyl)-4-phenylpiperidine-4-carbonitrile, and finally obtained 26 mg of white solid, yield 40%; $^1$H NMR (400 MHz, DMSO) δ 10.98 (s, 1H), 7.48 (t, J=7.7 Hz, 1H), 7.35-7.21 (m, 3H), 7.19-7.13 (m, 1H), 7.09 (dd, J=12.5, 5.1 Hz, 1H), 5.11 (dd, J=13.2, 5.0 Hz, 1H), 4.93 (s, 2H), 4.37 (d, J=17.4 Hz, 1H), 4.22 (d, J=17.4 Hz, 1H), 4.12 (t, J=6.1 Hz, 2H), 2.98-2.85 (m, 1H), 2.80 (d, J=9.9 Hz, 2H), 2.58 (s, 1H), 2.48-2.35 (m, 3H), 2.29 (t, J=11.4 Hz, 2H), 2.04-1.85 (m, 3H), 1.82-1.71 (m, 2H), 1.61 (d, J=12.7 Hz, 2H), 1.57-1.39 (m, 4H).

Example 145: 3-(4-(5-(2H-spiro[benzofuran-3,4'-piperidine]-1'-)pentyl-1-oxoisoindoline-2-)piperidine-2,6-dione (145)

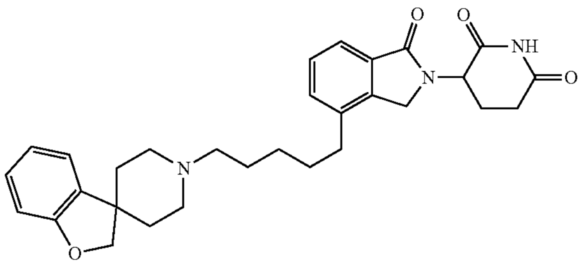 [SMILES: O=C1CCC(N2Cc3c(CCCCCN4CCC5(CC4)COc4ccccc45)cccc3C2=O)C(=O)N1]

The preparation method was the same as 3-(1-oxo-4-(5-(2-phenylpyrroline-1-)pentyl)indoline-2-)piperidine-2,6-dione, 15.5 mg, yield 50%; $^1$H NMR (400 MHz, DMSO) δ 11.00 (s, 1H), 7.63-7.53 (m, 1H), 7.45 (dd, J=7.1, 5.7 Hz, 2H), 7.19 (d, J=7.1 Hz, 1H), 7.11 (dd, J=11.2, 4.2 Hz, 1H), 6.85 (t, J=7.3 Hz, 1H), 6.75 (d, J=7.9 Hz, 1H), 5.14 (dd, J=13.2, 5.1 Hz, 1H), 4.47 (d, J=17.2 Hz, 1H), 4.36-4.28 (m, 3H), 3.00-2.82 (m, 3H), 2.73-2.57 (m, 3H), 2.49-2.30 (m, 3H), 2.12-1.96 (m, 3H), 1.86 (td, J=12.8, 3.1 Hz, 2H), 1.63 (d, J=13.2 Hz, 4H), 1.57-1.44 (m, 2H), 1.41-1.28 (m, 2H).

Example 146: 3-(4-((5-(6-methyl-3H-spiro[isobenzofuran-1,4'-piperidine]-1'-)pentyl)oxy)-1-oxoisoindoline-2-)piperidine-2,6-dione (146)

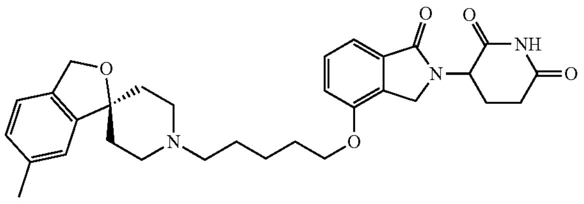

The preparation method was the same as 1-(3-((2-(2,6-dioxopiperidine-3-)-1-oxoisoindoline-4-)oxy)propyl)-4-phenylpiperidine-4-carbonitrile, and finally obtained 19 mg of white solid, yield 20%; $^1$H NMR (400 MHz, DMSO) δ 10.98 (s, 1H), 7.48 (t, J=7.8 Hz, 1H), 7.31 (d, J=7.5 Hz, 1H), 7.25 (d, J=8.2 Hz, 1H), 7.14 (d, J=7.6 Hz, 1H), 7.07 (d, J=7.8 Hz, 1H), 7.02 (s, 1H), 5.11 (dd, J=13.3, 5.1 Hz, 1H), 4.91 (s, 2H), 4.38 (d, J=17.4 Hz, 1H), 4.23 (d, J=17.4 Hz, 1H), 4.13 (t, J=6.2 Hz, 2H), 2.97-2.74 (m, 3H), 2.56 (d, J=16.4 Hz, 1H), 2.47-2.25 (m, 8H), 2.03-1.94 (m, 1H), 1.93-1.83 (m, 2H), 1.77 (dd, J=13.5, 6.5 Hz, 2H), 1.64-1.40 (m, 6H).

Example 147: 3-(1-oxo-4-(5-(4-oxo-1-phenyl-1,3,8-triazaspiro[4.5]decane-8-)pentyl)isoindoline-2-)piperidine-2,6-dione (147)

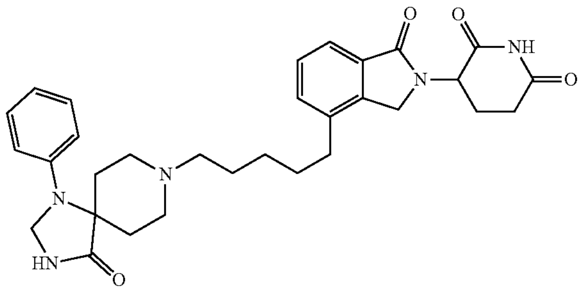 [SMILES: O=C1CCC(N2Cc3c(CCCCCN4CCC5(CC4)C(=O)NCN5c4ccccc4)cccc3C2=O)C(=O)N1]

The preparation method was the same as 3-(1-oxo-4-(5-(2-phenylpyrroline-1-)pentyl)indoline-2-)piperidine-2,6-dione, 33.8 mg, yield 52%; $^1$H NMR (400 MHz, DMSO) δ 11.00 (s, 1H), 8.73 (s, 1H), 8.28 (s, 1H), 7.57 (dd, J=6.3, 2.2 Hz, 1H), 7.52-7.42 (m, 2H), 7.22 (t, J=7.9 Hz, 2H), 6.87 (d, J=8.2 Hz, 2H), 6.75 (t, J=7.3 Hz, 1H), 5.13 (dd, J=13.3, 5.1 Hz, 1H), 4.58 (s, 2H), 4.47 (d, J=17.2 Hz, 1H), 4.31 (d, J=17.1 Hz, 1H), 3.20-2.73 (m, 5H), 2.71-2.52 (m, 7H), 2.40 (ddd, J=26.3, 13.2, 4.3 Hz, 1H), 2.07-1.95 (m, 1H), 1.75-1.60 (m, 4H), 1.56 (dd, J=14.2, 7.6 Hz, 2H), 1.42-1.28 (m, 2H).

Example 148: 3-(4-((6-(2H-spiro[benzofuran-3,4'-piperidine]-1'-)hexyl)oxy)-1-oxoisoindoline-2-)piperidine-2,6-dione (148)

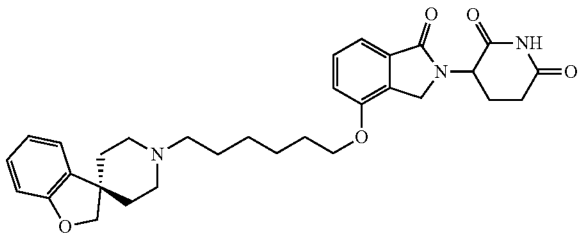

The preparation method was the same as 1-(3-((2-(2,6-dioxopiperidine-3-)-1-oxoisoindoline-4-)oxy)propyl)-4-phenylpiperidine-4-carbonitrile, and finally obtained 21 mg of white solid, yield 22%; 1H NMR (400 MHz, DMSO) δ 10.99 (s, 1H), 7.48 (t, J=7.8 Hz, 1H), 7.30 (d, J=7.4 Hz, 1H), 7.24 (d, J=8.1 Hz, 1H), 7.18 (d, J=7.2 Hz, 1H), 7.10 (td, J=7.9, 1.2 Hz, 1H), 6.84 (t, J=7.4 Hz, 1H), 6.75 (d, J=7.9 Hz, 1H), 5.11 (dd, J=13.3, 5.1 Hz, 1H), 4.37 (d, J=17.4 Hz, 1H), 4.33 (s, 2H), 4.22 (d, J=17.4 Hz, 1H), 4.12 (t, J=6.3 Hz, 2H), 2.97-2.87 (m, 1H), 2.83 (d, J=11.7 Hz, 2H), 2.57 (d, J=17.9 Hz, 1H), 2.48-2.38 (m, 1H), 2.36-2.25 (m, 2H), 1.97 (t, J=10.8 Hz, 3H), 1.83 (td, J=12.8, 3.6 Hz, 2H), 1.79-1.68 (m, 2H), 1.61 (d, J=12.4 Hz, 2H), 1.53-1.40 (m, 4H), 1.39-1.30 (m, 2H).

Example 149: 3-(4-(4-(3H-spiro[isobenzofuran-1,4'-piperidine]-1'-)butyl)-1-oxoisoindoline-2-)piperidine-2,6-dione (149)

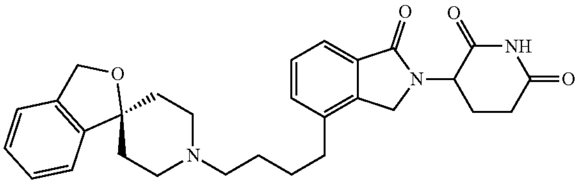

The preparation method was the same as 3-(1-oxo-4-(5-(2-phenylpyrroline-1-)pentyl)indoline-2-)piperidine-2,6-dione, 36.9 mg, yield 42%; $^1$H NMR (400 MHz, DMSO) δ 11.02 (s, 1H), 7.62-7.56 (m, 1H), 7.51-7.45 (m, 2H), 7.31-7.21 (m, 4H), 5.15 (dd, J=13.3, 5.1 Hz, 1H), 4.96 (s, 2H), 4.49 (d, J=17.2 Hz, 1H), 4.33 (d, J=17.1 Hz, 1H), 2.94 (ddd, J=17.6, 13.9, 5.5 Hz, 1H), 2.84-2.75 (m, 2H), 2.69 (t, J=7.5 Hz, 2H), 2.65-2.57 (m, 1H), 2.47-2.37 (m, 3H), 2.31 (t, J=10.9 Hz, 2H), 2.03 (dtd, J=12.6, 5.1, 2.0 Hz, 1H), 1.90 (td, J=13.1, 4.3 Hz, 2H), 1.65 (ddd, J=21.1, 10.2, 4.5 Hz, 4H), 1.53 (dt, J=14.9, 7.6 Hz, 2H).

Example 150: 3-(4-((6-(6-chloro-3H-spiro[isobenzofuran-1,4'-piperidine]-1'-)hexyl)oxy)-1-oxoisoindoline-2-)piperidine-2,6-dione (150)

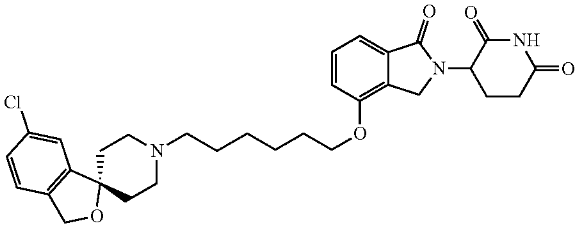

The preparation method was the same as 1-(3-((2-(2,6-dioxopiperidine-3-)-1-oxoisoindoline-4-)oxy)propyl)-4-phenylpiperidine-4-carbonitrile, and finally obtained 27 mg of white solid, yield 26%; $^1$H NMR (400 MHz, DMSO) δ 10.98 (s, 1H), 7.48 (t, J=7.8 Hz, 1H), 7.35 (s, 1H), 7.33-7.27 (m, 3H), 7.24 (d, J=8.1 Hz, 1H), 5.11 (dd, J=13.3, 5.1 Hz, 1H), 4.93 (s, 2H), 4.37 (d, J=17.4 Hz, 1H), 4.22 (d, J=17.4 Hz, 1H), 4.12 (t, J=6.3 Hz, 2H), 3.00-2.85 (m, 1H), 2.78 (d, J=10.6 Hz, 2H), 2.63-2.54 (m, 1H), 2.48-2.39 (m, 1H), 2.38-2.31 (m, 2H), 2.27 (t, J=11.3 Hz, 2H), 2.04-1.83 (m, 3H), 1.80-1.68 (m, 2H), 1.60 (d, J=12.6 Hz, 2H), 1.47 (q, J=16.3 Hz, 4H), 1.35 (dd, J=13.0, 6.3 Hz, 2H).

Example 151: 3-(4-(4-(6-chloro-3H-spiro[isobenzofuran-1,4-piperidine]-1-)butyl)-1-oxo isoindoline-2-)piperidine-2,6-dione (151)

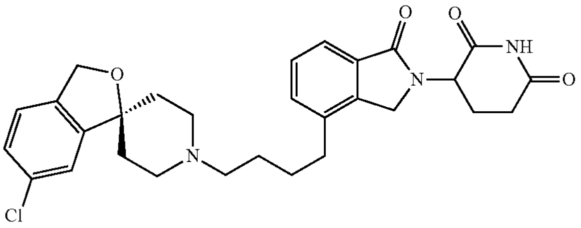

The preparation method was the same as 3-(1-oxo-4-(5-(2-phenylpyrroline-1-)pentyl)indoline-2-)piperidine-2,6-dione, 34.7 mg, yield 37%; $^1$H NMR (400 MHz, DMSO) δ 11.01 (s, 1H), 8.18 (s, 1H), 7.60-7.54 (m, 1H), 7.50-7.44 (m, 2H), 7.37 (d, J=1.4 Hz, 1H), 7.35-7.27 (m, 2H), 5.14 (dd, J=13.3, 5.1 Hz, 1H), 4.94 (s, 2H), 4.48 (d, J=17.2 Hz, 1H), 4.32 (d, J=17.2 Hz, 1H), 2.99-2.88 (m, 1H), 2.82 (d, J=11.0 Hz, 2H), 2.68 (t, J=7.5 Hz, 2H), 2.60 (dd, J=17.0, 2.8 Hz, 1H), 2.48-2.41 (m, 3H), 2.34 (t, J=10.8 Hz, 2H), 2.02 (ddd, J=9.6, 5.5, 2.0 Hz, 1H), 1.94 (ddd, J=14.4, 10.7, 3.8 Hz, 2H), 1.70-1.59 (m, 4H), 1.57-1.47 (m, 2H).

Example 152: 3-(4-((5-(6-chloro-3H-spiro[isobenzofuran-1,4'-piperidine]-1'-)-5-oxopentyl)oxy)-1-oxoisoindoline-2-)piperidine-2,6-dione 152)

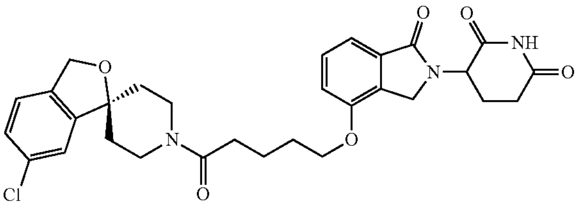

The synthesis method was the same as N-(3-chloro-4-methylphenyl)-4-((2-(2,6-dioxopiperidine-3-)-1-oxoisoindoline-4-)oxy)butanamide, and obtained 31 mg of final product, as a white solid, yield 39%; 1H NMR (400 MHz, DMSO) δ 10.96 (s, 1H), 7.48 (t, J=7.8 Hz, 1H), 7.42 (s, 1H), 7.32 (q, J=8.1 Hz, 3H), 7.25 (d, J=8.1 Hz, 1H), 5.10 (dd, J=13.0, 4.7 Hz, 1H), 4.47-4.34 (m, 2H), 4.22 (d, J=17.4 Hz, 1H), 4.15 (t, J=6.1 Hz, 2H), 3.87 (d, J=12.3 Hz, 1H), 3.27 (s, 1H), 2.87 (ddd, J=31.9, 19.7, 9.4 Hz, 2H), 2.62-2.53 (m, 1H), 2.45 (d, J=6.8 Hz, 5H), 1.94 (dd, J=23.7, 11.7 Hz, 2H), 1.87-1.57 (m, 7H).

Example 153: 3-(4-(4-(6-chloro-3H-spiro[isobenzofuran-1,4'-piperidine]-1'-)-4-oxobutyl)-1-oxoisoindoline-2-)piperidine-2,6-dione (153)

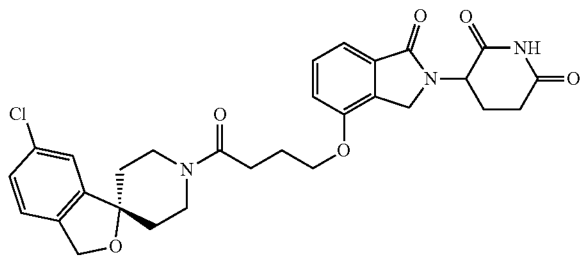

The synthesis method was the same as N-(3-chloro-4-methylphenyl)-4-((2-(2,6-dioxopiperidine-3-)-1-oxoisoindoline-4-)oxy)butanamide, and obtained 18 mg of final product, as a white solid, yield 23%; 1H NMR (400 MHz, DMSO) δ 10.97 (s, 1H), 7.49 (t, J=7.8 Hz, 1H), 7.39 (s, 1H), 7.35-7.24 (m, 4H), 5.11 (dd, J=13.3, 5.1 Hz, 1H), 4.99 (s, 2H), 4.48-4.36 (m, 2H), 4.24 (d, J=17.4 Hz, 1H), 4.17 (t, J=6.3 Hz, 2H), 3.87 (d, J=11.9 Hz, 1H), 3.27 (s, 1H), 2.99-2.79 (m, 2H), 2.65-2.52 (m, 3H), 2.48-2.35 (m, 1H), 2.01 (dt, J=14.6, 7.3 Hz, 3H), 1.82 (ddd, J=19.2, 17.3, 8.8 Hz, 2H), 1.63 (d, J=13.0 Hz, 2H).

Example 154: 6-chloro-N-(4-((2-(2,6-dioxopiperidine-3-)-1-oxoisoindoline-4-)-oxy-)butyl)-3H-spiro[isobenzofuran-1,4-piperidine]-1-carboxamide (154)

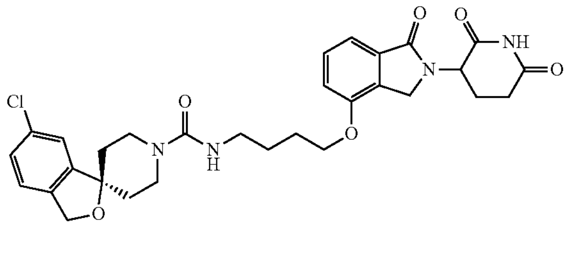

The preparation method was the same as 1-(3-chloro-4-methylphenyl)-3-(2-((2-(2,6-dioxopiperidine-3-)-1-oxoisoindoline-4-)oxy)ethyl)urea, white solid compound, 50.6 mg, yield 65%; $^{1}$H NMR (400 MHz, DMSO) δ 10.96 (s, 1H), 7.48 (t, J=7.8 Hz, 1H), 7.38 (s, 1H), 7.35-7.28 (m, 3H), 7.24 (d, J=8.1 Hz, 1H), 6.54 (t, J=5.2 Hz, 1H), 5.11 (dd, J=13.3, 5.1 Hz, 1H), 4.97 (s, 2H), 4.39 (d, J=17.5 Hz, 1H), 4.23 (d, J=17.4 Hz, 1H), 4.14 (t, J=6.3 Hz, 2H), 3.95 (d, J=11.5 Hz, 2H), 3.12 (dd, J=12.4, 6.7 Hz, 2H), 2.99-2.85 (m, 3H), 2.60-2.52 (m, 1H), 2.44 (dd, J=17.5, 8.9 Hz, 1H), 2.04-1.92 (m, 1H), 1.83-1.72 (m, 4H), 1.62-1.55 (m, 4H).

Example 155: 6-chloro-N-(2-((2-(2,6-dioxopiperidine-3-)-1-oxoisoindoline-4-)oxy)ethyl)-3H-spiro[isobenzofuran-1,4-piperidine]-1-carboxamide (155)

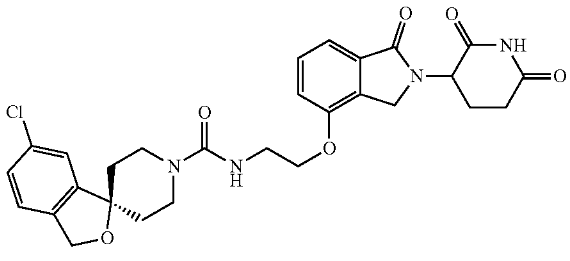

The preparation method was the same as 1-(3-chloro-4-methylphenyl)-3-(2-((2-(2,6-dioxopiperidine-3-)-1-oxoisoindoline-4-)oxy)ethyl)urea, white solid compound, 49 mg, yield 60%; $^{1}$H NMR (400 MHz, DMSO) δ 10.97 (s, 1H), 7.49 (t, J=7.8 Hz, 1H), 7.37 (s, 1H), 7.34-7.28 (m, 4H), 6.76 (t, J=5.3 Hz, 1H), 5.11 (dd, J=13.2, 5.0 Hz, 1H), 4.97 (s, 2H), 4.39 (d, J=17.4 Hz, 1H), 4.25 (d, J=17.4 Hz, 1H), 4.17 (t, J=6.1 Hz, 2H), 3.96 (d, J=12.7 Hz, 2H), 3.43 (dd, J=11.5, 5.8 Hz, 2H), 3.02-2.95 (m, 2H), 2.94-2.86 (m, 1H), 2.58 (d, J=18.0 Hz, 1H), 2.46-2.34 (m, 1H), 2.04-1.94 (m, 1H), 1.79 (td, J=13.0, 4.5 Hz, 2H), 1.58 (d, J=12.8 Hz, 2H).

Example 156: 3-(4-(5-(6-fluoro-3H-spiro[isobenzofuran-1,4'-piperidine]-1'-)pentyl)-1-oxoisoindoline-2-)piperidine-2,6-dione (156)

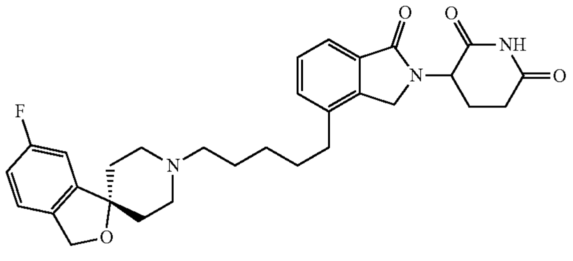

The preparation method was the same as 3-(1-oxo-4-(5-(2-phenylpyrroline-1-)pentyl)indoline-2-)piperidine-2,6-dione, 37 mg, yield 37%; $^{1}$H NMR (400 MHz, DMSO) δ 11.00 (s, 1H), 7.60-7.54 (m, 1H), 7.49-7.44 (m, 2H), 7.29 (dd, J=8.0, 4.9 Hz, 1H), 7.18-7.06 (m, 2H), 5.14 (dd, J=13.2, 5.2 Hz, 1H), 4.93 (s, 2H), 4.47 (d, J=17.4 Hz, 1H), 4.31 (d, J=17.2 Hz, 1H), 3.00-2.79 (m, 3H), 2.68-2.56 (m, 3H), 2.38 (dt, J=26.6, 15.4 Hz, 5H), 2.05-1.91 (m, 3H), 1.63 (d, J=11.3 Hz, 4H), 1.58-1.48 (m, 2H), 1.35 (dd, J=15.8, 6.9 Hz, 2H).

Example 157: 3-(4-(5-(6-methyl-3H-spiro[isobenzofuran-1,4'-piperidine]-1-)pentyl)-1-oxoisoindoline-2-)piperidine-2,6-dione (157)

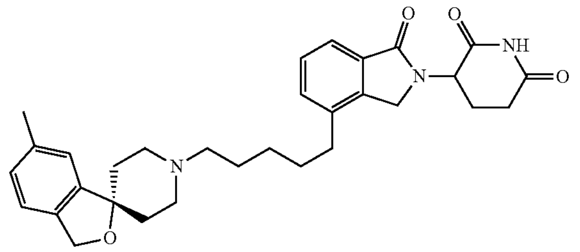

The preparation method was the same as 3-(1-oxo-4-(5-(2-phenylpyrroline-1-)pentyl)indoline-2-)piperidine-2,6-dione, 27.5 mg, yield 28%; $^1$H NMR (400 MHz, DMSO) δ 11.00 (s, 1H), 7.57 (dd, J=5.4, 3.1 Hz, 1H), 7.51-7.41 (m, 2H), 7.13 (d, J=7.6 Hz, 1H), 7.07 (d, J=7.7 Hz, 1H), 7.02 (s, 1H), 5.14 (dd, J=13.3, 5.1 Hz, 1H), 4.91 (s, 2H), 4.47 (d, J=17.2 Hz, 1H), 4.31 (d, J=17.1 Hz, 1H), 2.98-2.87 (m, 1H), 2.80 (d, J=10.8 Hz, 2H), 2.70-2.56 (m, 3H), 2.47-2.27 (m, 8H), 2.03-1.98 (m, 1H), 1.92-1.81 (m, 2H), 1.69-1.47 (m, 6H), 1.40-1.30 (m, 2H).

Example 158: N-(3-chloro-4-methylphenyl)-4-((2-(2,6-dioxopiperidine-3-)-1-oxoisoindoline-4-)oxy)butanamide (158)

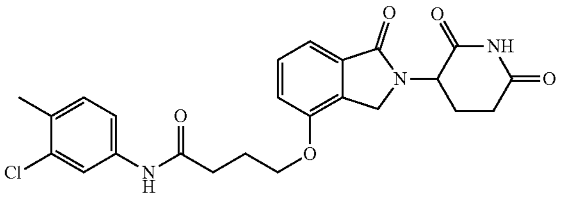 [SMILES: Cc1ccc(NC(=O)CCCOc2cccc3c2CN(C2CCC(=O)NC2=O)C3=O)cc1Cl]

Step 1: 4-bromobutyric acid (3.0 g, 16.57 mmol, 1.0 eq) was dissolved in 20 mL of anhydrous tetrahydrofuran, cooled to −40° C., trifluoroacetic anhydride (6.96 g, 33.14 mmol, 2.0 eq) was added dropwise, stirred at −40° C. for 30 min. Then tert-butanol (9.83 g, 132.56 mmol, 8.0 eq) was added, gradually raised to room temperature, and reacted overnight. After the reaction was completed, the reaction system was poured into saturated sodium bicarbonate solution, extracted with ethyl acetate, washed with saturated sodium chloride, and concentrated under reduced pressure to obtain 3.75 g of light-yellow oil with a yield of 95%. $^1$H NMR (400 MHz, $CDCl_3$) δ 3.41 (t, J=6.7 Hz, 2H), 2.25 (t, J=7.3 Hz, 2H), 1.94-1.85 (m, 2H), 1.79-1.68 (m, 2H), 1.44 (s, 9H).

Step 2: methyl 5-amino-4-(4-hydroxy-1-oxoisoindoline-2-)-5-oxopentanoate (400 mg, 1.37 mmol, 1.0 eq), and tert-butyl 4-bromobutyrate (1.62 g, 6.85 mmol, 5.0 eq) were dissolved in 20 mL DMSO, anhydrous potassium carbonate (379 mg, 2.74 mmol, 2.0 eq) was added and reacted at 50° C. for 24 h. After the reaction was completed, the solution was diluted with ethyl acetate, washed with saturated sodium chloride, dried, concentrated under reduced pressure, and purified by column chromatography to obtain 530 mg of colorless oil with a yield of 86%. $^1$H NMR (400 MHz, DMSO) δ 7.61 (s, 1H), 7.44 (t, J=7.8 Hz, 1H), 7.27 (d, J=7.4 Hz, 1H), 7.20 (d, J=8.3 Hz, 1H), 4.72 (dd, J=10.4, 4.8 Hz, 1H), 4.50 (d, J=17.6 Hz, 1H), 4.35 (d, J=17.6 Hz, 1H), 4.11 (t, J=6.0 Hz, 1H), 3.50 (s, 1H), 2.31-2.14 (m, 2H), 2.06 (ddd, J=13.7, 10.3, 6.5 Hz, 1H), 1.79-1.62 (m, 2H), 1.38 (s, 3H).

Step 3: methyl 5-amino-4-(4-(4-(tert-butoxy)-4-oxobutoxy)-1-oxoisoindoline-2-)-5-oxopentanoate (530 mg, 1.18 mmol, 1.0 eq) was dissolved in 20 mg of anhydrous tetrahydrofuran under ice bath for 15 min. Potassium tert-butoxide (146 mg, 1.30 mmol, 1.1 eq) was added, and the reaction was continued for 90 min under ice bath. After the reaction was completed, 50 uL formic acid was added to quench the reaction. The solvent was spun off under reduced pressure and purified by column chromatography to obtain 463 mg of yellow solid with a yield of 94%; $^1$H NMR (400 MHz, DMSO) δ 10.98 (s, 1H), 7.46 (d, J=7.8 Hz, 1H), 7.30 (d, J=7.4 Hz, 1H), 7.23 (d, J=8.1 Hz, 1H), 5.11 (dd, J=13.3, 5.0 Hz, 1H), 4.37 (d, J=17.3 Hz, 1H), 4.21 (d, J=17.2 Hz, 1H), 4.12 (t, J=5.9 Hz, 2H), 2.98-2.83 (m, 1H), 2.58 (d, J=18.0 Hz, 1H), 2.44 (dd, J=17.9, 8.8 Hz, 2H), 2.27 (t, J=7.1 Hz, 3H), 2.03-1.92 (m, 1H), 1.85-1.54 (m, 6H), 1.40-1.36 (m, 13H).

Step 4: tert-butyl 4-((2-(2,6-dioxopiperidine-3-)-1-oxoisoindoline-4-)oxy)butyrate (463 mg, 1.11 mmol) was added in a 100 mL round bottom flask, 20 mL of hydrochloric acid dioxane solution was added, and reacted at room temperature for 30 min. After the reaction was completed, the solvent was spun off, and directly used in the next step without further purification. $^1$H NMR (400 MHz, DMSO) δ 10.99 (s, 1H), 7.47 (t, J=7.8 Hz, 1H), 7.30 (d, J=7.4 Hz, 1H), 7.23 (d, J=8.1 Hz, 1H), 5.11 (dd, J=13.3, 5.1 Hz, 1H), 4.41-4.32 (m, 1H), 4.23 (t, J=12.9 Hz, 1H), 4.12 (t, J=6.0 Hz, 2H), 3.59-3.54 (m, 1H), 2.90 (ddd, J=13.6, 11.9, 5.4 Hz, 1H), 2.57 (d, J=17.8 Hz, 1H), 2.47-2.35 (m, 1H), 2.33-2.25 (m, 2H), 2.02-1.92 (m, 1H), 1.71 (ddd, J=19.0, 13.1, 5.6 Hz, 4H).

Step 5: 4-((2-(2,6-dioxopiperidine-3-)-1-oxoisoindoline-4-)oxy)butanoic acid (50 mg, 0.139 mmol, 1.0 eq) was dissolved in 3 mL dimethyl sulfoxide, 3-chloro-4-methylaniline (0.208 mmol, 1.5 eq), 0-(7-nitrobenzotriazole)-N,N,N,N-tetramethylurea hexafluorophosphate (79 mg, 0.208 mmol, 1.5 eq), 1-hydroxybenzotriazole (28 mg, 0.208 mmol, 1.5 eq), and triethylamine (141 mg, 1.39 mmol, 10 eq) were added, and reacted at room temperature for hour.

After the reaction was completed, the solution was diluted with ethyl acetate, washed with saturated sodium chloride, and purified by thin layer chromatography and high performance liquid chromatography to obtain 18 mg of the product, as a white solid, yield 26%; $^1$H NMR (400 MHz, DMSO) δ 10.96 (s, 1H), 10.03 (s, 1H), 7.83 (d, J=1.8 Hz, 1H), 7.48 (t, J=7.8 Hz, 1H), 7.35-7.28 (m, 2H), 7.24 (dd, J=8.2, 3.6 Hz, 2H), 5.07 (dd, J=13.4, 5.0 Hz, 1H), 4.27 (d, J=17.4 Hz, 1H), 4.14 (d, J=17.1 Hz, 3H), 2.96-2.84 (m, 1H), 2.59-2.52 (m, 1H), 2.25 (s, 3H), 2.21-1.87 (m, 4H), 1.24 (s, 2H).

Example 159: N-(3-chloro-4-methylphenyl)-5-((2-(2,6-dioxopiperidine-3-)-1-oxoisoindoline-4-)oxy) valeramide (159)

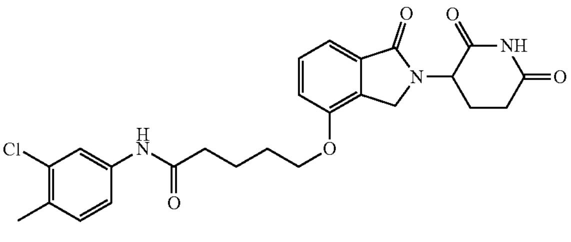 [SMILES: Cc1ccc(NC(=O)CCCCOc2cccc3c2CN(C2CCC(=O)NC2=O)C3=O)cc1Cl]

The synthesis method was the same as N-(3-chloro-4-methylphenyl)-4-((2-(2,6-dioxopiperidine-3-)-1-oxoisoindoline-4-)oxy)butanamide, and finally obtained 14 mg of product, as a white solid, yield 21%; $^1$H NMR (400 MHz, DMSO) δ 10.96 (s, 1H), 10.00 (s, 1H), 7.80 (d, J=1.9 Hz, 1H), 7.47 (t, J=7.8 Hz, 1H), 7.36-7.28 (m, 2H), 7.24 (d, J=8.4 Hz, 2H), 5.10 (dd, J=13.3, 5.1 Hz, 1H), 4.37 (d, J=17.4 Hz, 1H), 4.22 (d, J=17.4 Hz, 1H), 4.14 (d, J=5.4 Hz, 2H), 2.98-2.85 (m, 1H), 2.56 (d, J=19.3 Hz, 1H), 2.46-2.32 (m, 3H), 2.25 (s, 3H), 2.03-1.93 (m, 1H), 1.78 (d, J=3.5 Hz, 4H).

Example 160: 1-(3-chloro-4-methylphenyl)-3-(2-((2-(2,6-dioxopiperidine-3-)-1-oxoisoindoline-4-)oxy)ethyl)ure

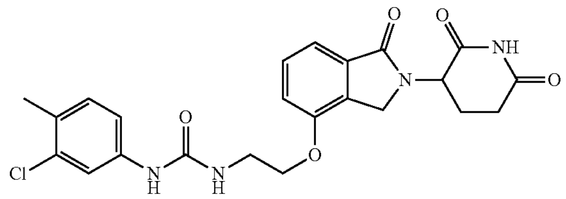

Step 1: methyl 5-amino-4-(4-hydroxy-1-oxoisoindoline-2-)-5-oxopentanoate (500 mg, 1.71 mmol), N-BoC-2-aminoethanol (413 mg, 2.56 mmol) and triphenylphosphine (672 mg, 2.56 mmol) were dissolved in dry tetrahydrofuran (30 mL), DIAD (504 μL, 2.56 mmol) was added with stirring at room temperature, the resulting reaction solution was stirred to reacted at room temperature for 30 min. After the reaction was completed, the solvent was removed under reduced pressure, and the resulting residue was purified by silica gel column chromatography to obtain 468 mg of methyl 5-amino-4-(4-(2-(tert-butoxycarbonylamino)ethoxy)-1-oxoisoindoline-2-)-5-oxopentanoate, 63%.

Step 2: methyl 5-amino-4-(4-(2-(tert-butoxycarbonylamino)ethoxy)-1-oxoisoindoline-2-)-5-oxopentanoate (468 mg, 1.07 mmol) was dissolved in dry tetrahydrofuran (40 mL), the reaction solution was cooled to 0° C., potassium tert-butoxide (133 mg, 1.18 mmol) was added under stirring, continued to stir under ice bath for 10 min. After the reaction was completed, the reaction solution was quenched with 60 μL of formic acid, the solvent was removed under reduced pressure, and the residue was purified by silica gel column chromatography to obtain 350 mg of target product, 81%.

Step 3: the product obtained in step 2 was dissolved in 20 mL of 1,4-dioxane solution of hydrogen chloride, and reacted under stirring at room temperature for 2 h. After the reaction was completed, the solvent was removed under reduced pressure to obtain the target product as a white powder solid.

Step 4: 3-(4-(2-aminoethoxy)-1-oxoisoindoline-2-)piperidine-2,6-dione hydrochloride (50 mg, 0.147 mmol) was dissolved in 3 mL of dry DMSO, triethylamine (61 μL, 0.44 mmol) and 3-chloro-4-methylphenyl isocyanate (37 mg, 0.22 mmol) were added to the reaction solution successively. The resulting reaction solution was heated at 40° C. to react for 3 h. After the reaction was completed, the obtained reaction solution was separated by HPLC to obtain 48 mg of target product 1-(3-chloro-4-methylphenyl)-3-(2-((2-(2,6-dioxopiperidine)-3-)-1-oxoisoindoline-4-)oxy)ethyl)urea, yield 69%; $^1$H NMR (400 MHz, DMSO) δ 10.96 (s, 1H), 8.78 (s, 1H), 7.66 (d, J=2.0 Hz, 1H), 7.48 (t, J=7.8 Hz, 1H), 7.32 (d, J=7.4 Hz, 1H), 7.27 (d, J=8.1 Hz, 1H), 7.21-7.00 (m, 4H), 6.46 (t, J=5.6 Hz, 1H), 5.11 (dd, J=13.3, 5.1 Hz, 1H), 4.39 (d, J=17.4 Hz, 1H), 4.24 (d, J=17.3 Hz, 1H), 4.17 (t, J=5.5 Hz, 2H), 3.49 (dd, J=5.4, 1.9 Hz, 2H), 2.91 (ddd, J=17.6, 13.7, 5.4 Hz, 1H), 2.58 (dt, J=6.8, 3.3 Hz, 1H), 2.33 (ddd, J=26.6, 13.4, 4.5 Hz, 1H), 2.22 (s, 3H), 2.03-1.91 (m, 1H).

Example 161: 1-(4-chloro-3-methylphenyl)-3-(3-((2-(2,6-dioxopiperidine-3-)-1-oxoisoindoline-4-)oxy)propyl)urea (161)

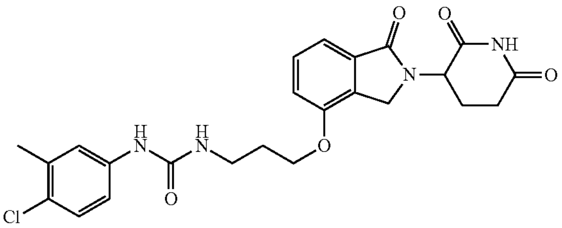 [SMILES: Cc1cc(NC(=O)NCCCOc2cccc3c2CN(C2CCC(=O)NC2=O)C3=O)ccc1Cl]

The preparation method was the same as 1-(3-chloro-4-methylphenyl)-3-(2-((2-(2,6-dioxopiperidine-3-)-1-oxoisoindoline-4-)oxy)ethyl)urea, 13.2 mg of white solid compound was obtained, yield 31%; $^1$H NMR (400 MHz, DMSO) δ 10.96 (s, 1H), 8.64-8.55 (m, 1H), 7.64 (d, J=2.1 Hz, 1H), 7.48 (t, J=7.8 Hz, 1H), 7.31 (d, J=7.4 Hz, 1H), 7.25 (d, J=8.0 Hz, 1H), 7.15 (d, J=8.5 Hz, 1H), 7.08 (dd, J=8.3, 2.1 Hz, 1H), 6.32 (s, 1H), 5.09 (dd, J=13.3, 5.2 Hz, 1H), 4.39 (d, J=17.4 Hz, 1H), 4.24 (d, J=17.4 Hz, 1H), 4.17 (t, J=5.9 Hz, 2H), 3.33-3.24 (m, 2H), 2.95-2.85 (m, 1H), 2.63-2.55 (m, 1H), 2.45-2.32 (m, 1H), 2.22 (s, 3H), 2.01-1.88 (m, 3H).

Example 162: 1-(3-chloro-4-methylphenyl)-3-(4-((2-(2,6-dioxopiperidine-3-)-1-oxoisoindoline-4-)oxy)butyl)urea (162)

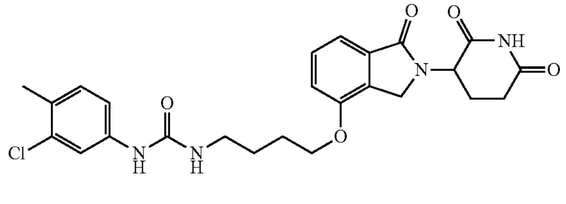 [SMILES: Cc1ccc(NC(=O)NCCCCOc2cccc3c2CN(C2CCC(=O)NC2=O)C3=O)cc1Cl]

The preparation method was the same as 1-(3-chloro-4-methylphenyl)-3-(2-((2-(2,6-dioxopiperidine-3-)-1-oxoisoindoline-4-)oxy)ethyl)urea, white solid compound, 44.2 mg, yield 65%; $^1H$ NMR (400 MHz, DMSO) δ 10.96 (s, 1H), 8.52 (s, 1H), 7.63 (d, J=2.0 Hz, 1H), 7.47 (t, J=7.8 Hz, 1H), 7.30 (d, J=7.4 Hz, 1H), 7.24 (d, J=8.1 Hz, 1H), 7.16 (d, J=8.4 Hz, 1H), 7.09 (dd, J=8.3, 2.1 Hz, 1H), 6.22 (t, J=5.8 Hz, 1H), 5.10 (dd, J=13.3, 5.0 Hz, 1H), 4.38 (d, J=17.4 Hz, 1H), 4.22 (d, J=17.3 Hz, 1H), 4.15 (t, J=6.2 Hz, 2H), 3.15 (dd, J=12.8, 6.6 Hz, 2H), 2.96-2.85 (m, 1H), 2.56 (d, J=17.6 Hz, 1H), 2.47-2.36 (m, 1H), 2.22 (s, 3H), 2.03-1.94 (m, 1H), 1.76 (dd, J=14.3, 6.4 Hz, 2H), 1.61 (dd, J=14.4, 6.9 Hz, 2H).

Example 163: 1-(3,4-dichlorophenyl)-3-(2-((2-(2,6-dioxopiperidine-3-)-1-oxoisoindoline-4-oxoethyl) urea (163)

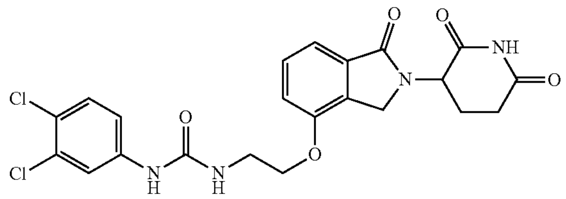 [SMILES: O=C1CCC(N2Cc3c(OCCNC(=O)Nc4ccc(Cl)c(Cl)c4)cccc3C2=O)C(=O)N1]

The preparation method was the same as 1-(3-chloro-4-methylphenyl)-3-(2-((2-(2,6-dioxopiperidine-3-)-1-oxoisoindoline-4-)oxy)ethyl)urea, white solid compound, 50 mg, yield 69%; $^1H$ NMR (400 MHz, DMSO) δ 10.97 (s, 1H), 8.96 (s, 1H), 7.85 (d, J=2.5 Hz, 1H), 7.65-7.54 (m, 1H), 7.59-7.52 (m, 1H), 7.52-7.42 (m, 2H), 7.27 (ddd, J=13.5, 11.3, 5.0 Hz, 3H), 6.56 (t, J=5.7 Hz, 1H), 5.11 (dd, J=13.3, 5.1 Hz, 1H), 4.38 (d, J=17.4 Hz, 1H), 4.25 (d, J=17.3 Hz, 1H), 4.18 (t, J=5.5 Hz, 2H), 3.55-3.47 (m, 1H), 2.91 (ddd, J=18.6, 13.6, 5.2 Hz, 1H), 2.57 (d, J=17.0 Hz, 2H), 2.41-2.28 (m, 2H), 2.02-1.93 (m, 1H).

Example 164: (2S)-2-acetylamino-5-(2-(2,6-dioxopiperidine-3-)-1-oxoisoindoline-4-)-N-phenylpentanamide (164)

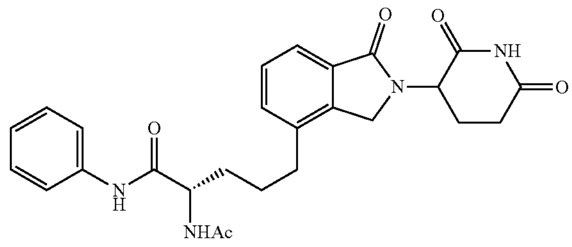 [SMILES: CC(=O)N[C@@H](CCCc1cccc2c1CN(C1CCC(=O)NC1=O)C2=O)C(=O)Nc1ccccc1]

Step 1: aniline (15 μL, 0.163 mmol) and compound (2R)-2-tert-butoxycarbonylamino-5-(2-(2,6-dioxopiperidine-3-)-1-oxoisoindoline-4-)pentanoic acid (50 mg, 0.109 mmol) were dissolved in 10 mL of dichloromethane, and triethylamine (46 μL, 0.326 mmol), HOBt (mg, mmol) and HATU (62 mg, 0.163 mmol) were added successively under stirring at room temperature. The reaction solution was stirred to react at room temperature for 2 h. LC-MS monitored the reaction until completed. The reaction solution was diluted with ethyl acetate, washed with saturated sodium chloride solution, and the ethyl acetate layer was dried over anhydrous sodium sulfate, filtered, removed the solvent under reduced pressure, and the crude product was used directly in the next step.

Step 2: the crude reaction product obtained in Step 1 was dissolved in 10 mL of hydrogen chloride in saturated 1,4-dioxane. The reaction solution was reacted at room temperature for 2 h. -LC-MS monitored that the reaction was completed. The solvent was removed under reduced pressure, and residue was diluted with ethyl acetate, washed with saturated sodium bicarbonate solution and saturated sodium chloride solution successively. The ethyl acetate layer was dried over anhydrous sodium sulfate, filtered, and dried under reduced pressure to obtain the crude product and directly used in the next reaction.

Step 3: the crude product in step 2 was dissolved in 10 mL of dry dichloromethane, and triethylamine (152 μL, 1.09 mmol) and acetyl chloride (16 μL, 0.218 mmol) were added successively under stirring at room temperature. The reaction solution was stirred to react overnight at room temperature. LC-MS monitored that the reaction was completed-, the solvent was removed under reduced pressure, the residue was dissolved in ethyl acetate, and washed with saturated sodium bicarbonate and saturated sodium chloride solution successively. The ethyl acetate layer was dried over anhydrous sodium sulfate, filtered, and the filtrate was dried under reduced pressure. The resulting crude product was separated by reverse phase HPLC to obtain 10.2 mg of (2S)-2-acetamido-5-(2-(2,6-dioxopiperidine-3-)-1-oxoisoindoline-4-)-N-phenylpentanamide, yield 19%; $^1H$ NMR (400 MHz, DMSO) δ 10.95 (s, 1H), 10.08 (d, J=5.3 Hz, 1H), 8.18 (d, J=7.8 Hz, 1H), 7.63-7.51 (m, 3H), 7.48-7.40 (m, 2H), 7.29 (t, J=7.8 Hz, 2H), 7.04 (t, J=7.3 Hz, 1H), 5.12 (dd, J=13.3, 5.0 Hz, 1H), 4.47 (dd, J=12.1, 6.8 Hz, 1H), 4.39 (d, J=17.3 Hz, 1H), 4.26 (dd, J=17.1, 6.3 Hz, 1H), 2.99-2.85 (m, 1H), 2.73-2.56 (m, 3H), 2.30 (dtd, J=16.3, 12.3, 3.0 Hz, 1H), 2.05-1.92 (m, 1H), 1.86 (s, 3H), 1.80-1.50 (m, 4H).

Example 165: N-((2S)-1-(benzylamino)-5-(2-(2,6-dioxopiperidine-3-)-1-oxoisoindoline-4-)-1-oxopentyl-2-)cyclopropylformamide (165)

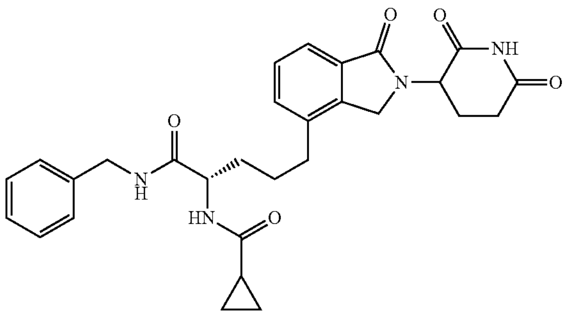 [SMILES: O=C1CCC(N2Cc3c(CCC[C@H](NC(=O)C4CC4)C(=O)NCc4ccccc4)cccc3C2=O)C(=O)N1]

The synthesis method was the same as (2S)-2-acetylamino-5-(2-(2,6-dioxopiperidine-3-)-1-oxoisoindoline-4-)-N-phenylpentanamide, 20.1 mg, yield 60%; $^1H$ NMR (400 MHz, DMSO) δ 11.00 (s, 1H), 8.48 (dd, J=9.2, 5.9 Hz, 1H), 8.26 (d, J=8.2 Hz, 1H), 7.57 (d, J=7.3 Hz, 1H), 7.46 (t, J=7.5 Hz, 1H), 7.40 (d, J=7.2 Hz, 1H), 7.29 (dd, J=10.4, 4.2 Hz, 2H), 7.24-7.18 (m, 3H), 5.75 (s, 2H), 5.14 (ddd, J=8.5, 4.9, 4.1 Hz, 1H), 4.48-4.34 (m, 2H), 4.33-4.20 (m, 3H), 2.99-2.86 (m, 1H), 2.63 (dd, J=19.4, 12.7 Hz, 3H), 2.46-2.29 (m, 1H), 2.06-1.95 (m, 1H), 1.79-1.49 (m, 5H), 0.73-0.57 (m, 4H).

Example 166: (2S)-2-acetylamino-N-benzyl-5-(2-(2,6-dioxopiperidine-3-)-1-oxoisoindoline-4-)pentanamide (166)

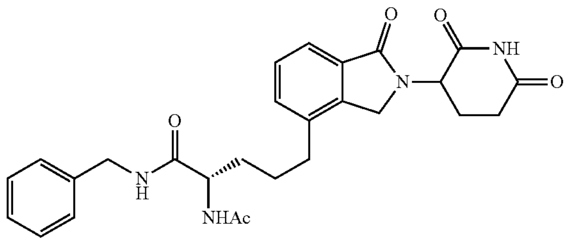 [SMILES: CC(=O)N[C@@H](CCCc1cccc2c1CN(C1CCC(=O)NC1=O)C2=O)C(=O)NCc1ccccc1]

The synthesis method was the same as (2S)-2-acetylamino-5-(2-(2,6-dioxopiperidine-3-)-1-oxoisoindoline-4-)-N-phenylpentanamide, 10.2 mg, yield 18%; $^1$H NMR (400 MHz, DMSO) δ 11.00 (s, 1H), 8.46 (td, J=5.7, 2.6 Hz, 1H), 8.04 (d, J=7.9 Hz, 1H), 7.57 (d, J=7.1 Hz, 1H), 7.49-7.37 (m, 2H), 7.33-7.17 (m, 3H), 5.14 (ddd, J=13.0, 5.7, 1.1 Hz, 1H), 4.43 (dd, J=17.4, 7.0 Hz, 1H), 4.36-4.23 (m, 3H), 2.99-2.87 (m, 1H), 2.69-2.57 (m, 3H), 2.37 (ddd, J=18.1, 10.9, 5.9 Hz, 1H), 2.05-1.94 (m, 1H), 1.85 (s, 3H), 1.63 (ddd, J=35.4, 18.8, 7.9 Hz, 4H).

Example 167: (2S)-N-benzyl-5-(2-(2,6-dioxopiperidine-3-)-1-oxoisoindoline-4-)-2-iso butyramidopentaneamide (167)

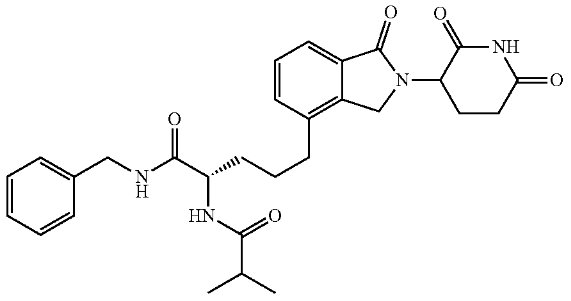 [SMILES: CC(C)C(=O)N[C@@H](CCCc1cccc2c1CN(C1CCC(=O)NC1=O)C2=O)C(=O)NCc1ccccc1]

The synthesis method was the same as (2S)-2-acetylamino-5-(2-(2,6-dioxopiperidine-3-)-1-oxoisoindoline-4-)-N-phenylpentanamide, 12.3 mg, yield 36%; $^1$H NMR (400 MHz, DMSO) δ 11.00 (s, 1H), 8.42 (dd, J=9.5, 5.9 Hz, 1H), 7.89 (d, J=8.2 Hz, 1H), 7.57 (d, J=7.4 Hz, 1H), 7.46 (t, J=7.5 Hz, 1H), 7.40 (d, J=7.0 Hz, 1H), 7.29 (dd, J=10.2, 4.3 Hz, 2H), 7.22 (dd, J=6.9, 3.5 Hz, 3H), 5.14 (ddd, J=13.2, 5.0, 3.1 Hz, 1H), 4.43 (dd, J=17.1, 6.0 Hz, 1H), 4.38-4.31 (m, 1H), 4.31-4.20 (m, 3H), 2.99-2.87 (m, 1H), 2.69-2.56 (m, 3H), 2.49-2.43 (m, 1H), 2.37 (ddd, J=17.8, 11.3, 4.4 Hz, 1H), 2.05-1.95 (m, 1H), 1.72 (dt, J=8.9, 5.6 Hz, 1H), 1.66-1.45 (m, 3H), 0.98 (dd, J=6.8, 3.2 Hz, 6H).

Example 168: (2S)-2-acetylamino-N-tert-butyl-(2-(2,6-dioxopiperidine-3-)-1-oxoisoindoline-4-)pentanamide (168)

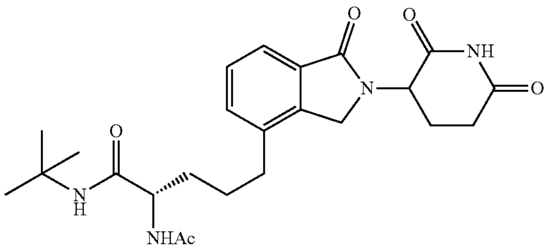 [SMILES: CC(=O)N[C@@H](CCCc1cccc2c1CN(C1CCC(=O)NC1=O)C2=O)C(=O)NC(C)(C)C]

The synthesis method was the same as (2S)-2-acetylamino-5-(2-(2,6-dioxopiperidine-3-)-1-oxoisoindoline-4-)-N-phenylpentanamide, 6.3 mg, yield 13%; $^1$H NMR (400 MHz, DMSO) δ 10.99 (s, 1H), 7.86 (d, J=8.4 Hz, 1H), 7.59-7.51 (m, 2H), 7.45 (dt, J=7.4, 6.9 Hz, 2H), 5.15 (dd, J=13.2, 5.1 Hz, 1H), 4.44 (dd, J=17.1, 7.2 Hz, 1H), 4.28 (dd, J=18.7, 8.9 Hz, 2H), 3.00-2.86 (m, 1H), 2.70-2.56 (m, 3H), 2.40 (ddd, J=28.4, 14.4, 5.0 Hz, 1H), 2.02 (dt, J=12.1, 4.9 Hz, 1H), 1.82 (s, 3H), 1.66-1.43 (m, 4H), 1.23 (d, J=0.8 Hz, 9H).

Example 169: (2S)-2-acetylamino-5-(2-(2,6-dioxopiperidine-3-)-1-oxoisoindoline-4-)-N—((R)-1-phenethyl)pentanoamide (169)

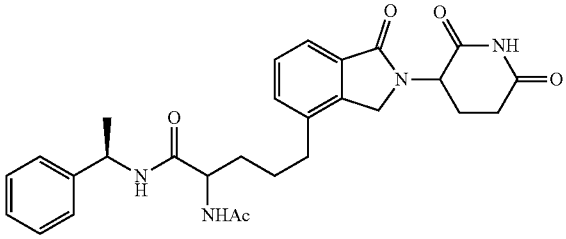 [SMILES: CC(=O)NC(CCCc1cccc2c1CN(C1CCC(=O)NC1=O)C2=O)C(=O)N[C@H](C)c1ccccc1]

The synthesis method was the same as (2S)-2-acetylamino-5-(2-(2,6-dioxopiperidine-3-)-1-oxoisoindoline-4-)-N-phenylpentanamide, 17.3 mg, yield 53%; $^1$H NMR (400 MHz, DMSO) δ 11.01 (s, 1H), 8.37 (dd, J=8.0, 5.0 Hz, 1H), 7.97 (d, J=8.3 Hz, 1H), 7.58 (dd, J=6.9, 1.6 Hz, 1H), 7.50-7.42 (m, 2H), 7.30 (d, J=4.3 Hz, 4H), 7.26-7.18 (m, 1H), 5.15 (dd, J=13.3, 5.1 Hz, 1H), 4.95-4.85 (m, 1H), 4.45 (dd, J=17.2, 6.5 Hz, 1H), 4.36 (dd, J=14.4, 6.6 Hz, 1H), 4.29 (d, J=17.0 Hz, 1H), 2.94 (ddd, J=17.5, 13.8, 5.4 Hz, 1H), 2.74-2.58 (m, 3H), 2.41 (ddd, J=16.8, 13.5, 4.2 Hz, 1H), 2.02 (ddd, J=9.6, 4.7, 2.2 Hz, 1H), 1.81 (s, 3H), 1.75-1.51 (m, 4H), 1.32 (d, J=7.0 Hz, 3H).

Example 170: (2S)-2-amino-5-(2-(2,6-dioxopiperidine-3-)-1-oxoisoindoline-4-)-N-(2-(pyridine-2-)phenyl)pentanamide (170)

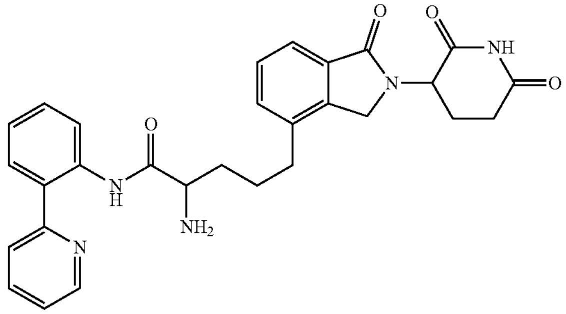 [SMILES: NC(CCCc1cccc2c1CN(C1CCC(=O)NC1=O)C2=O)C(=O)Nc1ccccc1-c1ccccn1]

The synthesis method was the same as (2S)-2-acetylamino-5-(2-(2,6-dioxopiperidine-3-)-1-oxoisoindoline-4-)-N-phenylpentanamide, deprotected with trifluoroacetic acid, directly separated by HPLC, 37 mg, yield 66%; $^1$H NMR (400 MHz, DMSO) δ 10.99 (s, 1H), 8.63 (t, J=6.1 Hz, 1H), 8.29 (dd, J=8.2, 1.3 Hz, 1H), 7.90 (tt, J=7.8, 1.9 Hz, 1H), 7.81 (d, J=7.8 Hz, 1H), 7.73 (dt, J=7.8, 1.6 Hz, 1H), 7.56 (d, J=7.4 Hz, 1H), 7.48-7.40 (m, 2H), 7.39-7.32 (m, 2H), 7.23 (td, J=7.7, 1.1 Hz, 1H), 5.12 (dd, J=13.2, 4.8 Hz, 1H), 4.40 (d, J=17.0 Hz, 1H), 4.25 (d, J=17.1 Hz, 1H), 3.66 (d, J=4.6 Hz, 1H), 2.99-2.84 (m, 1H), 2.69-2.55 (m, 3H), 2.39-2.22 (m, 1H), 1.98 (dd, J=11.4, 6.1 Hz, 1H), 1.87-1.72 (m, 1H), 1.63 (s, 3H).

Example 171: (2S)-2-acetylamino-5-(2-(2,6-dioxopiperidine-3-)-1-oxoisoindoline-4-)-N—((S)-1-phenethyl)pentanamide (171)

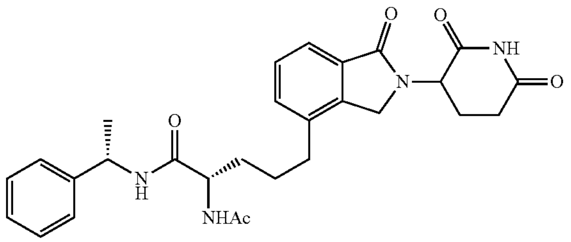 [SMILES: CC(=O)N[C@@H](CCCc1cccc2c1CN(C1CCC(=O)NC1=O)C2=O)C(=O)N[C@@H](C)c1ccccc1]

The synthesis method was the same as (2S)-2-acetylamino-5-(2-(2,6-dioxopiperidine-3-)-1-oxoisoindoline-4-)-N-phenylpentanamide, the preparation method was the same as in Example 127, 16.0 mg, yield 49%; $^1$H NMR (400 MHz, DMSO) δ 11.00 (d, J=2.7 Hz, 1H), 8.46 (d, J=8.0 Hz, 1H), 7.97 (d, J=8.3 Hz, 1H), 7.57 (dd, J=7.5, 1.0 Hz, 1H), 7.44 (td, J=7.5, 1.6 Hz, 1H), 7.33 (d, J=7.5 Hz, 1H), 7.31-7.15 (m, 5H), 5.13 (ddd, J=13.2, 5.0, 2.4 Hz, 1H), 4.96-4.85 (m, 1H), 4.44-4.33 (m, 2H), 4.23 (dd, J=17.1, 9.9 Hz, 1H), 2.99-2.86 (m, 1H), 2.64 (ddd, J=13.5, 7.7, 4.6 Hz, 3H), 2.45-2.31 (m, 1H), 1.99 (ddd, J=6.8, 5.2, 2.2 Hz, 1H), 1.84 (d, J=1.8 Hz, 3H), 1.69-1.41 (m, 4H), 1.34 (dd, J=7.0, 2.7 Hz, 3H).

Example 172: (2S)-2-amino-5-(2-(2,6-dioxopiperidine-3-)-1-oxoisoindoline-4-)-N-(2-(pyridine-3-)phenyl)pentaneamide (172)

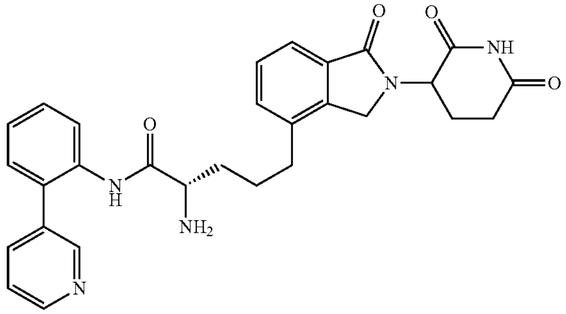 [SMILES: N[C@@H](CCCc1cccc2c1CN(C1CCC(=O)NC1=O)C2=O)C(=O)Nc1ccccc1-c1cccnc1]

The synthesis method was the same as (2S)-2-acetylamino-5-(2-(2,6-dioxopiperidine-3-)-1-oxoisoindoline-4-)-N-phenylpentanamide. After deprotected with trifluoroacetic acid, the product was directly separated by HPLC, 38 mg, yield 68%; $^1$H NMR (400 MHz, DMSO) δ 11.00 (s, 1H), 8.58 (s, 1H), 8.54 (dd, J=4.8, 1.5 Hz, 1H), 8.23 (s, 1H), 7.85 (d, J=7.9 Hz, 1H), 7.80 (d, J=7.8 Hz, 1H), 7.58 (dd, J=7.0, 1.2 Hz, 1H), 7.51-7.38 (m, 4H), 7.34 (dd, J=7.5, 1.4 Hz, 1H), 7.28 (t, J=7.4 Hz, 1H), 5.14 (dd, J=13.2, 5.1 Hz, 1H), 4.45 (d, J=17.1 Hz, 1H), 4.30 (d, J=17.1 Hz, 1H), 3.41 (dd, J=6.8, 5.2 Hz, 1H), 2.99-2.85 (m, 1H), 2.66-2.54 (m, 3H), 2.45-2.31 (m, 1H), 2.05-1.95 (m, 1H), 1.73-1.62 (m, 1H), 1.57 (dt, J=14.8, 7.4 Hz, 2H), 1.51-1.40 (m, 1H).

Example 173: N-((2S)-1-(benzylamine)-5-(2-(2,6-dioxopiperidine-3-)-1-oxoisoindoline-4-)-1-oxopentyl-2-)cyclobutylcarboxamide (173)

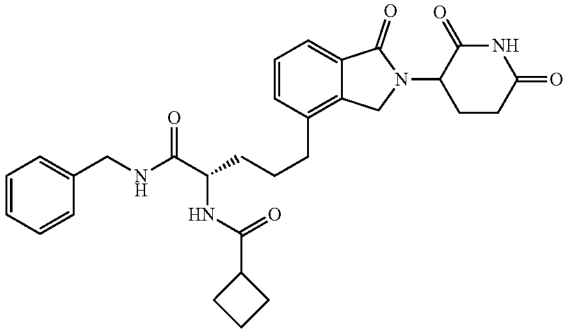 [SMILES: O=C1CCC(N2Cc3c(CCC[C@H](NC(=O)C4CCC4)C(=O)NCc4ccccc4)cccc3C2=O)C(=O)N1]

The synthesis method was the same as (2S)-2-acetylamino-5-(2-(2,6-dioxopiperidine-3-)-1-oxoisoindoline-4-)-N-phenylpentanamide, 12.8 mg, yield 37%; $^1$H NMR (400 MHz, DMSO) δ 10.96 (s, 1H), 8.43 (dd, J=9.3, 5.8 Hz, 1H), 7.79 (d, J=8.2 Hz, 1H), 7.57 (d, J=7.3 Hz, 1H), 7.45 (t, J=7.5 Hz, 1H), 7.39 (d, J=7.3 Hz, 1H), 7.28 (dd, J=10.3, 4.3 Hz, 2H), 7.24-7.17 (m, 3H), 5.75 (s, 2H), 5.18-5.10 (m, 1H), 4.43 (dd, J=17.2, 6.3 Hz, 1H), 4.35 (dd, J=13.7, 7.9 Hz, 1H), 4.30-4.20 (m, 3H), 3.09 (p, J=8.2 Hz, 1H), 3.00-2.85 (m, 1H), 2.71-2.56 (m, 3H), 2.39 (tdd, J=16.9, 8.3, 3.8 Hz, 1H), 2.18-1.93 (m, 5H), 1.87 (dt, J=17.6, 8.7 Hz, 1H), 1.74 (ddd, J=14.4, 9.0, 3.5 Hz, 2H), 1.63-1.49 (m, 3H).

Example 174: (2S)—N-((3R,5R,7R)-adamantane-1-)-2-amino-5-(2-(2,6-dioxopiperidine-3-)-1-oxoisoindoline-4-)pentanamide (174)

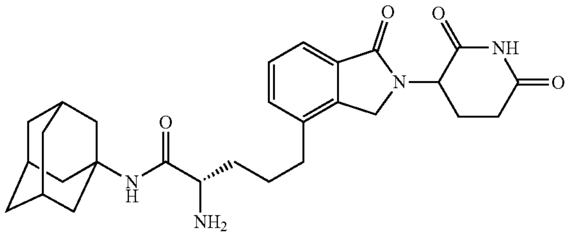 [SMILES: N[C@@H](CCCc1cccc2c1CN(C1CCC(=O)NC1=O)C2=O)C(=O)NC12CC3CC(CC(C3)C1)C2]

The synthesis method was the same as (2S)-2-acetylamino-5-(2-(2,6-dioxopiperidine-3-)-1-oxoisoindoline-4-)-N-phenylpentanamide. After deprotected with trifluoroacetic acid, the product was directly separated by HPLC, 51 mg, yield 94%; $^1$H NMR (400 MHz, DMSO) δ 11.04 (s, 1H), 8.10 (d, J=7.5 Hz, 1H), 7.58 (d, J=7.1 Hz, 1H), 7.50-7.40 (m, 2H), 5.75 (s, 1H), 5.15 (dd, J=13.2, 5.0 Hz, 1H), 4.45 (d, J=17.1 Hz, 1H), 4.29 (dd, J=17.0, 4.2 Hz, 1H), 3.85 (d, J=6.5 Hz, 1H), 3.71-3.64 (m, 1H), 3.00-2.87 (m, 1H), 2.71-2.56 (m, 3H), 2.39 (ddd, J=26.3, 13.2, 4.3 Hz, 1H), 2.06-1.90 (m, 2H), 1.63 (ddd, J=68.6, 36.4, 13.9 Hz, 17H).

Example 175: (2S)-2-acetylamino-N—((S)-2,3-dihydro-1H-indene-1-)-5-(2-(2,6-dioxopiperidine-3-)-1-oxoisoindoline-4-pentanamide (175)

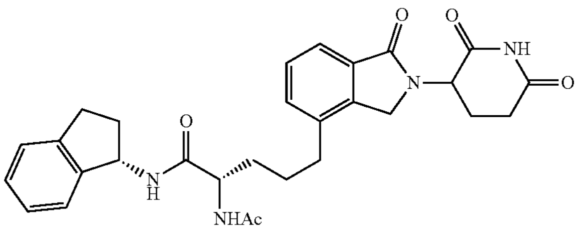 [SMILES: CC(=O)N[C@@H](CCCc1cccc2c1CN(C1CCC(=O)NC1=O)C2=O)C(=O)N[C@H]1CCc2ccccc21]

The synthesis method was the same as (2S)-2-acetylamino-5-(2-(2,6-dioxopiperidine-3-)-1-oxoisoindoline-4-)-N-phenylpentanamide, 16.8 mg, yield 50%; $^1$H NMR (400 MHz, DMSO) δ 10.99 (s, 1H), 8.32 (d, J=8.3 Hz, 1H), 8.01 (dd, J=8.2, 3.7 Hz, 1H), 7.57 (d, J=6.9 Hz, 1H), 7.44 (dt, J=7.4, 6.9 Hz, 2H), 7.26-7.09 (m, 3H), 7.05 (d, J=6.9 Hz, 1H), 5.27 (q, J=8.1 Hz, 1H), 5.13 (ddd, J=13.3, 4.8, 3.8 Hz, 1H), 4.36 (ddd, J=32.6, 31.1, 17.1 Hz, 3H), 2.99-2.85 (m, 2H), 2.84-2.73 (m, 1H), 2.72-2.55 (m, 3H), 2.45-2.29 (m, 2H), 1.98 (dddd, J=15.4, 9.8, 4.8, 2.6 Hz, 1H), 1.84 (s, 3H), 1.82-1.68 (m, 2H), 1.63 (dd, J=18.5, 6.0 Hz, 3H).

Example 176: (2S)—N-((1S,3S,5S,7 S)-adamantane-2-)-2-amino-5-(2-(2,6-dioxopiperidine-3-)-1-oxoisoindoline-4-)pentanamide (176)

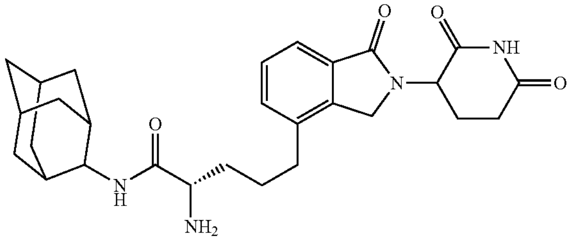 [SMILES: N[C@@H](CCCc1cccc2c1CN(C1CCC(=O)NC1=O)C2=O)C(=O)NC1C2CC3CC(C2)CC1C3]

The synthesis method was the same as (2S)-2-acetylamino-5-(2-(2,6-dioxopiperidine-3-)-1-oxoisoindoline-4-)—N-phenylpentanamide. After deprotected with trifluoroacetic acid, the product was directly separated by HPLC, 47 mg, yield 87%; $^1$H NMR (400 MHz, DMSO) δ 11.01 (s, 1H), 7.72 (s, 1H), 7.59 (d, J=7.1 Hz, 1H), 7.51-7.42 (m, 2H), 5.75 (s, 1H), 5.15 (dd, J=13.3, 4.9 Hz, 1H), 4.45 (d, J=17.1 Hz, 1H), 4.30 (dd, J=17.1, 3.2 Hz, 1H), 3.51 (s, 1H), 3.02-2.87 (m, 1H), 2.70-2.57 (m, 3H), 2.46-2.31 (m, 1H), 2.01 (s, 4H), 1.89 (s, 6H), 1.73-1.48 (m, 10H).

Example 177: (2S)-2-acetylamino-N—((R)-2,3-dihydro-1H-indene-1-)-5-(2-(2,6-dioxopiperidine-3-)-1-oxoisoindoline-4-)pentanamide (177)

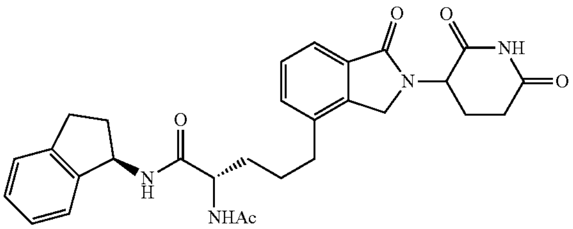 [SMILES: CC(=O)N[C@@H](CCCc1cccc2c1CN(C1CCC(=O)NC1=O)C2=O)C(=O)N[C@@H]1CCc2ccccc21]

The synthesis method was the same as (2S)-2-acetylamino-5-(2-(2,6-dioxopiperidine-3-)-1-oxoisoindoline-4-)-N-phenylpentaneamide, 24.3 mg, yield 72%; $^1$H NMR (400 MHz, DMSO) δ 11.01 (s, 1H), 8.33 (d, J=8.0 Hz, 1H), 8.01 (d, J=7.8 Hz, 1H), 7.58 (d, J=6.6 Hz, 1H), 7.51-7.41 (m, 2H), 7.29-7.12 (m, 4H), 5.33-5.21 (m, 1H), 5.15 (dd, J=13.0, 4.4 Hz, 1H), 4.45 (dd, J=17.4, 6.7 Hz, 1H), 4.30 (t, J=11.8 Hz, 2H), 2.92 (ddd, J=13.1, 10.9, 3.5 Hz, 2H), 2.83-2.73 (m, 1H), 2.72-2.57 (m, 3H), 2.46-2.29 (m, 2H), 2.02 (dd, J=8.8, 4.7 Hz, 1H), 1.85 (s, 3H), 1.79-1.68 (m, 2H), 1.68-1.51 (m, 3H).

Example 178: (2S)-2-acetylamino-N-(2,4-difluorobenzyl)-5-(2-(2,6-dioxopiperidine-3-)-1-oxoisoindoline-4-)oxoisoindoline (178)

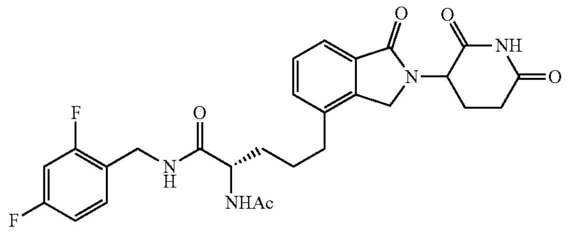 [SMILES: CC(=O)N[C@@H](CCCc1cccc2c1CN(C1CCC(=O)NC1=O)C2=O)C(=O)NCc1ccc(F)cc1F]

The synthesis method was the same as (2S)-2-acetylamino-5-(2-(2,6-dioxopiperidine-3-)-1-oxoisoindoline-4-)-N-phenylpentanamide, 37 mg, yield 65%; $^1H$ NMR (400 MHz, DMSO) δ 11.01 (s, 1H), 8.48 (td, J=5.7, 1.8 Hz, 1H), 8.06 (dd, J=7.9, 1.4 Hz, 1H), 7.57 (d, J=7.2 Hz, 1H), 7.45 (t, J=7.5 Hz, 1H), 7.39 (d, J=7.2 Hz, 1H), 7.32 (td, J=8.6, 6.8 Hz, 1H), 7.23-7.15 (m, 1H), 7.02 (td, J=8.6, 2.5 Hz, 1H), 5.14 (dd, J=13.4, 5.2 Hz, 1H), 4.43 (dd, J=17.0, 4.8 Hz, 1H), 4.34-4.23 (m, 4H), 2.99-2.87 (m, 1H), 2.68-2.55 (m, 3H), 2.40 (ddd, J=16.7, 13.2, 5.1 Hz, 1H), 2.06-1.96 (m, 1H), 1.84 (s, 3H), 1.73-1.64 (m, 1H), 1.62-1.48 (m, 3H).

Example 179: (2S)-2-acetylamino-5-(2-(2,6-dioxopiperidine-3-)-1-oxoisoindoline-4-)-N—((S)-1,2,3,4-tetrahydronaphthyl-1-)pentanamide (179)

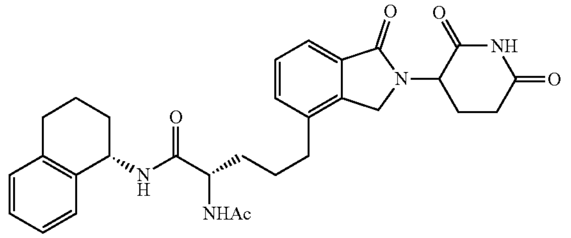 [SMILES: CC(=O)N[C@@H](CCCc1cccc2c1CN(C1CCC(=O)NC1=O)C2=O)C(=O)N[C@H]1CCCc2ccccc21]

The synthesis method was the same as (2S)-2-acetylamino-5-(2-(2,6-dioxopiperidine-3-)-1-oxoisoindoline-4-)-N-phenylpentanamide, 22.4 mg, yield 67%; $^1H$ NMR (400 MHz, DMSO) δ 10.99 (s, 1H), 8.26 (dd, J=8.6, 1.2 Hz, 1H), 7.97 (dd, J=8.1, 2.6 Hz, 1H), 7.57 (d, J=6.2 Hz, 1H), 7.44 (dt, J=7.5, 6.9 Hz, 2H), 7.17-7.10 (m, 1H), 7.06 (dt, J=12.5, 5.3 Hz, 3H), 5.13 (ddd, J=13.2, 4.9, 3.3 Hz, 1H), 4.95 (t, J=7.5 Hz, 1H), 4.36 (ddd, J=37.5, 31.1, 17.1 Hz, 3H), 2.92 (tdd, J=17.3, 5.1, 1.6 Hz, 1H), 2.80-2.55 (m, 5H), 2.46-2.30 (m, 1H), 2.04-1.94 (m, 1H), 1.91-1.80 (m, 5H), 1.77-1.55 (m, 6H).

Example 180: (2S)-2-acetylamino-N-(2,4-dimethoxybenzyl)-5-(2-(2,6-dipiperidine-3-)-1-oxoisoindoline-4-)pentanamide (180)

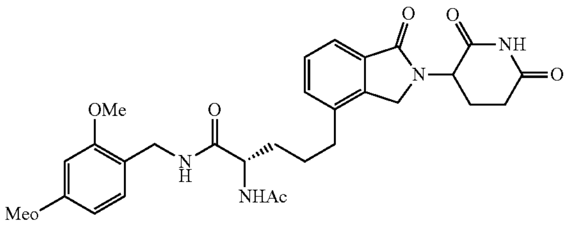

The synthesis method was the same as (2S)-2-acetylamino-5-(2-(2,6-dioxopiperidine-3-)-1-oxoisoindoline-4-)-N-phenylpentanamide, 39.3 mg, yield 65%; $^1H$ NMR (400 MHz, DMSO) δ 11.03 (s, 1H), 8.20 (td, J=5.9, 1.9 Hz, 1H), 8.04 (dd, J=8.2, 2.0 Hz, 1H), 7.58 (d, J=7.3 Hz, 1H), 7.46 (t, J=7.4 Hz, 1H), 7.41 (d, J=7.5 Hz, 1H), 7.03 (d, J=8.4 Hz, 1H), 6.52 (d, J=2.4 Hz, 1H), 6.42 (dd, J=8.3, 2.4 Hz, 1H), 5.15 (dd, J=12.9, 4.9 Hz, 1H), 4.44 (dd, J=17.0, 6.9 Hz, 1H), 4.38-4.32 (m, 1H), 4.28 (dd, J=17.1, 3.9 Hz, 1H), 4.17 (dd, J=15.2, 5.8 Hz, 1H), 4.10 (ddd, J=15.4, 5.7, 1.6 Hz, 1H), 3.74 (s, 3H), 3.73 (s, 3H), 3.01-2.87 (m, 1H), 2.72-2.56 (m, 3H), 2.47-2.31 (m, 1H), 2.06-1.94 (m, 1H), 1.84 (s, 3H), 1.75-1.47 (m, 4H).

Example 181: (2S)-2-acetylamino-N-benzhydryl-5-(2-(2,6-dioxopiperidine-3-)-1-oxoisoindoline-4-) pentanamide (181)

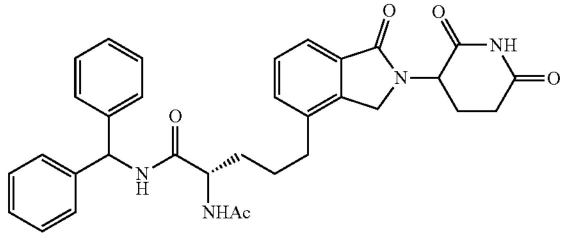 [SMILES: CC(=O)N[C@@H](CCCc1cccc2c1CN(C1CCC(=O)NC1=O)C2=O)C(=O)NC(c1ccccc1)c1ccccc1]

The synthesis method was the same as (2S)-2-acetylamino-5-(2-(2,6-dioxopiperidine-3-)-1-oxoisoindoline-4-)-N-phenylpentanamide, 21.5 mg, yield 58%; $^1H$ NMR (400 MHz, DMSO) δ 11.00 (d, J=3.3 Hz, 1H), 8.92 (dd, J=8.5, 5.9 Hz, 1H), 8.03 (d, J=8.2 Hz, 1H), 7.57 (d, J=7.5 Hz, 1H), 7.44 (t, J=7.5 Hz, 1H), 7.38-7.18 (m, 10H), 6.10 (d, J=8.7 Hz, 1H), 5.13 (dd, J=12.9, 5.2 Hz, 1H), 4.49 (dt, J=7.8, 5.2 Hz, 1H), 4.39 (dd, J=17.1, 2.3 Hz, 1H), 4.24 (dd, J=17.1, 7.2 Hz, 1H), 3.00-2.86 (m, 1H), 2.69-2.56 (m, 3H), 2.45-2.29 (m, 1H), 2.07-1.94 (m, 1H), 1.83 (d, J=1.5 Hz, 3H), 1.74-1.44 (m, 4H).

Example 182: (2S)-2-acetylamino-N-(3-bromobenzyl)-5-(2-(2,6-dioxopiperidine-3-)-1-oxoisoindoline-4-)pentanamide (182)

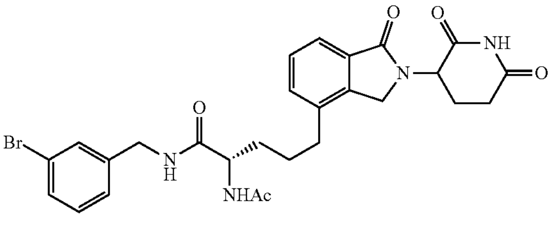 [SMILES: CC(=O)N[C@@H](CCCc1cccc2c1CN(C1CCC(=O)NC1=O)C2=O)C(=O)NCc1cccc(Br)c1]

The synthesis method was the same as (2S)-2-acetylamino-5-(2-(2,6-dioxopiperidine-3-)-1-oxoisoindoline-4-)-N-phenylpentanamide, 38.8 mg, yield 63%; $^1$H NMR (400 MHz, DMSO) δ 11.03 (s, 1H), 8.54 (td, J=6.1, 2.3 Hz, 1H), 8.10 (dd, J=8.0, 1.0 Hz, 1H), 7.57 (d, J=7.2 Hz, 1H), 7.49-7.38 (m, 4H), 7.29-7.19 (m, 2H), 5.14 (ddd, J=13.3, 4.9, 1.2 Hz, 1H), 4.43 (dd, J=17.2, 7.6 Hz, 1H), 4.30 (ddd, J=17.4, 11.1, 4.4 Hz, 4H), 3.00-2.87 (m, 1H), 2.72-2.56 (m, 3H), 2.47-2.31 (m, 1H), 2.05-1.95 (m, 1H), 1.85 (s, 3H), 1.71 (dt, J=11.5, 7.0 Hz, 1H), 1.64-1.51 (m, 3H).

Example 183: (2S)—N-(3-chloro-4-methylphenyl)-5-(2-(2,6-dioxopiperidine-3-)-1-oxoisoindoline-4-)-2-isobutyrylaminopentanamide (183)

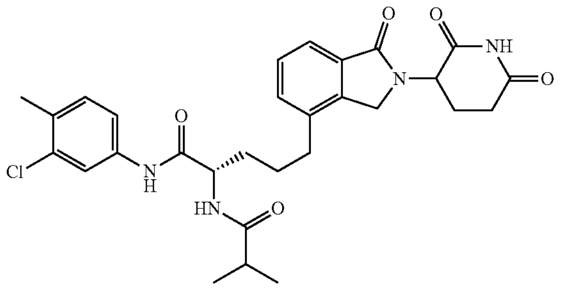 [SMILES: Cc1ccc(NC(=O)[C@H](CCCc2cccc3c2CN(C2CCC(=O)NC2=O)C3=O)NC(=O)C(C)C)cc1Cl]

The synthesis method was the same as (2S)-2-acetylamino-5-(2-(2,6-dioxopiperidine-3-)-1-oxoisoindoline-4-)-N-phenylpentanamide, 26.5 mg, yield 44%; $^1$H NMR (400 MHz, DMSO) δ 11.00 (d, J=4.2 Hz, 1H), 10.17 (d, J=2.4 Hz, 1H), 8.03 (d, J=7.7 Hz, 1H), 7.83-7.77 (m, 1H), 7.57 (dd, J=6.6, 1.8 Hz, 1H), 7.50-7.40 (m, 2H), 7.36 (dd, J=8.3, 2.1 Hz, 1H), 7.26 (d, J=8.4 Hz, 1H), 5.13 (dd, J=13.7, 5.7 Hz, 1H), 4.42 (dd, J=17.0, 11.7 Hz, 2H), 4.28 (dd, J=17.1, 5.4 Hz, 1H), 2.99-2.87 (m, 1H), 2.68 (t, J=7.1 Hz, 2H), 2.65-2.55 (m, 2H), 2.34 (ddd, J=15.4, 13.2, 5.0 Hz, 1H), 2.26 (s, 3H), 2.05-1.94 (m, 1H), 1.82-1.53 (m, 4H), 1.05-0.93 (m, 6H).

Example 184: (2S)-2-acetylamino-N-(3-chlorobenzyl)-5-(2-(2,6-dioxopiperidine-3-)-1-oxoisoindoline-4-)pentanamide (184)

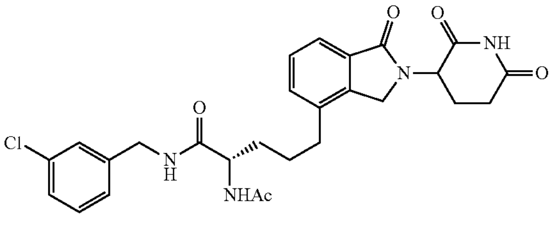 [SMILES: CC(=O)N[C@@H](CCCc1cccc2c1CN(C1CCC(=O)NC1=O)C2=O)C(=O)NCc1cccc(Cl)c1]

The synthesis method was the same as (2S)-2-acetylamino-5-(2-(2,6-dioxopiperidine-3-)-1-oxoisoindoline-4-)-N-phenylpentanamide, 34 mg, yield 60%; $^1$H NMR (400 MHz, DMSO) δ 11.03 (s, 1H), 8.54 (td, J=5.9, 2.4 Hz, 1H), 8.10 (dd, J=7.9, 8.1 Hz, 1H), 7.57 (d, J=7.2 Hz, 1H), 7.45 (t, J=7.4 Hz, 1H), 7.40 (d, J=7.2 Hz, 1H), 7.35 (td, J=8.6, 6.8 Hz, 1H), 7.18-7.15 (m, 1H), 5.14 (td, J=13.5, 1.0 Hz, 1H), 4.43 (dd, J=17.2, 7.3 Hz, 1H), 4.35 (dd, J=17.0, 4.8 Hz, 1H), 3.00-2.86 (m, 1H), 2.72-2.56 (m, 1H), 2.47-2.31 (m, 3H), 2.00 (ddd, J=10.4, 13.2, 5.7 Hz, 1H), 1.85-1.96 (m, 1H), 1.84 (s, 3H), 1.77-1.65 (m, 1H), 1.65-1.49 (m, 3H).

Example 185: N-((2S)-1-((3-chloro-4-methylphenyl)amino)-5-(2-(2,6-dioxopiperidine-3-)-1-oxoisoindoline-4-)-1-oxopentyl-2-)cyclopropylformamide (185)

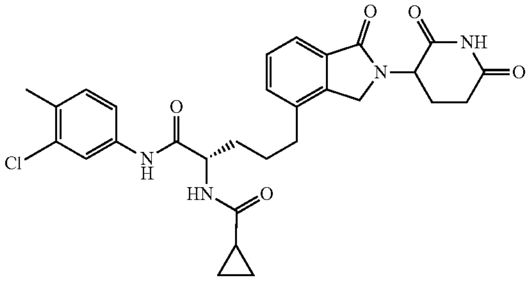 [SMILES: Cc1ccc(NC(=O)[C@H](CCCc2cccc3c2CN(C2CCC(=O)NC2=O)C3=O)NC(=O)C2CC2)cc1Cl]

The synthesis method was the same as (2S)-2-acetylamino-5-(2-(2,6-dioxopiperidine-3-)-1-oxoisoindoline-4-)-N-phenylpentanamide, 21.9 mg, yield 36%; $^1$H NMR (400 MHz, DMSO) δ 11.00 (d, J=3.7 Hz, 1H), 10.22 (d, J=4.1 Hz, 1H), 8.43 (d, J=7.9 Hz, 1H), 7.82 (dd, J=3.5, 2.2 Hz, 1H), 7.58 (dd, J=5.9, 2.6 Hz, 1H), 7.49-7.42 (m, 2H), 7.36 (dd, J=8.3, 2.0 Hz, 1H), 7.27 (d, J=8.3 Hz, 1H), 5.13 (dd, J=14.0, 4.9 Hz, 1H), 4.50-4.37 (m, 2H), 4.28 (dd, J=17.1, 7.1 Hz, 1H), 3.00-2.87 (m, 1H), 2.69 (t, J=7.1 Hz, 2H), 2.65-2.56 (m, 1H), 2.44-2.29 (m, 1H), 2.27 (s, 3H), 2.00 (tdd, J=9.9, 6.2, 3.9 Hz, 1H), 1.83-1.55 (m, 5H), 0.65 (dd, J=6.1, 2.6 Hz, 4H).

Example 186: (2S)-2-acetylamino-5-(2-(2,6-dioxopiperidine-3-)-1-oxoisoindoline-4-)-N-(4-(pyrrolidine-1-)benzyl)pentanamide (186)

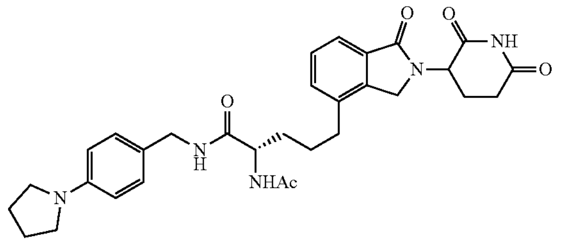 [SMILES: CC(=O)N[C@@H](CCCc1cccc2c1CN(C1CCC(=O)NC1=O)C2=O)C(=O)NCc1ccc(N2CCCC2)cc1]

The synthesis method was the same as (2S)-2-acetylamino-5-(2-(2,6-dioxopiperidine-3-)-1-oxoisoindoline-4-)-N-phenylpentanamide, 32 mg, yield 52%; $^1$H NMR (400 MHz, DMSO) δ 11.02 (s, 1H), 8.31 (td, J=5.8, 1.6 Hz, 1H), 8.01 (dd, J=8.3, 2.0 Hz, 1H), 7.56 (d, J=7.3 Hz, 1H), 7.44 (t, J=7.5 Hz, 1H), 7.38 (d, J=7.3 Hz, 1H), 7.01 (d, J=8.3 Hz, 2H), 6.43 (dd, J=8.7, 2.4 Hz, 2H), 5.14 (dd, J=13.5, 5.2 Hz, 1H), 4.42 (dd, J=17.1, 10.4 Hz, 1H), 4.29 (ddd, J=22.5, 11.9, 4.6 Hz, 2H), 4.20-4.04 (m, 2H), 3.16 (td, J=6.4, 2.2 Hz, 4H), 2.99-2.87 (m, 1H), 2.60 (dt, J=5.9, 4.6 Hz, 3H), 2.46-2.31 (m, 1H), 2.04-1.96 (m, 1H), 1.96-1.90 (m, 4H), 1.83 (s, 3H), 1.73-1.64 (m, 1H), 1.61-1.49 (m, 3H).

Example 187: N-((2S)-1-((3-chloro-4-methylphenyl)amino)-5-(2-(2,6-dioxopiperidine-3-)-1-oxoisoindoline-4-)-1-oxopentyl-2-)cyclobutylcarboxamide (187)

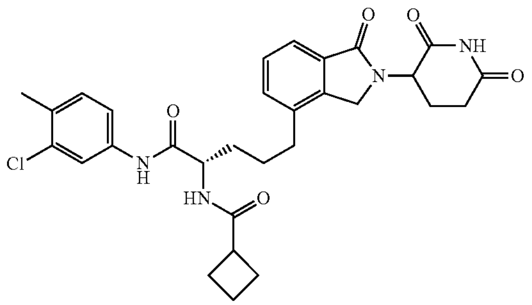 [SMILES: Cc1ccc(NC(=O)[C@H](CCCc2cccc3c2CN(C2CCC(=O)NC2=O)C3=O)NC(=O)C2CCC2)cc1Cl]

The synthesis method was the same as (2S)-2-acetylamino-5-(2-(2,6-dioxopiperidine-3-)-1-oxoisoindoline-4-)-N-phenylpentanamide, 24.2 mg, yield 39%; $^1$H NMR (400 MHz, DMSO) δ 11.00 (d, J=3.7 Hz, 1H), 10.18 (d, J=3.3 Hz, 1H), 7.95 (d, J=7.9 Hz, 1H), 7.80 (dd, J=3.2, 2.3 Hz, 1H), 7.57 (dd, J=6.6, 1.7 Hz, 1H), 7.49-7.40 (m, 2H), 7.36 (dd, J=8.3, 2.1 Hz, 1H), 7.26 (d, J=8.3 Hz, 1H), 5.12 (ddd, J=13.3, 5.0, 1.5 Hz, 1H), 4.47-4.35 (m, 2H), 4.27 (dd, J=17.1, 5.2 Hz, 1H), 3.11 (p, J=8.3 Hz, 1H), 3.01-2.87 (m, 1H), 2.67 (t, J=7.2 Hz, 2H), 2.64-2.56 (m, 1H), 2.42-2.29 (m, 1H), 2.26 (s, 3H), 2.17-2.05 (m, 2H), 2.04-1.95 (m, 3H), 1.87 (dt, J=17.7, 8.7 Hz, 1H), 1.79-1.71 (m, 2H), 1.70-1.53 (m, 3H).

Example 188: (2S)-2-acetylamino-5-(2-(2,6-dioxopiperidine-3-)-1-oxoisoindoline-4-)-N-(2-phenylpropyl-2-)pentanamide (188)

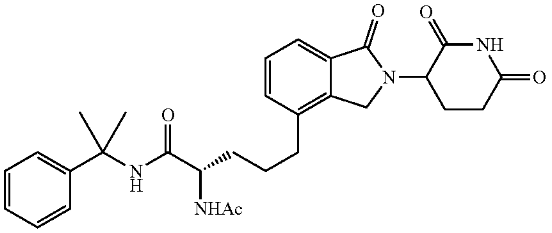 [SMILES: CC(=O)N[C@@H](CCCc1cccc2c1CN(C1CCC(=O)NC1=O)C2=O)C(=O)NC(C)(C)c1ccccc1]

The synthesis method was the same as (2S)-2-acetylamino-5-(2-(2,6-dioxopiperidine-3-)-1-oxoisoindoline-4-)-N-phenylpentanamide, 36.5 mg, yield 65%; $^1$H NMR (400 MHz, DMSO) δ 11.02 (s, 1H), 8.16 (d, J=3.4 Hz, 1H), 7.89 (d, J=8.1 Hz, 1H), 7.60-7.56 (m, 1H), 7.47 (ddd, J=13.4, 9.8, 4.2 Hz, 2H), 7.29 (dd, J=5.7, 4.2 Hz, 2H), 7.23 (td, J=7.6, 1.8 Hz, 2H), 7.18-7.11 (m, 1H), 5.15 (ddd, J=13.1, 5.1, 1.3 Hz, 1H), 4.49-4.36 (m, 2H), 4.28 (dd, J=17.3, 6.2 Hz, 1H), 3.00-2.88 (m, 1H), 2.71-2.57 (m, 3H), 2.45-2.31 (m, 1H), 2.06-1.96 (m, 1H), 1.83 (s, 3H), 1.72-1.45 (m, 10H).

Example 189: 6-amino-N-((2S)-1-((3-chloro-4-methylphenyl)amino)-5-(2-(2,6-dioxopiperidine-3-)-1-oxoisoindoline-4-)-1-oxopentyl-2-)hexanamide (189)

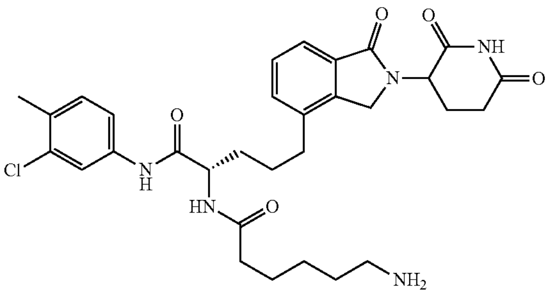 [SMILES: Cc1ccc(NC(=O)[C@H](CCCc2cccc3c2CN(C2CCC(=O)NC2=O)C3=O)NC(=O)CCCCCN)cc1Cl]

The synthesis method was the same as (2S)-2-acetylamino-5-(2-(2,6-dioxopiperidine-3-)-1-oxoisoindoline-4-)-N-phenylpentanamide, 23.9 mg, yield 37%; $^1$H NMR (400 MHz, DMSO) δ 11.00 (d, J=3.2 Hz, 1H), 10.29 (s, 1H), 8.20 (d, J=6.9 Hz, 1H), 7.83 (dd, J=8.8, 6.4 Hz, 4H), 7.57 (dd, J=6.6, 1.9 Hz, 1H), 7.42 (ddd, J=11.3, 10.3, 4.7 Hz, 3H), 7.26 (d, J=8.4 Hz, 1H), 5.13 (dd, J=13.3, 5.0 Hz, 1H), 4.43 (dd, J=17.1, 11.9 Hz, 2H), 4.28 (dd, J=17.1, 4.6 Hz, 1H), 2.93 (ddd, J=17.6, 11.8, 4.9 Hz, 1H), 2.70 (dt, J=19.6, 6.6 Hz, 4H), 2.60 (d, J=17.0 Hz, 1H), 2.43-2.30 (m, 1H), 2.26 (s, 3H), 2.15 (t, J=7.4 Hz, 2H), 1.99 (dd, J=10.8, 5.2 Hz, 1H), 1.84-1.57 (m, 4H), 1.51 (tt, J=15.6, 7.7 Hz, 4H), 1.26 (dt, J=13.7, 6.9 Hz, 2H).

Example 190: (2S)-2-acetylamino-N-(4-(2-(dimethylamino)ethoxy)benzyl)-5-(2-(2,6-dioxopiperidine)-3-)-1-oxoisoindoline-4-)pentanamide (190)

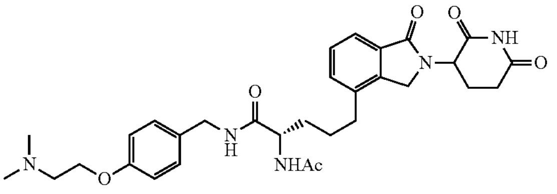 [SMILES: CC(=O)N[C@@H](CCCc1cccc2c1CN(C1CCC(=O)NC1=O)C2=O)C(=O)NCc1ccc(OCCN(C)C)cc1]

The synthesis method was the same as (2S)-2-acetylamino-5-(2-(2,6-dioxopiperidine-3-)-1-oxoisoindoline-4-)-N-phenylpentanamide, 35.4 mg, yield 56%; $^{1}$H NMR (400 MHz, DMSO) δ 11.03 (s, 1H), 8.42 (t, J=5.2 Hz, 1H), 8.16 (s, 1H), 8.04 (d, J=8.4 Hz, 1H), 7.57 (d, J=7.3 Hz, 1H), 7.45 (t, J=7.5 Hz, 1H), 7.39 (d, J=7.3 Hz, 1H), 7.13 (d, J=8.4 Hz, 2H), 6.85 (d, J=8.3 Hz, 2H), 5.14 (dd, J=13.6, 4.8 Hz, 1H), 4.43 (dd, J=16.8, 7.5 Hz, 1H), 4.34-4.23 (m, 2H), 4.22-4.14 (m, 2H), 4.04 (t, J=5.5 Hz, 2H), 3.00-2.87 (m, 1H), 2.76 (t, J=5.4 Hz, 2H), 2.61 (dd, J=25.9, 7.7 Hz, 3H), 2.43-2.36 (m, 1H), 2.32 (s, 6H), 2.05-1.95 (m, 1H), 1.84 (s, 3H), 1.73-1.64 (m, 1H), 1.63-1.49 (m, 3H).

Example 191: N-((2S)-1-((3-chloro-4-methylphenyl) amino)-5-(2-(2,6-dioxopiperidine-3-) -1-oxoisoindoline-4-)-1-oxopentyl-2-)piperidine-4-carboxamide (191)

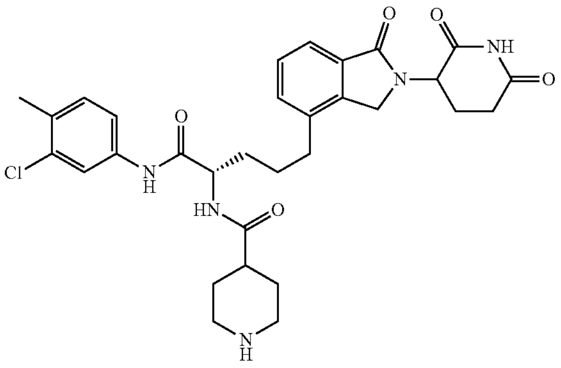 [SMILES: Cc1ccc(NC(=O)[C@H](CCCc2cccc3c2CN(C2CCC(=O)NC2=O)C3=O)NC(=O)C2CCNCC2)cc1Cl]

The synthesis method was the same as (2S)-2-acetylamino-5-(2-(2,6-dioxopiperidine-3-)-1-oxoisoindoline-4-)-N-phenylpentanamide, 33.8 mg, yield 52%; $^{1}$H NMR (400 MHz, DMSO) δ 11.00 (d, J=4.8 Hz, 1H), 10.31 (s, 1H), 8.97 (d, J=9.3 Hz, 1H), 8.67-8.49 (m, 1H), 8.31 (d, J=7.8 Hz, 1H), 7.82 (t, J=2.3 Hz, 1H), 7.57 (dd, J=6.6, 1.8 Hz, 1H), 7.48-7.41 (m, 2H), 7.38 (dd, J=8.3, 2.0 Hz, 1H), 7.26 (d, J=8.4 Hz, 1H), 5.13 (dd, J=13.2, 4.9 Hz, 1H), 4.49-4.38 (m, 2H), 4.28 (dt, J=5.9, 3.5 Hz, 1H), 3.30-3.17 (m, 2H), 3.01-2.76 (m, 3H), 2.68 (t, J=6.9 Hz, 2H), 2.65-2.52 (m, 2H), 2.37 (ddd, J=26.3, 13.1, 4.2 Hz, 1H), 2.26 (s, 3H), 2.00 (td, J=10.3, 5.1 Hz, 1H), 1.91-1.53 (m, 8H).

Example 192: (2S)-2-acetylamino-5-(2-(2,6-dioxopiperidine-3-)-1-oxoisoindoline-4-)-N-(4-phenoxybenzyl)pentanamide (192)

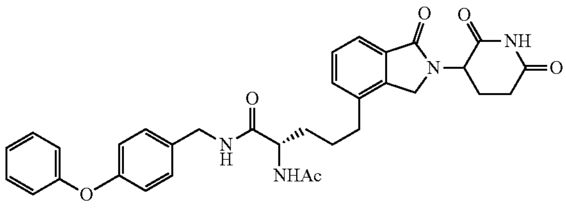 [SMILES: CC(=O)N[C@@H](CCCc1cccc2c1CN(C1CCC(=O)NC1=O)C2=O)C(=O)NCc1ccc(Oc2ccccc2)cc1]

The synthesis method was the same as (2S)-2-acetylamino-5-(2-(2,6-dioxopiperidine-3-)-1-oxoisoindoline-4-)-N-phenylpentanamide, 39 mg, yield 61%; $^{1}$H NMR (400 MHz, DMSO) δ 11.02 (s, 1H), 8.49 (td, J=5.9, 2.1 Hz, 1H), 8.06 (dd, J=8.0, 1.2 Hz, 1H), 7.56 (dd, J=7.0, 1.5 Hz, 1H), 7.45-7.34 (m, 4H), 7.24 (d, J=8.6 Hz, 2H), 7.13 (td, J=7.4, 0.5 Hz, 1H), 6.99-6.91 (m, 4H), 5.14 (dd, J=13.2, 5.0 Hz, 1H), 4.43 (dd, J=17.2, 7.4 Hz, 1H), 4.32 (ddd, J=13.6, 8.5, 3.6 Hz, 2H), 4.25 (d, J=6.1 Hz, 2H), 2.99-2.86 (m, 1H), 2.71-2.55 (m, 3H), 2.40 (ddd, J=17.5, 13.8, 5.6 Hz, 1H), 2.00 (ddd, J=8.4, 5.8, 3.2 Hz, 1H), 1.84 (s, 3H), 1.75-1.66 (m, 1H), 1.65-1.47 (m, 3H).

Example 193: N-((2S)-1-(3-chloro-4-methylaniline)-5-(2-(2,6-dioxopiperidine-3-)-1-oxoisoindoline-4-)-1-oxopentyl-2-)-6-hydroxyhexanamide (193)

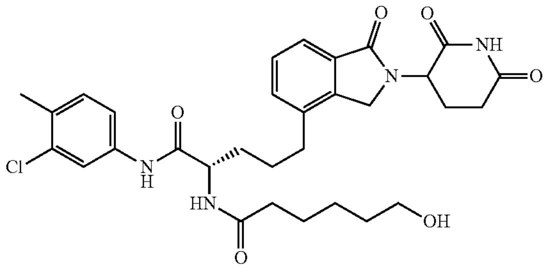 [SMILES: Cc1ccc(NC(=O)[C@H](CCCc2cccc3c2CN(C2CCC(=O)NC2=O)C3=O)NC(=O)CCCCCO)cc1Cl]

The synthesis method was the same as (2S)-2-acetylamino-5-(2-(2,6-dioxopiperidine-3-)-1-oxoisoindoline-4-)-N-phenylpentanamide, white solid, 48 mg, yield 69%; $^{1}$H NMR (400 MHz, DMSO) δ 10.98 (s, 1H), 10.16 (d, J=3.4 Hz, 1H), 8.11 (d, J=7.8 Hz, 1H), 7.83-7.76 (m, 1H), 7.57 (dd, J=6.4, 2.0 Hz, 1H), 7.49-7.41 (m, 2H), 7.36 (dd, J=8.3, 2.0 Hz, 1H), 7.26 (d, J=8.3 Hz, 1H), 5.12 (dd, J=13.3, 3.5 Hz, 1H), 4.47-4.37 (m, 2H), 4.29 (dt, J=17.1, 5.6 Hz, 2H), 3.37-3.33 (m, 2H), 2.93 (t, J=13.9 Hz, 1H), 2.68 (t, J=7.0 Hz, 2H), 2.59 (d, J=17.3 Hz, 1H), 2.43-2.29 (m, 1H), 2.26 (s, 3H), 2.13 (t, J=7.2 Hz, 2H), 1.99 (dd, J=12.0, 5.2 Hz, 1H), 1.78-1.56 (m, 4H), 1.48 (dt, J=15.1, 7.5 Hz, 2H), 1.43-1.34 (m, 2H), 1.30-1.19 (m, 2H).

Example 194: (2S)-2-acetylamino-5-(2-(2,6-dioxopiperidine-3-)-1-oxoisoindoline-4-)-N-(2-(pyridine-2-)phenyl)pentanamide (194)

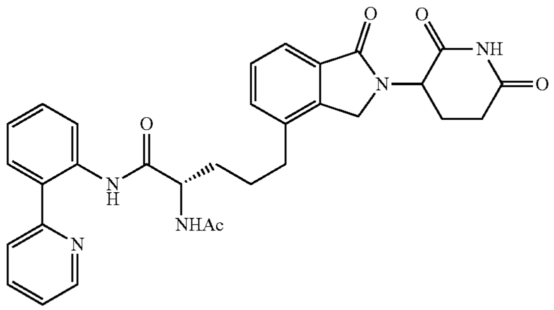 [SMILES: CC(=O)N[C@@H](CCCc1cccc2c1CN(C1CCC(=O)NC1=O)C2=O)C(=O)Nc1ccccc1-c1ccccn1]

The synthesis method was the same as (2S)-2-acetylamino-5-(2-(2,6-dioxopiperidine-3-)-1-oxoisoindoline-4-)-N-phenylpentanamide, 19.5 mg, yield 67%; $^1$H NMR (400 MHz, DMSO) δ 12.17 (s, 1H), 11.01 (s, 1H), 8.72-8.68 (m, 1H), 8.43 (dd, J=7.2, 1.9 Hz, 1H), 8.37 (dd, J=8.2, 0.6 Hz, 1H), 7.99-7.93 (m, 1H), 7.89 (d, J=8.3 Hz, 1H), 7.78 (dd, J=8.0, 1.3 Hz, 1H), 7.56 (dd, J=7.2, 1.2 Hz, 1H), 7.42 (ddd, J=12.4, 9.6, 4.5 Hz, 3H), 7.21 (td, J=7.9, 1.3 Hz, 1H), 5.13 (dd, J=13.3, 5.2 Hz, 1H), 4.43 (d, J=17.2 Hz, 1H), 4.33-4.22 (m, 2H), 3.00-2.86 (m, 1H), 2.71-2.56 (m, 3H), 2.44-2.27 (m, 1H), 1.99 (dtd, J=12.5, 5.1, 2.4 Hz, 1H), 1.95-1.76 (m, 4H), 1.75-1.55 (m, 3H).

Example 195: 3-(4-((S)-4-amino-4-(7-bromo-1H-benzo[d]imidazole-2-)butyl)-1-oxoisoindoline-2-)piperidine-2,6-dione (195)

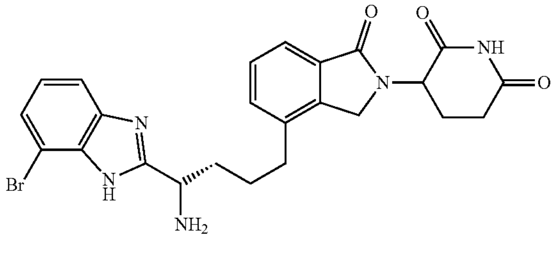

3-bromo-o-phenylenediamine (75 mg, 0.4 mmol), (2R)-2-tert-butoxycarbonylamino-5-(2-(2,6-dioxopiperidine-3-)-1-oxoisoindoline-4-)pentanoic acid (92 mg, 0.2 mmol), and HOBt (54 mg, 0.4 mmol) were dissolved in 10 mL of dichloromethane, and triethylamine (84 μL, 0.6 mmol) and HATU (152 mg, 0.4 mmol) were added with stirring at room temperature. The resulting solution was reacted with stirring at room temperature for 4 h. LC-MS monitored that the condensation reaction was completed. The solvent was removed under reduced pressure, 5 mL of acetic acid was added to the resulting residue, the reaction solution was warmed to 110° C. to reflux for 2 h. -LC-MS monitored that the reaction was completed. The solvent was removed under reduced pressure, and the residue was separated by HPLC to obtain 84 mg of target product 3-(4-((S)-4-amino-4-(7-bromo-1H-benzo[d]imidazole-2-)butyl)-1-oxoisoindoline-2-)piperidine-2,6-dione, as a white solid, yield 82%; $^1$H NMR (400 MHz, DMSO) δ 7.56 (dd, J=8.2, 3.0 Hz, 2H), 7.43 (q, J=7.6 Hz, 3H), 7.14 (t, J=7.9 Hz, 1H), 5.12 (dd, J=13.2, 4.9 Hz, 1H), 4.50 (t, J=6.5 Hz, 1H), 4.31 (ddd, J=24.0, 19.8, 12.0 Hz, 3H), 3.00-2.86 (m, 1H), 2.64 (dd, J=19.6, 12.5 Hz, 3H), 2.54 (s, 2H), 2.41-2.22 (m, 1H), 2.01 (dd, J=14.6, 8.4 Hz, 3H), 1.75-1.54 (m, 2H).

Example 196: (2S)-2-acetylamino-5-(2-(2,6-dioxopiperidine-3-)-1-oxoisoindoline-4-)-N-(2-(pyridine-3-)phenyl)pentanamide (196)

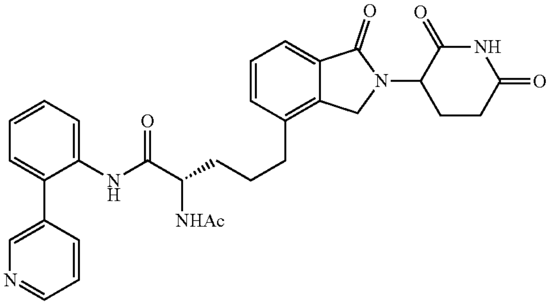 [SMILES: CC(=O)N[C@@H](CCCc1cccc2c1CN(C1CCC(=O)NC1=O)C2=O)C(=O)Nc1ccccc1-c1cccnc1]

The synthesis method was the same as (2S)-2-acetylamino-5-(2-(2,6-dioxopiperidine-3-)-1-oxoisoindoline-4-)-N-phenylpentanamide, 21.4 mg, yield 70%; $^1$H NMR (400 MHz, DMSO) δ 11.02 (d, J=3.0 Hz, 1H), 9.53 (d, J=3.8 Hz, 1H), 8.55-8.52 (m, 1H), 8.49 (dt, J=4.8, 1.6 Hz, 1H), 8.04 (dd, J=7.7, 1.7 Hz, 1H), 7.74 (ddd, J=7.7, 3.8, 1.8 Hz, 1H), 7.58 (d, J=7.4 Hz, 1H), 7.52-7.40 (m, 4H), 7.40-7.30 (m, 3H), 5.14 (dd, J=12.5, 5.2 Hz, 1H), 4.43 (dd, J=17.3, 9.0 Hz, 1H), 4.30 (ddd, J=18.9, 13.1, 3.5 Hz, 2H), 2.93 (t, J=14.7 Hz, 1H), 2.60 (t, J=7.1 Hz, 3H), 2.38 (ddd, J=20.5, 14.9, 4.7 Hz, 1H), 2.05-1.93 (m, 1H), 1.81 (s, 3H), 1.66-1.40 (m, 4H).

Example 197: N-((1S)-1-(7-bromo-1H-benzo[d]imidazole-2-)-4-(2-(2,6-dioxopiperidine-3-)-1-oxoisoindoline-4-)butyl)acetamide (197)

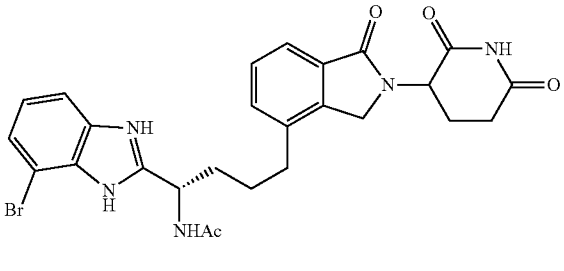 [SMILES: CC(=O)N[C@@H](CCCc1cccc2c1CN(C1CCC(=O)NC1=O)C2=O)c1nc2cccc(Br)c2[nH]1]

3-(4-((S)-4-amino-4-(7-bromo-1H-benzo[d]imidazole-2-)butyl)-1-oxoisoindoline-2-)piperidine-2,6-dione (31 mg, 0.061 mmol) was dissolved in 10 mL of dry dichloromethane. Triethylamine (85 μL, 0.61 mmol) and acetyl chloride (5 μL, 0.072 mmol) were added successively under stirring at room temperature, and continued to stir to react at room temperature for 2 h. After the reaction was completed, the solution was extracted with ethyl acetate, the organic phase was dried over anhydrous sodium sulfate, filtered, and dried under reduced pressure. The crude product obtained was separated by HPLC to obtain 15.5 mg of product with a yield of 46%; $^1$H NMR (400 MHz, DMSO) δ 12.63 (d, J=14.9 Hz, 1H), 11.00 (s, 1H), 8.51 (d, J=8.0 Hz, 1H), 7.56 (dd, J=5.3, 3.2 Hz, 1H), 7.45 (dd, J=8.1, 5.2 Hz, 3H), 7.36 (dd, J=7.6, 4.4 Hz, 1H), 7.09 (td, J=7.5, 3.0 Hz, 1H), 5.26-5.07 (m, 2H), 4.50-4.18 (m, 2H), 3.00-2.87 (m, 1H), 2.71 (dd, J=16.9, 8.1 Hz, 2H), 2.65-2.56 (m, 1H), 2.35 (ddd, J=12.5, 10.5, 4.4 Hz, 1H), 2.13-1.96 (m, 2H), 1.95-1.82 (m, 4H), 1.76-1.52 (m, 2H).

Example 198: (2S)-2-acetylamino-N-((3R,5R,7R)-adamantane-1-)-5-(2-(2,6-dioxopiperidine-3-)-1-oxoisoindoline-4-)pentanamide (198)

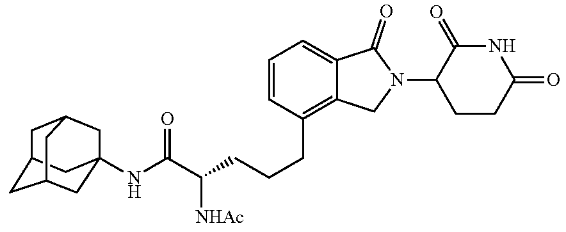 [SMILES: CC(=O)N[C@@H](CCCc1cccc2c1CN(C1CCC(=O)NC1=O)C2=O)C(=O)NC12CC3CC(CC(C3)C1)C2]

The synthesis method was the same as (2S)-2-acetylamino-5-(2-(2,6-dioxopiperidine-3-)-1-oxoisoindoline-4-)-N-phenylpentanamide, 15 mg, yield 49%; $^1$H NMR (400 MHz, DMSO) δ 11.01 (s, 1H), 7.85 (d, J=8.3 Hz, 1H), 7.57 (dd, J=7.1, 1.1 Hz, 1H), 7.44 (ddd, J=13.0, 10.7, 6.4 Hz, 3H), 5.15 (dd, J=13.4, 5.3 Hz, 1H), 4.43 (dd, J=16.9, 6.6 Hz, 1H), 4.33-4.23 (m, 2H), 3.00-2.87 (m, 1H), 2.62 (ddd, J=19.9, 7.6, 3.5 Hz, 3H), 2.46-2.32 (m, 1H), 2.07-1.94 (m, 4H), 1.81 (d, J=2.1 Hz, 9H), 1.67-1.43 (m, 10H).

Example 199: 3-(4-((S)-4-amino-4-(1H-benzo(d)imidazole-2-)butyl)-1-oxoisoindoline-2-)piperidine-2,6-dione (199)

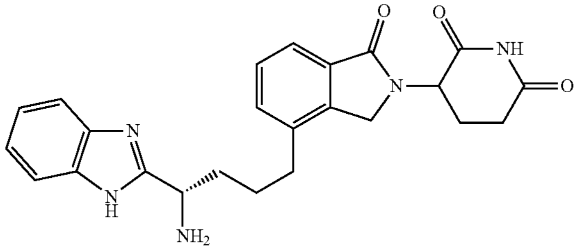 [SMILES: N[C@@H](CCCc1cccc2c1CN(C1CCC(=O)NC1=O)C2=O)c1nc2ccccc2[nH]1]

The preparation method was the same as 3-(4-((S)-4-amino-4-(7-bromo-1H-benzo[d]imidazole-2-)butyl)-1-oxoisoindoline-2-)piperidine-2,6-dione, 37 mg, yield 43%; $^1$H NMR (400 MHz, DMSO) δ 10.99 (s, 1H), 8.24 (s, 1H), 7.55 (dd, J=5.6, 2.9 Hz, 1H), 7.53-7.47 (m, 2H), 7.46-7.40 (m, 2H), 7.17-7.09 (m, 2H), 5.11 (dd, J=13.3, 5.1 Hz, 1H), 4.37 (dd, J=21.6, 17.2 Hz, 1H), 4.23 (dd, J=14.5, 7.8 Hz, 2H), 2.98-2.85 (m, 1H), 2.70-2.56 (m, 3H), 2.30 (tdd, J=26.1, 13.0, 4.4 Hz, 2H), 1.96 (ddd, J=17.0, 12.2, 6.0 Hz, 2H), 1.89-1.78 (m, 1H), 1.73-1.55 (m, 2H).

Example 200: (2S)-2-acetylamino-N-((1S,3S,5S,7S)-adamantane-2-)-5-(2-(2,6-dioxopiperidine-3-)-1-oxoisoindoline-4-)pentanamide (200)

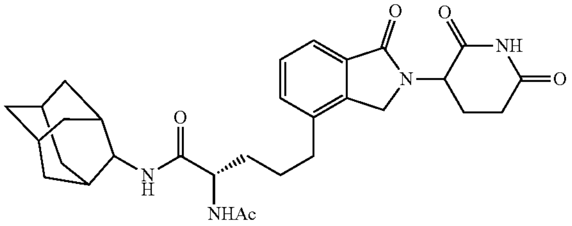 [SMILES: CC(=O)N[C@@H](CCCc1cccc2c1CN(C1CCC(=O)NC1=O)C2=O)C(=O)NC1C2CC3CC(C2)CC1C3]

The synthesis method was the same as (2S)-2-acetylamino-5-(2-(2,6-dioxopiperidine-3-)-1-oxoisoindoline-4-)-N-phenylpentanamide, 15.3 mg, yield 47%; $^1$H NMR (400 MHz, DMSO) δ 10.99 (s, 1H), 7.96 (d, J=8.4 Hz, 1H), 7.76 (dd, J=7.3, 2.7 Hz, 1H), 7.57 (dd, J=6.9, 1.4 Hz, 1H), 7.49-7.39 (m, 2H), 5.14 (dd, J=13.2, 5.1 Hz, 1H), 4.46 (ddd, J=19.3, 15.4, 4.6 Hz, 2H), 4.27 (d, J=17.1 Hz, 1H), 3.80 (d, J=6.8 Hz, 1H), 3.01-2.85 (m, 1H), 2.73-2.57 (m, 3H), 2.40 (ddd, J=22.7, 13.5, 4.5 Hz, 1H), 2.11-1.92 (m, 2H), 1.91-1.38 (m, 20H).

Example 201: 3-(4-((S)-4-amino-4-(3H-imidazole[4,5-c]pyridine-2-)butyl)-1-oxoindoline-2-)piperidine-2,6-dione (201)

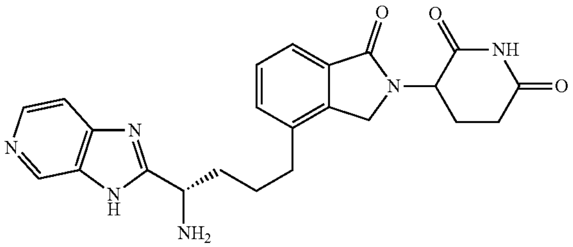 [SMILES: N[C@@H](CCCc1cccc2c1CN(C1CCC(=O)NC1=O)C2=O)c1nc2ccncc2[nH]1]

The preparation method was the same as 3-(4-((S)-4-amino-4-(7-bromo-1H-benzo[d]imidazole-2-)butyl)-1-oxoisoindoline-2-)piperidine-2,6-dione, 47 mg, yield 54%; $^1$H NMR (400 MHz, DMSO) δ 11.00 (s, 1H), 9.50 (s, 1H), 9.04 (d, J=53.3 Hz, 2H), 8.58 (dd, J=29.1, 6.2 Hz, 1H), 8.13 (dd, J=51.3, 6.3 Hz, 1H), 7.63-7.51 (m, 1H), 7.43 (d, J=4.0 Hz, 2H), 5.12 (d, J=11.0 Hz, 1H), 4.88 (s, 1H), 4.55-4.39 (m, 1H), 4.34-4.21 (m, 1H), 3.00-2.85 (m, 1H), 2.76-2.58 (m, 3H), 2.44-2.30 (m, 1H), 2.18 (d, J=6.0 Hz, 2H), 2.05-1.87 (m, 1H), 1.78-1.61 (m, 2H).

Example 202: (2S)-2-acetylamino-N-(3-chloro-4-methylphenyl)-5-(2-(2,6-dioxopiperidine-3-)-1-oxoisoindoline-4-)pentanamide (202)

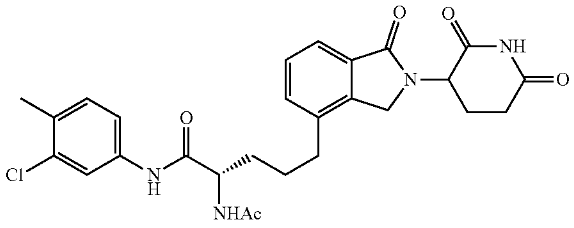 [SMILES: CC(=O)N[C@@H](CCCc1cccc2c1CN(C1CCC(=O)NC1=O)C2=O)C(=O)Nc1ccc(C)c(Cl)c1]

The synthesis method was the same as (2S)-2-acetylamino-5-(2-(2,6-dioxopiperidine-3-)-1-oxoisoindoline-4-)-N-phenylpentanamide, 34 mg, yield 60%; $^1$H NMR (400 MHz, DMSO) δ 10.99 (s, 1H), 10.17 (d, J=3.8 Hz, 1H), 8.20 (d, J=7.8 Hz, 1H), 7.81 (dd, J=3.3, 2.2 Hz, 1H), 7.57 (dd, J=5.9, 2.6 Hz, 1H), 7.49-7.41 (m, 2H), 7.37 (dd, J=8.3, 2.0 Hz, 1H), 7.26 (d, J=8.4 Hz, 1H), 5.13 (dd, J=13.3, 5.1 Hz, 1H), 4.42 (dd, J=16.9, 13.3 Hz, 2H), 4.27 (dd, J=17.1, 4.5 Hz, 1H), 3.00-2.86 (m, 1H), 2.68 (t, J=6.8 Hz, 2H), 2.59 (ddd, J=7.4, 6.7, 2.4 Hz, 1H), 2.42-2.29 (m, 1H), 2.26 (s, 3H), 1.99 (dd, J=12.4, 5.2 Hz, 1H), 1.86 (s, 3H), 1.80-1.53 (m, 4H).

Example 203: N-((1S)-1-(1H-benzo[d]imidazole-2-)-4-(2-(2,6-dioxopiperidine-3-)-1-oxoisoindoline-4-)butyl)amide (203)

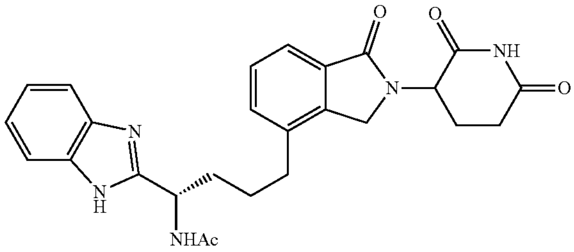 [SMILES: CC(=O)N[C@@H](CCCc1cccc2c1CN(C1CCC(=O)NC1=O)C2=O)c1nc2ccccc2[nH]1]

The preparation method was the same as N-((1S)-1-(7-bromo-1H-benzo[d]imidazole-2-)-4-(2-(2,6-dioxopiperidine-3-)-1-oxoisoindoline-4-)butyl)acetamide, 18.5 mg, yield 74%; $^1$H NMR (400 MHz, DMSO) δ 10.99 (s, 1H), 8.24 (s, 1H), 7.55 (dd, J=5.6, 2.9 Hz, 1H), 7.53-7.47 (m, 2H), 7.46-7.40 (m, 2H), 7.17-7.09 (m, 2H), 5.11 (dd, J=13.3, 5.1 Hz, 1H), 4.37 (dd, J=21.6, 17.2 Hz, 1H), 4.23 (dd, J=14.5, 7.8 Hz, 2H), 2.98-2.85 (m, 1H), 2.70-2.56 (m, 3H), 2.30 (tdd, J=26.1, 13.0, 4.4 Hz, 2H), 1.96 (ddd, J=17.0, 12.2, 6.0 Hz, 2H), 1.91 (s, 3H), 1.89-1.78 (m, 1H), 1.73-1.55 (m, 2H).

Example 204: (2S)-2-acetylamino-N-benzyl-5-(2-(2,6-oxopiperidine-3-)-1-oxoisoindoline-4-)-N-methylpentanamide (204)

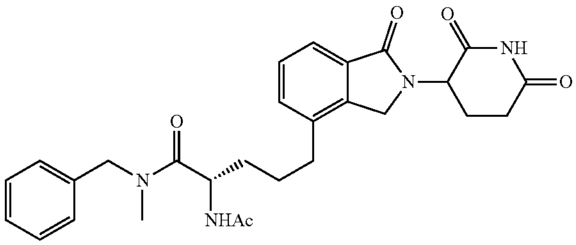

The synthesis method was the same as (2S)-2-acetylamino-5-(2-(2,6-dioxopiperidine-3-)-1-oxoisoindoline-4-)-N-phenylpentanamide, 17 mg, yield 52%; $^1$H NMR (400 MHz, DMSO) δ 11.00 (s, 1H), 8.20 (ddd, J=9.9, 9.0, 1.7 Hz, 1H), 7.56 (t, J=6.4 Hz, 1H), 7.49-7.40 (m, 2H), 7.39-7.29 (m, 2H), 7.28-7.20 (m, 2H), 7.18 (d, J=7.2 Hz, 1H), 5.17-5.09 (m, 1H), 4.79 (s, 1H), 4.64-4.18 (m, 4H), 2.99-2.75 (m, 4H), 2.64 (ddd, J=20.4, 15.7, 4.6 Hz, 3H), 2.39 (ddd, J=22.0, 16.2, 7.2 Hz, 1H), 2.01 (dd, J=10.9, 5.0 Hz, 1H), 1.80 (d, J=34.8 Hz, 3H), 1.73-1.40 (m, 4H).

Example 205: N-((1S)-4-(2-(2,6-dioxopiperidine-3-)-1-oxoisoindoline-4-)-1-(3H-imidazole[4,5-c]pyridine-2-)butyl)acetamide (205)

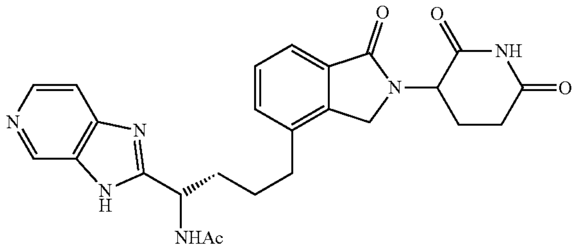

The preparation method was the same as N-((1S)-1-(7-bromo-1H-benzo[d]imidazole-2-)-4-(2-(2,6-dioxopiperidine-3-)-1-oxoisoindoline-4-)butyl)acetamide, 9.2 mg, yield 29%; $^1$H NMR (400 MHz, DMSO) δ 11.04 (s, 1H), 8.84 (s, 1H), 8.52 (d, J=8.0 Hz, 1H), 8.26 (d, J=5.5 Hz, 1H), 8.17 (s, 1H), 7.60-7.54 (m, 1H), 7.52-7.48 (m, 1H), 7.47-7.42 (m, 2H), 5.21-5.09 (m, 2H), 4.43 (t, J=16.5 Hz, 1H), 4.28 (d, J=17.1 Hz, 1H), 3.01-2.88 (m, 1H), 2.76-2.57 (m, 3H), 2.45-2.29 (m, 1H), 2.13-1.96 (m, 2H), 1.91 (s, 3H), 1.76-1.59 (m, 2H).

Example 206: (2S)—N-benzyl-5-(2-(2,6-dioxopiperidine-3-)-1-oxoisoindoline-4-)-2-propionamidopentaneamide (206)

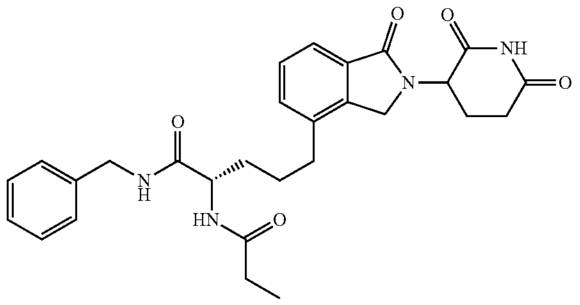 [SMILES: CCC(=O)N[C@@H](CCCc1cccc2c1CN(C1CCC(=O)NC1=O)C2=O)C(=O)NCc1ccccc1]

The synthesis method was the same as (2S)-2-acetylamino-5-(2-(2,6-dioxopiperidine-3-)-1-oxoisoindoline-4-)-N-phenylpentanamide, 32 mg, yield 58%; $^1$H NMR (400 MHz, DMSO) δ 11.00 (s, 1H), 8.44 (d, J=1.9 Hz, 1H), 7.94 (d, J=7.8 Hz, 1H), 7.57 (d, J=7.2 Hz, 1H), 7.46 (t, J=7.3 Hz, 1H), 7.40 (d, J=7.4 Hz, 1H), 7.32-7.25 (m, 2H), 7.22 (d, J=7.1 Hz, 3H), 5.75 (d, J=2.3 Hz, 1H), 5.14 (dd, J=11.8, 3.1 Hz, 1H), 4.43 (dd, J=17.0, 6.9 Hz, 1H), 4.38-4.20 (m, 4H), 3.01-2.85 (m, 1H), 2.61 (d, J=19.4 Hz, 3H), 2.39 (dd, J=27.6, 13.5 Hz, 1H), 2.14 (dd, J=14.8, 7.2 Hz, 2H), 2.05-1.94 (m, 1H), 1.77-1.46 (m, 4H), 0.98 (t, J=7.5 Hz, 3H).

Example 207: N-((2S)-5-(2-(2,6-dioxopiperidine-3-)-1-oxoisoindoline-4-)-1-oxo-1-(3H-spiro[isobenzofuran-1,4'-piperidine]-1'-)pentyl-2-)acetamide (207)

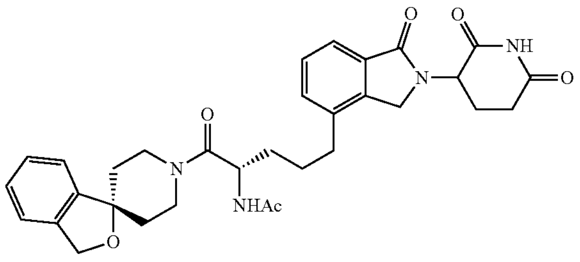

The synthesis method was the same as (2S)-2-acetylamino-5-(2-(2,6-dioxopiperidine-3-)-1-oxoisoindoline-4-)-N-phenylpentanamide, 32.3 mg, yield 51%; $^1$H NMR (400 MHz, DMSO) δ 11.01 (s, 1H), 8.17 (dd, J=18.4, 7.4 Hz, 1H), 7.64-7.54 (m, 1H), 7.47 (dd, J=6.9, 3.2 Hz, 2H), 7.29 (d, J=8.5 Hz, 3H), 7.24-7.06 (m, 1H), 5.15 (dd, J=13.2, 4.3 Hz, 1H), 5.01 (d, J=3.8 Hz, 2H), 4.81 (dd, J=7.5, 4.3 Hz, 1H), 4.55-4.23 (m, 3H), 3.88 (d, J=9.4 Hz, 1H), 3.32-3.24 (m, 1H), 3.04-2.82 (m, 2H), 2.80-2.55 (m, 3H), 2.41 (ddd, J=22.3, 15.0, 9.5 Hz, 1H), 2.02 (dd, J=14.8, 5.4 Hz, 1H), 1.85 (d, J=5.0 Hz, 3H), 1.78-1.48 (m, 7H).

Example 208: 3-(1-oxo-4-(4-(4-(phenyl-d5)piperazine-1-)butyl)isoindoline-2-)piperidine-2, 6-dione (208)

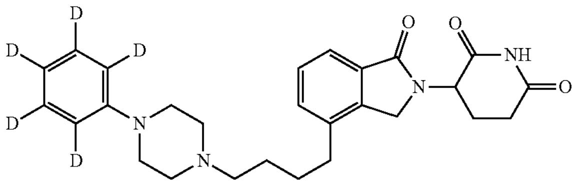 [SMILES: [2H]c1c([2H])c([2H])c(N2CCN(CCCCc3cccc4c3CN(C3CCC(=O)NC3=O)C4=O)CC2)c([2H])c1[2H]]

The preparation method was the same as 3-(1-oxo-4-(5-(2-phenylpyrroline-1-)pentyl)indoline-2-)piperidine-2,6-dione, 9.8 mg, yield 14%; $^1$H NMR (400 MHz, DMSO) δ 10.99 (s, 1H), 7.57 (dd, J=5.5, 3.1 Hz, 1H), 7.48-7.44 (m, 2H), 5.13 (dd, J=13.3, 5.1 Hz, 1H), 4.47 (d, J=17.1 Hz, 1H), 4.32 (d, J=17.1 Hz, 1H), 3.14-3.06 (m, 4H), 2.97-2.85 (m, 1H), 2.68 (t, J=7.6 Hz, 2H), 2.59-2.53 (m, 1H), 2.49-2.38 (m, 5H), 2.35 (t, J=7.1 Hz, 2H), 2.05-1.96 (m, 1H), 1.64 (dt, J=15.1, 7.5 Hz, 2H), 1.51 (dt, J=14.3, 7.3 Hz, 2H).

Example 209: 3-(1-oxo-4-(6-(4-(phenyl-d5)piperazine-1-)hexyl)isoindoline-2-)piperidine-2,6-dione (209)

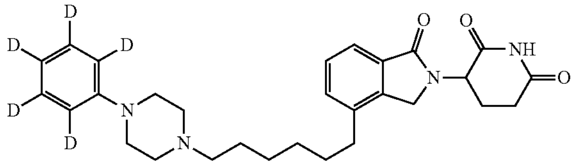 [SMILES: [2H]c1c([2H])c([2H])c(N2CCN(CCCCCCc3cccc4c3CN(C3CCC(=O)NC3=O)C4=O)CC2)c([2H])c1[2H]]

The preparation method was the same as 3-(1-oxo-4-(5-(2-phenylpyrroline-1-)pentyl)indoline-2-)piperidine-2,6-dione, 51.1 mg, yield 68%; $^1$H NMR (400 MHz, DMSO) δ 10.99 (s, 1H), 7.56 (dd, J=8.1, 4.6 Hz, 1H), 7.48-7.42 (m, 2H), 5.13 (dd, J=13.3, 5.1 Hz, 1H), 4.46 (d, J=17.2 Hz, 1H), 4.30 (d, J=17.1 Hz, 1H), 3.32 (s, 4H), 3.14-3.06 (m, 4H), 2.98-2.85 (m, 1H), 2.69-2.56 (m, 3H), 2.46-2.37 (m, 1H), 2.32 (t, J=7.2 Hz, 2H), 2.05-1.98 (m, 1H), 1.66-1.58 (m, 2H), 1.52-1.41 (m, 2H), 1.38-1.32 (m, 4H).

Example 210: 3-(1-oxo-4-(5-(4-(phenyl-d5)piperazine-1-)pentyl)isoindoline-2-)piperazine-2,6-dione (210)

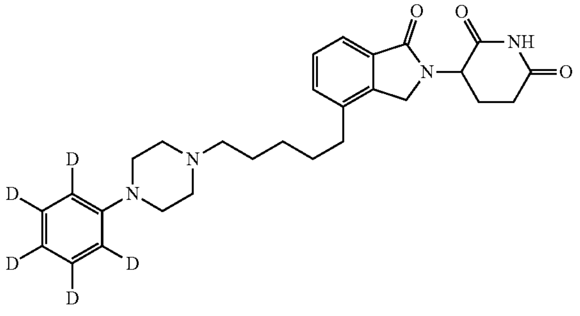 [SMILES: [2H]c1c([2H])c([2H])c(N2CCN(CCCCCc3cccc4c3CN(C3CCC(=O)NC3=O)C4=O)CC2)c([2H])c1[2H]]

The preparation method was the same as 3-(1-oxo-4-(5-(2-phenylpyrroline-1-)pentyl)indoline-2-)piperidine-2,6-dione, 24 mg, yield 32.7%; $^1$H NMR (400 MHz, DMSO) δ 11.00 (s, 1H), 7.56 (dd, J=5.9, 2.7 Hz, 1H), 7.49-7.43 (m, 2H), 5.14 (dd, J=13.2, 5.1 Hz, 1H), 4.47 (d, J=17.2 Hz, 1H), 4.31 (d, J=17.1 Hz, 1H), 3.32 (s, 4H), 3.10 (s, 4H), 2.99-2.86 (m, 1H), 2.69-2.55 (m, 3H), 2.46-2.27 (m, 3H), 2.05-1.95 (m, 1H), 1.63 (dd, J=15.1, 7.7 Hz, 2H), 1.56-1.46 (m, 2H), 1.36 (dd, J=13.8, 6.9 Hz, 2H).

Example 211: 3-(6-fluoro-1-oxy-4-(4-(quinoline-4-oxy)butoxy)-1-oxoisoindoline-2-)piperidine-2,6-dione (211)

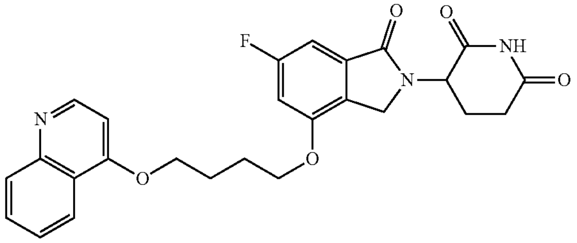 [SMILES: O=C1CCC(N2Cc3c(OCCCCOc4ccnc5ccccc45)cc(F)cc3C2=O)C(=O)N1]

The preparation method was the same as 3-(6-fluoro-4-(4-((2-methylquinoline-4-)oxy)butoxy)-1-oxoisoindoline-2-)piperidine-2,6-dione (Example 212), 19.0 mg of white solid was obtained, yield 43.2%; $^1$H NMR (400 MHz, DMSO) δ 10.97 (s, 1H), 8.73 (d, J=5.2 Hz, 1H), 8.12 (d, J=7.2 Hz, 1H), 7.93 (d, J=8.5 Hz, 1H), 7.74 (t, J=7.0 Hz, 1H), 7.53 (t, J=7.5 Hz, 1H), 7.20 (dd, J=11.5, 2.0 Hz, 1H), 7.11-7.02 (m, 2H), 5.08 (dd, J=13.4, 5.1 Hz, 1H), 4.35 (t, J=5.8 Hz, 2H), 4.27 (dd, J=11.5, 5.3 Hz, 3H), 4.14 (d, J=17.4 Hz, 1H), 2.95-2.85 (m, 1H), 2.63-2.55 (m, 1H), 2.45-2.32 (m, 1H), 2.11-1.91 (m, 5H).

Example 212: 3-(6-fluoro-4-(4-((2-methylquinoline-4-)oxy)butoxy)-1-oxoisoindoline-2-)piperidine-2,6-dione (212)

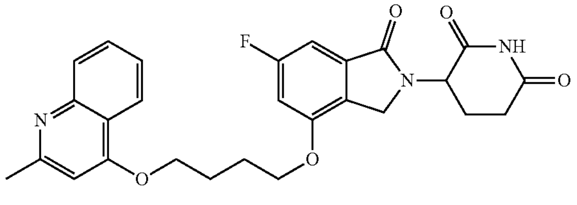 [SMILES: Cc1cc(OCCCCOc2cc(F)cc3c2CN(C2CCC(=O)NC2=O)C3=O)c2ccccc2n1]

Step 1: 5-fluoro-2-methyl-3-nitrobenzoic acid was dissolved in 20 ml methanol, thionyl chloride (728 ul, 10.04 mmol) was added under ice bath condition, heated to reflux for 3 h. After the reaction was completed, spin-dried, diluted with ethyl acetate, washed with saturated sodium bicarbonate and saturated sodium chloride, and dried to obtain 1.025 g of the target product with a yield of 96%.

Step 2: methyl 5-fluoro-2-methyl-3-nitrobenzoate (1.02 g, 4.8 mmol) was dissolved in 20 ml methanol, 10% Pd/C (110 mg) was added, and reacted with hydrogen at room temperature under normal pressure overnight. After TLC monitored the reaction was completed, the reaction solution was suction filtered, the solid was washed with methanol (20 ml×1), and the filtrate was concentrated to obtain 918 mg of colorless liquid methyl 3-amino-5-fluoro-2-methyl-benzene formate, directly used in the next step.

Step 3: methyl 3-amino-5-fluoro-2-methyl-benzoate (918 mg, crude product) and 10% $H_2SO_4$ (1.54 ml, 28.71 mmol), sodium nitrite (505 mg, 7.32) aqueous solution (5 ml) was added dropwise at 0° C., and reacted at the same temperature for 1 h, then 50% $H_2SO_4$ (7.65 ml, 143.55 mmol) was added, and heated 100° C. to react for 1 h. After TLC monitored the reaction was completed, the reaction solution was concentrated, and 20 ml of water and 100 ml of ethyl acetate were added, and shook to uniform and separated, the aqueous phase was extracted with ethyl acetate (50 ml×2), Combined organic phase was dried with anhydrous sodium sulfate, concentrated under reduced pressure, and purified by column chromatography to obtain 415 mg of product, two-step yield 47%.

Step 4: methyl 5-fluoro-3-hydroxy-2-methyl-benzoate (410 mg, 2.23 mmol) was dissolved in 20 ml DMF, 60% sodium hydride (107 mg, 2.67 mmol) was added at 0° C. condition, and reacted for 1 h. Chloromethyl methyl ether (203 ul, 2.67 mmol) was added dropwise at the same temperature, then warmed to room temperature and reacted for 2 h. The reaction was monitored by TLC until completed, quenched with water, extracted with ethyl acetate, separated, and the organic phase was sequentially washed with water and saturated sodium chloride solution, dried, and purified by column chromatography to obtain 430 mg of product with a yield of 84%.

Step 5: methyl 5-fluoro-3-methoxymethoxy-2-methyl benzoate (425 mg, 1.86 mmol) and NBS (398 mg, 2.23 mmol) were dissolved in 15 ml carbon tetrachloride, then 70% benzoyl peroxide (65 mg, 0.186 mmol) was added, heated to reflux for 3 h, concentrated under reduced pressure, and separated by flash column chromatography to obtain 545 mg of yellow solid, yield 95.4%.

Step 6: N,N-diisopropylethylamine (873 ul, 5.28 mmol) was added to suspension of methyl 2-bromomethyl-5-fluoro-3-methoxymethoxybenzoate (540 mg, 1.76 mmol) and methyl 4,5-diamino-5-oxopentanoate hydrochloride (413 mg, 2.11 mmol) in acetonitrile (20 ml), reacted at 40° C. overnight. After the reaction was completed, the solution was concentrated under reduced pressure, diluted with ethyl acetate, washed with water and saturated sodium chloride successively, dried, concentrated and directly used in the next step.

Step 7: the crude product from the previous step in a 50 ml round bottom flask, 10 ml 4M hydrochloric acid dioxane and 1 ml methanol were added, and reacted at room temperature for 1 h, then spin-dried, and purified by column chromatography to obtain 300 mg of target product, yield (two steps) 55%.

Step 8: methyl 5-amino-4-(6-fluoro-4-hydroxy-1-oxoisoindoline-2-)-5-oxopentanoate (35 mg, 0.11 mmol) was added into 50 ml round-bottom flask, then 4-((2-methylquinoline-4-)oxy)-1-butanol (51 mg, 0.22 mmol, 2 eq) and triphenylphosphine (58 mg, 0.22 mmol, 2 eq) were added. The reaction system was replaced with nitrogen, and 5 mL of dry tetrahydrofuran was added. Diisopropyl azodicarboxylate (43 μL, 0.22 mmol, 2 eq) was added to the reaction system to react at room temperature for 1 h. TLC monitored that the reaction was completed, and concentrated under reduced pressure, and 56.8 mg of product was obtained by column chromatography purification with a yield of 98%.

Step 9: the product obtained in the previous step (56.8 mg, 0.108 mmol) was dissolved in dry THF, and potassium tert-butoxide (13 mg, 0.12 mmol) was added at 0° C., and reacted at the same temperature for 30 min, 1N HCl was added to quench, diluted with ethyl acetate, washed with saturated sodium chloride, dried, and purified by HPLC to obtain 20.1 mg of white solid, yield 37.9%; $^1$H NMR (400 MHz, DMSO) δ 10.97 (s, 1H), 8.04 (d, J=8.3 Hz, 1H), 7.82 (d, J=8.5 Hz, 1H), 7.67 (t, J=7.0 Hz, 1H), 7.43 (t, J=7.6 Hz, 1H), 7.20 (d, J=11.6 Hz, 1H), 7.08 (dd, J=7.4, 1.8 Hz, 1H), 6.93 (s, 1H), 5.08 (dd, J=13.5, 4.9 Hz, 1H), 4.36-4.23 (m, 5H), 4.14 (d, J=17.3 Hz, 1H), 2.95-2.85 (m, 1H), 2.62-2.54 (m, 4H), 2.36-2.25 (m, 1H), 2.10-1.91 (m, 5H).

Example 213: 3-(4-(4-((2-methylquinoline-4-)methoxy)butoxy)-1-oxoisoindoline-2-)piperidine-2,6-dione (213)

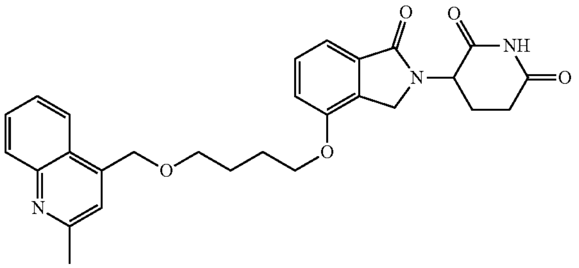 [SMILES: Cc1cc(COCCCCOc2cccc3c2CN(C2CCC(=O)NC2=O)C3=O)c2ccccc2n1]

Step 1: indoline-2,3-dione (1 g, 6.87 mmol) was added to a 100 ml round bottom flask, KOH (3.6 g, 54.4 mmol) in water (7.2 ml) was added, and stirred for 5 min, 12 ml Acetone was added, heated and refluxed overnight. After the reaction was completed, the pH was adjusted to 5-6 with 1N HCl, solid was precipitated and 666 mg of product was obtained by filtration with a yield of 52%.

Step 2: quinoline-4-carboxylic acid (665 mg, 3.55 mmol) was dissolved in 25 ml of dry THF, triethylamine (598 ul, 4.62 mmol) was added, and isopropyl chloroformate (635 ul, 4.62 mmol) was added dropwise under ice bath. After 0.5 h, sodium borohydride (403 mg, 10.65 mmol) in water (5 ml) was added, and reacted at the same temperature for 2 h. After the reaction was completed, the solution was spin-dried, diluted with ethyl acetate, washed with saturated sodium chloride, dried, and purified by column chromatography to obtain the product 390 mg, yield 63%.

Step 3: quinoline-4-methanol (100 mg, 0.577 mmol) was dissolved in 6 ml dry THF, fully cooled at 0° C. 60% Sodium hydride (35 mg, 0.87 mmol) was added, and reacted at the same temperature for 0.5 h, then 1,4-dibromobutane (206 ul, 0.866 mmol) was added, and heated to reflux overnight. After the reaction was completed, quenched with water, extracted with ethyl acetate, the organic layer was washed with saturated sodium chloride, dried, and purified by column chromatography, 83 mg, yield 47%.

Step 4: 4-((4-bromobutoxy)methyl)-2-methylquinoline (44.7 mg, 0.145 mmol) and methyl 5-amino-4-(4-hydroxy-1-oxoisoindoline-2-)-5-oxopentanoate (42 mg, 0.145 mmol) were dissolved in 6 ml of acetonitrile, and anhydrous potassium carbonate (20 mg, 0.145 mmol) was added and warmed to 80° C. to react for 48 h. After the reaction was completed, the solution was filtered and spin-dried, purified by column chromatography to obtain 38.3 mg of product with a yield of 51%.

Step 5: the product obtained in the previous step (38.3 mg, 0.074 mmol) was dissolved in 6 ml THF, potassium tert-butoxide (9 mg, 0.081 mmol) was added at 0° C. and reacted for 0.5 h at the same temperature, 1N HCl was added to quench, and the solution was diluted with ethyl acetate, washed with saturated sodium chloride, dried, spin-dried, purified by HPLC to obtain 17.7 mg of white solid, yield 49% $^1$H NMR (400 MHz, DMSO) δ 10.96 (s, 1H), 8.00 (d, J=8.2 Hz, 1H), 7.93 (d, J=8.3 Hz, 1H), 7.70 (t, J=7.3 Hz, 1H), 7.53 (t, J=7.4 Hz, 1H), 7.46 (t, J=7.8 Hz, 1H), 7.40 (s, 1H), 7.30 (d, J=7.4 Hz, 1H), 7.20 (d, J=8.1 Hz, 1H), 5.09 (dd, J=13.3, 5.0 Hz, 1H), 4.96 (s, 2H), 4.36 (d, J=17.4 Hz, 1H), 4.21 (d, J=17.4 Hz, 1H), 4.14 (t, J=5.9 Hz, 2H), 3.65 (t, J=5.9 Hz, 2H), 2.96-2.83 (m, 1H), 2.63 (s, 3H), 2.56 (d, J=17.5 Hz, 1H), 2.45-2.32 (m, 1H), 2.02-1.92 (m, 1H), 1.89-1.74 (m, 4H).

Example 214: 3-(4-(4-((2-ethylquinoline-4-)methoxy)butoxy)-1-oxoisoindoline-2-)piperidine-2,6-dione (214)

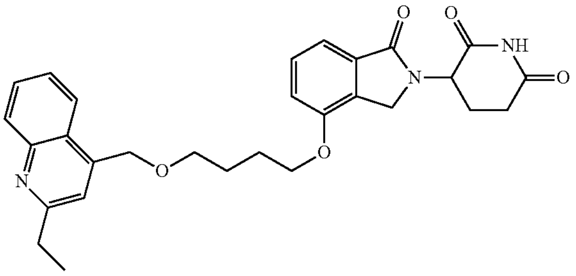 [SMILES: CCc1cc(COCCCCOc2cccc3c2CN(C2CCC(=O)NC2=O)C3=O)c2ccccc2n1]

The preparation method was the same as 3-(4-(4-((2-methylquinoline-4-)methoxy)butoxy)-1-oxoisoindoline-2-)piperidine-2,6-dione, 16.5 mg of white solid was obtained, yield 35.1%; $^1$H NMR (400 MHz, DMSO) δ 10.96 (s, 1H), 8.01 (d, J=8.4 Hz, 1H), 7.95 (d, J=8.3 Hz, 1H), 7.70 (t, J=7.7 Hz, 1H), 7.53 (t, J=7.6 Hz, 1H), 7.45 (dd, J=13.6, 5.7 Hz, 2H), 7.30 (d, J=7.4 Hz, 1H), 7.20 (d, J=8.2 Hz, 1H), 5.09 (dd, J=13.3, 5.1 Hz, 1H), 4.97 (s, 2H), 4.35 (d, J=17.4 Hz, 1H), 4.21 (d, J=17.4 Hz, 1H), 4.14 (t, J=5.9 Hz, 2H), 3.66 (t, J=5.9 Hz, 2H), 2.91 (q, J=7.5 Hz, 2H), 2.56 (d, J=18.5 Hz, 1H), 2.44-2.31 (m, 1H), 2.01-1.91 (m, 1H), 1.89-1.74 (m, 4H), 1.29 (t, J=7.6 Hz, 3H).

Example 215: 3-(4-(4-(4-(2-chlorophenyl)piperazine-1-yl)butyl)-1-oxoisoindoline-2-yl) piperidine-2,6-dione (215)

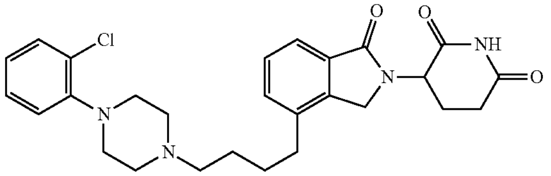 [SMILES: O=C1CCC(N2Cc3c(CCCCN4CCN(c5ccccc5Cl)CC4)cccc3C2=O)C(=O)N1]

Preparation method referred synthesis method 1 and Example 21. $^1$H NMR (400 MHz, DMSO) δ 11.00 (s, 1H), 7.57 (dd, J=5.5, 3.1 Hz, 1H), 7.50-7.45 (m, 2H), 7.39 (dd, J=7.9, 1.4 Hz, 1H), 7.32-7.26 (m, 1H), 7.14 (dd, J=8.1, 1.3 Hz, 1H), 7.03 (td, J=7.7, 1.4 Hz, 1H), 5.14 (dd, J=13.3, 5.1 Hz, 1H), 4.48 (d, J=17.1 Hz, 1H), 4.32 (d, J=17.1 Hz, 1H), 3.02-2.84 (m, 5H), 2.68 (t, J=7.6 Hz, 2H), 2.59 (d, J=20.8 Hz, 5H), 2.48-2.36 (m, 3H), 2.06-1.97 (m, 1H). 1.70-1.60

(m, 2H), 1.57-1.47 (m, 2H). UPLC-MS (ESI) calculated for $C_{27}H_{31}ClN_4O_3$ $[M+H]^+$: 495.21, found 495.52.

Example 216: 3-(4-(4-(4-(2-nitrophenyl)piperazine-1-yl)butyl)-1-oxoisoindoline-2-yl) piperidine-2,6-dione (216)

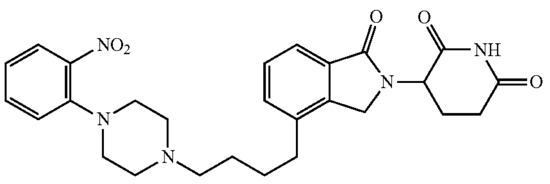

Preparation method referred synthesis method 1 and Example 21. $^1$H NMR (400 MHz, DMSO) δ 11.00 (s, 1H), 7.78 (dd, J=8.1, 1.5 Hz, 1H), 7.57 (ddd, J=7.4, 4.3, 1.6 Hz, 2H), 7.50-7.44 (m, 2H), 7.30 (d, J=7.7 Hz, 1H), 7.11 (t, J=7.2 Hz, 1H), 5.14 (dd, J=13.2, 5.0 Hz, 1H), 4.47 (d, J=17.2 Hz, 1H), 4.32 (d, J=17.2 Hz, 1H), 3.00-2.87 (m, 5H), 2.67 (t, J=7.6 Hz, 2H), 2.62-2.53 (m, 1H), 2.48-2.43 (m, 4H), 2.43-2.34 (m, 3H), 2.02 (ddd, J=12.1, 7.1, 5.1 Hz, 1H), 1.63 (dt, J=14.7, 7.5 Hz, 2H), 1.55-1.45 (m, 2H). UPLC-MS (ESI) calculated $C_{27}H_{31}N_5O_5$ $[M+H]^+$: 506.23, found 506.44.

Example 217: 3-(1-oxo-4-(4-(4-(o-tolyl)piperazine-1-yl)butyl)isoindoline-2-yl)piperidine-2,6-dione (217)

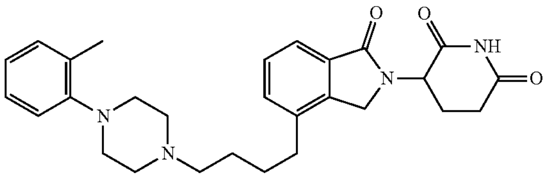 [SMILES: Cc1ccccc1N1CCN(CCCCc2cccc3c2CN(C2CCC(=O)NC2=O)C3=O)CC1]

Preparation method referred synthesis method 1 and Example 21. $^1$H NMR (400 MHz, DMSO) δ 11.00 (s, 1H), 7.57 (dd, J=5.6, 3.0 Hz, 1H), 7.50-7.45 (m, 2H), 7.13 (t, J=7.7 Hz, 2H), 6.99 (d, J=7.7 Hz, 1H), 6.94 (t, J=7.3 Hz, 1H), 5.14 (dd, J=13.3, 5.1 Hz, 1H), 4.48 (d, J=17.2 Hz, 1H), 4.32 (d, J=17.1 Hz, 1H), 2.93 (ddd, J=17.3, 13.7, 5.4 Hz, 1H), 2.83 (t, 4H), 2.68 (t, J=7.5 Hz, 2H), 2.64-2.53 (m, 5H), 2.48-2.38 (m, 3H), 2.22 (s, 3H), 2.06-1.96 (m, 1H), 1.70-1.59 (m, 2H), 1.52 (dt, J=15.5, 7.8 Hz, 2H). UPLC-MS (ESI) calculated for $C_{28}H_{34}N_4O_3$ $[M+H]^+$: 475.26, found 475.49.

Example 218: 3-(4-(4-(4-(2-fluorophenyl)piperazine-1-yl)butyl)-1-oxoisoindoline-2-yl)piperidine-2,6-dione (218)

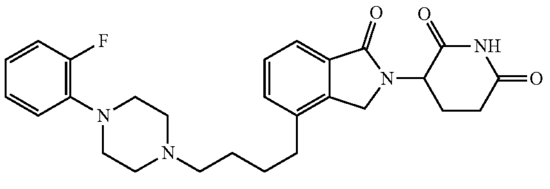 [SMILES: O=C1CCC(N2Cc3c(CCCCN4CCN(c5ccccc5F)CC4)cccc3C2=O)C(=O)N1]

Preparation method referred synthesis method 1 and Example 21. $^1$H NMR (400 MHz, DMSO) δ 11.00 (s, 1H), 7.57 (dd, J=5.5, 3.2 Hz, 1H), 7.49-7.45 (m, 2H), 7.15-7.06 (m, 2H), 7.05-6.92 (m, 2H), 5.14 (dd, J=13.4, 5.1 Hz, 1H), 4.48 (d, J=17.2 Hz, 1H), 4.32 (d, J=17.2 Hz, 1H), 3.05-2.98 (m, 4H), 2.92 (ddd, J=17.6, 13.7, 5.5 Hz, 1H), 2.68 (t, J=7.5 Hz, 2H), 2.67-2.52 (m, 5H), 2.46-2.35 (m, 3H), 2.06-1.97 (m, 1H), 1.70-1.58 (m, 2H), 1.57-1.47 (m, 2H). UPLC-MS (ESI) calculated for $C_{27}H_{31}FN_4O_3$ $[M+H]^+$: 479.24, found 479.47.

Example 219: 3-(1-oxo-4-(4-(4-(2-(trifluoromethyl)phenyl)piperazine-1-yl)butyl)isoindoline-2-yl)piperidine-2,6-dione (219)

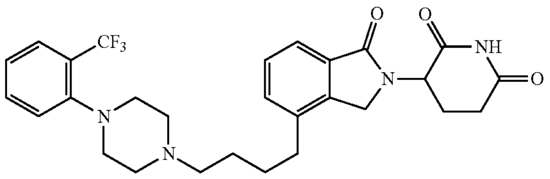 [SMILES: O=C1CCC(N2Cc3c(CCCCN4CCN(c5ccccc5C(F)(F)F)CC4)cccc3C2=O)C(=O)N1]

Preparation method referred synthesis method 1 and Example 21. $^1$H NMR (400 MHz, DMSO) δ 11.00 (s, 1H), 7.65 (t, J=7.4 Hz, 2H), 7.60-7.52 (m, 2H), 7.50-7.45 (m, 2H), 7.33 (t, J=7.6 Hz, 1H), 5.15 (dd, J=13.3, 5.1 Hz, 1H), 4.48 (d, J=17.2 Hz, 1H), 4.32 (d, J=17.2 Hz, 1H), 3.00-2.85 (m, 5H), 2.68 (t, J=7.6 Hz, 2H), 2.65-2.53 (m, 5H), 2.48-2.36 (m, 3H), 2.07-1.98 (m, 1H), 1.70-1.58 (m, 2H), 1.58-1.48 (m, 2H). UPLC-MS (ESI) calculated for $C_{28}H_{31}F_3N_4O_3$ $[M+H]^+$: 529.23, found 529.39.

Example 220: 3-(1-oxo-4-(4-(4-(3-(trifluoromethyl)phenyl)piperazine-1-yl)butyl)isoindoline-2-yl)piperidine-2,6-dione (220)

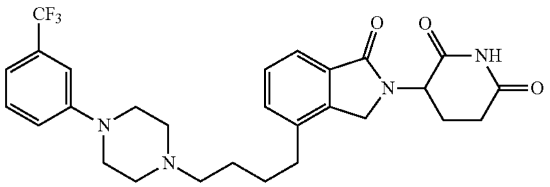 [SMILES: O=C1CCC(N2Cc3c(CCCCN4CCN(c5cccc(C(F)(F)F)c5)CC4)cccc3C2=O)C(=O)N1]

Preparation method referred synthesis method 1 and Example 21. $^1$H NMR (400 MHz, DMSO) δ 10.99 (s, 1H), 7.57 (dt, J=7.6, 3.8 Hz, 1H), 7.49-7.45 (m, 2H), 7.42 (dd, J=14.7, 6.4 Hz, 1H), 7.21 (dd, J=8.4, 1.8 Hz, 1H), 7.15 (s, 1H), 7.06 (d, J=7.7 Hz, 1H), 5.14 (dd, J=13.3, 4.9 Hz, 1H), 4.47 (d, J=17.2 Hz, 1H), 4.32 (d, J=17.2 Hz, 1H), 3.22 (t, 4H), 2.97-2.86 (m, 1H), 2.68 (t, J=7.5 Hz, 2H), 2.65-2.53 (m, 5H), 2.45-2.35 (m, 3H), 2.06-1.96 (m, 1H), 1.70-1.58 (m, 2H), 1.57-1.48 (m, 2H). UPLC-MS (ESI) calculated for $C_{28}H_{31}F_3N_4O_3$ $[M+H]^+$: 529.23, found 529.41.

Example 221: 3-(4-(4-(4-(benzothiophene-7-yl)piperazin-1-yl)butyl)-1-oxoisoindoline-2-yl)piperidine-2,6-dione (221)

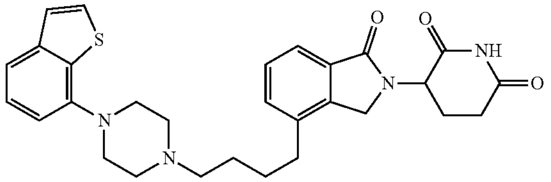 [SMILES: O=C1CCC(N2Cc3c(CCCCN4CCN(c5cccc6ccsc56)CC4)cccc3C2=O)C(=O)N1]

Preparation method referred synthesis method 1 and Example 21. $^{1}H$ NMR (400 MHz, DMSO) δ 11.00 (s, 1H), 7.69 (d, J=5.5 Hz, 1H), 7.61 (d, J=8.1 Hz, 1H), 7.57 (dd, J=6.1, 2.5 Hz, 1H), 7.51-7.44 (m, 2H), 7.39 (d, J=5.5 Hz, 1H), 7.27 (t, J=7.8 Hz, 1H), 6.88 (d, J=7.5 Hz, 1H), 5.14 (dd, J=13.2, 5.0 Hz, 1H), 4.49 (d, J=17.2 Hz, 1H), 4.33 (d, J=17.2 Hz, 1H), 3.06 (s, 4H), 2.98-2.87 (m, 1H), 2.69 (t, J=7.5 Hz, 2H), 2.64-2.54 (m, 5H), 2.47-2.38 (m, 3H), 2.06-1.98 (m, 1H), 1.72-1.62 (m, 2H), 1.58-1.48 (m, 2H). UPLC-MS (ESI) calculated for $C_{29}H_{32}N_4O_3S$ $[M+H]^+$: 519.22, found 517.47.

Example 222: 3-(4-(4-(4-(2,4-dichlorophenyl)piperazine-1-yl)butyl)-1-oxoisoindoline-2-yl)piperidine-2,6-dione (222)

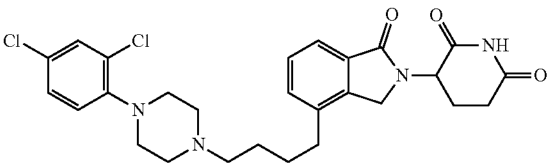 [SMILES: O=C1CCC(N2Cc3c(CCCCN4CCN(c5ccc(Cl)cc5Cl)CC4)cccc3C2=O)C(=O)N1]

Preparation method referred synthesis method 1 and Example 21. $^{1}H$ NMR (400 MHz, DMSO) δ 11.00 (s, 1H), 7.57 (dd, J=5.2, 3.4 Hz, 1H), 7.52 (d, J=2.4 Hz, 1H), 7.48-7.45 (m, 2H), 7.35 (dd, J=8.6, 2.5 Hz, 1H), 7.14 (d, J=8.7 Hz, 1H), 5.14 (dd, J=13.2, 5.1 Hz, 1H), 4.47 (d, J=17.1 Hz, 1H), 4.32 (d, J=17.1 Hz, 1H), 2.99-2.87 (m, 5H), 2.67 (t, J=7.5 Hz, 2H), 2.64-2.56 (m, 1H), 2.46-2.34 (m, 3H), 2.08-1.95 (m, 1H), 1.70-1.58 (m, 2H), 1.56-1.44 (m, 2H). UPLC-MS (ESI) calculated for $C_{27}H_3OCl_2N_4O_3$ $[M+H]^+$: 529.17, found 529.35.

Example 223: 3-(4-(4-(4-(3,5-dichlorophenyl)piperazine-1-yl)butyl)-1-oxoisoindoline-2-yl) piperidine-2,6-dione (223)

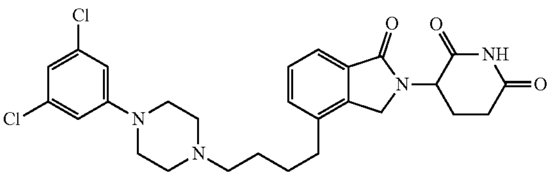 [SMILES: O=C1CCC(N2Cc3c(CCCCN4CCN(c5cc(Cl)cc(Cl)c5)CC4)cccc3C2=O)C(=O)N1]

Preparation method referred synthesis method 1 and Example 21. $^{1}H$ NMR (400 MHz, DMSO) δ 10.99 (s, 1H), 7.59-7.54 (m, 1H), 7.50-7.42 (m, 2H), 6.91 (d, J=1.6 Hz, 2H), 6.84 (t, J=1.5 Hz, 1H), 5.13 (dd, J=13.3, 5.1 Hz, 1H), 4.47 (d, J=17.2 Hz, 1H), 4.31 (d, J=17.2 Hz, 1H), 3.22-3.15 (m, 4H), 2.98-2.86 (m, 1H), 2.67 (t, J=7.5 Hz, 2H), 2.63-2.56 (m, 1H), 2.47-2.38 (m, 5H), 2.33 (t, J=7.0 Hz, 2H), 2.08-1.95 (m, 1H), 1.69-1.57 (m, 2H), 1.55-1.42 (m, 2H). UPLC-MS (ESI) calculated for $C_{27}H_3OCl_2N_4O_3$ $[M+H]^+$: 529.17, found 529.53.

Example 224: 3-(4-(4-(4-(2-methoxyphenyl)piperazine-1-yl)butyl)-1-isoindoline-2-yl)piperidine-2,6-dione (224)

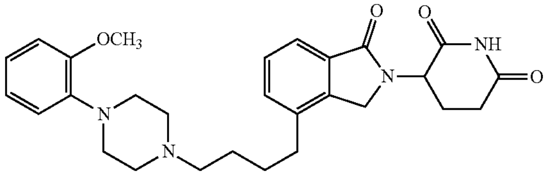 [SMILES: COc1ccccc1N1CCN(CCCCc2cccc3c2CN(C2CCC(=O)NC2=O)C3=O)CC1]

Preparation method referred synthesis method 1 and Example 21. $^{1}H$ NMR (400 MHz, DMSO) δ 11.00 (s, 1H), 7.57 (dt, J=7.7, 3.9 Hz, 1H), 7.49-7.45 (m, 2H), 6.95-6.89 (m, 2H), 6.86 (d, J=2.6 Hz, 2H), 5.14 (dd, J=13.3, 5.1 Hz, 1H), 4.47 (d, J=17.2 Hz, 1H), 4.32 (d, J=17.2 Hz, 1H), 2.98-2.87 (m, 5H), 2.68 (t, J=7.5 Hz, 2H), 2.64-2.55 (m, 1H), 2.48-2.42 (m, 2H), 2.39-2.34 (m, 2H), 2.06-1.97 (m, 1H), 1.69-1.58 (m, 2H), 1.55-1.44 (m, 2H). UPLC-MS (ESI) calculated for $C_{28}H_{34}N_4O_4$ $[M+H]^+$: 491.26, found 491.53.

Example 225: 3-(4-(5-(4-(benzothiophene-7-yl)piperazin-1-yl)pentyl)-1-oxoisoindoline-2-yl)piperidine-2,6-dione (225)

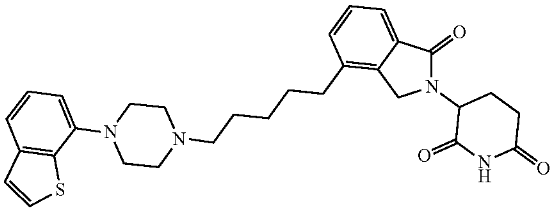 [SMILES: O=C1CCC(N2Cc3c(CCCCCN4CCN(c5cccc6ccsc56)CC4)cccc3C2=O)C(=O)N1]

Preparation method referred synthesis method 1 and Example 21. $^{1}H$ NMR (400 MHz, DMSO) δ 11.00 (s, 1H), 7.69 (d, J=5.5 Hz, 1H), 7.62 (d, J=8.0 Hz, 1H), 7.57 (dd, J=6.2, 2.3 Hz, 1H), 7.51-7.42 (m, 2H), 7.39 (d, J=5.5 Hz, 1H), 7.27 (t, J=7.9 Hz, 1H), 6.89 (d, J=7.6 Hz, 1H), 5.14 (dd, J=13.3, 5.0 Hz, 1H), 4.48 (d, J=17.1 Hz, 1H), 4.32 (d, J=17.2 Hz, 1H), 3.10-3.01 (m, 4H), 2.98-2.87 (m, 1H), 2.73-2.56 (m, 5H), 2.44 (dd, J=13.3, 4.4 Hz, 3H), 2.06-1.96 (m, 1H), 1.72-1.59 (m, 2H), 1.59-1.47 (m, 2H), 1.36 (dt, J=8.6, 5.6 Hz, 2H), 1.28-1.18 (m, 2H). UPLC-MS (ESI) calculated for $C_{30}H_{34}N_4O_3S$ $[M+H]^+$: 531.24, found 531.47.

Example 226: 3-(4-(5-(4-(6-fluorobenzisoxazole-3-yl)piperidin-1-yl)pentyl)-1-oxoisoindoline-2-yl)piperidine-2,6-(226)

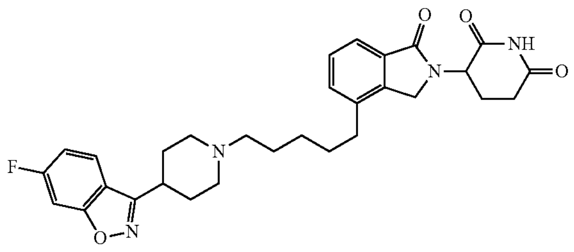 [SMILES: O=C1CCC(N2Cc3c(CCCCCN4CCC(c5noc6cc(F)ccc56)CC4)cccc3C2=O)C(=O)N1]

Preparation method referred synthesis method 1 and Example 21. $^1$H NMR (400 MHz, DMSO) δ 11.00 (s, 1H), 8.00 (dd, J=8.7, 5.3 Hz, 1H), 7.69 (dd, J=9.1, 2.0 Hz, 1H), 7.57 (dd, J=5.9, 2.6 Hz, 1H), 7.50-7.42 (m, 2H), 7.28 (td, J=9.2, 2.0 Hz, 1H), 5.14 (dd, J=13.2, 5.1 Hz, 1H), 4.47 (d, J=17.2 Hz, 1H), 4.31 (d, J=17.2 Hz, 1H), 3.20-3.08 (m, 1H), 3.04-2.87 (m, 3H), 2.70-2.64 (m, 2H), 2.60 (d, J=17.8 Hz, 1H), 2.47-2.30 (m, 3H), 2.17-1.95 (m, 5H), 1.83 (dd, J=22.7, 12.1 Hz, 2H), 1.64 (dt, J=15.2, 7.6 Hz, 2H), 1.51 (dd, J=13.1, 6.9 Hz, 2H), 1.36 (dd, J=13.4, 6.3 Hz, 2H). UPLC-MS (ESI) calculated for $C_{30}H_{33}FN_4O_4$ [M+H]$^+$: 533.25, found 533.51.

Example 227: 3-(4-(4-(4-(6-fluorobenzisoxazole-3-yl)piperidin-1-yl)butyl)-1-oxoisoindoline-2-yl)piperidine-2,6-dione (227)

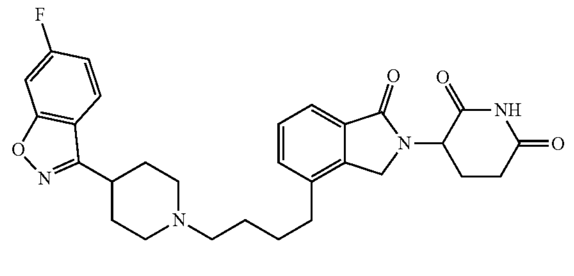 [SMILES: O=C1CCC(N2Cc3c(CCCCN4CCC(c5noc6cc(F)ccc56)CC4)cccc3C2=O)C(=O)N1]

Preparation method referred synthesis method 1 and Example 21. $^1$H NMR (400 MHz, DMSO) δ 10.99 (s, 1H), 8.00 (dd, J=8.8, 5.3 Hz, 1H), 7.69 (dd, J=9.1, 2.1 Hz, 1H), 7.57 (dd, J=5.9, 2.7 Hz, 1H), 7.51-7.43 (m, 2H), 7.28 (td, J=9.2, 2.2 Hz, 1H), 5.14 (dd, J=13.3, 5.1 Hz, 1H), 4.48 (d, J=17.2 Hz, 1H), 4.32 (d, J=17.2 Hz, 1H), 3.20-3.08 (m, 1H), 3.04-2.96 (m, 2H), 2.96-2.86 (m, 1H), 2.68 (t, J=7.5 Hz, 2H), 2.60 (d, J=16.8 Hz, 1H), 2.47-2.38 (m, 3H), 2.17 (t, J=10.2 Hz, 2H), 2.04 (dd, J=13.4, 9.5 Hz, 3H), 1.84 (dd, J=24.4, 11.9 Hz, 2H), 1.64 (dt, J=15.3, 7.8 Hz, 2H), 1.53 (dt, J=14.7, 7.5 Hz, 2H). UPLC-MS (ESI) calculated for $C_{29}H_{31}FN_4O_4$ [M+H]$^+$: 519.23, found 519.53.

Example 228: 3-(4-(4-(4-(benzisoxazole-3-yl)piperazine-1-yl)butyl)-1-oxoisoindoline-2-yl)piperidine-2,6-dione (228)

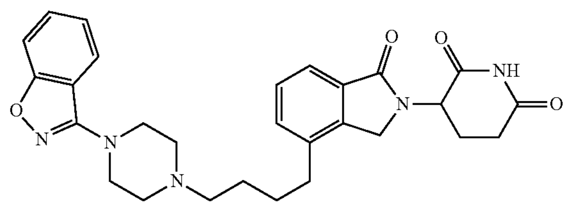

Preparation method referred synthesis method 1 and Example 21. $^1$H NMR (400 MHz, DMSO) δ 11.00 (s, 1H), 7.97 (d, J=8.0 Hz, 1H), 7.61-7.54 (m, 3H), 7.50-7.43 (m, 2H), 7.29 (dt, J=8.0, 4.0 Hz, 1H), 5.14 (dd, J=13.3, 5.1 Hz, 1H), 4.48 (d, J=17.2 Hz, 1H), 4.32 (d, J=17.2 Hz, 1H), 3.46 (t, J=4.1 Hz, 4H), 2.97-2.87 (m, 1H), 2.68 (t, J=7.5 Hz, 2H), 2.62-2.56 (m, 1H), 2.54 (t, J=4.1 Hz, 4H), 2.47-2.41 (m, 1H), 2.38 (t, J=6.8 Hz, 2H), 2.05-1.97 (m, 1H), 1.68-1.61 (m, 2H), 1.56-1.47 (m, 2H). UPLC-MS (ESI) calculated for $C_{28}H_{31}N_5O_4$ [M+H]$^+$: 502.24, found 502.53.

Example 229: 3-(4-(4-(4-(2,5-dichlorophenyl)piperazine-1-yl)butyl)-1-oxoisoindoline-2-yl) piperidine-2,6-dione (229)

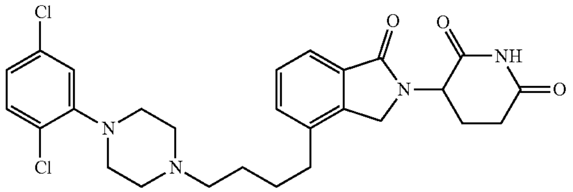 [SMILES: O=C1CCC(N2Cc3c(CCCCN4CCN(c5cc(Cl)ccc5Cl)CC4)cccc3C2=O)C(=O)N1]

Preparation method referred synthesis method 1 and Example 21. $^1$H NMR (400 MHz, DMSO-d6) δ 11.00 (s, 1H), 7.59-7.55 (m, 1H), 7.48-7.44 (m, 2H), 7.42 (d, J=8.5 Hz, 1H), 7.14 (d, J=2.4 Hz, 1H), 7.09 (dd, J=8.5, 2.4 Hz, 1H), 5.14 (dd, J=13.3, 5.1 Hz, 1H), 4.47 (d, J=17.2 Hz, 1H), 4.32 (d, J=17.2 Hz, 1H), 2.97 (t, J=5.6 Hz, 4H), 2.94-2.87 (m, 1H), 2.67 (t, J=7.5 Hz, 2H), 2.64-2.56 (m, 1H), 2.48 (t, J=5.6 Hz, 4H), 2.46-2.41 (m, 1H), 2.36 (t, J=7.5 Hz, 2H), 2.05-1.98 (m, 1H), 1.69-1.58 (m, 2H), 1.46-1.53 (m, 2H). UPLC-MS (ESI) calculated for $C_{27}H_3OCl_2N_4O_3$ [M+H]$^+$: 529.17, found 529.45.

Example 230: 3-(4-(4-(4-(benzisothiazol-3-yl)piperazine-1-yl)butyl)-1-oxoisoindoline-2-yl) piperidine-2,6-dione (230)

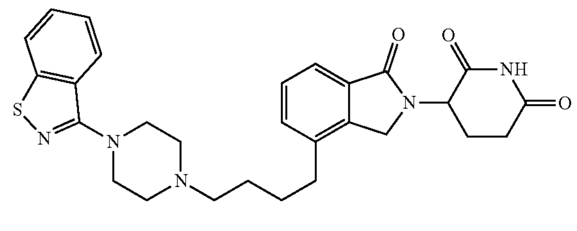 [SMILES: O=C1CCC(N2Cc3c(CCCCN4CCN(c5nsc6ccccc56)CC4)cccc3C2=O)C(=O)N1]

Preparation method referred synthesis method 1 and Example 21. $^{1}H$ NMR (400 MHz, DMSO) δ 11.00 (s, 1H), 8.08-8.02 (m, 2H), 7.61-7.52 (m, 2H), 7.51-7.40 (m, 3H), 5.14 (dd, J=13.3, 5.1 Hz, 1H), 4.48 (d, J=17.2 Hz, 1H), 4.33 (d, J=17.1 Hz, 1H), 3.48-3.38 (m, 4H), 2.99-2.86 (m, 1H), 2.69 (t, J=7.6 Hz, 2H), 2.65-2.54 (m, 5H), 2.47-2.35 (m, 3H), 2.07-1.96 (m, 1H), 1.71-1.60 (m, 2H), 1.60-1.48 (m, 2H). UPLC-MS (ESI) calculated for $C_{28}H_{31}N_5O_3S$ $[M+H]^+$: 518.21, found 518.45.

Example 231: 3-(4-(5-(4-(benzisoxazole-3-yl)piperazin-1-yl)pentyl)-1-oxoisoindoline-2-yl) piperidine-2,6-dione (231)

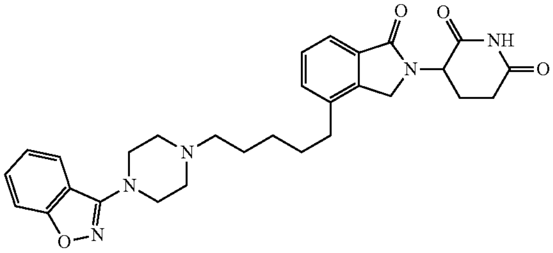 [SMILES: O=C1CCC(N2Cc3c(CCCCCN4CCN(c5noc6ccccc56)CC4)cccc3C2=O)C(=O)N1]

Preparation method referred synthesis method 1 and Example 22. $^{1}H$ NMR (400 MHz, DMSO) δ 11.00 (s, 1H), 7.97 (d, J=8.1 Hz, 1H), 7.62-7.52 (m, 3H), 7.51-7.41 (m, 2H), 7.33-7.24 (m, 1H), 5.14 (dd, J=13.3, 5.1 Hz, 1H), 4.47 (d, J=17.2 Hz, 1H), 4.31 (d, J=17.2 Hz, 1H), 3.53-3.39 (m, 4H), 2.92 (ddd, J=18.4, 13.6, 5.2 Hz, 1H), 2.66 (t, J=7.7 Hz, 2H), 2.59 (dd, J=11.2, 8.5 Hz, 1H), 2.55-2.51 (m, 4H), 2.46-2.38 (m, 1H), 2.33 (t, J=7.0 Hz, 2H), 2.04-1.97 (m, 1H), 1.64 (dt, J=15.3, 7.8 Hz, 2H), 1.57-1.44 (m, 2H), 1.41-1.30 (m, 2H). UPLC-MS (ESI) calculated for $C_{29}H_{33}N_5O_4$ $[M+H]^+$: 516.25, found 516.51.

Example 232: 3-(4-(5-(4-(benzisothiazol-3-yl)piperazin-1-yl)pentyl)-1-oxoisoindoline-2-yl) piperidine-2,6-dione (232)

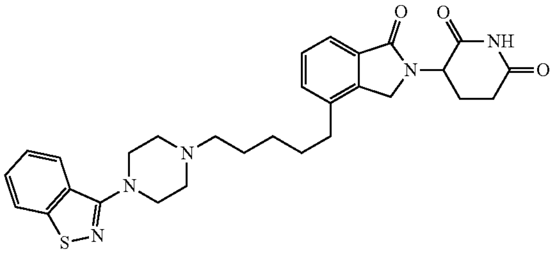 [SMILES: O=C1CCC(N2Cc3c(CCCCCN4CCN(c5nsc6ccccc56)CC4)cccc3C2=O)C(=O)N1]

Preparation method referred synthesis method 1 and Example 22. $^{1}H$ NMR (400 MHz, DMSO) δ 11.00 (s, 1H), 8.04 (t, J=7.3 Hz, 2H), 7.59-7.52 (m, 2H), 7.49-7.42 (m, 3H), 5.14 (dd, J=13.4, 5.3 Hz, 1H), 4.47 (d, J=17.2 Hz, 1H), 4.32 (d, J=17.3 Hz, 1H), 3.47-3.37 (m, 4H), 2.92-2.86 (m, 1H), 2.70-2.54 (m, 7H), 2.48-2.40 (m, 1H), 2.34 (d, J=8.1 Hz, 2H), 2.06-1.97 (m, 1H), 1.70-1.60 (m, 2H), 1.53 (dt, J=10.4, 5.1 Hz, 2H), 1.41-1.30 (m, 2H). UPLC-MS (ESI) calculated for $C_{29}H_{33}N_5O_3S$ $[M+H]^+$: 532.23, found 532.53.

Example 233: 3-(4-(5-(4-(2,5-dichlorophenyl)piperazine-1-yl)pentyl)-1-oxoisoindoline-2-yl) piperidine-2,6-dione (233)

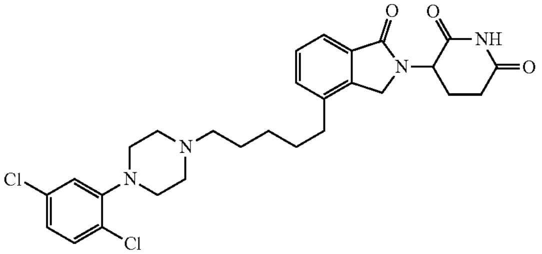 [SMILES: O=C1CCC(N2Cc3c(CCCCCN4CCN(c5cc(Cl)ccc5Cl)CC4)cccc3C2=O)C(=O)N1]

Preparation method referred synthesis method 1 and Example 22. $^{1}H$ NMR (400 MHz, DMSO-$d_6$) δ 11.00 (s, 1H), 7.58-7.54 (m, 1H), 7.44-7.48 (m, 2H), 7.42 (d, J=8.5 Hz, 1H), 7.14 (d, J=2.4 Hz, 1H), 7.09 (dd, J=8.5, 2.4 Hz, 1H), 5.14 (dd, J=13.4, 5.0 Hz, 1H), 4.47 (d, J=17.2 Hz, 1H), 4.31 (d, J=17.2 Hz, 1H), 2.99-2.95 (m, 4H), 2.94-2.87 (m, 1H), 2.70-2.63 (m, 2H), 2.61-2.57 (m, 1H), 2.49-2.47 (m, 4H), 2.45-2.38 (m, 1H), 2.49-2.47 (m, 2H), 2.01-1.98 (m, 1H), 1.67-1.59 (m, 2H), 1.54-1.46 (m, 2H), 1.39-1.31 (m, 2H). UPLC-MS (ESI) calculated for $C_{28}H_{32}Cl_2N_4O_3$ $[M+H]^+$: 543.19, found 543.47.

Example 234: 3-(4-(5-(4-(3,4-dichlorophenyl)piperazine-1-yl)pentyl)-1-oxoisoindoline-2-yl)piperidine-2,6-dione (234)

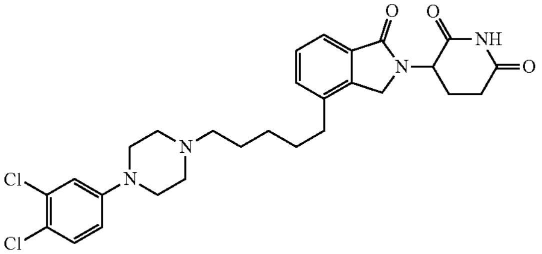 [SMILES: O=C1CCC(N2Cc3c(CCCCCN4CCN(c5ccc(Cl)c(Cl)c5)CC4)cccc3C2=O)C(=O)N1]

Preparation method referred synthesis method 1 and Example 22. $^{1}H$ NMR (400 MHz, DMSO-$d_6$) δ 11.00 (s, 1H), 7.58-7.54 (m, 1H), 7.47-7.43 (m, 2H), 7.37 (d, J=8.8 Hz, 1H), 7.10 (d, J=2.4 Hz, 1H), 6.91 (dd, J=8.8, 2.4 Hz, 1H), 5.13 (dd, J=13.2, 5.2 Hz, 1H), 4.47 (d, J=17.1 Hz, 1H), 4.30 (d, J=17.1 Hz, 1H), 3.14 (t, J=2.4 Hz, 4H), 2.97-2.88 (m, 1H), 2.65 (t, J=8.0 Hz, 2H), 2.62-2.57 (m, 1H), 2.45 (t, J=8.0 Hz, 4H), 2.42-2.37 (m, 1H), 2.29 (t, J=8.0 Hz, 2H), 2.04-1.96 (m, 1H), 1.66-1.58 (m, 2H), 1.53-1.45 (m, 2H), 1.37-1.29 (m, 2H). UPLC-MS (ESI) calculated for $C_{28}H_{32}Cl_2N_4O_3$ $[M+H]^+$: 543.19, found 543.42.

Example 235: 3-(4-(5-(4-(2,6-dichlorophenyl)piperazine-1-yl)pentyl)-1-oxoisoindoline-2-yl)piperidine-2,6-dione (235)

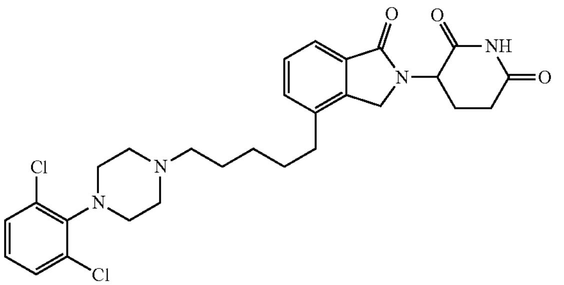 [SMILES: O=C1CCC(N2Cc3c(CCCCCN4CCN(c5c(Cl)cccc5Cl)CC4)cccc3C2=O)C(=O)N1]

Preparation method referred synthesis method 1 and Example 22. $^1$H NMR (400 MHz, DMSO-$d_6$) δ 11.00 (s, 1H), 7.57 (dd, J=6.1, 2.3 Hz, 1H), 7.49-7.44 (m, 1H), 7.41 (d, J=8.0 Hz, 2H), 7.15 (t, J=8.0 Hz, 1H), 5.14 (dd, J=13.3, 5.2 Hz, 1H), 4.47 (d, J=17.2 Hz, 1H), 4.31 (d, J=17.2 Hz, 1H), 3.12 (t, J=3.2 Hz, 4H), 2.98-2.88 (m, 1H), 2.71-2.63 (m, 2H), 2.62-2.56 (m, 1H), 2.49-2.43 (m, 4H), 2.42-2.37 (m, 1H), 2.35-2.27 (m, 2H), 2.05-1.98 (m, 1H), 1.69-1.59 (m, 2H), 1.54-1.45 (m, 2H), 1.39-1.32 (m, 2H). UPLC-MS (ESI) calculated for $C_{28}H_{32}Cl_2N_4O_3$ $[M+H]^+$: 543.19, found 543.51.

Example 236: 3-(4-(5-(4-(2,4-dichlorophenyl)piperazine-1-yl)pentyl)-1-oxoisoindoline-2-yl)piperidine-2,6-dione (236)

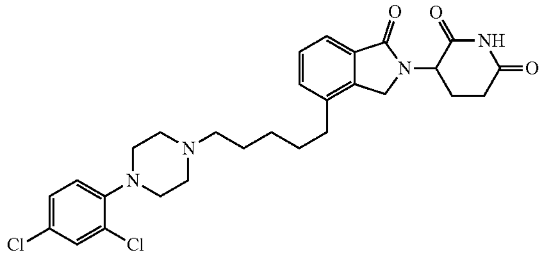 [SMILES: O=C1CCC(N2Cc3c(CCCCCN4CCN(c5ccc(Cl)cc5Cl)CC4)cccc3C2=O)C(=O)N1]

Preparation method referred synthesis method 1 and Example 22. $^1$H NMR (400 MHz, DMSO-$d_6$) δ 11.00 (s, 1H), 7.57-7.54 (m, 1H), 7.53 (d, J=2.4 Hz, 1H), 7.49-7.43 (m, 2H), 7.36 (dd, J=8.7, 2.4 Hz, 1H), 7.15 (d, J=8.7 Hz, 1H), 5.14 (dd, J=13.2, 5.1 Hz, 1H), 4.47 (d, J=17.1 Hz, 1H), 4.31 (d, J=17.1 Hz, 1H), 2.97-2.92 (m, 4H), 2.90-2.88 (m, 1H), 2.65 (t, J=4.0 Hz, 2H), 2.62-2.56 (m, 1H), 2.48-2.47 (m, 4H), 2.45-2.38 (m, 1H), 2.32 (t, J=5.6 Hz, 2H), 2.06-1.97 (m, 1H), 1.67-1.59 (m, 2H), 1.54-1.44 (m, 2H), 1.38-1.30 (m, 2H). UPLC-MS (ESI) calculated for $C_{28}H_{32}Cl_2N_4O_3$ $[M+H]^+$: 543.19, found 543.42.

Example 237: 3-(4-(5-(4-(3,5-dichlorophenyl)piperazine-1-yl)pentyl)-1-oxoisoindoline-2-yl)piperidine-2,6-dione (237)

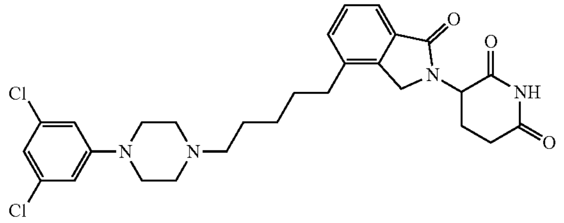 [SMILES: O=C1CCC(N2Cc3c(CCCCCN4CCN(c5cc(Cl)cc(Cl)c5)CC4)cccc3C2=O)C(=O)N1]

Preparation method referred synthesis method 1 and Example 22. $^1$H NMR (400 MHz, DMSO-$d_6$) δ 11.00 (s, 1H), 7.58-7.54 (m, 1H), 7.47-7.43 (m, 2H), 6.92 (d, J=1.6 Hz 2H), 6.85 (t, J=1.6 Hz, 1H), 5.14 (dd, J=13.3, 5.1 Hz, 1H), 4.47 (d, J=17.2 Hz, 1H), 4.31 (d, J=17.2 Hz, 1H), 3.19 (t, J=4.0 Hz, 4H), 2.97-2.88 (m, 1H), 2.65 (t, J=8 Hz, 2H), 2.62-2.57 (m, 1H), 2.43 (t, J=4.0 Hz, 4H), 2.40-2.36 (m, 1H), 2.29 (t, J=6.6 Hz, 2H), 2.04-1.97 (m, 1H), 1.67-1.59 (m, 2H), 1.53-1.46 (m, 2H), 1.38-1.30 (m, 2H). UPLC-MS (ESI) calculated for $C_{28}H_{32}C_{12}N_4O_3$ $[M+H]^+$: 543.19, found 543.43.

Example 238: 3-(4-(3-(4-(2,3-dichlorophenyl)piperazine-1-yl)propoxy)-1-oxoisoindoline-2-yl)piperidine-2,6-dione (238)

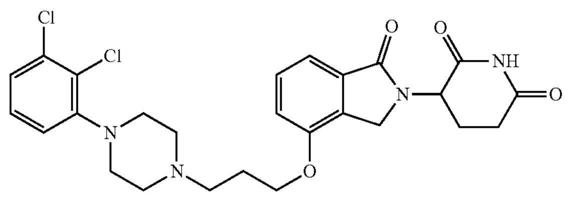 [SMILES: O=C1CCC(N2Cc3c(OCCCN4CCN(c5cccc(Cl)c5Cl)CC4)cccc3C2=O)C(=O)N1]

Preparation method referred synthesis method 6 and Example 21. $^1$H NMR (400 MHz, DMSO) δ 10.98 (s, 1H), 7.48 (t, J=7.8 Hz, 1H), 7.33-7.28 (m, 3H), 7.25 (d, J=8.1 Hz, 1H), 7.14 (dd, J=6.4, 3.2 Hz, 1H), 5.11 (dd, J=13.3, 5.1 Hz, 1H), 4.39 (d, J=17.5 Hz, 1H), 4.24 (d, J=17.4 Hz, 1H), 4.18 (t, J=6.2 Hz, 2H), 3.02-2.86 (m, 5H), 2.63-2.52 (m, 7H), 2.48-2.38 (m, 1H), 2.03-1.90 (m, 3H). UPLC-MS (ESI) calculated for $C_{26}H_{28}Cl_2N_4O_4$ $[M+H]^+$: 531.15, found 531.35.

Example 239: 3-(4-(4-(4-(benzothiophene-7-yl)piperazine-1-yl)butoxy)-1-oxoisoindoline-2-yl)piperidine-2,6-dione (239)

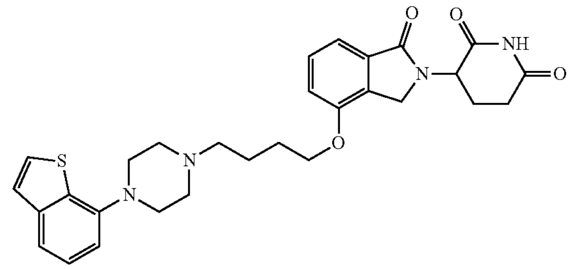 [SMILES: O=C1CCC(N2Cc3c(OCCCCN4CCN(c5cccc6ccsc56)CC4)cccc3C2=O)C(=O)N1]

Preparation method referred synthesis method 6 and Example 21. $^1$H NMR (400 MHz, DMSO) δ 10.98 (s, 1H), 7.69 (d, J=5.5 Hz, 1H), 7.61 (d, J=8.1 Hz, 1H), 7.48 (t, J=7.8 Hz, 1H), 7.39 (d, J=5.5 Hz, 1H), 7.31-7.25 (m, 3H), 6.89 (d, J=7.5 Hz, 1H), 5.10 (dd, J=13.4, 5.1 Hz, 1H), 4.39 (d, J=17.4 Hz, 1H), 4.24 (d, J=17.4 Hz, 1H), 4.17 (t, J=6.2 Hz, 2H), 3.11-2.99 (m, 4H), 2.96-2.84 (m, 1H), 2.69-2.53 (m, 5H), 2.46-2.42 (m, 3H), 2.03-1.95 (m, 1H), 1.86-1.73 (m, 2H), 1.72-1.59 (m, 2H). UPLC-MS (ESI) calculated for $C_{29}H_{32}N_4O_4S$ [M+H]$^+$: 533.21, found 533.51.

Example 240: 3-(4-(4-(4-(2,3-dichlorophenyl)piperazine-1-yl)butoxy)-1-oxoisoindoline-2-yl)piperidine-2,6-dione (240)

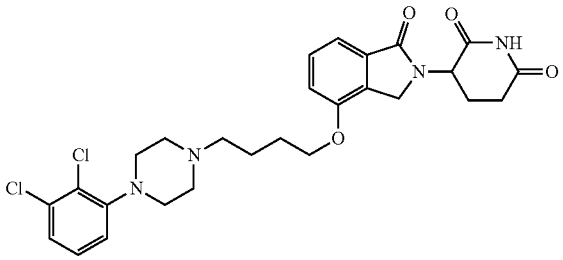

Preparation method referred synthesis method 6 and Example 21. $^1$H NMR (400 MHz, DMSO) δ 10.98 (s, 1H), 7.49 (t, J=7.8 Hz, 1H), 7.35-7.28 (m, 3H), 7.26 (d, J=8.1 Hz, 1H), 7.14 (dd, J=6.2, 3.3 Hz, 1H), 5.12 (dd, J=13.3, 5.1 Hz, 1H), 4.39 (d, J=17.5 Hz, 1H), 4.24 (d, J=17.5 Hz, 1H), 4.16 (t, J=6.3 Hz, 2H), 3.06-2.85 (m, 5H), 2.71-2.52 (m, 5H), 2.49-2.38 (m, 3H), 1.99 (td, J=5.5, 2.7 Hz, 1H), 1.85-1.74 (m, 2H), 1.69-1.59 (m, 2H). UPLC-MS (ESI) calculated for $C_{27}H_{30}Cl_2N_4O_4$ [M+H]$^+$: 545.16, found 545.37.

Example 241: 3-(4-(4-(4-(6-fluorobenzisoxazole-3-yl)piperidin-1-yl)butoxy)-1-oxoisoindoline-2-yl)piperidine-2,6-dione (241)

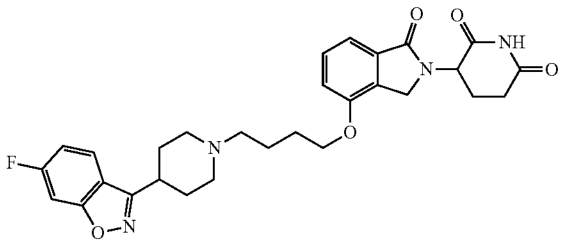

Preparation method referred synthesis method 6 and Example 21. $^1$H NMR (400 MHz, DMSO) δ 10.98 (s, 1H), 7.99 (dd, J=8.7, 5.3 Hz, 1H), 7.69 (dd, J=9.1, 2.1 Hz, 1H), 7.48 (t, J=7.8 Hz, 1H), 7.35-7.20 (m, 3H), 5.11 (dd, J=13.3, 5.0 Hz, 1H), 4.38 (d, J=17.4 Hz, 1H), 4.23 (d, J=17.4 Hz, 1H), 4.16 (t, J=6.2 Hz, 2H), 3.23-3.12 (m, 2H), 3.05 (d, J=11.0 Hz, 2H), 2.95-2.86 (m, 1H), 2.62-2.50 (m, 2H), 2.47-2.40 (m, 1H), 2.30-2.14 (m, 2H), 2.10-2.01 (m, 2H), 1.98 (ddd, J=12.3, 5.4, 2.1 Hz, 1H), 1.92-1.82 (m, 2H), 1.78 (dd, J=13.9, 6.3 Hz, 2H), 1.72-1.60 (m, 2H). UPLC-MS (ESI) calculated for $C_{29}H_{31}FN_4O_5$ [M+H]$^+$: 535.23, found 535.49.

Example 242: 3-(4-(4-(4-(benzisoxazole-3-yl)piperazine-1-yl)butoxy)-1-oxoisoindoline-2-yl)piperidine-2,6-dione (242)

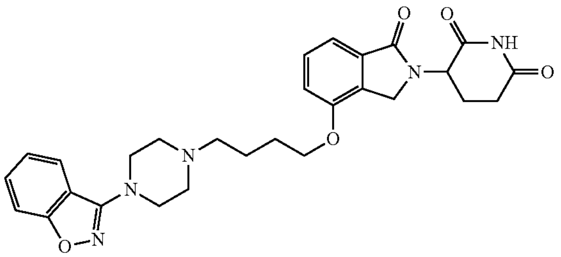 [SMILES: O=C1CCC(N2Cc3c(OCCCCN4CCN(c5noc6ccccc56)CC4)cccc3C2=O)C(=O)N1]

Preparation method referred synthesis method 6 and Example 21. $^1$H NMR (400 MHz, DMSO) δ 10.98 (s, 1H), 7.97 (d, J=8.1 Hz, 1H), 7.58 (d, J=3.8 Hz, 2H), 7.48 (t, J=7.8 Hz, 1H), 7.35-7.19 (m, 3H), 5.11 (dd, J=13.3, 5.1 Hz, 1H), 4.39 (d, J=17.4 Hz, 1H), 4.23 (d, J=17.4 Hz, 1H), 4.16 (t, J=6.3 Hz, 2H), 3.56-3.38 (m, 4H), 2.96-2.84 (m, 1H), 2.58 (d, J=13.0 Hz, 5H), 2.47-2.34 (m, 3H), 2.03-1.94 (m, 1H), 1.85-1.73 (m, 2H), 1.70-1.60 (m, 2H). UPLC-MS (ESI) calculated for $C_{28}H_{31}N_5O_5$ [M+H]$^+$: 518.23, found 518.47.

Example 243: 3-(4-(4-(4-(3,4-dichlorophenyl)piperazine-1-yl)butoxy)-1-oxoisoindoline-2-yl)piperidine-2,6-dione (243)

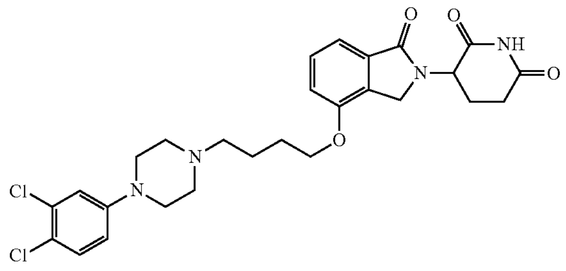 [SMILES: O=C1CCC(N2Cc3c(OCCCCN4CCN(c5ccc(Cl)c(Cl)c5)CC4)cccc3C2=O)C(=O)N1]

Preparation method referred synthesis method 6 and Example 21. ¹H NMR (400 MHz, DMSO-$d_6$) δ 10.98 (s, 1H), 7.47 (t, J=7.9 Hz, 1H), 7.38 (d, J=9.0 Hz, 1H), 7.30 (d, J=7.9 Hz, 1H), 7.24 (d, J=7.9 Hz, 1H), 7.11 (d, J=2.8 Hz, 1H), 6.92 (dd, J=9.0, 2.8 Hz, 1H), 5.11 (dd, J=13.3, 5.1 Hz, 1H), 4.38 (d, J=17.4 Hz, 1H), 4.23 (d, J=17.4 Hz, 1H), 4.15 (t, J=6.3 Hz, 2H), 3.15 (t, J=4.0 Hz, 4H), 2.96-2.87 (m, 1H), 2.61-2.55 (m, 1H), 2.47 (t, J=4.0 Hz, 4H), 2.40-2.44 (m, 1H), 2.37 (t, J=6.4 Hz, 2H), 2.03-1.95 (m, 1H), 1.82-1.73 (m, 2H), 1.67-1.58 (m, 2H). UPLC-MS (ESI) calculated for $C_{27}H_3OCl_2N_4O_4$ $[M+H]^+$: 545.16, found 545.49.

Example 244: 4-(3,5-dichlorophenyl)-1-(4-(2-(2,6-dioxopiperidine-3-yl)-1-oxoisoindoline-4-yl)butyl) piperidine-4-carbonitrile 244)

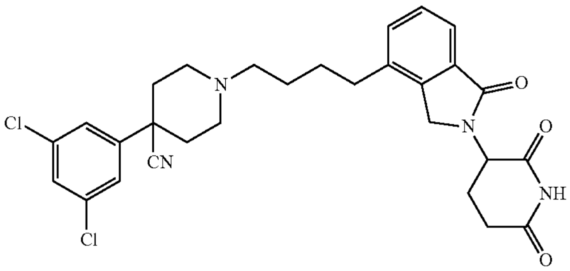 [SMILES: N#CC1(c2cc(Cl)cc(Cl)c2)CCN(CCCCc2cccc3c2CN(C2CCC(=O)NC2=O)C3=O)CC1]

Preparation method referred synthesis method 1 and Example 51. ¹H NMR (400 MHz, DMSO) δ 11.00 (s, 1H), 7.68 (s, 1H), 7.60 (s, 2H), 7.57 (dt, J=7.7, 3.9 Hz, 1H), 7.52-7.41 (m, 2H), 5.14 (dd, J=13.2, 5.0 Hz, 1H), 4.47 (d, J=17.2 Hz, 1H), 4.32 (d, J=17.2 Hz, 1H), 3.14-2.86 (m, 3H), 2.68 (t, J=7.0 Hz, 2H), 2.60 (dd, J=17.2, 1.6 Hz, 1H), 2.47-2.36 (m, 3H), 2.30-2.10 (m, 4H), 2.10-1.87 (m, 3H), 1.74-1.42 (m, 4H). UPLC-MS (ESI) calculated for $C_{29}H_3OCl_2N_4O_3$ $[M+H]^+$: 553.17, found 553.49.

Example 245: 4-(2-chloro-4-methoxyphenyl)-1-(4-(2-(2,6-dioxopiperidine-3-yl)-1-oxoisoindoline-4-yl) butyl)piperidine-4-carbonitrile (245)

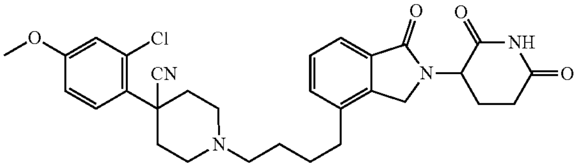 [SMILES: COc1ccc(C2(C#N)CCN(CCCCc3cccc4c3CN(C3CCC(=O)NC3=O)C4=O)CC2)c(Cl)c1]

Preparation method reference synthesis method 1 and examples 51. 1H NMR (500 MHz, DMSO) δ 10.99 (s, 1H), 7.57 (dd, J=5.7, 2.9 Hz, 1H), 7.48-7.45 (m, 2H), 7.42 (d, J=9.0 Hz, 1H), 7.13 (d, J=2.7 Hz, 1H), 6.98 (dd, J=8.9, 2.7 Hz, 1H), 5.13 (dd, J=13.3, 5.1 Hz, 1H), 4.47 (d, J=17.1 Hz, 1H), 4.32 (d, J=17.1 Hz, 1H), 3.79 (s, 3H), 2.98 (d, J=11.1 Hz, 2H), 2.94-2.86 (m, 1H), 2.67 (t, J=7.7 Hz, 2H), 2.58 (d, J=17.0 Hz, 1H), 2.44-2.37 (m, 5H), 2.30 (t, J=11.9 Hz, 2H), 2.03-1.97 (m, 1H), 1.91 (t, J=14.0 Hz, 2H), 1.63 (d, J=7.9 Hz, 2H), 1.56-1.46 (m, 2H). UPLC-MS (ESI) calculated for $C_{30}H_{33}ClN_4O_4$ $[M+H]^+$: 549.22, found 549.43.

Example 246: 4-(2,5-dimethoxyphenyl)-1-(4-(2-(2,6-dioxopiperidine-3-yl)-1-oxoisoindoline-4-yl)butyl) piperidine-4-carbonitrile (246)

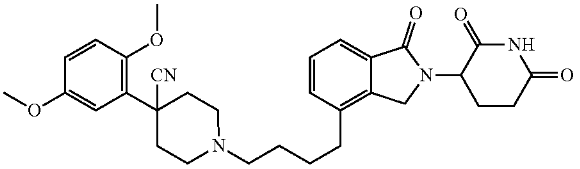 [SMILES: COc1ccc(OC)c(C2(C#N)CCN(CCCCc3cccc4c3CN(C3CCC(=O)NC3=O)C4=O)CC2)c1]

Preparation method referred synthesis method 1 and Example 51. ¹H NMR (400 MHz, DMSO) δ 10.98 (s, 1H), 7.56 (dt, J=7.7, 3.9 Hz, 1H), 7.49-7.44 (m, 2H), 7.06 (d, J=9.0 Hz, 1H), 6.95-6.90 (m, 1H), 6.84 (d, J=2.9 Hz, 1H), 5.13 (dd, J=13.3, 5.1 Hz, 1H), 4.47 (d, J=17.2 Hz, 1H), 4.31 (d, J=17.1 Hz, 1H), 3.80 (s, 3H), 3.72 (s, 3H), 2.90 (dd, J=22.3, 8.8 Hz, 3H), 2.67 (t, J=7.6 Hz, 2H), 2.58 (d, J=17.6 Hz, 1H), 2.41 (dd, J=17.8, 4.7 Hz, 3H), 2.27 (d, J=11.5 Hz, 4H), 2.04-1.96 (m, 1H), 1.90 (d, J=13.3 Hz, 2H), 1.62 (dd, J=13.9, 6.7 Hz, 2H), 1.55-1.45 (m, 2H). UPLC-MS (ESI) calculated for $C_{31}H_{36}N_4O_5$ $[M+H]^+$: 545.27, found 545.56.

Example 247: 4-(2,5-dimethoxyphenyl)-1-(5-(2-(2,6-dioxopiperidine-3-yl)-1-oxoisoindoline-4-yl)pentyl)piperidine-4-carbonitrile (247)

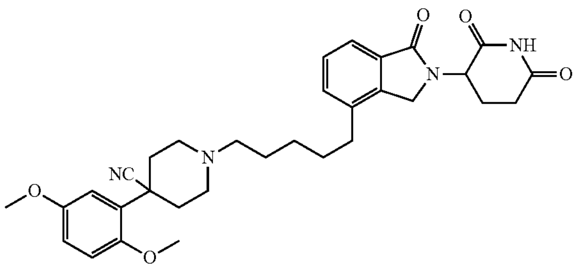 [SMILES: COc1ccc(OC)c(C2(C#N)CCN(CCCCCc3cccc4c3CN(C3CCC(=O)NC3=O)C4=O)CC2)c1]

Preparation method reference synthesis method 1 and examples 51. $^1$H NMR (400 MHz, DMSO) δ 11.00 (s, 1H), 7.56 (dt, J=7.7, 3.9 Hz, 1H), 7.51-7.39 (m, 2H), 7.06 (d, J=8.9 Hz, 1H), 6.93 (dd, J=8.9, 2.9 Hz, 1H), 6.84 (d, J=2.9 Hz, 1H), 5.13 (dd, J=13.2, 5.0 Hz, 1H), 4.46 (d, J=17.2 Hz, 1H), 4.31 (d, J=17.2 Hz, 1H), 3.80 (s, 3H), 3.73 (s, 3H), 3.04-2.82 (m, 3H), 2.72-2.55 (m, 3H), 2.45-2.40 (m, 1H), 2.39-2.30 (m, 2H), 2.25 (t, J=3.6 Hz, 4H), 2.04-1.97 (m, 1H), 1.88 (t, J=12.2, 10.8 Hz, 2H), 1.68-1.59 (m, 2H), 1.53-1.45 (m, 2H), 1.39-1.28 (m, 2H). UPLC-MS (ESI) calculated for $C_{32}H_{38}N_4O_5$ [M+H]$^+$: 559.28, found 559.51.

Example 248: 4-(2,5-dichlorophenyl)-1-(5-(2-(2,6-dioxopiperidine-3-yl)-1-oxoisoindoline-4-yl)pentyl) piperidine-4-carbonitrile (248)

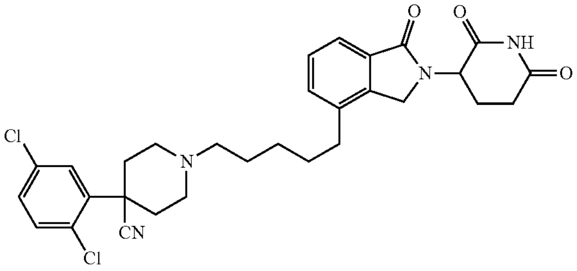 [SMILES: N#CC1(c2cc(Cl)ccc2Cl)CCN(CCCCCc2cccc3c2CN(C2CCC(=O)NC2=O)C3=O)CC1]

Preparation method reference synthesis method 1 and examples 51. $^1$H NMR (400 MHz, DMSO-$d_6$) δ 11.00 (s, 1H), 7.60 (d, J=8.5 Hz, 1H), 7.58-7.50 (m, 3H), 7.47-7.43 (m, 2H), 5.13 (dd, J=13.2, 5.1 Hz, 1H), 4.46 (d, J=17.2 Hz, 1H), 4.30 (d, J=17.2 Hz, 1H), 3.00 (d, J=12.5 Hz, 2H), 2.95-2.87 (m, 1H), 2.69-2.62 (m, 2H), 2.60-2.56 (m, 1H), 2.45-2.41 (m, 3H), 2.39-2.32 (m, 2H), 2.32-2.20 (m, 2H), 2.05-1.89 (m, 3H), 1.66-1.59 (m, 2H), 1.56-1.44 (m, 2H), 1.41-1.28 (m, 2H). UPLC-MS (ESI) calculated for $C_{30}H_{32}Cl_2N_4O_3$ [M+H]$^+$: 567.19, found 567.48.

Example 249: 4-(3,4-dimethoxyphenyl)-1-(5-(2-(2,6-dioxopiperidine-3-yl)-1-oxoisoindoline-4-yl)pentyl)piperidine-4-carbonitrile (249)

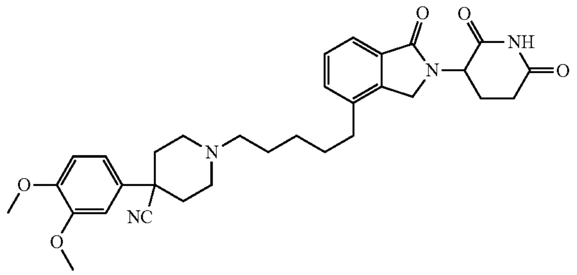 [SMILES: COc1ccc(C2(C#N)CCN(CCCCCc3cccc4c3CN(C3CCC(=O)NC3=O)C4=O)CC2)cc1OC]

Preparation method referred synthesis method 1 and Example 51. $^1$H NMR (400 MHz, DMSO-$d_6$) δ 11.00 (s, 1H), 7.56 (dd, J=5.8, 2.8 Hz, 1H), 7.48-7.31 (m, 2H), 7.04-7.03 (m, 2H), 6.97 (d, J=9.1 Hz, 1H), 5.13 (dd, J=13.3, 5.1 Hz, 1H), 4.47 (d, J=17.2 Hz, 1H), 4.31 (d, J=17.2 Hz, 1H), 3.78 (s, 3H), 3.75 (s, 3H), 3.00-2.93 (m, 2H), 2.92-2.88 (m, 1H), 2.65 (t, J=7.2 Hz, 2H), 2.61-2.56 (m, 1H), 2.45-2.41 (m, 1H), 2.34 (t, J=7.2 Hz, 2H), 2.22 (t, J=11.4 Hz, 2H), 2.09 (d, J=13.4 Hz, 2H), 2.05-1.89 (m, 3H), 1.67-1.59 (m, 2H), 1.53-1.46 (m, 2H), 1.37-1.30 (m, 2H). UPLC-MS (ESI) calculated for $C_{32}H_{38}N_4O_5$ [M+H]$^+$: 559.28, found 559.59.

Example 250: 4-(2,6-dichlorophenyl)-1-(5-(2-(2,6-dioxopiperidin-3-yl)-1-oxoisoindoline-4-yl)pentyl) piperidine-4-carbonitrile 1

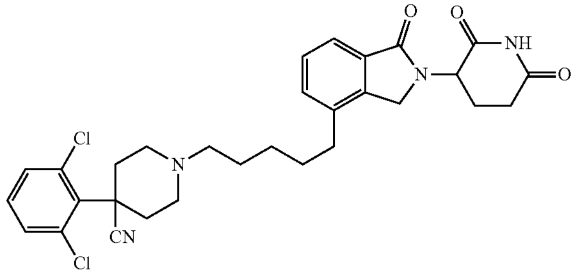 [SMILES: N#CC1(c2c(Cl)cccc2Cl)CCN(CCCCCc2cccc3c2CN(C2CCC(=O)NC2=O)C3=O)CC1]

Preparation method referred synthesis method 1 and Example 51. $^1$H NMR (400 MHz, DMSO-$d_6$) δ 11.00 (s, 1H), 7.61-7.52 (m, 3H), 7.48-7.43 (m, 2H), 7.40 (dd, J=8.5, 7.6 Hz, 1H), 5.13 (dd, J=13.3, 5.1 Hz, 1H), 4.47 (d, J=17.2 Hz, 1H), 4.31 (d, J=17.2 Hz, 1H), 3.11-3.03 (m, 2H), 2.97-2.88 (m, 1H), 2.70-2.63 (m, 2H), 2.61-2.57 (m, 1H), 2.55-2.52 (m, 4H), 2.47-2.43 (m, 1H), 2.42-2.31 (m, 4H), 2.04-1.98 (m, 1H), 1.67-1.59 (m, 2H), 1.55-1.47 (m, 2H), 1.37-1.30 (m, 2H). UPLC-MS (ESI) calculated for $C_{30}H_{32}Cl_2N_4O_3$ [M+H]$^+$: 567.19, found 567.48.

Example 251: 4-(3,5-dichlorophenyl)-1-(5-(2-(2,6-dioxopiperidin-3-yl)-1-oxoisoindoline-4-yl)pentyl) piperidine-4-carbonitrile (251)

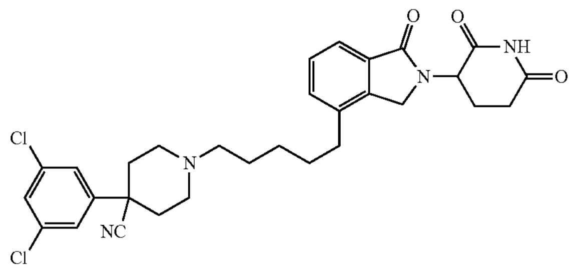 [SMILES: N#CC1(c2cc(Cl)cc(Cl)c2)CCN(CCCCCc2cccc3c2CN(C2CCC(=O)NC2=O)C3=O)CC1]

Preparation method referred synthesis method 1 and Example 51. $^1$H NMR (400 MHz, DMSO-$d_6$) δ 11.00 (s, 1H), 7.67 (d, J=1.6 Hz, 1H), 7.60 (d, J=1.6 Hz, 2H), 7.56 (dd, J=7.7, 4.0 Hz, 1H), 7.48-7.43 (m, 2H), 5.14 (dd, J=13.3, 5.0 Hz, 1H), 4.47 (d, J=17.2 Hz, 1H), 4.31 (d, J=17.2 Hz, 1H), 3.04-2.87 (m, 3H), 2.70-2.63 (m, 2H), 2.60-2.56 (m, 1H), 2.45-2.41 (m, 1H), 2.40-2.29 (m, 2H), 2.29-2.09 (m, 4H), 2.06-1.91 (m, 3H), 1.69-1.58 (m, 2H), 1.57-1.43 (m, 2H), 1.37-1.29 (m, 2H). UPLC-MS (ESI) calculated for $C_{30}H_{32}Cl_2N_4O_3$ [M+H]$^+$: 567.19, found 567.52.

Example 252: 1-(5-(2-(2,6-dioxopiperidin-3-yl)-1-oxoisoindolin-4-yl)pentyl)-4-(4-(((S)-tetrahydro-furan-3-yl)oxy)phenyl)piperidine-4-carbonitrile 252

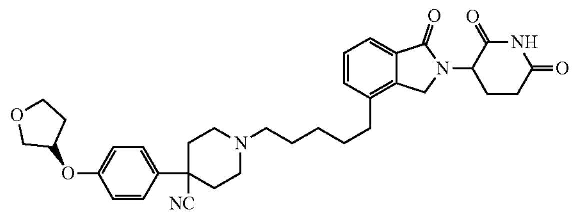

Preparation method referred synthesis method 1 and Example 51. $^1$H NMR (400 MHz, DMSO) δ 11.00 (s, 1H), 7.58-7.53 (m, 1H), 7.49-7.39 (m, 4H), 6.96 (d, J=8.8 Hz, 2H), 5.14 (dd, J=13.2, 5.1 Hz, 1H), 5.05-5.00 (m, 1H), 4.47 (d, J=17.2 Hz, 1H), 4.31 (d, J=17.2 Hz, 1H), 3.92-3.71 (m, 4H), 3.00-2.86 (m, 3H), 2.71-2.54 (m, 3H), 2.47-2.30 (m, 3H), 2.27-2.16 (m, 3H), 2.11-1.84 (m, 6H), 1.65-1.57 (m, 2H), 1.55-1.44 (m, 2H), 1.38-1.29 (m, 2H). UPLC-MS (ESI) calculated for $C_{34}H_{40}N_4O_5$ $[M+H]^+$:585.30, found 585.56.

Example 253: 1-(4-(2-(2,6-dioxopiperidin-3-yl)-1-oxoisoindolin-4-yl)butyl)-4-(2,3,4-trimethoxyphenyl)piperidine-4-carbonitrile (253)

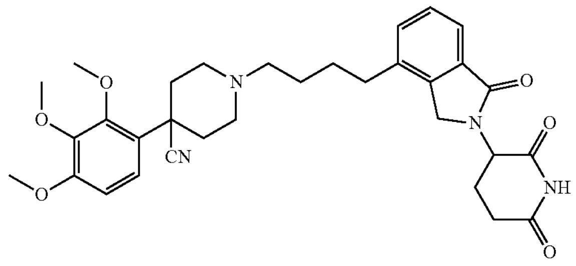 [SMILES: COc1ccc(C2(C#N)CCN(CCCCc3cccc4c3CN(C3CCC(=O)NC3=O)C4=O)CC2)c(OC)c1OC]

Preparation method referred synthesis method 1 and Example 51. $^1$H NMR (400 MHz, DMSO) δ 11.00 (s, 1H), 7.64-7.53 (m, 1H), 7.53-7.40 (m, 2H), 6.87 (dd, J=76.8, 8.9 Hz, 2H), 5.13 (dd, J=13.2, 5.0 Hz, 1H), 4.47 (d, J=17.2 Hz, 1H), 4.32 (d, J=17.1 Hz, 1H), 3.92 (s, 3H), 3.80 (s, 3H), 3.76 (s, 3H), 3.03-2.84 (m, 3H), 2.67 (t, J=7.4 Hz, 2H), 2.62-2.53 (m, 1H), 2.48-2.12 (m, 7H), 2.06-1.95 (m, 1H), 1.91-1.74 (m, 2H), 1.70-1.56 (m, 2H), 1.56-1.44 (m, 2H). UPLC-MS (ESI) calculated for $C_{32}H_{38}N_4O_6$ $[M+H]^+$: 575.28, found 575.57.

Example 254: 1-(5-(2-(2,6-dioxopiperidin-3-yl)-1-oxoisoindolin-4-yl)pentyl)-4-(2,3,4-trimethoxyphenyl)piperidine-4-carbonitrile (254)

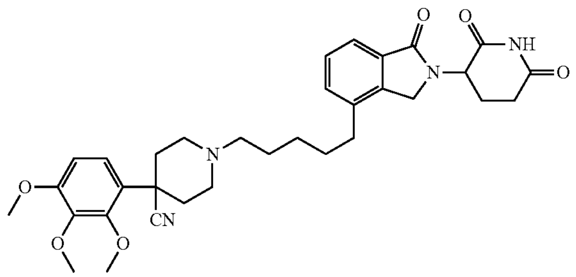 [SMILES: COc1ccc(C2(C#N)CCN(CCCCCc3cccc4c3CN(C3CCC(=O)NC3=O)C4=O)CC2)c(OC)c1OC]

Preparation method referred synthesis method 1 and Example 51. $^1$H NMR (400 MHz, DMSO) δ 11.00 (s, 1H), 7.61-7.52 (m, J=2.9 Hz, 1H), 7.50-7.41 (m, 2H), 6.88 (dd, J=74.6, 8.9 Hz, 2H), 5.18-5.08 (m, 1H), 4.46 (d, J=17.2 Hz, 1H), 4.31 (d, J=17.2 Hz, 1H), 3.92 (s, 3H), 3.80 (s, 3H), 3.76 (s, 3H), 3.06-2.85 (m, 3H), 2.71-2.54 (m, 3H), 2.46-2.12 (m, 7H), 2.05-1.96 (m, 1H), 1.91-1.73 (m, 2H), 1.70-1.57 (m, 2H), 1.56-1.41 (m, 3H), 1.38-1.27 (m, 2H). UPLC-MS (ESI) calculated for $C_{33}H_{40}N_4O_6$ $[M+H]^+$: 589.30, found 589.58.

Example 255: 4-(2,4-dimethoxyphenyl)-1-(5-(2-(2,6-dioxopiperidin-3-yl)-1-oxoisoindoline-4-yl)pentyl) piperidine-4-carbonitrile (255)

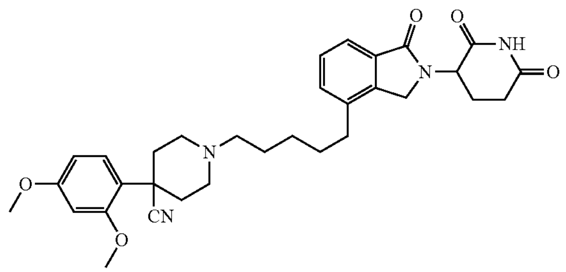 [SMILES: COc1ccc(C2(C#N)CCN(CCCCCc3cccc4c3CN(C3CCC(=O)NC3=O)C4=O)CC2)c(OC)c1]

Preparation method referred synthesis method 1 and Example 51. $^1$H NMR (400 MHz, DMSO) δ 11.00 (s, 1H), 7.60-7.52 (m, 1H), 7.49-7.41 (m, 2H), 7.19 (d, J=8.7 Hz, 1H), 6.70-6.41 (m, 1H), 6.59-6.51 (m, 1H), 5.14 (dd, J=13.2, 5.1 Hz, 1H), 4.46 (d, J=17.2 Hz, 1H), 4.31 (d, J=17.2 Hz, 1H), 3.84 (s, 3H), 3.77 (s, 3H), 3.05-2.82 (m, 3H), 2.70-2.54 (m, 3H), 2.46-2.13 (m, 7H), 2.06-1.95 (m, 1H), 1.92-1.76 (m, 2H), 1.68-1.57 (m, 2H), 1.56-1.42 (m, 2H), 1.38-1.26 (m, 2H). UPLC-MS (ESI) calculated for $C_{32}H_{38}N_4O_5$ $[M+H]^+$: 559.28, found 559.54.

Example 256: 4-(2,4-dimethoxyphenyl)-1-(4-(2-(2,6-dioxopiperidin-3-yl)-1-oxoisoindoline-4-yl)butyl)piperidine-4-carbonitrile (256)

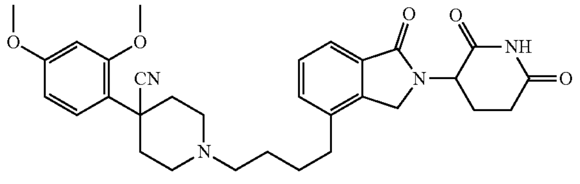 [SMILES: COc1ccc(C2(C#N)CCN(CCCCc3cccc4c3CN(C3CCC(=O)NC3=O)C4=O)CC2)c(OC)c1]

Preparation method referred synthesis method 1 and Example 51. $^1H$ NMR (400 MHz, DMSO) δ 11.00 (s, 1H), 7.60-7.53 (m, 1H), 7.49-7.43 (m, 2H), 7.19 (d, J=8.7 Hz, 1H), 6.69-6.30 (m, 1H), 6.57-6.51 (m, 1H), 5.13 (dd, J=13.2, 5.0 Hz, 1H), 4.47 (d, J=17.1 Hz, 1H), 4.31 (d, J=17.1 Hz, 1H), 3.84 (s, 3H), 3.77 (s, 3H), 2.99-2.82 (m, 3H), 2.67 (t, J=7.3 Hz, 2H), 2.62-2.53 (m, 1H), 2.46-2.11 (m, 8H), 2.05-1.94 (m, 1H), 1.89-1.77 (m, 2H), 1.69-1.56 (m, 2H), 2.46-2.11 (m, 2H). UPLC-MS (ESI) calculated for $C_{31}H_{36}N_4O_5$ $[M+H]^+$: 545.27, found 545.53.

Example 257: 4-(2-chloro-4-(trifluoromethoxy)phenyl)-1-(4-(2-(2,6-dioxopiperidin-3-yl)-1-oxoisoindolin-4-yl)butyl)piperidine-4-carbonitrile (257)

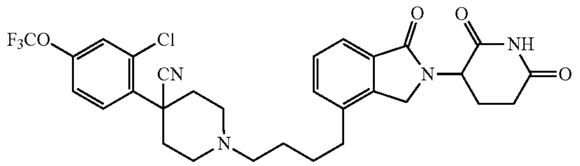 [SMILES: N#CC1(c2ccc(OC(F)(F)F)cc2Cl)CCN(CCCCc2cccc3c2CN(C2CCC(=O)NC2=O)C3=O)CC1]

Preparation method referred synthesis method 1 and Example 51. $^1H$ NMR (400 MHz, DMSO) δ 11.00 (s, 1H), 7.72-7.64 (m, 2H), 7.59-7.54 (m, 1H), 7.51-7.44 (m, 3H), 5.13 (dd, J=13.3, 5.1 Hz, 1H), 4.47 (d, J=17.1 Hz, 1H), 4.31 (d, J=17.1 Hz, 1H), 3.06-2.84 (m, 3H), 2.73-2.54 (m, 3H), 2.47-2.23 (m, 7H), 2.04-1.90 (m, 3H), 1.67-1.58 (m, 2H), 1.56-1.44 (m, 2H). UPLC-MS (ESI) calculated for $C_{30}H_{30}ClF_3N_4O_4$ $[M+H]^+$: 603.19, found 603.51.

Example 258: 4-(2-chloro-4-(trifluoromethoxy)phenyl)-1-(5-(2-(2,6-dioxopiperidin-3-yl)-1-oxoisoindolin-4-yl)pentyl)piperidine-4-carbonitrile (258)

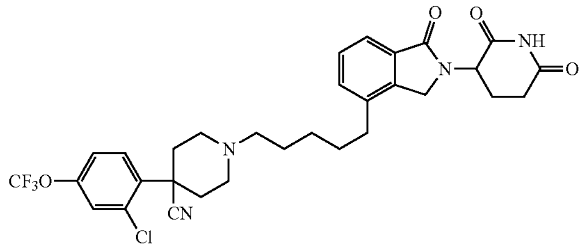

Preparation method referred synthesis method 1 and Example 51. $^1H$ NMR (400 MHz, DMSO) δ 10.99 (s, 1H), 7.23-7.64 (m, 2H), 7.58-7.63 (m, 1H), 7.52-7.41 (m, 3H), 5.14 (dd, J=13.3, 5.0 Hz, 1H), 4.46 (d, J=17.2 Hz, 1H), 4.31 (d, J=17.1 Hz, 1H), 3.05-2.87 (m, 3H), 2.69-2.56 (m, 3H), 2.47-2.22 (m, 7H), 2.06-1.89 (m, 3H), 1.69-1.57 (m, 2H), 1.55-1.43 (m, 2H), 1.41-1.29 (m, 2H). UPLC-MS (ESI) calculated for $C_{31}H_{32}ClF_3N_4O_4$ $[M+H]^+$: 617.21, found 617.58.

Example 259: 4-(2,3-dimethoxyphenyl)-1-(4-(2-(2,6-dioxopiperidin-3-yl)-1-oxoisoindoline-4-yl)butyl)piperidine-4-carbonitrile (259)

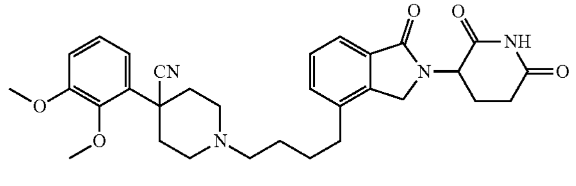 [SMILES: COc1cccc(C2(C#N)CCN(CCCCc3cccc4c3CN(C3CCC(=O)NC3=O)C4=O)CC2)c1OC]

Preparation method referred synthesis method 1 and Example 51. $^1H$ NMR (400 MHz, DMSO) δ 10.99 (s, 1H), 7.56 (dt, J=7.7, 3.8 Hz, 1H), 7.49-7.42 (m, 2H), 7.13-7.04 (m, 2H), 6.90 (dd, J=7.4, 1.9 Hz, 1H), 5.13 (dd, J=13.3, 5.1 Hz, 1H), 4.46 (d, J=17.2 Hz, 1H), 4.31 (d, J=17.2 Hz, 1H), 3.87 (s, 3H), 3.83 (s, 3H), 2.98-2.85 (m, 3H), 2.67 (t, J=7.6 Hz, 2H), 2.62-2.55 (m, 1H), 2.47-2.33 (m, 3H), 2.33-2.16 (m, 4H), 2.04-1.95 (m, 1H), 1.84 (t, J=12.3 Hz, 2H), 1.68-1.56 (m, 2H), 1.55-1.45 (m, 2H). UPLC-MS (ESI) calculated for $C_{31}H_{36}N_4O_5$ $[M+H]^+$: 545.27, found 545.49.

Example 260: 4-(2,3-dimethoxyphenyl)-1-(5-(2-(2,6-dioxopiperidin-3-yl)-1-oxoisoindoline-4-yl)pentyl)piperidine-4-carbonitrile (260)

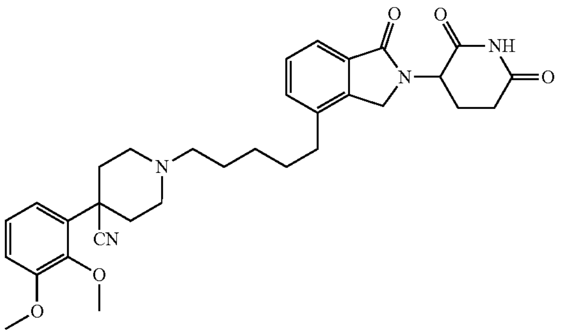 [SMILES: COc1cccc(C2(C#N)CCN(CCCCCc3cccc4c3CN(C3CCC(=O)NC3=O)C4=O)CC2)c1OC]

Preparation method referred synthesis method 1 and Example 51. $^{1}$H NMR (400 MHz, DMSO) δ 11.00 (s, 1H), 7.57 (dd, J=7.1, 4.0 Hz, 1H), 7.51-7.42 (m, 2H), 7.14-7.12 (m, 2H), 6.90 (d, J=7.1 Hz, 1H), 5.14 (dd, J=13.2, 5.2 Hz, 1H), 4.47 (d, J=17.1 Hz, 1H), 4.31 (d, J=17.0 Hz, 1H), 3.89 (s, 3H), 3.84 (s, 3H), 3.14-3.05 (m, 2H), 2.99-2.89 (m, 1H), 2.68-2.57 (m, 3H), 2.49-2.36 (m, 3H), 2.36-2.07 (m, 4H), 2.04-1.98 (m, 1H), 1.88-1.84 (m, 2H), 1.68-1.58 (m, 2H), 1.53-1.46 (m, 2H), 1.27-1.20 (m, 2H). UPLC-MS (ESI) calculated for $C_{32}H_{38}N_4O_5$ [M+H]$^+$: 559.28, found 559.56.

Example 261: 1-(4-(2-(2,6-dioxopiperidin-3-yl)-1-oxoisoindolin-4-yl)butyl)-4-sym-trimethylphenylpiperidine-4-carbonitrile (261)

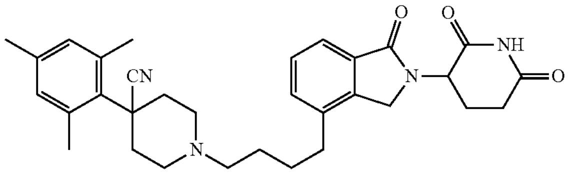 [SMILES: Cc1cc(C)c(C2(C#N)CCN(CCCCc3cccc4c3CN(C3CCC(=O)NC3=O)C4=O)CC2)c(C)c1]

Preparation method referred synthesis method 1 and Example 51. $^{1}$H NMR (400 MHz, DMSO-$d_6$) δ 10.99 (s, 1H), 7.57 (dd, J=5.6, 2.7 Hz, 1H), 7.51-7.42 (m, 2H), 6.86 (s, 2H), 5.13 (dd, J=13.1, 4.9 Hz, 1H), 4.47 (d, J=17.0 Hz, 1H), 4.32 (d, J=17.1 Hz, 1H), 3.01-2.86 (m, 3H), 2.73-2.64 (m, 2H), 2.63-2.56 (m, 1H), 2.51 (s, 6H), 2.49-2.39 (m, 3H), 2.39-2.21 (m, 6H), 2.17 (s, 3H), 2.09-2.03 (m, 1H), 1.69-1.58 (m, 2H), 1.56-1.43 (m, 2H). UPLC-MS (ESI) calculated for $C_{32}H_{38}N_4O_3$ [M+H]$^+$: 527.29, found 527.56.

Example 262: 1-(5-(2-(2,6-dioxopiperidin-3-yl)-1-oxoisoindolin-4-yl)pentyl)-4-sym-trimethylphenylpiperidine-4-carbonitrile (262)

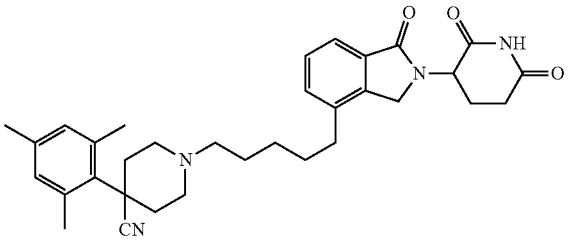 [SMILES: Cc1cc(C)c(C2(C#N)CCN(CCCCCc3cccc4c3CN(C3CCC(=O)NC3=O)C4=O)CC2)c(C)c1]

The preparation method referred to synthesis method 1 and Example 51. (q, J=4.0, 3.5 Hz, 2H), 6.86 (s, 2H), 5.14 (dd, J=13.4, 5.0 Hz, 1H), 4.47 (d, J=17.2 Hz, 1H), 4.31 (d, J=17.3 Hz, 1H), 3.00-2.86 (m, 3H), 2.69-2.56 (m, 3H), 2.51 (s, 6H), 2.49-2.36 (m, 3H), 2.36-2.20 (m, 6H), 2.18 (s, 3H), 2.05-1.97 (m, 1H), 1.70-1.58 (m, 2H), 1.56-1.44 (m, 2H), 1.41-1.29 (m, 2H). UPLC-MS (ESI) calculated for $C_{33}H_{40}N_4O_3$ [M+H]$^+$: 541.31, found 541.45.

Example 263: 1-(5-(2-(2,6-dioxopiperidin-3-yl)-1-oxoisoindolin-4-yl)pentyl)-4-(4-(((S)-tetrahydrofuran-3-yl)oxy)phenyl)piperidine-4-carbonitrile (263)

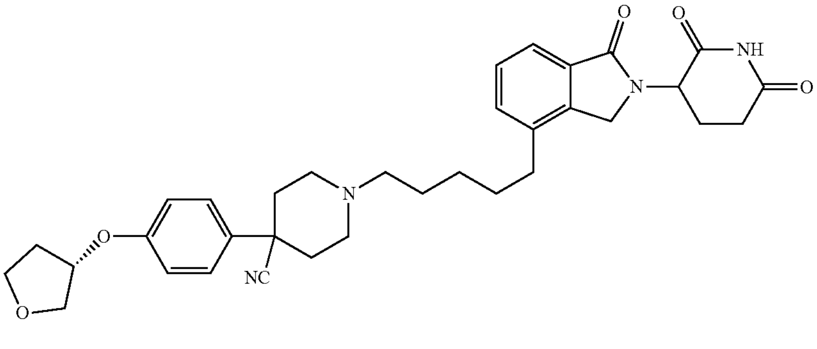 [SMILES: N#CC1(c2ccc(O[C@H]3CCOC3)cc2)CCN(CCCCCc2cccc3c2CN(C2CCC(=O)NC2=O)C3=O)CC1]

Preparation method referred synthesis method 1 and Example 51. $^{1}H$ NMR (400 MHz, DMSO-$d_6$) δ 11.00 (s, 1H), 7.56 (dd, J=5.7, 2.8 Hz, 1H), 7.46 (q, J=4.1, 3.4 Hz, 2H), 7.42 (d, J=8.9 Hz, 2H), 6.96 (d, J=8.8 Hz, 2H), 5.14 (dd, J=13.4, 5.1 Hz, 1H), 5.08-4.97 (m, 1H), 4.47 (d, J=17.2 Hz, 1H), 4.31 (d, J=17.2 Hz, 1H), 3.89 (dd, J=10.1, 4.6 Hz, 1H), 3.86-3.80 (m, 1H), 3.76 (ddd, J=16.5, 8.7, 4.9 Hz, 2H), 3.07-2.84 (m, 3H), 2.68-2.56 (m, 3H), 2.43-2.36 (m, 3H), 2.29-2.15 (m, 3H), 2.14-1.80 (m, 6H), 1.70-1.56 (m, 2H), 1.56-1.42 (m, 2H), 1.33 (p, J=8.7, 8.3 Hz, 2H). UPLC-MS (ESI) calculated for $C_{34}H_{40}N_4O_5$ $[M+H]^+$: 585.30, found 585.53.

Example 264: 1-(5-(2-(2,6-dioxopiperidin-3-yl)-1-oxoisoindolin-4-yl)pentyl)-4-(4-(2-methoxyethoxy)phenyl)piperidine-4-carbonitrile (264)

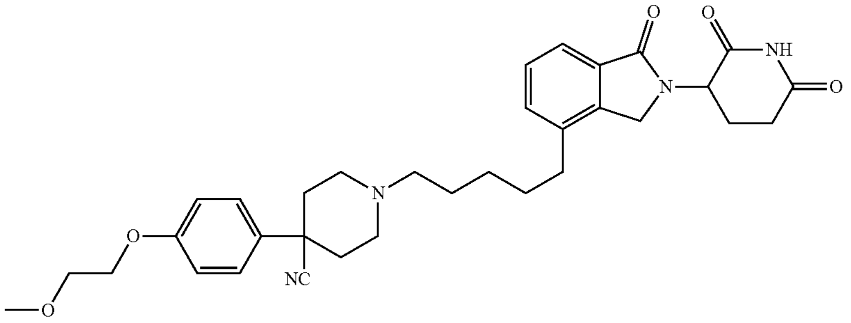 [SMILES: COCCOc1ccc(C2(C#N)CCN(CCCCCc3cccc4c3CN(C3CCC(=O)NC3=O)C4=O)CC2)cc1]

Preparation method referred synthesis method 1 and Example 51. $^{1}H$ NMR (400 MHz, DMSO) δ 11.01 (s, 1H), 7.57 (dd, J=5.4, 3.2 Hz, 1H), 7.45 (dt, J=18.7, 6.6 Hz, 4H), 7.00 (d, J=8.8 Hz, 2H), 5.14 (dd, J=13.3, 5.1 Hz, 1H), 4.47 (d, J=17.2 Hz, 1H), 4.31 (d, J=17.1 Hz, 1H), 4.12-4.07 (m, 2H), 3.68-3.61 (m, 2H), 3.47-3.35 (m, 3H), 3.30 (s, 3H), 3.23-3.04 (m, 2H), 2.99-2.87 (m, 1H), 2.70-2.56 (m, 3H), 2.46-2.35 (m, 2H), 2.27-2.12 (m, 2H), 2.09-1.94 (m, 3H), 1.69-1.52 (m, 4H), 1.41-1.29 (m, 2H). UPLC-MS (ESI) calculated for $C_{33}H_{40}N_4O_5$ $[M+H]^+$: 573.30, found 573.53.

Example 265: 1-(5-(2-(2,6-dioxopiperidin-3-yl)-1-oxoisoindolin-4-yl)pentyl)-4-(4-methoxyphenyl)piperidine-4-carbonitrile (265)

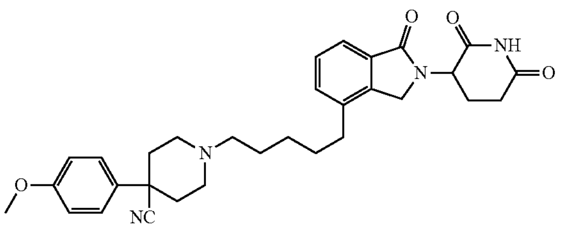 [SMILES: COc1ccc(C2(C#N)CCN(CCCCCc3cccc4c3CN(C3CCC(=O)NC3=O)C4=O)CC2)cc1]

The preparation method referred to synthesis method 1 and Example 51. $^{1}H$ NMR (400 MHz, DMSO) δ 11.02 (s, 1H), 7.61-7.55 (m, 1H), 7.50-7.41 (m, 4H), 7.01 (d, J=8.6 Hz, 2H), 5.15 (dd, J=13.3, 5.0 Hz, 1H), 4.48 (d, J=17.2 Hz, 1H), 4.32 (d, J=17.0 Hz, 1H), 3.77 (s, 3H), 3.44-3.23 (m, 6H), 3.01-2.87 (m, 1H), 2.70-2.56 (m, 3H), 2.46-2.35 (m, 1H), 2.29-2.14 (m, 2H), 2.07-1.94 (m, 3H), 1.70-1.50 (m, 4H), 1.40-1.27 (m, 2H). UPLC-MS (ESI) calculated for $C_{31}H_{36}N_4O_4$ $[M+H]^+$: 529.27, found 529.58.

Example 266: 4-(2,6-dichlorophenyl)-1-(4-(2-(2,6-dioxopiperidin-3-yl)-1-oxoisoindoline-4-yl)butyl)piperidine-4-carbonitrile

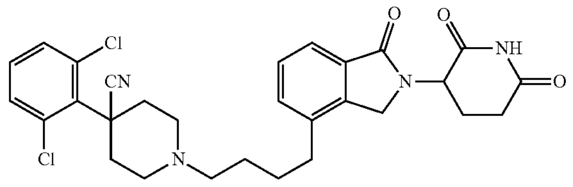 [SMILES: N#CC1(c2c(Cl)cccc2Cl)CCN(CCCCc2cccc3c2CN(C2CCC(=O)NC2=O)C3=O)CC1]

Preparation method referred synthesis method 1 and Example 51. $^{1}H$ NMR (400 MHz, DMSO) δ 11.02 (s, 1H), 7.62-7.56 (m, 3H), 7.51-7.47 (m, 2H), 7.43 (dd, J=13.8, 6.0 Hz, 1H), 5.15 (dd, J=13.3, 5.0 Hz, 1H), 4.48 (d, J=17.1 Hz, 1H), 4.33 (d, J=17.1 Hz, 1H), 3.52-3.17 (m, 4H), 2.99-2.88 (m, 1H), 2.80-2.58 (m, 9H), 2.46-2.35 (m, 1H), 2.08-1.98 (m, 1H), 1.72-1.50 (m, 4H). UPLC-MS (ESI) calculated for $C_{29}H_{30}Cl_2N_4O_3$ $[M+H]^+$: 553.17, found 553.50.

Example 267: 4-(2-chloro-4-methoxyphenyl)-1-(5-(2-(2,6-dioxopiperidin-3-yl)-1-oxoisoindoline-4-yl)pentyl)piperidine-4-carbonitrile (267)

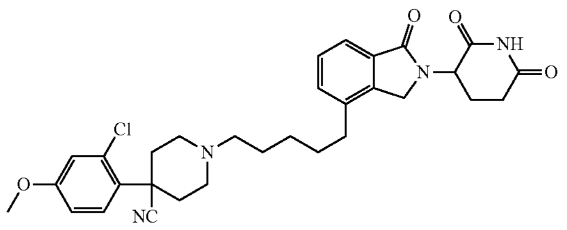 [SMILES: COc1ccc(C2(C#N)CCN(CCCCCc3cccc4c3CN(C3CCC(=O)NC3=O)C4=O)CC2)c(Cl)c1]

Preparation method referred synthesis method 1 and Example 51. $^{1}H$ NMR (400 MHz, DMSO) δ 11.00 (s, 1H), 7.58-7.53 (m, 1H), 7.49-7.39 (m, 3H), 7.13 (d, J=2.7 Hz, 1H), 6.98 (dd, J=8.9, 2.7 Hz, 1H), 5.14 (dd, J=13.3, 5.1 Hz, 1H), 4.46 (d, J=17.2 Hz, 1H), 4.31 (d, J=17.1 Hz, 1H), 3.79 (s, 3H), 3.07-2.86 (m, 3H), 2.68-2.56 (m, 3H), 2.46-2.36 (m, 3H), 2.37-2.32 (m, 2H), 2.28 (t, J=11.7 Hz, 2H), 2.05-1.95 (m, 1H), 1.89 (t, J=11.1 Hz, 2H), 1.68-1.56 (m, 2H), 1.50 (dt, J=14.8, 7.6 Hz, 2H), 1.34 (dd, J=14.1, 7.2 Hz, 2H). UPLC-MS (ESI) calculated for $C_{31}H_{35}ClN_4O_4$ $[M+H]^+$: 563.23, found 563.52.

Example 268: 4-(4-cyanophenyl)-1-(5-(2-(2,6-dioxopiperidin-3-yl)-1-oxoisoindoline-4-yl)pentyl) piperidine-4-carbonitrile (268)

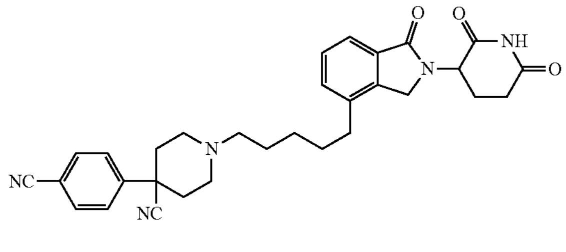 [SMILES: N#Cc1ccc(C2(C#N)CCN(CCCCCc3cccc4c3CN(C3CCC(=O)NC3=O)C4=O)CC2)cc1]

Preparation method referred synthesis method 1 and Example 51. $^1H$ NMR (400 MHz, DMSO) δ 11.00 (s, 1H), 7.93 (d, J=8.4 Hz, 2H), 7.75 (d, J=8.5 Hz, 2H), 7.56 (dd, J=5.5, 3.0 Hz, 1H), 7.49-7.41 (m, 2H), 5.14 (dd, J=13.2, 5.1 Hz, 1H), 4.47 (d, J=17.2 Hz, 1H), 4.31 (d, J=17.1 Hz, 1H), 3.12-2.86 (m, 3H), 2.70-2.56 (m, 3H), 2.46-2.38 (m, 3H), 2.35-2.20 (m, 2H), 2.19-2.09 (m, 2H), 2.08-1.94 (m, 3H), 1.63 (dt, J=15.5, 7.7 Hz, 2H), 1.53 (dd, J=12.5, 7.1 Hz, 2H), 1.40-1.29 (m, 2H). UPLC-MS (ESI) calculated for $C_{31}H_{33}N_5O_3$ $[M+H]^+$: 524.26, found 524.55.

Example 269: 4-(2,5-dichlorophenyl)-1-(4-(2-(2,6-dioxopiperidin-3-yl)-1-oxoisoindoline-4-yl)butyl) piperidine-4-carbonitrile (269)

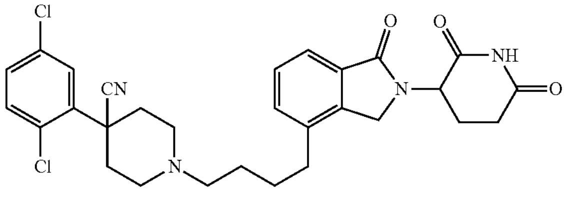 [SMILES: N#CC1(c2cc(Cl)ccc2Cl)CCN(CCCCc2cccc3c2CN(C2CCC(=O)NC2=O)C3=O)CC1]

Preparation method referred synthesis method 1 and Example 51. $^1H$ NMR (400 MHz, DMSO) δ 11.00 (s, 1H), 7.61 (d, J=8.3 Hz, 1H), 7.59-7.51 (m, 3H), 7.49-7.43 (m, 2H), 5.13 (dd, J=13.3, 5.1 Hz, 1H), 4.47 (d, J=17.1 Hz, 1H), 4.31 (d, J=17.2 Hz, 1H), 3.08-2.86 (m, 3H), 2.66 (t, J=7.6 Hz, 2H), 2.59 (d, J=17.1 Hz, 1H), 2.47-2.23 (m, 7H), 2.05-1.93 (m, 3H), 1.63 (dd, J=15.5, 7.8 Hz, 2H), 1.58-1.45 (m, 2H). UPLC-MS (ESI) calculated for $C_{29}H_3OCl_2N_4O_3$ $[M+H]^+$: 553.17, found 553.52.

Example 270: 1-(5-(2-(2,6-dioxopiperidin-3-yl)-1-oxoisoindolin-4-yl)pentyl)-4-(4-(oxetan-3-yloxy) phenyl)piperidine-4-carbonitrile (270)

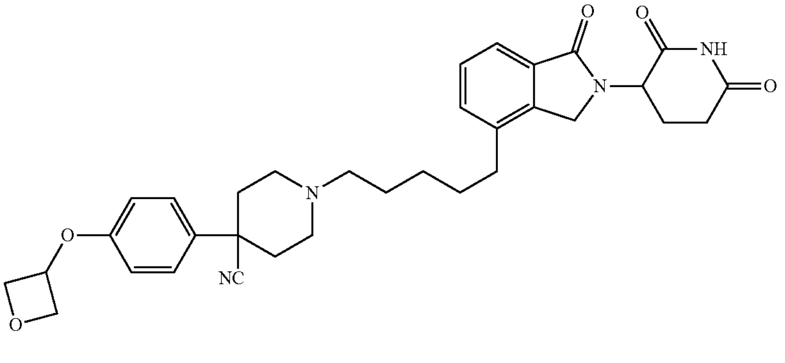 [SMILES: N#CC1(c2ccc(OC3COC3)cc2)CCN(CCCCCc2cccc3c2CN(C2CCC(=O)NC2=O)C3=O)CC1]

Preparation method referred synthesis method 1 and Example 51. $^1H$ NMR (400 MHz, DMSO) δ 11.01 (s, 1H), 7.57 (dt, J=7.7, 3.9 Hz, 1H), 7.49-7.42 (m, 4H), 6.86 (d, J=8.5 Hz, 2H), 5.34-5.25 (m, 1H), 5.14 (dd, J=13.3, 5.0 Hz, 1H), 4.93 (t, J=6.7 Hz, 2H), 4.54 (dd, J=7.4, 5.1 Hz, 2H), 4.47 (d, J=17.2 Hz, 1H), 4.31 (d, J=17.2 Hz, 1H), 3.24-3.05 (m, 2H), 3.04-2.83 (m, 3H), 2.72-2.64 (m, 2H), 2.60-2.56 (m, 1H), 2.48-2.31 (m, 3H), 2.23-2.09 (m, 2H), 2.04-1.98 (m, 3H), 1.70-1.47 (m, 4H), 1.40-1.29 (m, 2H). UPLC-MS (ESI) calculated for $C_{33}H_{38}N_4O_5$ $[M+H]^+$: 571.28, found 571.53.

Example 271: 1-(5-(2-(2,6-dioxopiperidin-3-yl)-1-oxoisoindolin-4-yl)pentyl)-4-(4-(trifluoromethyl)phenyl)piperidine-4-carbonitrile (271)

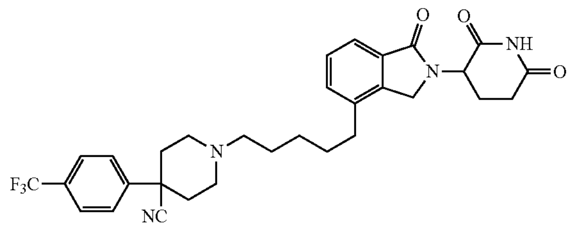 [SMILES: N#CC1(c2ccc(C(F)(F)F)cc2)CCN(CCCCCc2cccc3c2CN(C2CCC(=O)NC2=O)C3=O)CC1]

Preparation method referred synthesis method 1 and Example 51. $^1$H NMR (400 MHz, DMSO) δ 11.00 (s, 1H), 7.80 (q, J=8.6 Hz, 4H), 7.56 (dd, J=5.7, 2.8 Hz, 1H), 7.49-7.44 (m, 2H), 5.14 (dd, J=13.2, 5.1 Hz, 1H), 4.47 (d, J=17.2 Hz, 1H), 4.31 (d, J=17.2 Hz, 1H), 3.03-2.95 (m, 2H), 2.94-2.86 (m, 1H), 2.69-2.54 (m, 3H), 2.43 (dd, J=13.2, 4.5 Hz, 1H), 2.39-2.33 (m, 2H), 2.24 (t, J=11.4 Hz, 2H), 2.12 (d, J=12.3 Hz, 2H), 2.06-1.95 (m, 3H), 1.68-1.58 (m, 2H), 1.55-1.46 (m, 2H), 1.40-1.29 (m, 2H). UPLC-MS (ESI) calculated for $C_{31}H_{33}F_3N_4O_3$ [M+H]$^+$: 567.25, found 567.53.

Example 272: 4-(3,4-dichlorophenyl)-1-(4-(2-(2,6-dioxopiperidin-3-yl)-1-oxoisoindoline-4-yl)butyl)piperidine-4-carbonitrile (272)

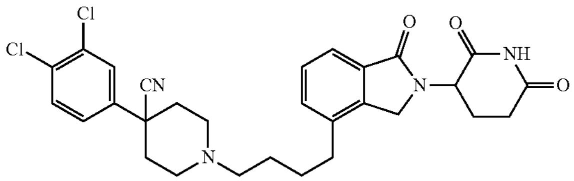 [SMILES: N#CC1(c2ccc(Cl)c(Cl)c2)CCN(CCCCc2cccc3c2CN(C2CCC(=O)NC2=O)C3=O)CC1]

Preparation method referred synthesis method 1 and Example 51. $^1$H NMR (400 MHz, DMSO) δ 11.00 (s, 1H), 7.79 (d, J=1.8 Hz, 1H), 7.73 (d, J=8.5 Hz, 1H), 7.59-7.53 (m, 2H), 7.50-7.45 (m, 2H), 5.14 (dd, J=13.2, 5.0 Hz, 1H), 4.47 (d, J=17.1 Hz, 1H), 4.32 (d, J=17.1 Hz, 1H), 3.40-3.28 (m, 4H), 3.10-2.86 (m, 3H), 2.68 (t, J=7.0 Hz, 2H), 2.59 (d, J=16.6 Hz, 1H), 2.42 (dd, J=13.2, 4.3 Hz, 1H), 2.29-2.10 (m, 3H), 2.05-1.94 (m, 2H), 1.69-1.40 (m, 4H). UPLC-MS (ESI) calculated for $C_{29}H_3OCl_2N_4O_3$ [M+H]$^+$: 553.17, found 553.52.

Example 273: 3-(4-(5-(5-fluoro-3H-spiro[isobenzofuran-1,4'-piperidine]-1'-)pentyl)-1-oxoisoindoline-2-yl)piperidine-2,6-dione (273)

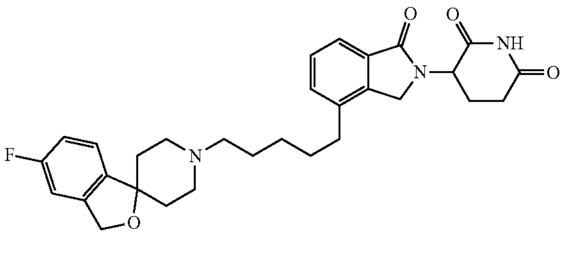 [SMILES: O=C1CCC(N2Cc3c(CCCCCN4CCC5(CC4)OCc4cc(F)ccc45)cccc3C2=O)C(=O)N1]

Preparation method referred synthesis method 1 and Example 120. $^1$H NMR (400 MHz, DMSO) δ 11.01 (s, 1H), 7.58 (dd, J=5.3, 3.1 Hz, 1H), 7.47 (dd, J=7.8, 5.4 Hz, 2H), 7.17 (dd, J=16.5, 8.1 Hz, 3H), 5.15 (dd, J=13.3, 5.0 Hz, 1H), 5.02 (s, 2H), 4.48 (d, J=17.2 Hz, 1H), 4.31 (d, J=17.2 Hz, 1H), 3.50 (d, J=6.9 Hz, 2H), 3.20-3.06 (m, 2H), 3.00-2.88 (m, 1H), 2.68 (t, J=7.4 Hz, 2H), 2.64-2.56 (m, 1H), 2.44-2.34 (m, 3H), 2.19 (t, J=13.5 Hz, 2H), 2.06-1.97 (m, 1H), 1.86 (d, J=13.6 Hz, 2H), 1.78-1.62 (m, 4H), 1.41-1.33 (m, 2H). UPLC-MS (ESI) calculated for $C_{30}H_{34}FN_3O_4$ [M+H]$^+$: 520.25, found 520.53.

Example 274: 3-(4-(5-(5-chloro-3H-spiro[isobenzofuran-1,4'-piperidin]-1-yl)pentyl)-1-oxoisoindoline-2-yl)piperidine-2,6-dione (274)

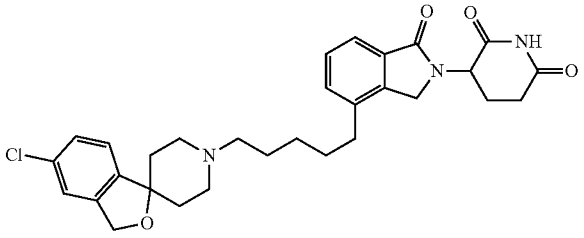 [SMILES: O=C1CCC(N2Cc3c(CCCCCN4CCC5(CC4)OCc4cc(Cl)ccc45)cccc3C2=O)C(=O)N1]

Preparation method referred synthesis method 1 and Example 120. $^1$H NMR (400 MHz, DMSO) δ 11.01 (s, 1H), 7.62-7.55 (m, 1H), 7.48 (d, J=3.5 Hz, 2H), 7.45-7.37 (m, 2H), 7.20 (d, J=8.1 Hz, 1H), 5.15 (dd, J=13.3, 5.1 Hz, 1H), 5.03 (s, 2H), 4.48 (d, J=17.1 Hz, 1H), 4.31 (d, J=17.1 Hz, 1H), 3.51 (d, J=12.2 Hz, 2H), 3.20-3.08 (m, 2H), 3.00-2.87 (m, 1H), 2.72-2.57 (m, 3H), 2.41 (dd, J=17.7, 8.7 Hz, 1H), 2.14 (t, J=12.0 Hz, 2H), 2.07-1.95 (m, 2H), 1.88 (d, J=13.2 Hz, 2H), 1.80-1.60 (m, 5H), 1.42-1.32 (m, 2H). UPLC-MS (ESI) calculated for $C_{30}H_{34}ClN_3O_4$ [M+H]$^+$: 536.22, found 536.52.

Example 275: 3-(4-(5-(6-chloro-2-oxospiro[dihydroindole-3,4-piperidin]-1-yl)pentyl)-1-oxoisoindoline-2-yl)piperidine-2,6-dione (275)

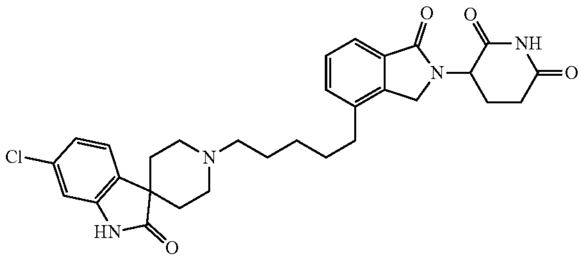 [SMILES: O=C1CCC(N2Cc3c(CCCCCN4CCC5(CC4)C(=O)Nc4cc(Cl)ccc45)cccc3C2=O)C(=O)N1]

Preparation method referred synthesis method 1 and Example 120. $^1$H NMR (400 MHz, DMSO) δ 11.00 (s, 1H), 10.56 (s, 1H), 7.57 (dd, J=5.9, 2.6 Hz, 1H), 7.49-7.43 (m, 3H), 7.00 (dd, J=8.0, 1.9 Hz, 1H), 6.86 (d, J=1.9 Hz, 1H), 5.14 (dd, J=13.3, 5.1 Hz, 1H), 4.48 (d, J=17.1 Hz, 1H), 4.31 (d, J=17.1 Hz, 1H), 2.99-2.85 (m, 3H), 2.70-2.60 (m, 4H), 2.59-2.52 (m, 3H), 2.47-2.37 (m, 1H), 2.06-1.97 (m, 1H), 1.87-1.77 (m, 2H), 1.72-1.61 (m, 4H), 1.55 (dd, J=14.3, 7.0 Hz, 2H), 1.43-1.29 (m, 2H). UPLC-MS (ESI) calculated for $C_{30}H_{33}ClN_4O_4$ [M+H]$^+$: 549.22, found 549.53.

Example 276: 3-(4-(5-(4-chloro-2-oxospiro[dihydroindole-3,4-piperidin]-1-yl)pentyl)-1-oxoisoindoline-2-yl)piperidine-2,6-dione (276)

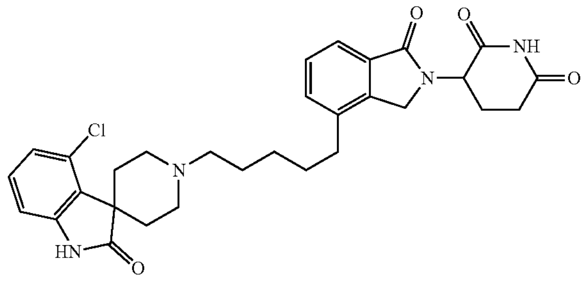 [SMILES: O=C1CCC(N2Cc3c(CCCCCN4CCC5(CC4)C(=O)Nc4cccc(Cl)c45)cccc3C2=O)C(=O)N1]

Preparation method referred synthesis method 1 and Example 120. $^1$H NMR (400 MHz, DMSO) δ 11.01 (s, 1H), 10.66 (s, 1H), 7.58 (dd, J=6.1, 2.5 Hz, 1H), 7.51-7.46 (m, 2H), 7.22 (t, J=8.0 Hz, 1H), 6.97 (d, J=8.2 Hz, 1H), 6.82 (d, J=7.6 Hz, 1H), 5.15 (dd, J=13.3, 5.1 Hz, 1H), 4.49 (d, J=17.2 Hz, 1H), 4.32 (d, J=17.2 Hz, 1H), 3.15-2.88 (m, 5H), 2.75-2.57 (m, 6H), 2.47-2.38 (m, 2H), 2.07-1.98 (m, 3H), 1.76-1.58 (m, 6H), 1.42-1.32 (m, 2H). UPLC-MS (ESI) calculated for $C_{30}H_{33}ClN_4O_4$ $[M+H]^+$: 549.22, found 549.49.

Example 277: 3-(4-(5-(6-chloro-2-oxo-1,2-dihydrospiro[benzo[1,3]oxazine-4,4'-piperidine]-1'-yl)pentyl)-1-oxoisoindolin-2-yl)piperidine-2,6-dione (277)

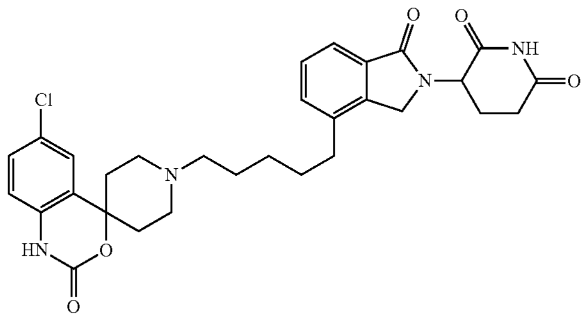 [SMILES: O=C1CCC(N2Cc3c(CCCCCN4CCC5(CC4)OC(=O)Nc4ccc(Cl)cc45)cccc3C2=O)C(=O)N1]

Preparation method referred synthesis method 1 and Example 120. $^1$H NMR (400 MHz, DMSO) δ 11.00 (s, 1H), 10.35 (s, 1H), 7.57 (dd, J=5.6, 3.0 Hz, 1H), 7.49-7.45 (m, 2H), 7.38 (d, J=2.1 Hz, 1H), 7.31 (dd, J=8.5, 2.2 Hz, 1H), 6.89 (d, J=8.5 Hz, 1H), 5.14 (dd, J=13.3, 5.1 Hz, 1H), 4.47 (d, J=17.2 Hz, 1H), 4.31 (d, J=17.2 Hz, 1H), 2.98-2.87 (m, 1H), 2.75 (d, J=10.3 Hz, 2H), 2.68-2.54 (m, 3H), 2.43 (dd, J=13.1, 4.4 Hz, 1H), 2.39-2.28 (m, 4H), 2.07-1.98 (m, 3H), 1.90 (d, J=13.0 Hz, 2H), 1.68-1.58 (m, 2H), 1.56-1.45 (m, 2H), 1.39-1.32 (m, 2H). UPLC-MS (ESI) calculated for $C_{30}H_{33}ClN_4O_5$ $[M+H]^+$: 565.21, found 565.53.

Example 278: 3-(4-(5-(5-fluoro-2-oxospiro[dihydroindole-3,4-piperidin]-1-yl)pentyl)-1-oxoisoindolin-2-yl)piperidine-2,6-dione (278)

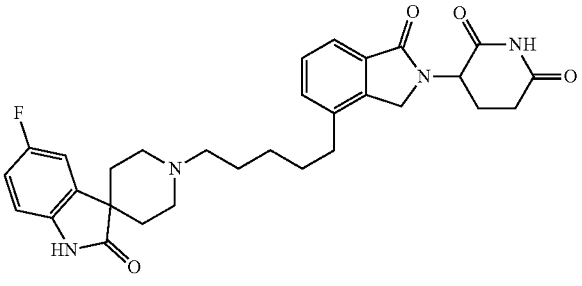 [SMILES: O=C1CCC(N2Cc3c(CCCCCN4CCC5(CC4)C(=O)Nc4ccc(F)cc45)cccc3C2=O)C(=O)N1]

Preparation method referred synthesis method 1 and Example 120. $^1$H NMR (400 MHz, DMSO) δ 11.00 (s, 1H), 10.39 (s, 1H), 7.57 (dd, J=6.0, 2.6 Hz, 1H), 7.52-7.41 (m, 2H), 7.34 (dd, J=8.6, 2.4 Hz, 1H), 7.01 (td, J=9.5, 2.4 Hz, 1H), 6.82 (dd, J=8.6, 4.6 Hz, 1H), 5.14 (dd, J=13.3, 5.2 Hz, 1H), 4.48 (d, J=17.2 Hz, 1H), 4.32 (d, J=17.2 Hz, 1H), 2.99-2.81 (m, 3H), 2.67 (t, J=7.8 Hz, 2H), 2.65-2.55 (m, 3H), 2.46-2.40 (m, 3H), 2.06-1.98 (m, 1H), 1.86-1.75 (m, 2H), 1.74-1.59 (m, 4H), 1.59-1.50 (m, 2H), 1.42-1.32 (m, 2H). UPLC-MS (ESI) calculated for $C_{30}H_{33}FN_4O_4$ $[M+H]^+$: 533.25, found 533.52.

Example 279: 3-(4-(5-(7-chloro-2-oxospiro[dihydroindole-3,4-piperidin]-1-yl)pentyl)-1-oxoisoindoline-2-yl)piperidine-2,6-dione (279)

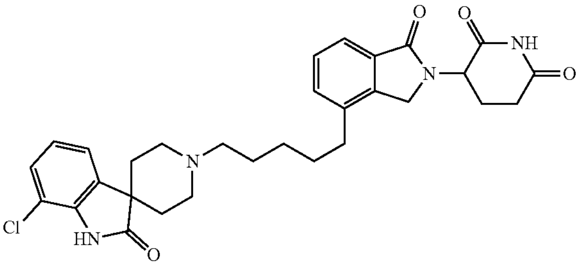 [SMILES: O=C1CCC(N2Cc3c(CCCCCN4CCC5(CC4)C(=O)Nc4c(Cl)cccc45)cccc3C2=O)C(=O)N1]

Preparation method referred synthesis method 1 and Example 120. $^1$H NMR (400 MHz, DMSO) δ 11.01 (s, 1H), 10.92 (s, 1H), 7.58 (dd, J=5.8, 2.6 Hz, 1H), 7.48 (d, J=5.9 Hz, 2H), 7.44-7.35 (m, 1H), 7.29 (d, J=8.1 Hz, 1H), 7.02 (t, J=7.8 Hz, 1H), 5.14 (dd, J=13.3, 5.1 Hz, 1H), 4.48 (d, J=17.0 Hz, 1H), 4.32 (d, J=17.1 Hz, 1H), 3.22-3.14 (m, 2H), 3.05-2.88 (m, 3H), 2.87-2.76 (m, 2H), 2.72-2.64 (m, 2H), 2.64-2.57 (m, 1H), 2.46-2.36 (m, 1H), 2.06-1.98 (m, 1H), 1.97-1.84 (m, 4H), 1.73-1.58 (m, 4H), 1.44-1.33 (m, 2H). UPLC-MS (ESI) calculated for $C_{30}H_{33}ClN_4O_4$ $[M+H]^+$: 549.22, found 549.48.

Example 280: 3-(4-(5-(4-chloro-3H-spiro[isobenzofuran-1,4'-piperidin]-1-yl)pentyl)-1-oxoisoindoline-2-yl)piperidine-2,6-dione (280)

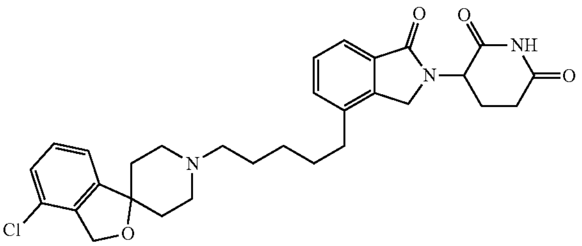 [SMILES: O=C1CCC(N2Cc3c(CCCCCN4CCC5(CC4)OCc4c(Cl)cccc45)cccc3C2=O)C(=O)N1]

Preparation method referred synthesis method 1 and Example 120. $^1$H NMR (400 MHz, DMSO) δ 11.02 (s, 1H), 7.61-7.56 (m, 1H), 7.48 (d, J=3.5 Hz, 2H), 7.44-7.40 (m, 2H), 7.20-7.15 (m, 1H), 5.15 (dd, J=13.4, 5.1 Hz, 1H), 5.08 (s, 2H), 4.48 (d, J=17.2 Hz, 1H), 4.31 (d, J=17.2 Hz, 1H), 3.53 (d, J=11.8 Hz, 2H), 3.23-3.10 (m, 4H), 3.01-2.85 (m, 1H), 2.73-2.65 (m, 2H), 2.61 (d, J=18.7 Hz, 1H), 2.44-2.36 (m, 1H), 2.20-2.08 (m, 2H), 2.07-1.99 (m, 2H), 1.98-1.91 (m, 1H), 1.77-1.63 (m, 4H), 1.42-1.30 (m, 2H). UPLC-MS (ESI) calculated for $C_{30}H_{34}ClN_3O_4$ [M+H]$^+$: 536.22, found 536.53.

2. Test Examples

Method of tumor cell proliferation inhibition test: the inventors tested all the example compounds on hematologic tumor cells, multiple myeloma MMTs cell line and acute leukemia cell MV-4-11 cell line of some examples. The activity test method and results are as follows.

1. The Compound's Inhibitory Effect on the Proliferation of MM.1S, MTS Cell Viability Test:

1). Experimental Method:

MM.1S cells were cultured and collected with 1640 plus 10% fetal bovine serum. The cell concentration was diluted according to 7 days, and 180 ul cell suspension was added to each well of the 96-well cell plate to 20,000 cells. 20 ul of DMSO with a final concentration of 0.2% was added to the control wells. The compound was 5-fold diluted—from the 10 mM stock solution, and 20 ul was also added to each compound cell well (the final concentration of DMSO was 0.2%). The cells were placed in a 37° C., 5% $CO_2$ incubator to incubate for 7 days. After the reaction solution was prepared according to the MTS kit (Promega, G5430), 20 μL was added to each well and incubated in a 37° C., 5% $CO_2$ incubator for 3-4 h. Absorbance value at 490 nm was read with a microtiter plate, and 690 nm absorbance value was used as the background value. OD490-OD690 was used as the final initial data. The formula for calculating the inhibition rate of the compound is: inhibition rate=$(OD_{DMSO}-OD_{compound})/(OD_{DMSO}-O_{blank})\times100\%$. The compound's proliferation inhibition IC50 was fitted by Graph Pad Prism 5.0. The experiment was repeated three times, and the average and standard deviation was calculated according to the three parallel experiments.

Cell viability test results: ** represents cell viability $IC_{50}>20$ μM,  represents cell viability 1 μM<$IC_{50}$<20 μM, ** represents cell viability 100 nM<$IC_{50}$<1 μM, * represents cell viability $IC_{50}$<100 nM.

2). Experimental Results

| Serial number | Tumor cell inhibitory activity (μM) | Serial number | Tumor cell inhibitory activity (μM) |
|---|---|---|---|
| Lenalidomide | ** | CC-122 | * |
| Pomalidomide | * | CC-220 | * |
| 1 | * | 2 | ** |
| 3 | * | 4 | *** |
| 5 | ** | 6 | * |
| 7 | ** | 8 | * |
| 9 | * | 10 | * |
| 11 | * | 12 | ** |
| 13 | * | 14 | * |
| 15 | * | 16 | ** |
| 17 | * | 18 | * |
| 19 | * | 20 | **** |
| 21 | * | 22 | * |
| 23 | * | 24 | * |
| 25 | *** | 26 | * |
| 27 | *** | 28 | * |
| 29 | * | 30 | * |
| 31 | * | 32 | ** |
| 33 | * | 34 | *** |
| 35 | * | 36 | * |
| 37 | * | 38 | * |
| 39 | * | 40 | * |
| 41 | * | 42 | * |
| 43 | * | 44 | * |
| 45 | * | 46 | ** |
| 47 | * | 48 | * |
| 49 | * | 50 | *** |
| 51 | * | 52 | *** |
| 53 | * | 54 | *** |
| 55 | * | 56 | *** |
| 57 | * | 58 | *** |
| 59 | * | 60 | *** |
| 61 | ** | 62 | *** |
| 63 | ** | 64 | ** |
| 65 | ** | 66 | ** |
| 67 | ** | 68 | * |
| 69 | ** | 70 | * |
| 71 | * | 72 | * |
| 73 | * | 74 | * |
| 75 | ** | 76 | * |
| 77 | ** | 78 | * |
| 79 | * | 80 | *** |
| 81 | * | 82 | ** |
| 83 | * | 84 | ** |
| 85 | * | 86 | * |
| 87 | * | 88 | ** |
| 89 | * | 90 | *** |
| 91 | * | 92 | * |
| 93 | * | 94 | * |
| 95 | * | 96 | * |
| 97 | * | 98 | * |
| 99 | * | 100 | * |
| 101 | * | 102 | * |
| 103 | ** | 104 | ** |
| 105 | ** | 106 | ** |
| 107 | * | 108 | *** |
| 109 | *** | 110 | * |
| 111 | ** | 112 | * |
| 113 | ** | 114 | ** |
| 115 | ** | 116 | * |
| 117 | ** | 118 | * |
| 119 | * | 120 | * |
| 121 | * | 122 | * |
| 123 | * | 124 | * |
| 125 | ** | 126 | * |
| 127 | ** | 128 | * |
| 129 | ** | 130 | * |
| 131 | ** | 132 | * |
| 133 | * | 134 | * |
| 135 | ** | 136 | ** |
| 137 | ** | 138 | * |
| 139 | ** | 140 | * |
| 141 | ** | 142 | ** |
| 143 | * | 144 | * |

-continued

| Serial number | Tumor cell inhibitory activity (μM) | Serial number | Tumor cell inhibitory activity (μM) |
|---|---|---|---|
| 145 | ** | 146 | * |
| 147 | ** | 148 | * |
| 149 | ** | 150 | * |
| 151 | ** | 152 | * |
| 153 | ** | 154 | * |
| 155 | * | 156 | * |
| 157 | * | 158 | * |
| 159 | * | 160 | * |
| 161 | ** | 162 | * |
| 163 | ** | 164 | * |
| 165 | * | 166 | ** |
| 167 | * | 168 | *** |
| 169 | * | 170 | **** |
| 171 | *** | 172 | **** |
| 173 | * | 174 | **** |
| 175 | ** | 176 | **** |
| 177 | ** | 178 | ** |
| 179 | * | 180 | ** |
| 181 | ** | 182 | * |
| 183 | * | 184 | ** |
| 185 | * | 186 | ** |
| 187 | * | 188 | ** |
| 189 | ** | 190 | *** |
| 191 | ** | 192 | ** |
| 193 | * | 194 | ** |
| 195 | ** | 196 | *** |
| 197 | ** | 198 | * |
| 199 | **** | 200 | ** |
| 201 | **** | 202 | * |
| 203 | ** | 204 | *** |
| 205 | **** | 206 | * |
| 207 | ** | 208 | ** |
| 209 | * | 210 | ** |
| 211 | * | 212 | * |
| 213 | ** | 214 | ** |
| 215 | * | 216 | * |
| 217 | * | 218 | * |
| 219 | * | 220 | * |
| 221 | * | 222 | * |
| 223 | * | 224 | * |
| 225 | *** | 226 | *** |
| 227 | *** | 228 | *** |
| 229 | ** | 230 | *** |
| 231 | *** | 232 | *** |
| 233 | ** | 234 | ** |
| 235 | ** | 236 | *** |
| 237 | ** | 238 | ** |
| 239 | *** | 240 | *** |
| 241 | *** | 242 | *** |
| 243 | ** | 244 | ** |
| 245 | ** | 246 | ** |
| 247 | ** | 248 | *** |
| 249 | ** | 250 | ** |
| 251 | ** | 252 | ** |
| 253 | *** | 254 | *** |
| 255 | *** | 256 | *** |
| 257 | ** | 258 | ** |
| 259 | ** | 260 | ** |
| 261 | *** | 262 | *** |
| 263 | ** | 264 | ** |
| 265 | *** | 266 | ** |
| 267 | ** | 268 | ** |
| 269 | ** | 270 | ** |
| 271 | *** | 272 | ** |
| 273 | ** | 274 | ** |
| 275 | ** | 276 | ** |
| 277 | ** | 278 | ** |
| 279 | ** | 280 | ** |

Based on the cell growth inhibitory activity test results of the above compounds, the compounds of some embodiments of the present invention have good inhibitory activity on the growth of multiple myeloma MM1s cells, and the activities of some compounds are equivalent or superior to the positive compounds. On the other hand, the development of these structurally diverse compounds provides an alternative source for obtaining more active drug molecules and molecules with better pharmaceutical properties. Therefore, the compounds of the present invention can be used to prevent and treat diseases related to the regulation of CRBN (CRL4 $^{CRBN}$ E3 ubiquitin ligase) activity, such as multiple myeloma or including but not limited to other potential tumor diseases, pain, nervous system diseases and immune system diseases.

2. The Inhibitory Effect of Compounds on the Proliferation of MV-4-11 Cells, MTS Cell Viability Test: 1). Experimental Method:

MV-4-11 cells were cultured and collected with IMDM and 10% fetal bovine serum. The cell concentration was diluted according to 7 days, and 180 ul of cell suspension was added to each well of a 96-well cell plate to 2000 cells. 20 ul of DMSO with a final concentration of 0.2% was added to the control wells. The compound was diluted 5-fold from the 10 mM stock solution, and 20 ul was also added to the compound cell wells (the final concentration of DMSO was 0.2%). The cells were placed in a 37° C., 5% $CO_2$ incubator and incubated for 7 days. After the reaction solution was prepared according to the MTS kit (Promega, G5430), 20 μL was added to each well, incubated in a 37° C., 5% $CO_2$ incubator for 3-4 h. The 490 nm absorbance value was read with a microtiter plate, and the 690 nm absorbance value was used as the background value. OD490-OD690 was used as the final initial data. The formula for calculating the inhibition rate of the compound was: inhibition rate= $(OD_{DMSO}\text{-}OD_{compound})/(OD_{DMSO}\text{-}O_{blank})\times 100\%$. The compound's proliferation inhibition IC50 was fitted by Graph Pad Prism 5.0. The experiment was repeated three times, and the average and standard deviation was calculated according to three parallel experiments each time.

2). Experimental Results:

| Serial number | Tumor cell inhibitory activity (μM) |
|---|---|
| Lenalidomide | >20 |
| Pomalidomide | >20 |
| CC-122 | >20 |
| CC-220 | >20 |
| 22 | 0.11 |
| 51 | 0.57 |
| 107 | 0.18 |
| 114 | 0.22 |
| 143 | 0.61 |
| 158 | 0.014 |
| 164 | 0.25 |
| 166 | 0.20 |
| 167 | 0.035 |
| 173 | 0.029 |
| 182 | 0.017 |
| 221 | 0.60 |
| 226 | 0.51 |
| 235 | 0.48 |
| 248 | 0.66 |
| 275 | 0.63 |

Based on the test results of the cell growth inhibitory activity of the above compounds, the compounds of some examples of the present invention have very good inhibitory activity against acute leukemia cells MV-4-11 cells. The IC50 of multiple compounds is at nanomolar level, and the best activity of the tested compounds in the table can reach 17 nM. The cytostatic activity (IC50) of the positive compounds (either lenalidomide or pomalidomide), which are already commercial available, and those compounds (CC- 122 or CC-220) which are currently in clinical practice on acute leukemia cell MV-4-11 cells is greater than 20 μM. From the test results in the above table, it is found that the inhibitory activity of some compounds of the present invention on the proliferation of acute leukemia cells MV-4-11 cells is better than that of the related positive compounds, and the best compound has an activity 1000 times better than that of the positive compound. Therefore, the compound of the present invention broadens the scope of application of dosamine drugs in the treatment of hematoma diseases, and can be used to expand to other indications of hematological tumors, such as an inhibitor of acute leukemia, and as a medicine for the treatment of such diseases. The compound of the present invention can be used as a powerful new type of CRBN modulator for the prevention and treatment of diseases related to the regulation of CRBN (CRL4CRBNE3 ubiquitin ligase) activity, such as multiple myeloma or including but not limited to other potential tumor diseases, pain, nervous system diseases and immune system diseases.

In summary, the present invention provides a class of substituted isoindoline compounds with novel structures, in which some representative compounds exhibit very strong proliferation inhibitory activity on the tested hematoma cells. In addition, some of the representative compounds provided by the present invention can effectively overcome the application limitations of existing doxamine drugs, which can not only effectively make up for the shortcomings of existing doxamine drugs, but also expand their indications to new areas. Therefore, it has very strong research potential and application prospects.

The invention claimed is:

1. A compound represented by formula (I) or a tautomer, enantiomer, diastereomer, racemate, isotopic compound, pharmaceutically acceptable salt, ester, or hydrate thereof:

(I)

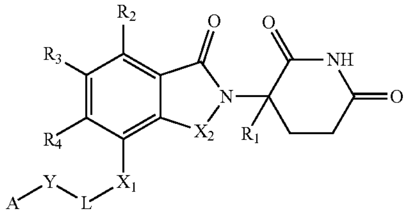

wherein, $X_1$ is —$CH_2$— or —O—;

$X_2$ is —$CH_2$— or —CO—;

$R_1$ is hydrogen, deuterium, fluorine or linear or branched $C_1$-$C_6$ hydrocarbon group;

$R_2$ and $R_4$ are each independently hydrogen or deuterium;

$R_3$ is hydrogen, deuterium or halogen;

L is a substituted or unsubstituted linear alkylene group containing 2-8 carbon atoms, and the "substituted" means that one or more hydrogen atoms in the alkylene group are optionally substituted by the following substituents: deuterium, halogen, carbonyl, hydroxyl, amino, cyano, $C_1$-$C_6$ alkyl, $C_1$-$C_6$ haloalkyl, $C_3$-$C_8$ cycloalkyl, —NHC(O) $Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl unsubstituted or substituted by halogen, hydroxyl, cyano, or nitro, and $C_{3-6}$ cycloalkyl unsubstituted or substituted by halogen, hydroxyl, cyano, or nitro;

Y is absent, —CO— or —CO—NH—, the corresponding placement of Y, A and L is A-L-, A-CO-L-, and A-CO—NH-L-, A is: i) heterocyclyl selected from the following:

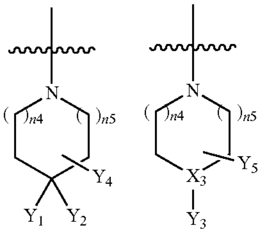

$X_3$ is N;

$n_4$ is 0, 1, 2 or 3;

$n_5$ is 0, 1, 2 or 3, $Y_1$ is hydrogen, deuterium, halogen, cyano, carboxyl, nitro, hydroxyl, amino, aminocarbonyl, $C_1$-$C_6$ alkyl, $C_1$-$C_6$alkoxyl, $C_1$-$C_6$haloalkyl, or $C_1$-$C_6$haloalkoxyl;

$Y_2$ is substituted or unsubstituted 6-10 membered aryl, or substituted or unsubstituted 6-10 membered heteroaryl, wherein the substituted 6-10 membered aryl or 6-10 membered heteroaryl is substituted by one or more substituents selected from: deuterium, halogen, cyano, nitro, hydroxyl, aminocarbonyl, $C_1$-$C_3$ alkyl, $C_1$-$C_3$ alkoxyl, $C_1$-$C_3$alkylcarbonyl, $C_1$-$C_3$alkoxycarbonyl, $C_1$-$C_3$alkylsulfonyl, $C_1$-$C_3$alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl;

$Y_3$ is substituted or unsubstituted 6-10 membered aryl, or substituted or unsubstituted 6-10 membered heteroaryl, wherein the substituted 6-10 membered aryl or 6-10 membered heteroaryl is substituted by one or more substituents selected from: deuterium, halogen, cyano, nitro, hydroxyl, aminocarbonyl, $C_1$-$C_3$ alkyl, $C_1$-$C_3$ alkoxyl, $C_1$-$C_3$alkylcarbonyl, $C_1$-$C_3$alkoxycarbonyl, $C_1$-$C_3$alkylsulfonyl, $C_1$-$C_3$alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl;

$Y_4$ and $Y_5$ are absent, or one or more substituents on the heterocyclic ring, $Y_4$ and $Y_5$ are each independently deuterium, halogen, oxo, $C_1$-$C_3$ alkyl, $C_3$ cycloalkyl, $C_1$-$C_3$ haloalkyl or phenyl;

ii) fused heterocyclyl selected from:

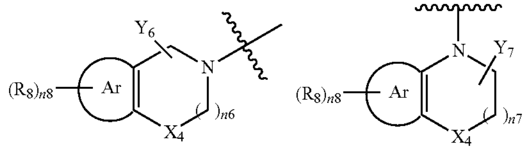

$X_4$ is C, N or O;

$n_6$ is 0, 1, 2 or 3;

$n_7$ is 0, 1, 2 or 3;

$n_8$ is 0, 1, 2, 3 or 4;

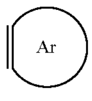

is 6-10 membered aryl ring or 5-10 membered heteroaryl ring;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-Czalkylaminocarbonyl, $C_1$-$C_3$alkoxycarbonyl, nitro, amino, cyano, $C_1$-$C_3$ haloalkyl, hydroxyl, $C_1$-$C_3$alkylsulfonyl, $C_1$-$C_3$ alkylamino, $C_1$-$C_3$ acylamino, aminocarbonyl, $C_3$-$C_6$ heterocyclyl, $C_1$-$C_3$haloalkoxyl, phenyl or 5-6 membered heteroaryl;

with the proviso that when Ra is selected from the following substituents: hydrogen, deuterium, $C_1$-$C_3$ alkoxyl, halogen, $C_1$-$C_3$ alkyl, $C_3$-$C_6$ cycloalkyl, carboxyl, $C_1$-$C_3$ alkyl aminocarbonyl, $C_1$-$C_3$alkoxycarbonyl, nitro, amino, cyano, $C_1$-$C_3$ haloalkyl, hydroxyl, $C_1$-$C_3$alkylsulfonyl, and Y is absent, then $X_1$ is other than —O—;

$Y_6$ and $Y_7$ are absent, or one or more substituents on the heterocyclic ring independently selected from deuterium, halogen, $C_1$-$C_3$ alkyl, $C_3$ cycloalkyl, $C_1$-$C_3$ haloalkyl;

or iii) spiroheterocyclic group selected from:

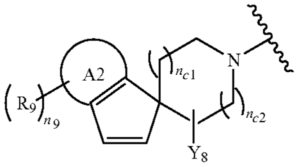

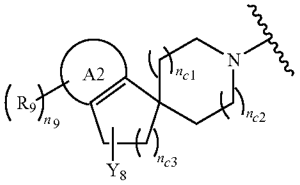

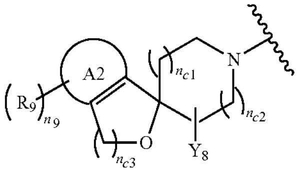

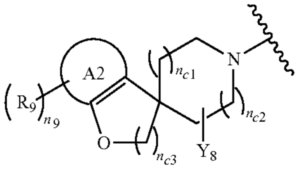

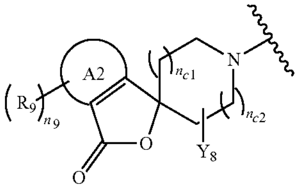

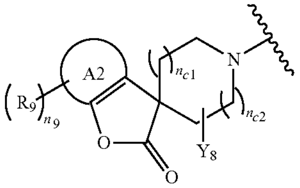

-continued

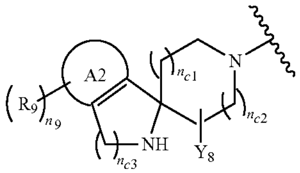

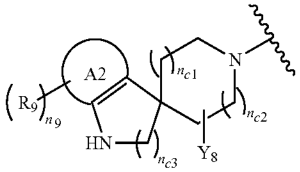

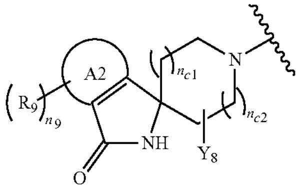

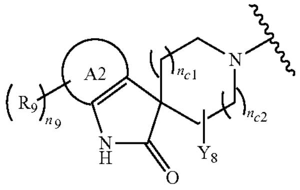

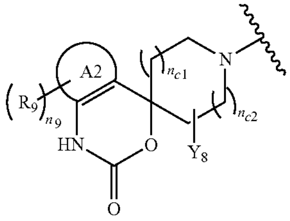

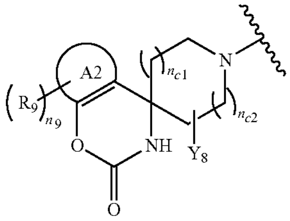

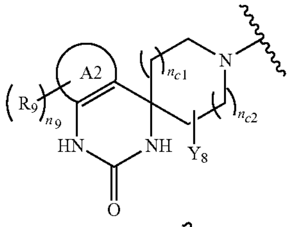

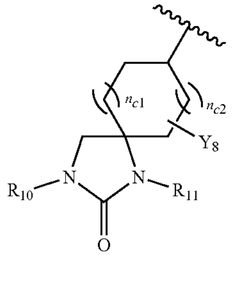

$n_{c1}$ is 0, 1, 2 or 3;

$n_{c2}$ is 0, 1, 2 or 3;

$n_{c3}$ is 1, 2 or 3;

$n_9$ is 0, 1, 2, 3 or 4;

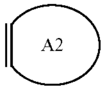

is 6-10 membered aryl ring or 5-10 heteroaryl ring;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl;

$R_{10}$ and $R_{11}$ are independently selected from hydrogen, substituted or unsubstituted 6-10 membered aryl, substituted or unsubstituted 5-10 membered heteroaryl, and the species of substituent is the same as the above-mentioned substituent $R_9$ on the

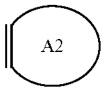

ring;

$Y_8$ is a substituent which optionally replaces the hydrogen atom in the non-aromatic moiety of the spiro ring structure, and $Y_8$ is optionally substituted by deuterium, halogen, $C_1$-$C_3$ alkyl, $C_3$ cycloalkyl or $C_1$-$C_3$ haloalkyl.

2. The compound of claim 1, or the tautomer, enantiomer, diastereomer, racemate, isotopic compound, pharmaceutically acceptable salt, ester, or hydrate thereof, wherein $X_1$ is —$CH_2$— or —O—;

$X_2$ is —$CH_2$— or —CO—;

$R_1$ is hydrogen, deuterium, fluorine or $C_1$-$C_3$ linear or branched hydrocarbon group;

$R_2$ and $R_4$ are each independently hydrogen or deuterium;

$R_3$ is hydrogen, deuterium or halogen;

L is a substituted or unsubstituted linear alkylene group comprising 2-8 carbon atoms, and the "substituted" means that one or more hydrogen atoms in the alkylene group are optionally replaced by substituents selected from: deuterium, halogen, carbonyl, hydroxyl, amino, cyano, $C_1$-$C_3$ alkyl, $C_1$-$C_3$ haloalkyl, $C_3$-$C_6$ cycloalkyl, —NHC(O) $Ra_1$, —NHC(O)O$Ra_2$, —N$Ra_3$$Ra_4$, wherein $Ra_1$, $Ra_2$, $Ra_3$ and $Ra_4$ are each independently selected from hydrogen, $C_{1-6}$ alkyl substituted by halogen, hydroxyl, cyano, or nitro, and $C_{3-6}$ cycloalkyl substituted by halogen, hydroxyl, cyano, or nitro Y is absent or —CO— or —CO—NH—, the corresponding placement of Y, A and L is A-L-, A-CO-L- or A-CO—NH-L-, A is:

i) heterocyclyl selected from the following:

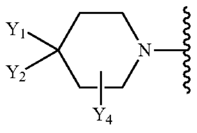

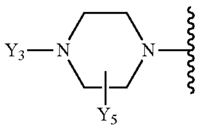

wherein, $Y_1$ is hydrogen, deuterium, halogen, cyano, carboxyl, nitro, hydroxyl, amino, aminocarbonyl, $C_1$-$C_6$ alkyl, $C_1$-$C_6$alkoxyl, $C_1$-$C_6$haloalkyl, or $C_1$-$C_6$haloalkoxyl;

$Y_2$ is substituted or unsubstituted 6-10 membered aryl or substituted or unsubstituted 6-10 membered heteroaryl, wherein the substituted 6-10 membered aryl or 6-10 membered heteroaryl is substituted by one or more of the following substituents: deuterium, halogen, cyano, nitro, hydroxyl, aminocarbonyl, $C_1$-$C_3$ alkyl, $C_1$-$C_3$ alkoxyl, $C_1$-$C_3$alkylcarbonyl, $C_1$-$C_3$alkoxycarbonyl, $C_1$-$C_3$alkylsulfonyl, $C_1$-$C_3$alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl;

$Y_3$ is substituted or unsubstituted 6-10 membered aryl, or substituted or unsubstituted 6-10 membered heteroaryl wherein the substituted 6-10 membered aryl or 6-10 membered heteroaryl is substituted by one or more of the following substituents: deuterium, halogen, cyano, nitro, hydroxyl, aminocarbonyl, $C_1$-$C_3$ alkyl, $C_1$-$C_3$ alkoxyl, $C_1$-$C_3$alkylcarbonyl, $C_1$-$C_3$alkoxycarbonyl, $C_1$-$C_3$alkylsulfonyl, $C_1$-$C_3$alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl;

$Y_4$ and $Y_5$ are absent, or one or more substituents on the heterocyclic ring, $Y_4$ and $Y_5$ are each independently deuterium, halogen, oxo, $C_1$-$C_3$ alkyl, $C_3$ cycloalkyl or phenyl;

ii) fused heterocyclyl selected from:

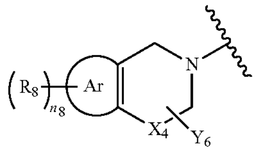

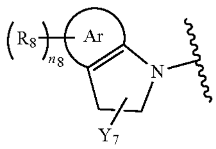

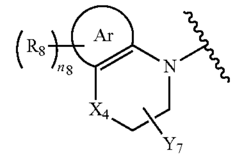

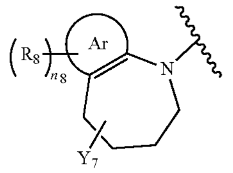

$n_8$ is 0, 1, 2, 3 or 4;

$X_4$ is C, N or O;

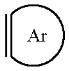

is 6-10 membered aryl ring or 5-10 membered heteroaryl ring, $R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$alkylaminocarbonyl, $C_1$-$C_3$alkoxycarbonyl, nitro, amino, cyano, $C_1$-$C_3$ haloalkyl, hydroxyl, $C_1$-$C_3$alkylsulfonyl, $C_1$-$C_3$ alkylamino, $C_1$-$C_3$ acylamino, aminocarbonyl, $C_3$-$C_6$ heterocyclyl, $C_1$-$C_3$ haloalkoxyl, phenyl or 5-6 membered heteroaryl;

with the proviso that when the above $R_8$ is each independently selected from any of the following substituents: hydrogen, deuterium, $C_1$-$C_3$ alkoxyl, halogen, $C_1$-$C_3$ alkyl, $C_3$-$C_6$ cycloalkyl, carboxyl, $C_1$-$C_3$alkylaminocarbonyl, $C_1$-$C_3$alkoxycarbonyl, nitro, amino, cyano, $C_1$-$C_3$ haloalkyl, hydroxyl, $C_1$-$C_3$alkylsulfonyl, and when Y is absent, then $X_1$ is other than —O—;

$Y_6$ and $Y_7$ are absent, or one or more substituents on the heterocyclic ring, and each is independently selected from deuterium, halogen, $C_1$-$C_3$ alkyl, $C_3$ cycloalkyl, $C_1$-$C_3$ haloalkyl;

or iii) spiroheterocyclic group selected from:

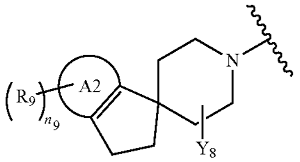

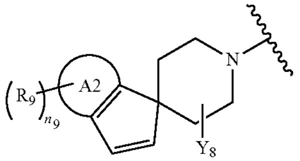

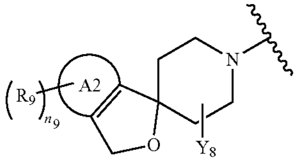

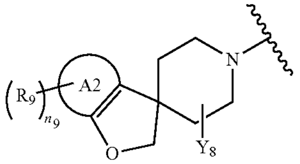

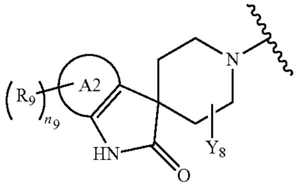

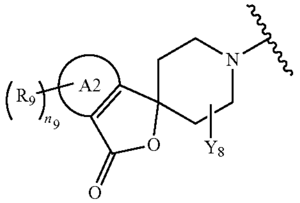

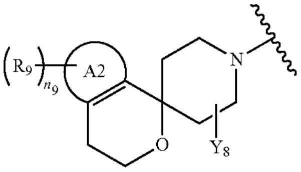

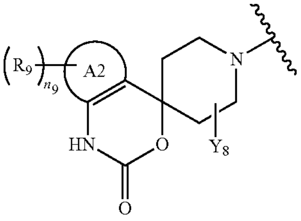

-continued

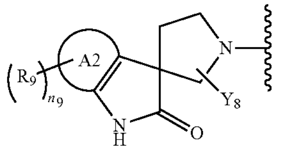

wherein, $n_9$ is 0, 1, 2, 3 or 4:

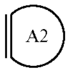

is 6-10 membered aryl ring or 5-10 heteroaryl ring;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl; wherein when $n_9$>1, each $R_9$ can be the same or different;

$Y_8$ is a substituent which optionally replace the hydrogen atom in the non-aromatic moiety of the spiro ring structure, and $Y_8$ is optionally substituted by deuterium, halogen, $C_1$-$C_3$ alkyl, $C_3$ cycloalkyl or $C_1$-$C_3$ haloalkyl.

3. The compound of claim 1, or the tautomer, enantiomer, diastereomer, racemate, isotopic compound, pharmaceutically acceptable salt, ester, or hydrate thereof, wherein the compound of formula (I) is the compound of any of formula (I-1) to (I-8):

I-1

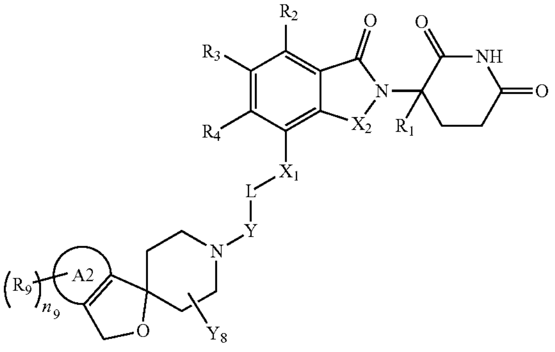

-continued

I-2

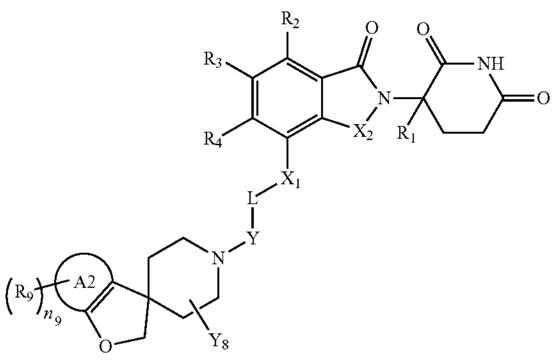

I-3

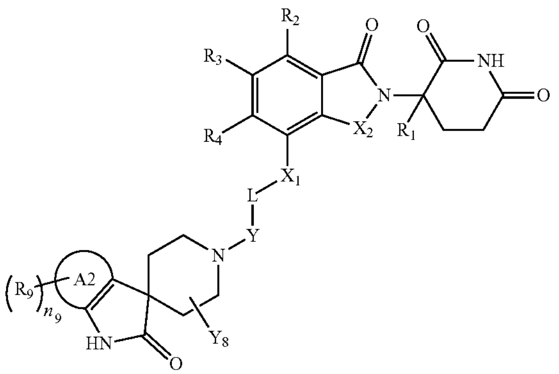

I-4

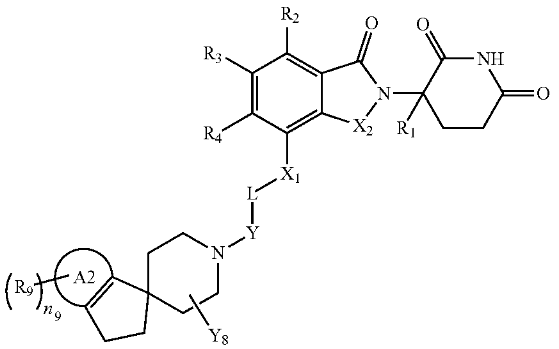

I-5

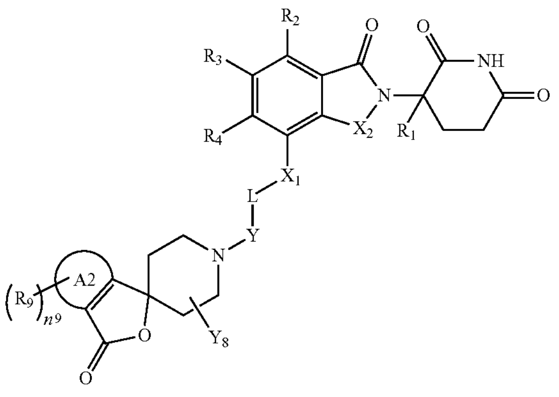

-continued

I-6

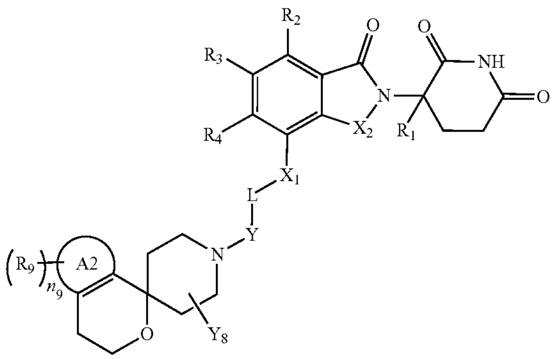

I-7

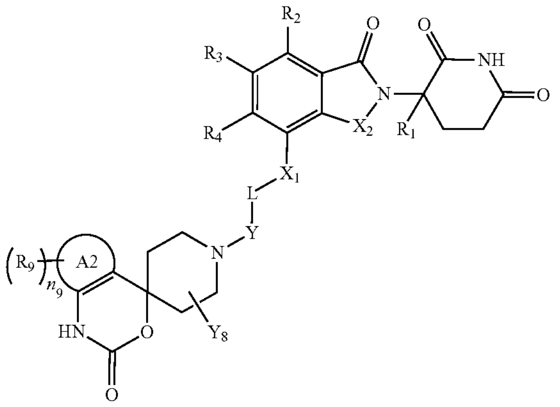

I-8

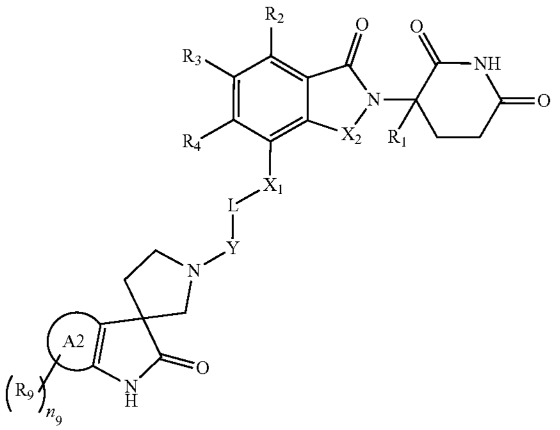

wherein, $X_1$ is —$CH_2$— or —O—;

$X_2$ is —$CH_2$— or —CO—;

$R_1$ is hydrogen, deuterium or fluorine;

$R_2$ and $R_4$ are each independently selected from hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O) $Ra_1$, —NHC(O)O$Ra_2$, —$NRa_3Ra_4$, wherein $Ra_1$, $Ra_2$, $Ra_3$ and $Ra_4$ are each independently selected from hydrogen, $C_{1-6}$ alkyl substituted or unsubstituted by one or more halogens, or $C_{3-6}$ cycloalkyl substituted or unsubstituted by one or more halogens;

Y is absent, or is —CO— or —CO—NH—;

$n_9$ is 0, 1, 2, 3 or 4;

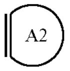

is a 6-10 membered aryl ring or 5-10 heteroaryl ring,

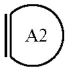

is fused with the spiro ring nucleus to form a spiro heterocyclic group;

$Y_8$ is a substituent which optionally replaces the hydrogen atom in the non-aromatic moiety of the spiro ring structure, and $Y_8$ is optionally substituted by deuterium, halogen, methyl, ethyl, cyclopropyl, or trifluoromethyl;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl; wherein when $n_{9>1}$, each $R_9$ can be the same or different.

4. The compound of claim 1, or the tautomer, enantiomer, diastereomer, racemate, isotopic compound, pharmaceutically acceptable salt, ester or hydrate thereof, wherein the compound of formula (I) is the compound of any of formula (I-9) to (I-16):

I-9

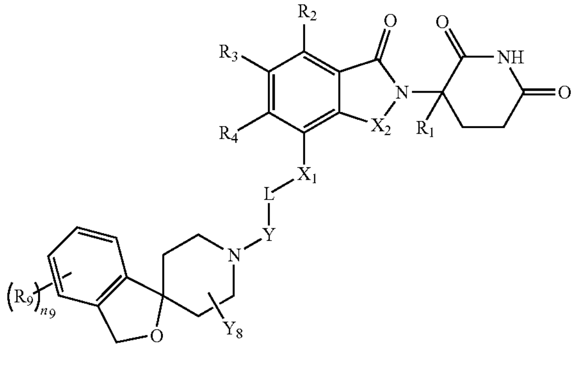

-continued

I-10

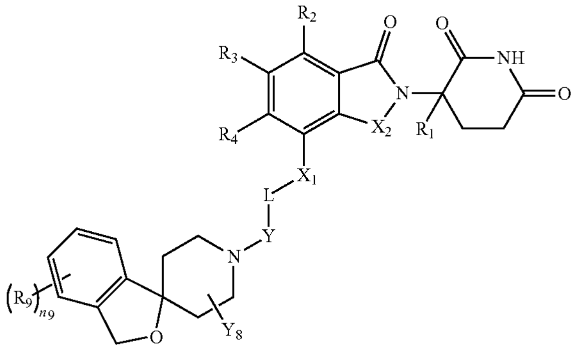

I-11

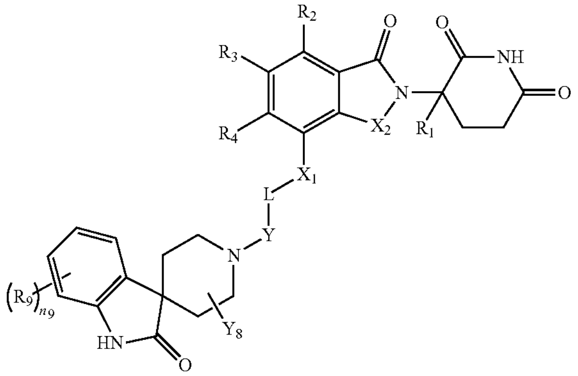

I-12

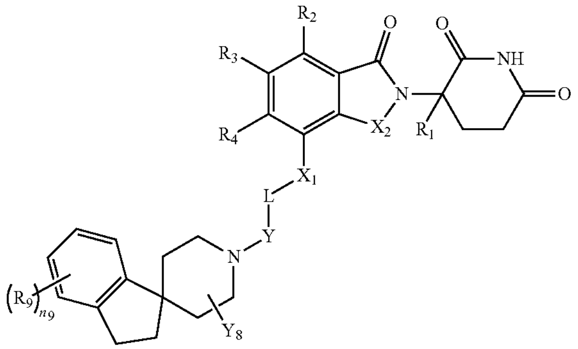

I-13

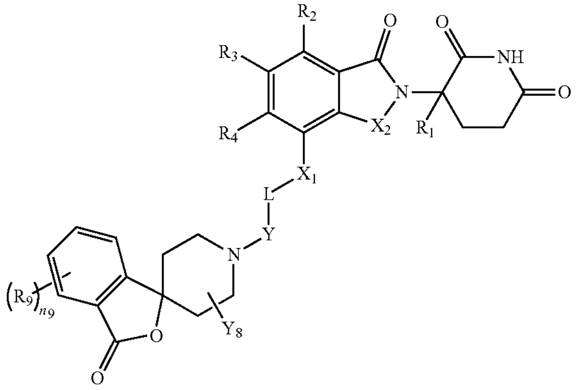

-continued

I-14

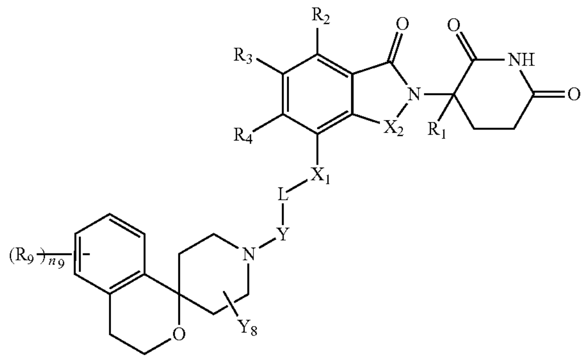

I-15

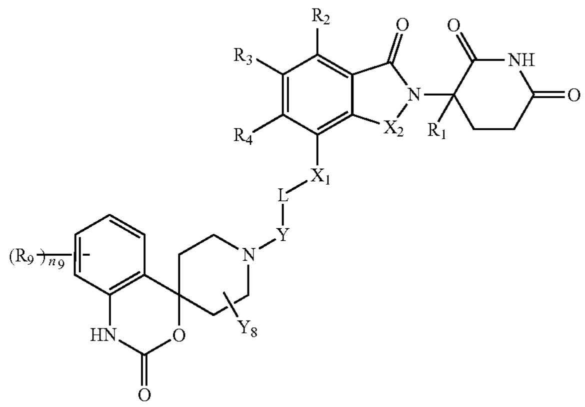

I-16

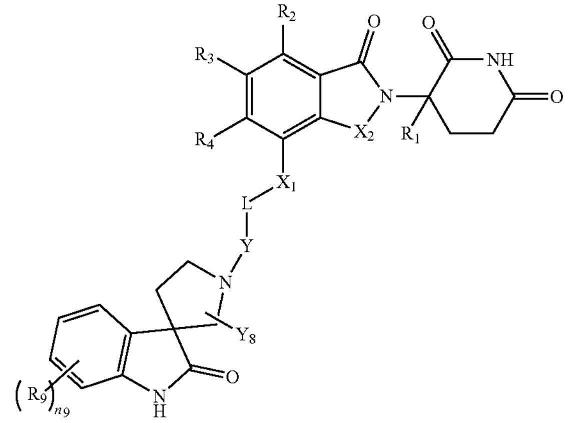

wherein, $X_1$ is —$CH_2$— or —O—;

$X_2$ is —$CH_2$— or —CO—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O) $Ra_1$, —NHC(O)O$Ra_2$, —N$Ra_3$$Ra_4$, wherein $Ra_1$, $Ra_2$, $Ra_3$ and $Ra_4$ are each independently selected from hydrogen atom, $C_{1-6}$ alkyl substituted or unsubstituted by one or more halogens, or $C_{3-6}$ cycloalkyl substituted or unsubstituted by one or more halogens;

Y is absent, or is —CO— or —CO—NH—;

$n_9$ is 0, 1, 2, 3 or 4;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl; wherein when $n_9$>1, each $R_9$ can be the same or different;

$Y_8$ is a substituent which optionally replaces the hydrogen atom in the non-aromatic moiety of the spiro ring structure, and $Y_8$ is optionally substituted by deuterium, halogen, methyl, ethyl, cyclopropyl, or trifluoromethyl.

5. The compound of claim 1, or the tautomer, enantiomer, diastereomer, racemate, isotopic compound, pharmaceutically acceptable salt, ester or hydrate thereof, wherein the compound of formula (I) is the compound of any of formula (I-24) to (I-32):

I-24

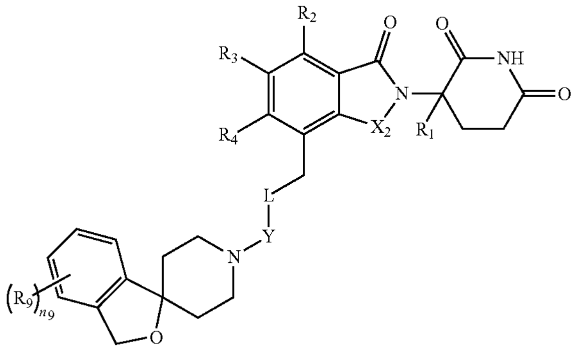

I-25

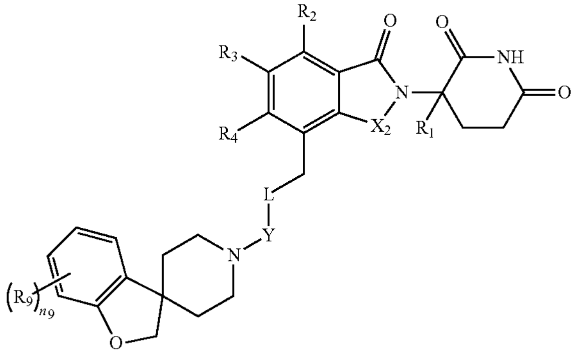

-continued

I-26

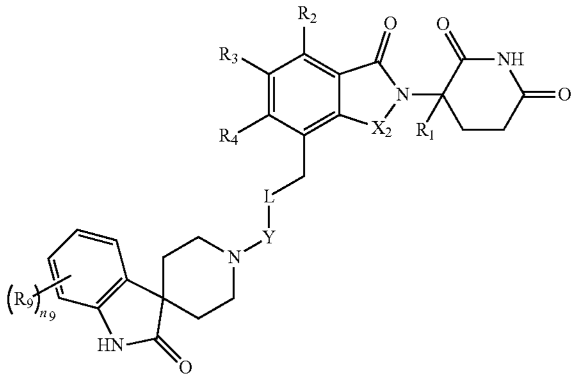

I-27

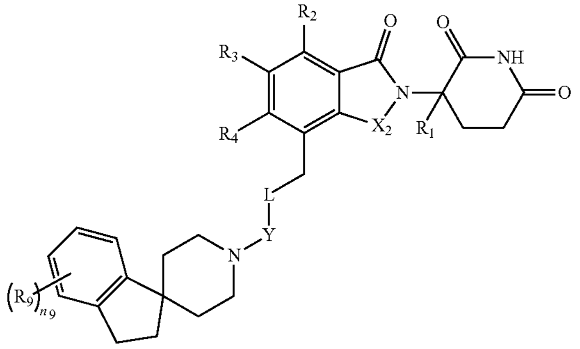

I-29

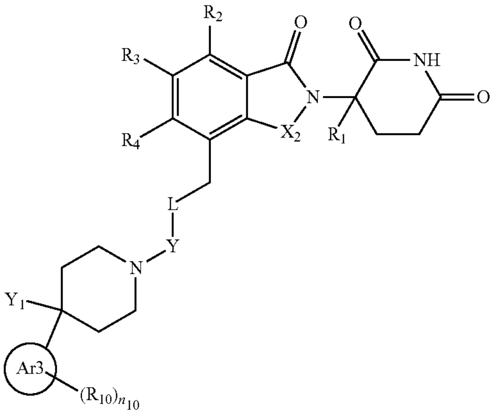

I-30

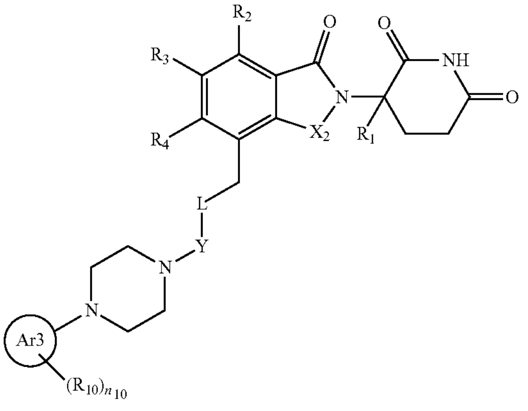

-continued

I-31

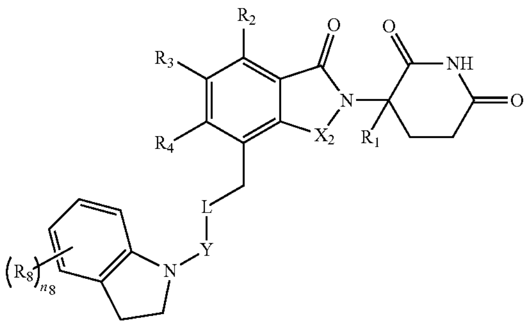

I-32

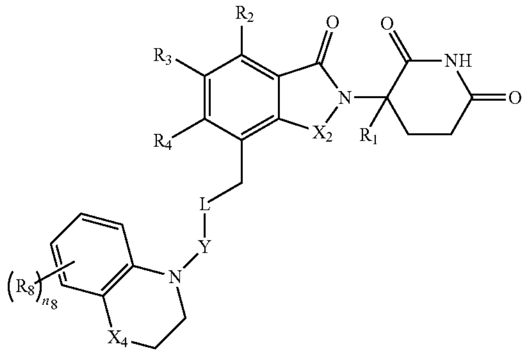

wherein, $X_2$ is —$CH_2$— or —CO—;

$R_1$ is hydrogen, deuterium or fluorine;

$R_2$ and $R_4$ are each independently hydrogen or deuterium;

$R_3$ is selected from hydrogen, deuterium or fluorine;

L is substituted or unsubstituted linear alkylene group containing 2-8 carbon atoms, and the “substituted” means that one or more hydrogen atoms in the alkylene group are optionally substituted by the following substituents: deuterium, halogen, cyano, $C_1$-$C_3$ alkyl, $C_1$-$C_3$ haloalkyl, —NHC(O) $Ra_1$, —NHC(O)$ORa_2$, —$NRa_3Ra_4$, wherein $Ra_1$, $Ra_2$, $Ra_3$ and $Ra_4$ are each independently selected from hydrogen atom, $C_{1-6}$ alkyl unsubstituted or substituted by one or more halogens or $C_{3-6}$ cycloalkyl unsubstituted or substituted by one or more halogens;

Y is absent, or —CO— or —CO—NH—;

$n_8$, $n_9$ and $n_{10}$ are each independently selected from 0, 1, 2, 3, or 4;

$X_4$ is C, N or O;

$R_9$ is selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl; wherein when $n_9$>1, each $R_9$ can be the same or different;

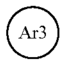

is selected from substituted or unsubstituted 6-10 membered aryl, substituted or unsubstituted 6-10 membered heteroaryl, and the 6-10 membered aryl or 6-10 membered heteroaryl is selected from thienyl, pyridyl, phenyl, benzothienyl, benzimidazolyl, indolyl, naphthyl, quinolinyl, isoquinolinyl;

$R_{10}$ is each independently selected from deuterium, halogen, cyano, nitro, hydroxyl, aminocarbonyl, $C_1$-$C_3$ alkyl, $C_1$-$C_3$ alkoxyl, $C_1$-$C_3$alkylcarbonyl, $C_1$-$C_3$alkoxycarbonyl, $C_1$-$C_3$alkylsulfonyl, $C_1$-$C_3$alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl, when $n_{10>1}$, each $R_{10}$ can be the same or different;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$alkylaminocarbonyl, $C_1$-$C_3$alkoxycarbonyl, nitro, amino, cyano, $C_1$-$C_3$ haloalkyl, hydroxyl, $C_1$-$C_3$alkylsulfonyl, $C_1$-$C_3$ alkylamino, $C_1$-$C_3$ acylamino, aminocarbonyl, $C_3$-$C_6$ heterocyclyl, $C_1$-$C_3$haloalkoxyl, phenyl or 5-6 membered heteroaryl; wherein when $n_8>1$, each $R_8$ can be the same or different.

6. The compound of claim 1, or the tautomer, enantiomer, diastereomer, racemate, isotopic compound, pharmaceutically acceptable salt, ester or hydrate thereof, wherein the compound of formula (I) is the compound of any one of formula (I-33) to (I-40):

I-33

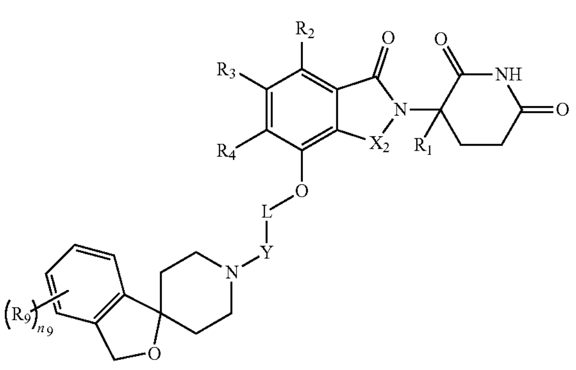

I-34

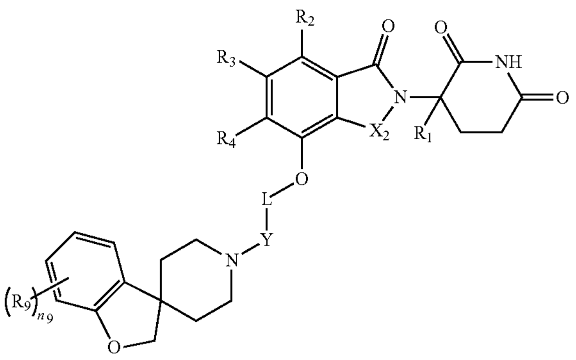

-continued

I-35

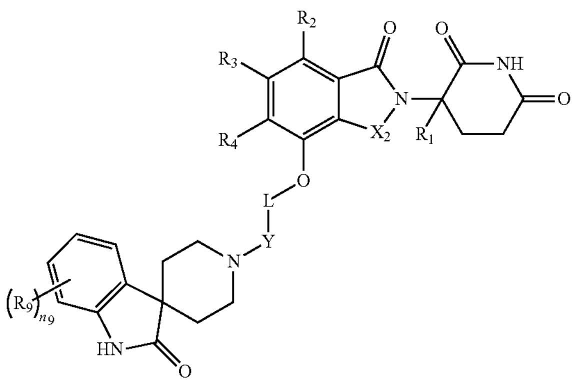

I-36

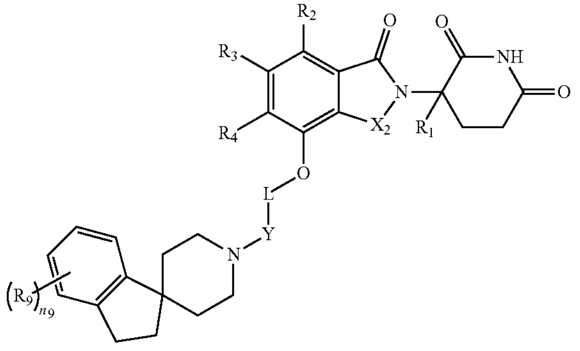

I-37

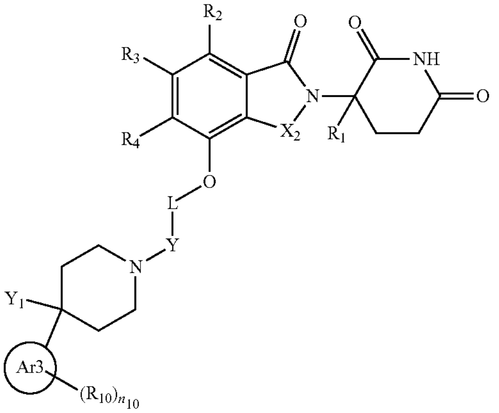

I-38

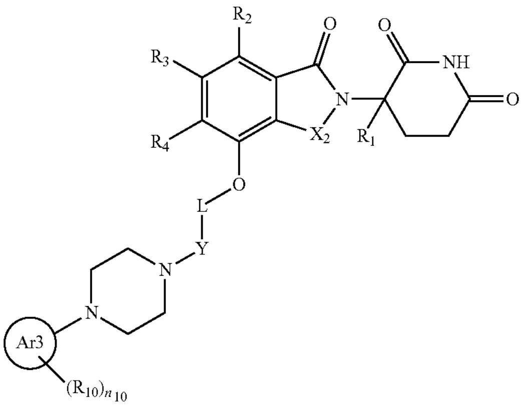

-continued

I-39

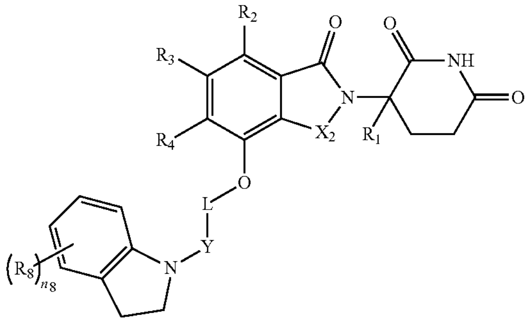

I-40

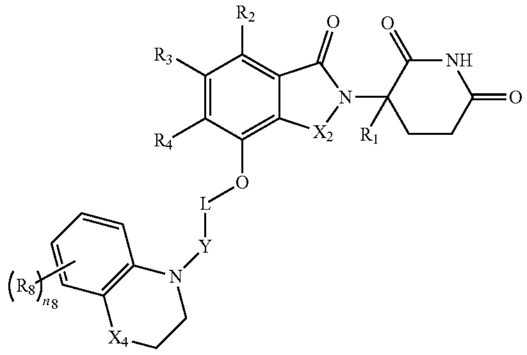

wherein, $X_2$ is —$CH_2$— or —CO—;

$R_1$ is hydrogen, deuterium or fluorine;

$R_2$ and $R_4$ are each independently hydrogen or deuterium;

$R_3$ is hydrogen, deuterium or fluorine;

L is substituted or unsubstituted linear alkylene group containing 2-8 carbon atoms, and the "substituted" means that one or more hydrogen atoms in the alkylene group are optionally substituted by the following substituents: deuterium, halogen, cyano, $C_1$-$C_3$ alkyl, $C_1$-$C_3$ haloalkyl, —NHC(O) $Ra_1$, —NHC(O)O$Ra_2$, —N$Ra_3$$Ra_4$, wherein $Ra_1$, $Ra_2$, $Ra_3$ and $Ra_4$ are each independently selected from hydrogen atom, $C_{1-6}$ alkyl unsubstituted or substituted by one or more halogens or $C_{3-6}$ cycloalkyl unsubstituted or substituted by one or more halogens;

Y is absent, or —CO— or —CO—NH—;

$n_8$, $n_9$ and $n_{10}$ are each independently 0, 1, 2, 3, or 4;

$X_4$ is selected from C, N or O;

$R_9$ are each independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl; when $n_9$>1, each $R_9$ can be the same or different;

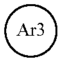

is selected from substituted or unsubstituted 6-10 membered aryl, substituted or unsubstituted 6-10 membered heteroaryl, and the 6-10 membered aryl or 6-10 membered heteroaryl is selected from thienyl, pyridyl, phenyl, benzothienyl, benzimidazolyl, indolyl, naphthyl, quinolinyl, isoquinolinyl;

$R_{10}$ is each independently selected from deuterium, halogen, cyano, nitro, hydroxyl, #aminocarbonyl, $C_1$-$C_3$ alkyl, $C_1$-$C_3$ alkoxyl, $C_1$-$C_3$alkylcarbonyl, $C_1$-$C_3$alkoxycarbonyl, $C_1$-$C_3$alkylsulfonyl, $C_1$-$C_3$alkylaminocarbonyl, $C_3$-$C_6$ cycloalkyl or heterocyclyl, $C_1$-$C_3$ acylamino, $C_1$-$C_3$ haloalkyl, $C_1$-$C_3$haloalkoxyl, when $n_{10}$>1, each $R_{10}$ can be the same or different;

$R_8$ is each independently selected from hydrogen, deuterium, $C_1$-$C_3$ alkoxyl, halogen, $C_1$-$C_3$ alkyl, $C_3$-$C_6$ cycloalkyl, carboxyl, $C_1$-$C_3$alkylaminocarbonyl, $C_1$-$C_3$alkoxycarbonyl, nitro, amino, cyano, $C_1$-$C_3$ haloalkyl, hydroxyl, $C_1$-$C_3$alkylsulfonyl, $C_1$-$C_3$ alkylamino, $C_1$-$C_3$ acylamino, aminocarbonyl, $C_3$-$C_6$ heterocyclyl, $C_1$-$C_3$haloalkoxyl, phenyl or 5-6 membered heteroaryl; wherein when $n_8$>1, each $R_8$ can be the same or different;

with the proviso that when $R_8$ is selected from any of the following substituents: deuterium, $C_1$-$C_3$ alkoxyl, halogen, $C_1$-$C_3$ alkyl, $C_3$-$C_6$ cycloalkyl, carboxyl, $C_1$-$C_3$alkylaminocarbonyl, $C_1$-$C_3$alkoxycarbonyl, nitro, amino, cyano, $C_1$-$C_3$ haloalkyl, hydroxyl, $C_1$-$C_3$alkylsulfonyl, and when Y is absent, $X_1$ is other than —O—.

7. A compound selected from the following compounds:

| Serial number | Compound |
| --- | --- |
| 1 | 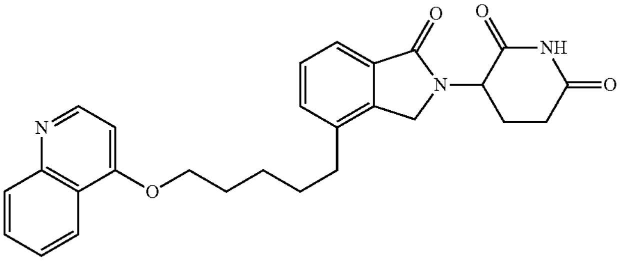 [SMILES: O=C1CCC(N2Cc3c(CCCCCOc4ccnc5ccccc45)cccc3C2=O)C(=O)N1] |

-continued
| Serial number | Compound |
|---|---|
| 2 | 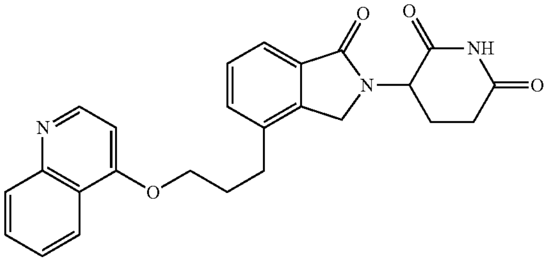 [SMILES: O=C1CCC(N2Cc3c(CCCOc4ccnc5ccccc45)cccc3C2=O)C(=O)N1] |
| 3 | 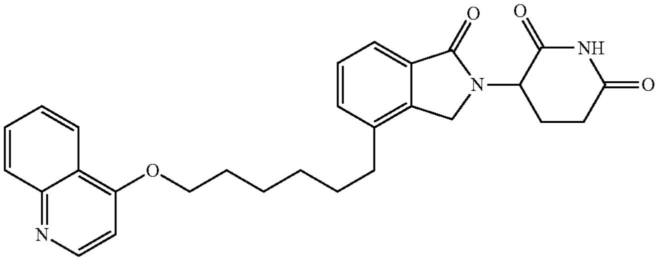 [SMILES: O=C1CCC(N2Cc3c(CCCCCCOc4ccnc5ccccc45)cccc3C2=O)C(=O)N1] |
| 4 | 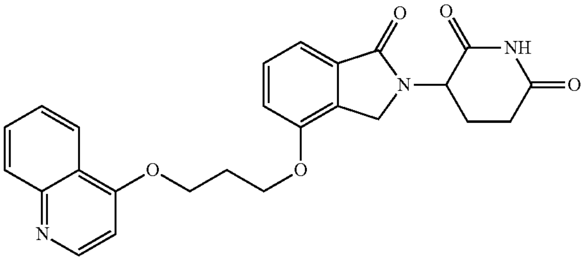 [SMILES: O=C1CCC(N2Cc3c(OCCCOc4ccnc5ccccc45)cccc3C2=O)C(=O)N1] |
| 5 | 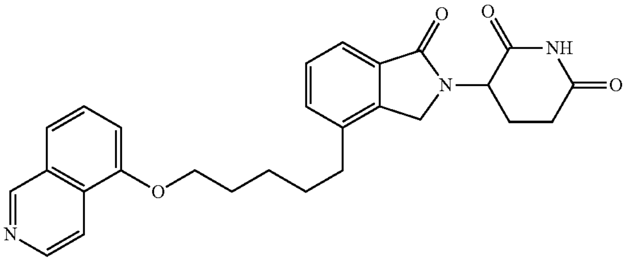 [SMILES: O=C1CCC(N2Cc3c(CCCCCOc4cccc5cnccc45)cccc3C2=O)C(=O)N1] |
| 6 | 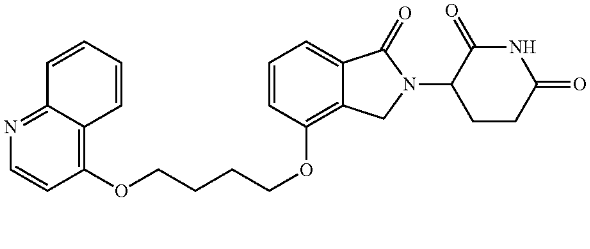 [SMILES: O=C1CCC(N2Cc3c(OCCCCOc4ccnc5ccccc45)cccc3C2=O)C(=O)N1] |

-continued
| Serial number | Compound |
| --- | --- |
| 7 | 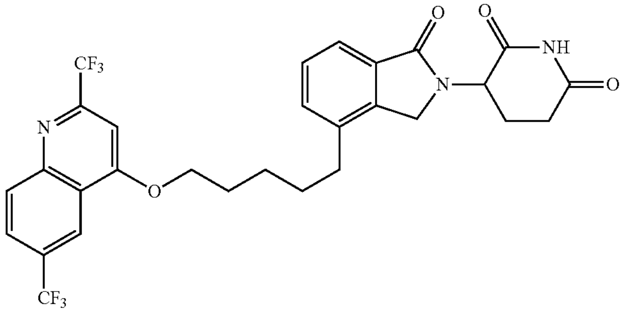 |
| 8 | 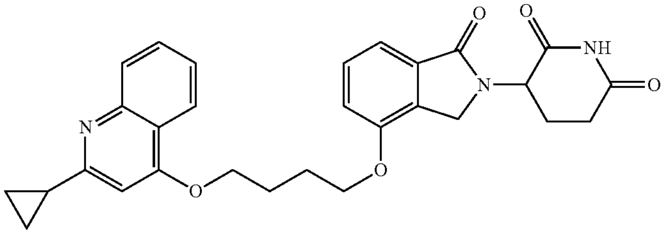 [SMILES: O=C1CCC(N2Cc3c(OCCCCOc4cc(C5CC5)nc5ccccc45)cccc3C2=O)C(=O)N1] |
| 9 | 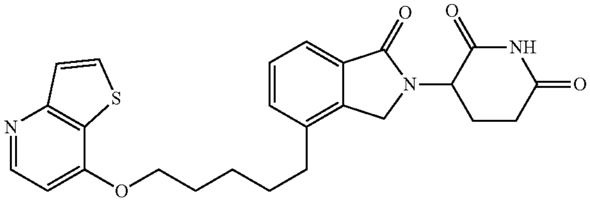 [SMILES: O=C1CCC(N2Cc3c(CCCCCOc4ccnc5ccsc45)cccc3C2=O)C(=O)N1] |
| 10 | 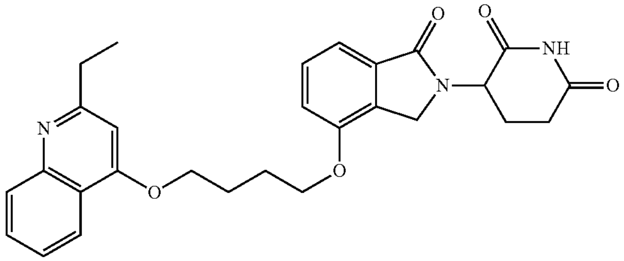 |
| 11 | 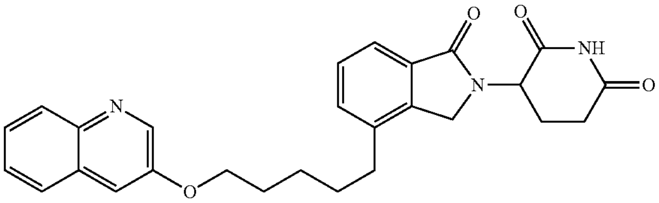 [SMILES: O=C1CCC(N2Cc3c(CCCCCOc4cnc5ccccc5c4)cccc3C2=O)C(=O)N1] |
| 12 | 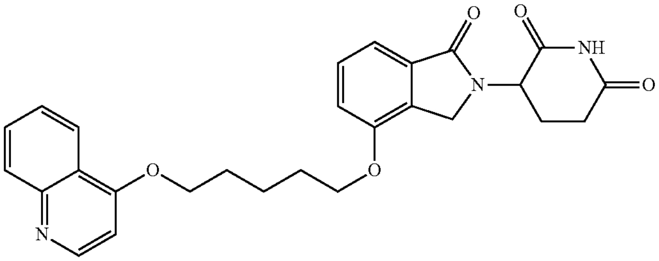 |

-continued
| Serial number | Compound |
|---|---|
| 13 | 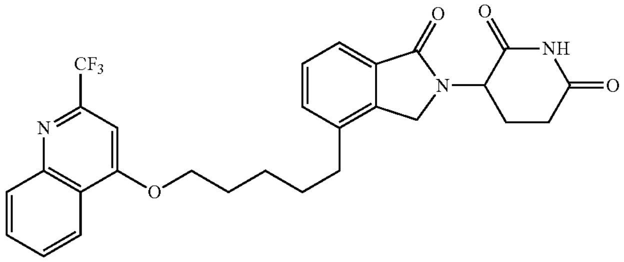 [SMILES: O=C1CCC(N2Cc3c(CCCCCOc4cc(C(F)(F)F)nc5ccccc45)cccc3C2=O)C(=O)N1] |
| 14 | 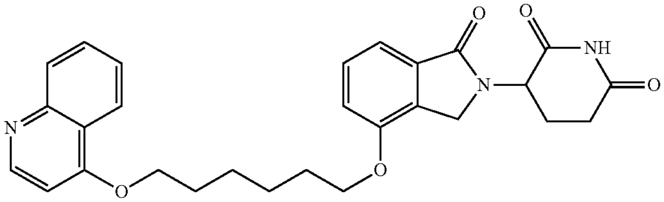 [SMILES: O=C1CCC(N2Cc3c(OCCCCCCOc4ccnc5ccccc45)cccc3C2=O)C(=O)N1] |
| 15 | 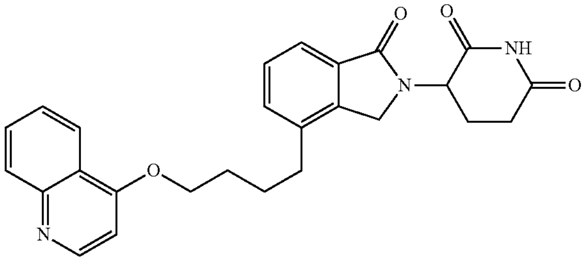 [SMILES: O=C1CCC(N2Cc3c(CCCCOc4ccnc5ccccc45)cccc3C2=O)C(=O)N1] |
| 16 | 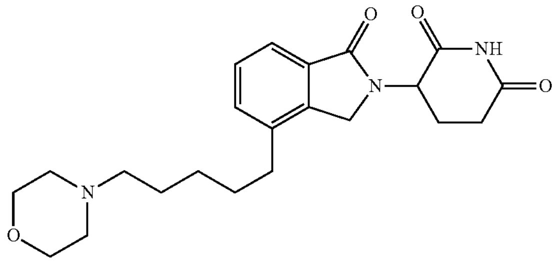 [SMILES: O=C1CCC(N2Cc3c(CCCCCN4CCOCC4)cccc3C2=O)C(=O)N1] |
| 17 | 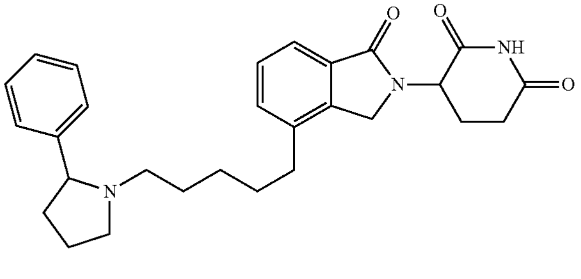 [SMILES: O=C1CCC(N2Cc3c(CCCCCN4CCCC4c4ccccc4)cccc3C2=O)C(=O)N1] |

-continued
| Serial number | Compound |
|---|---|
| 18 | 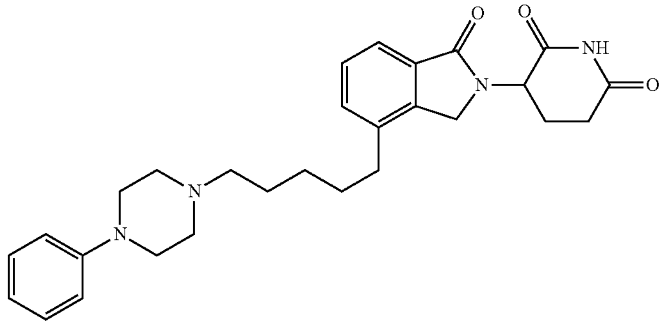 [SMILES: O=C1CCC(N2Cc3c(CCCCCN4CCN(c5ccccc5)CC4)cccc3C2=O)C(=O)N1] |
| 19 | 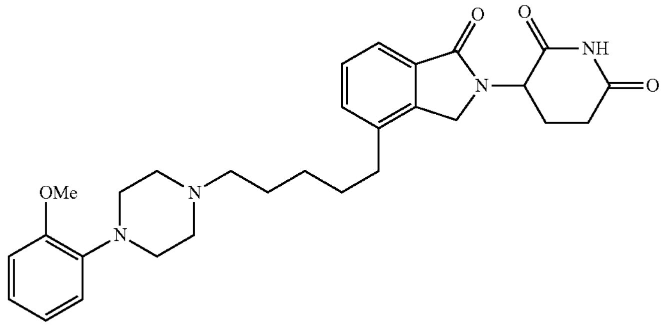 [SMILES: COc1ccccc1N1CCN(CCCCCc2cccc3c2CN(C2CCC(=O)NC2=O)C3=O)CC1] |
| 20 | 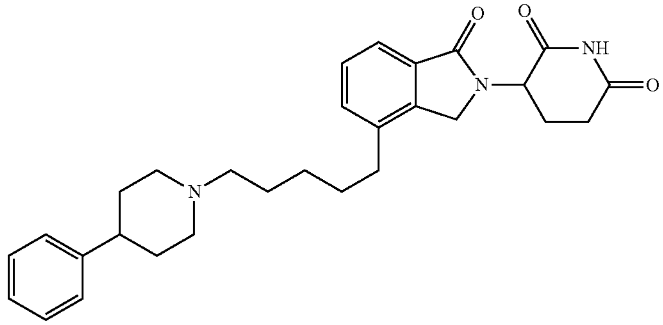 |
| 21 | 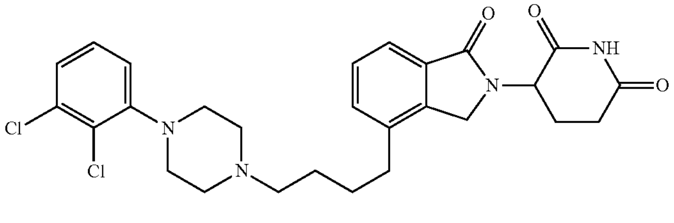 [SMILES: O=C1CCC(N2Cc3c(CCCCN4CCN(c5cccc(Cl)c5Cl)CC4)cccc3C2=O)C(=O)N1] |
| 22 | 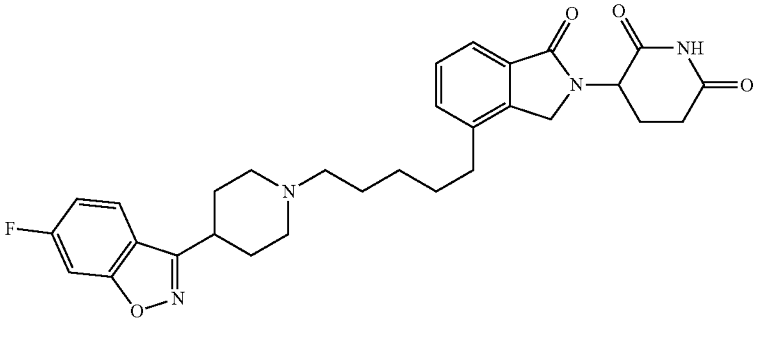 [SMILES: O=C1CCC(N2Cc3c(CCCCCN4CCC(c5noc6cc(F)ccc56)CC4)cccc3C2=O)C(=O)N1] |

-continued
| Serial number | Compound |
|---|---|
| 23 | 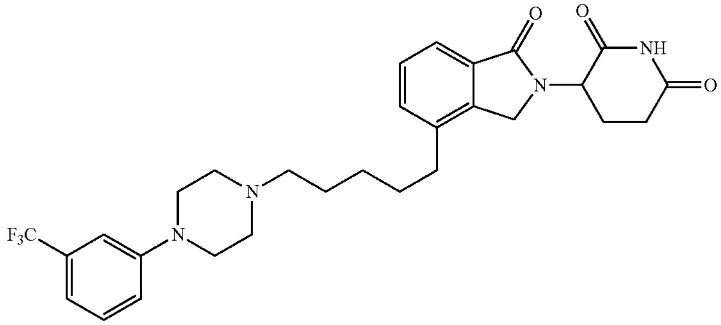 [SMILES: O=C1CCC(N2Cc3c(CCCCCN4CCN(c5cccc(C(F)(F)F)c5)CC4)cccc3C2=O)C(=O)N1] |
| 24 | 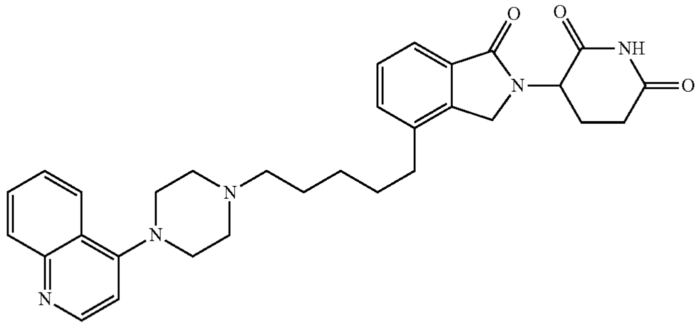 [SMILES: O=C1CCC(N2Cc3c(CCCCCN4CCN(c5ccnc6ccccc56)CC4)cccc3C2=O)C(=O)N1] |
| 25 | 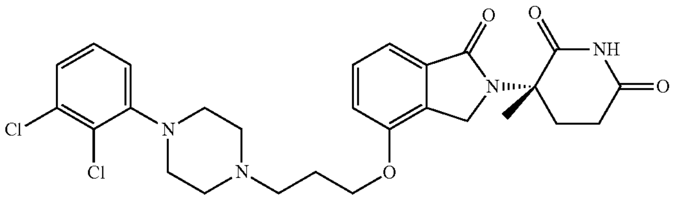 [SMILES: C[C@]1(N2Cc3c(OCCCN4CCN(c5cccc(Cl)c5Cl)CC4)cccc3C2=O)CCC(=O)NC1=O] |
| 26 | 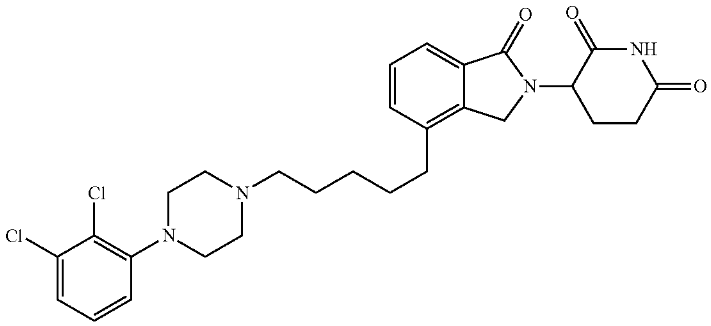 |
| 27 | 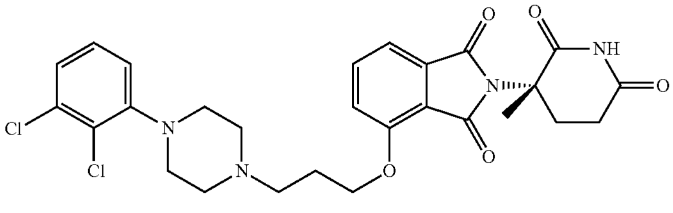 [SMILES: C[C@]1(N2C(=O)c3cccc(OCCCN4CCN(c5cccc(Cl)c5Cl)CC4)c3C2=O)CCC(=O)NC1=O] |

-continued
| Serial number | Compound |
|---|---|
| 28 | 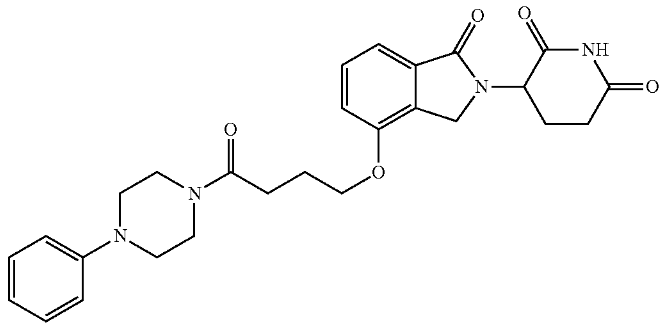 [SMILES: O=C1CCC(N2Cc3c(OCCCC(=O)N4CCN(c5ccccc5)CC4)cccc3C2=O)C(=O)N1] |
| 29 | 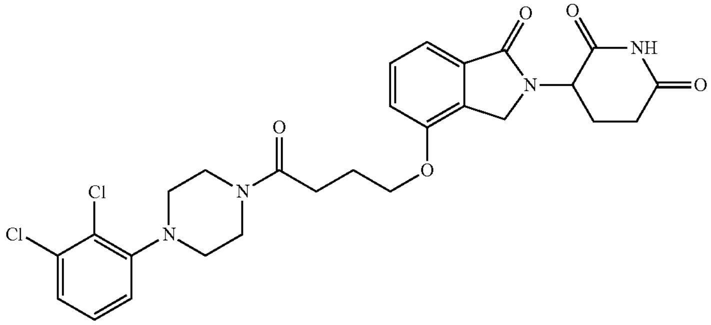 [SMILES: O=C1CCC(N2Cc3c(OCCCC(=O)N4CCN(c5cccc(Cl)c5Cl)CC4)cccc3C2=O)C(=O)N1] |
| 30 | 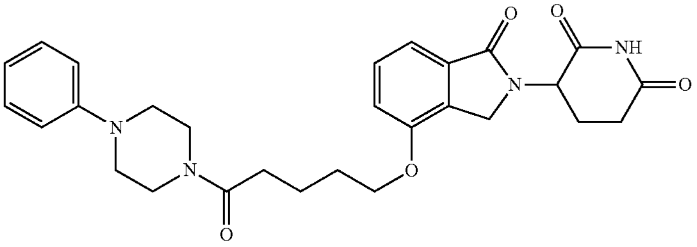 [SMILES: O=C1CCC(N2Cc3c(OCCCCC(=O)N4CCN(c5ccccc5)CC4)cccc3C2=O)C(=O)N1] |
| 31 | 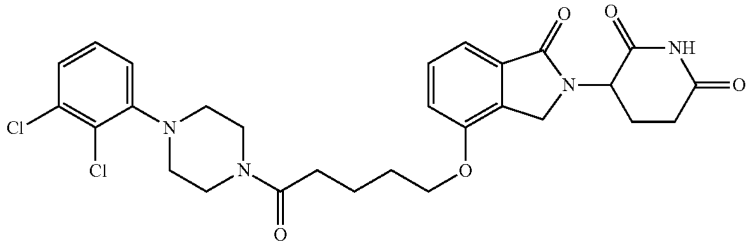 [SMILES: O=C1CCC(N2Cc3c(OCCCCC(=O)N4CCN(c5cccc(Cl)c5Cl)CC4)cccc3C2=O)C(=O)N1] |
| 32 | 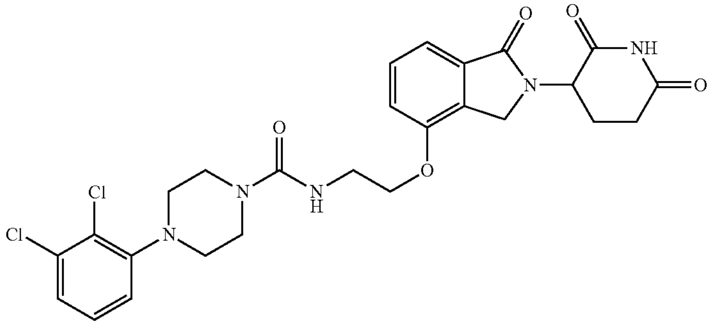 [SMILES: O=C1CCC(N2Cc3c(OCCNC(=O)N4CCN(c5cccc(Cl)c5Cl)CC4)cccc3C2=O)C(=O)N1] |

-continued
| Serial number | Compound |
|---|---|
| 33 | 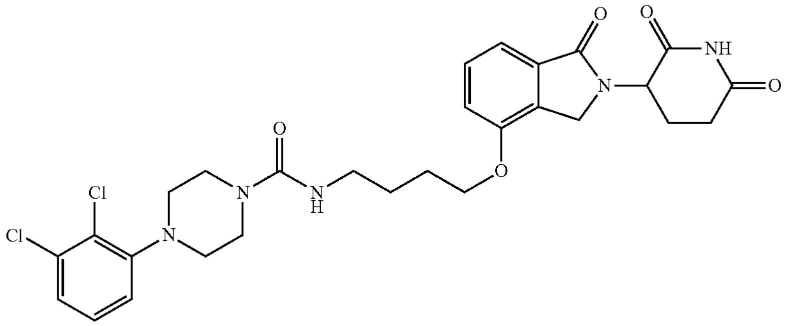 [SMILES: O=C1CCC(N2Cc3c(OCCCCNC(=O)N4CCN(c5cccc(Cl)c5Cl)CC4)cccc3C2=O)C(=O)N1] |
| 34 | 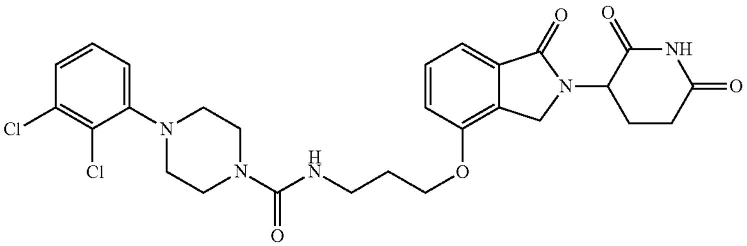 |
| 35 | 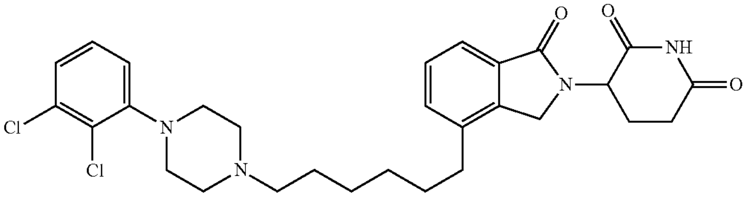 [SMILES: O=C1CCC(N2Cc3c(CCCCCCN4CCN(c5cccc(Cl)c5Cl)CC4)cccc3C2=O)C(=O)N1] |
| 36 | 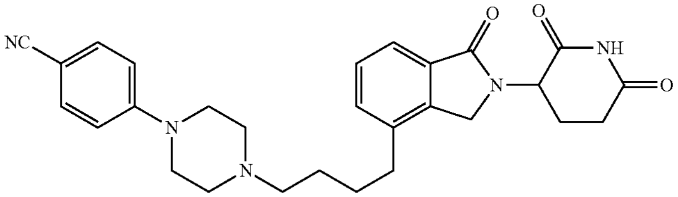 [SMILES: N#Cc1ccc(N2CCN(CCCCc3cccc4c3CN(C3CCC(=O)NC3=O)C4=O)CC2)cc1] |
| 37 | 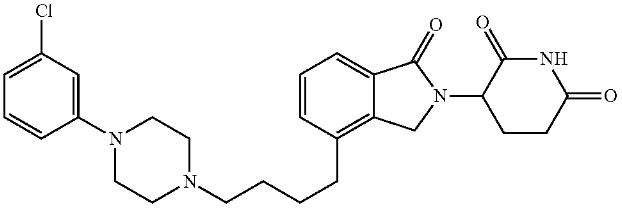 [SMILES: O=C1CCC(N2Cc3c(CCCCN4CCN(c5cccc(Cl)c5)CC4)cccc3C2=O)C(=O)N1] |
| 38 | 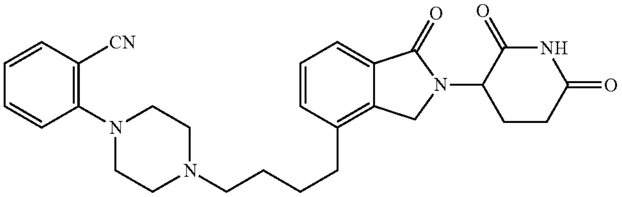 |

-continued
| Serial number | Compound |
|---|---|
| 39 | 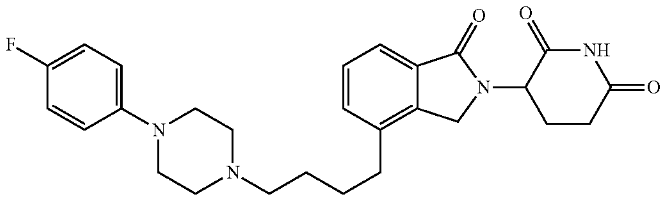 [SMILES: O=C1CCC(N2Cc3c(CCCCN4CCN(c5ccc(F)cc5)CC4)cccc3C2=O)C(=O)N1] |
| 40 | 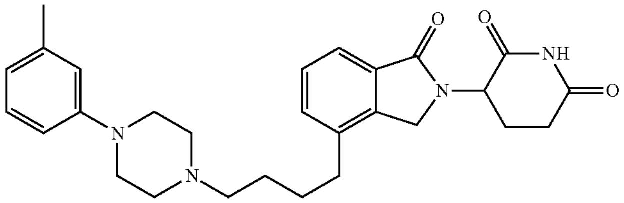 [SMILES: Cc1cccc(N2CCN(CCCCc3cccc4c3CN(C3CCC(=O)NC3=O)C4=O)CC2)c1] |
| 41 | 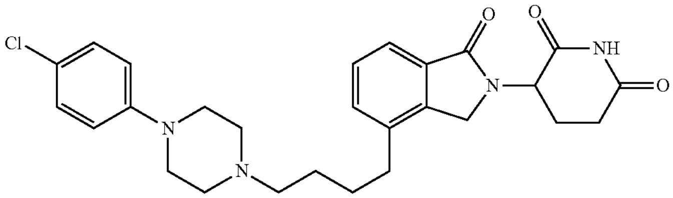 [SMILES: O=C1CCC(N2Cc3c(CCCCN4CCN(c5ccc(Cl)cc5)CC4)cccc3C2=O)C(=O)N1] |
| 42 | 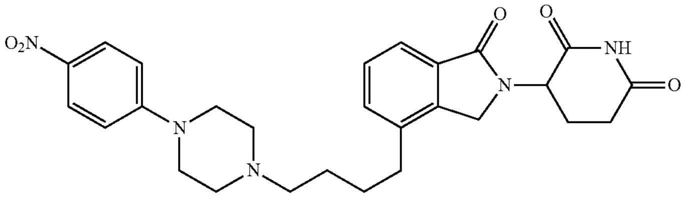 [SMILES: O=C1CCC(N2Cc3c(CCCCN4CCN(c5ccc([N+](=O)[O-])cc5)CC4)cccc3C2=O)C(=O)N1] |
| 43 | 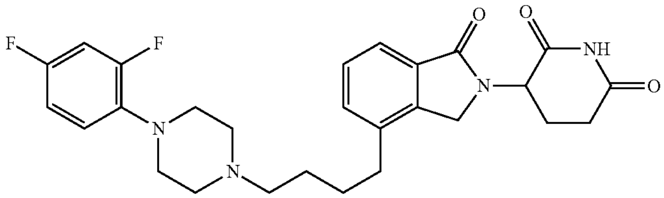 [SMILES: O=C1CCC(N2Cc3c(CCCCN4CCN(c5ccc(F)cc5F)CC4)cccc3C2=O)C(=O)N1] |
| 44 | 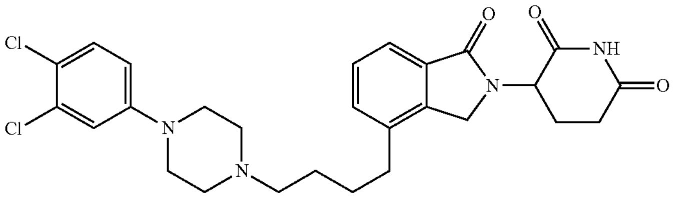 [SMILES: O=C1CCC(N2Cc3c(CCCCN4CCN(c5ccc(Cl)c(Cl)c5)CC4)cccc3C2=O)C(=O)N1] |
| 45 | 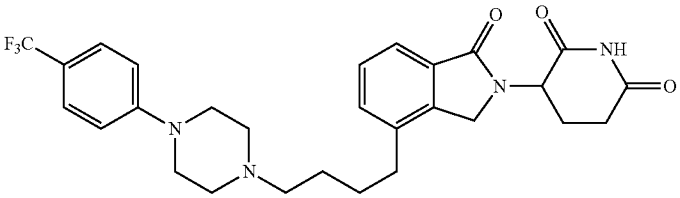 |

-continued
| Serial number | Compound |
|---|---|
| 46 | 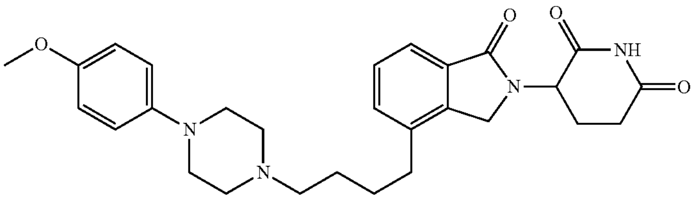 [SMILES: COc1ccc(N2CCN(CCCCc3cccc4c3CN(C3CCC(=O)NC3=O)C4=O)CC2)cc1] |
| 47 | 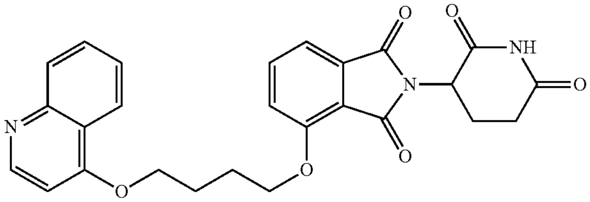 [SMILES: O=C1CCC(N2C(=O)c3cccc(OCCCCOc4ccnc5ccccc45)c3C2=O)C(=O)N1] |
| 48 | 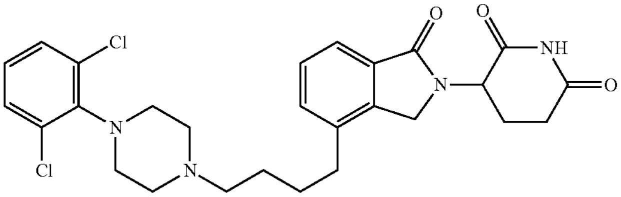 |
| 49 | 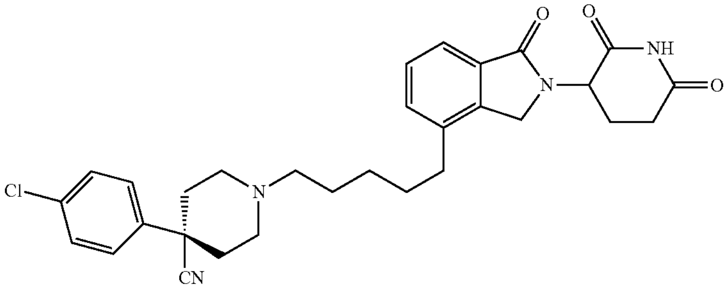 |
| 50 | 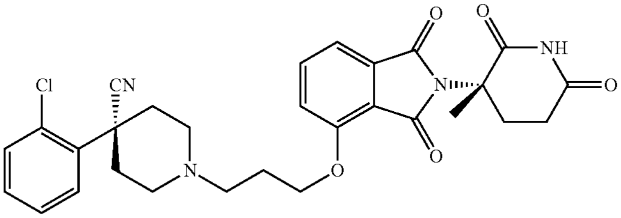 |
| 51 | 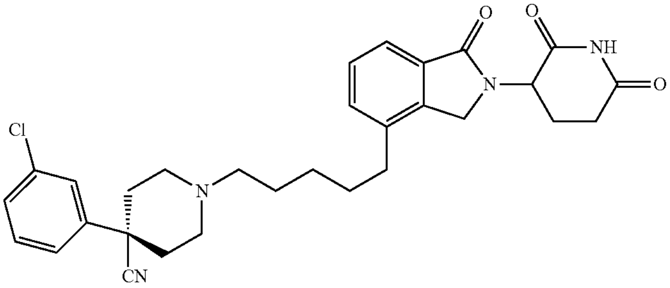 |

-continued
| Serial number | Compound |
|---|---|
| 52 | 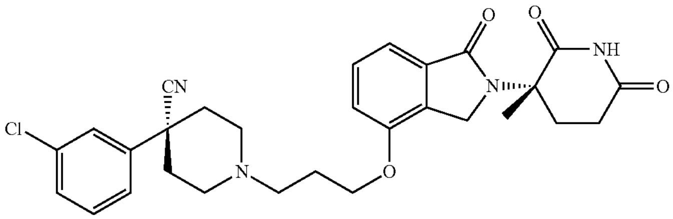 |
| 53 | 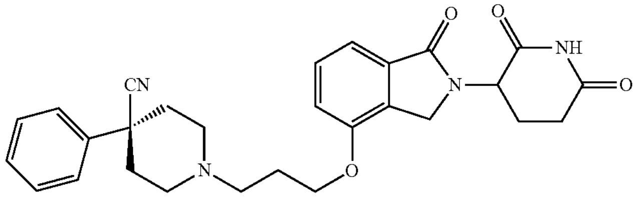 |
| 54 | 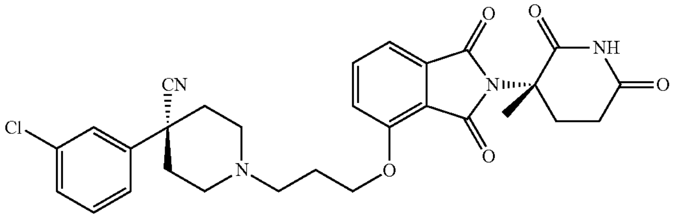 |
| 55 | 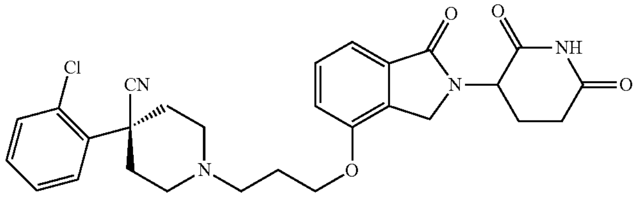 |
| 56 | 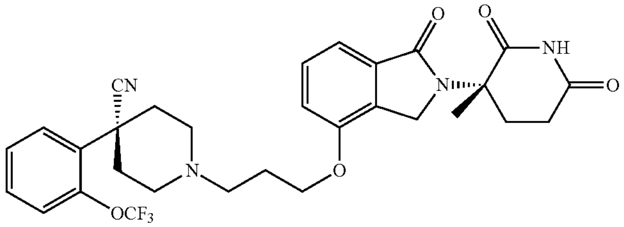 |
| 57 | 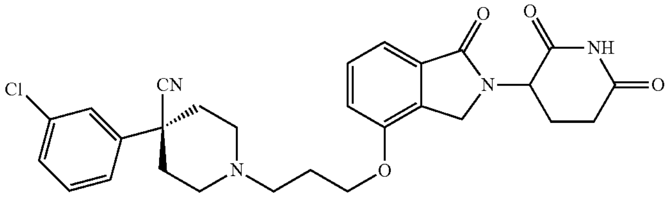 |
| 58 | 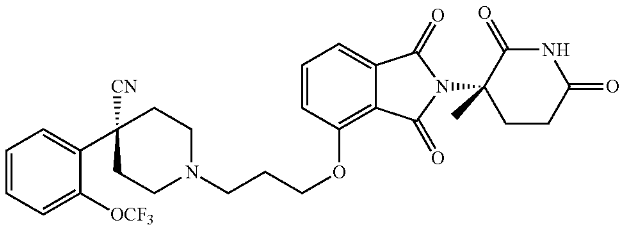 |

-continued
| Serial number | Compound |
|---|---|
| 59 | 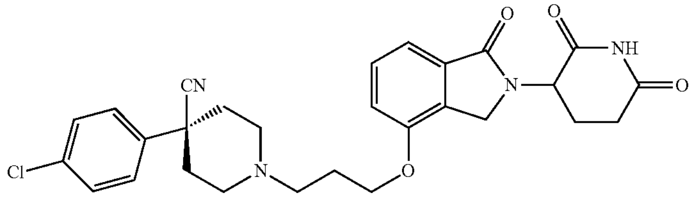 |
| 60 | 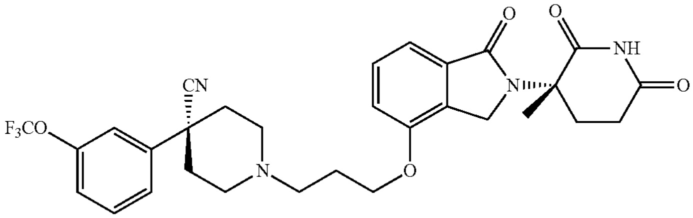 |
| 61 | 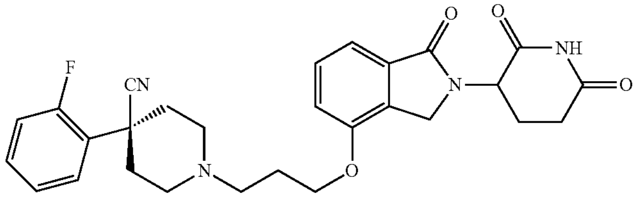 |
| 62 | 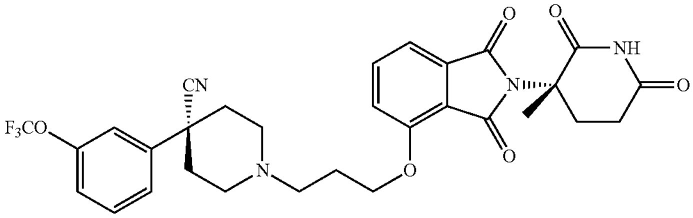 |
| 63 | 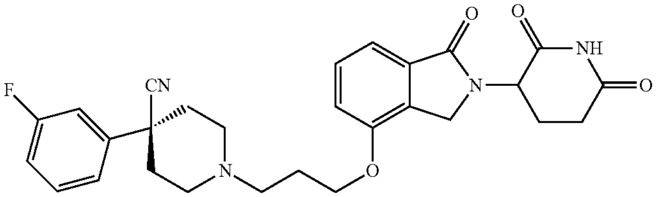 |
| 64 | 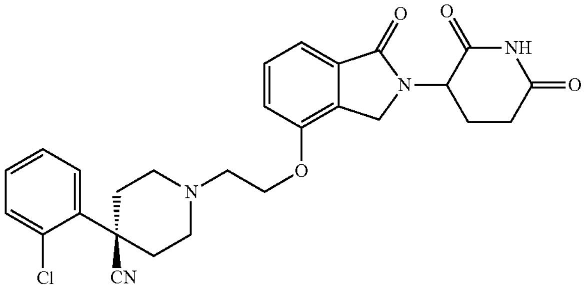 |
| 65 | 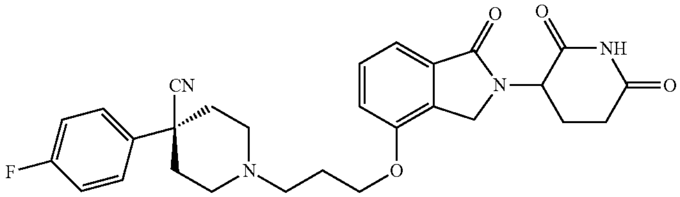 |

-continued
| Serial number | Compound |
|---|---|
| 66 | 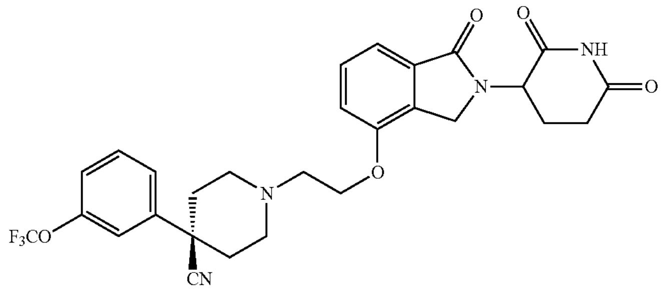 |
| 67 | 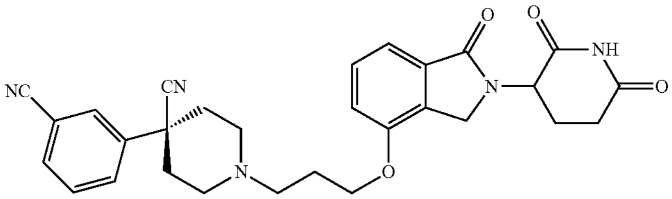 |
| 68 | 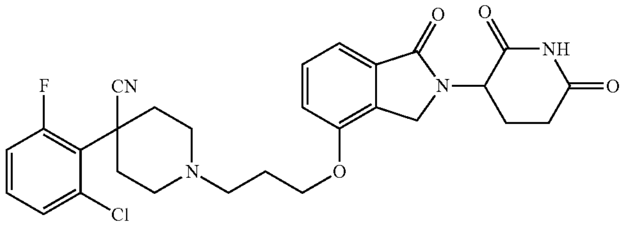 |
| 69 | 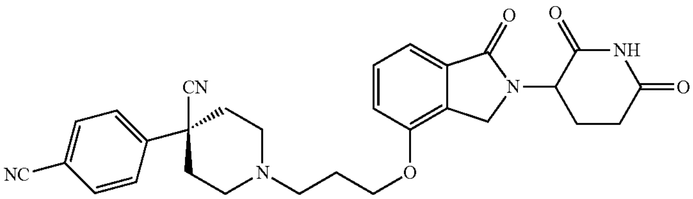 |
| 70 | 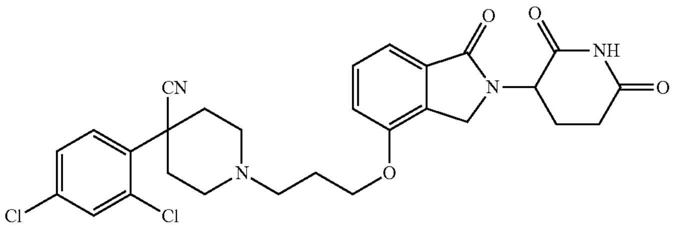 |
| 71 | 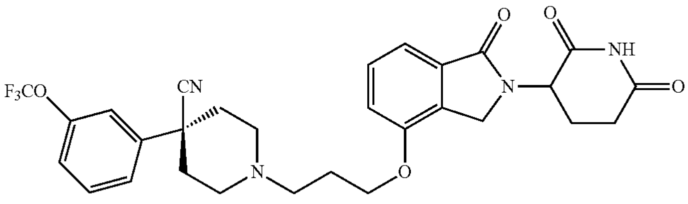 |

-continued
| Serial number | Compound |
|---|---|
| 72 | 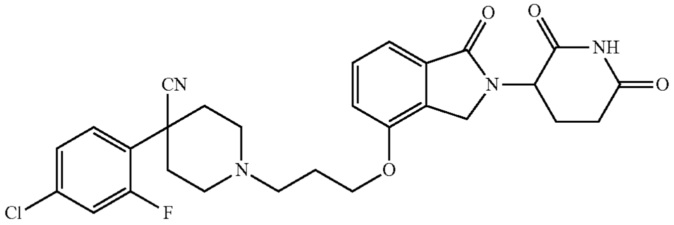 |
| 73 | 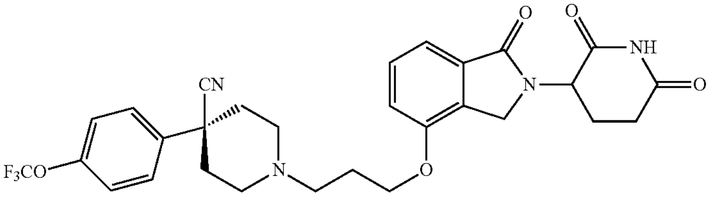 |
| 74 | 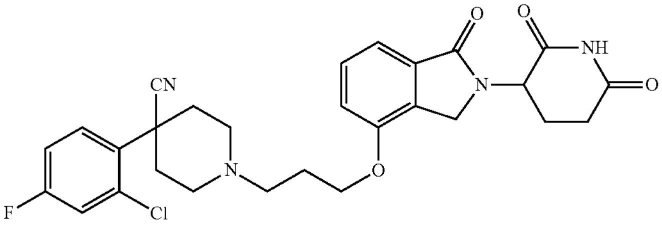 [SMILES: N#CC1(c2ccc(F)cc2Cl)CCN(CCCOc2cccc3c2CN(C2CCC(=O)NC2=O)C3=O)CC1] |
| 75 | 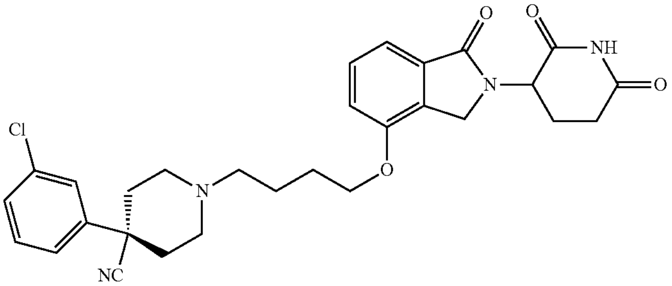 |
| 76 | 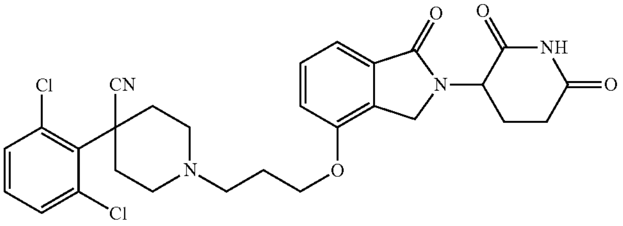 |
| 77 | 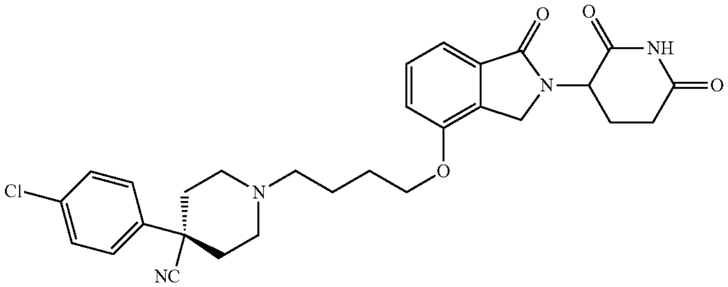 |

-continued
| Serial number | Compound |
|---|---|
| 78 | 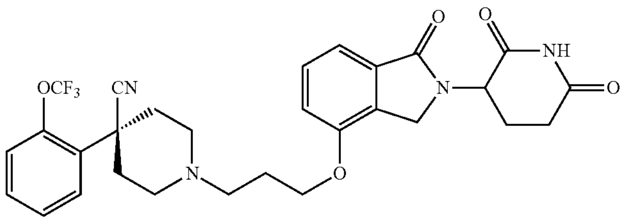 |
| 79 | 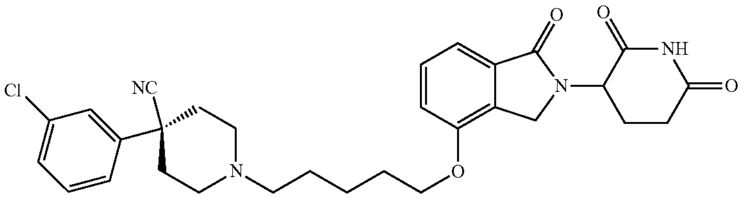 |
| 80 | 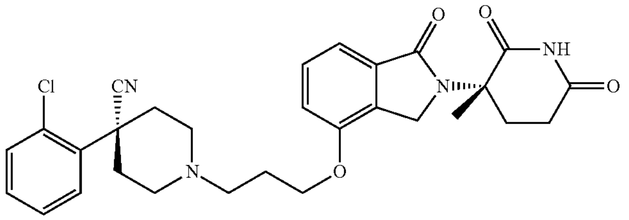 |
| 81 | 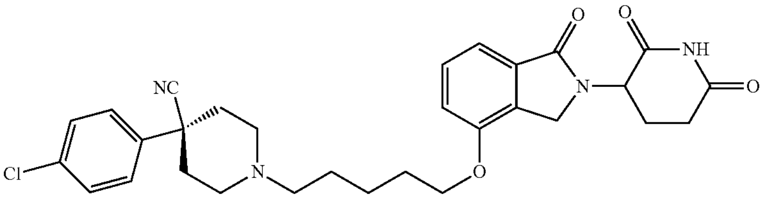 |
| 82 | 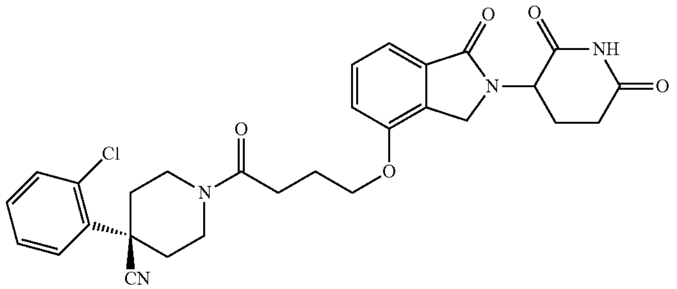 |
| 83 | 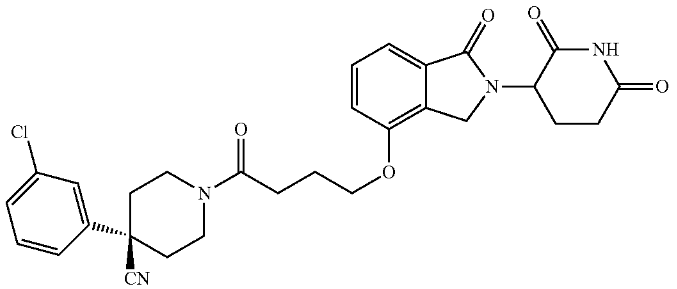 |

-continued
| Serial number | Compound |
|---|---|
| 84 | 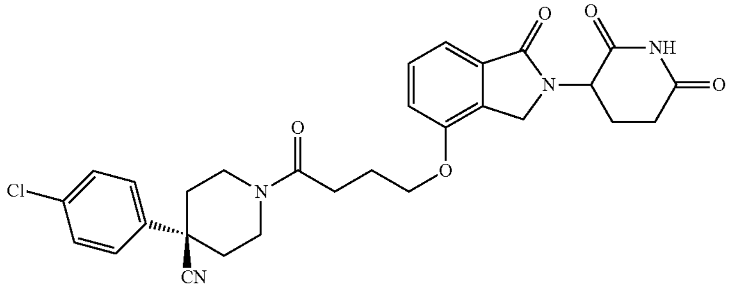 |
| 85 | 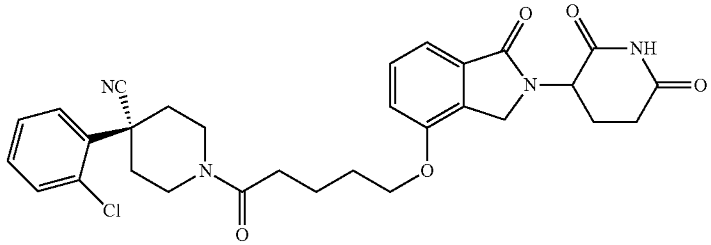 |
| 86 | 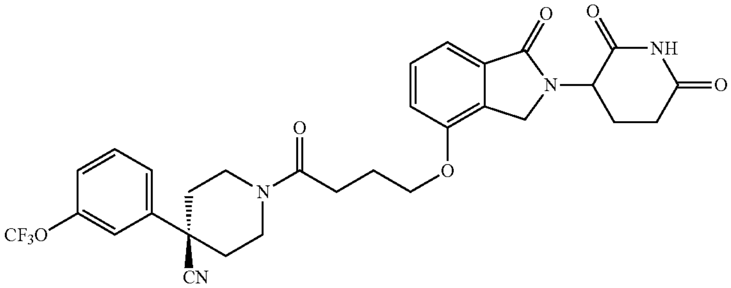 |
| 87 | 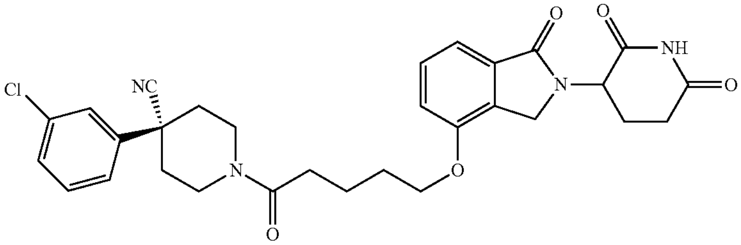 |
| 88 | 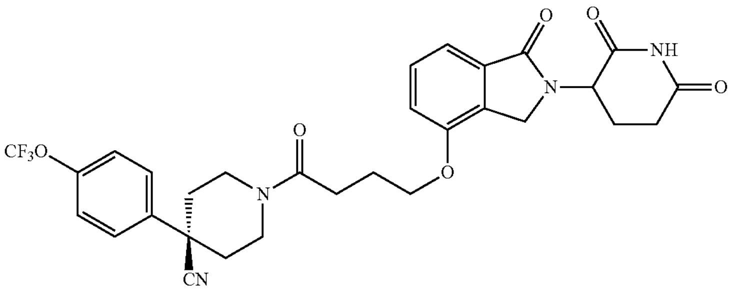 |

-continued
| Serial number | Compound |
|---|---|
| 89 | 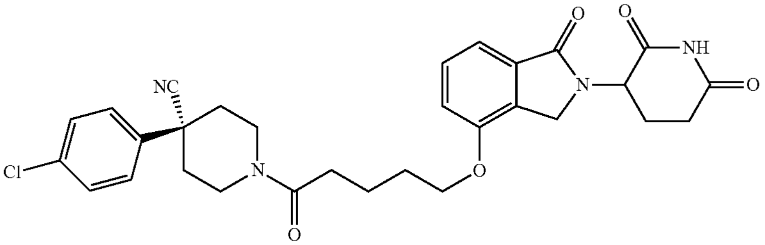 |
| 90 | 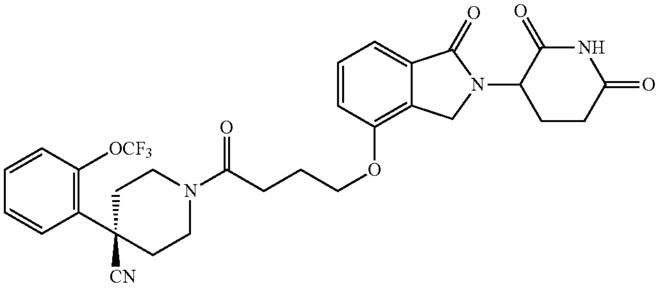 |
| 91 | 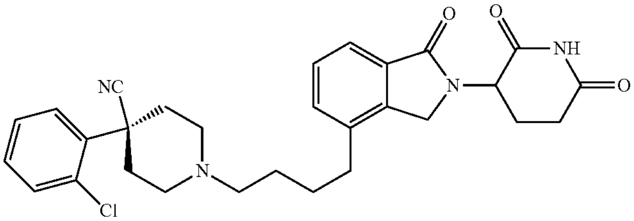 |
| 92 | 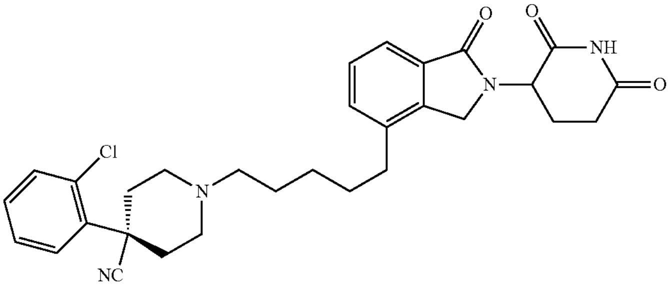 |
| 93 | 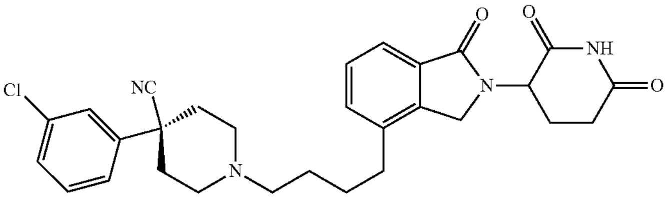 |
| 94 | 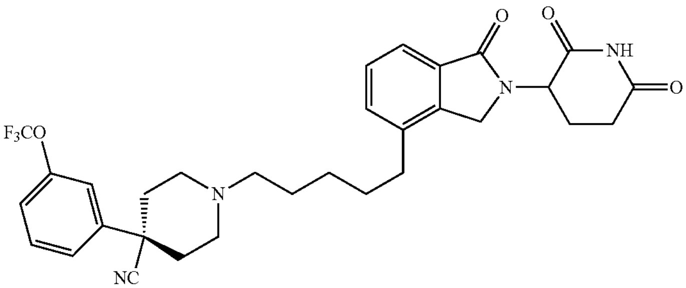 |

-continued
| Serial number | Compound |
|---|---|
| 95 | 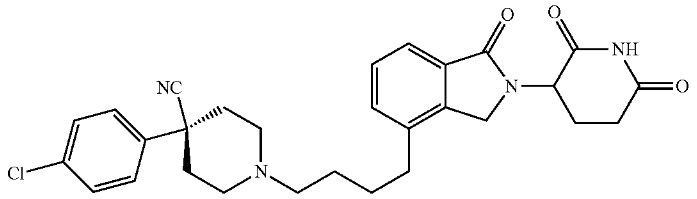 |
| 96 | 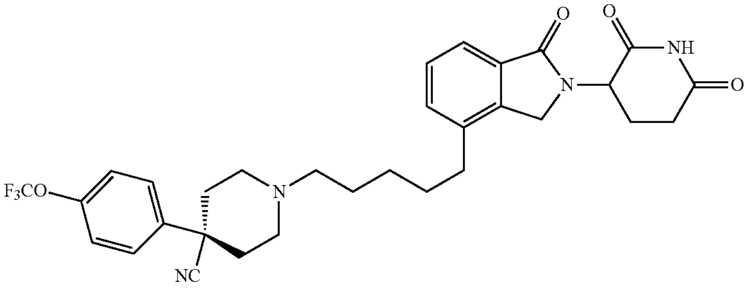 |
| 97 | 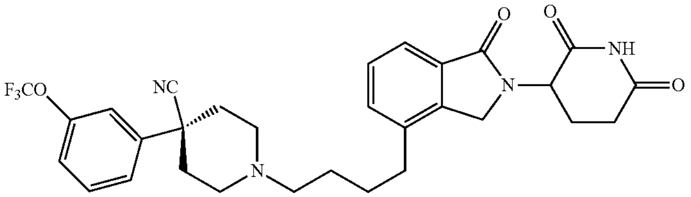 |
| 98 | 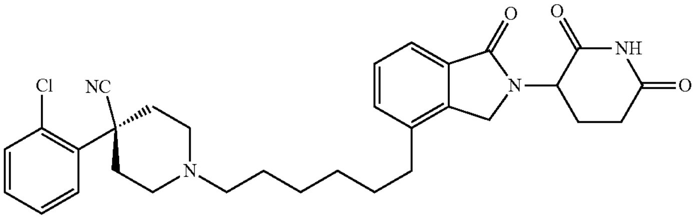 |
| 99 | 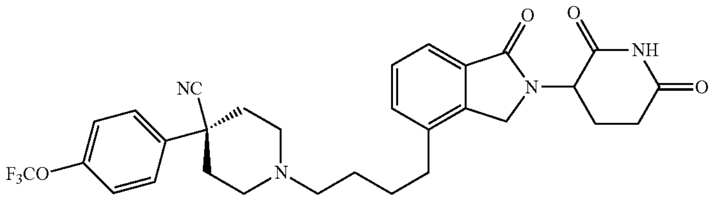 |
| 100 | 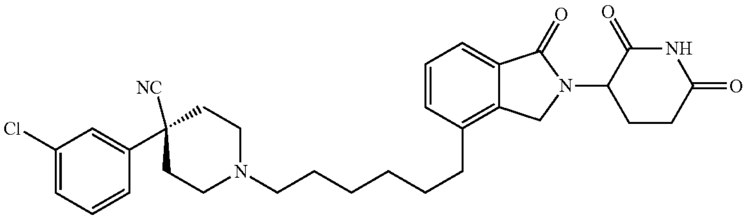 |

-continued
| Serial number | Compound |
|---|---|
| 101 | 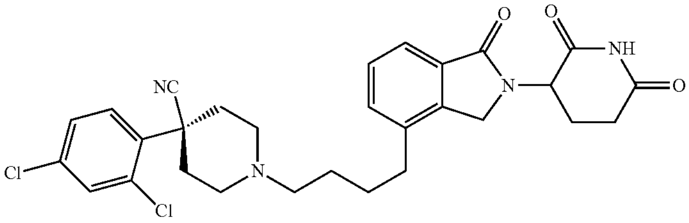 |
| 102 | 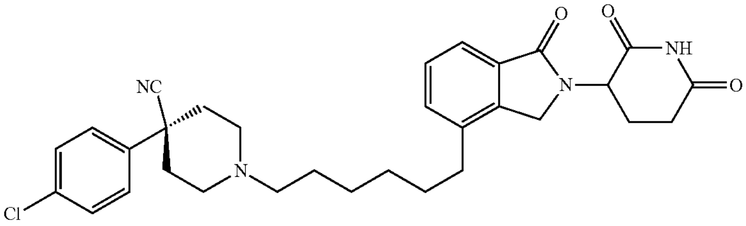 |
| 103 | 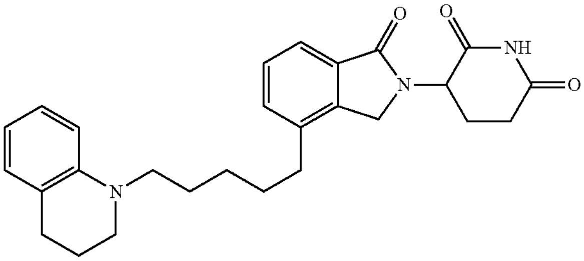 |
| 104 | 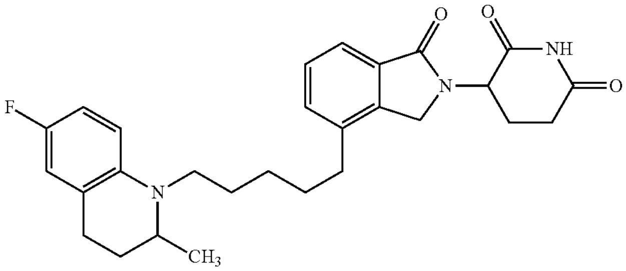 [SMILES: CC1CCc2cc(F)ccc2N1CCCCCc1cccc2c1CN(C1CCC(=O)NC1=O)C2=O] |
| 105 | 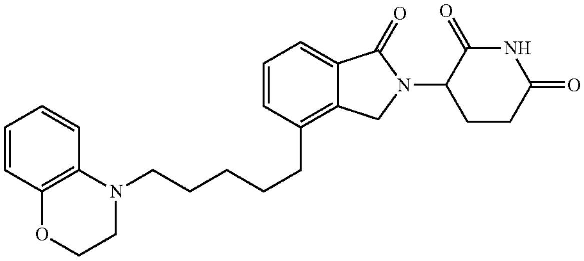 |
| 106 | 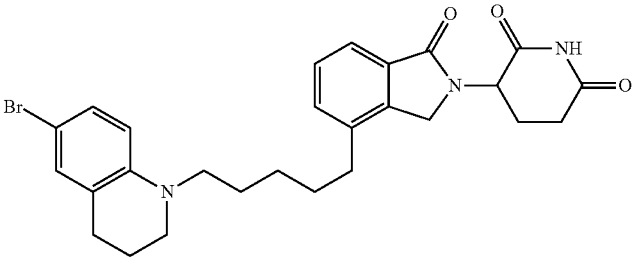 |

-continued
| Serial number | Compound |
|---|---|
| 107 | 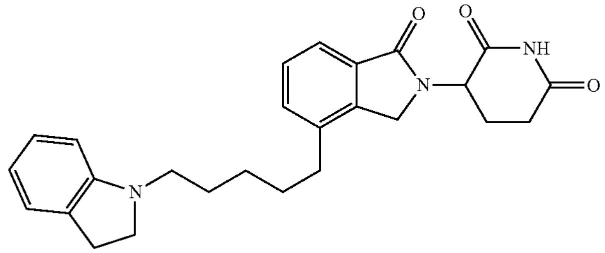 [SMILES: O=C1CCC(N2Cc3c(CCCCCN4CCc5ccccc54)cccc3C2=O)C(=O)N1] |
| 108 | 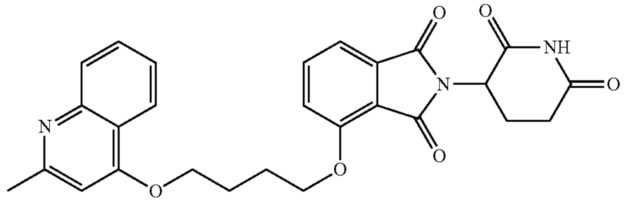 [SMILES: Cc1cc(OCCCCOc2cccc3c2C(=O)N(C2CCC(=O)NC2=O)C3=O)c2ccccc2n1] |
| 109 | 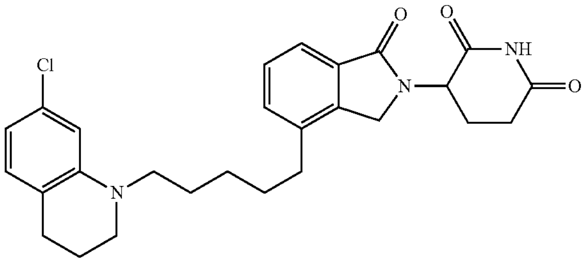 [SMILES: O=C1CCC(N2Cc3c(CCCCCN4CCCc5ccc(Cl)cc54)cccc3C2=O)C(=O)N1] |
| 110 | 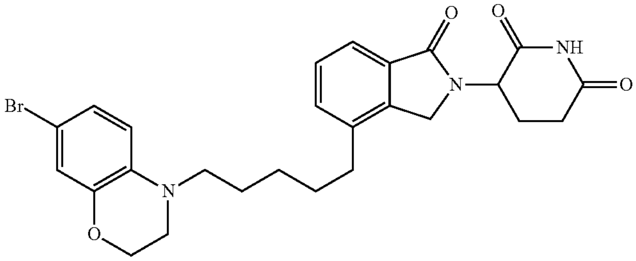 |
| 111 | 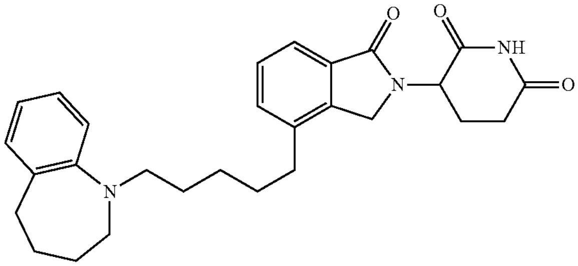 [SMILES: O=C1CCC(N2Cc3c(CCCCCN4CCCCc5ccccc54)cccc3C2=O)C(=O)N1] |
| 112 | 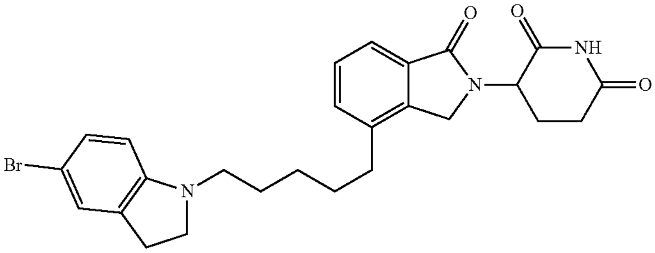 [SMILES: O=C1CCC(N2Cc3c(CCCCCN4CCc5cc(Br)ccc54)cccc3C2=O)C(=O)N1] |

-continued
| Serial number | Compound |
|---|---|
| 113 | 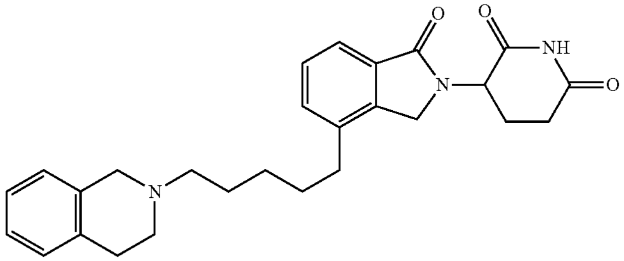 [SMILES: O=C1CCC(N2Cc3c(CCCCCN4CCc5ccccc5C4)cccc3C2=O)C(=O)N1] |
| 114 | 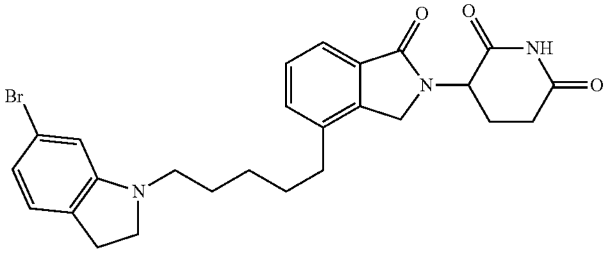 [SMILES: O=C1CCC(N2Cc3c(CCCCCN4CCc5ccc(Br)cc54)cccc3C2=O)C(=O)N1] |
| 115 | 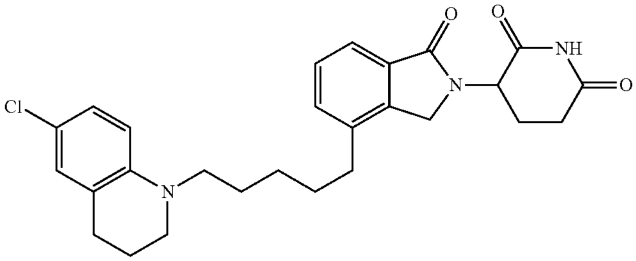 [SMILES: O=C1CCC(N2Cc3c(CCCCCN4CCCc5cc(Cl)ccc54)cccc3C2=O)C(=O)N1] |
| 116 | 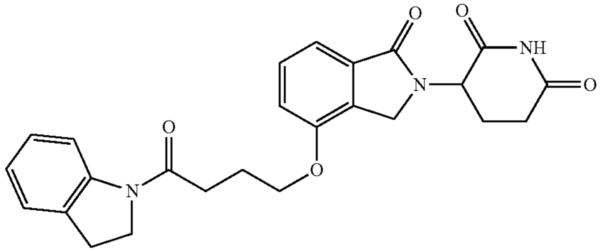 [SMILES: O=C1CCC(N2Cc3c(OCCCC(=O)N4CCc5ccccc54)cccc3C2=O)C(=O)N1] |
| 117 | 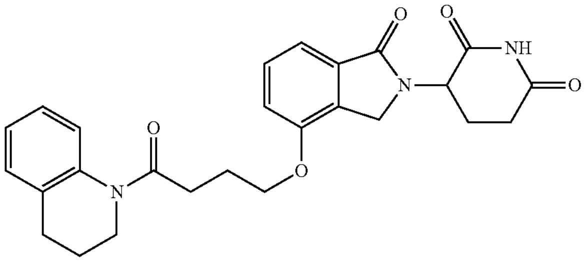 [SMILES: O=C1CCC(N2Cc3c(OCCCC(=O)N4CCCc5ccccc54)cccc3C2=O)C(=O)N1] |
| 118 | 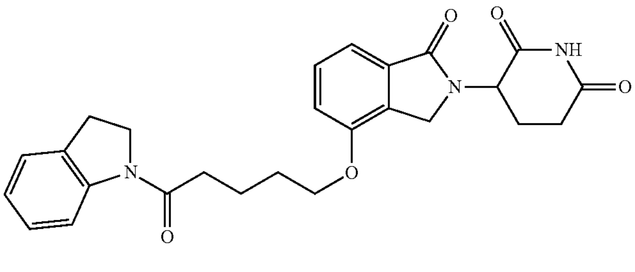 [SMILES: O=C1CCC(N2Cc3c(OCCCCC(=O)N4CCc5ccccc54)cccc3C2=O)C(=O)N1] |

-continued
| Serial number | Compound |
|---|---|
| 119 | 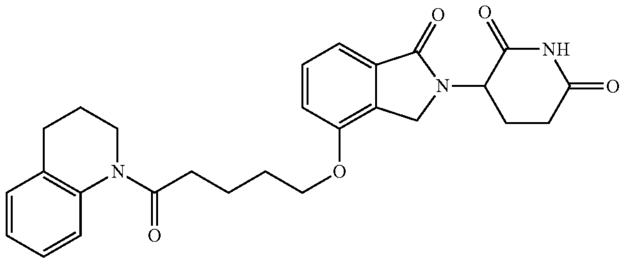 [SMILES: O=C1CCC(N2Cc3c(OCCCCC(=O)N4CCCc5ccccc54)cccc3C2=O)C(=O)N1] |
| 120 | 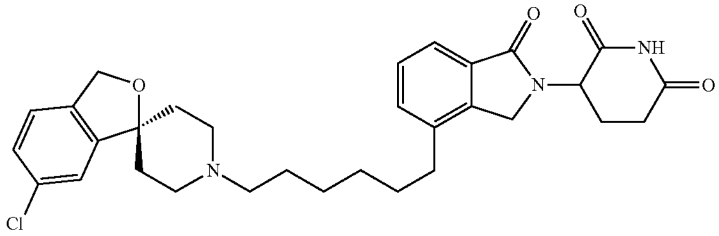 |
| 121 | 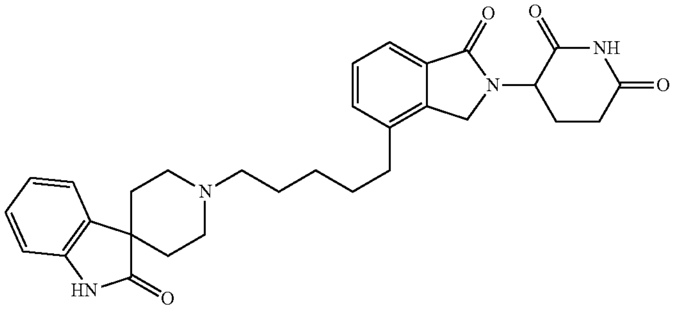 [SMILES: O=C1CCC(N2Cc3c(CCCCCN4CCC5(CC4)C(=O)Nc4ccccc45)cccc3C2=O)C(=O)N1] |
| 122 | 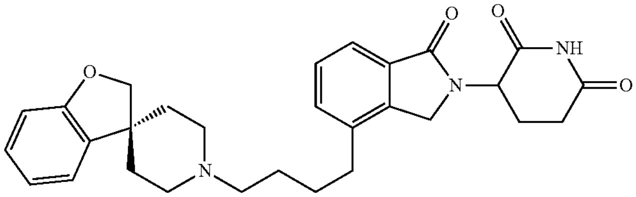 |
| 123 | 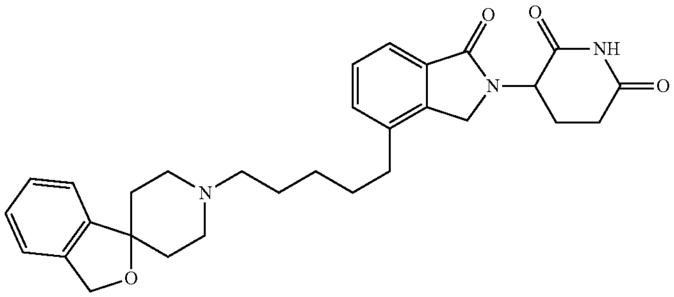 [SMILES: O=C1CCC(N2Cc3c(CCCCCN4CCC5(CC4)OCc4ccccc45)cccc3C2=O)C(=O)N1] |

-continued
| Serial number | Compound |
| --- | --- |
| 124 | 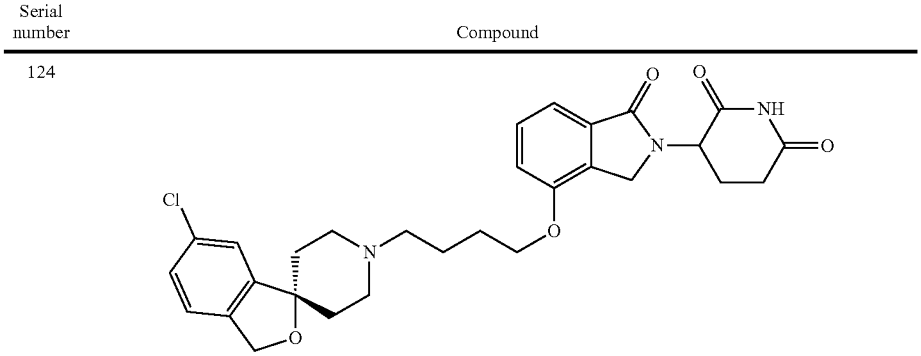 |
| 125 | 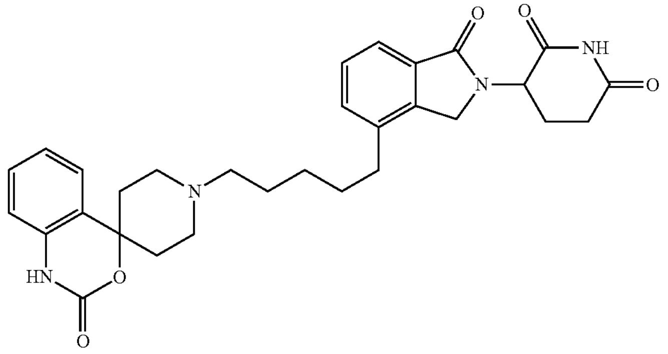 [SMILES: O=C1CCC(N2Cc3c(CCCCCN4CCC5(CC4)OC(=O)Nc4ccccc45)cccc3C2=O)C(=O)N1] |
| 126 | 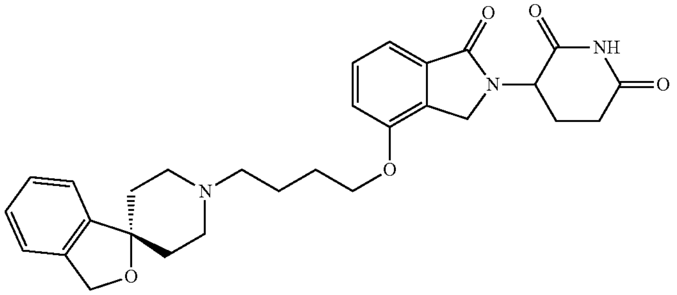 |
| 127 | 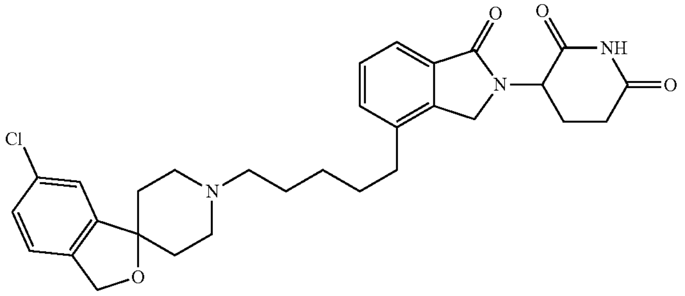 [SMILES: O=C1CCC(N2Cc3c(CCCCCN4CCC5(CC4)OCc4ccc(Cl)cc45)cccc3C2=O)C(=O)N1] |
| 128 | 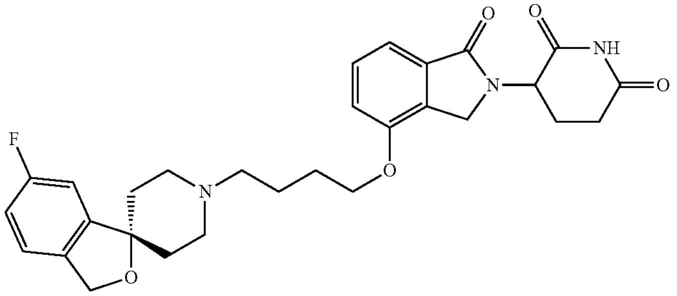 |

-continued
| Serial number | Compound |
|---|---|
| 129 | 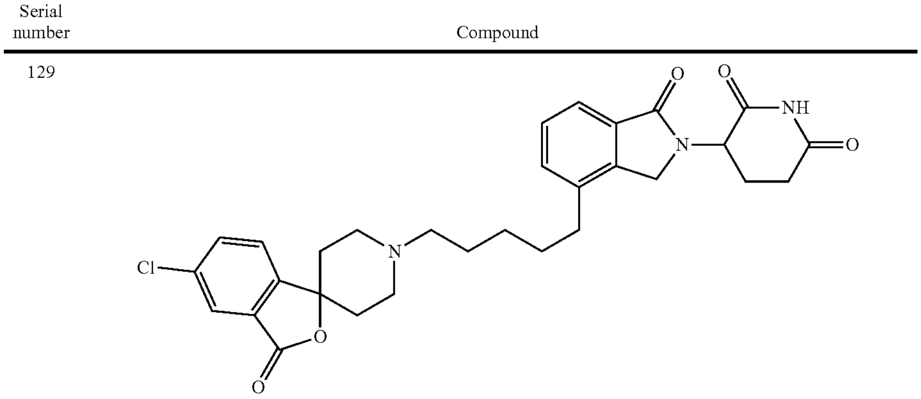 |
| 130 | 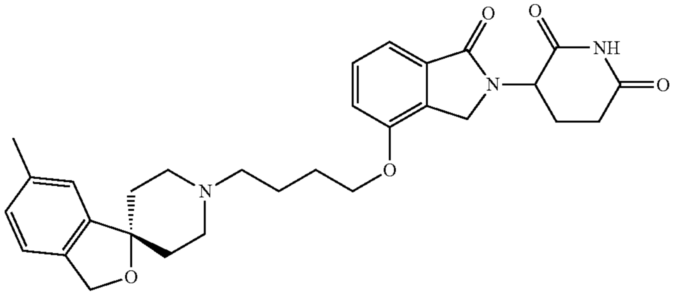 |
| 131 | 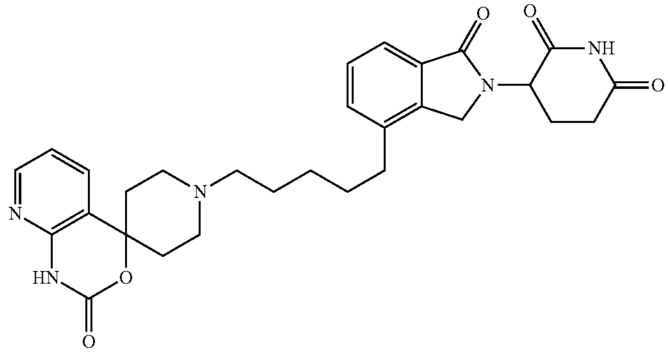 [SMILES: O=C1CCC(N2Cc3c(CCCCCN4CCC5(CC4)OC(=O)Nc4ncccc45)cccc3C2=O)C(=O)N1] |
| 132 | 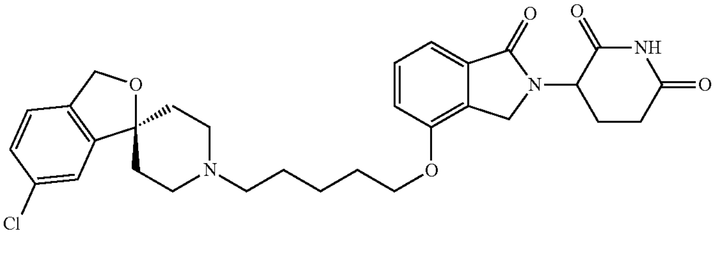 |
| 133 | 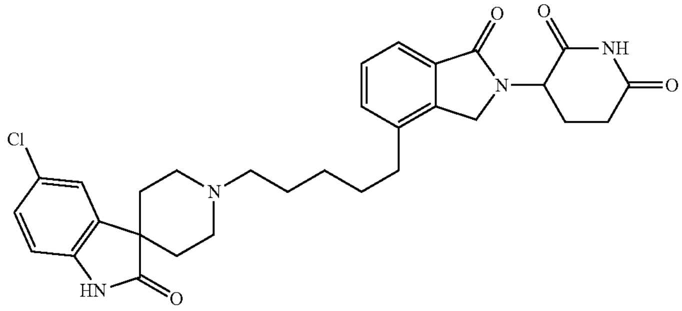 [SMILES: O=C1CCC(N2Cc3c(CCCCCN4CCC5(CC4)C(=O)Nc4ccc(Cl)cc45)cccc3C2=O)C(=O)N1] |

-continued
| Serial number | Compound |
|---|---|
| 134 | 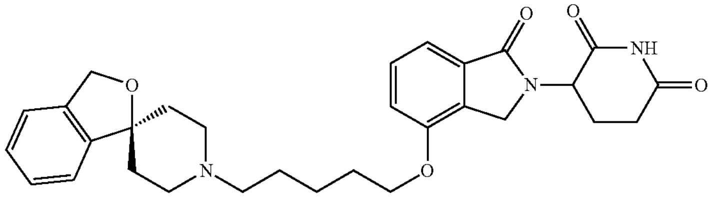 |
| 135 | 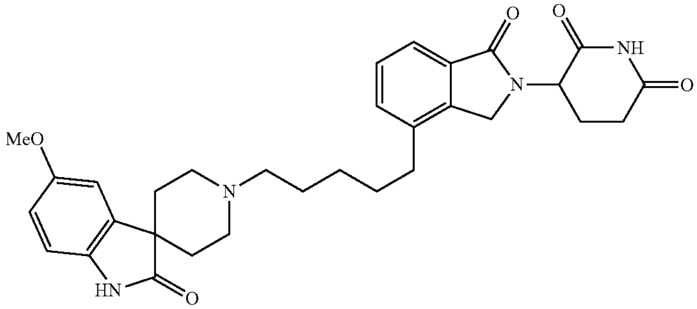 [SMILES: COc1ccc2c(c1)C1(CCN(CCCCCc3cccc4c3CN(C3CCC(=O)NC3=O)C4=O)CC1)C(=O)N2] |
| 136 | 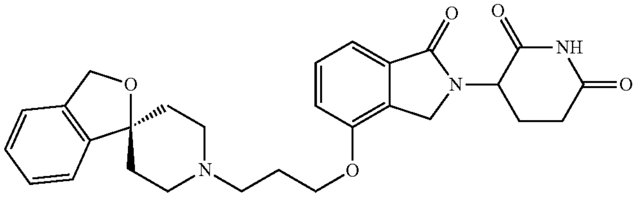 |
| 137 | 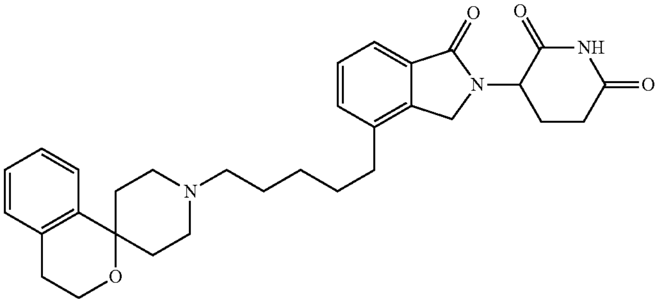 [SMILES: O=C1CCC(N2Cc3c(CCCCCN4CCC5(CC4)OCCc4ccccc45)cccc3C2=O)C(=O)N1] |
| 138 | 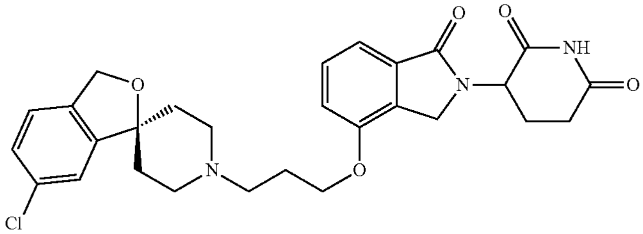 |
| 139 | 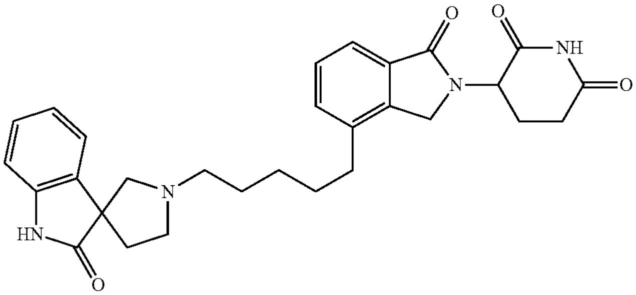 [SMILES: O=C1CCC(N2Cc3c(CCCCCN4CCC5(C4)C(=O)Nc4ccccc45)cccc3C2=O)C(=O)N1] |

-continued
| Serial number | Compound |
|---|---|
| 140 | 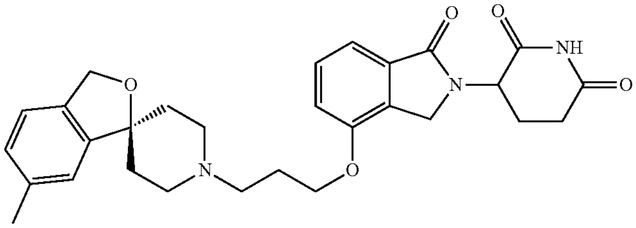 |
| 141 | 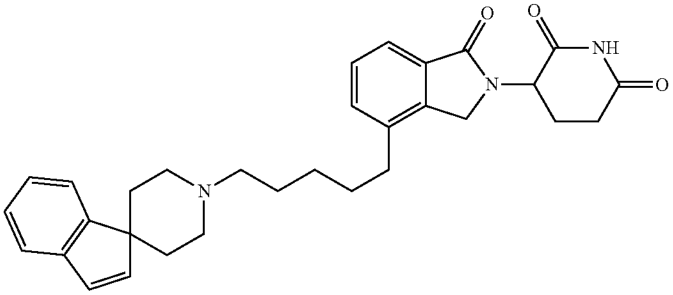 [SMILES: O=C1CCC(N2Cc3c(CCCCCN4CCC5(C=Cc6ccccc65)CC4)cccc3C2=O)C(=O)N1] |
| 142 | 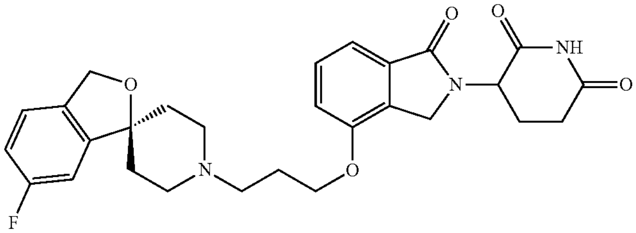 |
| 143 | 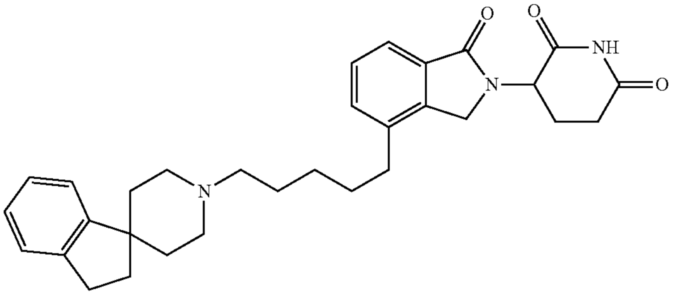 |
| 144 | 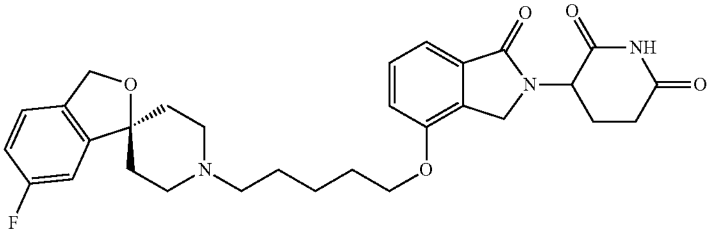 |

-continued
| Serial number | Compound |
|---|---|
| 145 | 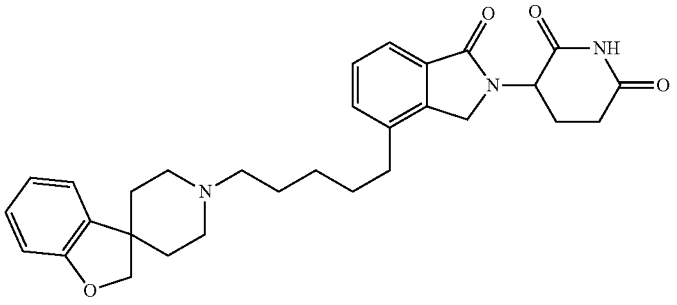 [SMILES: O=C1CCC(N2Cc3c(CCCCCN4CCC5(CC4)COc4ccccc45)cccc3C2=O)C(=O)N1] |
| 146 | 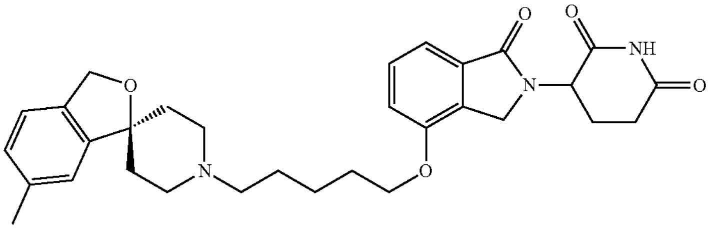 |
| 147 | 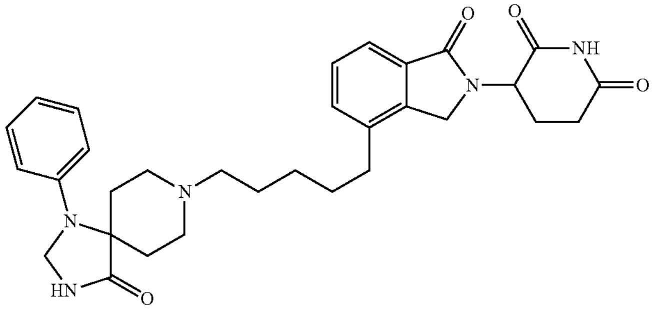 [SMILES: O=C1CCC(N2Cc3c(CCCCCN4CCC5(CC4)C(=O)NCN5c4ccccc4)cccc3C2=O)C(=O)N1] |
| 148 | 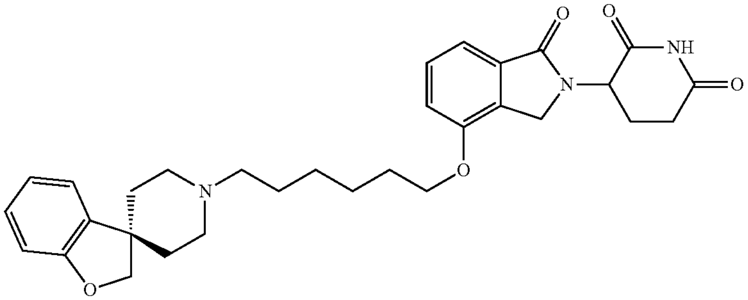 |
| 149 | 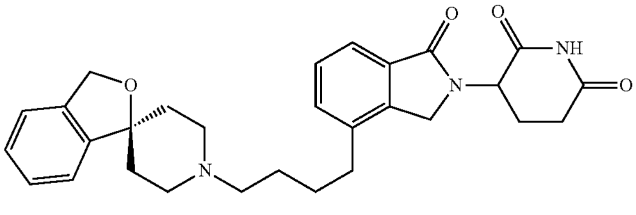 |

-continued
| Serial number | Compound |
|---|---|
| 150 | 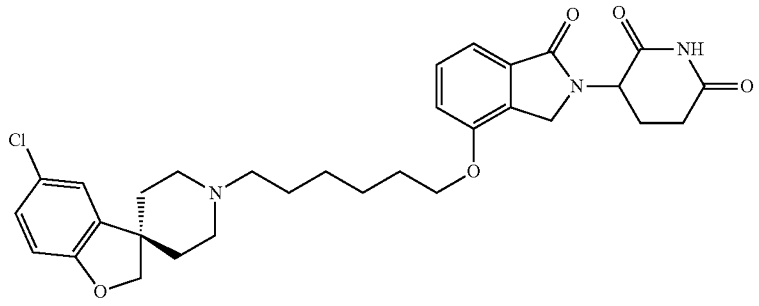 |
| 151 | 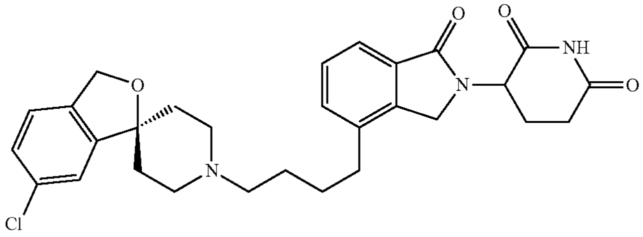 |
| 152 | 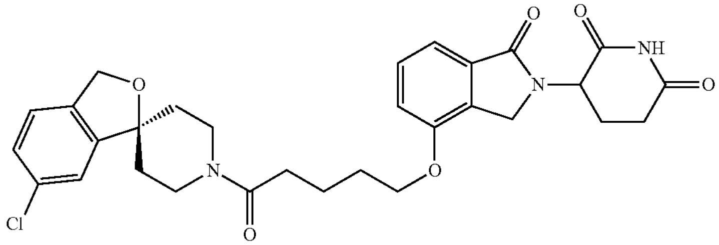 |
| 153 | 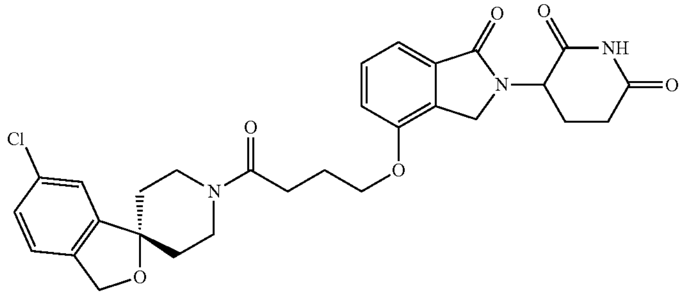 |
| 154 | 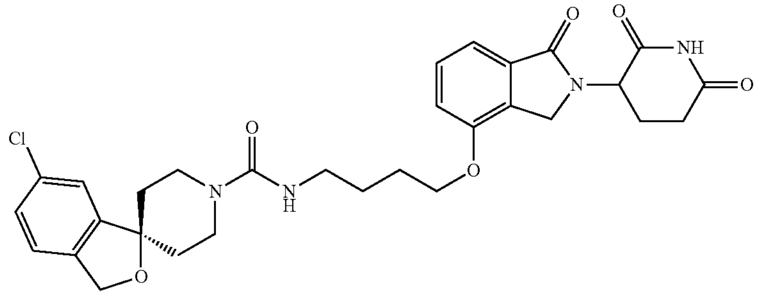 |

-continued
| Serial number | Compound |
|---|---|
| 155 | 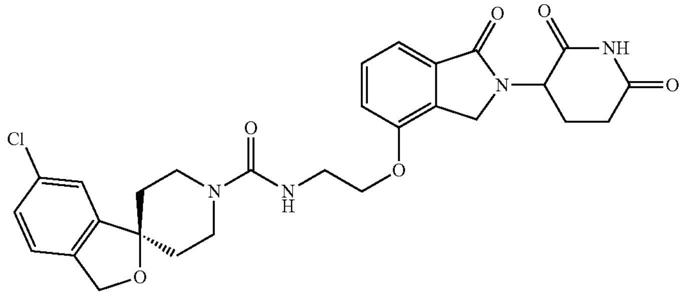 |
| 156 | 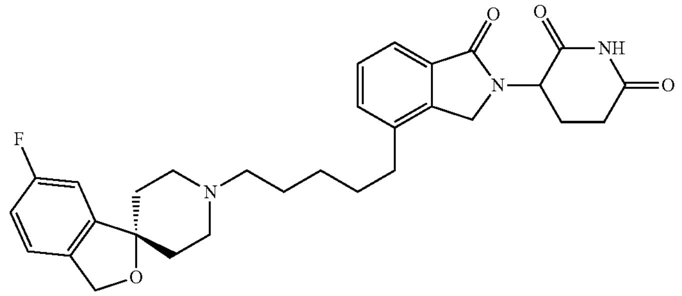 |
| 157 | 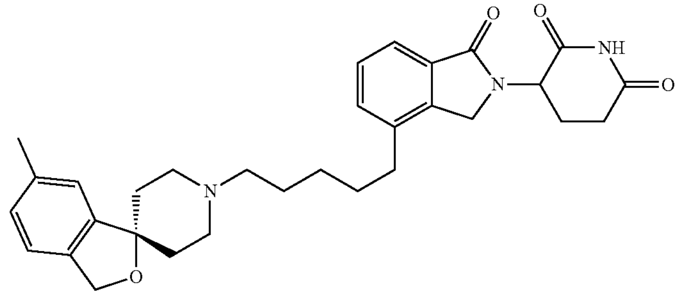 |
| 158 | 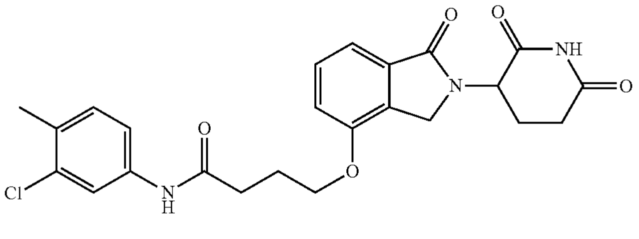 [SMILES: Cc1ccc(NC(=O)CCCOc2cccc3c2CN(C2CCC(=O)NC2=O)C3=O)cc1Cl] |
| 159 | 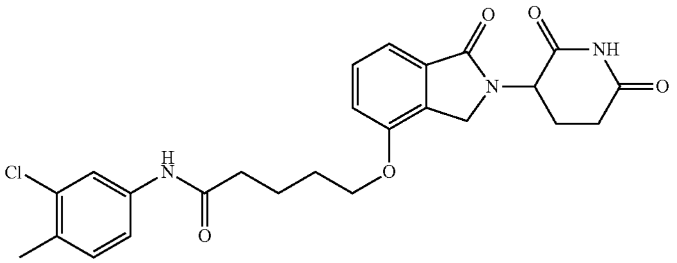 [SMILES: Cc1ccc(NC(=O)CCCCOc2cccc3c2CN(C2CCC(=O)NC2=O)C3=O)cc1Cl] |

-continued
| Serial number | Compound |
|---|---|
| 160 | 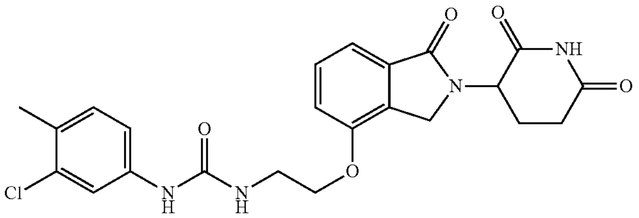 |
| 161 | 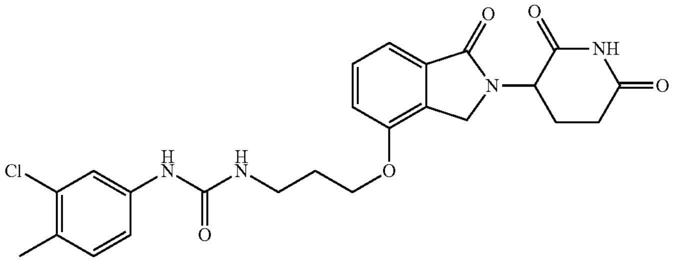 [SMILES: Cc1ccc(NC(=O)NCCCOc2cccc3c2CN(C2CCC(=O)NC2=O)C3=O)cc1Cl] |
| 162 | 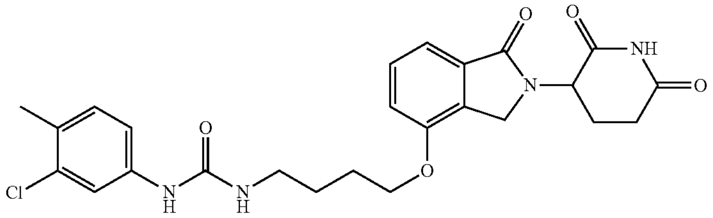 [SMILES: Cc1ccc(NC(=O)NCCCCOc2cccc3c2CN(C2CCC(=O)NC2=O)C3=O)cc1Cl] |
| 163 | 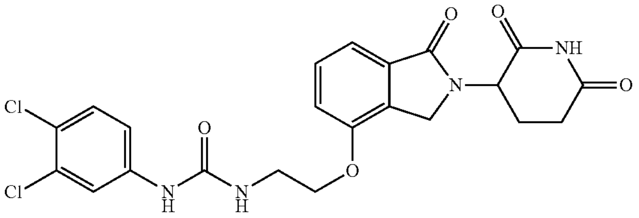 [SMILES: O=C1CCC(N2Cc3c(OCCNC(=O)Nc4ccc(Cl)c(Cl)c4)cccc3C2=O)C(=O)N1] |
| 164 | 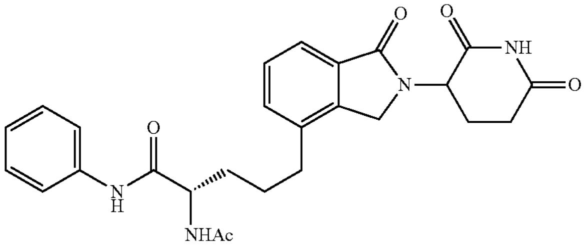 [SMILES: CC(=O)N[C@@H](CCCc1cccc2c1CN(C1CCC(=O)NC1=O)C2=O)C(=O)Nc1ccccc1] |
| 165 | 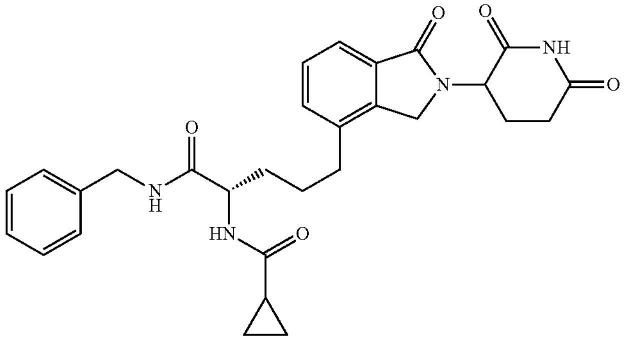 [SMILES: O=C1CCC(N2Cc3c(CCC[C@H](NC(=O)C4CC4)C(=O)NCc4ccccc4)cccc3C2=O)C(=O)N1] |

-continued
| Serial number | Compound |
|---|---|
| 166 | 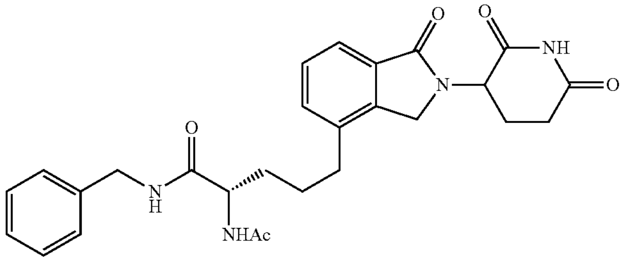 [SMILES: CC(=O)N[C@@H](CCCc1cccc2c1CN(C1CCC(=O)NC1=O)C2=O)C(=O)NCc1ccccc1] |
| 167 | 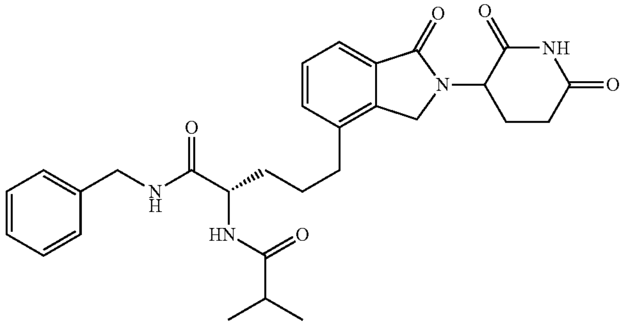 [SMILES: CC(C)C(=O)N[C@@H](CCCc1cccc2c1CN(C1CCC(=O)NC1=O)C2=O)C(=O)NCc1ccccc1] |
| 168 | 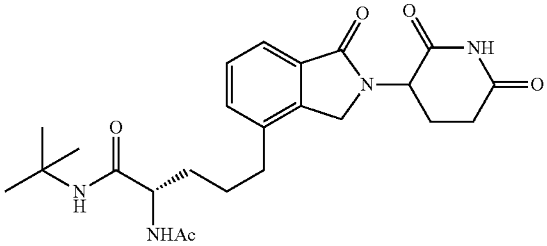 [SMILES: CC(=O)N[C@@H](CCCc1cccc2c1CN(C1CCC(=O)NC1=O)C2=O)C(=O)NC(C)(C)C] |
| 169 | 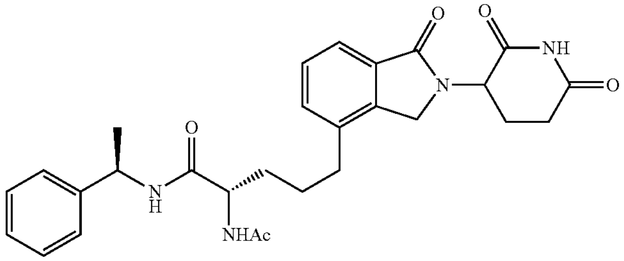 [SMILES: CC(=O)N[C@@H](CCCc1cccc2c1CN(C1CCC(=O)NC1=O)C2=O)C(=O)N[C@H](C)c1ccccc1] |
| 170 | 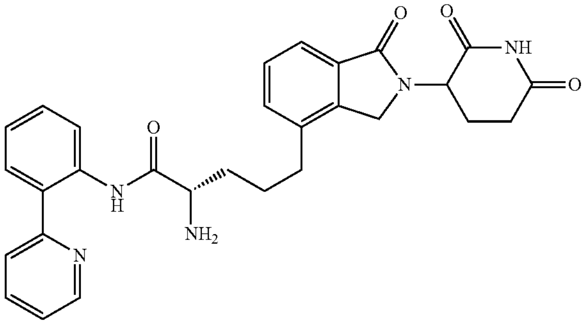 |

-continued
| Serial number | Compound |
|---|---|
| 171 | 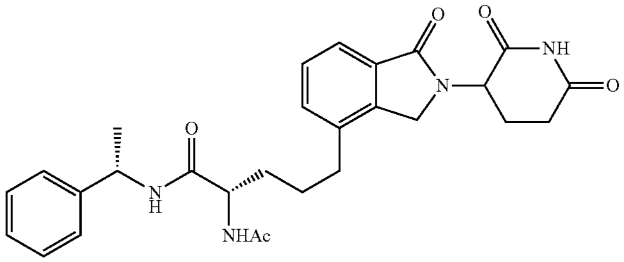 [SMILES: CC(=O)N[C@@H](CCCc1cccc2c1CN(C1CCC(=O)NC1=O)C2=O)C(=O)N[C@@H](C)c1ccccc1] |
| 172 | 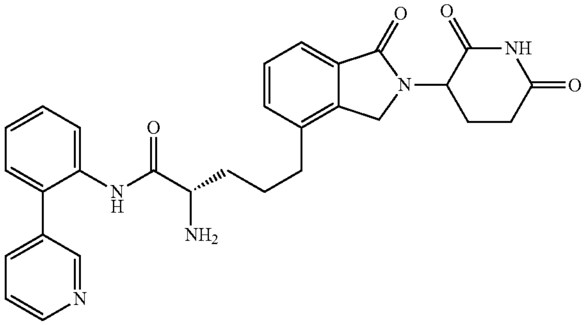 [SMILES: N[C@@H](CCCc1cccc2c1CN(C1CCC(=O)NC1=O)C2=O)C(=O)Nc1ccccc1-c1cccnc1] |
| 173 | 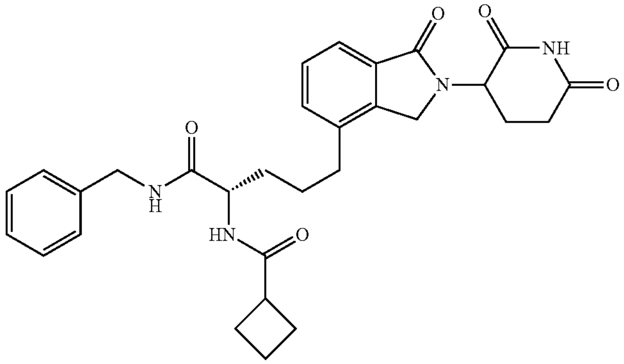 [SMILES: O=C1CCC(N2Cc3c(CCC[C@H](NC(=O)C4CCC4)C(=O)NCc4ccccc4)cccc3C2=O)C(=O)N1] |
| 174 | 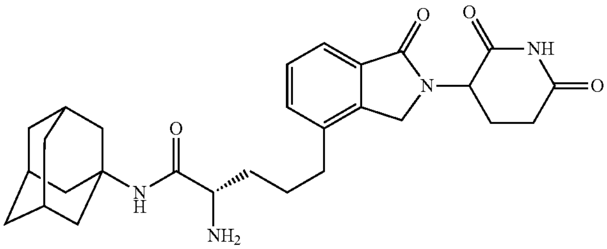 [SMILES: N[C@@H](CCCc1cccc2c1CN(C1CCC(=O)NC1=O)C2=O)C(=O)NC12CC3CC(CC(C3)C1)C2] |
| 175 | 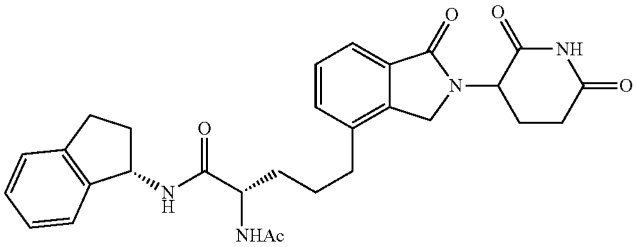 [SMILES: CC(=O)N[C@@H](CCCc1cccc2c1CN(C1CCC(=O)NC1=O)C2=O)C(=O)N[C@H]1CCc2ccccc21] |

-continued
| Serial number | Compound |
|---|---|
| 176 | 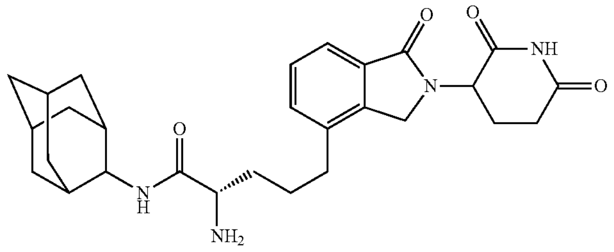 [SMILES: N[C@@H](CCCc1cccc2c1CN(C1CCC(=O)NC1=O)C2=O)C(=O)NC1C2CC3CC(C2)CC1C3] |
| 177 | 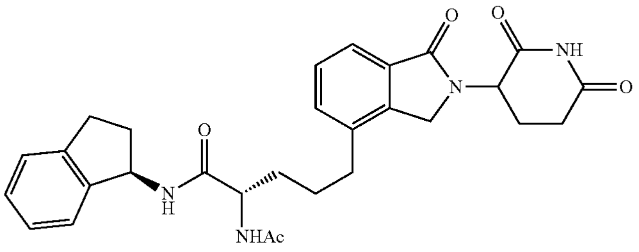 [SMILES: CC(=O)N[C@@H](CCCc1cccc2c1CN(C1CCC(=O)NC1=O)C2=O)C(=O)N[C@@H]1CCc2ccccc21] |
| 178 | 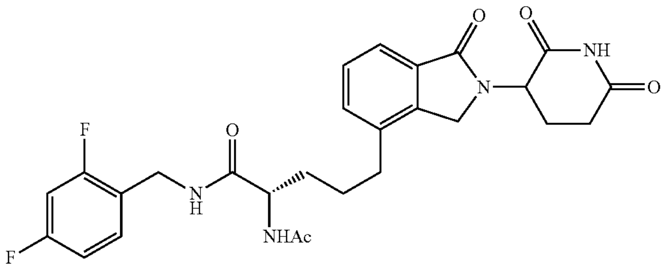 [SMILES: CC(=O)N[C@@H](CCCc1cccc2c1CN(C1CCC(=O)NC1=O)C2=O)C(=O)NCc1ccc(F)cc1F] |
| 179 | 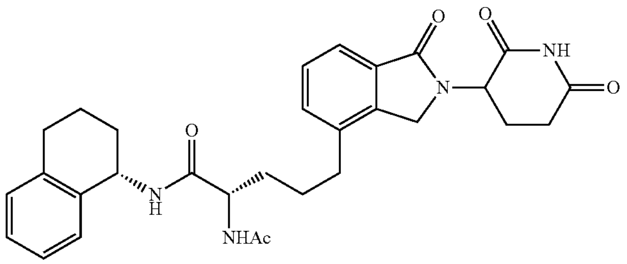 [SMILES: CC(=O)N[C@@H](CCCc1cccc2c1CN(C1CCC(=O)NC1=O)C2=O)C(=O)N[C@H]1CCCc2ccccc21] |
| 180 | 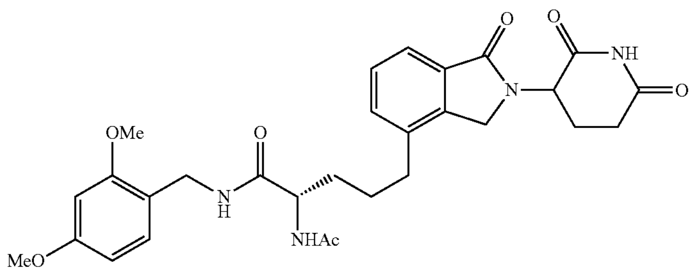 [SMILES: COc1ccc(CNC(=O)[C@H](CCCc2cccc3c2CN(C2CCC(=O)NC2=O)C3=O)NC(C)=O)c(OC)c1] |

-continued
| Serial number | Compound |
|---|---|
| 181 | 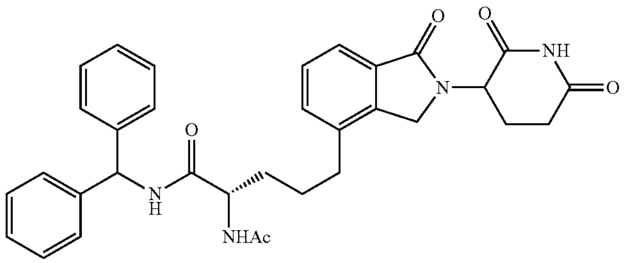 [SMILES: CC(=O)N[C@@H](CCCc1cccc2c1CN(C1CCC(=O)NC1=O)C2=O)C(=O)NC(c1ccccc1)c1ccccc1] |
| 182 | 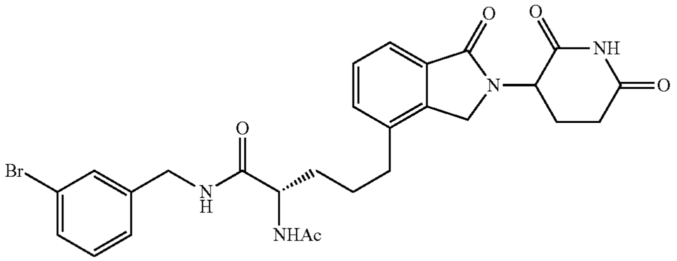 |
| 183 | 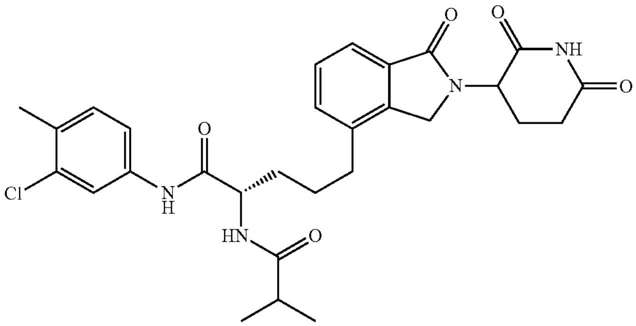 [SMILES: Cc1ccc(NC(=O)[C@H](CCCc2cccc3c2CN(C2CCC(=O)NC2=O)C3=O)NC(=O)C(C)C)cc1Cl] |
| 184 | 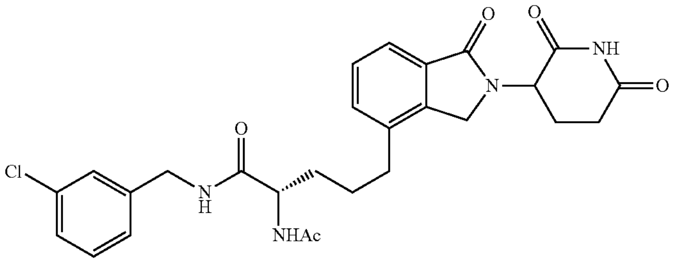 [SMILES: CC(=O)N[C@@H](CCCc1cccc2c1CN(C1CCC(=O)NC1=O)C2=O)C(=O)NCc1cccc(Cl)c1] |
| 185 | 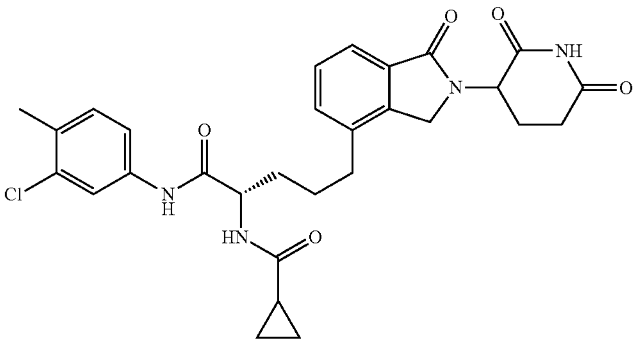 [SMILES: Cc1ccc(NC(=O)[C@H](CCCc2cccc3c2CN(C2CCC(=O)NC2=O)C3=O)NC(=O)C2CC2)cc1Cl] |

-continued
| Serial number | Compound |
|---|---|
| 186 | 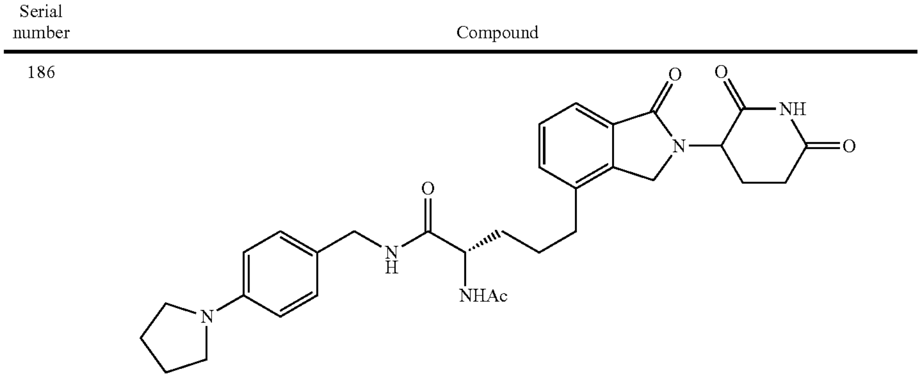 |
| 187 | 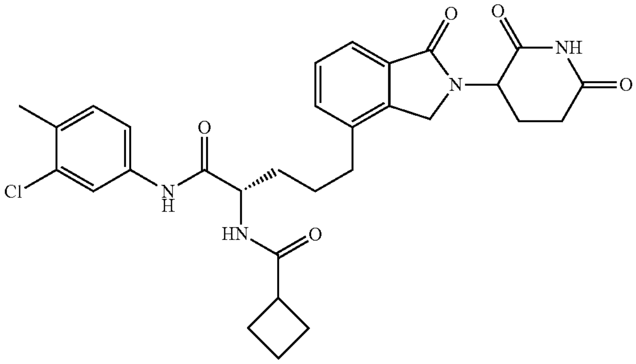 [SMILES: Cc1ccc(NC(=O)[C@H](CCCc2cccc3c2CN(C2CCC(=O)NC2=O)C3=O)NC(=O)C2CCC2)cc1Cl] |
| 188 | 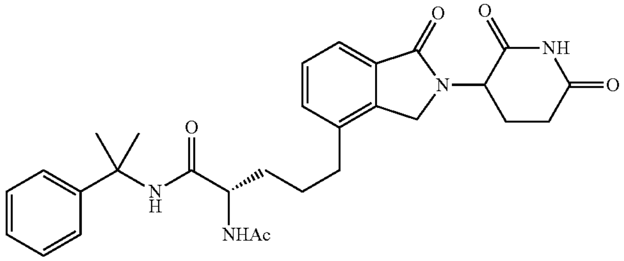 [SMILES: CC(=O)N[C@@H](CCCc1cccc2c1CN(C1CCC(=O)NC1=O)C2=O)C(=O)NC(C)(C)c1ccccc1] |
| 189 | 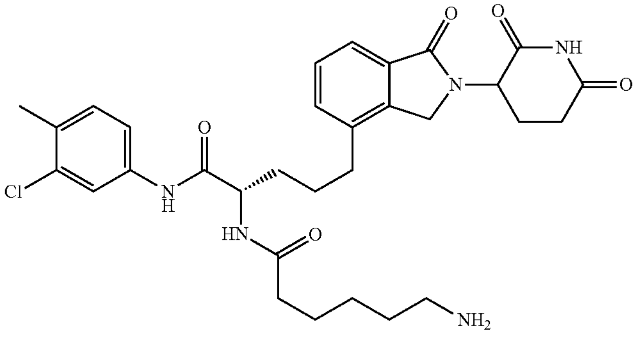 [SMILES: Cc1ccc(NC(=O)[C@H](CCCc2cccc3c2CN(C2CCC(=O)NC2=O)C3=O)NC(=O)CCCCCN)cc1Cl] |
| 190 | 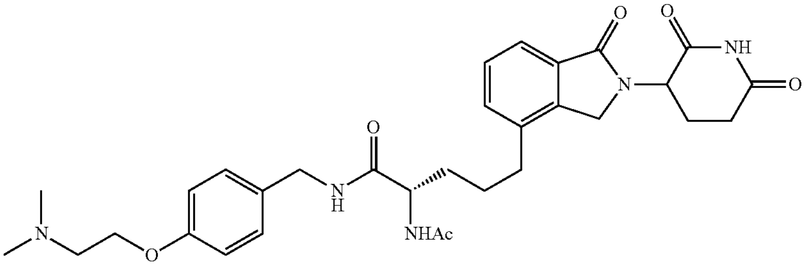 [SMILES: CC(=O)N[C@@H](CCCc1cccc2c1CN(C1CCC(=O)NC1=O)C2=O)C(=O)NCc1ccc(OCCN(C)C)cc1] |

-continued
| Serial number | Compound |
|---|---|
| 191 | 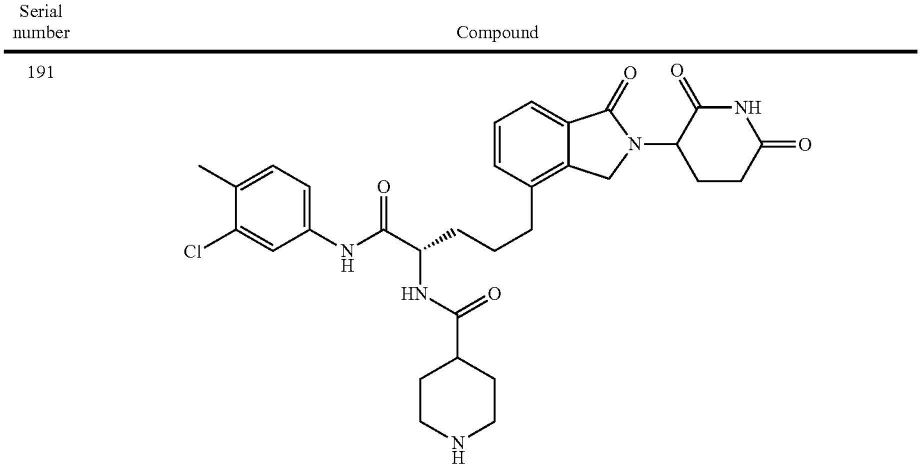 |
| 192 | 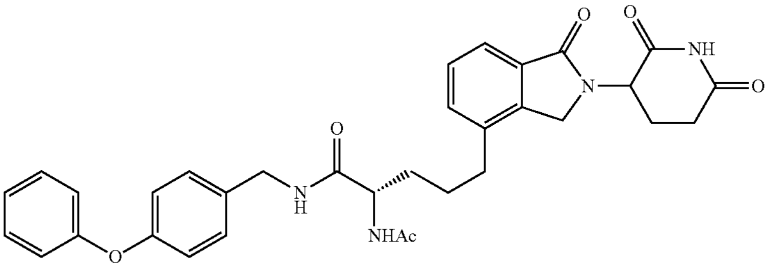 [SMILES: CC(=O)N[C@@H](CCCc1cccc2c1CN(C1CCC(=O)NC1=O)C2=O)C(=O)NCc1ccc(Oc2ccccc2)cc1] |
| 193 | 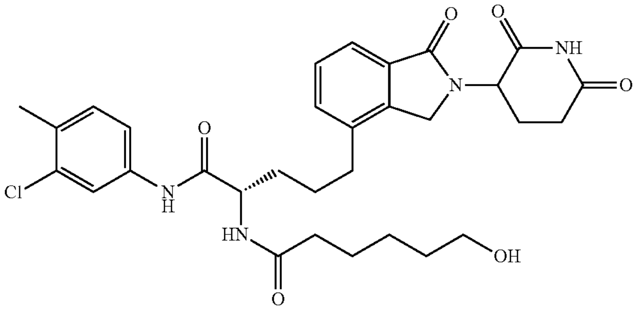 [SMILES: Cc1ccc(NC(=O)[C@H](CCCc2cccc3c2CN(C2CCC(=O)NC2=O)C3=O)NC(=O)CCCCCO)cc1Cl] |
| 194 | 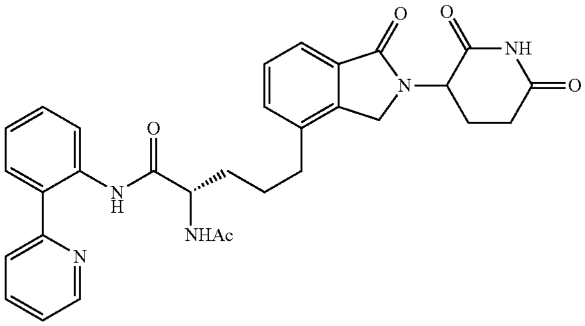 [SMILES: CC(=O)N[C@@H](CCCc1cccc2c1CN(C1CCC(=O)NC1=O)C2=O)C(=O)Nc1ccccc1-c1ccccn1] |
| 195 | 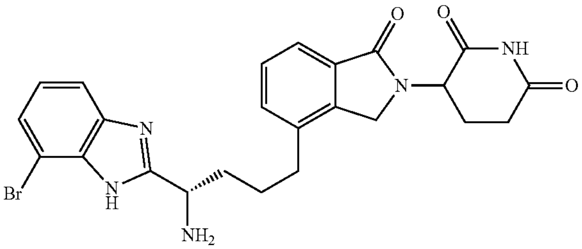 [SMILES: N[C@@H](CCCc1cccc2c1CN(C1CCC(=O)NC1=O)C2=O)c1nc2cccc(Br)c2[nH]1] |

-continued
| Serial number | Compound |
|---|---|
| 196 | 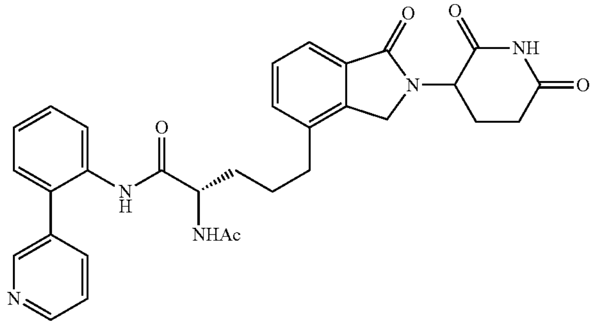 [SMILES: CC(=O)N[C@@H](CCCc1cccc2c1CN(C1CCC(=O)NC1=O)C2=O)C(=O)Nc1ccccc1-c1cccnc1] |
| 197 | 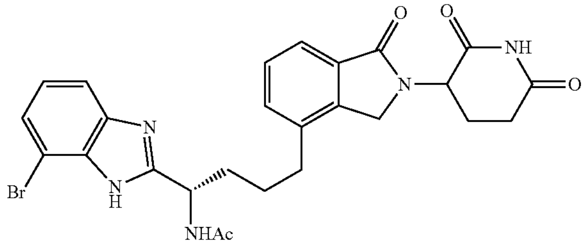 [SMILES: CC(=O)N[C@@H](CCCc1cccc2c1CN(C1CCC(=O)NC1=O)C2=O)c1nc2cccc(Br)c2[nH]1] |
| 198 | 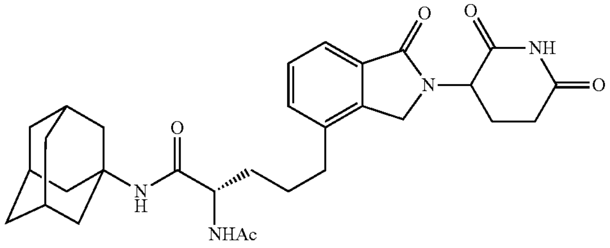 [SMILES: CC(=O)N[C@@H](CCCc1cccc2c1CN(C1CCC(=O)NC1=O)C2=O)C(=O)NC12CC3CC(CC(C3)C1)C2] |
| 199 | 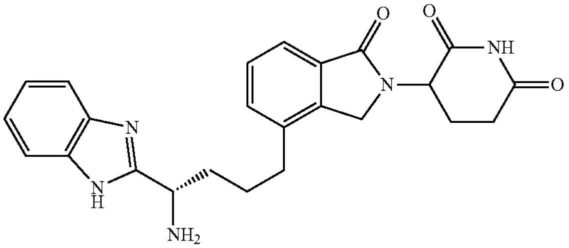 [SMILES: N[C@@H](CCCc1cccc2c1CN(C1CCC(=O)NC1=O)C2=O)c1nc2ccccc2[nH]1] |
| 200 | 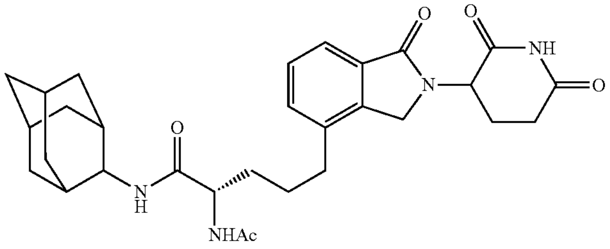 [SMILES: CC(=O)N[C@@H](CCCc1cccc2c1CN(C1CCC(=O)NC1=O)C2=O)C(=O)NC1C2CC3CC(C2)CC1C3] |

-continued
| Serial number | Compound |
|---|---|
| 201 | 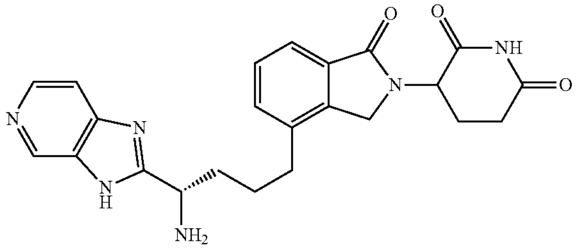 [SMILES: N[C@@H](CCCc1cccc2c1CN(C1CCC(=O)NC1=O)C2=O)c1nc2ccncc2[nH]1] |
| 202 | 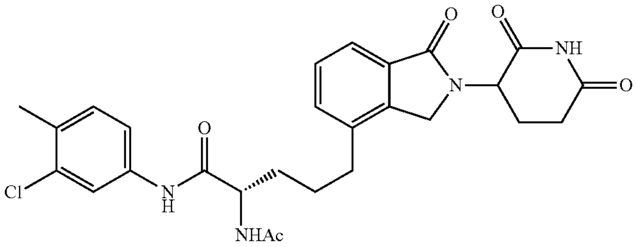 [SMILES: CC(=O)N[C@@H](CCCc1cccc2c1CN(C1CCC(=O)NC1=O)C2=O)C(=O)Nc1ccc(C)c(Cl)c1] |
| 203 | 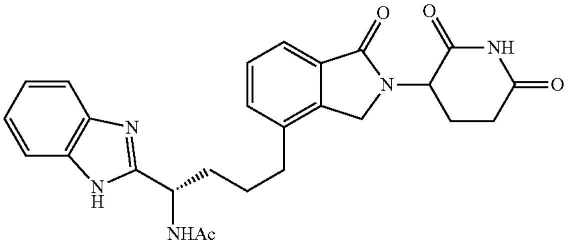 [SMILES: CC(=O)N[C@@H](CCCc1cccc2c1CN(C1CCC(=O)NC1=O)C2=O)c1nc2ccccc2[nH]1] |
| 204 | 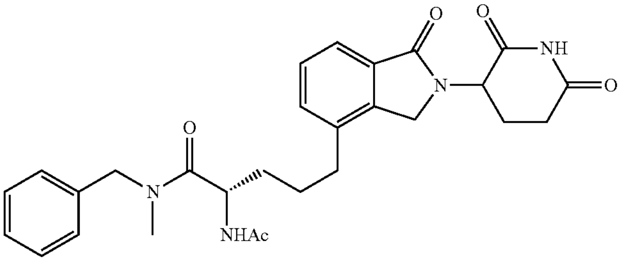 [SMILES: CC(=O)N[C@@H](CCCc1cccc2c1CN(C1CCC(=O)NC1=O)C2=O)C(=O)N(C)Cc1ccccc1] |
| 205 | 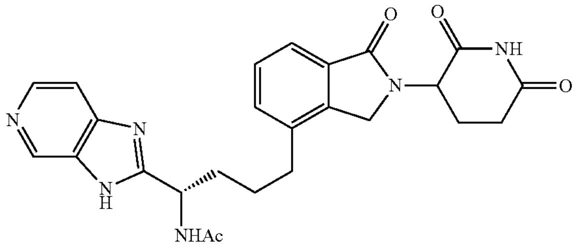 [SMILES: CC(=O)N[C@@H](CCCc1cccc2c1CN(C1CCC(=O)NC1=O)C2=O)c1nc2ccncc2[nH]1] |

-continued
| Serial number | Compound |
|---|---|
| 206 | 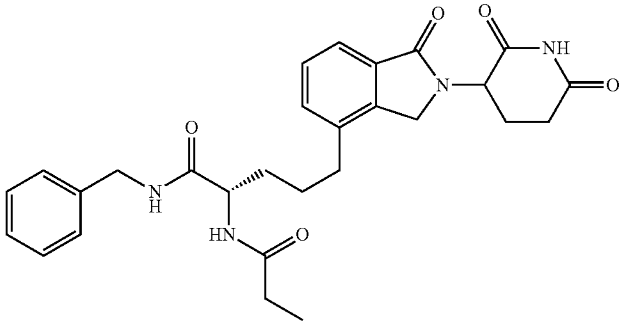 [SMILES: CCC(=O)N[C@@H](CCCc1cccc2c1CN(C1CCC(=O)NC1=O)C2=O)C(=O)NCc1ccccc1] |
| 207 | 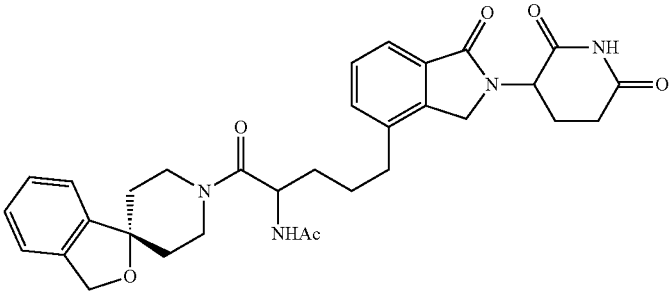 |
| 208 | 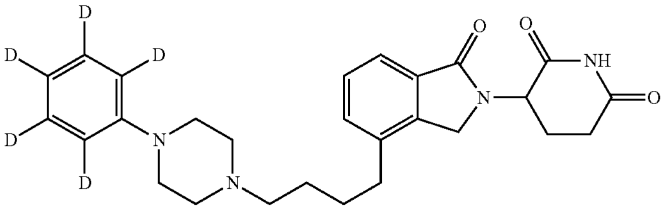 [SMILES: [2H]c1c([2H])c([2H])c(N2CCN(CCCCc3cccc4c3CN(C3CCC(=O)NC3=O)C4=O)CC2)c([2H])c1[2H]] |
| 209 | 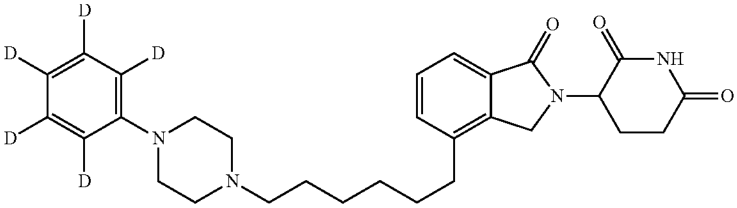 [SMILES: [2H]c1c([2H])c([2H])c(N2CCN(CCCCCCc3cccc4c3CN(C3CCC(=O)NC3=O)C4=O)CC2)c([2H])c1[2H]] |
| 210 | 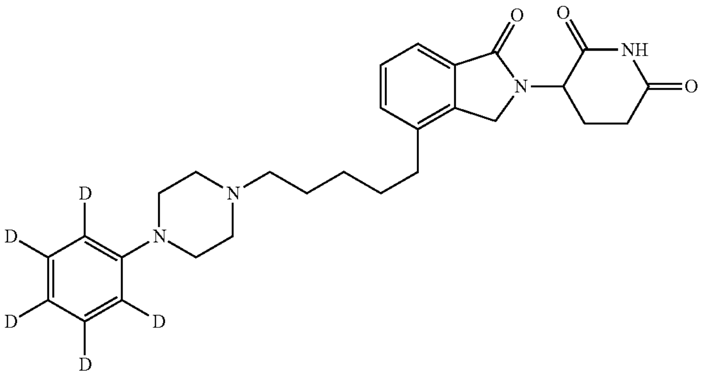 [SMILES: [2H]c1c([2H])c([2H])c(N2CCN(CCCCCc3cccc4c3CN(C3CCC(=O)NC3=O)C4=O)CC2)c([2H])c1[2H]] |

-continued
| Serial number | Compound |
|---|---|
| 211 | 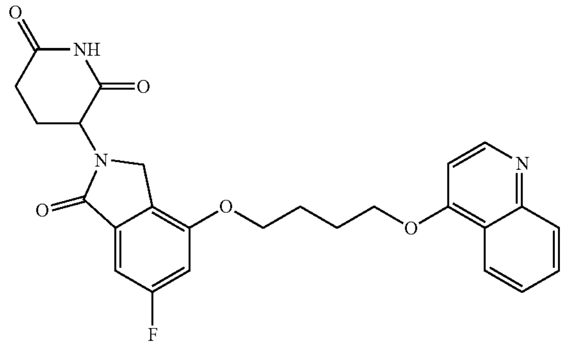 [SMILES: O=C1CCC(N2Cc3c(OCCCCOc4ccnc5ccccc45)cc(F)cc3C2=O)C(=O)N1] |
| 212 | 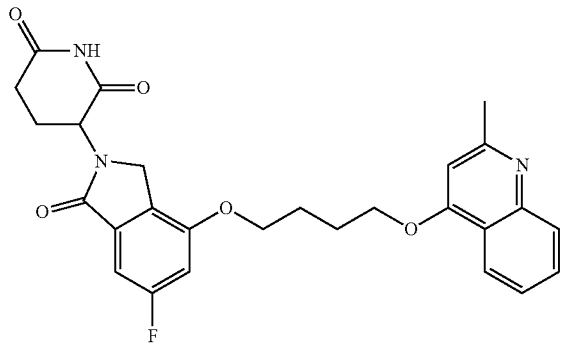 [SMILES: Cc1cc(OCCCCOc2cc(F)cc3c2CN(C2CCC(=O)NC2=O)C3=O)c2ccccc2n1] |
| 213 | 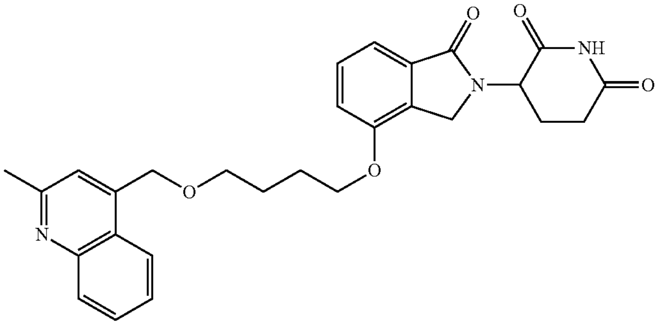 [SMILES: Cc1cc(COCCCCOc2cccc3c2CN(C2CCC(=O)NC2=O)C3=O)c2ccccc2n1] |
| 214 | 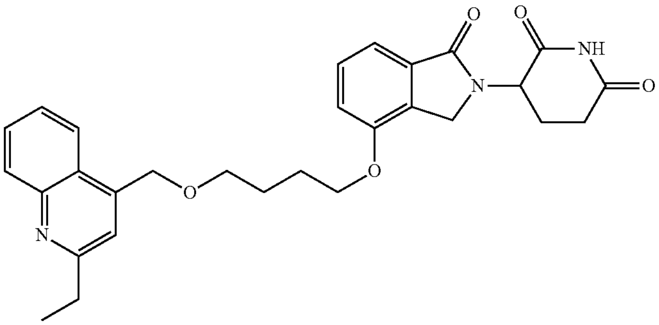 [SMILES: CCc1cc(COCCCCOc2cccc3c2CN(C2CCC(=O)NC2=O)C3=O)c2ccccc2n1] |
| 215 | 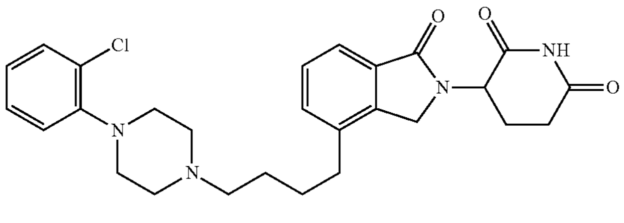 [SMILES: O=C1CCC(N2Cc3c(CCCCN4CCN(c5ccccc5Cl)CC4)cccc3C2=O)C(=O)N1] |

-continued
| Serial number | Compound |
| --- | --- |
| 216 | 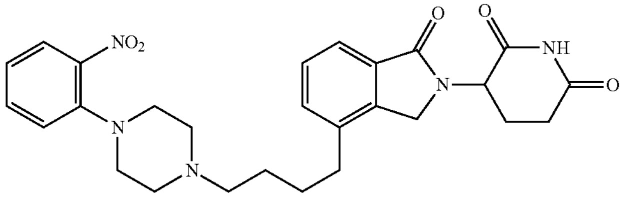 |
| 217 | 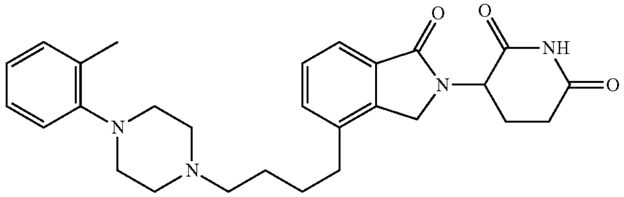 |
| 218 | 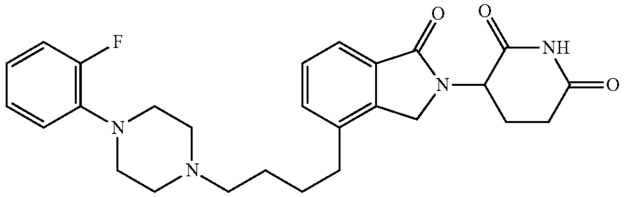 |
| 219 | 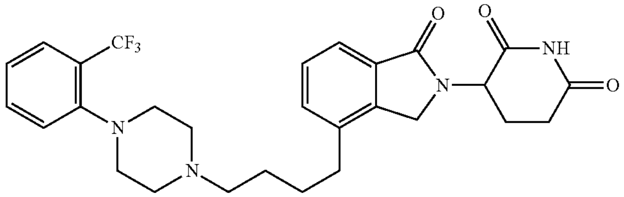 |
| 220 | 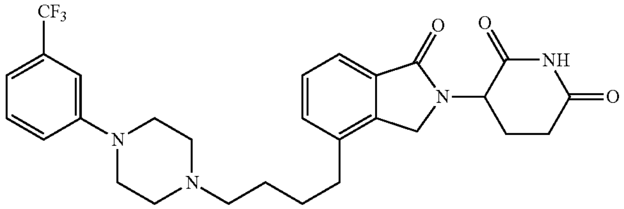 |
| 221 | 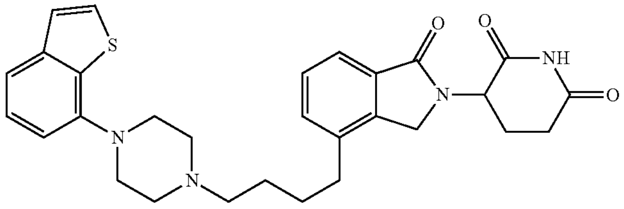 [SMILES: O=C1CCC(N2Cc3c(CCCCN4CCN(c5cccc6ccsc56)CC4)cccc3C2=O)C(=O)N1] |
| 222 | 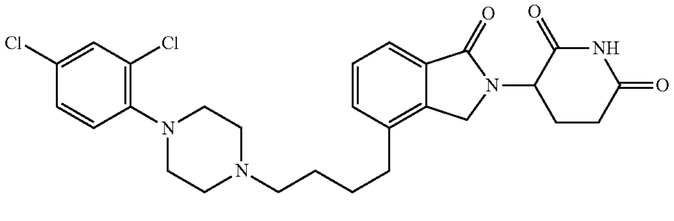 |

-continued
| Serial number | Compound |
|---|---|
| 223 | 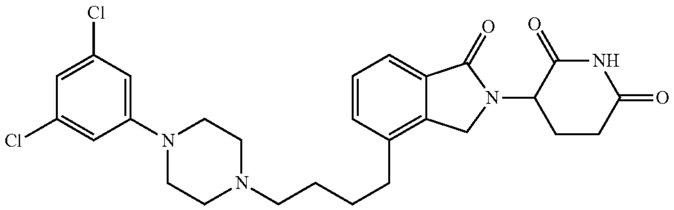 [SMILES: O=C1CCC(N2Cc3c(CCCCN4CCN(c5cc(Cl)cc(Cl)c5)CC4)cccc3C2=O)C(=O)N1] |
| 224 | 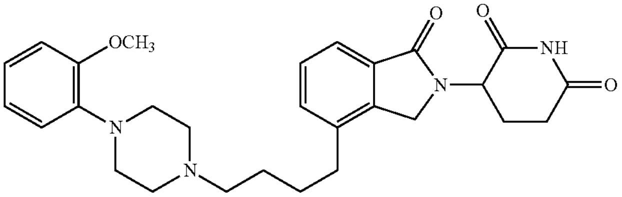 |
| 225 | 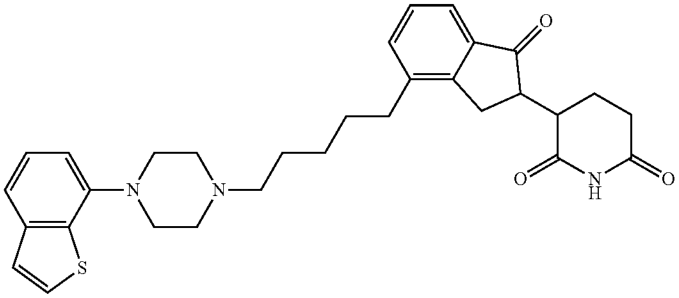 [SMILES: O=C1CCC(C2Cc3c(CCCCCN4CCN(c5cccc6ccsc56)CC4)cccc3C2=O)C(=O)N1] |
| 226 | 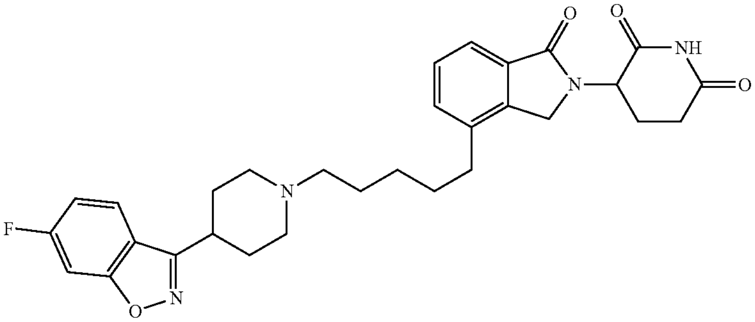 [SMILES: O=C1CCC(N2Cc3c(CCCCCN4CCC(c5noc6cc(F)ccc56)CC4)cccc3C2=O)C(=O)N1] |
| 227 | 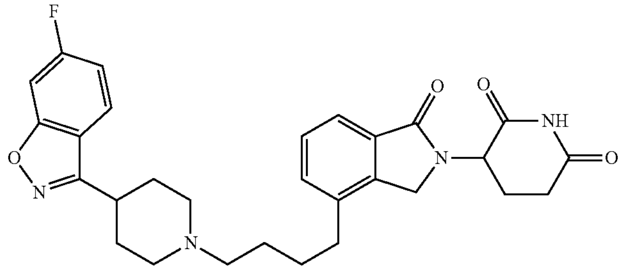 [SMILES: O=C1CCC(N2Cc3c(CCCCN4CCC(c5noc6cc(F)ccc56)CC4)cccc3C2=O)C(=O)N1] |
| 228 | 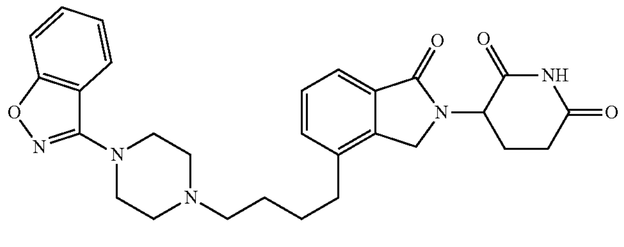 [SMILES: O=C1CCC(N2Cc3c(CCCCN4CCN(c5noc6ccccc56)CC4)cccc3C2=O)C(=O)N1] |

-continued
| Serial number | Compound |
|---|---|
| 229 | 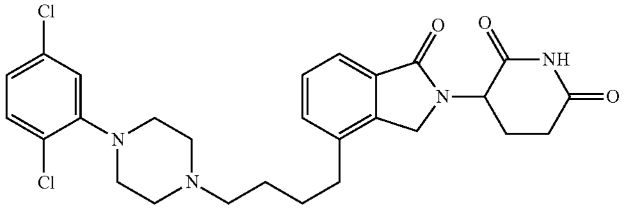 [SMILES: O=C1CCC(N2Cc3c(CCCCN4CCN(c5cc(Cl)ccc5Cl)CC4)cccc3C2=O)C(=O)N1] |
| 230 | 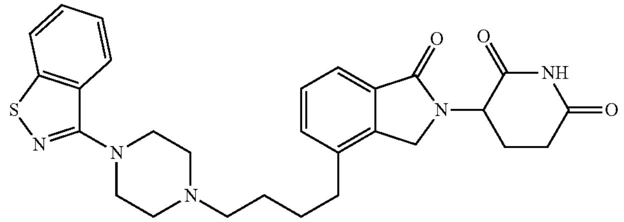 [SMILES: O=C1CCC(N2Cc3c(CCCCN4CCN(c5nsc6ccccc56)CC4)cccc3C2=O)C(=O)N1] |
| 231 | 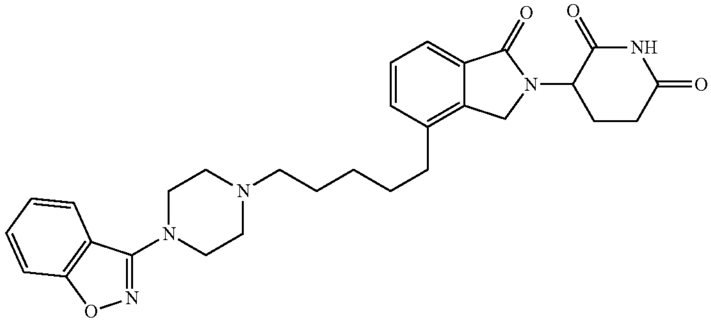 [SMILES: O=C1CCC(N2Cc3c(CCCCCN4CCN(c5nsc6ccccc56)CC4)cccc3C2=O)C(=O)N1] |
| 232 | 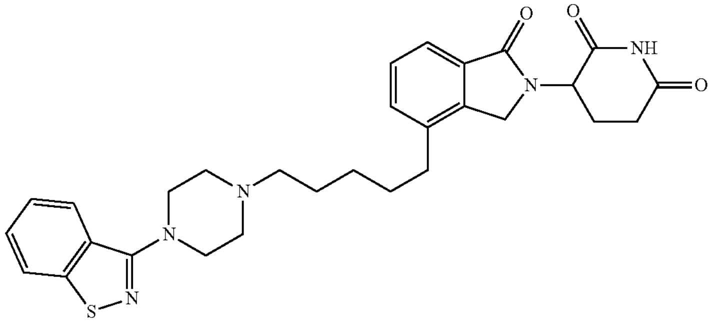 |
| 233 | 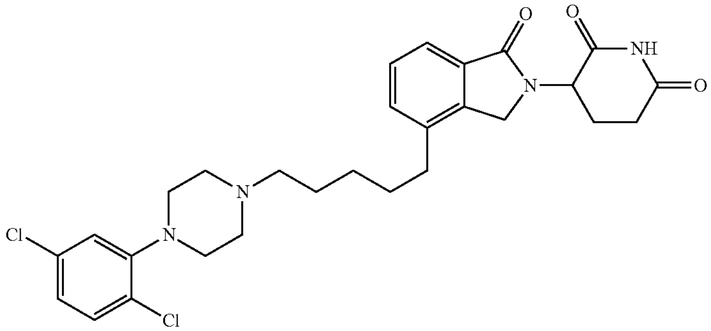 [SMILES: O=C1CCC(N2Cc3c(CCCCCN4CCN(c5cc(Cl)ccc5Cl)CC4)cccc3C2=O)C(=O)N1] |

-continued
| Serial number | Compound |
|---|---|
| 234 | 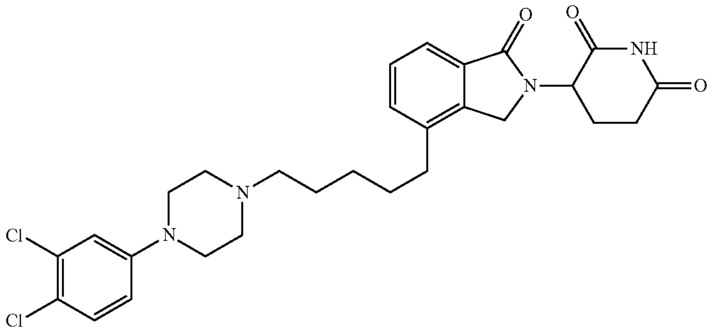 [SMILES: O=C1CCC(N2Cc3c(CCCCCN4CCN(c5ccc(Cl)c(Cl)c5)CC4)cccc3C2=O)C(=O)N1] |
| 235 | 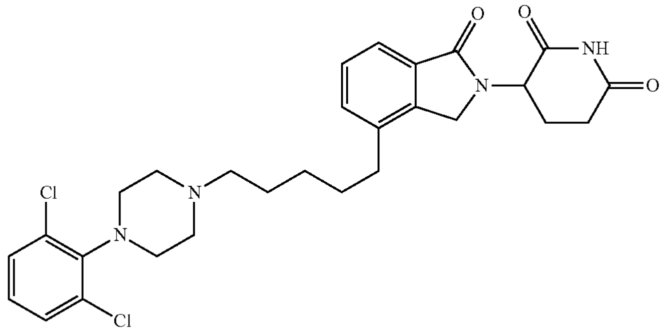 [SMILES: O=C1CCC(N2Cc3c(CCCCCN4CCN(c5c(Cl)cccc5Cl)CC4)cccc3C2=O)C(=O)N1] |
| 236 | 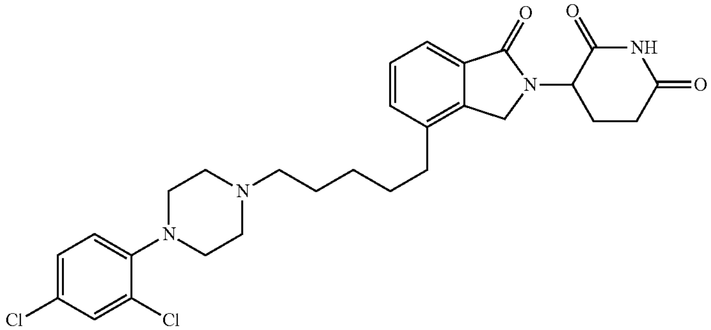 [SMILES: O=C1CCC(N2Cc3c(CCCCCN4CCN(c5ccc(Cl)cc5Cl)CC4)cccc3C2=O)C(=O)N1] |
| 237 | 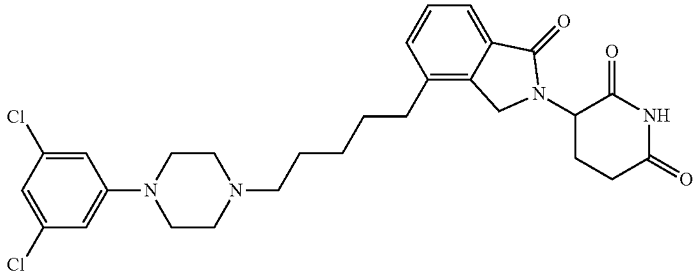 [SMILES: O=C1CCC(N2Cc3c(CCCCCN4CCN(c5cc(Cl)cc(Cl)c5)CC4)cccc3C2=O)C(=O)N1] |
| 238 | 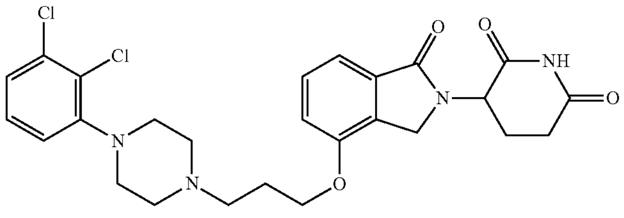 [SMILES: O=C1CCC(N2Cc3c(OCCCN4CCN(c5cccc(Cl)c5Cl)CC4)cccc3C2=O)C(=O)N1] |

-continued
| Serial number | Compound |
| --- | --- |
| 239 | 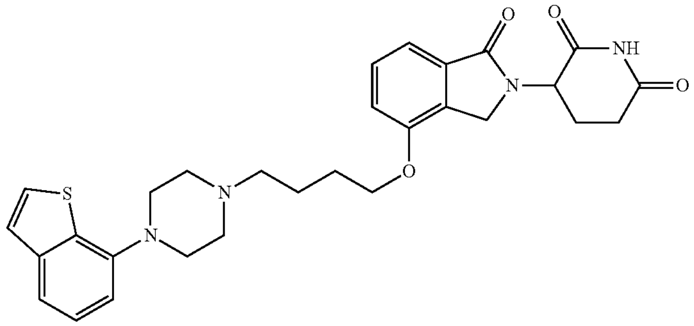 [SMILES: O=C1CCC(N2Cc3c(OCCCCN4CCN(c5cccc6ccsc56)CC4)cccc3C2=O)C(=O)N1] |
| 240 | 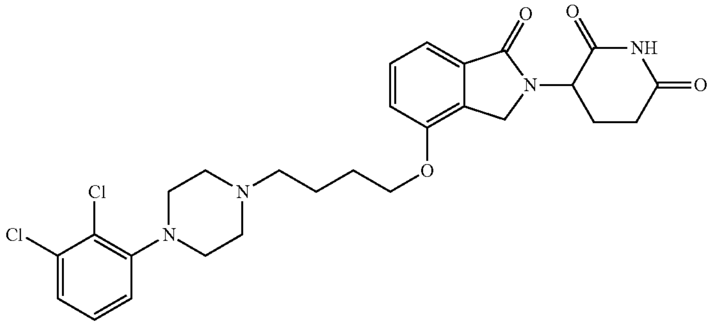 |
| 241 | 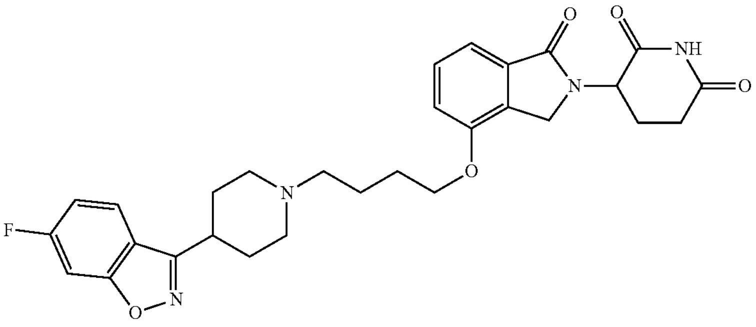 |
| 242 | 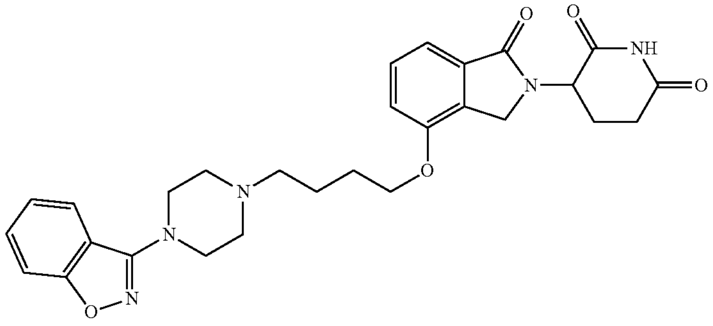 |

-continued
| Serial number | Compound |
|---|---|
| 243 | 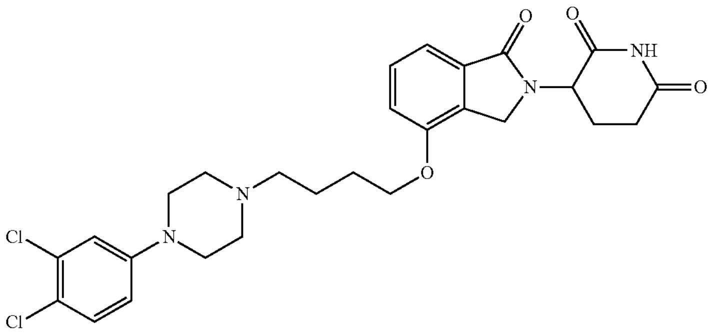 |
| 244 | 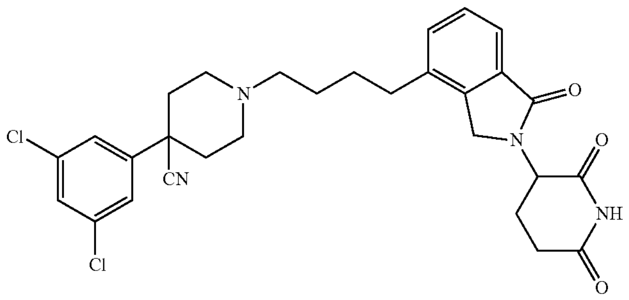 [SMILES: N#CC1(c2cc(Cl)cc(Cl)c2)CCN(CCCCc2cccc3c2CN(C2CCC(=O)NC2=O)C3=O)CC1] |
| 245 | 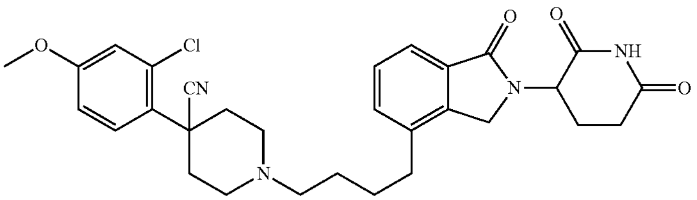 [SMILES: COc1ccc(C2(C#N)CCN(CCCCc3cccc4c3CN(C3CCC(=O)NC3=O)C4=O)CC2)c(Cl)c1] |
| 246 | 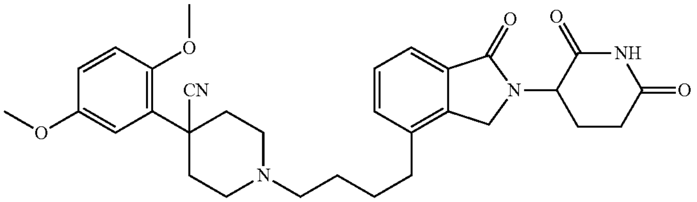 [SMILES: COc1ccc(OC)c(C2(C#N)CCN(CCCCc3cccc4c3CN(C3CCC(=O)NC3=O)C4=O)CC2)c1] |
| 247 | 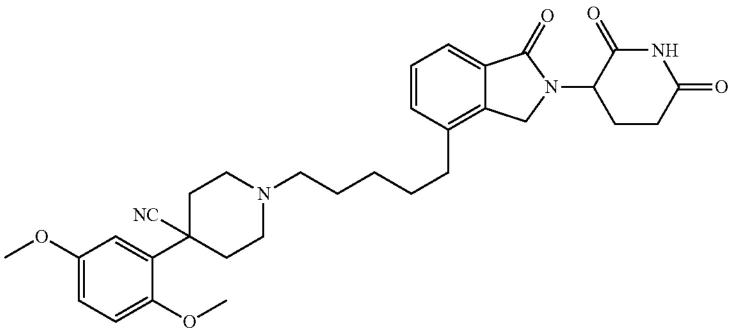 [SMILES: COc1ccc(OC)c(C2(C#N)CCN(CCCCCc3cccc4c3CN(C3CCC(=O)NC3=O)C4=O)CC2)c1] |

-continued
| Serial number | Compound |
|---|---|
| 248 | 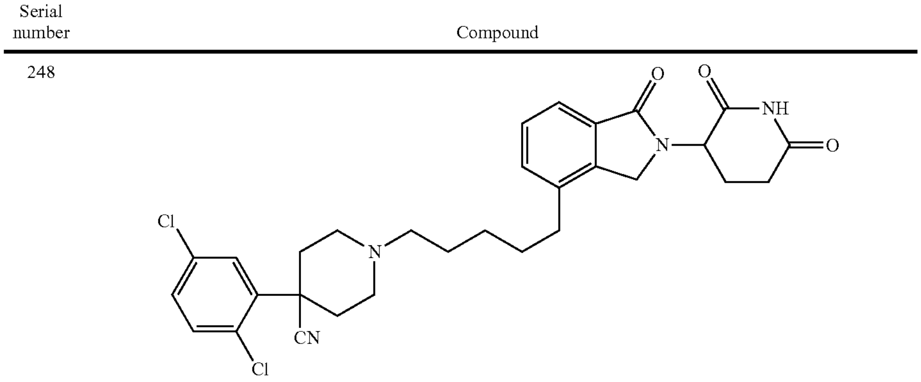 |
| 249 | 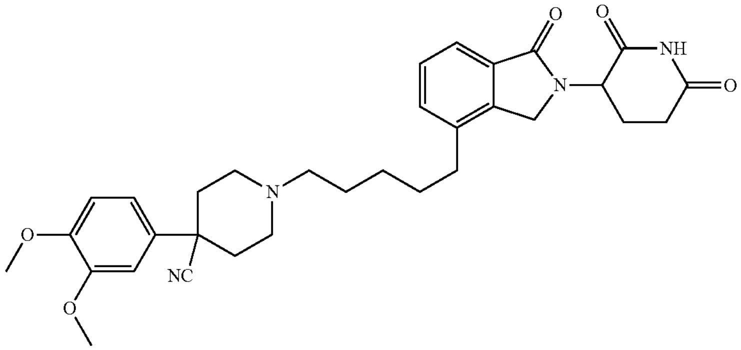 [SMILES: COc1ccc(C2(C#N)CCN(CCCCCc3cccc4c3CN(C3CCC(=O)NC3=O)C4=O)CC2)cc1OC] |
| 250 | 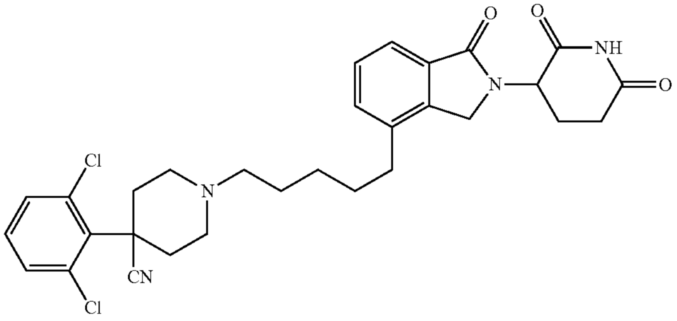 [SMILES: N#CC1(c2c(Cl)cccc2Cl)CCN(CCCCCc2cccc3c2CN(C2CCC(=O)NC2=O)C3=O)CC1] |
| 251 | 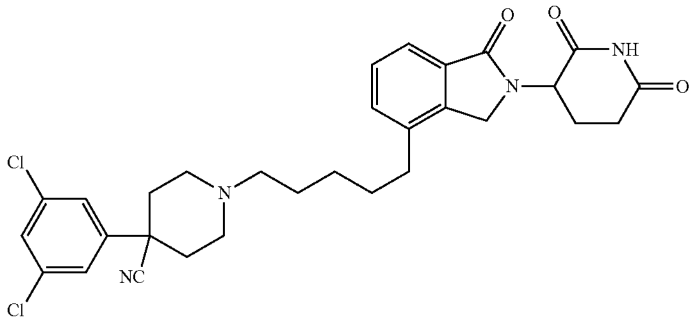 [SMILES: N#CC1(c2cc(Cl)cc(Cl)c2)CCN(CCCCCc2cccc3c2CN(C2CCC(=O)NC2=O)C3=O)CC1] |

-continued
| Serial number | Compound |
|---|---|
| 252 | 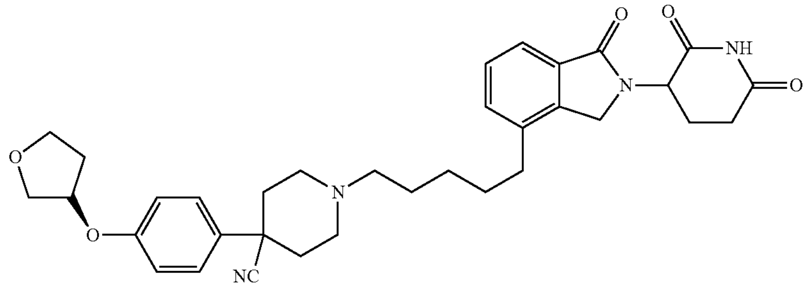 |
| 253 | 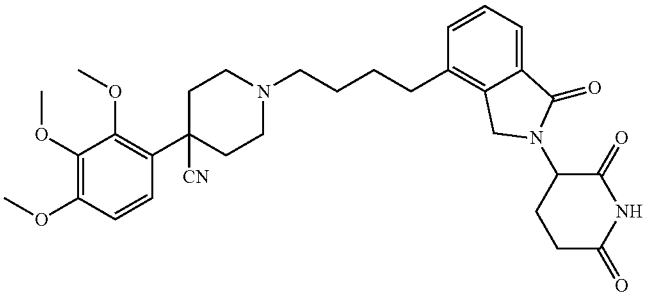 [SMILES: COc1ccc(C2(C#N)CCN(CCCCc3cccc4c3CN(C3CCC(=O)NC3=O)C4=O)CC2)c(OC)c1OC] |
| 254 | 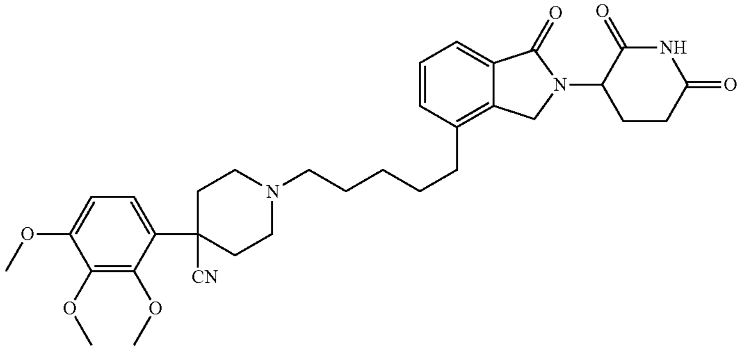 [SMILES: COc1ccc(C2(C#N)CCN(CCCCCc3cccc4c3CN(C3CCC(=O)NC3=O)C4=O)CC2)c(OC)c1OC] |
| 255 | 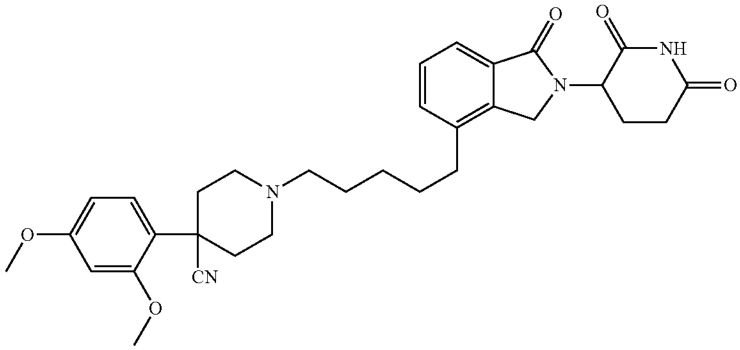 [SMILES: COc1ccc(C2(C#N)CCN(CCCCCc3cccc4c3CN(C3CCC(=O)NC3=O)C4=O)CC2)c(OC)c1] |
| 256 | 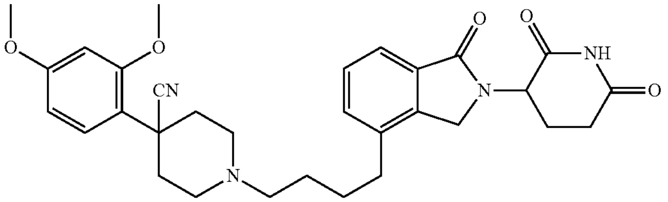 [SMILES: COc1ccc(C2(C#N)CCN(CCCCc3cccc4c3CN(C3CCC(=O)NC3=O)C4=O)CC2)c(OC)c1] |

-continued
| Serial number | Compound |
| --- | --- |
| 257 | 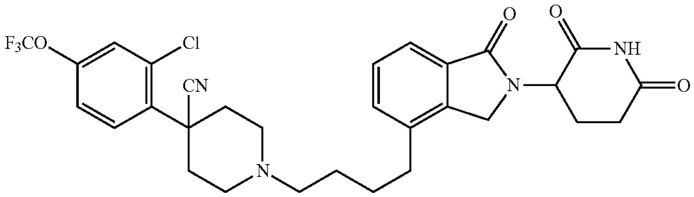 [SMILES: N#CC1(c2ccc(OC(F)(F)F)cc2Cl)CCN(CCCCc2cccc3c2CN(C2CCC(=O)NC2=O)C3=O)CC1] |
| 258 | 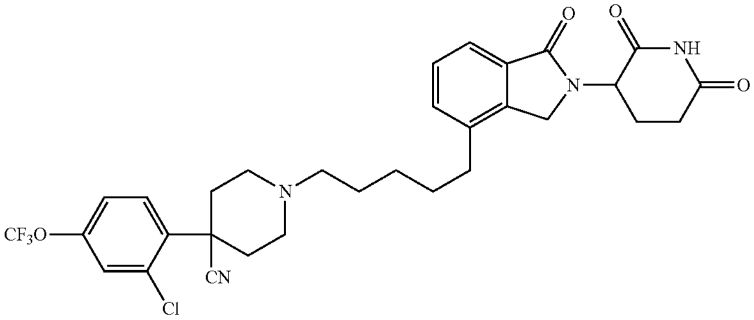 |
| 259 | 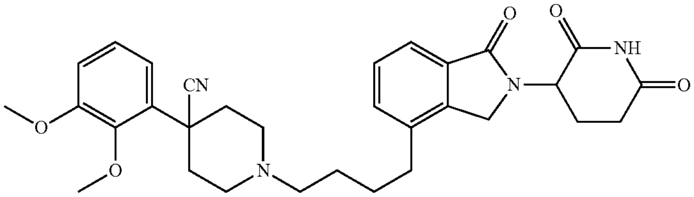 [SMILES: COc1cccc(C2(C#N)CCN(CCCCc3cccc4c3CN(C3CCC(=O)NC3=O)C4=O)CC2)c1OC] |
| 260 | 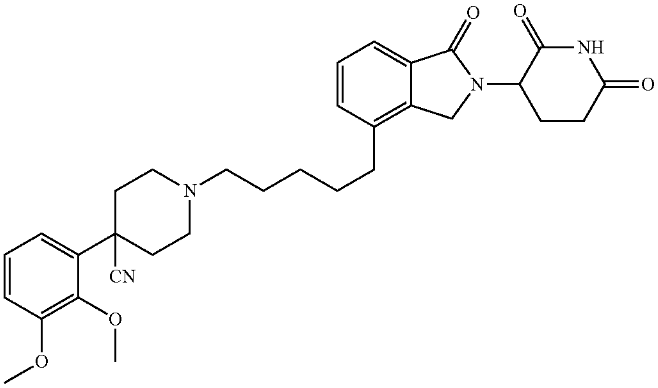 [SMILES: COc1cccc(C2(C#N)CCN(CCCCCc3cccc4c3CN(C3CCC(=O)NC3=O)C4=O)CC2)c1OC] |
| 261 | 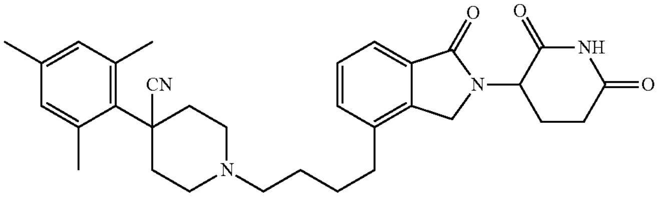 [SMILES: Cc1cc(C)c(C2(C#N)CCN(CCCCc3cccc4c3CN(C3CCC(=O)NC3=O)C4=O)CC2)c(C)c1] |

-continued
| Serial number | Compound |
|---|---|
| 262 | 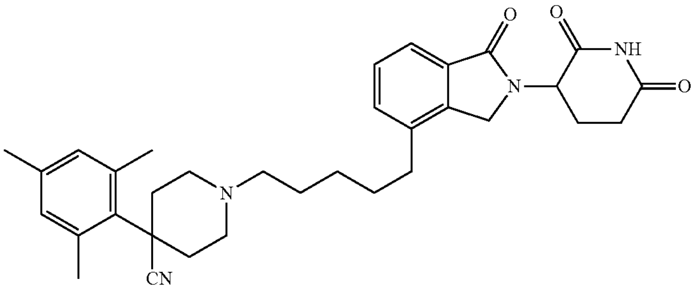 [SMILES: Cc1cc(C)c(C2(C#N)CCN(CCCCCc3cccc4c3CN(C3CCC(=O)NC3=O)C4=O)CC2)c(C)c1] |
| 263 | 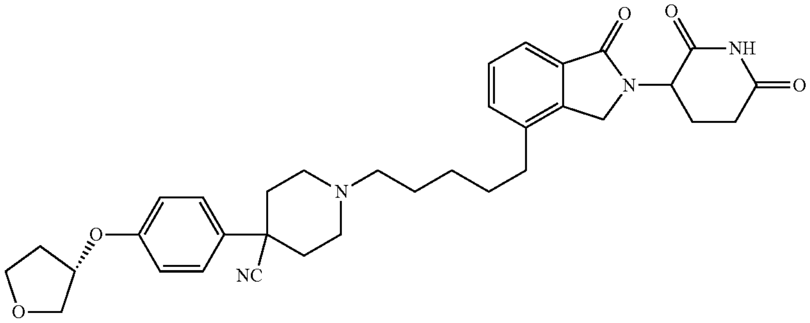 [SMILES: N#CC1(c2ccc(O[C@H]3CCOC3)cc2)CCN(CCCCCc2cccc3c2CN(C2CCC(=O)NC2=O)C3=O)CC1] |
| 264 | 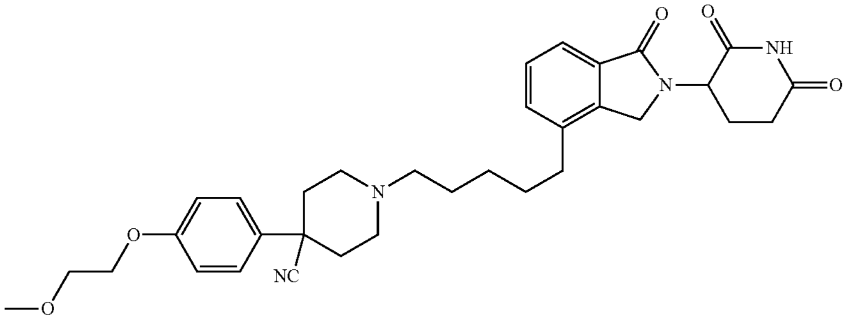 [SMILES: COCCOc1ccc(C2(C#N)CCN(CCCCCc3cccc4c3CN(C3CCC(=O)NC3=O)C4=O)CC2)cc1] |
| 265 | 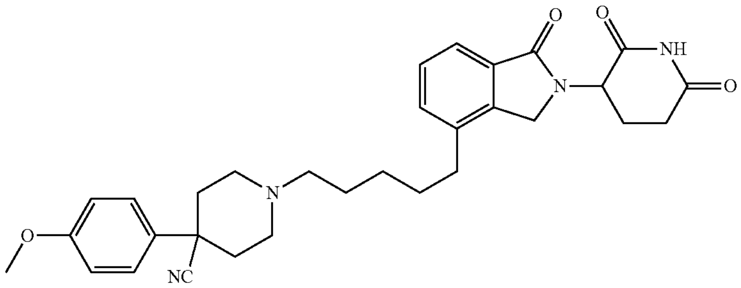 [SMILES: COc1ccc(C2(C#N)CCN(CCCCCc3cccc4c3CN(C3CCC(=O)NC3=O)C4=O)CC2)cc1] |
| 266 | 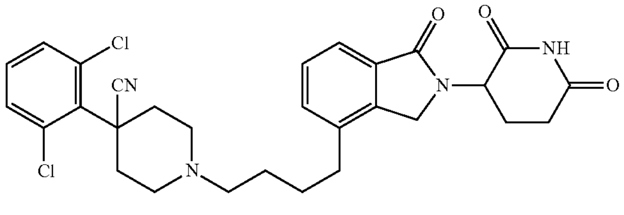 [SMILES: N#CC1(c2c(Cl)cccc2Cl)CCN(CCCCc2cccc3c2CN(C2CCC(=O)NC2=O)C3=O)CC1] |

-continued
| Serial number | Compound |
|---|---|
| 267 | 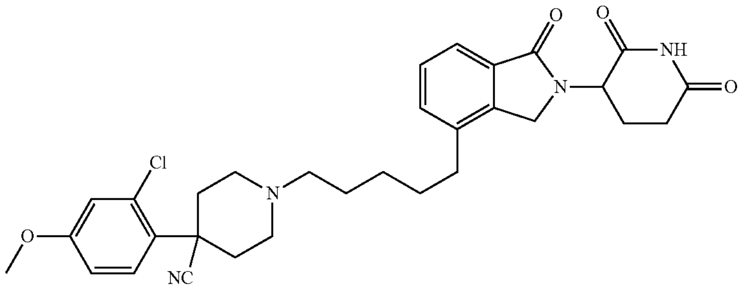 |
| 268 | 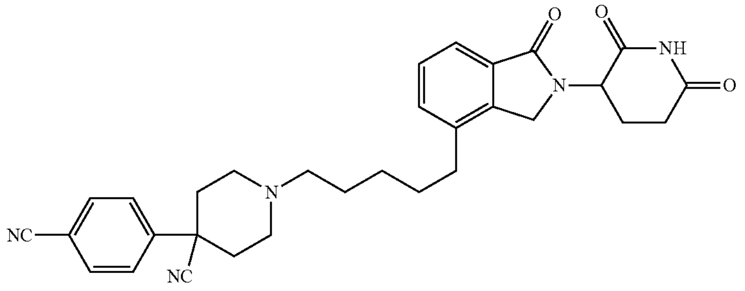 [SMILES: N#Cc1ccc(C2(C#N)CCN(CCCCCc3cccc4c3CN(C3CCC(=O)NC3=O)C4=O)CC2)cc1] |
| 269 | 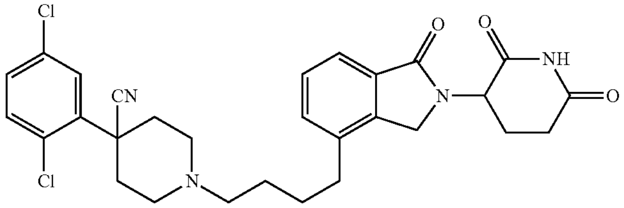 [SMILES: N#CC1(c2cc(Cl)ccc2Cl)CCN(CCCCc2cccc3c2CN(C2CCC(=O)NC2=O)C3=O)CC1] |
| 270 | 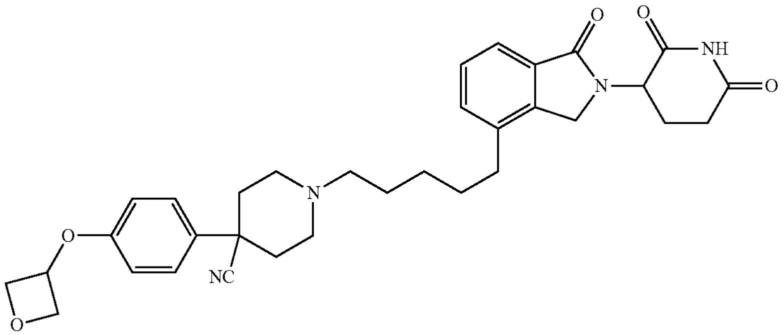 [SMILES: N#CC1(c2ccc(OC3COC3)cc2)CCN(CCCCCc2cccc3c2CN(C2CCC(=O)NC2=O)C3=O)CC1] |
| 271 | 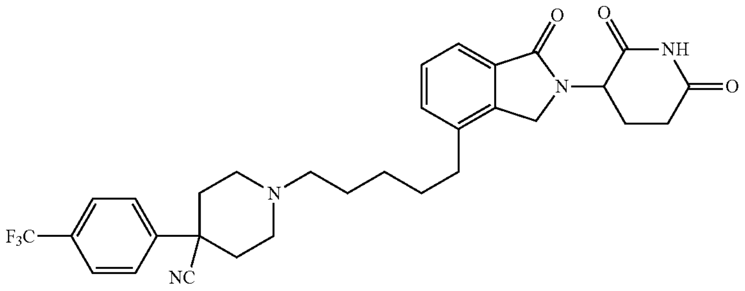 [SMILES: N#CC1(c2ccc(C(F)(F)F)cc2)CCN(CCCCCc2cccc3c2CN(C2CCC(=O)NC2=O)C3=O)CC1] |

-continued
| Serial number | Compound |
| --- | --- |
| 272 | 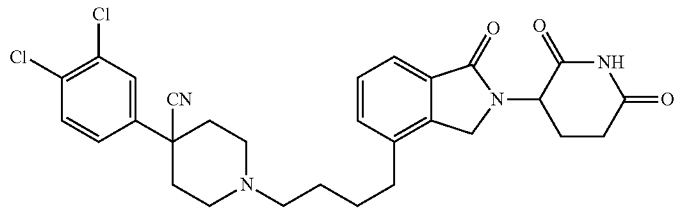 [SMILES: N#CC1(c2ccc(Cl)c(Cl)c2)CCN(CCCCc2cccc3c2CN(C2CCC(=O)NC2=O)C3=O)CC1] |
| 273 | 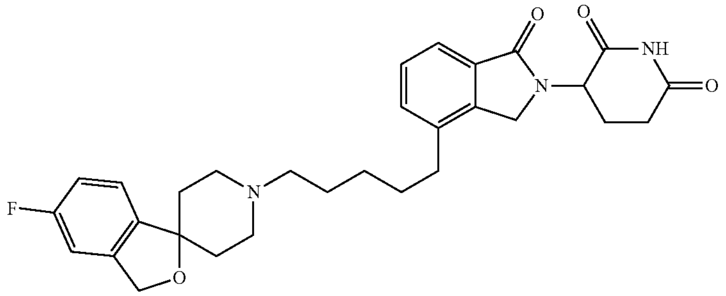 [SMILES: O=C1CCC(N2Cc3c(CCCCCN4CCC5(CC4)OCc4cc(F)ccc45)cccc3C2=O)C(=O)N1] |
| 274 | 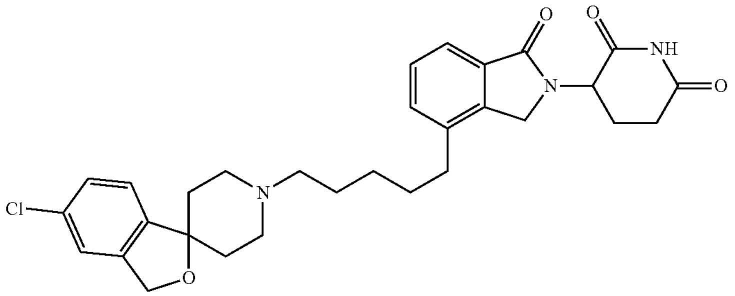 [SMILES: O=C1CCC(N2Cc3c(CCCCCN4CCC5(CC4)OCc4cc(Cl)ccc45)cccc3C2=O)C(=O)N1] |
| 275 | 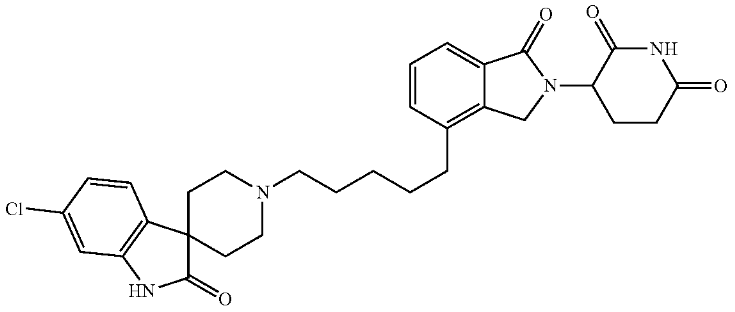 [SMILES: O=C1CCC(N2Cc3c(CCCCCN4CCC5(CC4)C(=O)Nc4cc(Cl)ccc45)cccc3C2=O)C(=O)N1] |
| 276 | 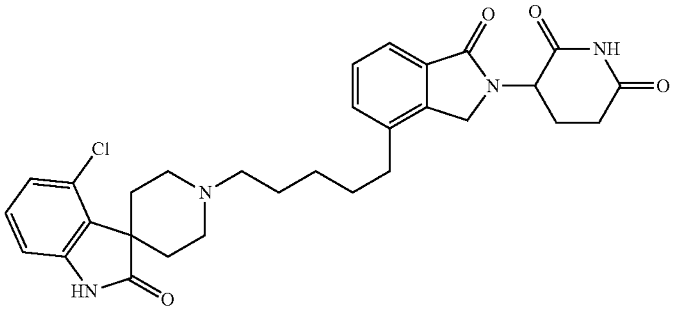 [SMILES: O=C1CCC(N2Cc3c(CCCCCN4CCC5(CC4)C(=O)Nc4cccc(Cl)c45)cccc3C2=O)C(=O)N1] |

-continued
| Serial number | Compound |
|---|---|
| 277 | 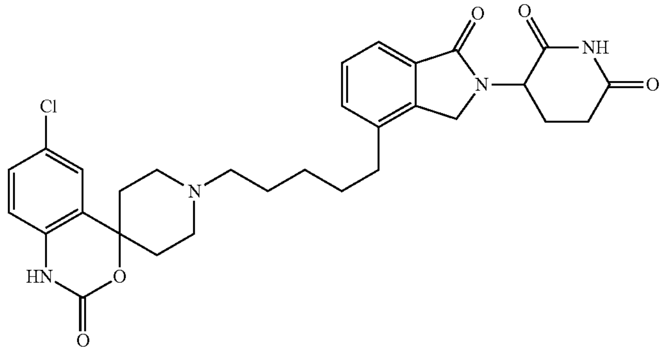 [SMILES: O=C1CCC(N2Cc3c(CCCCCN4CCC5(CC4)OC(=O)Nc4ccc(Cl)cc45)cccc3C2=O)C(=O)N1] |
| 278 | 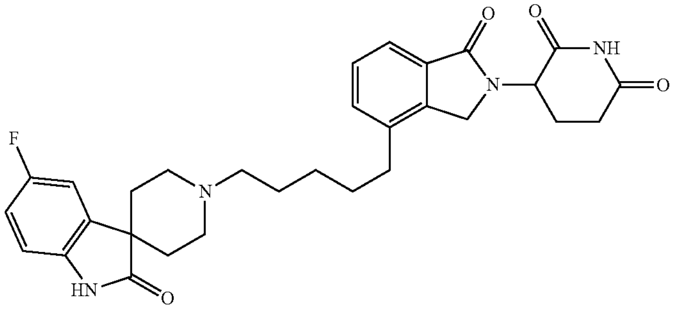 [SMILES: O=C1CCC(N2Cc3c(CCCCCN4CCC5(CC4)C(=O)Nc4ccc(F)cc45)cccc3C2=O)C(=O)N1] |
| 279 | 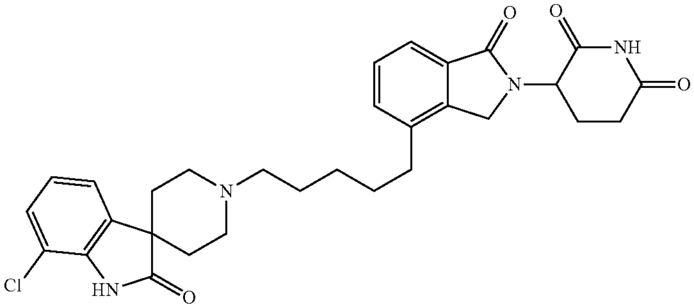 [SMILES: O=C1CCC(N2Cc3c(CCCCCN4CCC5(CC4)C(=O)Nc4c(Cl)cccc45)cccc3C2=O)C(=O)N1] |
| 280 | 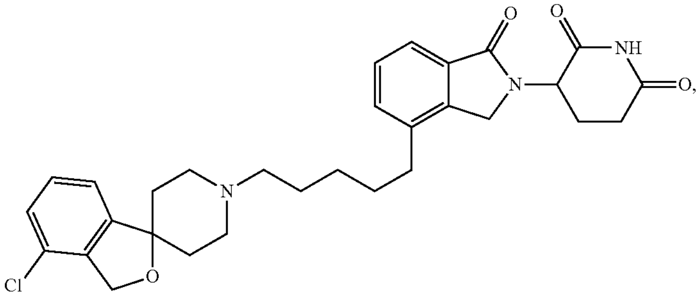 [SMILES: O=C1CCC(N2Cc3c(CCCCCN4CCC5(CC4)OCc4c(Cl)cccc45)cccc3C2=O)C(=O)N1] |
or a tautomer, enantiomer, diastereomer, racemate, isotopic compound, pharmaceutically acceptable salt, ester or hydrate thereof.

8. A method for preparing the compound represented by the general formula (I) of claim 1, wherein the method is selected from one of the following:

Synthesis method 1:

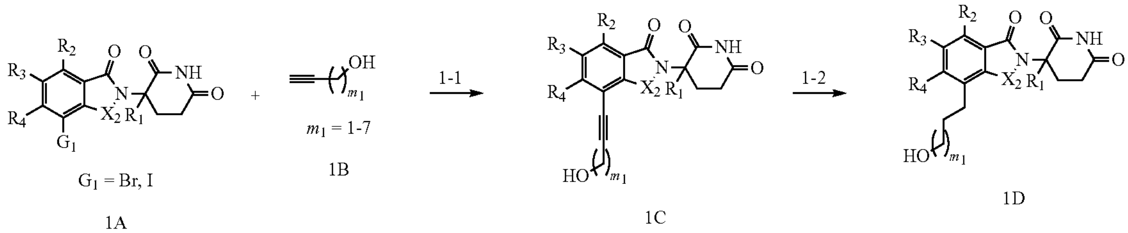

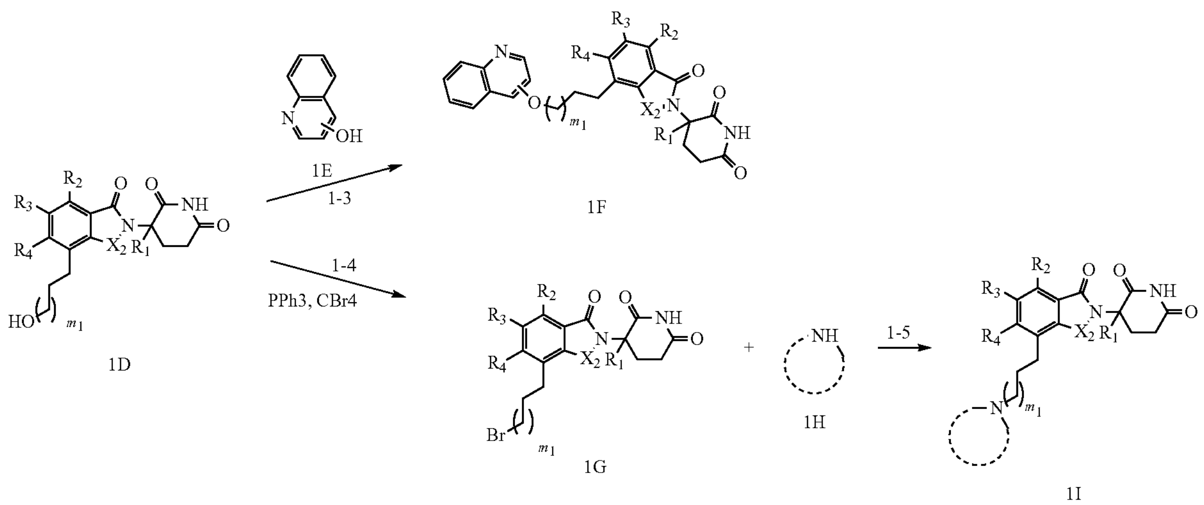

wherein, the definitions of $R_1$, $R_2$, $R_3$, $R_4$ and $X_2$ are the same as those in claim 1;

$m_1$ is an integer from 1 to 7;

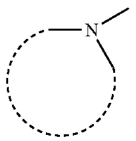

has the same definition as i) heterocyclyl, ii) fused heterocyclyl, and iii) spiroheterocyclic group in the definition of A in claim 1;

Step 1-1: compound 1C is obtained by Sonogashira coupling reaction of compounds 1A and 1B at room temperature or under heating conditions in the presence of dipole organic solvent, Pd catalyst, monovalent copper catalyst and base;

Step 1-2: compound 1C is reduced to compound 1D by hydrogen under catalytic condition of Pd/C, raney nickel or Wilkinson's catalyst, Step 1-3: compound 1F is obtained by reacting compound 1D with hydroxyquinoline 1E under the condition of triphenylphosphine and diisopropylazodiformate;

Step 1-4: compound 1D is reacted to obtain compound 1G in the presence of triphenylphosphine and carbon tetrabromide;

Step 1-5: compound 1I is obtained by reacting compound 1G with nitrogen-containing heterocyclic compound 1H in the presence of sodium iodide, wherein the compound 1H is amine compound containing A group in claim 1;

Synthesis method 2:

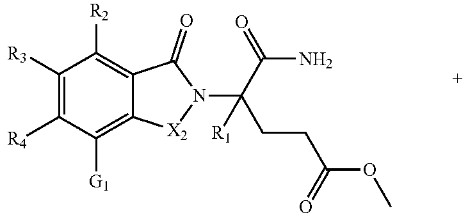

G1 = Br, I

2A

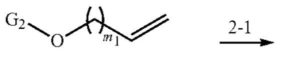

$m_1$ = 1-7

2B

-continued

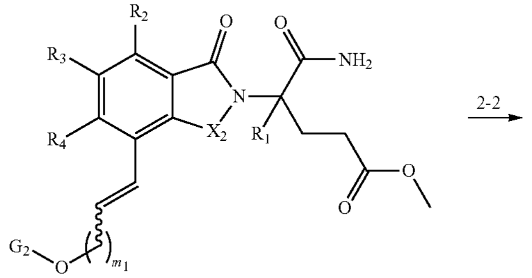

2C

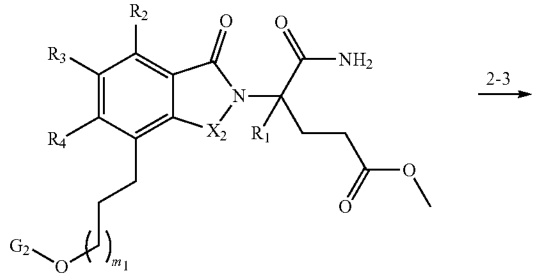

2D

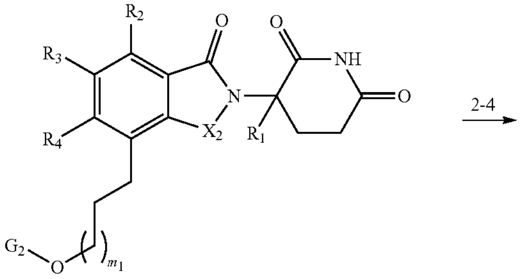

2E

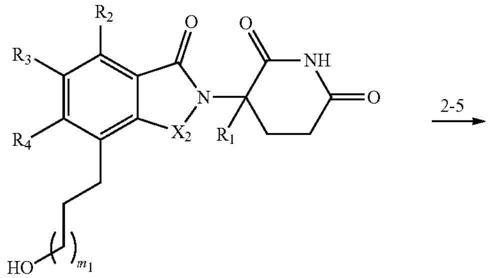

2F

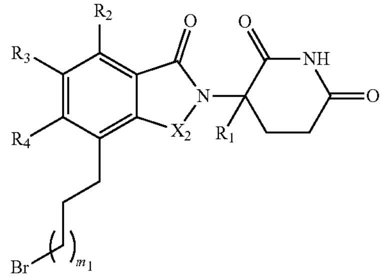

2G

+

-continued

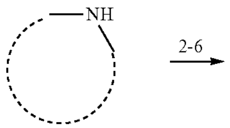

2H

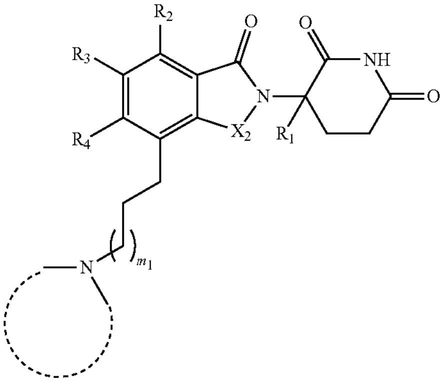

2I wherein, the definitions of $R_1$, $R_2$, $R_3$, $R_4$ and $X_2$ are the same as those in claim 1;

$m_1$ is an integer from 1 to 7;

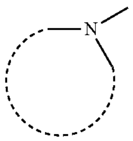

has the same definition as i) heterocyclyl, ii) fused heterocyclyl, and iii) spiroheterocyclic group in the definition of A in claim 1;

G2 is a protecting group selected from TBS, Trit or benzyl;

Step 2-1: multi-substituted olefin derivative 2C is obtained by reacting compounds 2A and 2B under heating conditions in the presence of aprotic solvent, Pd catalyst phosphine ligand and organic base;

Step 2-2: compound 2C is reduced to compound 2D by hydrogen under catalytic condition of Pd/C or Wilkinson's catalyst;

Step 2-3: piperidone derivative 2E is obtained by ring-closing reaction in the presence of potassium tert-butoxide in dry tetrahydrofuran;

Step 2-4: compound 2F is obtained by removing the protective group of compound 2E under acidic condition or in the presence of TBAF;

Step 2-5: compound 2F is reacted to obtain compound 2G in the presence of triphenylphosphine and carbon tetrabromide;

Step 2-6: compound 21 is obtained by reacting compound 2G with nitrogen-containing heterocyclic compound 2H in the presence of sodium iodide, wherein the compound 2H is amine compound containing A group in claim 1;

Synthesis method 3:

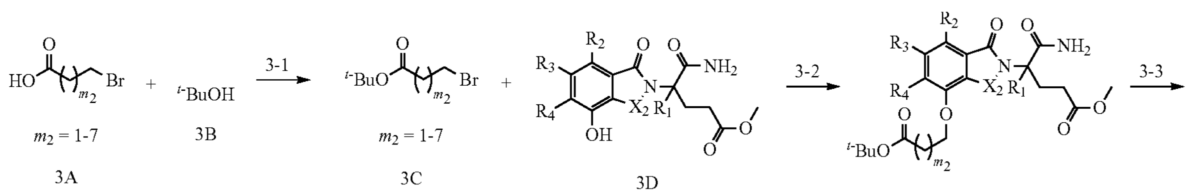

3A 3B 3C 3D 3E

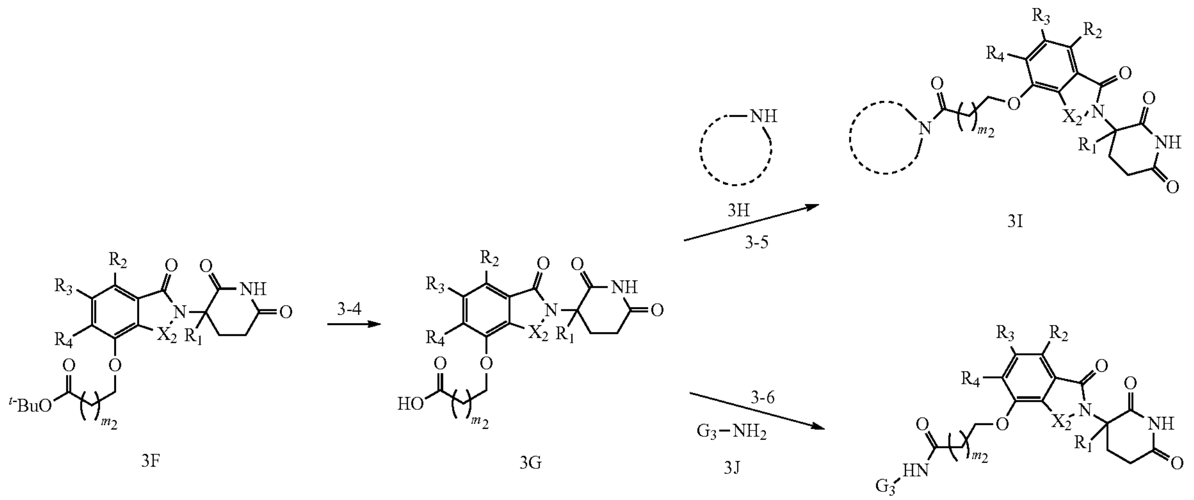

3F 3G 3H 3I 3J 3K wherein, the definitions of $R_1$, $R_2$, $R_3$, $R_4$, and $X_2$ are the same as those in claim 1;

$m_2$ is an integer from 1 to 7:

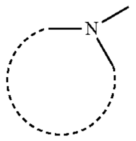

has the same definition as i) heterocyclyl, ii) fused heterocyclyl, and iii) spiroheterocyclic group in the definition of A in claim 1;

$G_3$-$NH_2$ is various aromatic amine or aliphatic amine compounds used in the examples of the present invention;

Step 3-1: compound 3A and 3B are reacted in the presence of trifluoroacetic anhydride and tert-butanol to obtain compound 3C;

Step 3-2: compounds 3C and 3D are reacted in the presence of potassium carbonate to obtain compound 3E;

Step 3-3: piperidone derivative 3F is obtained by ring-closing of compound 3E in the presence of potassium tert-butoxide;

Step 3-4: compound 3G is obtained by removing the protective group of compound 3F under hydrochloric acid condition;

Step 3-5: compound 3I is obtained by condensation reaction of compound 3G and nitrogen-containing heterocyclic compound 3H in the presence of condensing agent and base, wherein compound 3H is the variety amine compounds containing A group in claim 1;

Step 3-6: compound 3G and compound 3J are condensed in the presence of condensing agent and base to obtain compound 3K;

Synthesis method 5:

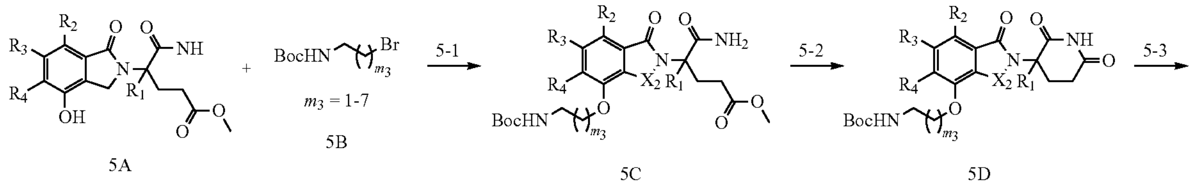

5A 5B 5C 5D

-continued

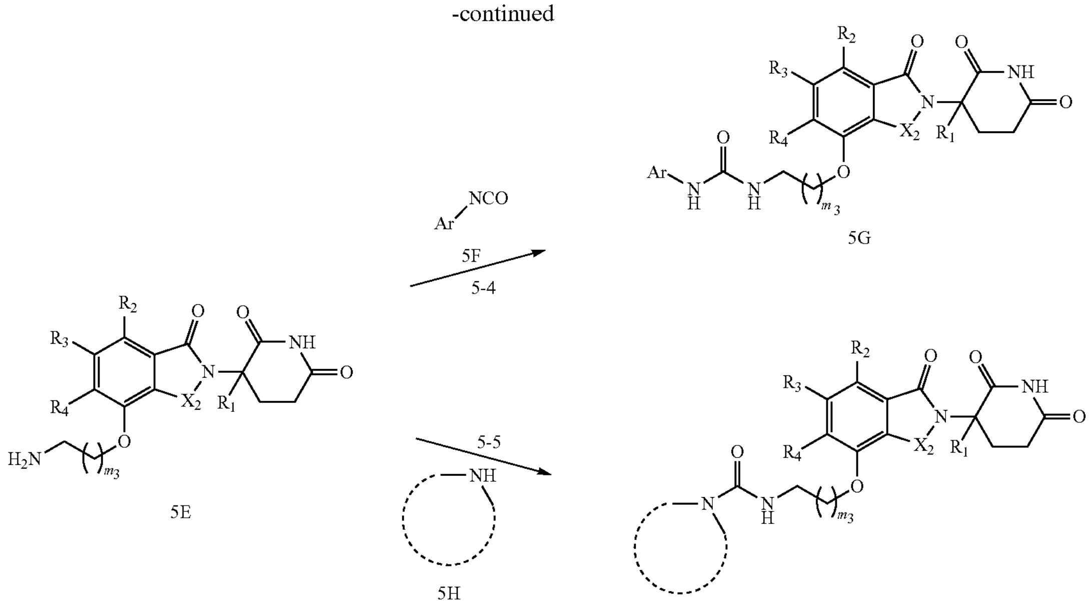

5G

5E

5H

5I wherein, the definitions of $R_1$, $R_2$, $R_3$, $R_4$, and $X_2$ are the same as those in claim 1;

$m_3$ is an integer from 1 to 7;

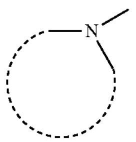

has the same definition as heterocyclyl, fused heterocyclyl, spiroheterocyclic group in the definition of A in claim 1;

Ar is 6-10 membered aryl, or 5-10 membered heteroaryl, the aryl or heteroaryl is optionally substituted by one or more $R_5$ substituents, and $R_5$ is the same as in claim 1;

Step 5-1: compound 5A and 5B are reacted under condition of triphenylphosphine and diisopropyl azodicarboxylate to obtain compound 5C;

Step 5-2: compound 5C is reacted in the presence of potassium carbonate to obtain compound 5D;

Step 5-3: compound 5E is obtained by removing the protective group under hydrochloric acid condition;

Step 5-4: compound 5E and compound 5F are reacted under basic condition to obtain compound 5G;

Step 5-5: compound 5I is obtained by reacting compound 5E with nitrogen-containing heterocyclic Compound 5H under N,N-carbonyldiimidazole and basic condition, wherein the Compound 5H is the amine compound containing A group in claim 1;

Synthesis method 6:

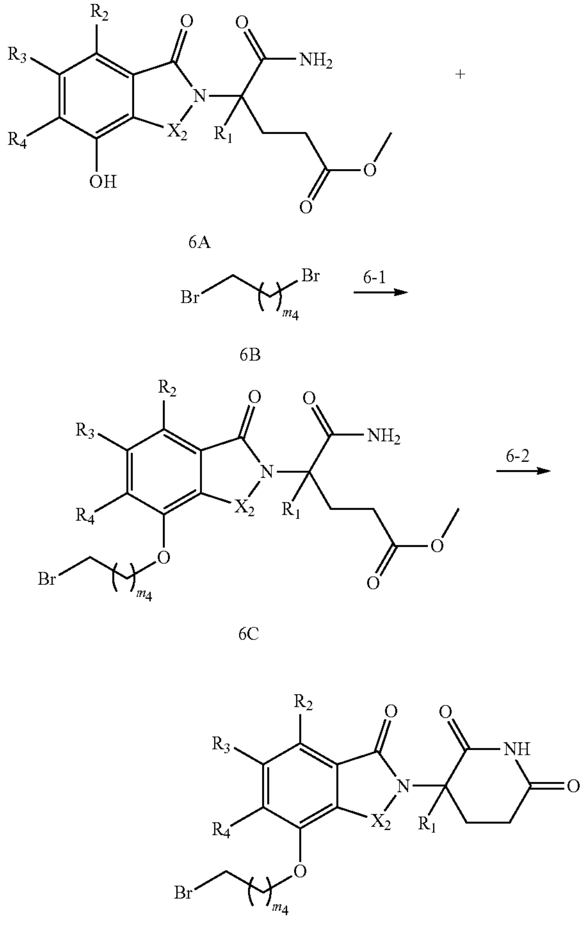

6A

6B

6C

6D

-continued

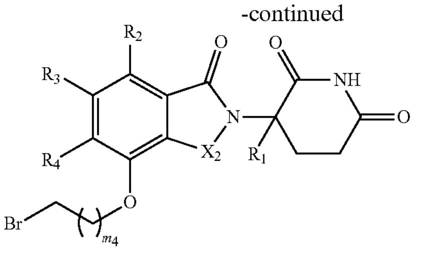

6D

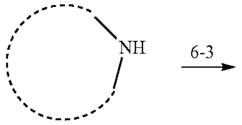

6E

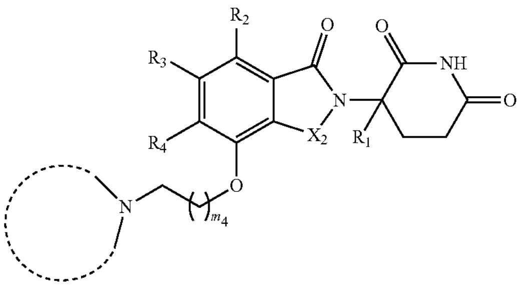

6F wherein, the definitions of $R_1$, $R_2$, $R_3$, $R_4$, and $X_2$ are the same as those in claim 1;

$m_4$ is an integer from 1 to 7;

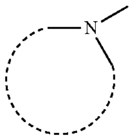

has the same definition as heterocyclyl, fused heterocyclyl, spiroheterocyclic group in the definition of A in claim 1;

Step 6-1: compound 6A and 6B are reacted in the presence of potassium carbonate to obtain compound 6C;

Step 6-2: compound 6C is reacted in the presence of potassium tert-butoxide to obtain compound 6D;

Step 6-3: compound 6F is obtained by reacting compound 6D with nitrogen-containing heterocyclic compound 6E under basic condition, wherein compound 6E is amine compounds containing A group in claim 1;

Synthesis method 7

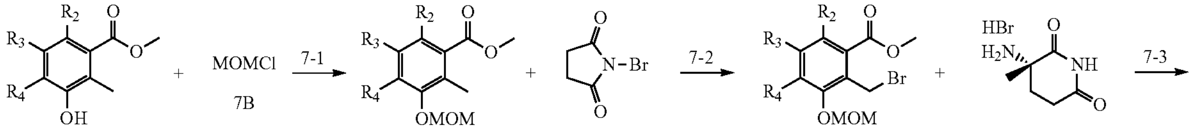

7A 7C 7D 7E 7F

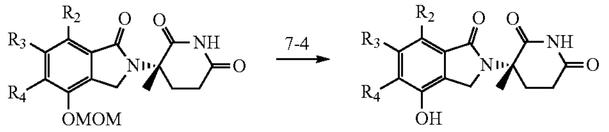

7G 7H

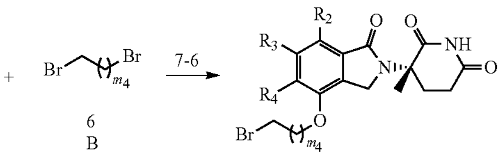

7J

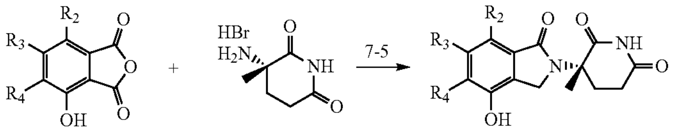

7I 7F 7H

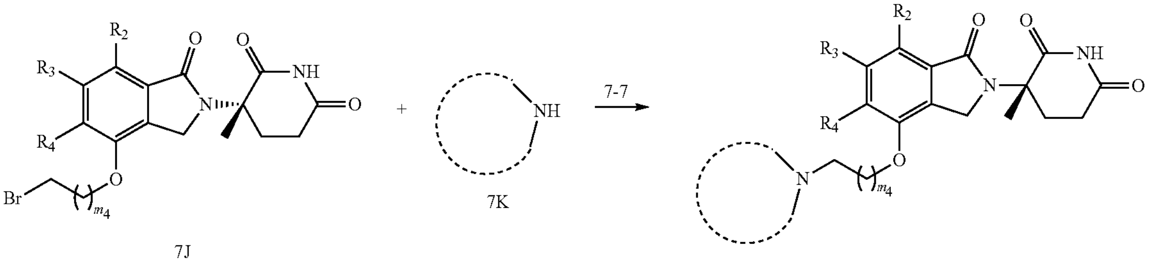

7J 7L wherein, the definitions of $R_1$, $R_2$, $R_3$, and $R_4$ are the same as those in claim 1;

$m_4$ is an integer from 1 to 7;

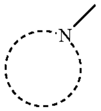

has the same definition as heterocyclyl, fused heterocyclyl, spiroheterocyclic group in the definition of A in claim 1;

Step 7-1: compound 7A and 7B chloromethyl methyl ether are reacted in the presence of sodium hydride to obtain compound 7C;

Step 7-2: compound 7C is reacted in the presence of 7D and azodiisobutyronitrile to obtain compound 7E;

Step 7-3: compounds 7E and 7F are reacted under basic condition to obtain compound 7G;

Step 7-4: compound 7G is reacted under acidic condition to obtain compound 7H;

Step 7-5: compound 7I and 7F are reacted under basic condition to obtain compound 7H;

Step 7-6: compound 7H and 6B are reacted in the presence of potassium carbonate to obtain compound 7J;

Steps 7-7: compound 7L is obtained by reacting compound 7J with nitrogen-containing heterocyclic compound 7K under basic condition, wherein the compound 7K is amine compound containing A group in claim 1.

9. The compound of claim 1, or the enantiomer, diastereomer, racemate, pharmaceutically acceptable salt, ester or hydrate thereof, for use in regulating the activity of $CRL4^{CRBN}$ E3 ubiquitin ligase.

10. A pharmaceutical composition, wherein the pharmaceutical composition contains a therapeutically effective dose of the compound of claim 1, or the enantiomer, diastereomer, racemate, pharmaceutically acceptable salt, ester or hydrate thereof, and at least one pharmaceutically acceptable carrier.

11. A method of treating a disease related to $CRL4^{CRBN}$ E3 ubiquitin ligase in a subject in need thereof, the method comprising administering to the subject a therapeutically amount of the compound of claim 1, enantiomer, diastereomer, racemate, pharmaceutically acceptable salt, ester, or hydrate thereof of claim 1, wherein the diseases is selected from the group consisting of cancer, inflammation, pain, neurological disease and immune system disease.

12. The compounds of claim 2, or the tautomer, enantiomer, diastereomer, racemate, isotopic compound, pharmaceutically acceptable salt, ester, or hydrate thereof, wherein

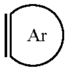

ring is selected from the group consisting of benzene ring, pyridine ring, thiophene ring, indole ring, benzothiophene ring, benzimidazole ring, naphthalene ring, quinoline ring and isoquinoline ring.

13. The compounds of claim 3, or the tautomer, enantiomer, diastereomer, racemate, isotopic compound, pharmaceutically acceptable salt, ester, or hydrate thereof, wherein

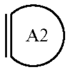

is selected from the group consisting of thiophene ring, pyrrole ring, benzene ring, pyridine ring, benzothiophene ring, benzimidazole ring, indole ring, quinoline ring and isoquinoline ring.

14. The compound of claim 1, or the tautomer, enantiomer, diastereomer, racemate, isotopic compound, pharmaceutically acceptable salt, ester, or hydrate thereof, wherein $R_1$ is hydrogen, deuterium or fluorine;

$R_3$ is hydrogen, deuterium or fluorine;

L is substituted or unsubstituted linear alkylene group containing 2-8 carbon atoms, and the "substituted" means one or more hydrogen atoms in the alkylene group are optionally replaced by the following substituents: deuterium, halogen, cyano, $C_1$-$C_3$ alkyl, $C_1$-$C_3$ haloalkyl, —NHC(O) $Ra_1$, —NHC(O)O$Ra_2$, —N$Ra_3$$Ra_4$, wherein $Ra_1$, $Ra_2$, $Ra_3$ and $Ra_4$ are each independently selected from hydrogen atom, $C_{1-6}$ alkyl unsubstituted or substituted by one or more halogens, or $C_{3-6}$ cycloalkyl unsubstituted or substituted by one or more halogens;

Y is absent, or is —CO— or —CO—NH—, the corresponding placement of Y, A and L is -A-CO-L-,-A-CO—NH-L-,-A-L-, A moiety comprises at least one nitrogen atom and Y is connected to the nitrogen atom, A is spiroheterocyclic group selected from:

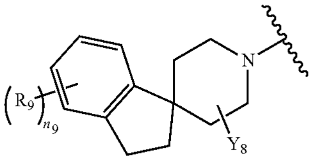

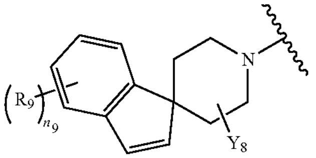

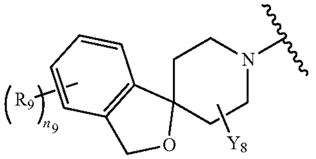

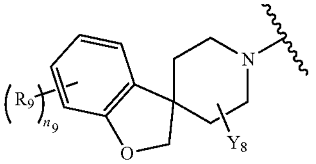

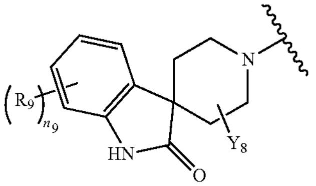

-continued

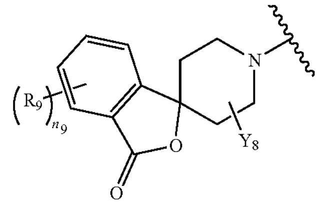

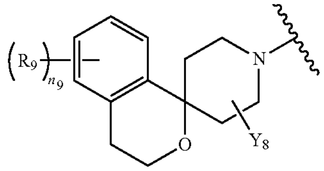

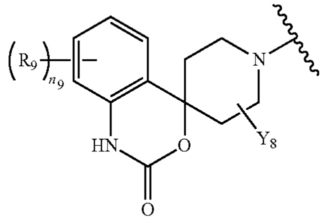

-continued

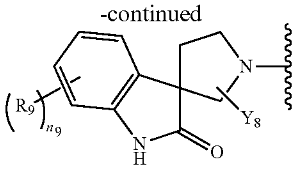

wherein, $n_9$ is 0, 1, 2, 3 or 4;

$R_9$ is independently selected from the following substituents: deuterium, halogen, cyano, nitro, hydroxyl, amino, $C_1$-$C_3$ alkylamino, $C_1$-$C_3$ acylamino, aminocarbonyl, linear or branched $C_1$-$C_6$ alkyl, linear or branched $C_1$-$C_6$ alkoxyl, $C_3$-$C_6$cycloalkyloxyl, $C_3$-$C_6$ cycloalkyl or heterocycloalkyl, $C_1$-$C_3$alkylaminocarbonyl, $C_1$-$C_3$alkoxycarbonyl, $C_1$-$C_3$alkylsulfonyl, $C_1$-$C_3$ haloalkyl, $C_1$-$C_3$haloalkoxyl, phenyl, 5-6 membered heteroaryl; wherein when $n_9>1$, each $R_9$ can be the same or different;

$Y_8$ is a substituent which optionally replace the hydrogen atom in the non-aromatic moiety of the spiro ring structure, and $Y_8$ is optionally substituted by deuterium, halogen, methyl, ethyl, cyclopropyl, or trifluoromethyl.

* * * * *